United States Patent
Lu et al.

(10) Patent No.: US 9,221,834 B2
(45) Date of Patent: Dec. 29, 2015

(54) CYCLIC AMINE SUBSTITUTED OXAZOLIDINONE CETP INHIBITOR

(75) Inventors: Zhijian Lu, Clinton, NJ (US); Yi-Heng Chen, Whippany, NJ (US); Cameron Smith, Lawrenceville, NJ (US); Hong Li, Edison, NJ (US); Christopher F. Thompson, Arlington, MA (US); Julianne Hunt, Montclair, NJ (US); Florida Kallashi, Lawrence Harbor, NJ (US); Ramzi Sweis, Lake Bluff, IL (US); Peter Sinclair, Doylestown, PA (US); Samantha E. Adamson, Charlottesville, VA (US); Guizhen Dong, Dayton, NJ (US); Debra L. Ondeyka, Fanwood, NJ (US); Xiaoxia Qian, New York, NY (US); Wanying Sun, Edison, NJ (US); Petr Vachal, Summit, NJ (US); Kake Zhao, Westfield, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 160 days.

(21) Appl. No.: 13/881,896

(22) PCT Filed: Oct. 25, 2011

(86) PCT No.: PCT/US2011/057584
§ 371 (c)(1), (2), (4) Date: Apr. 26, 2013

(87) PCT Pub. No.: WO2012/058187
PCT Pub. Date: May 3, 2012

(65) Prior Publication Data
US 2013/0331372 A1    Dec. 12, 2013

Related U.S. Application Data

(60) Provisional application No. 61/408,308, filed on Oct. 29, 2010.

(51) Int. Cl.
*A61K 31/4439* (2006.01)
*A61K 31/506* (2006.01)
(Continued)

(52) U.S. Cl.
CPC .............. *C07D 491/08* (2013.01); *A61K 31/42* (2013.01); *A61K 31/444* (2013.01); *A61K 31/4439* (2013.01); *A61K 31/4545* (2013.01); *A61K 31/497* (2013.01); *A61K 31/506* (2013.01); *A61K 31/5377* (2013.01); *A61K 45/06* (2013.01); *C07D 413/06* (2013.01); *C07D 413/14* (2013.01); *C07D 417/14* (2013.01)

(58) Field of Classification Search
CPC .. C07D 491/08; C07D 417/14; C07D 413/14; A61K 31/4439; A61K 31/506; A61K 31/5377; A61K 31/4545; A61K 31/497; A61K 45/06; A61K 31/444

USPC .............. 514/210.18, 210.2, 235.8, 275, 318, 514/343; 544/122, 325, 405; 546/194, 256, 546/269.7, 271.4
See application file for complete search history.

(56) References Cited

U.S. PATENT DOCUMENTS

| | | | |
|---|---|---|---|
| 7,652,049 B2 | 1/2010 | Ali et al. | |
| 7,781,426 B2 | 8/2010 | Ali et al. | |
| 8,871,738 B2 | 10/2014 | Shao et al. | |
| 2015/0111866 A1 | 4/2015 | Acton, III et al. | |

(Continued)

FOREIGN PATENT DOCUMENTS

| | | | |
|---|---|---|---|
| WO | 2007/081569 | * | 7/2007 |
| WO | 2007081569 A1 | | 7/2007 |
| WO | 2011/028395 | * | 3/2011 |

OTHER PUBLICATIONS

Abu Khalaf; et al., "Discovery of new cholesteryl ester transfer protein inhibitors via ligand-based pharmacophore modeling and QSAR analysis followed by synthetic exploration", European Journal of Medicinal Chemistry, vol. 45, pp. 1598-1617; 1599, Sec 2.1, 1604, Sec 2.5, 1605-1606, Sec 4.1.1(2010).

*Primary Examiner* — James O Wilson
*Assistant Examiner* — Ebenezer O Sackey
(74) *Attorney, Agent, or Firm* — Eric A. Meade; Catherine D. Fitch

(57) ABSTRACT

Compounds having the structure of Formula I, including pharmaceutically acceptable salts of the compounds, are CETP inhibitors and are useful for raising HDL-cholesterol, reducing LDL-cholesterol, and for treating or preventing atherosclerosis. In the compound of Formula I, $A^3$ is a substituted phenyl group or indanyl group. Formula (I).

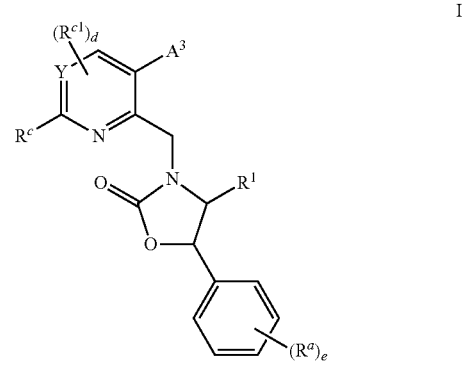

14 Claims, No Drawings

(51) Int. Cl.
*A61K 31/5377* (2006.01)
*A61K 31/4545* (2006.01)
*A61K 31/497* (2006.01)
*A61K 31/444* (2006.01)
*C07D 491/08* (2006.01)
*C07D 417/14* (2006.01)
*C07D 413/14* (2006.01)
*A61K 31/42* (2006.01)
*A61K 45/06* (2006.01)
*C07D 413/06* (2006.01)

(56) References Cited

U.S. PATENT DOCUMENTS 7,910,592 B2 3/2011 Ali et al.
7,915,271 B2 3/2011 Ali et al.
(Continued)

* cited by examiner

CYCLIC AMINE SUBSTITUTED OXAZOLIDINONE CETP INHIBITOR

FIELD OF THE INVENTION

This invention relates to chemical compounds that inhibit cholesterol ester transfer protein (CETP) and are expected to have utility in raising HDL-C, lowering LDL-C, and in the treatment and prevention of atherosclerosis.

BACKGROUND OF THE INVENTION

Atherosclerosis and its clinical consequences, including coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA reductase inhibitors, especially the statins, in reducing coronary events is based on the reduction of circulating low density lipoprotein cholesterol (LDL-C), levels of which correlate directly with an increased risk for atherosclerosis. More recently, epidemiologic studies have demonstrated an inverse relationship between high density lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoprotein and transports cholesterol ester from HDL to the apoB lipoprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-L, Yamashita, S, and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering LDL-C.

Despite the significant therapeutic advance that statins such as simvastatin and atorvastatin represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin provides an effective therapy for raising HDL-C but suffers from patient compliance issues, due in part to side effects such as flushing. Drugs that inhibit CETP (CETP inhibitors) have been under development with the expectation that they will effectively raise HDL cholesterol levels and also reduce the incidence of atherosclerosis in patients. Torcetrapib was the first drug that was tested in a long-term outcomes clinical trial. The clinical trial of torcetrapib was terminated early due to a higher incidence of mortality in patients to whom torcetrapib and atorvastatin were administered concomitantly compared with patients who were treated with atorvastatin alone. The cause of the increased mortality is not completely understood, but it is not believed to be associated with the CETP inhibiting effects of the drug.

Two other drug candidates, dalcetrapib and anacetrapib, are currently being tested in Phase III clinical trials, including large scale outcomes trials. Data from the recently completed DEFINE Phase III trial of anacetrapib are promising. Patients who were treated with anacetrapib along with baseline statin therapy showed an increase of HDL-C of 138% and a decrease of LDL-C of 40% compared with patients who were treated with just a statin. See: *N. Engl. J. Med.* 2010:363: 2406-15. The data in the DEFINE trial were sufficient to indicate that an increase in mortality for patients treated with anacetrapib is unlikely. Additional drug candidates are still being sought that may have properties that are advantageous compared with the CETP inhibitors that have so far been studied or are currently being studied. Such properties may include, for example, higher potency, reduced off-target activity, better pharmacodynamics, higher bioavailability, or a reduced food effect compared with many of the highly lipophilic compounds that have so far been studied. "Food effect" refers to the variability in exposure to the active drug that occurs depending on when the patient had last eaten, whether or not the drug is administered with food, and the fat content of the food.

SUMMARY OF THE INVENTION

The compound of Formula I, or a pharmaceutically acceptable salt thereof, is a potent CETP inhibitor, having the utilities described below:

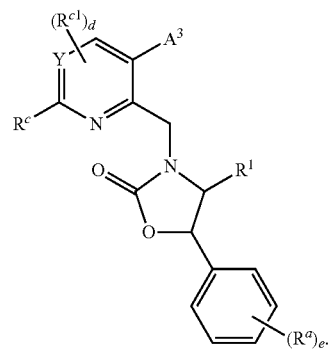

In the compound of Formula I, $A^3$ is represented by Formula II or Formula III:

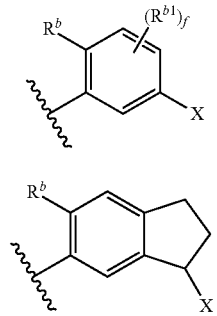

In the compound of Formula I:

$Y$ is N or CH, where CH may be substituted with $R^{e1}$ if $R^{e1}$ is present in the structure and is not H;

$R^1$ is H, $CF_3$, or $C_{1-3}$ alkyl;

Each $R^a$ is independently $C_{1-3}$alkyl optionally substituted with 1-5 halogens, —$OC_{1-3}$alkyl optionally substituted with 1-5 halogens, halogen, —CN, or $C_{3-4}$cycloalkyl optionally substituted with 1-3 halogens;

$R^c$ is (a) a 4-7 membered monocyclic heterocycle comprising one N which is bonded to the heteroaromatic ring to which $R^c$ is connected, wherein the monocyclic heterocycle optionally comprises 1-3 double bonds, one carbonyl, and 1-3 additional heteroatom groups which are each independently N, O, S, S(O), or $S(O)_2$, or (b) a 5-8 membered bicyclic heterocycle comprising one N which is bonded to the heteroaromatic ring to which $R^c$ is connected, wherein the bicyclic heterocycle optionally comprises 1-3 double bonds, one carbonyl, and 1-3 additional heteroatom groups which are each independently N, O, S, S(O), or $S(O)_2$, wherein $R^c$ as defined in (a) or (b) is optionally substituted with 1-3 substituent groups which are independently halogen, —OH, —CN, $C_{1-3}$ alkyl, or —$OC_{1-3}$ alkyl, wherein $C_{1-3}$ alkyl and —$OC_{1-3}$ alkyl are optionally substituted with 1-3 halogens;

Each $R^{e1}$ is independently $C_{1-3}$ alkyl, —$OC_{1-3}$ alkyl, or halogen, wherein alkyl in either case is optionally substituted with 1-5 halogens;

$R^b$ is H, $C_{1-3}$ alkyl, —$OC_{1-3}$ alkyl, —$OC_{3-6}$ cycloalkyl, halogen, —CN, —$NO_2$, or —OH, wherein $C_{1-3}$ alkyl and —$OC_{1-3}$ alkyl are optionally substituted with 1-5 halogens, and —$OC_{3-6}$ cycloalkyl is optionally substituted with 1-3 halogens;

Each $R^{b1}$ is independently $C_{1-3}$ alkyl, —$OC_{1-3}$ alkyl, or halogen, wherein $C_{1-3}$ alkyl and —$OC_{1-3}$ alkyl are optionally substituted with 1-5 halogens;

X is:

(a) (i) halogen, (ii) —$C_{1-4}$alkyl, (iii) —$C_{3-6}$cycloalkyl-Y or $C_{1-3}$alkyl-Y, wherein Y is —CN, —OH, or —$OCH_3$, or (iv) -phenyl which is substituted with 1-3 groups which are independently halogen, —CN, —OH, —$C_{1-4}$alkyl, —$OC_{1-4}$ alkyl, or —C(=O)$C_{1-2}$alkyl, wherein alkyl and cycloalkyl in all uses are optionally substituted with 1-3 halogens;

(b) $D^1$, wherein $D^1$ is —$CO_2H$, —$CO_2C_{1-4}$alkyl, or —C(=O)$NR^2R^3$;

(c) —$C_{1-4}$alkyl-$D^1$, wherein alkyl is optionally substituted with 1-3 halogens;

(d) —$C_{3-6}$cycloalkyl-$D^1$, wherein cycloalkyl is optionally substituted with 1-2 groups which are independently —$C_{1-2}$ alkyl or halogen, wherein —$C_{1-2}$ alkyl is optionally substituted with 1-3 halogens;

(e) —$C_{3-6}$cycloalkyl-$CH_2$-$D^1$, wherein cycloalkyl is optionally substituted with 1-2 groups which are independently —$C_{1-2}$ alkyl or halogen, wherein —$C_{1-2}$ alkyl is optionally substituted with 1-3 halogens;

(f) -phenyl-$D^1$, wherein phenyl is optionally substituted with 1-3 substituents which are independently halogen, —CN, —OH, —$CH_3$, —$CF_3$, —$OCH_3$, or —$OCF_3$;

(g) -Het-$D^1$, wherein Het is a 5-6-membered heteroaromatic ring having 1-4 heteroatom groups which are each independently N, O, S, S(O), or $S(O)_2$, wherein Het is optionally substituted with 1-3 groups which are independently halogen, —$CH_3$, —$CF_3$, —$OCH_3$, or —$OCF_3$; or (h) —$C_{1-2}$alkyl-Het, wherein Het is optionally substituted with 1-3 groups which are independently —$CH_3$, —$CF_3$, —$OCH_3$, —$OCF_3$ or halogen;

$R^2$ and $R^3$ are each independently H or —$C_{1-3}$alkyl, or $R^2$ and $R^3$ are optionally joined to form a bridging group having 3-5 carbons, thereby yielding a 4-6 membered cyclic amide group;

d is an integer from 0-2;

e is an integer from 0-3; and f is an integer from 0-2.

It should be noted that in the definition of $R^c$ above and in definitions of other heterocycles, when the definition includes 5-6-membered heterocycles that optionally have 1-3 double bonds, some of the heterocycles that have 2-3 double bonds are aromatic. They are still heterocycles as defined herein.

In the compound of Formula I, and in subgroups and other embodiments of the invention, alkyl groups and substituents based on alkyl groups, such as alkoxy, may be linear or branched unless otherwise indicated.

In general, references to the compound(s) of formula I or to the compound(s) of the invention herein are meant to also include subsets of compounds of formula I as may be defined herein, and specifically also are meant to include the specific numbered examples provided herein.

DETAILED DESCRIPTION OF THE INVENTION

In further embodiments of the invention, the substituent groups defined above may have alternative values independently of one another, as written below. Such embodiments include pharmaceutically acceptable salts when such salts are possible.

In subgroups of the compounds, $R^1$ is H or $C_{1-3}$alkyl. In preferred subgroups, $R^1$ is $CH_3$.

In subgroups of the compounds, each $R^a$ is independently $CF_3$, —$OCF_3$, $CH_3$, —$OCH_3$, halogen, —CN, or cyclopropyl which is optionally substituted with 1-3 halogens. In preferred subgroups, each $R^a$ is independently $CF_3$, $CH_3$, —$OCF_3$, Cl, F, cyclopropyl, or —CN.

In subgroups of the compounds, $R^c$ is (a) a 4-6 membered monocyclic heterocycle comprising one N which is bonded to the heteroaromatic ring to which $R^c$ is connected, wherein the monocyclic heterocycle optionally comprises 1-2 double bonds, one carbonyl, and 1-2 additional heteroatom groups which are each independently O, N, or —$S(O)_2$—, or (b) a 6-7 membered bicyclic heterocycle comprising one N which is bonded to the heteroaromatic ring to which $R^c$ is connected, wherein the bicyclic heterocycle optionally comprises 1-2 double bonds, one carbonyl, and 1-2 additional heteroatom groups which are each independently N, O, or —$S(O)_2$—, wherein $R^c$ as defined in (a) or (b) is optionally substituted with 1-2 substituent groups which are each independently halogen, —OH, $CH_3$, —$OCH_3$, $CF_3$, or —$OCF_3$.

In other subgroups of the compounds, $R^c$ is (a) a 4-6 membered monocyclic heterocycle comprising one N which is bonded to the heteroaromatic ring to which $R^c$ is connected, wherein the monocyclic heterocycle optionally comprises one carbonyl and 1 additional heteroatom group which is O, N, or —S(O)$_2$—; (b) a 5 membered monocyclic heteroaromatic ring comprising one N which is bonded to the heteroaromatic ring to which $R^c$ is connected, wherein the 5 membered monocyclic heteroaromatic ring optionally comprises 1 additional heteroatom group which is N; or (c) a 6-7 membered bicyclic heterocycle comprising one N which is bonded to the heteroaromatic ring to which $R^c$ is connected, wherein the bicyclic heterocycle optionally comprises 1 additional heteroatom group which is N or O; wherein $R^c$ as defined in (a), (b), or (c) is optionally substituted with 1-2 substituent groups which are each independently F, —OH, CH$_3$, —OCH$_3$, CF$_3$, or —OCF$_3$.

In additional subgroups of compounds, $R^c$ is azetidine, azetidinone, pyrrolidine, piperidine, morpholine, imidazole, pyrazole, isothiazolidine 1,1-dioxide, a morpholine ring comprising a methylene group bridging between two ring members, or a pyrrolidine ring comprising a fused cyclopropyl ring, wherein $R^c$ is optionally substituted with 1-3 substituents which are each independently halogen, —OH, —CH$_3$, —OCH$_3$, —CF$_3$, or —OCF$_3$.

In preferred embodiments, $R^c$ is optionally substituted with 1-2 substituents which are each independently F, —CH$_3$, —OH, or —OCH$_3$.

In subsets of the compounds of formula I, $R^{c1}$ is independently CH$_3$, CF$_3$, —OCH$_3$, —OCF$_3$ or halogen. In further subgroups, each $R^{c1}$ is independently —CH$_3$ or Br.

In further subsets of the compounds of formula I, $R^b$ is H, C$_{1-3}$ alkyl, —OC$_{1-3}$ alkyl, —OC$_{3-6}$ cycloalkyl, or halogen, wherein C$_{1-3}$ alkyl, —OC$_{1-3}$ alkyl, and —OC$_{3-6}$ cycloalkyl are optionally substituted with 1-3 halogens. In preferred subgroups, $R^b$ is H, —C$_{1-2}$ alkyl, —OCH$_3$, Cl, F, or —O-cyclopropyl.

In further subgroups of the compounds of formula I, each $R^b$ is independently halogen, CF$_3$, or CH$_3$. In preferred subgroups, $R^{b1}$ is F.

In additional embodiments of the invention, X is as provided in the two descriptions below. Individual choices for X as provided below can be substituted for the corresponding choices for X above or in the other list below, so that for example, (a) in the definition of X in either list below can replace (a) in the other list below or in the definition of X provided above. The same is true for selections (b) (c), (d), (e), (f), (g) and (h).

In one embodiment or set of embodiments, X is:

(a) (i) Cl, (ii) —C$_{2-4}$alkyl, (iii) —C$_{5-6}$cycloalkyl-Y or —C$_{1-3}$alkyl-Y wherein Y is —CN, —OH, or —OCH$_3$, or (iv) -phenyl which is substituted with 1-3 groups which are independently halogen, —CN, —OH, —C$_{1-4}$alkyl, —OC$_{1-4}$alkyl, or —C(=O)C$_{1-2}$alkyl, wherein alkyl and cycloalkyl in all occurrences are optionally substituted with 1-3 halogens;

(b) D$^1$, wherein D$^1$ is —CO$_2$H, —CO$_2$C$_{1-4}$alkyl, or —C(=O)NR$^2$R$^3$;

(c) —C$_{1-4}$alkyl-D$^1$, wherein alkyl is optionally substituted with 1-3 F;

(d) —C$_{3-6}$cycloalkyl-D$^1$, wherein cycloalkyl is optionally substituted with 1-2 groups which are independently —CH$_3$, CF$_3$, or halogen;

(e) —C$_{3-6}$cycloalkyl-CH$_2$-D$^1$, wherein cycloalkyl is optionally substituted with 1-2 groups which are independently —CH$_3$, CF$_3$, or halogen;

(f) -phenyl-D$^1$, wherein phenyl is optionally substituted with 1-3 substituent groups which are independently halogen, —CH$_3$, —CF$_3$, —OCH$_3$, or —OCF$_3$;

(g) -HET(1)-D$^1$, wherein HET(1) is a 5-6 membered heteroaromatic ring having 1-2 heteroatom groups which are independently N, O, S, S(O), or S(O)$_2$, wherein HET(1) is optionally substituted with 1-3 substituents which are independently halogen, —CH$_3$, —CF$_3$, —OCH$_3$, or —OCF$_3$; or (h) —(CH$_2$)$_{1-2}$-HET(2), wherein HET(2) is a 5-membered heteroaromatic ring having 2-4 heteroatom groups which are N, O, or S, wherein HET(2) is optionally substituted with 1-2 groups which are independently —CH$_3$ or halogen.

In another embodiment or set of embodiments, X is as listed below, and the individual choices for X as provided below can be substituted for the corresponding choices for X above, as explained previously, so that for example (a) in the list below can replace (a) under earlier definitions of X above. The same is true for selections (b) (c), (d), (e), (f), (g) and (h).

X is:

(a) Cl, —CH$_2$CN, —(CH$_2$)$_{1-3}$OH, —(CH$_2$)$_{1-3}$OCH$_3$, —CH(CH$_3$)$_2$ optionally substituted with 1-3 F and one —OH, -cyclopentyl-OH, -cyclohexyl-CN, or phenyl substituted with 2 substituents which are —OH and —C(=O)CH$_3$;

(b) D$^1$, wherein D$^1$ is —CO$_2$H or —CO$_2$C$_{1-4}$alkyl;

(c) —C$_{1-4}$alkyl-D$^2$, wherein D$^2$ is —CO$_2$H, —CO$_2$C$_{1-4}$alkyl, or —C(=O)NR$^2$R$^3$;

(d) —C$_{3-6}$cycloalkyl-D$^2$;

(e) —C$_{3-6}$cycloalkyl-CH$_2$-D$^1$;

(f) -phenyl-D$^1$, wherein phenyl is optionally substituted with 1-3 substituent groups which are independently halogen or —CH$_3$;

(g) -HET(1)-D$^1$, wherein HET(1) is a 5-6 membered heteroaromatic ring having 1-2 heteroatoms which are independently N, O, or S, wherein HET(1) is optionally substituted with 1-3 substituents which are independently halogen, —CH$_3$, —CF$_3$, —OCH$_3$, or —OCF$_3$; or (h) —(CH$_2$)$_{1-2}$-HET(2), wherein HET(2) is a 5-membered heteroaromatic ring having 2-4 N atoms, wherein HET(2) is optionally substituted with 1-2 groups which are independently —CH$_3$ or halogen.

In preferred embodiments, HET(1) as defined above is isoxazole, pyrazole, pyrazine, thiophene, furan, thiazole, pyrrole, pyridine, or imidazole.

In preferred embodiments, HET(2) is triazole, tetrazole, or imidazole.

In other embodiments, e is an integer from 1-3.

In other embodiments, d is 0 or 1.

In other embodiments, d is 0.

In other embodiments, f is 0 or 1.

In other embodiments, f is 0.

In an alternative embodiment, the invention is defined as a compound having Formula IV, as described below, including pharmaceutically acceptable salts:

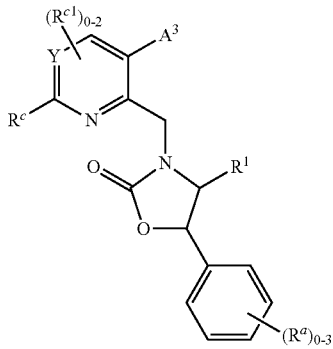

IV wherein A³ has a structure which has Formula V or Formula VI:

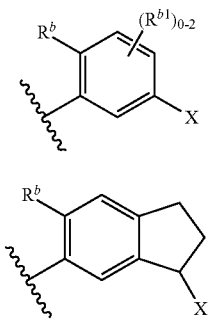

V

VI wherein Y is N or CH, wherein CH may be substituted with $R^{c1}$ if $R^{c1}$ is present in the structure;

$R^1$ is H or $C_{1-3}$ alkyl;

Each $R^a$ is independently $CF_3$, $CH_3$, halogen, or CN;

$R^c$ is a 4-7 membered saturated cyclic amine group containing one N which is attached to the heteroaromatic ring of formula I through the N, wherein $R^c$ is optionally substituted with 1-3 substituent groups which are independently halogen, $C_{1-3}$ alkyl, or —$OC_{1-3}$ alkyl, wherein $C_{1-3}$ alkyl and —$OC_{1-3}$ alkyl are optionally substituted with 1-3 halogens;

Each $R^{c1}$ is independently $C_{1-3}$ alkyl or halogen;

$R^b$ is H, $C_{1-3}$ alkyl, —$OC_{1-3}$ alkyl, —$OC_{3-6}$ cycloalkyl, or halogen, wherein $C_{1-3}$ alkyl and —$OC_{1-3}$ alkyl are optionally substituted with 1-3 halogens, and —$OC_{3-6}$ cycloalkyl is optionally substituted with 1-2 groups which are each independently halogen, $CF_3$, or $CH_3$;

Each $R^{b1}$ is independently halogen, $CF_3$, or $CH_3$;

X is:

(a) halogen;

(b) $D^1$, wherein $D^1$ is selected from the group consisting of H, —CN, —OH, —$OC_{1-3}$alkyl wherein alkyl is optionally substituted with 1-3 halogens, —$CO_2H$, —$CO_2C_{1-5}$ alkyl wherein alkyl is optionally substituted with 1-3 halogens, and —C(=O)$NR^2R^3$;

(c) —$C_{1-5}$alkyl-$D^1$;

(d) —$C_{3-6}$cycloalkyl-$D^2$, wherein cycloalkyl is optionally substituted with 1-2 groups independently selected from —$C_{1-2}$ alkyl and halogen; wherein $D^2$ is selected from $D^1$, —$C_{1-4}$alkyl-$CO_2H$, and —$C_{1-4}$alkyl-$CO_2C_{1-4}$ alkyl, wherein alkyl is optionally substituted with 1-3 halogens;

(e) -phenyl-$D^2$, wherein phenyl is optionally substituted with 1-3 substituents independently selected from halogen, —CN, —OH, —$C_{1-4}$alkyl, —$OC_{1-4}$alkyl, and —C(=O)$C_{1-2}$ alkyl;

(f) -phenyl optionally substituted with 1-3 groups independently selected from halogen, —CN, —OH, —$C_{1-4}$alkyl, —$OC_{1-4}$alkyl, and —C(=O)$C_{1-2}$alkyl; or (g) —$C_{0-2}$alkyl-Het-$D^2$, wherein Het is a 5-6-membered heteroaromatic ring having 1-4 heteroatoms independently selected from N, S and O, wherein Het is optionally substituted with 1-3 groups independently selected from halogen, —$C_{1-3}$alkyl optionally substituted with 1-3 halogens, and —$OC_{1-3}$alkyl optionally substituted with 1-3 halogens, and $R^2$ and $R^3$ are independently selected from the group consisting of H and —$C_{1-3}$alkyl, or $R^2$ and $R^3$ are joined to form a bridging group having 3-5 carbons, thereby yielding a 4-6 membered cyclic amine group when $R^2$ and $R^3$ are attached to the same N atom.

DEFINITIONS AND ABBREVIATIONS

"Ac" is acetyl, which is $CH_3C$(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, n-butyl, sec-butyl, tert-butyl, pentyl, hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group. Alkyl groups that are shown as difunctional are alkylene groups, even if they are referred to as alkyl groups.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" when used to describe a substituent or group in a structure means a monocyclic or bicyclic compound in which the rings are aromatic and which contain only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocyclyl," "heterocycle," and "heterocyclic" means a fully or partially saturated or aromatic 5-7 membered ring containing 1 or more heteroatom groups independently selected from N, S, O, S(O), S(O)$_2$, and (N)R and optionally having 1-3 double bonds unless otherwise stated, where R is H or alkyl. In general, when the terms are used herein, they will include the number of ring members, the number of double bonds (if any), and the specific heteroatoms. The heterocycles in some cases will be aromatic, depending on the number of double bonds (e.g. 6-membered ring with 3 double bonds). S(O), S(O)$_2$, and N(R) are referred to as heteroatom groups, and each heteroatom group is counted as one ring member, as is also the case for N, S, and O.

"Benzoheterocycle" represents a phenyl ring fused to a 5-7-membered heterocyclic ring having 1-2 heteroatoms, each of which is O, N, S, or (NR) wherein the heterocyclic ring optionally has 1-3 double bonds, and R is as defined above. Examples include indole, benzofuran, 2,3-dihydrobenzofuran and quinoline.

"AIBN" is azobisisobutyryonitrile.
"BISPIN" is bis(pinacoloto)diboron.
"Celite®" is a trade name for diatomaceous earth. Celite® 521 is the name of a specific product for laboratory use.
"CV" is a column volume (volume of a chromatography column).
"DIPEA" is diisopropylethylamine.
"DCM" is dichloromethane.
"DEA" is diethylamine.
"DMF" is N,N-dimethylformamide.
"DMSO" is dimethyl sulfoxide.
"ETOAc" is ethyl acetate.
"Halogen" includes fluorine, chlorine, bromine and iodine.
"HOBT" is 1-Hydroxybenzotriazole.
"HPLC" is high pressure liquid chromatography.
"IPAC" is isopropyl acetate.
"LCMS" is liquid chromatography mass spectrometry.
"Me" represents methyl.
"MeOH" is methanol.
"MsCL" is methanesulfonyl chloride.
"mCPBA" is meta-chloroperoxybenzoic acid.
"NaHMDS" is sodium hexamethyldisilazide.
"NCS" is N-chlorosuccinimide.
"NMP" is N-methyl-2-pyrrolidone.
"r.b.f." is a round bottom flask.
"RP" means reverse phase.
"r.t." and "RT" are abbreviations for room temperature.
"SFC" is supercritical fluid chromatography.
"SM" is starting material
"S-Phos" is 2-Dicyclohexylphosphino-2',6'-dimethoxybiphenyl (CAS#657408-07-6).
"TEA" is triethylamine.
"TFA" is trifluoroacetic acid.
"THF" is tetrahydrofuran.
"TLC" is thin layer chromatography.
"uw" is microwave.

The term "composition," as in pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers-Diastereomers-Geometric Isomers-Tautomers

The compounds disclosed herein generally have at least two asymmetric centers, and can thus occur as pure stereoisomers and as mixtures of stereoisomers, including racemates, racemic mixtures, single enantiomers, mixtures of enantiomers, diastereomeric mixtures and individual diastereomers. Different stereoisomers having the same 2-dimensional chemical structure may have different levels of activity with respect to CETP inhibition, so that some stereoisomers may have higher activity than others. The compounds that are potent inhibitors of CETP may have utility in patients for raising HDL-C, lowering LDL-C, treating dyslipidemia, and for preventing, treating or delaying the onset of conditions that are related to atherosclerosis. Stereoisomers that have little or no activity may have utility as research tools for better understanding CETP inhibition. All stereoisomers of the claimed compounds thus have utility. The compounds of Formula I may also occur as atropisomers (rotamers), which may be observable by NMR spectroscopy, and in some cases may be stable enough to conversion to other atropisomers that they can be isolated and assayed.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, triethanolamine, trimethylamine, tripropylamine, tromethamine, and the like.

When the compound of the present invention is basic, salts may be prepared from pharmaceutically acceptable non-toxic acids, including inorganic and organic acids. Such acids include acetic, adipic, ascorbic, benzenesulfonic, benzoic, camphorsulfonic, citric, diethylacetic, ethanesulfonic, formic, fumaric, gluconic, glutamic, hydrobromic, hydrochloric, isethionic, isonicotinic, lactic, maleic, malic, malonic, mandelic, methanesulfonic, mucic, naphthalendisulfonic, nitric, oxalic, pamoic, pantothenic, phenylpropionic, phosphoric, pimelic, pivalic, propionic, salicylic, succinic, sulfuric, sulfaminic, tartaric, p-toluenesulfonic acid, trifluoroacetic and the like. Particularly preferred are citric, hydrobromic, hydrochloric, maleic, phosphoric, sulfuric, and tartaric acids.

It will be understood that, as used herein, references to the compounds of the invention are also meant to be references to the compounds of Formula I and to the examples, and are meant to also include the pharmaceutically acceptable salts, where such salts are possible.

Prodrugs

Prodrugs, which are compounds that are converted to the compound of Formula I as they are being administered to a patient or after they have been administered to a patient, are also compounds of this invention in the sense that they provide the claimed pharmaceutically active drug moiety to the patient.

Utilities

The compounds disclosed herein, including pharmaceutically acceptable salts thereof, are potent inhibitors of CETP. The compounds are therefore useful in treating mammalian patients, preferably human patients, having diseases and conditions that are treated by inhibition of CETP.

One aspect of the present invention provides a method for treating or reducing the risk of developing a disease or condition that may be treated or prevented by inhibition of CETP by administering a therapeutically effective amount of the compound of Formula I to a patient in need of treatment. The patient is a human or mammal, but is most often a human. A "therapeutically effective amount" is the amount of compound that is effective in obtaining a desired clinical outcome in the treatment of a specific disease.

Diseases or conditions that may be treated with the compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds disclosed herein are particularly effective in raising HDL-C and/or increasing the ratio of HDL-C to LDL-C. The compounds may also be effective in reducing LDL-C, and may be effective in treating dyslipidemia. These changes in HDL-C and LDL-C may be beneficial in treating atherosclerosis, reducing or reversing the development of atherosclerosis, reducing the risk of developing atherosclerosis, or preventing atherosclerosis. The compounds disclosed herein are thus expected to be beneficial in treating atherosclerosis, reducing or reversing the development of atherosclerosis, reducing the risk of developing atherosclerosis, and preventing atherosclerosis.

Likely indications for atherosclerosis and dyslipidemia using the compounds described herein are written below, where the drug product is titled "CETP inhibitor:"

Atherosclerosis.

In patients at high risk of cardiovascular events because of existing coronary, cerebrovascular, or peripheral vascular disease, CETP inhibitor co-administered with an HMG-CoA reductase inhibitor is indicated to reduce the risk of coronary mortality, myocardial infarction, coronary revascularization procedures, ischemic stroke, and cardiovascular death.

Dyslipidemia.

CETP inhibitor co-administered with a statin is indicated to reduce elevated LDL-C, apolipoprotein B (ApoB), lipoprotein a (Lp(a)), non-HDL-C, and total cholesterol; and increase HDL-C and apolipoprotein A-1 (Apo A-1) in patients with mixed or primary dyslipidemia.

Administration and Dose Ranges

Any suitable route of administration may be employed for providing a mammal, especially a human, with an effective dose of the compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably the compound of Formula I is administered orally.

When treating the diseases for which the compound of Formula I is indicated, generally satisfactory results are expected when the compound of the present invention is administered at a daily dosage of from about 0.1 milligram to about 1000 milligram in one dose daily or divided into more than one dose per day.

Oral administration will usually be carried out using tablets. Examples of doses in tablets include 0.1 mg, 0.5 mg, 1 mg, 2 mg, 5 mg, 10 mg, 25 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 300 mg, 350 mg, 400 mg, 450 mg, 500 mg, and 1000 mg. Other oral forms can also have the same dosages (e.g. capsules). A preferred dose is in the range of 50-200 mg.

Pharmaceutical Compositions

Another aspect of the present invention provides pharmaceutical compositions which comprise the compound of Formula I and a pharmaceutically acceptable carrier. The pharmaceutical compositions of the present invention comprise the compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. A pharmaceutical composition may also consist essentially of the compound of Formula I, or a pharmaceutically acceptable salt of the compound, and a pharmaceutically acceptable carrier, without other therapeutic ingredients.

Pharmaceutical compositions may be formulated to be suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compound of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compound can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The Compound of formula I may also be administered parenterally. Solutions or suspensions of the compound can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

The compound of Formula I, including pharmaceutically acceptable salts, may be used in combination with other drugs that may also be useful in the treatment or amelioration of the diseases or conditions for which the compound of Formula I is useful. Such other drugs may be administered, by a route and in an amount commonly used therefor, contemporaneously or sequentially with the compound of Formula I. When the compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered concomitantly, on the same or different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); rivastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for uses described above, such as improving a patient's lipid profile (i.e. raising HDL-C and lowering LDL-C) and for treating, preventing, or reducing the risk of developing atherosclerosis, include one or both of statins and cholesterol absorption inhibitors. Particularly preferred are combinations of the compounds of this invention with a statin, with ezetimibe, or with both a statin and ezetimibe. Statins that may be used in these combinations include simvastatin, lovastatin, rosuvastatin, pravastatin, fluvastatin, atorvastatin, rivastatin, and pitavastatin. Preferred statins for use in combination therapy include simvastatin, atorvastatin, and rosuvastatin. Preferred combinations include combinations of a CETP inhibitor as disclosed herein and one or more cholesterol reducing agents, such as (a) atorvastatin; (b) simvastatin; (c) rosuvastatin; (d) ezetimibe; (e) atorvastatin and ezetimibe; (f) simvastatin and ezetimibe; or (g) rosuvastatin and ezetimibe.

Finally the compound of this invention can be used with compounds that are useful for treating other diseases, such as diabetes, hypertension and obesity, as well as other anti-atherosclerotic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these diseases, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818);

(b) biguanides such as metformin and phenformin;

(c) protein tyrosine phosphatase-1B (PTP-1B) inhibitors;

(d) dipeptidyl peptidase IV (DP-IV) inhibitors, including sitagliptin, vildagliptin, saxagliptin, alogliptin, linagliptin, dutogliptin, and gemigliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1; and (m) Non-sulfonylurea insulin secretagogues, such as the meglitinides (e.g. nateglinide and rapeglinide).

Preferred combinations with antidiabetic compounds include combinations of the compounds disclosed herein with DP-IV inhibitors (sitagliptin, alogliptin, vildagliptin, saxagliptin, linagliptin, dutogliptin, or gemigliptin), combinations with biguanides, and combinations with both a DP-IV inhibitor and a biguanide. The preferred DP-IV inhibitor is sitagliptin, and the preferred biguanide is metformin.

These other active ingredients that may be used in combination with the current invention also include antiobesity compounds, including 5-HT(serotonin) inhibitors, neuropeptide Y5 (NPY5) inhibitors, melanocortin 4 receptor (Mc4r) agonists, cannabinoid receptor 1 (CB-1) antagonists/inverse agonists, and β$_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as candesartan, eprosartan, irbesartan, losartan, olmesartan, telmisartan, and valsartan; (2) angiotensin converting enzyme inhibitors (ACE inhibitors), such as alacepril, benazepril, captopril, ceronapril, cilazapril, delapril, enalapril, enalaprilat, fosinopril, imidapril, lisinopril, moexepril, moveltipril, perindopril, quinapril, ramipril, spirapril, temocapril, or trandolapril; (3) calcium channel blockers such as nifedipine and diltiazam; and (4) endothelin antagonists.

Preferred antihypertensives that may be used in combination with the CETP inhibitors disclosed herein include one or more of an angiotensin II antagonist (losartan), an ACE inhibitor (enalapril or captopril), and hydrochlorothiazide.

Anti-obesity compounds may be administered in combination with the compounds of this invention, including: (1) growth hormone secretagogues and growth hormone secretagogue receptor agonists/antagonists, such as NN703 and hexarelin; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, amrinone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14]Bn(6-14) and [D-Phe6, Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

ASSAYS

Protocol: Scintillation Proximity Assay (SPA) for CETP Activity

First low density lipoprotein (LDL) (Meridian) was biotinylated by incubating LDL with biotin for 1 hour on ice, after which it was dialyzed to remove free biotin. Then compounds at varying concentrations were incubated with 15 nM CETP (reagent production group, In Vitro Pharmacology, MRL Rahway) and 50 ug/ml of the biotinylated LDL in 50 mM HEPES, 150 mM NaCl, pH 7.4, for 1 hour at 37° C. The reaction was started by adding $^3$H-cholesterol ester high density lipoprotein (HDL) (American Radiochemicals Corp) at a concentration of ~0.6 nM. The reaction proceeded for 2 hours at 37° C., after which time it was quenched by the addition of 12% acetic acid. PVT streptavadin-coated scintillation proximity beads, which had been brought to room temperature, were then added at a concentration of 4 mg/ml. The assay was then mixed and counted after one half hour in a Microbeta plate reader.

In Vitro Radioactive Assays of CETP-Catalyzed CE and TG Transfer (RTA Assay)

Reagents and sources are: [3H] cholesteryl oleate (GE #TRK.886), [3H] Triolein (Perkin-Elmer NET-431), Butylated hydroxyl toluene (Aldrich, #D4740-4), DOPC (Sigma, #P6354), Sodium Bromide (Fisher scientific #5255-500), PEG 8000 (Fisher, #BP233-1), and human HDL (Intracel Corp #RP-036).

An in vitro assay for determining $IC_{50}$'s to identify compounds that inhibit CETP transfer activity is performed based on a modification of a published method (Morton and Zilversmit, (1981) A plasma inhibitor of triglyceride and cholesteryl ester transfer activities, J. Biol. Chem. 256(23), 11992-11995). The ability of inhibitors to alter CETP activity is performed using two different assays: one using recombinant CETP and one using an edogenous plasma source of CETP. Both assays measure the transfer of [3H] cholesteryl oleate or [3H]triolein from exogenous LDL to HDL.

Radiolabeled donor particles are generated by first combining 100 µl of 200 µM butylated hydroxyl toluene in CHCl$_3$, 216 µL of 21.57 mM DOPC in EtOH, and either 500 µCi [3H]-triolein (Perkin Elmer #NET-431) or 500 µCi [3H]-cholesteryl oleate (GE #TRK886) in a glass tube. Reagents are mixed, dried under nitrogen, and then resuspended in 2 mL of 50 mM Tris, 27 µM EDTA at pH 7.4. After a brief vortex, the solution is sonicated until clear and mixed with 20 mL of fresh human serum. The mixture is incubated overnight at 37° C. The [3H] labeled LDL substrate is separated at 1.063 g/ml density by sequential ultracentrifugal flotation in NaBr according to the method by (Havel, Eder et al. 1955; Chapman, Goldstein et al. 1981). Once isolated the particles are dialyzed 3× in CETP buffer (50 mM Tris, pH 7.4, 100 mM NaCl, 1 mM EDTA). Human HDL is purchased from Intracel and used as the acceptor particles.

Transfer assays are performed in a 96-well v-bottom polypropylene plate. For the RTA using recombinant CETP (2% RTA), an assay cocktail is prepared with the final concentrations 128 µg/mL HDL, 20 nM rCETP, 2% human serum, and 1×CETP buffer. 1 µL of each test compound diluted in DMSO is added to 47 µL of assay cocktail per well and incubated at 37° C. for 1 hour. To initiate the transfer reaction, 2 µL radiolabeled LDL is added. After an additional 60 min of incubation at 37° C., the transfer action is terminated by precipitation of LDL with an equal volume of 20% W/V PEG 8000. The plates are centrifuged at 2000 rpm for 30 minutes at 4° C. A 40 µL aliquot of the HDL-containing supernatant is transferred to a Packard Optiplate with 200 µL of MicroScint 20. After mixing, plates are counted by liquid scintillation. Counts present in the supernatant for blanks (wells containing only HDL acceptor, CETP buffer and DMSO) are subtracted from those containing test compounds and used to correct for non-specific transfer.

For the transfer assay using endogenous CETP from serum (95% RTA), the same procedure is used except that human serum is added such that a final concentration of serum of 95% of the total assay volume is achieved, yielding a concentration of approximately 15 nM endogenous CETP in the assay. This is then combined with HDL and CETP buffer and the reaction proceeds as above and is terminated as described.

Comparison of the counts of samples with inhibitors to an uninhibited (DMSO only) positive control yield a percent inhibition. A plot of percent inhibition vs. log of inhibitor concentration, fit to a Sigmoidal 4 parameter equation is used to calculate IC50.

Assay Data

The table below provides data using the assays described herein. The data were obtained using the RTA assay in 2% human serum. In a few cases (Examples 142, 170 and 277), the RTA assays were carried out in 95% human serum. These measurements are labeled with an asterisk(*). Examples which are marked "N/A" were selected based on the assays, but the actual IC50's are not available in the databases. The IC50's for these examples are believed to be less then 1000 nM. Finally, the data for a few examples are included with the structures in the examples and are not in the table.

| Example | IC50 (nM) | Example | IC50 (nM) | Example | IC50 (nM) |
|---|---|---|---|---|---|
| 1 | 8 | 32 | 107 | 63 | 5 |
| 2 | 33 | 33 | N/A | 64 | 13 |
| 3 | 6 | 34 | N/A | 65 | 24 |
| 4 | 6 | 35 | 439 | 66 | 8 |
| 5 | 7 | 36 | 26 | 67 | 14 |
| 6 | 7 | 37 | 17 | 68 | 4 |
| 7 | 12 | 38 | 5 | 69 | 5 |
| 8 | 12 | 39 | 3 | 70 | 4 |
| 9 | 15 | 40 | 3 | 71 | 5 |
| 10 | 63 | 41 | 4 | 72 | 7 |
| 11 | 186 | 42 | 102 | 73 | 8 |
| 12 | 227 | 43 | 3 | 74 | 9 |
| 13 | 498 | 44 | 344 | 75 | 9 |
| 14 | 87 | 45 | N/A | 76 | 14 |
| 15 | 159 | 46 | 10 | 77 | 15 |
| 16 | 94 | 47 | 34 | 78 | 18 |
| 17 | 181 | 48 | 65 | 79 | 18 |
| 18 | 62 | 49 | 98 | 80 | 36 |
| 19 | 381 | 50 | 15 | 81 | 161 |
| 20 | 96 | 51 | 12 | 82 | 484 |
| 21 | 22 | 52 | 15 | 83 | 134 |
| 22 | 11 | 53 | 61 | 84 | 73 |
| 23 | 18 | 54 | 189 | 85 | 84 |
| 24 | 2 | 55 | N/A | 86 | 415 |
| 25 | 14 | 56 | 5 | 87 | 7 |
| 26 | 7 | 57 | 7 | 88 | 9 |
| 27 | 3 | 58 | 29 | 89 | 29 |
| 28 | 80 | 59 | 195 | 90 | 6 |
| 29 | 14 | 60 | 11 | 91 | 10 |
| 30 | 133 | 61 | 5 | 92 | 5 |
| 31 | 97 | 62 | 49 | 93 | 18 |
| 94 | 12 | 139 | 13 | 184 | 12 |
| 95 | 34 | 140 | 344 | 185 | 12 |
| 96 | 8 | 141 | N/A | 186 | 137 |
| 97 | 4 | 142 | 145* | 187 | 4 |
| 98 | 223 | 143 | 7 | 188 | 18 |
| 99 | 177 | 144 | 17 | 189 | 5 |
| 100 | N/A | 145 | 16 | 190 | 146 |
| 101 | 37 | 146 | 160 | 191 | 9 |
| 102 | 8 | 147 | 94 | 192 | N/A |
| 103 | 31 | 148 | 84 | 193 | 105 |
| 104 | 4 | 149 | 4 | 194 | 145 |
| 105 | 51 | 150 | 7 | 195 | 44 |
| 106 | 12 | 151 | 99 | 196 | 381 |
| 107 | 72 | 152 | 10 | 197 | 59 |
| 108 | 5 | 153 | 53 | 198 | 50 |
| 109 | 9 | 154 | 27 | 199 | 237 |
| 110 | 44 | 155 | 40 | 200 | 55 |
| 111 | 5 | 156 | 42 | 201 | 166 |
| 112 | 184 | 157 | 10 | 202 | 16 |
| 113 | 29 | 158 | 21 | 203 | 106 |
| 114 | 50 | 159 | 55 | 204 | 114 |
| 115 | 285 | 160 | 9 | 205 | 54 |
| 116 | 77 | 161 | 7 | 206 | 203 |
| 117 | 25 | 162 | 6 | 207 | 44 |
| 118 | N/A | 163 | 14 | 208 | 25 |
| 119 | 5 | 164 | 16 | 209 | 99 |
| 120 | 33 | 165 | 11 | 210 | 22 |
| 121 | 28 | 166 | 46 | 211 | 23 |
| 122 | 15 | 167 | 771 | 212 | 75 |
| 123 | N/A | 168 | 6 | 213 | 14 |
| 124 | 33 | 169 | 187 | 214 | 8 |
| 125 | 60 | 170 | 110* | 215 | 6 |
| 126 | 134 | 171 | 60 | 216 | 9 |
| 127 | 114 | 172 | 35 | 217 | 19 |
| 128 | 1085 | 173 | 21 | 218 | 12 |
| 129 | 18 | 174 | 18 | 219 | 44 |
| 130 | 32 | 175 | 72 | 220 | 330 |
| 131 | 10 | 176 | 415 | 221 | 145 |
| 132 | 4 | 177 | 19 | 222 | 115 |
| 133 | 39 | 178 | 6 | 223 | 289 |
| 134 | N/A | 179 | 5 | 224 | 14 |
| 135 | 89 | 180 | 56 | 225 | 66 |
| 136 | 55 | 181 | 7 | 226 | 110 |
| 137 | 605 | 182 | 297 | 227 | 65 |
| 138 | 2028 | 183 | 14 | 228 | 47 |
| 229 | 161 | 253 | 23 | 277 | 35* |
| 230 | 95 | 254 | 15 | 278 | N/A |
| 231 | 403 | 255 | 395 | 279 | 189 |
| 232 | 54 | 256 | 5 | 280 | 23 |
| 233 | 38 | 257 | 90 | 281 | N/A |
| 234 | 267 | 258 | 7 | 282 | N/A |
| 235 | 6 | 259 | 4 | 283 | 9 |
| 236 | 13 | 260 | 12 | 284 | 16 |
| 237 | 10 | 261 | 42 | 285 | 4 |
| 238 | 5 | 262 | 3 | 286 | 4 |
| 239 | 7 | 263 | 5 | 287 | 3 |
| 240 | 7 | 264 | 2 | 288 | 11 |
| 241 | 475 | 265 | 23 | 289 | 7 |
| 242 | 6 | 266 | 79 | 290 | 9 |
| 243 | 3 | 267 | 67 | 291 | 49 |
| 244 | 431 | 268 | 91 | 292 | 7 |
| 245 | 9 | 269 | 175 | 293 | 7 |
| 246 | 12 | 270 | 7 | 294 | 102 |
| 247 | 44 | 271 | 96 | 295 | 114 |
| 248 | 19 | 272 | 165 | 296 | 8 |
| 249 | 105 | 273 | 2295 | 297 | 375 |
| 250 | 54 | 274 | 1624 | 298 | 14 |
| 251 | 24 | 275 | 605 | | |
| 252 | 63 | 276 | 76 | | |

EXAMPLES

The following schemes and examples are provided so that the invention will be more fully appreciated and understood. These examples are illustrative and are not to be construed as limiting the invention in any way. The claims appended hereto define the scope of the invention.

Starting materials are commercially available or are made using known procedures or as shown below. The examples may be synthesized using the general schemes provided below. The compounds listed as examples all have IC50 values that were measured using the RTA or SPA assay between about 2 nM and 2295 nM. Preferred compounds have an IC50 less than about 500 nM. More preferred compounds have an IC50 less than about 100 nM. Highly preferred compounds have an IC50 less than about 50 nM.

Synthetic Schemes

SCHEME 1

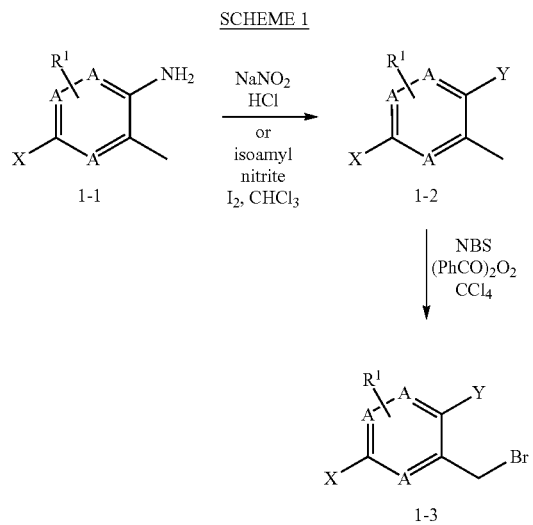

A = C, N
X, Y = Cl, Br or I

Intermediates of the present invention can be prepared as shown in Scheme 1. The aryl halide 1-2 can be obtained by treatment of an appropriately substituted pyridyl amine 1-1, which can be purchased or prepared by known methods, with reagents such as isoamylnitrite, n-pentylnitrite, t-butyl nitrite or the like in the presence of diiodomethane (see for example: Smith et al., *J. Org. Chem.* 55, 2543, (1990) and references cited therein) either neat or in a solvent such as THF or acetonitrile. Alternatively, the pyridyl halide can be prepared first by diazonium formation using isoamyl nitrite, n-pentyl nitrite, t-butyl nitrite, sodium nitrite in hydrochloric acid, nitrous acid or the like followed by the addition of bromine, iodine or an halo salt such as copper chloride, copper bromide, copper iodide, sodium iodide, potassium iodide, tetrabutylammonium iodide or the like. Heating pyridyl methyl derivative 1-2 with brominating agents such as N-bromosuccinimide or the like and a radical initiator such as benzoyl bromide, AIBN or the like in carbon tetrachloride affords the corresponding bromomethyl pyridines 1-3.

SCHEME 2

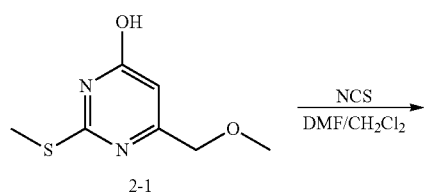

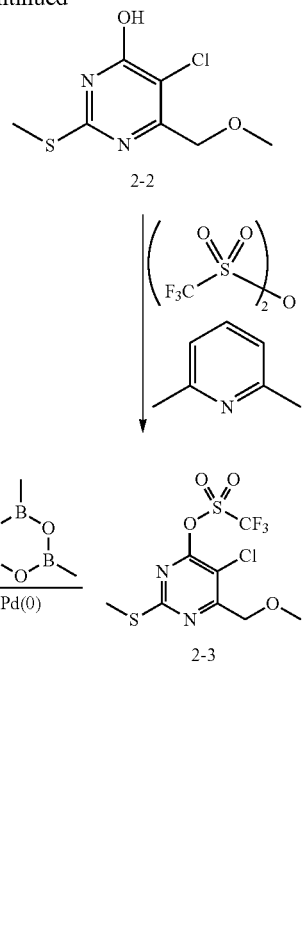

Intermediates 2-5 of the present invention can be prepared as shown in Scheme 2. Commercially available 2-1 can be halogenated using NCS in dichloromethane to afford Intermediate 2-2. Activation of the hydroxyl group by reaction with trifluoromethanesulfonic anhydride in the presence of a suitable base, such as 2,6-lutidine can afford the corresponding triflate Intermediate 2-3. Intermediate 2-4 can be prepared via an organotransition metal catalyzed cross-coupling reaction commonly referred to as the Suzuki reaction. In this method, Intermediate 2-3 can be reacted with trimethylboroxine in the presence of a suitable palladium catalyst, such as [1,1'-bis(diphenylphosphino)ferrocene]dichloropalladium (II) or tetrakistriphenylphosphine-palladium(0) or the like, and a base such as aqueous sodium carbonate or aqueous tribasic sodium phosphate or the like (Pure Appl. Chem. 1991, 63, 419-422). The reaction is usually performed in an inert organic solvent such as a toluene-EtOH mixture or dioxane, at temperatures above room temperature, for a period of 3-24 h. Recent advancements in the Suzuki reaction have allowed this type of transformation to be conducted in many cases at room temperature (for example, see: J. Am. Chem. Soc. 2000, 122, 4020-4028 and references cited therein. The methoxymethyl ether intermediate 2-4 can be de-alkylated via reaction with boron tribromide in dichloromethane to afford intermediates of the present invention 2-5.

SCHEME 3

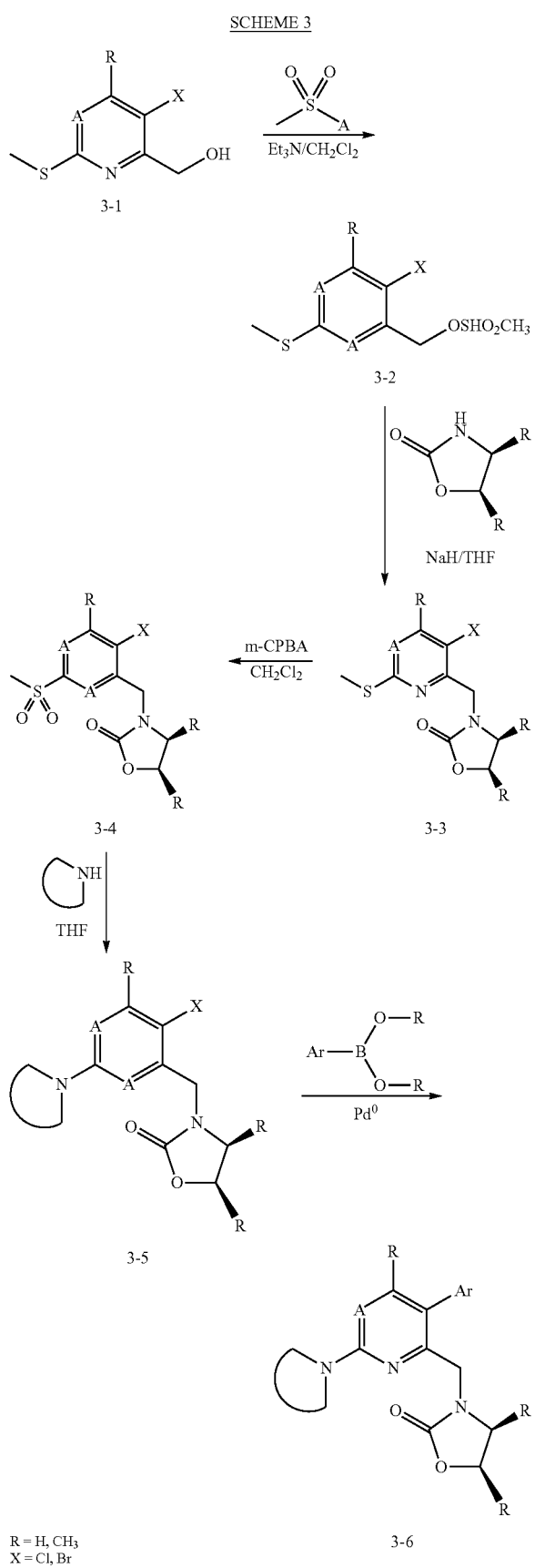

R = H, CH₃
X = Cl, Br

Compounds of the present invention can be prepared as shown in Scheme 3. Intermediates 3-1 can be obtained as shown in Scheme 2 or by reduction of the carboxylic acid group of commercially available pyrimidine or pyridine carboxylic acids. The transformation may be effected first by formation of the corresponding acid chloride, as by treatment with oxalyl chloride in dichloromethane in the presence of catalytic DMF, and subsequent reduction with sodium borohydride or the like. Activation of the hydroxyl group as by preparation of the corresponding methanesulfonate by treatment with methansulfonyl chloride in an aprotic solvent such as dichloromethane in the presence of a base such as triethylamine affords intermediate 3-2. Appropriately substituted oxazolidinones, prepared as shown in Scheme 5 can be alkylated by 3-2 using bases such as sodium hexamethyldisiliazide or sodium hydride in solvents like tetrahydrofuran, dimethoxyethane, diethyl ether or the like to afford Intermediates 3-3. Treatment of 3-3 with a suitable oxidizing agent such as m-CPBA, OXONE®, or the like in dichloromethane affords the methyl sulfone intermediate 3-4. Subsequent treatment of intermediate 3-4 with an appropriately substituted amine, neat or in an aprotic solvent such as THF or the like, affords aminopyrimidine 3-5. Compounds of the present invention, 3-6, can be prepared via an organotransition metal catalyzed cross-coupling reaction commonly referred to as the Suzuki reaction. In this method, Intermediate 3-5 is reacted with a boronic acid or boronate coupling partner in the presence of a suitable palladium catalyst, such as [1,1'-bis (diphenylphosphino)ferrocene]dichloropalladium(II) or tetrakistriphenylphosphine-palladium(0) or the like, and a base such as aqueous sodium carbonate or aqueous tribasic sodium phosphate or the like (Pure Appl, Chem. 1991, 63, 419-422). The reaction is usually performed in an inert organic solvent such as a toluene-EtOH mixture or dioxane, at temperatures above room temperature, for a period of 3-24 h. Recent advancements in the Suzuki reaction have allowed this type of transformation to be conducted in many cases at room temperature (for example, see: J. Am. Chem. Soc. 2000, 122, 4020-4028 and references cited therein).

SCHEME 4

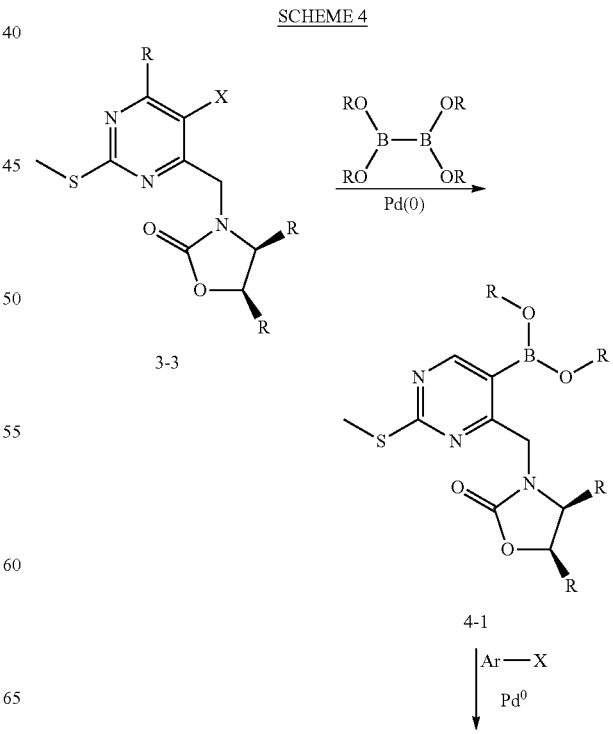

-continued

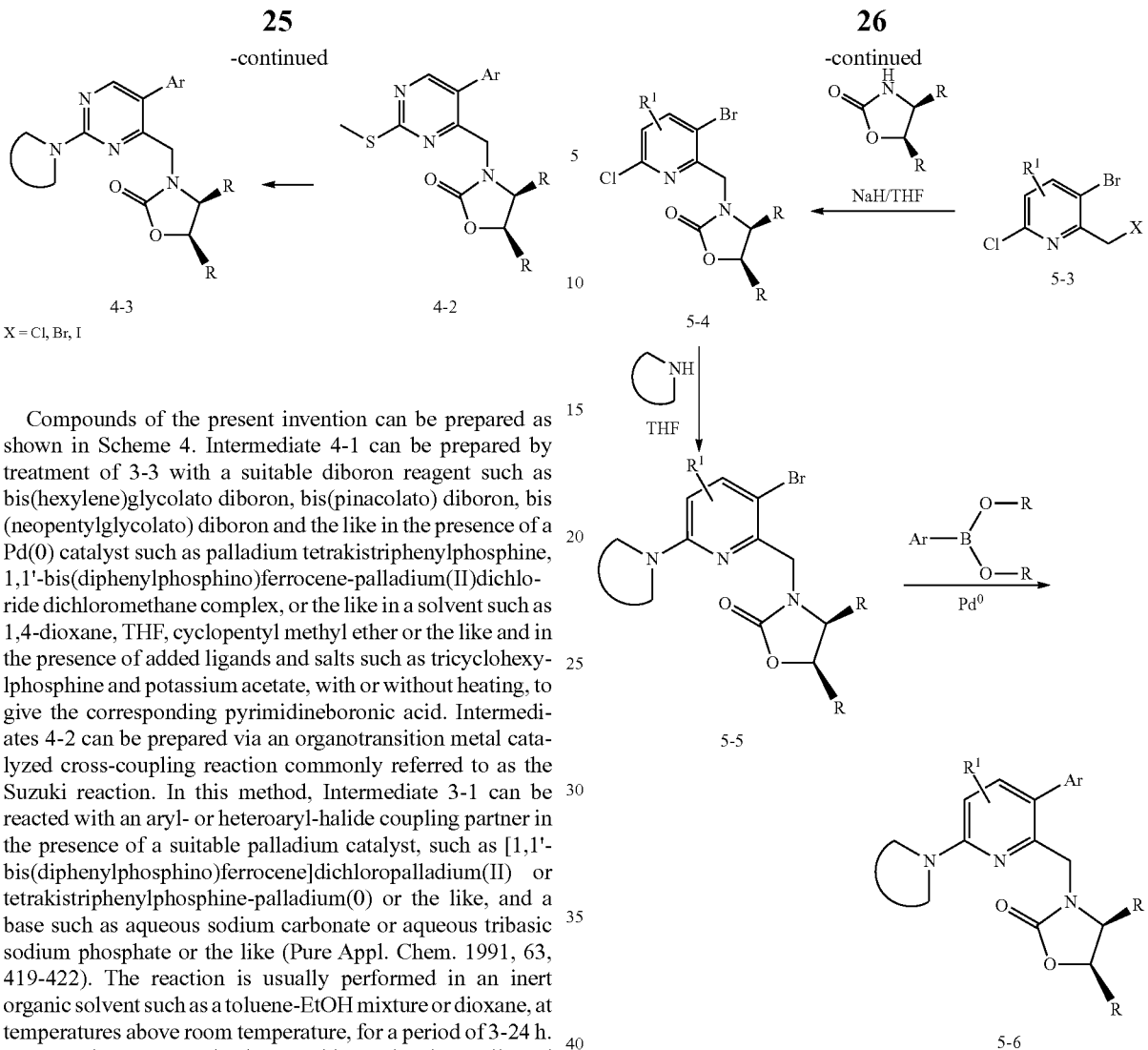

4-3    4-2

X = Cl, Br, I

Compounds of the present invention can be prepared as shown in Scheme 4. Intermediate 4-1 can be prepared by treatment of 3-3 with a suitable diboron reagent such as bis(hexylene)glycolato diboron, bis(pinacolato) diboron, bis (neopentylglycolato) diboron and the like in the presence of a Pd(0) catalyst such as palladium tetrakistriphenylphosphine, 1,1'-bis(diphenylphosphino)ferrocene-palladium(II)dichloride dichloromethane complex, or the like in a solvent such as 1,4-dioxane, THF, cyclopentyl methyl ether or the like and in the presence of added ligands and salts such as tricyclohexylphosphine and potassium acetate, with or without heating, to give the corresponding pyrimidineboronic acid. Intermediates 4-2 can be prepared via an organotransition metal catalyzed cross-coupling reaction commonly referred to as the Suzuki reaction. In this method, Intermediate 3-1 can be reacted with an aryl- or heteroaryl-halide coupling partner in the presence of a suitable palladium catalyst, such as [1,1'-bis(diphenylphosphino)ferrocene]dichloropalladium(II) or tetrakistriphenylphosphine-palladium(0) or the like, and a base such as aqueous sodium carbonate or aqueous tribasic sodium phosphate or the like (Pure Appl. Chem. 1991, 63, 419-422). The reaction is usually performed in an inert organic solvent such as a toluene-EtOH mixture or dioxane, at temperatures above room temperature, for a period of 3-24 h. Recent advancements in the Suzuki reaction have allowed this type of transformation to be conducted in many cases at room temperature (for example, see: J. Am. Chem. Soc. 2000, 122, 4020-4028 and references cited therein). Compounds 3-3 of the present invention are then prepared by oxidation of the sulfide with a suitable oxidizing agent such as m-CPBA, oxone or the like in dichloromethane, followed by displacement with an appropriately substituted amine, neat or in a solvent such as THF, 2-methyl THF or the like. Alternatively, an amine salt may be used along with the addition of an appropriate scavenger base such as triethylamine, diisopropylethylamine of the like.

SCHEME 5

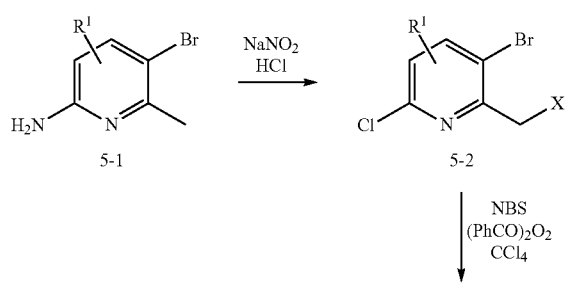

5-1    5-2

Compounds of the present invention can be prepared as shown in Scheme 5. The 2-halopyridine 5-2 can be obtained by treatment of an appropriately substituted pyridyl amine 5-1, which can be purchased or prepared by known methods, with reagents such as isoamylnitrite, n-pentylnitrite, t-butyl nitrite or the like in the presence of diiodomethane (see for example: Smith et al., J. Org. Chem. 55, 2543, (1990) and references cited therein) either neat or in a solvent such as THF or acetonitrile. Alternatively, the pyridyl halide can be prepared first by diazonium formation using isoamyl nitrite, n-pentyl nitrite, t-butyl nitrite, sodium nitrite in hydrochloric acid, nitrous acid or the like followed by the addition of bromine iodine or an halo salt such as copper chloride, copper bromide, copper iodide, sodium iodide, potassium iodide, tetrabutylammonium iodide or the like. Heating pyridyl methyl derivative 5-2 with brominating agents such as N-bromosuccinimide or the like and a radical initiator such as benzoyl bromide, AIBN or the like in carbon tetrachloride affords the corresponding bromomethyl pyridines 5-3. Appropriately substituted oxazolidinones, prepared as shown in Scheme 5 can be alkylated with aryl methyl bromides 5-3 using bases such as sodium hexamethyldisiliazide or sodium hydride in solvents like tetrahydrofuran, dimethoxyethane, diethyl ether or the like to afford Intermediates 5-4. Treatment of Intermediates 5-4 with appropriately substituted amines, neat or in a solvent such as THF, 2-methyl THF or the like, affords Intermediates 5-5. Alternatively, an amine salt may be used along with the addition of an appropriate scavenger base such as triethylamine, diisopropylethylamine of the like. Compounds 5-6 of the present invention can be prepared via an organotransition metal catalyzed cross-coupling reaction commonly referred to as the Suzuki reaction. In this method, Intermediate 5-5, is reacted with a boronic acid or boronate coupling partner in the presence of a suitable palladium catalyst, such as [1,1'-bis(diphenylphosphino)ferrocene]dichloropalladium(II) or tetrakistriphenylphosphine-palladium(0) or the like, and a base such as aqueous sodium carbonate or aqueous tribasic sodium phosphate or the like (Pure Appl. Chem. 1991, 63, 419-422). The reaction is usually performed in an inert organic solvent such as a toluene-EtOH mixture or dioxane, at temperatures above room temperature, for a period of 3-24 h. Recent advancements in the Suzuki reaction have allowed this type of transformation to be conducted in many cases at room temperature (for example, see: J. Am. Chem. Soc. 2000, 122, 4020-4028 and references cited therein).

SCHEME 6

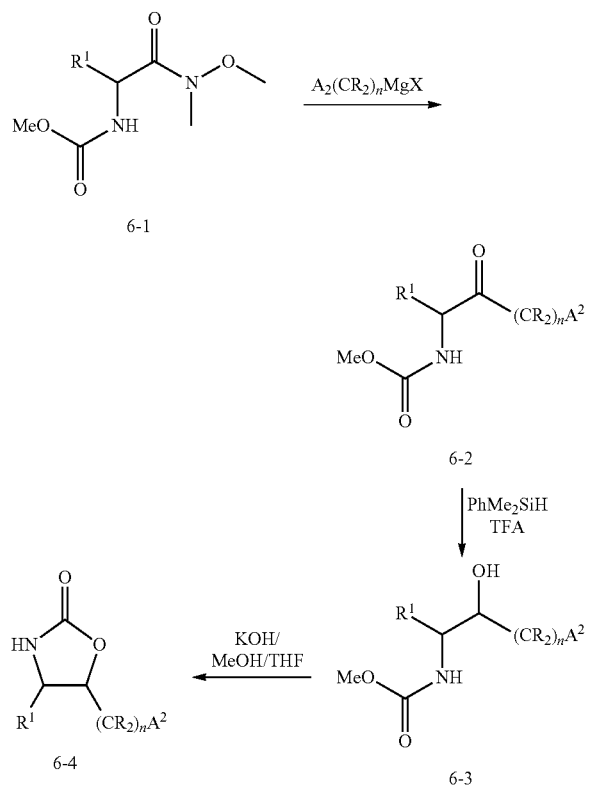

Intermediates 6-4 of the present invention can be prepared as shown in Scheme 6. Treatment of an N-carbamoyl-(N-methoxy-N-methyl)amide of an amino acid 6-1, which can be purchased or prepared by known methods, with a Grignard or other organometallic reagent such as an organolithium affords the corresponding ketone 6-2. Reduction of the ketone with sodium borohydride or zinc borohydride in alcoholic solvents or THF or the like or with other reducing agents such as phenyldimethyl silane in trifluoroacetic acid affords alcohol 6-3 which can be cyclized to oxazolidinone 6-4 upon treatment with base such as KOH in solvents such as MeOH, EtOH or the like and THF, dioxane, dimethoxyethane or the like.

INTERMEDIATE 1

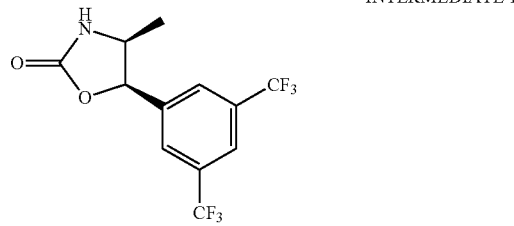

(4S,5R)-5-[3,5-bis(trifluoromethyl)phenyl]-4-methyl-1,3-oxazolidin-2-one

The synthesis of INTERMEDIATE 1 has been described previously. See, for example, INTERMEDIATE 1 of WO2007081569.

INTERMEDIATE 2

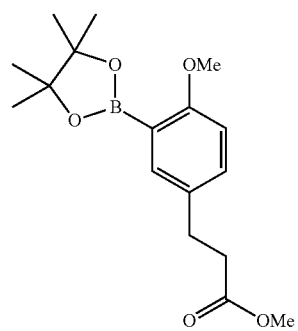

Methyl 3-[4-methoxy-3-(4,4,5,5-tetramethyl-1,3,2-dioxaborolan-2-1)phenyl]propanoate Step A: Methyl 3-(3-iodo-4-methoxyphenyl)propanoate To a solution of methyl 3-(4-methoxyphenyl)propanoate (5 g, 25.7 mmol) in MeOH (75 mL) was added $Ag_2SO_4$ (8.03 g, 25.7 mmol) followed by 12 (6.53 g, 25.7 mmol). The reaction was stirred vigorously at room temperature for 1 hour and then the solids were removed by filtration through Celite®. The filtrate was concentrated and the residue was taken up in EtOAc (150 mL), and washed with water (50 mL), aq. $NaHSO_3$ (2×50 mL), and brine (50 mL). The organic layer was dried over $Na_2SO_4$, filtered, and concentrated. Purification of the reside by flash chromatography on silica gel afforded methyl 3-(3-iodo-4-methoxyphenyl)propanoate. $^1$H NMR (500 MHz, $CDCl_3$) δ 7.61 (d, J=2.0 Hz, 1H), 7.14 (dd, J=8.2, 2.0 Hz, 1H), 6.74 (d, J=8.5 Hz, 1H), 3.85 (s, 3H), 3.67 (s, 3H), 2.85 (t, J=7.8 Hz, 2H), 2.59 (t, J=7.8 Hz, 2H).

Step B: Methyl 3-[4-methoxy-3-(4,4,5,5-tetramethyl-1,3,2-dioxaborolan-2-yl)phenyl]propanoate A round bottom flask was charged with methyl 3-(3-iodo-4-methoxyphenyl)propanoate (3 g, 9.37 mmol), bis(pinacolato)diboron (2.97 g, 11.71 mmol), $PdCl_2(dppf)CH_2Cl_2$ (765 mg, 0.937 mmol), KOAc (1.84 g, 18.74 mmol), dioxane (20 mL), and DMSO (80 mL). The reaction was degassed with N₂ and heated at 50° C. for 1 hour, and then 80° C. for 16 hours. The reaction was then cooled to r.t., diluted with EtOAc (200 mL), and washed with water (4×50 mL) and brine (50 mL). The organic layer was filtered through a plug of silica gel and concentrated. Purification of the residue by flash chromatography on silica gel (0 to 100% EtOAc/hexanes) afforded methyl 3-[4-methoxy-3-(4,4,5,5-tetramethyl-1,3,2-dioxaborolan-2-yl)phenyl]propanoate. ¹H NMR (CDCl₃, 500 MHz) δ 7.48 (d, J=2.5 Hz, 1H), 7.21 (dd, J=8.4, 2.3 Hz, 1H), 6.78 (d, J=8.5 Hz, 1H), 3.80 (s, 3H), 3.66 (s, 3H), 2.88 (t, J=7.8 Hz, 2H), 2.59 (t, J=7.8 Hz, 2H), 1.35 (s, 12H).

INTERMEDIATE 3

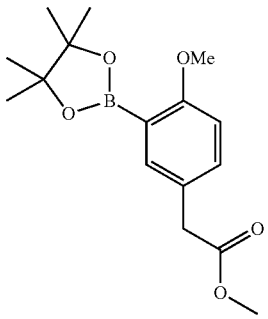

Methyl [4-methoxy-3-(4,4,5,5-tetramethyl-1,3,2-dioxaborolan-2-yl)phenyl]acetate

Step A: Methyl (3-iodo-4-methoxyphenyl)acetate

To a solution of methyl (4-methoxyphenyl)acetate (1 mL, 6.3 mmol) in MeOH (40 mL) was added Ag₂SO₄ (1.96 g, 6.3 mmol) followed by I₂ (1.6 g, 6.3 mmol). The reaction was stirred vigorously at room temperature for 1 hour and then the solids were removed by filtration. The filtrate was diluted with EtOAc (200 mL), and washed with aq. NaHSO₃ (2×50 mL) and brine (2×50 mL). The organic layer was dried over Na₂SO₄, filtered, and concentrated to afford methyl (3-iodo-4-methoxyphenyl)acetate. R_f=0.27 (15% EtOAc/hexanes). ¹H NMR (500 MHz, CDCl₃) δ 7.68 (d, J=2.0 Hz, 1H), 7.21 (dd, J=8.2, 1.8 Hz, 1H), 6.76 (d, J=8.4 Hz, 1H), 3.85 (s, 3H), 3.68 (s, 3H), 3.52 (s, 2H).

Step B: Methyl [4-methoxy-3-(4,4,5,5-tetramethyl-1,3,2-dioxaborolan-2-yl)phenyl]acetate A round bottom flask was charged with methyl (3-iodo-4-methoxyphenyl)acetate (503 mg, 1.64 mmol), bis(pinacolato)diboron (521 mg, 2.05 mmol), PdCl₂(dppf)-CH₂Cl₂ (134 mg, 0.164 mmol), KOAc (322 mg, 3.28 mmol), and DMSO (23 mL). The reaction was degassed with N₂ and heated at 40° C. for 1 hour, 60° C. for 1 hour, and then 80° C. for 12 hours. The reaction was diluted with EtOAc (50 mL) and washed with water (3×25 mL) and brine (25 mL). The organic layer was dried over Na₂SO₄, filtered, and concentrated. Purification of the residue by flash chromatography on silica gel (0 to 80% EtOAc/hexanes) afforded methyl [4-methoxy-3-(4,4,5,5-tetramethyl-1,3,2-dioxaborolan-2-yl)phenyl]acetate. ¹H NMR (CDCl₃, 500 MHz) δ 7.55 (d, J=2.3 Hz, 1H), 7.32 (dd, J=8.5, 2.3 Hz, 1H), 6.82 (d, J=8.4 Hz, 1H), 3.82 (s, 3H), 3.67 (s, 3H), 3.56 (s, 2H), 1.35 (s, 12H).

INTERMEDIATE 4

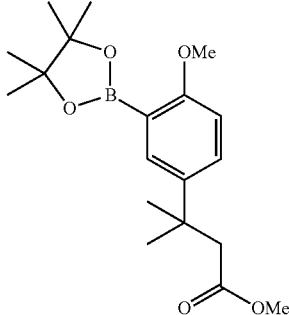

Methyl 3-[4-methoxy-3-(4,4,5,5-tetramethyl-1,3,2-dioxaborolan-2-yl)phenyl]-3-methylbutanoate Step A: 3-(4-Methoxyphenyl)-3-methylbutanoic acid In a dry flask was placed 3,3-dimethylacrylic acid (2.064 ml, 19.98 mmol). Dichloromethane (20 ml) and anisole (4.36 ml, 40.0 mmol) were added. Aluminum chloride (10.65 g, 80 mmol) was added in a single portion. After stirring at room temperature for 10 minutes, the reaction was heated to 65° C. After 2 hours, the reaction was cooled to room temperature and poured carefully onto 150 g of ice and 50 mL of concentrated HCl. The aqueous layer was extracted with CHCl₃ (3×50 mL). The combined organics were extracted with water (150 mL) and saturated NaHCO₃ (3×75 ml). These aqueous extracts were combined and acidified with 1N HCl. The acidified aqueous solution was extracted with 4×75 mL of Et₂O. The Et₂O extracts were dried over Mg₂SO₄, filtered, and concentrated. The residue was purified by flash chromatography on silica gel with 0 to 100% EtOAc/hexanes to afford 3-(4-methoxyphenyl)-3-methylbutanoic acid. ¹H NMR (CDCl₃, 500 MHz) δ 7.28 (d, J=8.8 Hz, 2H), 6.85 (d, J=8.8 Hz, 2H), 3.79 (s, 3H), 2.62 (s, 2H), 1.45 (s, 6H).

Step B: Methyl 3-(4-methoxyphenyl)-3-methylbutanoate 3-(4-methoxyphenyl)-3-methylbutanoic acid (513 mg, 2.463 mmol) was dissolved in toluene (13.3 ml) and methanol (2 ml). TMS-diazomethane (1.848 ml, 3.70 mmol) was added dropwise. Evolution of gas was observed, and a yellow color persisted. After 45 minutes, the reaction was quenched with acetic acid (200 uL, 3.5 mmol). The reaction was concentrated, and the residue was purified by flash chromatography on silica gel with 0 to 75% EtOAc/hexanes to afford methyl 3-(4-methoxyphenyl)-3-methylbutanoate. ¹H NMR (CDCl₃, 500 MHz) δ 7.28 (d, J=8.8 Hz, 2H), 6.85 (d, J=8.8 Hz, 2H), 3.79 (s, 3H), 3.54 (s, 3H), 2.59 (s, 2H), 1.43 (s, 6H).

Step C: Methyl 3-(3-iodo-4-methoxyphenyl)-3-methylbutanoate

Methyl 3-(4-methoxyphenyl)-3-methylbutanoate (475 mg, 2.137 mmol) was dissolved in ethanol (20 mL). Iodine (542 mg, 2.137 mmol) and silver sulfate (666 mg, 2.137 mmol) were added and the reaction was stirred vigorously at room temperature, protected from light, for 1 hr. The reaction was then diluted with ethyl acetate (40 mL) and filtered. The filtrate was washed with sodium bisulfite (2×50 mL), water (50 mL), and brine (50 mL). The organic layer was dried over sodium sulfate, filtered, and concentrated. The residue was purified by flash chromatography on silica gel with 0 to 50% ethyl acetate/hexanes to afford methyl 3-(3-iodo-4-methoxyphenyl)-3-methylbutanoate. $^1$H NMR (CDCl$_3$, 500 MHz) δ 7.73 (d, J=2.5 Hz, 1H), 7.29 (dd, J=8.6, 2.5 Hz, 1H), 6.75 (d, J=8.4 Hz, 1H), 3.86 (s, 3H), 3.55 (s, 3H), 2.57 (s, 2H), 1.41 (s, 6H).

Step D: Methyl 3-[4-methoxy-3-(4,4,5,5-tetramethyl-1,3,2-dioxaborolan-2-yl)phenyl]-3-methylbutanoate An oven-dried flask was charged with methyl 3-(3-iodo-4-methoxyphenyl)-3-methylbutanoate (250 mg, 0.718 mmol), bis(pinacolato)diboron (228 mg, 0.898 mmol), PdCl$_2$(dppf)·CH$_2$Cl$_2$ (58.6 mg, 0.072 mmol), potassium acetate (141 mg, 1.436 mmol), DMSO (5 mL), and dioxane (1 mL). The reaction was degassed with nitrogen and heated to 80° C. for 16 hours. The reaction was then cooled, diluted with ethyl acetate (25 mL), and washed with 1N NaOH (10 mL), water (2×10 mL), and brine (10 mL). The organic layer was dried over sodium sulfate, filtered, and concentrated. Purification of the residue by flash chromatography on silica gel (0 to 75% ethyl acetate/hexanes) afforded methyl 3-[4-methoxy-3-(4,4,5,5-tetramethyl-1,3,2-dioxaborolan-2-yl)phenyl]-3-methylbutanoate. $^1$H NMR (CDCl$_3$, 500 MHz) δ 7.63 (d, J=2.8 Hz, 1H), 7.38 (dd, J=8.7, 2.8 Hz, 1H), 6.79 (d, J=8.7 Hz, 1H), 3.81 (s, 3H), 3.55 (s, 3H), 2.59 (s, 2H), 1.44 (s, 6H), 1.35 (s, 12H).

INTERMEDIATE 5

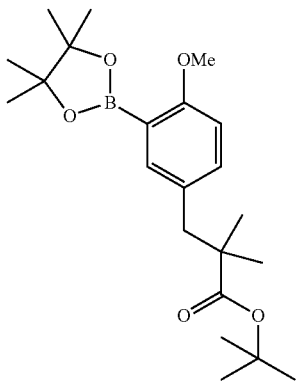

tert-Butyl 3-[4-methoxy-3-(4,4,5,5-tetramethyl-1,3,2-dioxaborolan-2-yl)phenyl]-2,2-dimethylpropanoate Step A: tert-Butyl 3-(4-methoxyphenyl)propanoate

[Reference: Wright, Hageman, Wright, and McClure, "Convenient Preparations of t-butyl esters and ethers from t-butanol" *Tetrahedron Letters*, Vol. 38, No. 42., pp. 7345-7348, 1997.]

To a fast stirring suspension of anhydrous magnesium sulfate (4.81 g, 40.0 mmol) in dichloromethane (40 ml) was added sulfuric acid (0.55 ml, 10.32 mmol). The reaction was vigorously stirred for 15 minutes at room temperature and then 3-(4-methoxyphenyl)propionic acid (1.8 g, 9.99 mmol) and tert-butanol (4.78 ml, 50.0 mmol) were added. The reaction was sealed and stirred at room temperature overnight. The reaction was quenched with 75 mL of saturated sodium bicarbonate solution and washed with water (2×50 mL) and brine (1×50 mL). The organic layer was dried over sodium sulfate, filtered, concentrated, and purified by flash chromatography on silica gel (0 to 80% ethyl acetate/hexanes) to afford tert-butyl 3-(4-methoxyphenyl)propanoate. $^1$H NMR (CDCl$_3$, 500 MHz) δ 7.11 (d, J=8.7 Hz, 2H), 6.82 (d, J=8.7 Hz, 2H), 3.78 (s, 3H), 2.85 (t, J=7.7 Hz, 2H), 2.50 (t, J=7.7 Hz, 2H), 1.42 (s, 9H).

Step B: tert-Butyl 3-(4-methoxyphenyl)-2-methylpropanoate

An oven dried flask was charged with THF (40 mL) under nitrogen and cooled to −78° C. and 2M LDA in THF (7.62 mL, 15.23 mmol) was added dropwise followed by DMPU (8 mL, 6.09 mmol). Tert-butyl 3-(4-methoxyphenyl)propanoate (1.44 g, 6.09 mmol) was added by cannula in THF (4×5 mL), and the reaction was stirred at −78° C. for 1 hr. Methyl iodide (1.143 mL, 18.28 mmol) was added dropwise, and the reaction was stirred 30 minutes at −78° C. and then warmed to room temperature for 1 hr. The reaction was then quenched with water (40 mL) and extracted with ethyl acetate (50 mL). The organic layer was washed with 1N HCl (2×30 mL) and brine (2×30 mL), dried over sodium sulfate, filtered, and concentrated. Purification of the residue by flash chromatography on silica gel (0 to 60% ethyl acetate/hexanes) afforded of tert-butyl 3-(4-methoxyphenyl)-2-methylpropanoate. $^1$H NMR (CDCl$_3$, 500 MHz) δ 7.09 (d, J=8.5 Hz, 2H), 6.81 (d, J=8.5 Hz, 2H), 3.78 (s, 3H), 2.89 (multiplet, 1H), 2.57 (multiplet, 2H), 1.38 (s, 9H), 1.10 (d, J=6.4 Hz, 3H).

Step C: tert-Butyl 3-(4-methoxyphenyl)-2,2-dimethylpropanoate

An oven dried flask was charged with THF (40 mL) under nitrogen and cooled to −78° C. and 2M LDA in THF (7.19 mL, 14.38 mmol) was added dropwise followed by DMPU (8 mL, 5.75 mmol). Tert-butyl 3-(4-methoxyphenyl)-2-methylpropanoate (1.44 g, 5.75 mmol) was added by cannula in THF (4×5 mL), and the reaction was stirred at −78° C. for 1 hr. Methyl iodide (1.079 mL, 17.26 mmol) was added dropwise, and the reaction was stirred 30 minutes at −78° C. and then warmed to room temperature for 1 hr. The reaction was quenched with water (40 mL) and extracted with ethyl acetate (50 mL). The organic layer was washed with 1N HCl (2×30 mL) and brine (2×30 mL), dried over sodium sulfate, filtered, and concentrated. Purification of the residue by flash chromatography on silica gel (0 to 60% ethyl acetate/hexanes) afforded tert-butyl 3-(4-methoxyphenyl)-2,2-dimethylpropanoate. $^1$H NMR (CDCl$_3$, 500 MHz) δ 7.07 (d, J=8.5 Hz, 2H), 6.79 (d, J=8.7 Hz, 2H), 3.78 (s, 3H), 2.76 (s, 2H), 1.43 (s, 9H), 1.11 (s, 6H).

Step D: tert-Butyl 3-(3-iodo-4-methoxyphenyl)-2,2-dimethylpropanoate

Tert-butyl 3-(4-methoxyphenyl)-2,2-dimethylpropanoate (1.45 g, 5.48 mmol) was dissolved in ethanol (55 mL). Iodine (1.392 g, 5.48 mmol) and silver sulfate (1.710 g, 5.48 mmol) were added, and the reaction was stirred vigorously at room temperature, protected from light, for 1 hr. The reaction was diluted with ethyl acetate (100 mL) and filtered. The filtrate was washed with sodium bisulfite (2×60 mL), water (70 mL), and brine (70 mL). The organic layer was dried over sodium sulfate, filtered, and concentrated. The residue was purified by flash chromatography on silica gel with 0 to 50% ethyl acetate/hexanes to afford tert-butyl 3-(3-iodo-4-methoxyphenyl)-2,2-dimethylpropanoate. $^1$H NMR (CDCl$_3$, 500 MHz) δ

7.58 (d, J=1.8 Hz, 1H), 7.08 (dd, J=8.4, 1.9 Hz, 1H), 6.71 (d, J=8.4 Hz, 1H), 3.85 (s, 3H), 2.71 (s, 2H), 1.44 (s, 9H), 1.11 (s, 6H).

Step E: tert-Butyl 3-[4-methoxy-3-(4,4,5,5-tetramethyl-1,3,2-dioxaborolan-2-yl)phenyl]-2,2-dimethylpropanoate An oven-dried flask was charged with tert-butyl 3-(3-iodo-4-methoxyphenyl)-2,2-dimethylpropanoate (1.9 g, 4.87 mmol), bis(pinacolato)diboron (1.545 g, 6.09 mmol), PdCl$_2$(dppf)CH$_2$Cl$_2$ (398 mg, 0.487 mmol), potassium acetate (956 mg, 9.74 mmol), DMSO (35 mL), and dioxane (10 mL). The reaction was degassed with nitrogen and heated to 80° C. for 16 hours. The reaction was then cooled to r.t., diluted with ethyl acetate (100 mL), and washed with 1N NaOH (2×75 mL), water (2×100 mL), and brine (100 mL). The organic layer was dried over sodium sulfate, filtered, and concentrated. Purification of the residue by flash chromatography on silica gel (0 to 75% ethyl acetate/hexanes) afforded tert-butyl 3-[4-methoxy-3-(4,4,5,5-tetramethyl-1,3,2-dioxaborolan-2-yl)phenyl]-2,2-dimethylpropanoate. $^1$H NMR (CDCl$_3$, 500 MHz) δ 7.47 (d, J=2.3 Hz, 1H), 7.16 (dd, J=8.5, 2.4 Hz, 1H), 6.74 (d, J=8.5 Hz, 1H), 3.80 (s, 3H), 2.76 (s, 2H), 1.44 (s, 9H), 1.33 (s, 12H), 1.12 (s, 6H).

INTERMEDIATE 6

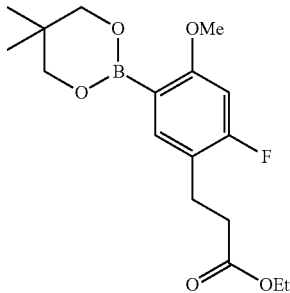

Ethyl 3-[5-(5,5-dimethyl-1,3,2-dioxaborinan-2-yl)-2-fluoro-4-methoxyphenyl]propanoate Step A: Ethyl 3-(2-fluoro-4-methoxyphenyl)propanoate An oven dried flask was charged with sodium hydride (60%) (389 mg, 9.73 mmol) and THF (25 mL) and cooled to 0° C. Triethyl phosphonoacetate (1.948 mL, 9.73 mmol) was added dropwise and the reaction was heated to 50° C. for 1 hr. The reaction was then cooled to 0° C., and 2-fluoro-4-methoxy-benzaldehyde (1000 mg, 6.49 mmol) was added via cannula in THF (4×5 mL). The reaction was then heated at reflux for 16 hours. Next, the reaction was cooled to room temperature and diluted with ethyl acetate (75 mL). The organic layer was washed with water (2×75 mL) and brine (75 mL), dried over sodium sulfate, filtered, and concentrated. The residue was dissolved in ethanol (20 mL) and 10% palladium on carbon (100 mg) was added. The reaction was placed under an atmosphere of H$_2$ (balloon) and stirred for 4 hours. The reaction was then filtered and concentrated. Purification of the residue via flash chromatography on silica gel (0 to 40% ethyl acetate/hexanes) afforded ethyl 3-(2-fluoro-4-methoxyphenyl)propanoate. $^1$H NMR (CDCl$_3$, 500 MHz) δ 7.09 (t, J=8.5 Hz, 1H), 6.60 (m, 2H), 4.12 (q, J=7.2 Hz, 2H), 3.77 (s, 3H), 2.90 (t, J=7.6 Hz, 2H), 2.58 (t, J=7.7 Hz, 2H), 1.23 (t, J=7.2 Hz, 3H).

Step B: Ethyl 3-(2-fluoro-5-iodo-4-methoxyphenyl)propanoate

Ethyl 3-(2-fluoro-4-methoxyphenyl)propanoate (1480 mg, 6.54 mmol) was dissolved in ethanol (60 mL). Iodine (1660 mg, 6.54 mmol) and silver sulfate (2040 mg, 6.54 mmol) were added and the reaction was stirred vigorously at room temperature, protected from light, for 1 hr. The reaction was then diluted with ethyl acetate (100 mL) and filtered. The filtrate was washed with sodium bisulfite (2×60 mL), water (70 mL), and brine (70 mL). The organic layer was dried over sodium sulfate, filtered, and concentrated. The residue was purified by flash chromatography on silica gel with 0 to 50% ethyl acetate/hexanes to afford ethyl 3-(2-fluoro-5-iodo-4-methoxyphenyl)propanoate. $^1$H NMR (CDCl$_3$, 500 MHz) δ 7.59 (d, J=8.4 Hz, 1H), 6.55 (d, J=11.6 Hz, 1H), 4.13 (q, J=7.1 Hz, 2H), 3.84 (s, 3H), 2.87 (t, J=7.6 Hz, 2H), 2.57 (t, J=7.6 Hz, 2H), 1.24 (t, J=7.1 Hz, 3H).

Step C: Ethyl 3-[5-(5,5-dimethyl-1,3,2-dioxaborinan-2-yl)-2-fluoro-4-methoxyphenyl]propanoate An oven dried flask was charged with ethyl 3-(2-fluoro-5-iodo-4-methoxyphenyl)propanoate (2.05 g, 5.82 mmol), bis(neopentyl glycolato)diboron (1.578 g, 6.99 mmol), 1,1'-bis(diphenylphosphino)ferrocene-palladium(II)dichloride dichloromethane complex (0.143 g, 0.175 mmol), potassium acetate (1.714 g, 17.46 mmol), and DMSO (50 mL). The reaction was degassed with nitrogen and heated at 60° C. for 2 hr. The reaction was then poured into ice water and extracted with ethyl acetate (2×75 mL). The combined extracts were washed with water (2×50 mL) and brine (2×50 mL), dried over sodium sulfate, filtered, and concentrated. The residue was purified via flash chromatography on silica gel (0 to 60% ethyl acetate/hexanes) to afford semi-pure ethyl 3-[5-(5,5-dimethyl-1,3,2-dioxaborinan-2-yl)-2-fluoro-4-methoxyphenyl]propanoate. $^1$H NMR (CDCl$_3$, 500 MHz) δ 7.50 (d, J=9.8 Hz, 1H), 6.54 (d, J=12.6 Hz, 1H), 4.12 (q, J=7.1 Hz, 2H), 3.79 (s, 3H), 3.77 (s, 4H), 2.91 (multiplet, 2H), 2.58 (multiplet, 2H), 1.23 (multiplet, 3H), 1.02 (s, 6H).

INTERMEDIATE 7

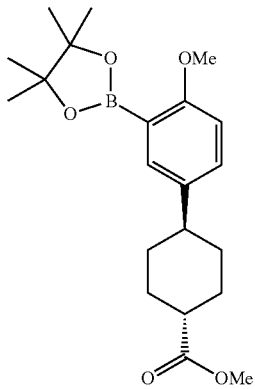

Methyl trans-4-[4-methoxy-3-(4,4,5,5-tetramethyl-1,3,2-dioxaborolan-2-yl)phenyl]cyclohexanecarboxylate Step A: 4-(4-Methoxyphenyl)cyclohexanone To a solution of 4-(4-hydroxyphenyl)cyclohexanone (1 g, 5.26 mmol) in DMF (50 ml) was added cesium carbonate (3.00 g, 9.20 mmol) followed by methyl iodide (0.411 ml, 6.57 mmol). The reaction was stirred at room temperature for 1 hour and then diluted with ethyl acetate (100 mL), washed with water (3×50 mL), and brine (50 mL). The organic layer was dried over $Na_2SO_4$, filtered, and concentrated. Purification of the residue by flash chromatography on silica gel with 0 to 100% EtOAc/hexanes afforded 4-(4-methoxyphenyl)cyclohexanone. $^1$H NMR (CDCl$_3$, 500 MHz) δ 7.16 (d, J=8.4 Hz, 2H), 6.87 (d, J=8.7 Hz, 2H), 3.80 (s, 3H), 2.99 (m, 1H), 2.45-2.55 (m, 4H), 2.16-2.23 (m, 2H), 1.86-1.96 (m, 2H).

Step B: trans-4-(4-Methoxyphenyl)cyclohexanecarbaldehyde

A suspension of (methoxymethyl)triphenylphosphonium chloride (4632 mg, 13.51 mmol) in THF (60 mL) was cooled to 0° C. Potassium hexamethyldisilazide (22.52 ml, 11.26 mmol) was added dropwise via syringe and the solution turned dark red. After the reaction was stirred at 0° C. for 15 minutes, 4-(4-methoxyphenyl)cyclohexanone (920 mg, 4.50 mmol) was added as a solution in THF (15 mL). The reaction was warmed to r.t. and stirred at r.t. for 2 hours. Next, 5 mL of concentrated HCl was added to 10 mL of water and this solution was added to the reaction dropwise via addition funnel. The reaction was allowed to stir for 16 hours at room temperature. The reaction was then diluted with EtOAc (150 mL). The organic layer was washed with $H_2O$ (3×50 mL), saturated $NaHCO_3$ (50 mL), and brine (50 mL). The organic layer was dried over $Na_2SO_4$, filtered, and concentrated. Purification of the residue by flash chromatography on silica gel with 0 to 50% EtOAc/hexanes and isolation of the major product afforded trans-4-(4-methoxyphenyl)cyclohexanecarbaldehyde. $^1$H NMR (CDCl$_3$, 500 MHz) δ 9.67 (s, 1H), 7.12 (d, J=8.4 Hz, 2H), 6.85 (d, J=8.7 Hz, 2H), 3.79 (s, 3H), 2.45 (m, 1H), 2.27 (m, 1H), 1.98-2.14 (m, 4H), 1.36-1.53 (m, 4H).

Step C: Methyl trans-4-(4-methoxyphenyl)cyclohexanecarboxylate

Trans-4-(4-methoxyphenyl)cyclohexanecarbaldehyde (774 mg, 3.55 mmol) was dissolved in tetrahydrofuran (7.2 ml) and t-BuOH (18 ml) was added followed by 2-methyl-2-butene (7.2 ml, 68.0 mmol). To this solution was added sodium dihydrogen phosphate, hydrate (1072 mg, 7.80 mmol) as a solution in water (4.1 mL). Finally, sodium chlorite (882 mg, 7.80 mmol) was added as a solution in water (4.1 mL). The reaction was stirred at room temperature for 2 hours and then diluted with EtOAc (100 mL) and washed with water (25 mL) and brine (25 mL). The aqueous washes were combined, acidified with 1N HCl and extracted with EtOAc (50 mL). The two EtOAc extracts (before and after acidification) were combined, dried over $Na_2SO_4$, filtered, and concentrated. The residue was taken up in toluene (20 ml) and MeOH (3 ml). TMS-diazomethane (2.82 ml, 5.64 mmol) was added dropwise. Evolution of gas was observed, and a yellow color persisted. After 45 minutes, the reaction was quenched with HOAc, diluted with EtOAc (75 mL), and washed with saturated $NaHCO_3$ and brine (20 mL each). The organic layer was dried over $Na_2SO_4$, filtered, and concentrated. Purification of the residue by flash chromatography on silica gel with 0 to 40% EtOAc/hexanes afforded methyl trans-4-(4-methoxyphenyl)cyclohexanecarboxylate. $^1$H NMR (CDCl$_3$, 500 MHz) δ 7.12 (d, J=8.7 Hz, 2H), 6.84 (d, J=8.5 Hz, 2H), 3.79 (s, 3H), 3.69 (s, 3H), 2.47 (m 1H), 2.35 (m, 1H), 1.92-2.12 (m, 4H), 1.53-1.63 (m, 2H), 1.40-1.49 (m, 2H).

Steps 4 and 5: Methyl trans-4-[4-methoxy-3-(4,4,5,5-tetramethyl-1,3,2-dioxaborolan-2-yl)phenyl]cyclohexanecarboxylate Methyl trans-4-(4-methoxyphenyl)cyclohexanecarboxylate was converted into methyl trans-4-[4-methoxy-3-(4,4,5,5-tetramethyl-1,3,2-dioxaborolan-2-yl)phenyl]cyclohexanecarboxylate via the intermediate iodide as in the examples above. See, for example, steps 1 and 2 in the synthesis of INTERMEDIATE 2.

INTERMEDIATE 8

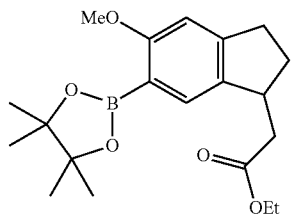

Ethyl [5-methoxy-6-(4,4,5,5-tetramethyl-1,3,2-dioxaborolan-2-yl)-2,3-dihydro-1H-inden-1-yl]acetate Step A: Ethyl (5-methoxy-2,3-dihydro-1H-inden-1-yl)acetate An oven dried flask was charged with sodium hydride (60 wt %) (173 mg, 4.32 mmol) and THF (15 mL) and cooled to 0° C. Triethyl phosphonoacetate (0.864 mL, 4.32 mmol) was added dropwise and the reaction was then heated to 50° C. for 1 hr. The reaction was then cooled to 0° C., and 5-methoxy-1-indanone (500 mg, 3.08 mmol) was added via cannula in THF (3×5 mL). The reaction was then refluxed for 17 hours. Next, the reaction was cooled to room temperature and diluted with ethyl acetate (50 mL). The organic layer was washed with water (2×50 mL) and brine (50 mL), dried over sodium sulfate, filtered, and concentrated. The residue was dissolved in ethanol (15 mL) and 10% palladium on carbon (150 mg) was added. The reaction was stirred at room temperature under an atmosphere of hydrogen (balloon) for 17 hours. At this point, the catalyst was removed by filtration, and the filtrate was concentrated. Purification of the residue via flash chromatography on silica gel (0 to 40% ethyl acetate/hexanes) afforded ethyl (5-methoxy-2,3-dihydro-1H-inden-1-yl)acetate. $^1$H NMR (CDCl$_3$, 500 MHz) δ 7.07 (d, J=8.5 Hz, 1H), 6.78 (s, 1H), 6.71 (dd, J=8.2, 2.3 Hz, 1H), 4.18 (m, 2H), 3.78 (s, 3H), 3.53 (m, 1H), 2.95-2.65 (m, 3H), 2.45-2.30 (m, 2H), 1.76 (m, 1H), 1.28 (t, J=7.2 Hz, 3H).

Step B: Ethyl (6-iodo-5-methoxy-2,3-dihydro-1H-inden-1-yl)acetate

Ethyl (5-methoxy-2,3-dihydro-1H-inden-1-yl)acetate (472 mg, 2.015 mmol) was dissolved in ethanol (20 mL). Iodine (511 mg, 2.015 mmol) and silver sulfate (628 mg, 2.015 mmol) were added and the reaction was stirred vigorously at room temperature, protected from light, for 1 hour. The reaction was diluted with ethyl acetate (75 mL) and filtered to remove solids. The filtrate was washed with sodium bisulfite (2×50 mL), water (70 mL), and brine (70 mL). The organic layer was dried over sodium sulfate, filtered, and concentrated. The residue was purified by flash chromatography on silica gel with 0 to 50% ethyl acetate/hexanes. Further purification by SFC on a chiral AD column with 15% IPA/heptanes removed a minor regioisomer and separated the two enantiomers of ethyl (6-iodo-5-methoxy-2,3-dihydro-1H-inden-1-yl)acetate. $^1$H NMR (CDCl$_3$, 500 MHz) δ 7.55 (s, 1H), 6.72 (s, 1H), 4.17 (m, 2H), 3.85 (s, 3H), 3.53 (m, 1H), 2.95-2.65 (m, 3H), 2.60-2.42 (m, 2H), 1.78 (m, 1H), 1.28 (t, J=7.1 Hz, 3H).

Step C: Ethyl [5-methoxy-6-(4,4,5,5-tetramethyl-1,3,2-dioxaborolan-2-yl)-2,3-dihydro-1H-inden-1-yl]acetate The two enantiomers of ethyl (6-iodo-5-methoxy-2,3-dihydro-1H-inden-1-yl)acetate were converted into the two enantiomers of ethyl [5-methoxy-6-(4,4,5,5-tetramethyl-1,3,2-dioxaborolan-2-yl)-2,3-dihydro-1H-inden-1-yl]acetate as in the examples above. See, for example, Step B in the synthesis of INTERMEDIATE 2.

INTERMEDIATE 9

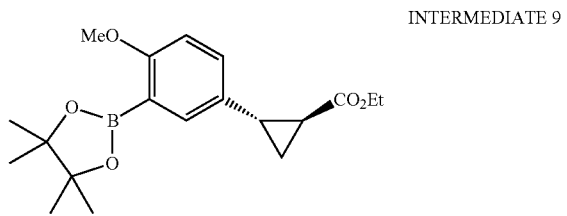 [SMILES: CCOC(=O)[C@H]1C[C@@H]1c1ccc(OC)c(B2OC(C)(C)C(C)(C)O2)c1]

Ethyl(1S,2S)-2-[4-methoxy-3-(4,4,5,5-tetramethyl-1,3,2-dioxaborolan-2-yl)phenyl]cyclopropanecarboxylate Step A: Ethyl (1S,2S)-2-(4-methoxyphenyl)cyclopropanecarboxylate and ethyl (1S,2R)-2-(4-methoxyphenyl)cyclopropanecarboxylate A solution of bis(copper(I) trifluoromethanesulfonate), benzene complex (0.049 g, 0.088 mmol) and (R,R)-(−)-2,2'-isopropylidenebis(4-tert-butyl-2-oxazoline) (0.103 g, 0.351 mmol) in dry ClCH$_2$CH$_2$Cl (10 mL) was stirred at room temperature for 30 min. 4-Methoxystyrene (11.8 mL, 88 mmol) was added and the solution was stirred for 30 min. The solution was cooled to −15° C. and a solution of ethyl diazoacetate (2.17 mL, 17.53 mmol) in dry ClCH$_2$CH$_2$Cl (15 mL) was added via syringe pump over 14 h. The reaction was aged a total of 18 h. This reaction mixture was purified by flash chromatography (Biotage Horizon, 65i, Si, ~60-70 mL/min, 100% hexanes for 360 mL, gradient to 20% EtOAc in hexanes over 4536 mL, gradient to 40% EtOAc in hexanes over 2448 mL) to afford in order of elution trans-1S,2S isomer (94% e.e., chiral HPLC AD column), and cis-1S,2R isomer (95% e.e., chiral HPLC OJ column), as colorless oils. trans-1S,2S isomer: R$_f$=0.64 (20% EtOAc/hexanes). $^1$H NMR (600 MHz, CDCl$_3$): δ 7.02 (d, J=8.4 Hz, 2H); 6.81 (d, J=8.5 Hz, 2H); 4.16 (q, J=7.2 Hz, 2H); 3.77 (s, 3H); 2.49-2.44 (m, 1H); 1.83-1.78 (m, 1H); 1.56-1.51 (m, 1H); 1.27 (t, J=7.1 Hz, 3H); 1.26-1.22 (m, 1H). cis-1S,2R isomer: R$_f$=0.56 (20% EtOAc/hexanes). $^1$H NMR (600 MHz, CHCl$_3$-d): δ 7.18 (d, J=8.4 Hz, 2H); 6.80 (d, J=8.5 Hz, 2H); 3.89 (q, J=7.1 Hz, 2H); 3.77 (s, 3H); 2.51 (q, J=8.4 Hz, 1H); 2.05-2.00 (m, 1H); 1.67-1.63 (m, 1H); 1.33-1.27 (m, 1H); 1.01 (t, J=7.1 Hz, 3H).

Step B: Ethyl (1S,2S)-2-(3-iodo-4-methoxyphenyl)cyclopropanecarboxylate

Silver sulfate (3.47 g, 11.12 mmol) and iodine (0.576 mL, 11.12 mmol) were added successively to a solution of ethyl (1S,2S)-2-(4-methoxyphenyl)cyclopropanecarboxylate (2.45 g, 11.12 mmol) in EtOH (55.6 mL) at 25° C. and the reaction was stirred vigorously for 4 h. After this time the reaction mixture was filtered through a plug of Celite®. The filtrate was diluted with EtOAc (100 mL), washed with water (2×25 mL), aq. NaHSO$_3$ (2×25 mL), and brine (25 mL), dried (MgSO$_4$) and concentrated in vacuo to give the crude product. This was purified by flash chromatography (Biotage Horizon, 40M, Si, ~30 mL/min, 100% hexanes for 360 mL, gradient to 20% EtOAc in hexanes over 2088 mL) to afford ethyl (1S,2S)-2-(3-iodo-4-methoxyphenyl)cyclopropanecarboxylate, as a colorless oil. R$_f$=0.61 (20% EtOAc/hexanes). $^1$H NMR (600 MHz, CDCl$_3$): δ 7.50 (d, J=2.3 Hz, 1H); 7.04 (dd, J=8.5, 2.3 Hz, 1H); 6.71 (d, J=8.5 Hz, 1H); 4.15 (q, J=7.2 Hz, 2H); 3.83 (s, 3H); 2.44-2.39 (m, 1H); 1.82-1.78 (m, 1H); 1.55-1.50 (m, 1H); 1.27 (t, J=7.2 Hz, 3H); 1.25-1.19 (m, 1H).

Step C: Ethyl(1S,2S)-2-[4-methoxy-3-(4,4,5,5-tetramethyl-1,3,2-dioxaborolan-2-yl)phenyl]cyclopropanecarboxylate Dioxane (19.75 mL) and DMSO (79 mL) were added to sequentially to a mixture of ethyl (1S,2S)-2-(3-iodo-4-methoxyphenyl)cyclopropanecarboxylate (3.76 g, 10.86 mmol), bis(pinacolato)diboron (3.45 g, 13.58 mmol), potassium acetate (2.132 g, 21.72 mmol) and 1,1'-bis(diphenylphosphino)ferrocene-palladium(ii)dichloride dichloromethane complex (0.887 g, 1.086 mmol) and the resulting solution was degassed with N$_2$. The reaction was heated at 50° C. for 1 h and then to 80° C. overnight. The reaction mixture was diluted with EtOAc (150 mL), washed with aq. 0.5N HCl (2×80 mL) and brine (2×40 mL), dried (Na$_2$SO$_4$) and concentrated in vacuo to give the crude product. This was purified by flash chromatography (Biotage Horizon, 40M, Si, ~30 mL/min, 100% hexanes for 360 mL, gradient to 30% EtOAc in hexanes over 4536 mL) to afford ethyl(1S,2S)-2-[4-methoxy-3-(4,4,5,5-tetramethyl-1,3,2-dioxaborolan-2-yl)phenyl]cyclopropanecarboxylate. R$_f$=0.34 (20% EtOAc/hexanes). LCMS calc.=347.20. found=347.06 (M+H)$^+$. $^1$H NMR (600 MHz, CDCl$_3$): δ 7.41 (d, J=2.5 Hz, 1H); 7.11 (dd, J=8.5, 2.5 Hz, 1H); 6.76 (d, J=8.5 Hz, 1H); 4.14 (t, J=5.4 Hz, 2H); 3.79 (s, 3H); 2.50-2.45 (m, 1H); 1.83-1.80 (m, 1H); 1.34 (s, 12H); 1.30-1.23 (m, 4H).

The following boronic esters (Table 1) were synthesized using methods analogous to those described for INTERMEDIATE 9 from commercially available materials.

TABLE 1

| Intermediate | Structure |
|---|---|
| 10 | MeO-, pinacol boronate, cyclopropane-CO₂Et (trans) |
| 11 | MeO-, pinacol boronate, cyclopropane-CO₂Et (1R,2R) |
| 12 | MeO-, pinacol boronate, cyclopropane-CO₂Et (1R,2S) |

INTERMEDIATE 13

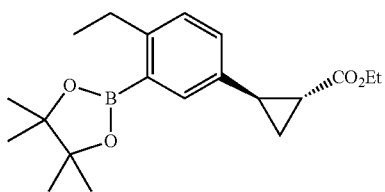

Ethyl (1R,2R)-2-[4-ethyl-3-(4,4,5,5-tetramethyl-1,3, 2-dioxaborolan-2-yl)phenyl]cyclopropanecarboxylate

Step A: 4-Ethyl-3-iodobenzaldehyde

Iodine (0.245 mL, 4.73 mmol) and sodium metaperiodate (0.340 g, 1.59 mmol) were added slowly portionwise successively to stirred 95% $H_2SO_4$ (30.0 mL) at 25° C. and the mixture was stirred for 30 min to afford a dark brown iodinating solution. The iodinating solution was added dropwise to a stirred suspension of 4-ethylbenzaldehyde (1.34 g, 10 mmol) in 95% $H_2SO_4$ (10.0 mL) over 45 min while maintaining the temperature at 25-30° C. Stirring was continued for a further 15 min and the reaction was quenched by slowly pouring into stirred ice-water (300 mL). The precipitate was collected by filtration, washed with water and dried under vacuum to afford 4-ethyl-3-iodobenzaldehyde, as a colorless solid. $^1$H NMR (600 MHz, CDCl$_3$): δ 9.87 (s, 1H); 8.28 (d, J=1.7 Hz, 1H); 7.77 (dd, J=7.8, 1.6 Hz, 1H); 7.36 (d, J=7.8 Hz, 1H); 2.78 (q, J=7.6 Hz, 2H); 1.23 (t, J=7.6 Hz, 4H).

Step B: 4-Ethenyl-1-ethyl-2-iodobenzene

Potassium hexamethyldisilazide (0.5 M in THF) (46.1 mL, 23.07 mmol) was added dropwise to a stirred suspension of methyltriphenylphosphohonium bromide (8.24 g, 23.1 mmol) in dry THF (62 mL) at 0° C. and the mixture was stirred for 20 min. A solution of 4-ethyl-3-iodobenzaldehyde (2.40 g, 9.23 mmol) in dry THF (31 mL) was added via cannula. The reaction mixture was allowed to warm to room temperature and stirred overnight. The reaction was quenched with satd NH$_4$Cl (50 mL) and the resulting mixture was extracted with EtOAc (3×50 mL). The combined extracts were dried (MgSO$_4$) and concentrated in vacuo to give the crude product. This was purified by flash chromatography (Biotage Horizon, 40M, Si, ~30 mL/min, 100% hexanes for 2448 mL) to afford 4-ethenyl-1-ethyl-2-iodobenzene, as a colorless oil. $R_f$=0.79 (hexanes). $^1$H NMR (500 MHz, CDCl$_3$): δ 7.37 (d, J=1.8 Hz, 1H); 6.83 (dd, J=7.9, 1.8 Hz, 1H); 6.68 (d, J=7.9 Hz, 1H); 6.11 (dd, J=17.6, 10.9 Hz, 1H); 5.21 (d, J=17.6 Hz, 1H); 4.72 (d, J=9.7 Hz, 1H); 2.23 (q, J=7.5 Hz, 2H); 0.72 (t, J=7.5 Hz, 3H).

Step C: Ethyl (1R,2R)-2-(4-ethyl-3-iodophenyl)cyclopropanecarboxylate and ethyl (1R,2S)-2-(4-ethyl-3-iodophenyl)cyclopropanecarboxylate A solution of bis(copper(I) trifluoromethanesulfonate), benzene complex (4.78 mg, 8.55 μmol) and (S,S)-(−)-2,2'-isopropylidenebis(4-tert-butyl-2-oxazoline) (10.07 mg, 0.034 mmol) in dry ClCH$_2$CH$_2$Cl (487 μL) was stirred at room temperature for 30 min. A solution of 4-ethenyl-1-ethyl-2-iodobenzene (2207 mg, 8.55 mmol) in dry ClCH$_2$CH$_2$Cl (487 μL) was added and the solution was stirred for 30 min. The solution was cooled to −15° C. and a solution of ethyl diazoacetate (212 μL, 1.71 mmol) in dry ClCH$_2$CH$_2$Cl (1462 μL) was added via syringe pump over ~17 h. The reaction was aged a total of 24 h. This reaction mixture was purified by flash chromatography (Biotage Horizon, 40M, Si, ~30 mL/min, 100% hexanes for 360 mL, gradient to 15% EtOAc in hexanes over 4536 mL) to afford in order of elution recovered starting styrene, ethyl (1R,2R)-2-(4-ethyl-3-iodophenyl)cyclopropanecarboxylate and ethyl (1R,2S)-2-(4-ethyl-3-iodophenyl)cyclopropanecarboxylate, as colorless oils. 1R,2R isomer: $R_f$=0.57 (10% EtOAc/hexanes). $^1$H NMR (600 MHz, CHCl$_3$-d): δ 7.55 (d, J=1.9 Hz, 1H); 7.11 (d, J=7.9 Hz, 1H); 7.01 (dd, J=7.8, 1.9 Hz, 1H); 4.17 (q, J=7.1 Hz, 2H); 2.69 (q, J=7.5 Hz, 2H); 2.45-2.40 (m, 1H); 1.89-1.83 (m, 1H); 1.57 (dt, J=9.2, 5.0 Hz, 1H); 1.30-1.23 (m, 4H); 1.18 (t, J=7.5 Hz, 3H). 1R,2S isomer: $R_f$=0.48 (10% EtOAc/hexanes). LCMS calc.=345.04. found=344.94 (M+H)$^+$. $^1$H NMR (600 MHz, CHCl$_3$-d): δ 7.72 (s, 1H); 7.17 (dd, J=7.9, 1.8 Hz, 1H); 7.10 (d, J=7.8 Hz, 1H); 3.92 (q, J=7.1 Hz, 2H); 2.68 (q, J=7.5 Hz, 2H); 2.48 (q, J=8.4 Hz, 1H); 2.08-2.01 (m, 1H); 1.67-1.62 (m, 1H); 1.33-1.26 (m, 1H); 1.17 (t, J=7.5 Hz, 3H); 1.02 (t, J=7.1 Hz, 3H).

Step D: Ethyl (1R,2R)-2-[4-ethyl-3-(4,4,5,5-tetramethyl-1,3,2-dioxaborolan-2-yl)phenyl]cyclopropanecarboxylate Dioxane (0.94 mL) and DMSO (3.8 mL) were added to sequentially to a mixture of ethyl (1R,2R)-2-(4-ethyl-3-iodophenyl)cyclopropanecarboxylate (0.1783 g, 0.518 mmol), bis(pinacolato)diboron (0.164 g, 0.648 mmol), potassium acetate (0.102 g, 1.036 mmol) and 1,1'-bis(diphenylphosphino)ferrocene-palladium(II)dichloride dichloromethane complex (0.042 g, 0.052 mmol) and the resulting solution was degassed with N$_2$. The reaction was heated at 50° C. for 1 h and then to 80° C. overnight. The reaction mixture was diluted with EtOAc (40 mL), washed with aq. 0.5 N HCl (2×40 mL) and brine (2×20 mL), dried (Na$_2$SO$_4$) and concentrated in vacuo to give the crude product. This was purified by flash chromatography (Biotage Horizon, 25M, Si, ~20 mL/min, 100% hexanes for 144 mL, gradient to 30% EtOAc in hexanes over 2394 mL) to afford ethyl (1R,2R)-2-[4-ethyl-3-(4,4,5,5-tetramethyl-1,3,2-dioxaborolan-2-yl)phenyl]cyclopropanecarboxylate. $R_f$=0.73 (20% EtOAc/hexanes). LCMS calc.=345.22. found=345.06 (M+H)$^+$. $^1$H NMR (600 MHz, CHCl$_3$-d): δ 7.57 (s, 1H); 7.13 (d, J=8.0 Hz, 1H); 7.08 (dd, J=8.0, 2.1 Hz, 1H); 4.18 (q, J=7.2 Hz, 2H); 2.91 (q, J=7.6 Hz, 2H); 2.57-2.52 (m, 1H); 1.93-1.88 (m, 1H); 1.61-1.56 (m, 1H); 1.45-1.25 (m, 13H); 1.30 (t, J=7.2 Hz, 3H); 1.20 (t, J=7.6 Hz, 3H).

INTERMEDIATE 14

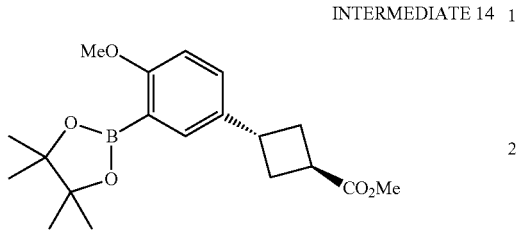

Methyl trans-3-[4-methoxy-3-(4,4,5,5-tetramethyl-1,3,2-dioxaborolan-2-yl)phenyl]cyclobutanecarboxylate Step A: 3-Methylidenecyclobutanecarboxylic acid 3-Methylenecyclobutanecarbonitrile (244 g; 2.62 mol) was added to a solution of potassium hydroxide (85 wt-% pellets; 750 g; 11.4 mol) in a mixture of water (2.7 L) and EtOH (2.7 L). The mixture was heated to obtain a gentle reflux. The reaction was complete, after approximately 2 h, when a moist pH paper did not color blue at the top of the reflux condenser, i.e. ammonia evolution had ceased. The mixture was cooled and was subsequently extracted with toluene (2×0.5 L) and Et$_2$O (4×0.5 L). The combined organic phases were dried over Na$_2$SO$_4$. After removal of the drying agent, the resulting solution was concentrated under reduced pressure yielding an oily residue. $^{13}$C NMR (CDCl$_3$): δ 179.3; 146.2; 107.5; 36.7; 34.8.

Step B: 3-Oxocyclobutanecarboxylic acid

To a solution of crude 3-methylenecyclobutane-carboxylic acid (280 g, 2.25 mol), water (5.5 L), THF (2.5 L) and potassium osmate dihydrate (2.11 g; 5.7 mmol), was charged portion-wise sodium periodate (1.1 kg, 5.14 mol) over a 1.5 h period. The inner temperature was kept below 28° C. To complete conversion additional potassium osmate dihydrate (0.5 g; 1.35 mmol) and sodium periodate (0.45 kg; 2.1 mol) were added. After 2 h stirring, the solids were removed via filtration and were subsequently washed with THF (1 L). The resulting filtrate was extracted with CH$_2$Cl$_2$ (7×1.5 L and 5×2 L) and EtOAc (9×2 L). The first 1.5 L CH$_2$Cl$_2$ extract was set aside because of the relative large amount of by-product present. The other organic phases were combined and concentrated under reduced pressure. The solid material (approximately 140 g) was redissolved in CH$_2$Cl$_2$ and was treated with charcoal (7 g). The charcoal was removed by filtration over Celite® and the resulting filtrate was concentrated under reduced pressure, yielding a crystalline mass. This material was redissolved in toluene (150 mL) and to the solution was dosed hexane (150 mL). This yielded 52 g light yellowish/brown crystals, which darkened upon standing. Concentration of the mother liquor and recrystallization of the solid mass (70 g) from toluene (150 mL) yielded 48 g yellowish/brown material. The first CH$_2$Cl$_2$ extract which was set aside, was concentrated yielding 70 g of residue. To the residue CH$_2$Cl$_2$ (30 mL) was added and the remaining solution was stored at −15° C., which initiated crystallization. From this slurry, 55 g of dark grey/black needle-like crystals were recovered. All crystalline material was combined and was dissolved in EtOAc (750 mL) upon heating, charcoal (7.5 g) was added and the mixture was stirred for 1 h at ambient temperature. The charcoal was removed by filtration over Celite®. Approximately 500 mL of EtOAc were removed under reduced pressure. At that point the product started to crystallize and severe foaming was observed. Hexane (500 mL) was added and the mixture was rotated on the rotary evaporator for 1 h. Filtration of the crystalline mass yielded pure product. Anal. Calcd. for C$_5$H$_6$O$_3$: C, 52.63; H, 5.30. Found: C, 52.67; H, 5.31. MS (FIA/ES; negative ionization mode): m/e 430 [M−H]$^-$. $^1$H NMR (CDCl$_3$): δ 11.47 (br s, 1H); 3.2-3.5 (m, 5H). $^{13}$C NMR (CDCl$_3$): δ 203.1; 180.1; 51.5; 27.2.

Step C: Methyl 3-oxocyclobutanecarboxylate

Trimethylsilyldiazomethane (21.0 mL of a 2 M solution in hexanes, 42.1 mmol) was added to a stirred solution of 3-oxocyclobutanecarboxylic acid (3.00 g, 26.3 mmol) in dry MeOH (11.1 mL) and dry CH$_2$Cl$_2$ (100 mL) at 25° C. under N$_2$. The reaction was stirred at 25° C. for 2 h. The reaction mixture was concentrated in vacuo to afford methyl 3-oxocyclobutanecarboxylate, as an oil. $^1$H NMR (500 MHz, CHCl$_3$): δ 3.75 (s, 3H); 3.44-3.37 (m, 2H); 3.31-3.17 (m, 3H).

Step D: Methyl 3-hydroxy-3-(4-methoxyphenyl)cyclobutanecarboxylate

4-Anisylmagnesium bromide (15.6 mL of 0.5 M solution in THF, 7.80 mmol) was added dropwise over 1 h to a stirred solution of methyl 3-oxocyclobutanecarboxylate (1.00 g, 7.80 mmol) in dry Et$_2$O (71.0 mL) at −78° C. under N$_2$. The reaction mixture was allowed to warm to room temperature and was stirred for 1 h. Satd aq. Na$_2$SO$_4$ was added and the mixture was stirred until a clear solution resulted. This mixture was extracted with Et$_2$O (3×50 mL). The combined extracts were dried (MgSO$_4$) and concentrated in vacuo to give the crude product. This was purified by flash chromatography (Biotage Horizon, 40M, Si, ~30 mL/min, 100% hexanes for 360 mL, gradient to 20% EtOAc in hexanes over 2088 mL, gradient to 40% EtOAc in hexanes over 2448 mL) to afford methyl 3-hydroxy-3-(4-methoxyphenyl)cyclobutanecarboxylate. $R_f$=0.18 (20% EtOAc/hexanes). LCMS calc.=259.10. found=259.01 (M+Na)$^+$. $^1$H NMR (500 MHz, CHCl$_3$): δ 3.75 (s, 3H); 3.44-3.37 (m, 2H); 3.32-3.18 (m, 3H).

Step E: Methyl trans-3-(4-methoxyphenyl)cyclobutanecarboxylate and methyl cis-3-(4-methoxyphenyl)cyclobutanecarboxylate Diphenylchlorosilane (0.806 mL, 3.71 mmol) was added to a mixture of indium(III) chloride (0.021 g, 0.093 mmol) and methyl 3-hydroxy-3-(4-methoxyphenyl)cyclobutanecarboxylate (0.438 g, 1.85 mmol) in dry ClCH$_2$CH$_2$Cl (3.71 mL) under N$_2$. The reaction mixture was stirred at 25° C. for 15 min. The reaction mixture was diluted with water (20 mL) and extracted with Et$_2$O (3×20 mL). The combined extracts were dried (MgSO$_4$) and concentrated in vacuo to give the crude product. This was purified by flash chromatography (Biotage Horizon, 25M, Si, ~20 mL/min, 100% hexanes for 144 mL, gradient to 20% EtOAc in hexanes over 2394 mL) to afford a mixture of diastereoisomers (0.37 g, 91% yield). The sample was resolved by chiral HPLC (OJ, 20×250 mm, 9 mL/min, 5% i-PrOH in heptanes) to afford in order of elution methyl trans-3-(4-methoxyphenyl)cyclobutanecarboxylate and methyl cis-3-(4-methoxyphenyl)cyclobutanecarboxylate. trans-diastereoisomer: R$_f$=0.54 (20% EtOAc/hexanes). LCMS calc.=221.12. found=221.15 (M+H)$^+$. $^1$H NMR (600 MHz, CHCl$_3$): δ 7.66 (d, J=8.4 Hz, 2H); 7.37 (d, J=8.4 Hz, 2H); 4.29 (s, 3H); 4.25 (s, 3H); 4.24-4.15 (m, 1H); 3.67-3.61 (m, 1H); 3.20-3.14 (m, 2H); 2.93-2.87 (m, 2H). cis-diastereoisomer: R$_f$=0.54 (20% EtOAc/hexanes), $^1$H NMR (600 MHz, CHCl$_3$): δ 7.68 (d, J=8.4 Hz, 2H); 7.36 (d, J=8.3 Hz, 2H); 4.28 (s, 3H); 4.20 (s, 3H); 3.93-3.84 (m, 1H); 3.63-3.54 (m, 1H); 3.12-3.06 (m, 2H); 2.94-2.86 (m, 2H).

Step F: Methyl trans-3-(3-iodo-4-methoxyphenyl) cyclobutanecarboxylate

Silver sulfate (0.671 g, 2.15 mmol) and iodine (0.11 mL, 2.15 mmol) were added successively to a solution of methyl trans-3-(4-methoxyphenyl)cyclobutanecarboxylate (0.474 g, 2.15 mmol) in MeOH (10.8 mL) at 25° C. and the reaction was stirred vigorously for 4 h. After this time the reaction mixture was filtered through a plug of Celite®. The filtrate was diluted with EtOAc (50 mL), washed with water (2×10 mL), aq. Na$_2$SO$_3$ (2×10 mL), and brine (10 mL), dried (Na$_2$SO$_4$) and concentrated in vacuo to give the crude product. This was purified by flash chromatography (Biotage Horizon, 25M, Si, ~20 mL/imin, 100% hexanes for 144 mL, gradient to 20% EtOAc in hexanes over 2394 mL) to afford methyl trans-3-(3-iodo-4-methoxyphenyl)cyclobutanecarboxylate, as a colorless oil. R$_f$=0.54 (20% EtOAc/hexanes). LCMS calc.=347.01. found=347.02 (M+H)$^+$. $^1$H NMR (500 MHz, CHCl$_3$): δ 7.58 (d, J=2.2 Hz, 1H); 7.08 (dd, J=8.4, 2.2 Hz, 1H); 6.69 (d, J=8.4 Hz, 1H); 3.76 (s, 3H); 3.67 (s, 3H); 3.65-3.54 (m, 1H); 3.07-3.00 (m, 1H); 2.61-2.55 (m, 2H); 2.32-2.25 (m, 2H).

Step G: Methyl trans-3-[4-methoxy-3-(4,4,5,5-tetramethyl-1,3,2-dioxaborolan-2-yl)phenyl]cyclobutanecarboxylate Dioxane (3.60 mL) and DMSO (14.4 mL) were added to sequentially to a mixture of methyl trans-3-(3-iodo-4-methoxyphenyl)cyclobutanecarboxylate (0.686 g, 1.98 mmol), bis(pinacolato)diboron (0.629 g, 2.48 mmol), potassium acetate (0.389 g, 3.96 mmol) and 1,1'-bis(diphenylphosphino)ferrocene-palladium(II)dichloride dichloromethane complex (0.162 g, 0.198 mmol) and the resulting solution was degassed with N$_2$. The reaction was heated at 50° C. for 1 h and then to 80° C. overnight. The reaction mixture was diluted with EtOAc (70 mL), washed with aq. 0.5 N HCl (2×40 mL) and brine (2×20 mL), dried (Na$_2$SO$_4$) and concentrated in vacuo to give the crude product. This was purified by flash chromatography (Biotage Horizon, 25M, Si, ~20 mL/min, 100% hexanes for 144 mL, gradient to 30% EtOAc in hexanes over 2394 mL) to afford methyl trans-3-[4-methoxy-3-(4,4,5,5-tetramethyl-1,3,2-dioxaborolan-2-yl)phenyl]cyclobutanecarboxylate. R$_f$=0.27 (20% EtOAc/hexanes). LCMS calc.=347.20. found=347.08 (M+H)$^+$. $^1$H NMR (600 MHz, CHCl$_3$): δ 8.01 (d, J=2.4 Hz, 1H); 7.77-7.74 (m, 1H); 7.31 (dd, J=8.5, 0.8 Hz, 1H); 4.30 (s, 3H); 4.23 (s, 3H); 4.22-4.15 (m, 1H); 3.66-3.60 (m, 1H); 3.17-3.11 (m, 2H); 2.94-2.87 (m, 2H); 1.85 (s, 12H).

INTERMEDIATE 15

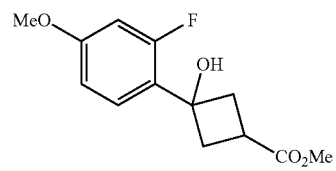

Methyl 3-(2-fluoro-4-methoxyphenyl)-3-hydroxycyclobutanecarboxylate

To a dry and N$_2$ flashed flask was added 4-bromo-3-fluoroanisole (1.04 g, 5.07 mmol) in THF (6 mL) under N$_2$. This was cooled to −78° C., and n-BuLi (1.72 mL, 4.29 mmol) was added. The reaction was stirred at −78° C. for 30 min. The mixture above was added via cannula to a stirred solution of methyl 3-oxocyclobutane carboxylate (500 mg, 3.90 mmol) in dry Et$_2$O (35 mL) at −78° C. under N$_2$. The reaction mixture was allowed to warm to room temperature and was stirred for 1 h. Satd aq. NH$_4$Cl was added and the mixture was stirred until a clear solution resulted. This mixture was extracted with Et$_2$O (3×). The combined extracts were dried (MgSO$_4$) and concentrated in vacuo to give the crude product, which was purified by flash chromatography (Biotage Horizon, 40M, Si, ~30 mL/min, 100% hexanes for 260 mL, gradient to 40% EtOAc in hexanes over 5184 mL) to afford methyl 3-(2-fluoro-4-methoxyphenyl)-3-hydroxycyclobutanecarboxylate (450 mg, 45%). $^1$H NMR (500 MHz, CDCl$_3$): δ 7.32 (t, J=8.9 Hz, 1H); 6.69-6.63 (m, 2H); 3.80 (s, 3H); 3.74 (s, 3H); 3.40 (s, 1H); 3.03-2.93 (m, 2H); 2.90-2.82 (m, 1H); 2.67-2.61 (m, 2H).

The following boronic esters (Table 2) were synthesized using methods analogous to those described for INTERMEDIATE 14 from INTERMEDIATE 15 and commercially available materials.

TABLE 2

| Intermediate | Molecular Structure |
|---|---|
| 16 | MeO-phenyl-cyclobutane-CO$_2$Me with pinacol boronate |
| 17 | MeO-phenyl(F)-cyclobutane-CO$_2$Me with pinacol boronate |

TABLE 2-continued

| Intermediate | Molecular Structure |
|---|---|
| 18 | (MeO, F, pinacol boronate, cyclobutyl-CO₂Me structure) |

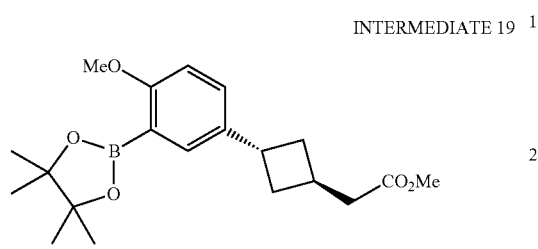

INTERMEDIATE 19

Methyl {trans-3-[4-methoxy-3-(4,4,5,5-tetramethyl-1,3,2-dioxaborolan-2-yl)phenyl]cyclobutyl}acetate

Step A: Methyl [trans-3-(4-methoxyphenyl)cyclobutyl]acetate

A solution of n-butyllithium (1.25 mL of a 2.5 M soln in hexanes, 3.12 mmol) was added to a stirred solution of 2,2,6,6-tetramethylpiperidine (0.56 mL, 3.33 mmol) in dry THF (4.37 mL) at 0° C. under $N_2$. Separately, a mixture of methyl trans-3-(4-methoxyphenyl)cyclobutanecarboxylate (INTERMEDIATE 14, Step E) (0.200 g, 0.908 mmol) and dibromomethane (0.22 mL, 3.12 mmol) in dry THF (4.37 mL) was cooled to −78° C. under $N_2$. After 30 min, the LiTMP solution was cooled to −78° C. and added to the ester/$CH_2Br_2$ solution dropwise via cannula. After 15 min a cold (−78° C.) solution of lithium bis(trimethylsilyl)amide (3.12 mL of a 1 M soln in THF, 3.12 mmol) was added dropwise via cannula. The mixture was allowed to warm to −20° C. and then recooled to −78° C., and a solution of sec-butyllithium (3.39 mL of a 1.4 M soln in cyclohexane, 4.74 mmol) was added dropwise. The mixture was then warmed to −20° C. and a solution of n-butyllithium (1.13 mL of a 2.5 M soln in hexanes, 2.82 mmol) was added. The mixture was warmed to room temperature, stirred for 1 h and then quenched over a 20 min period into a stirred solution of acidic methanol at 0° C. (prepared by slow addition of acetyl chloride (2.01 mL, 28.3 mmol) to ice-cooled dry MeOH (10.2 mL). The mixture was diluted with $Et_2O$ (40 mL) and washed with satd sq. $NaHCO_3$. The aqueous phase was re-extracted with $Et_2O$ (2×40 mL) and the combined organic extracts were dried ($MgSO_4$) and concentrated in vacuo to give the crude product. This was purified by flash chromatography (Biotage Horizon, 25M, Si, ~20 mL/min, 100% hexanes for 144 mL, gradient to 20% EtOAc in hexanes over 2394 mL) to afford methyl [trans-3-(4-methoxyphenyl)cyclobutyl]acetate, as a colorless oil. $R_f$=0.55 (20% EtOAc/hexanes). $^1$H NMR (500 MHz, $CDCl_3$): δ 7.18 (d, J=8.4 Hz, 2H); 6.87 (d, J=8.4 Hz, 2H); 3.80 (s, 3H); 3.69 (s, 3H); 3.59-3.54 (m, 1H); 2.74-2.71 (m, 1H); 2.62 (d, J=7.9 Hz, 2H); 2.38-2.31 (m, 2H); 2.19-2.13 (m, 2H).

Step B: Methyl [trans-3-(3-iodo-4-methoxyphenyl)cyclobutyl]acetate

Silver sulfate (0.149 g, 0.478 mmol) and iodine (0.025 mL, 0.478 mmol) were added successively to a solution of methyl [trans-3-(4-methoxyphenyl)cyclobutyl]acetate (0.1119 g, 0.478 mmol) in MeOH (2.4 mL) at 25° C. and the reaction was stirred vigorously for 4 h. After this time the reaction mixture was filtered through a plug of Celite®. The filtrate was diluted with EtOAc (50 mL), washed with water (2×10 mL), aq. $Na_2SO_3$ (2×10 mL), and brine (10 mL), dried ($Na_2SO_4$) and concentrated in vacuo to give the crude product. This was purified by flash chromatography (Biotage Horizon, 25M, Si, ~20 mL/min, 100% hexanes for 144 mL, gradient to 20% EtOAc in hexanes over 2394 mL) to afford methyl [trans-3-(3-iodo-4-methoxyphenyl)cyclobutyl]acetate, as a colorless oil. $R_f$=0.45 (20% EtOAc/hexanes), LCMS calc.=383.01. found=382.92 (M+Na). $^1$H NMR (500 MHz, $CDCl_3$): δ 7.64 (d, J=2.2 Hz, 1H); 7.16 (dd, J=8.4, 2.2 Hz, 1H); 6.76 (d, J=8.4 Hz, 1H); 3.85 (s, 3H); 3.68 (s, 3H); 3.56-3.46 (m, 1H); 2.74-2.66 (m, 1H); 2.60 (d, J=7.9 Hz, 2H); 2.35-2.27 (m, 2H); 2.17-2.10 (m, 2H).

Step C: Methyl {trans-3-[4-methoxy-3-(4,4,55-tetramethyl-1,3,2-dioxaborolan-2-yl)phenyl]cyclobutyl}acetate Dioxane (0.71 mL) and DMSO (2.8 mL) were added to sequentially to a mixture of methyl [trans-3-(3-iodo-4-methoxyphenyl)cyclobutyl]acetate (0.1406 g, 0.390 mmol), bis (pinacolato)diboron (0.124 g, 0.488 mmol), potassium acetate (0.077 g, 0.781 mmol) and 1,1′-bis(diphenylphosphino)ferrocene-palladium(II)dichloride dichloromethane complex (0.032 g, 0.039 mmol) and the resulting solution was degassed with N. The reaction was heated at 50° C. for 1 h and then to 80° C. overnight. The reaction mixture was diluted with EtOAc (70 mL), washed with aq. 0.5 N HCl (2×40 mL) and brine (2×20 mL), dried ($Na_2SO_4$) and concentrated in vacuo to give the crude product. This was purified by flash chromatography (Biotage Horizon, 25M, Si, ~20 mL/min, 100% hexanes for 144 mL, gradient to 30% EtOAc in hexanes over 2394 mL) to afford methyl {trans-3-[4-methoxy-3-(4,4,5,5-tetramethyl-1,3,2-dioxaborolan-2-yl)phenyl]cyclobutyl}acetate. $R_f$=0.34 (20% EtOAc/hexanes). LCMS calc.=361.22. found=361.11 (M+H)$^+$. $^1$H NMR (600 MHz, $CDCl_3$): δ 7.71 (d, J=2.5 Hz, 1H); 7.31 (dd, J=8.5, 2.5 Hz, 1H); 6.87 (d, J=8.5 Hz, 1H); 3.90 (s, 3H); 3.67 (s, 3H); 3.62-3.52 (m, 1H); 2.75-2.67 (m, 1H); 2.61 (d, J=7.7 Hz, 2H); 2.38-2.32 (m, 2H); 2.18-2.10 (m, 2H); 1.35 (s, 12H).

The following boronic esters (Table 3) were synthesized using methods analogous to those described for INTERMEDIATE 19 from commercially available materials.

TABLE 3

| Intermediate | Molecular Structure |
|---|---|
| 20 | (MeO, pinacol boronate, cyclobutyl-CH₂-CO₂Me structure) |

INTERMEDIATE 21

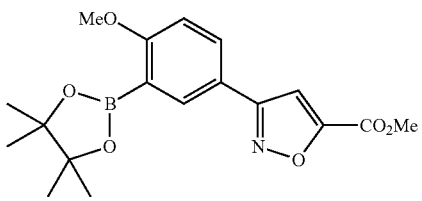

Methyl 3-[4-methoxy-3-(4,4,5,5-tetramethyl-1,3,2-dioxaborolan-2-yl)phenyl]isoxazole-5-carboxylate

Step A: Methyl 3-(4-methoxyphenyl)isoxazole-5-carboxylate

Trimethylsilyldiazomethane (3.50 mL of a 2 M soln in $Et_2O$, 7.01 mmol) was added to a stirred solution of 3-(4-methoxyphenyl)-5-isoxazolecarboxylic acid (0.96 g, 4.38 mmol) in dry MeOH (4.38 mL) and dry $CH_2Cl_2$ (39 mL) at 25° C. under $N_2$. The reaction was stirred at 25° C. for 2 h. The reaction mixture was concentrated in vacuo to afford methyl 3-(4-methoxyphenyl)isoxazole-5-carboxylate, as a colorless solid. LCMS calc.=234.08. found=233.98 (M+H)$^+$. $^1$H NMR (600 MHz, CDCl$_3$): δ 7.76 (d, J=8.4 Hz, 2H); 7.19 (s, 1H); 6.98 (d, J=8.4 Hz, 2H); 3.99 (s, 3H); 3.86 (s, 3H).

Step B: Methyl 3-(3-iodo-4-methoxyphenyl)isoxazole-5-carboxylate

Iodine (0.147 mL, 2.85 mmol) and [bis(trifluoroacetoxy)iodo]benzene (1.224 g, 2.85 mmol) were added successively to a solution of methyl 3-(4-methoxyphenyl)isoxazole-5-carboxylate (1.021 g, 4.38 mmol) in $CH_2Cl_2$ (13.2 mL) at 25° C. and the reaction was stirred overnight. After this time the solvent was removed in vacuo to give the crude product. This was purified by flash chromatography (Biotage Horizon, 40M, Si, ~30 mL/min, 100% hexanes for 360 mL, gradient to 20% EtOAc in hexanes over 2088 mL, gradient to 40% EtOAc in hexanes over 2448 mL) to afford methyl 3-(3-iodo-4-methoxyphenyl)isoxazole-5-carboxylate, as a colorless oil. LCMS calc.=359.97. found=359.81 (M+H)$^+$. $^1$H NMR (600 MHz, CDCl$_3$): δ 8.24 (d, J=2.1 Hz, 1H); 7.78 (dd, J=8.5, 2.2 Hz, 1H); 7.19 (s, 1H); 6.89 (d, J=8.5 Hz, 1H); 3.99 (s, 3H); 3.93 (s, 3H).

Step C: Methyl 3-[4-methoxy-3-(4,4,5,5-tetramethyl-1,3,2-dioxaborolan-2-yl)phenyl]isoxazole-5-carboxylate Dioxane (1.0 mL) and DMSO (4.0 mL) were added to sequentially to a mixture of methyl 3-(3-iodo-4-methoxyphenyl)isoxazole-5-carboxylate (0.200 g, 0.557 mmol), bis(pinacolato)diboron (0.177 g, 0.696 mmol), potassium acetate (0.109 g, 1.114 mmol) and 1,1'-bis(diphenylphosphino)ferrocene-palladium(II)dichloride dichloromethane complex (0.045 g, 0.056 mmol) and the resulting solution was degassed with $N_2$. The reaction was heated at 50° C. for 1 h and then to 80° C. overnight. The reaction mixture was diluted with EtOAc (70 mL), washed with aq. 0.5 N HCl (2×40 mL) and brine (2×20 mL), dried (Na$_2$SO$_4$) and concentrated in vacuo to give the crude product. This was purified by flash chromatography (Biotage Horizon, 25M, Si, ~20 mL/min, 100% hexanes for 144 mL, gradient to 30% EtOAc in hexanes over 2538 mL) to afford methyl 3-[4-methoxy-3-(4,4,5,5-tetramethyl-1,3,2-dioxaborolan-2-yl)phenyl]isoxazole-5-carboxylate. R$_f$=0.20 (20% EtOAc/hexanes). LCMS calc.=360.16. found=360.07 (M+H)$^+$. $^1$H NMR (600 MHz, CDCl$_3$): δ 8.05 (d, J=2.4 Hz, 1H); 7.88 (dd, J=8.6, 2.4 Hz, 1H); 7.24 (s, 1H); 6.90 (d, J=8.7 Hz, 1H); 3.94 (s, 3H); 3.84 (s, 3H); 1.18 (s, 12H).

INTERMEDIATE 22

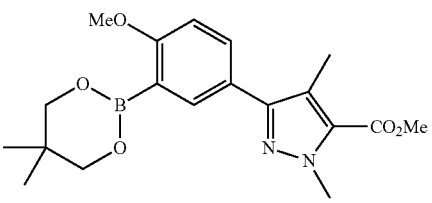

Methyl 3-[3-(5,5-dimethyl-1,3,2-dioxaborinan-2-yl)-4-methoxyphenyl]-1,4-dimethyl-1H-pyrazole-5-carboxylate

Step A: Methyl 3-(4-methoxyphenyl)-1-methyl-1H-pyrazole-5-carboxylate

Trimethylsilyldiazomethane (1.75 mL of a 2 M soln in $Et_2O$, 3.49 mmol) was added to a stirred solution of 3-(4-methoxyphenyl)-1-methyl-1H-pyrazole-5-carboxylic acid (0.507 g, 2.182 mmol) in dry MeOH (2.2 mL) and dry $CH_2Cl_2$ (19.6 mL) at 25° C. under $N_2$. The reaction was stirred at 25° C. for 2 h. The reaction mixture was concentrated in vacuo to afford methyl 3-(4-methoxyphenyl)-1-methyl-1H-pyrazole-5-carboxylate, as a colorless solid. LCMS calc.=247.11. found=247.03 (M+H)$^+$. $^1$H NMR (600 MHz, CDCl$_3$): δ 7.71 (d, J=8.5 Hz, 2H); 7.04 (s, 1H); 6.93 (d, J=8.5 Hz, 2H); 4.21 (s, 3H); 3.90 (s, 3H); 3.83 (s, 3H).

Step B: Methyl 4-iodo-3-(4-methoxyphenyl-1-methyl-1H-pyrazole-5-carboxylate Silver sulfate (640 mg, 2.053 mmol) and iodine (0.106 mL, 2.053 mmol) were added successively to a solution of methyl 3-(4-methoxyphenyl)-1-methyl-1H-pyrazole-5-carboxylate (405.8 mg, 1.648 mmol) in EtOH (20.0 mL) at 25° C. and the reaction was stirred vigorously for 4 h. The reaction mixture was filtered through a plug of Celite®. The filtrate was diluted with EtOAc (20 mL) and washed with satd Na$_2$SO$_3$ (10 mL). The organic layer was dried (Na$_2$SO$_4$) and concentrated in vacuo to give the crude product. This was purified by flash chromatography (Biotage Horizon, 25M, Si, ~20 mL/min, 100% hexanes for 144 mL, gradient to 20% EtOAc in hexanes over 2394 mL) to afford methyl 4-iodo-3-(4-methoxyphenyl)-1-methyl-1H-pyrazole-5-carboxylate, as a colorless solid. R$_f$=0.33 (20% EtOAc/hexanes). LCMS calc.=373.01. found=372.89 (M+H)$^+$. $^1$H NMR (600 MHz, CDCl$_3$): δ 7.68 (d, J=8.6 Hz, 2H); 6.97 (d, J=8.6 Hz, 2H); 4.22 (s, 3H); 3.96 (s, 3H); 3.85 (s, 3H).

Step C: Methyl 3-(4-methoxyphenyl)-1,4-dimethyl-1H-pyrazole-5-carboxylate

A solution of methyl 4-iodo-3-(4-methoxyphenyl)-1-methyl-1H-pyrazole-5-carboxylate (587.8 mg, 1.579 mmol), trimethylboroxine (883 μL, 6.32 mmol) and 1,1'-bis(di-tert-butylphosphino)ferrocene palladium dichloride (103 mg, 0.158 mmol) in THF (2.6 mL) was degassed by bubbling $N_2$ through the solution. 1N K$_2$CO$_3$ (2.6 mL) was added and N$_2$ was bubbled through the mixture for 30 s. The mixture was heated in a sealed tube at 60° C. overnight. Another 4 eq. of trimethylboroxine was added and the reaction was subjected to microwave irradiation (120° C., 30 min). The reaction mixture was filtered through a plug of silica, eluted with EtOAc and the filtrate was washed with 1N aq. NaOH (2×30 mL), dried (Na$_2$SO$_4$) and concentrated in vacuo to afford the crude product. This was purified by flash chromatography (Biotage Horizon, 25M, Si, ~20 mL/min, 100% hexanes for 144 mL, gradient to 20% EtOAc in hexanes over 2394 mL) to afford methyl 3-(4-methoxyphenyl)-1,4-dimethyl-1H-pyrazole-5-carboxylate, as a colorless solid. R$_f$=0.33 (20% EtOAc/hexanes). LCMS calc.=261.03. found=261.12 (M+H)$^+$. $^1$H NMR (600 MHz, CDCl$_3$): δ 7.51 (d, J=8.5 Hz, 2H); 6.96 (d, J=8.5 Hz, 2H); 4.16 (s, 3H); 3.92 (s, 3H); 3.83 (s, 3H); 2.36 (s, 3H).

Step D: Methyl 3-(3-iodo-4-methoxyphenyl-1,4-dimethyl-1H-pyrazole-5-carboxylate

Silver sulfate (261 mg, 0.837 mmol) and iodine (212 mg, 0.837 mmol) were added successively to a solution of methyl 3-(4-methoxyphenyl)-1,4-dimethyl-1H-pyrazole-5-carboxylate (217.8 mg, 0.837 mmol) in EtOH (8.4 mL) at 25° C. and the reaction was stirred vigorously overnight. The reaction mixture was filtered through a plug of Celite®. The filtrate was diluted with EtOAc (80 mL) and washed with satd Na$_2$SO$_3$ (30 mL). The organic layer was washed with brine (2×30 mL), dried (Na$_2$SO$_4$) and concentrated in vacuo to give the crude product. This was purified by flash chromatography (Biotage Horizon, 25M, Si, ~20 mL/min, 100% hexanes for 144 mL, gradient to 20% EtOAc in hexanes over 1125 mL) to afford methyl 3-(3-iodo-4-methoxyphenyl)-1,4-dimethyl-1H-pyrazole-5-carboxylate, as a colorless solid. R$_f$=0.31 (20% EtOAc/hexanes). LCMS calc.=387.02. found=386.91 (M+H)$^+$. $^1$H NMR (600 MHz, CDCl$_3$): δ 7.99 (d, J=2.1 Hz, 1H); 7.48 (dd, J=8.5, 2.2 Hz, 1H); 6.82 (d, J=8.5 Hz, 1H); 4.12 (s, 3H); 3.89 (s, 3H); 3.86 (s, 3H); 2.31 (s, 3H).

Step E: Methyl 3-[3-(5,5-dimethyl-1,3,2-dioxaborinan-2-yl)-4-methoxyphenyl]-1,4-dimethyl-1H-pyrazole-5-carboxylate Dry DMSO (2094 μL) was added to a mixture of 1,1'-bis(diphenylphosphino)ferrocene-palladium(II)dichloride dichloromethane complex (6.41 mg, 7.85 μmol), potassium acetate (77 mg, 0.785 mmol), bis(neopentyl glycolato)diboron (71.0 mg, 0.314 mmol), and methyl 3-(3-iodo-4-methoxyphenyl)-1,4-dimethyl-1H-pyrazole-5-carboxylate (101.1 mg, 0.262 mmol) and the resulting solution was degassed with N$_2$. The reaction was heated at 50° C. for 1 h then 80° C. for 2 h. The reaction mixture was poured into ice-water and extracted with EtOAc (3×40 mL) The combined extracts were washed with brine (2×40 mL), dried (Na$_2$SO$_4$) and concentrated in vacuo to afford methyl 3-[3-(5,5-dimethyl-1,3,2-dioxaborinan-2-yl)-4-methoxyphenyl]-1,4-dimethyl-1H-pyrazole-5-carboxylate. $^1$H NMR (500 MHz, CDCl$_3$): δ 7.87 (d, J=2.4 Hz, 1H); 7.54 (dd, J=8.5, 2.4 Hz, 1H); 6.91 (d, J=8.5 Hz, 1H); 4.16 (s, 3H); 3.91 (s, 3H); 3.86 (s, 3H); 3.78 (s, 4H); 2.34 (s, 3H); 1.03 (s, 6H).

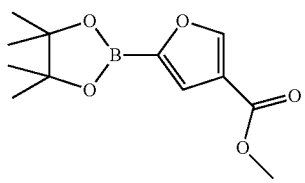

INTERMEDIATE 23

Methyl 5-(4,4,5,5-tetramethyl-1,3,2-dioxaborolan-2-yl)-3-furoate

4-Carboxyfuran-2-boronic acid pinacol ester (200 mg, 0.840 mmol) was dissolved in CH$_2$Cl$_2$ (4 mL) and MeOH (0.444 mL). Trimethylsilyldiazomethane (0.840 mL, 1.680 mmol) was added dropwise. After 45 min, the reaction was quenched with AcOH dropwise until the yellow color disappeared. The reaction was concentrated in vacuo to give methyl 5-(4,4,5,5-tetramethyl-1,3,2-dioxaborolan-2-yl)-3-furoate. $^1$H NMR (500 MHz, CDCl$_3$): δ 8.20 (s, 1H); 7.37 (s, 1H); 3.84 (s, 3H); 1.36 (s, 12H).

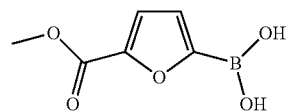

INTERMEDIATE 24

[5-(Methoxycarbonyl)-2-furyl]boronic acid 5-(Dihydroxyboryl)-2-furoic acid (200 mg, 1.283 mmol) was dissolved in CH$_2$Cl$_2$ (5 mL) and MeOH (0.556 mL). Trimethylsilyldiazomethane (1.283 mL, 2.57 mmol) was added dropwise. After 45 min, the reaction was quenched with AcOH dropwise until the yellow color disappeared. The reaction was concentrated in vacuo to give [5-(methoxycarbonyl)-2-furyl]boronic acid. $^1$H NMR (500 MHz, CD$_3$OD): δ 7.20 (d, J=3.5 Hz, 1H); 7.05 (d, J=3.6 Hz, 1H); 3.87 (s, 3H).

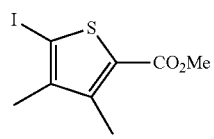

INTERMEDIATE 25

Methyl 5-iodo-3,4-dimethylthiophene-2-carboxylate

Step A: Methyl 3,4-dimethylthiophene-2-carboxylate

A solution of methyl 3-iodo-4-methylthiophene-2-carboxylate (400 mg, 1.418 mmol), trimethylboroxine (793 μL, 5.67 mmol) and 1,1'-bis(di-tert-butylphosphino)ferrocene palladium dichloride (92 mg, 0.142 mmol) in THF (2363 μL) was degassed by bubbling N$_2$ through the solution. 1N aq. K$_2$CO$_3$ (2363 μL) was added and N$_2$ was bubbled through the mixture for 30 s. The mixture was subjected to microwave irradiation in a sealed tube at 120° C. for 30 min. The reaction mixture was filtered through a plug of silica, eluted with EtOAc and the filtrate was washed with 1N aq. NaOH (2×), dried (Na$_2$SO$_4$) and concentrated in vacuo to afford the crude product. This was purified by flash chromatography (Biotage Horizon, 25M, Si, ~20 mL/min, 100% hexanes for 144 mL, gradient to 10% EtOAc in hexanes over 1140 mL) to afford methyl 3,4-dimethylthiophene-2-carboxylate.

Step B: Methyl 5-iodo-3,4-dimethylthiophene-2-carboxylate

To a solution of methyl 3,4-dimethylthiophene-2-carboxylate (80 mg, 0.470 mmol) in MeOH, was added silver sulfate (176 mg, 0.564 mmol) and $I_2$ (143 mg, 0.564 mmol). The mixture was stirred at room temperature. under $N_2$ overnight.

The reaction was quenched with sat. $Na_2SO_3$. The aqueous layer was extracted with EtOAc (3×).

The combined organic layers were washed with brine (1×), dried ($Na_2SO_4$) and concentrated in vacuo. The residue was purified by preparative TLC (1000 μm, hexanes/EtOAc (9:1)) to give methyl 5-iodo-3,4-dimethylthiophene-2-carboxylate. $^1$H NMR (500 MHz, $CDCl_3$): δ 3.86 (s, 3H); 2.54 (s, 3H); 2.18 (s, 3H).

INTERMEDIATE 26

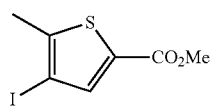

Methyl 4-iodo-5-methylthiophene-2-carboxylate

To a solution of methyl 5-methylthiophene-2-carboxylate (287 mg, 1.837 mmol) in MeOH (7 mL), was added silver sulfate (687 mg, 2.205 mmol) and $I_2$ (513 mg, 2.021 mmol). The mixture was stirred at room temperature under $N_2$ overnight. The reaction was quenched with sat. $Na_2SO_3$. The aqueous layer was extracted with EtOAc (3×). The combined organic layers were washed with brine (1×), dried ($Na_2SO_4$) and concentrated in vacuo. This was purified by flash chromatography (Biotage Horizon, 25M, Si, ~20 mL/min, 100% hexanes for 144 mL, gradient to 10% EtOAc in hexanes over 1140 mL) to afford in order of elution methyl 4-iodo-5-methylthiophene-2-carboxylate. LCMS calc.=207.1. found=206.9 (M+Na)$^+$. $^1$H NMR (500 MHz, $CDCl_3$): δ 767 (s, 1H); 3.87 (s, 3H); 2.46 (s, 3H).

INTERMEDIATE 27

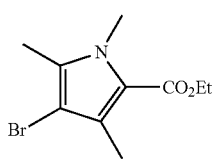

Ethyl 4-bromo-1,3,5-trimethyl-1H-pyrrole-2-carboxylate

To a solution of ethyl 4-bromo-3,5-dimethyl-1H-pyrrole-2-carboxylate (0.050 mL, 0.610 mmol) in THF (3 mL), was added NaH (36.6 mg, 0.914 mmol). The mixture was stirred for 10 min and then MeI (0.046 mL, 0.731 mmol) was added dropwise. The resulting mixture was stirred overnight. The reaction was quenched with sat. $NH_4Cl$. The aqueous layer was extracted with EtOAc (3×). The combined organic layers were washed with brine (1×), dried ($Na_2SO_4$) and concentrated in vacuo. The residue was purified by flash chromatography (Biotage Horizon, 12M, Si, ~10 mL/min, 100% hexanes for 36 mL, gradient to 20% EtOAc in hexanes over 1032 mL) to afford ethyl 4-bromo-1,3,5-trimethyl-1H-pyrrole-2-carboxylate. $^1$H NMR (500 MHz, $CDCl_3$): δ 4.31 (q, J=7.1 Hz, 2H); 3.82 (s, 3H); 2.31 (s, 3H); 2.26 (s, 3H); 1.38 (t, J=7.1 Hz, 3H).

INTERMEDIATE 28

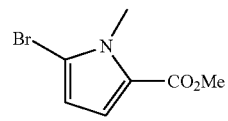

Methyl 5-bromo-1-methyl-1H-pyrrole-2-carboxylate

To a solution of methyl 1-methyl-1H-pyrrole-2-carboxylate (100 mg, 0.719 mmol) in $CHCl_3$ (5 mL) at 0° C. was added N-bromosuccinimide (128 mg, 0.719 mmol). The reaction was stirred at 0° C. for 5 min. The reaction was allowed to warm to room temperature and stirred overnight. The reaction mixture was filtered and concentrated in vacuo. The residue was purified by preparative TLC (1000 μm, hexanes/EtOAc (9:1)) to give methyl 5-bromo-1-methyl-1H-pyrrole-2-carboxylate. $^1$H NMR (500 MHz, $CDCl_3$): δ 6.94 (d, J=4.2 Hz, 1H); 6.21 (d, J=4.1 Hz, 1H); 3.94 (s, 3H); 3.82 (s, 3H).

INTERMEDIATE 29

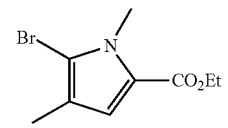

Ethyl 5-bromo-1,4-dimethyl-1H-pyrrole-2-carboxylate

Step A: Ethyl 1,4-dimethyl-1H-pyrrole-2-carboxylate

To a solution of 4-methyl-2-pyrrolecarboxylic acid ethyl ester (100 mg, 0.653 mmol) in THF (2.5 mL), was added NaH (31.3 mg, 0.783 mmol). The mixture was stirred for 10 min and then MeI (0.061 mL, 0.979 mmol) was added dropwise. The resulting mixture was stirred overnight. The reaction was quenched with sat. $NH_4Cl$. The aqueous layer was extracted with EtOAc (3×). The combined organic layers were washed with brine (1×), dried ($Na_2SO_4$) and concentrated in vacuo. The residue was purified by preparative TLC (1000 μm, hexanes/EtOAc (9:1)) to give ethyl 1,4-dimethyl-1H-pyrrole-2-carboxylate. $^1$H NMR (500 MHz, $CDCl_3$): δ 6.77 (s, 1H); 6.58 (s, 1H); 4.28 (q, J=7.1 Hz, 2H); 3.88 (s, 3H); 2.08 (s, 3H); 1.35 (t, J=7.1 Hz, 3H).

Step B: Ethyl 5-bromo-1,4-dimethyl-1H-pyrrole-2-carboxylate

To a solution of ethyl 1,4-dimethyl-1H-pyrrole-2-carboxylate (63 mg, 0.377 mmol) in $CHCl_3$ (3.5 mL) at 0° C. was added N-bromosuccinimide (67.1 mg, 0.377 mmol). The reaction was stirred at 0° C. for 15 min. The reaction was warmed to room temperature and stirred overnight. The reaction mixture was filtered and the filtrate was concentrated in vacuo. The residue was purified by preparative TLC (1000 μm, hexanes/EtOAc (9:1)) to give ethyl 5-bromo-1,4-dimethyl-1H-pyrrole-2-carboxylate. LCMS calc.=245.0. found=245.9 (M+H)⁺. ¹H NMR (500 MHz, CDCl₃): δ 6.83 (s, 1H); 4.27 (q, J=7.1 Hz, 2H); 3.91 (s, 3H); 2.05-2.02 (m, 3H); 1.34 (t, J=7.1 Hz, 3H).

INTERMEDIATE 30

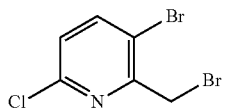

3-Bromo-2-(bromomethyl)-6-chloropyridine

Step A: 3-Bromo-6-chloro-2-methylpyridine

A solution of 6-amino-3-bromo-2-methylpyridine (239 g, 1278 mmol) in concentrated HCl (1.0 L) was cooled to −5° C. A solution of sodium nitrite (238 g, 3450 mmol) in water (1.0 L) was added dropwise over 1 hour while maintaining the temperature of the reaction between −5 and 5° C. After the addition was complete, the reaction was stirred for 1 hour, and then the cooling bath was removed and the reaction was warmed to r.t. and stirred for 16 hours. The reaction was then poured onto ice and 5N NaOH (1.7 L) was added to adjust the pH of the solution to 13. The mixture was extracted 3 times with EtOAc (3 L and 2×2 L). The combined organic layers were dried over Na₂SO₄, filtered, and concentrated. Purification of the residue by flash chromatography on silica gel with 100% methylene chloride afforded 3-bromo-6-chloro-2-methylpyridine. ¹H NMR (CDCl₃, 500 MHz) δ 7.76 (d, J=8.2 Hz, 1H), 7.07 (d, J=8.1 Hz, 1H), 2.66 (s, 3H).

Step B: 3-Bromo-2-(bromomethyl)-6-chloropyridine

To a stirred solution of 3-bromo-6-chloro-2-methylpyridine (105 g, 509 mmol) in CCl₄ (2 L) was added N-bromosuccinimide (95 g, 534 mmol) followed by AIBN (8.35 g, 50.9 mmol). The reaction was brought to reflux for 24 hours and then cooled to r.t., filtered, and concentrated. Purification of the residue by flash chromatography on silica gel with 60% methylene chloride/heptanes afforded semi-pure product. Further purification by SFC on a Chiralpak AD-H column with 20% IPA/CO₂ [the conditions of the preparative separation were as follows: column Chiralpak AD-H (2.1×25 cm, 5 μm particle size) (Chiral Technologies, West Chester, Pa., USA); mobile phase 20% 2-propanol/CO₂; elution mode isocratic pump-mixed; flow rate 50 mL/min; pressure 100 bar.] gave 3-bromo-2-(bromomethyl)-6-chloropyridine. LCMS=285.7 (M+H)⁺ ¹H NMR (CDCl₃, 500 MHz) δ 7.81 (d, J=8.4 Hz, 1H), 7.15 (d, J=8.3 Hz, 1H), 4.63 (s, 2H).

INTERMEDIATE 31

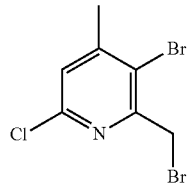

3-Bromo-2-(bromomethyl)-6-chloro-4-methylpyridine

Step A: 3-Bromo-6-chloro-2,4-dimethylpyridine

A stirred solution of 2-amino-5-bromo-4,6-dimethylpyridine (65 g, 323 mmol) in 37% hydrochloric acid (780 ml) was cooled to −10° C. Sodium nitrite (66.9 g, 970 mmol) was added in small portions over 10 min. The reaction was stirred for 15 min at −10° C. and then warmed to room temperature. After stirring for 1 hour at r.t., the reaction was quenched by pouring into ice/water (4 L). The mixture was stirred for 5 minutes and then extracted with EtOAc (4 L). The organic extract was washed with water (4 L) and brine (2 L). The organic layer was dried over Na₂SO₄, filtered, and concentrated. The resulting white solid was dissolved in CH₂Cl₂ (200 mL) and heptanes (700 mL) were added. The solution was stirred for 20 minutes and then filtered to remove solids. The filtrate was concentrated and the residue was purified by flash chromatography on silica gel with 0 to 15% EtOAc/heptanes to afford 3-bromo-6-chloro-2,4-dimethylpyridine. LCMS=219.9 and 221.9 (M+H)⁺ ¹H NMR (CDCl₃, 500 MHz) δ 7.05 (s, 1H), 2.65 (s, 3H), 2.39 (s, 3H).

Step B: 3-Bromo-6-chloro-2,4-dimethylpyridine 1-oxide

A suspension of urea hydrogen peroxide (33.9 g, 360 mmol) in CH₂Cl₂ (1.985 L) was cooled to 0° C. Trifluoroacetic anhydride (25.4 mL, 180 mmol) was added and the reaction was warmed to r.t. and stirred for 10 minutes. Next, 3-bromo-6-chloro-2,4-dimethylpyridine (39.7 g, 180 mmol) was added as a solution in CH₂Cl₂ (198 mL). The reaction was stirred for 2.5 hours at room temperature and then dimethyl sulfide (170 mL, 2305 mmol) was added and stirring was continued for an additional 30 minutes. Next, water (2 L) was added, and the mixture was stirred for 10 minutes. The layers were separated and the aqueous layer was extracted with CH₂Cl₂ (3×500 mL). The combined organic layers were dried over Na₂SO₄, filtered, and concentrated. Purification of the residue by flash chromatography on silica gel with 0 to 75% EtOAc/heptanes afforded 3-bromo-6-chloro-2,4-dimethylpyridine 1-oxide. LCMS=235.9 and 237.9 (M+H)⁺ ¹H NMR (CDCl₃, 500 MHz) δ 7.29 (s, 1H), 2.79 (s, 3H), 2.40 (s, 3H).

Step C: (3-Bromo-6-chloro-4-methylpyridin-2-yl)methanol

To a solution of 3-bromo-6-chloro-2,4-dimethylpyridine 1-oxide (28.7 g, 121 mmol) in CH₂Cl₂ (240 mL) was added trifluoroacetic anhydride (240 mL, 1699 mmol). The reaction was stirred for 3 hours at room temperature and then concentrated. The residue was dissolved in MeOH (1.7 L) and cooled to 0° C. 1M K₂CO₃ (360 mL, 360 mmol) was added dropwise, and the reaction was stirred for 10 minutes at 0° C. and then warmed to r.t. for 1 hour. The reaction was then concentrated to a volume of 300 mL and diluted with EtOAc (1 L). Water (1 L) was added and the layers were separated. The aqueous layer was extracted with additional EtOAc (2×1 L). The organic layers were combined, washed with brine (1 L), dried over $Na_2SO_4$, filtered, and concentrated. Purification of the residue by flash chromatography on silica gel with 0 to 75% EtOAc/heptanes afforded (3-bromo-6-chloro-4-methylpyridin-2-yl)methanol. LCMS=236.1 and 238.1 (M+H)+ $^1$H NMR ($CDCl_3$, 500 MHz) δ 7.17 (s, 1H), 4.73 (s, 2H), 2.42 (s, 3H).

Step D:
3-Bromo-2-(bromomethyl)-6-chloro-4-methylpyridine

A solution of (3-bromo-6-chloro-4-methylpyridin-2-yl)methanol (22.9 g, 97 mmol) in $CH_2Cl_2$ (1.5 L) was cooled to 0° C. $CBr_4$ (48.2 g, 145 mmol) was added, followed by $Ph_3P$ (38.1 g, 145 mmol). The reaction was stirred at 0° C. for 20 minutes and then warmed to r.t. for 16 hours. The reaction was then concentrated and the residue was purified by flash chromatography on silica gel with 0 to 10% EtOAc/heptanes to afford of 3-bromo-2-(bromomethyl)-6-chloro-4-methylpyridine. $^1$H NMR ($CDCl_3$, 500 MHz) δ 7.16 (s, 1H), 4.67 (s, 2H), 2.43 (s, 3H).

INTERMEDIATE 32

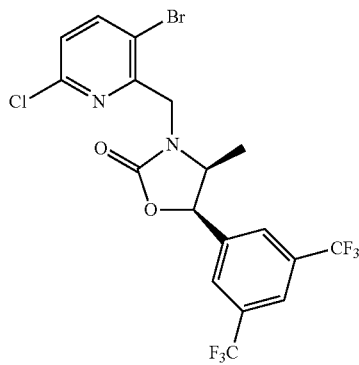

(4S,5R)-5-[3,5-Bis(trifluoromethyl)phenyl]-3-[(3-bromo-6-chloropyridin-2-yl)methyl]-4-methyl-1,3-oxazolidin-2-one To a solution of (4S,5R)-5-[3,5-bis(trifluoromethyl)phenyl]-4-methyl-1,3-oxazolidin-2-one (4.94 g, 15.77 mmol) in THF (75 mL) was added NaH (60% dispersion in mineral oil) (0.526 g, 13.14 mmol). After stirring the reaction at room temperature for 10 minutes, 3-bromo-2-(bromomethyl)-6-chloropyridine (3.0 g, 10.51 mmol) was added as a solution in THF (20 mL). The reaction was stirred at room temperature for 16 hours and then quenched with saturated $NH_4Cl$ (40 mL). The mixture was diluted with EtOAc (100 mL) and hexanes (50 mL). The organic layer was washed with water (2×100 mL) and brine (50 mL), dried over $Na_2SO_4$, filtered, and concentrated. Purification of the residue by flash chromatography on silica gel with 0 to 50% EtOAc/hexanes afforded (4S,5R)-5-[3,5-bis(trifluoromethyl)phenyl]-3-[(3-bromo-6-chloropyridin-2-yl)methyl]-4-methyl-1,3-oxazolidin-2-one. LCMS=518.8 (M+H)+ $^1$H NMR ($CDCl_3$, 500 MHz) δ 7.90 (s, 1H), 7.81-7.83 (m, 3H), 7.18 (d, J=8.5 Hz, 1H), 5.87 (d, J=8.5 Hz, 1H), 5.02 (d, J=17.2 Hz, 1H), 4.42 (m, 1H), 4.32 (d, J=17.1 Hz, 1H), 0.80 (d, J=6.6 Hz, 3H).

INTERMEDIATE 33

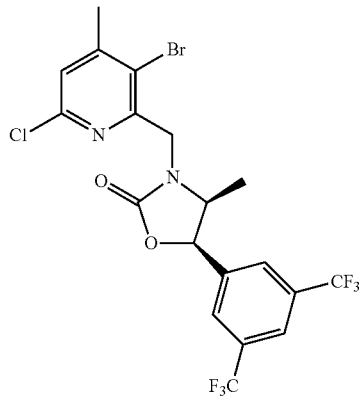

(4S,5R)-5-[3,5-Bis(trifluoromethyl)phenyl]-3-[(3-bromo-6-chloro-4-methylpyridin-2-yl)methyl]-4-methyl-1,3-oxazolidin-2-one To a solution of (4S,5R)-5-[3,5-bis(trifluoromethyl)phenyl]-4-methyl-1,3-oxazolidin-2-one (30.6 g, 98 mmol) in THF (800 mL) was added NaH (60% dispersion in mineral oil) (3.35 g, 84 mmol). After stirring the reaction at room temperature for 10 minutes, 3-bromo-2-(bromomethyl)-6-chloro-4-methylpyridine (16.7 g, 55.8 mmol) was added as a solution in THF (300 mL). The reaction was stirred at room temperature for 16 hours and then quenched with saturated $NH_4Cl$ (200 mL). The mixture was diluted with EtOAc (1 L). The organic layer was separated, washed with water (500 mL) and brine (500 mL), dried over $Na_2SO_4$, filtered, and concentrated. Purification of the residue by flash chromatography on silica gel with 0 to 50% EtOAc/heptanes afforded (4S,5R)-5-[3,5-bis(trifluoromethyl)phenyl]-3-[(3-bromo-6-chloro-4-methylpyridin-2-yl)methyl]-4-methyl-1,3-oxazolidin-2-one. LCMS=530.8, 532.8 (M+H)+ $^1$H NMR ($CDCl_3$, 500 MHz) δ 7.89 (s, 1H), 7.81 (s, 2H), 7.18 (s, 1H), 5.87 (d, J=8.3 Hz, 1H), 5.04 (d, J=17.2 Hz, 1H), 4.42 (m, 1H), 4.32 (d, J=17.3 Hz, 1H), 2.43 (s, 3H), 0.80 (d, J=6.6 Hz, 3H).

The following intermediates (Table 4) were synthesized using methods analogous to those described for INTERMEDIATE 32 and 33 from commercially available materials or intermediates whose syntheses are described above.

TABLE 4

| Intermediate | Molecular structure | LCMS (M + H)+ |
|---|---|---|
| 34 | (structure shown) | 416.8, 418.8 |

INTERMEDIATE 35

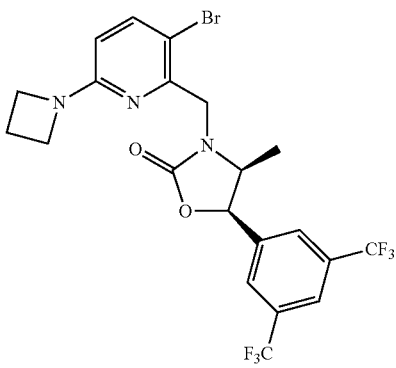

(4S,5R)-3-[(6-Azetidin-1-yl-3-bromopyridin-2-yl)methyl]-5-[3,5-bis(trifluoromethyl)phenyl]-4-methyl-1,3-oxazolidin-2-one To a microwave tube containing (4S,5R)-5-[3,5-bis(trifluoromethyl)phenyl]-3-[(3-bromo-6-chloropyridin-2-yl)methyl]-4-methyl-1,3-oxazolidin-2-one (330 mg, 0.637 mmol) was added a 2M solution of azetidine in THF (4 mL, 8 mmol). The tube was sealed and the reaction was heated at 150° C. for 30 minutes in the microwave. The reaction was cooled and concentrated. The residue was purified via flash chromatography on silica gel (0 to 75% ethyl acetate/hexanes) to afford (4S,5R)-3-[(6-azetidin-1-yl-3-bromopyridin-2-yl)methyl]-5-[3,5-bis(trifluoromethyl)phenyl]-4-methyl-1,3-oxazolidin-2-one. LCMS=537.9 and 539.8 (M+H)$^+$. $^1$H NMR (CDCl$_3$, 500 MHz) δ 7.88 (s, 1H), 7.78 (s, 2H), 7.51 (d, J=8.6 Hz, 1H), 6.10 (d, J=8.7 Hz, 1H), 5.77 (d, J=8.6 Hz, 1H), 4.86 (d, J=17.0 Hz, 1H), 4.35 (m, 1H), 4.20 (d, J=16.9 Hz, 1H), 4.01 (m, 4H), 2.40 (m, 2H), 0.78 (d, J=6.7 Hz, 3H).

INTERMEDIATE 36

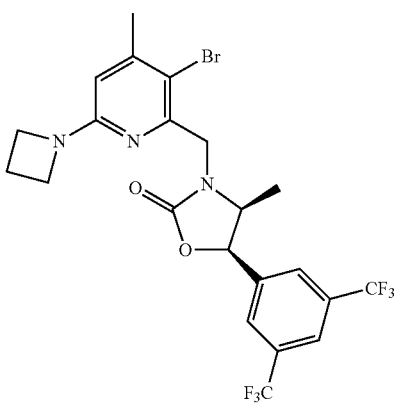

(4S,5R)-3-[(6-Azetidin-1-yl-3-bromo-4-methylpyridin-2-yl)methyl]-5-[3,5-bis(trifluoromethyl)phenyl]-4-methyl-1,3-oxazolidin-2-one In a microwave tube, (4S,5R)-5-[3,5-bis(trifluoromethyl)phenyl]-3-[(3-bromo-6-chloro-4-methylpyridin-2-yl)methyl]-4-methyl-1,3-oxazolidin-2-one (500 mg, 0.940 mmol) was dissolved in a 2M solution of azetidine in THF (8 mL, 16.0 mmol). The tube was sealed and the reaction was heated to 150° C. for 2 hr in the microwave. The reaction was then cooled and concentrated. The residue was purified via flash chromatography on silica gel (0 to 75% ethyl acetate/hexanes) to afford (4S,5R)-3-[(6-azetidin-1-yl-3-bromo-4-methylpyridin-2-yl)methyl]-5-[3,5-bis(trifluoromethyl)phenyl]-4-methyl-1,3-oxazolidin-2-one. LCMS=551.9 and 553.9 (M+H)$^+$. $^1$H NMR (CDCl$_3$, 500 MHz) δ 7.87 (s, 1H), 7.77 (s, 2H), 6.09 (s, 1H), 5.77 (d, J=8.7 Hz, 1H), 4.87 (d, J=17.2 Hz, 1H), 4.37 (m, 1H), 4.21 (d, J=16.9 Hz, 1H), 3.99 (m, 4H), 2.38 (m, 2H), 2.30 (s, 3H), 0.77 (d, J=6.7 Hz, 3H).

The following intermediates (Table 5) were synthesized using methods analogous to those described for INTERMEDIATE 35 and 36 from commercially available materials or intermediates whose syntheses are described above.

TABLE 5

| Intermediate | Molecular structure | LCMS (M + H)$^+$ |
|---|---|---|
| 37 | ![structure] | 437.9, 439.9 |
| 38 | ![structure] | 551.9, 553.9 |
| 39 | ![structure] | |

(4S,5R)-5-[3,5-Bis(trifluoromethyl)phenyl]-3-{[3-bromo-6-(3,3-difluoroazetidin-1-yl-pyridin-2-yl]methyl}-4-methyl-1,3-oxazolidin-2-one A reaction vessel was charged with (4S,5R)-5-[3,5-bis(trifluoromethyl)phenyl]-3-[(3-bromo-6-chloropyridin-2-yl)methyl]-4-methyl-1,3-oxazolidin-2-one (50 mg, 0.097 mmol), 3,3-difluoroazetidine hydrochloride (125 mg, 0.966 mmol) and sodium bicarbonate (162 mg, 1.932 mmol). DMSO (2 mL) was added. The reaction was heated to 150° C. under an atmosphere of $N_2$. After 16 hours, the reaction was cooled to r.t., diluted with EtOAc (40 mL), and washed with water and brine (10 mL each). The organic layer was dried over $Na_2SO_4$, filtered, and concentrated. Purification of the residue by flash chromatography on silica gel with 0 to 80% EtOAc/hexanes afforded (4S,5R)-5-[3,5-bis(trifluoromethyl)phenyl]-3-{[3-bromo-6-(3,3-difluoroazetidin-1-yl)pyridin-2-yl]methyl}-4-methyl-1,3-oxazolidin-2-one contaminated with a minor impurity. This material was used in subsequent reactions without further purification. LCMS=575.9 (M+H)$^+$ $^1$H NMR (CDCl$_3$, 500 MHz) δ 7.89 (s, 1H), 7.78 (s, 2H), 7.63 (d, J=8.7 Hz, 1H), 6.24 (d, J=8.7 Hz, 1H), 5.75 (d, J=8.4 Hz, 1H), 4.87 (d, J=17.1 Hz, 1H), 4.23-4.40 (m, 6H), 0.79 (d, J=7.6 Hz, 3H).

The following intermediates (Table 6) were synthesized using methods analogous to those described for INTERMEDIATE 39 from commercially available materials or intermediates whose syntheses are described above.

TABLE 6

| Intermediate | Molecular structure | LCMS (M + H)$^+$ |
|---|---|---|
| 40 | 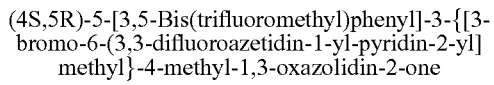 | 590.0 |
| INTERMEDIATE 41 | 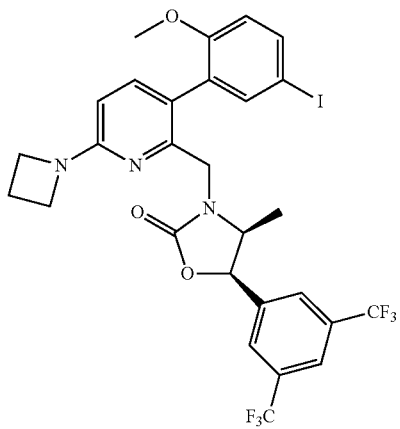 | |

(4S,5R)-3-{[6-Azetidin-1-yl-3-(5-iodo-2-methoxyphenyl)pyridin-2-yl]methyl}-5-[3,5-bis(trifluoromethyl)phenyl]-4-methyl-1,3-oxazolidin-2-one

Step A: 2-(2-Methoxy-5-nitrophenyl)-5,5-dimethyl-1,3,2-dioxaborinane

Dry DMSO (35 mL) was added to a mixture of PdCl$_2$ (dppf)-CH$_2$Cl$_2$ adduct (0.106 g, 0.129 mmol), potassium acetate (1.269 g, 12.93 mmol), bis(neopentyl glycolato)diboron (1.168 g, 5.17 mmol) and 2-bromo-4-nitroanisole (1 g, 4.31 mmol) and the resulting solution was degassed with $N_2$. The reaction was heated at 50° C. for 1 h then 80° C. for 2 h. The reaction mixture was poured into ice-water and extracted with EtOAc (3×) The combined extracts were washed with brine (2×), dried (Na$_2$SO$_4$) and concentrated in vacuo to give the crude product 2-(2-methoxy-5-nitrophenyl)-5,5-dimethyl-1,3,2-dioxaborinane, which was used in the next step without further purification. $^1$H NMR (500 MHz, CDCl$_3$): δ 8.56 (d, J=3.0 Hz, 1H); 8.27 (d, J=9.3 Hz, 1H); 6.92 (d, J=9.1 Hz, 1H); 3.95 (s, 3H); 3.82 (s, 4H); 1.07 (s, 6H).

Step B: (4S,5R)-3-{[6-azetidin-1-yl-3-(2-methoxy-5-nitrophenyl)pyridin-2-yl]methyl}-5-[3,5-bis(trifluoromethyl)phenyl]-4-methyl-1,3-oxazolidin-2-one A solution of (4S,5R)-3-{[6-azetidin-1-yl-3-bromopyridin-2-yl]methyl}-5-[3,5-bis(trifluoromethyl)phenyl]-4-methyl-1,3-oxazolidin-2-one (1.2 g, 2.229 mmol) and 2-(2-methoxy-5-nitrophenyl)-5,5-dimethyl-1,3,2-dioxaborinane in THF (20 mL) was degassed with N$_2$ at 25° C. 1N K$_2$CO$_3$ (20 mL) was added followed by 1,1-bis(di-tert-butylphosphino)ferrocene palladium dichloride (0.073 g, 0.111 mmol) and the reaction was stirred vigorously at 25° C. under N$_2$ for 4 h. The reaction was diluted with water (50 mL) and extracted with EtOAc (3×30 mL). The combined extracts were dried (Na$_2$SO$_4$) and concentrated in vacuo to afford the crude product. This was purified by flash chromatography (Biotage Horizon, 40M, Si, ~30 mL/min, 100% hexanes for 260 mL, gradient to 40% EtOAc in hexanes over 2240 mL) to give (4S,5R)-3-{[6-azetidin-1-yl-3-(2-methoxy-5-nitrophenyl)pyridin-2-yl]methyl}-5-[3,5-bis(trifluoromethyl)phenyl]-4-methyl-1,3-oxazolidin-2-one. LCMS calc.=610.2. found=611.1 (M+H)$^+$.

Step C: (4S,5R)-3-{[3-(5-Amino-2-methoxyphenyl)-6-azetidin-1-ylpyridin-2-yl]methyl}-5-[3,5-bis(trifluoromethyl)phenyl]-4-methyl-1,3-oxazolidin-2-one To a solution of (4S,5R)-3-{[6-azetidin-1-yl-3-(2-methoxy-5-nitrophenyl)pyridin-2-yl]methyl}-5-[3,5-bis(trifluoromethyl)phenyl]-4-methyl-1,3-oxazolidin-2-one (1.26 g, 2.064 mmol) in EtOH (80 mL) was added Pd—C (10%) (0.220 g, 0.206 mmol). The mixture was subjected to hydrogenation by using a Hz balloon for 6.5 h. The mixture was filtered through Celite® and the filtrate was concentrated in vacuo. This was purified by flash chromatography (Biotage Horizon, 40M, Si, ~30 mL/min, 100% hexanes for 260 mL, gradient to 50% EtOAc in hexanes over 2240 mL) to afford (4S,5R)-3-{[3-(5-amino-2-methoxyphenyl)-6-azetidin-1-ylpyridin-2-yl]methyl}-5-[3,5-bis(trifluoromethyl)phenyl]-4-methyl-1,3-oxazolidin-2-one. LCMS calc.=580.2. found=581.1 (M+H)$^+$. $^1$H NMR (500 MHz, CDCl$_3$): δ 7.86 (s, 1H); 7.75 (s, 2H); 7.32 (d, J=8.3 Hz, 1H); 6.79 (d, J=8.6 Hz, 1H); 6.68 (dd, J=8.6, 2.9 Hz, 1H); 6.54 (d, 2.9 Hz, 1H); 6.27 (d, J=8.3 Hz, 1H); 5.61 (d, J=8.5 Hz, 1H); 4.93-4.30 (m, 1H); 4.18-4.01 (m, 6H); 3.70 (s, 3H); 3.51 (s, br, 2H); 2.46-2.37 (m, 2H); 0.68 (s, br, 3H).

Step D: (4S,5R-3-{[6-Azetidin-1-yl-3-(5-iodo-2-methoxyphenyl)pyridin-2-yl]methyl}-5-[3,5-bis(trifluoromethyl)phenyl]-4-methyl-1,3-oxazolidin-2-one A solution of (4S,5R)-3-{[3-(5-amino-2-methoxyphenyl)-6-azetidin-1-ylpyridin-2-yl]methyl}-5-[3,5-bis(trifluoromethyl)phenyl]-4-methyl-1,3-oxazolidin-2-one (460 mg, 0.792 mmol) in toluene (7 mL) and diiodomethane (2 mL, 24.79 mmol) was added isoamyl nitrite (0.213 mL, 1.585 mmol) dropwise at room temperature. The mixture was stirred at 25° C. for 15 min. Then the mixture was heated at 80° C. for 45 min. The reaction mixture was loaded on a silica column directly and was purified by flash chromatography (Biotage Horizon, 25M, Si, ~20 mL/min, 100% hexanes for 270 mL, gradient to 35% EtOAc in hexanes over 972 mL) to afford (4S,5R)-3-{[6-azetidin-1-yl-3-(5-iodo-2-methoxyphenyl)pyridin-2-yl]methyl}-5-[3,5-bis(trifluoromethyl)phenyl]-4-methyl-1,3-oxazolidin-2-one. LCMS calc.=691.1. found=692.0 (M+H)$^+$. $^1$H NMR (500 MHz, CDCl$_3$): δ 7.87 (s, 1H); 7.75 (s, 2H); 7.62 (dd, J=8.7, 2.2 Hz, 1H); 7.54-7.38 (m, 1H); 7.29 (d, J=8.3 Hz, 1H); 6.74 (d, J=8.7 Hz, 1H); 6.28 (d, J=8.3 Hz, 1H); 5.75-5.30 (m, 1H); 4.81 (d, J=16.3 Hz, 1H); 4.21-4.00 (m, 6H); 3.79 (s, 3H); 2.48-2.38 (m, 2H); 0.67 (s, br, 3H).

INTERMEDIATE 42

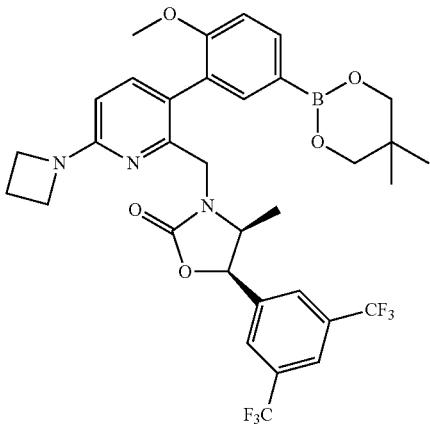

(4S,5R)-3-({6-Azetidin-1-yl-3-[5-(5,5-dimethyl-1,3,2-dioxaborinan-2-yl)-2-methoxyphenyl]pyridin-2-yl}methyl)-5-[3,5-bis(trifluoromethyl)phenyl]-4-methyl-1,3-oxazolidin-2-one Dry DMSO (3.6 mL) was added to a mixture of PdCl$_2$ (dppf)-CH$_2$Cl$_2$ adduct (9.39 mg, 0.011 mmol), potassium acetate (113 mg, 1.150 mmol), bis(neopentyl glycolato)diboron (104 mg, 0.460 mmol) and (4S,5R)-3-({[6-azetidin-1-yl-3-(5-iodo-2-methoxyphenyl)pyridin-2-yl]methyl}-5-[3,5-bis(trifluoromethyl)phenyl]-4-methyl-1,3-oxazolidin-2-one (265 mg, 0.383 mmol) and the resulting solution was degassed with N$_2$. The reaction was heated at 50° C. for 2.5 h. The reaction mixture was poured into ice-water and extracted with EtOAc (3×) The combined extracts were washed with brine (2×), dried (Na$_2$SO$_4$) and concentrated in vacuo to give the crude product (4S,5R)-3-({6-azetidin-1-yl-3-[5-(5,5-dimethyl-1,3,2-dioxaborinan-2-yl)-2-methoxyphenyl]pyridin-2-yl}methyl)-5-[3,5-bis(trifluoromethyl)phenyl]-4-methyl-1,3-oxazolidin-2-one. This product was used without further purification. $^1$H NMR (500 MHz, CDCl$_3$): δ 7.85 (s, br, 1H); 7.79 (d, J=7.0 Hz, 1H); 7.76-7.67 (m, 2H); 7.66-7.53 (m, 1H); 7.37 (d, J=8.5 Hz, 1H); 6.96 (dd, J=8.3 Hz, 1H); 6.29 (d, J=8.3 Hz, 1H); 5.77-5.09 (m, 1H); 4.99-4.71 (m, 1H); 4.19-4.03 (m, 6H); 3.84 (s, 3H); 3.75 (s, 4H); 2.46-2.37 (m, 2H); 0.71-0.48 (m, 3H).

INTERMEDIATE 43

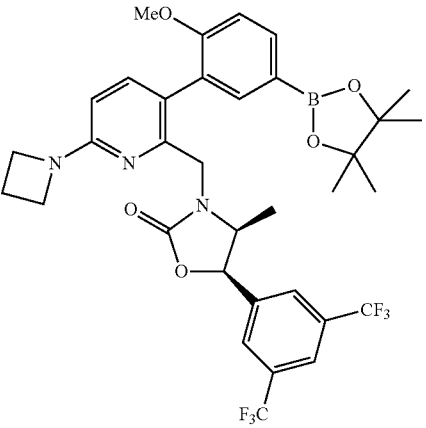

(4S,5R)-3-({6-(Azetidin-1-yl)-3-[2-methoxy-5-(4,4,5,5-tetramethyl-1,3,2-dioxaborolan-2-yl)phenyl]pyridin-2-yl}methyl)-5-[3,5-bis(trifluoromethyl)phenyl]-4-methyl-1,3-oxazolidin-2-one A solution of palladium (II) acetate (6.4 mg, 0.28 mmol) and dicyclohexyl[2',4',6'-tri(propan-2-yl)biphenyl-2-yl]phosphane (29.8 mg, 0.62 mmol) in cyclopropyl methyl ether (3.5 mL) was heated in a sealed tube at 85° C. under N$_2$ for 1 h. The resulting dark brown opaque solution was transferred to a mixture of (4S,5R)-3-{[6-(azetidin-1-yl)-3-(5-chloro-2-methoxyphenyl)pyridin-2-yl]methyl}-5-[3,5-bis(trifluoromethyl)phenyl]-4-methyl-1,3-oxazolidin-2-one (EXAMPLE 22) (851 mg, 1.42 mmol), potassium acetate (278 mg, 2.84 mmol) and bis(pinacolato)diboron (540 mg, 2.13 mmol) and the resulting mixture was heated in a sealed tube at 85° C. under N$_2$ for 20 h. The reaction mixture was diluted with EtOAc, washed with water and brine, dried (Na$_2$SO$_4$) and concentrated in vacuo to afford (4S,5R)-3-({6-(azetidin-1-yl)-3-[2-methoxy-5-(4,4,5,5-tetramethyl-1,3,2-dioxaborolan-2-yl)phenyl]pyridin-2-yl}methyl)-5-[3,5-bis(trifluoromethyl)phenyl]-4-methyl-1,3-oxazolidin-2-one. This was used without further purification. LCMS calc.=692.3. found=692.1 (M+H)$^+$. $^1$H NMR (500 MHz, CDCl$_3$): δ 7.87-7.77 (m, 2H); 7.81-7.65 (m, 2H); 7.71-7.51 (m, 1H); 7.45-7.24 (m, 1H); 7.07-6.93 (m, 1H); 6.28 (d, J=8.2 Hz, 1H); 5.77-5.20 (m, 1H); 4.92-4.77 (m, 1H); 4.28-3.95 (m, 7H); 3.85 (s, 3H); 2.46-2.37 (m, 2H); 1.28 (s, 12H); 0.72-0.52 (m, 3H).

INTERMEDIATE 44

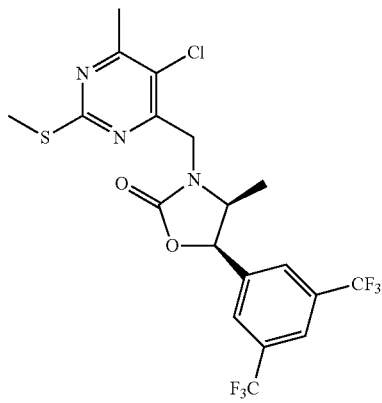

(4S,5R)-5-[3,5-bis(trifluoromethyl)phenyl]-3-{[5-chloro-6-methyl-2-(methylsulfanyl)pyrimidin-4-yl]methyl}-4-methyl-1,3-oxazolidin-2-one

Step A: 5-Chloro-6-(methoxymethyl)-2-(methylsulfanyl)pyrimidin-4-ol

The mixture of 4-hydroxy-6-methoxymethyl-2-(methylthio) pyrimidine (10.0 g, 53.7 mmol), NCS (14.34 g, 107 mmol), DMF (10 mL) and $CH_2Cl_2$ (200 mL) was stirred at room temperature for 4 h. TLC (EtOAc/hexane 40:60) showed no starting material left. The solvent was removed. The final product was recrystallized from EtOAc. The mother liquid was purified by column chromatography on silica gel using EtOAc/hexane=40:60 as the eluent.
$^1$H NMR ($CDCl_3$, 500 MHz) δ 4.58 (s, 2H), 3.55 (s, 3H), 2.62 (s, 3H).

Step B: 5-chloro-6-(methoxymethyl)-2-(methylsulfanyl)pyrimidin-4-yl trifluoromethanesulfonate A solution of the title compound from Step A (3.0 g, 13.59 mmol) in $CH_2Cl_2$ (20 ml) was cooled at 0° C. Trifluoromethanesulfonic anhydride ($Tf_2O$) (5.75 g, 20.39 mmol) and 2,6-lutidine (2.91 g, 27.2 mmol) were added. The mixture was stirred at 0° C. and room temperature for 2 h. Water (10 mL) was added and the mixture was extracted with $CH_2Cl_2$ (3×30 mL). The combined organic fractions were washed with brine (10 mL), dried over $Na_2SO_4$, filtered and the solvent was evaporated under reduced pressure. The residue was purified by column chromatography on silica gel Biotage 40M, eluting with EtOAc/hexane (1/9) to give the title compound as a light brown oil. $^1$H NMR ($CDCl_3$, 500 MHz) δ 4.68 (s, 2H), 3.58 (s, 3H), 2.60 (s, 3H).

Step C: 5-chloro-4-(methoxymethyl)-6-methyl-2-(methylsulfanyl)pyrimidine

A mixture of the title compound from Step B (1.00 g, 2.83 mmol), trimethyl boroxine (1.78 g, 14.18 mmol), $Cs_2CO_3$ (0.92 g, 2.83 mmol), and catalytic amount $Pd(PPh_3)_4$ was stirred at 140° C. under microwave for 1 h. The solvent was removed. $CH_2Cl_2$ and water were added. The organic was extracted with $CH_2Cl_2$ (3×10 mL), washed with brine and dried over $Na_2SO_4$. The residue was purified by column chromatography on silica gel Biotage 40M, eluting with EtOAc/hexane (1/9) to give as a colorless oil. $^1$H NMR ($CDCl_3$, 500 MHz) δ 4.61 (s, 2H), 3.55 (s, 3H), 2.60 (s, 3H), 2.58 (s, 3H).

Step D: [5-chloro-6-methyl-2-(methylsulfanyl)pyrimidin-4-yl]methanol

1M $BBr_3$ in $CH_2Cl_2$ (9.5 ml, 9.5 mmol) was added to a solution of the title compound from Step C (0.52 g, 2.78 mmol) in $CH_2Cl_2$ (5 mL) at 0° C. The mixture was stirred at 0° C. for 1 h. Water (1 mL) was added. The mixture was extracted with $CH_2Cl_2$ (3×10 mL), and dried over $Na_2SO_4$. The solvent was removed. The residue was purified by column chromatography on silica gel Biotage 40S, eluting with EtOAc/hexane (3/7) to give the title compound as a colorless gum. $^1$H NMR ($CDCl_3$, 500 MHz) δ 4.76 (d, J=4.5 Hz, 1H), 3.88 (m, 1H), 2.61 (s, 3H), 2.59 (s, 3H).

Step E: 5-chloro-4-methyl-2-(methylsulfanyl)-6-[(methylsulfonyl)methyl]pyrimidine MsCl (248 mg, 2.169 mmol) was added to a stirred, cooled 0° C. mixture of the title compound from Step D (370 mg, 1.808 mmol) in $CH_2Cl_2$ (10 mL), followed by addition of $Et_3N$ (274 mg, 2.71 mmol). The mixture was stirred at 0° C. for 30 min. TLC showed no starting material left. The mixture was quenched with water (5 mL) and the mixture was washed with more water (10 mL). The organic fraction were washed with brine (saturated, 10 mL), dried ($Na_2SO_4$), filtered and the solvent was evaporated under reduced pressure. The residue was purified by column chromatography on silica gel Biotage 40S, eluting with EtOAc/hexane (2/8) to give the title compound as a colorless solid. $^1$H NMR ($CDCl_3$, 500 MHz) δ 5.40 (s, 2H), 3.20 (s, 3H), 2.61 (s, 3H), 2.59 (s, 3H).

Step F: (4S,5R)-5-[3,5-bis(trifluoromethyl)phenyl]-3-{[5-chloro-6-methyl-2-(methylsulfanyl)pyrimidin-4-yl]methyl}-4-methyl-1,3-oxazolidin-2-one A solution of (4S,5R)-5-[3,5-bis(trifluoromethyl)phenyl]-4-methyl-1,3-oxazolidin-2-one (614 mg, 1.961 mmol) in THF (20 mL) was cooled to 0° C. NaH (58.8 mg, 2.451 mmol) was added. The mixture was stirred at 0° C. for 30 min. The title compound from Step E (462 mg, 1.63 mmol) in THF (30 mL) was added. The mixture was stirred at 0° C. and then room temperature for 4 h. Saturated $NH_4Cl$ (10 mL) was added. The mixture was extracted with ethyl acetate (3×10 mL). The combined organic fractions were washed with brine (saturated, 10 mL), dried ($Na_2SO_4$), filtered and the solvent was evaporated under reduced pressure. The residue was purified by column chromatography on silica gel Biotage 40S, eluting with EtOAc/hexane (30/70) to give the title compound as a colorless solid. $^1$H NMR ($CDCl_3$, 500 MHz) δ 7.94 (s, 1H), 7.82 (s, 2H), 5.85 (d, J=8.5 Hz, 1H), 5.00 (d, J=17.5 Hz, 1H), 4.46 (m, 1H), 4.31 (d, J=18.0 Hz, 1H), 2.60 (s, 6H), 0.83 (d, J=7.0 Hz, 3H).

INTERMEDIATE 45

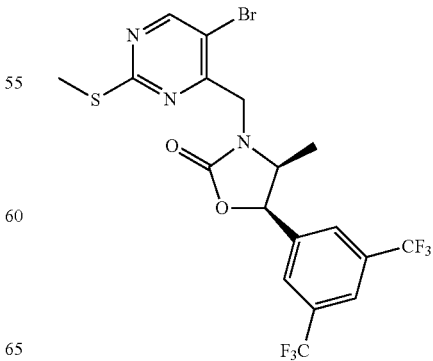

(4S,5R)-5-[3,5-bis(trifluoromethyl)phenyl]-3-{[5-bromo-2-(methylsulfanyl)pyrimidin-4-yl]methyl}-4-methyl-1,3-oxazolidin-2-one Step A: 5-Bromo-2-(methylsulfanyl)-4-[(methylsulfonyl)methyl]pyrimidine MsCl (5.85 g, 51.0 mmol) was added to a stirred, cooled 0° C. mixture of 2-methylthio-5-bromo-3-methylhydroxy pyrimidine (10 g, 42.5 mmol) in $CH_2Cl_2$ (200 mL), followed by addition of $Et_3N$ (6.46 g, 63.8 mmol). The mixture was stirred at 0° C. for 30 min. TLC showed no starting material left. The mixture was quenched with water (30 mL) and the mixture was washed with more water (50 mL). The organic fraction were washed with brine (saturated, 50 mL), dried ($Na_2SO_4$), filtered and the solvent was evaporated under reduced pressure. The residue was purified by column chromatography on silica gel Biotage 65i, eluting with EtOAc/hexane (3/7) to give the title compound as a colorless solid. $^1H$ NMR ($CDCl_3$, 500 MHz) δ 8.61 (s, 1H), 5.38 (s, 2H), 3.21 (s, 3H), 2.60 (s, 3H).

Step B: (4S,5R)-5-[3,5-bis(trifluoromethyl)phenyl]-3-{[5-bromo-2-(methylsulfanyl)pyrimidin-4-yl]methyl}-4-methyl-1,3-oxazolidin-2-one A solution of (4S,5R)-5-[3,5-bis(trifluoromethyl)phenyl]-4-methyl-1,3-oxazolidin-2-one (12.00 g, 38.3 mmol) in THF (200 mL) was cooled to 0° C. NaH (0.919 g, 38.3 mmol) was added. The mixture was stirred at 0° C. for 30 min. The title compound from Step A (10.0 g, 31.9 mmol) in THF (30 mL) was added. The mixture was stirred at 0° C. and then room temperature for 4 h. Saturated $NH_4Cl$ (10 mL) was added. The mixture was extracted with ethyl acetate (3×100 mL). The combined organic fractions were washed with brine (saturated, 20 mL), dried ($Na_2SO_4$), filtered and the solvent was evaporated under reduced pressure. The residue was purified by column chromatography on silica gel Biotage 65i, eluting with EtOAc/hexane (20/80) to give the title compound as a colorless solid. $^1H$ NMR ($CDCl_3$, 500 MHz) δ 8.57 (s, 1H), 7.94 (s, 1H), 7.82 (s, 2H), 5.86 (d, J=8.5 Hz, 1H), 4.97 (d, J=18.0 Hz, 1H), 4.46 (m, 1H), 4.28 (d, J=17.5 Hz, 1H), 2.60 (s, 3H), 0.83 (d, J=6.5 Hz, 3H).

The following intermediates (Table X) were synthesized using methods analogous to those described for INTERMEDIATE 45 from commercially available materials or intermediates whose syntheses are described above.

TABLE 6A

| Intermediate | Molecular structure | LCMS (M + H)+ |
| --- | --- | --- |
| 45(a) | 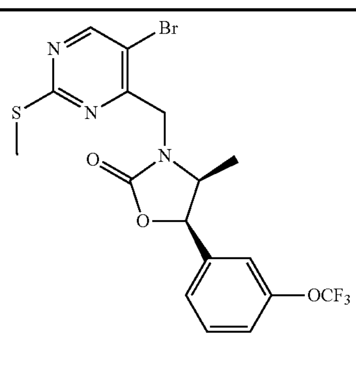 | 480.1 |

TABLE 6A-continued

| Intermediate | Molecular structure | LCMS (M + H)+ |
| --- | --- | --- |
| 45(b) | 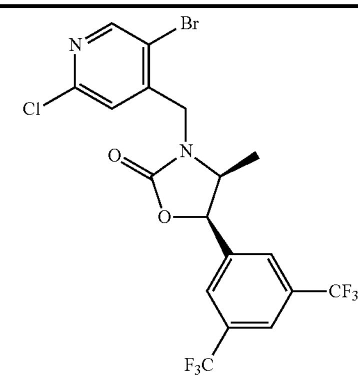 | 517.0, 519.0 |

INTERMEDIATE 46

(4S,5R)-3-{[2-(azetidin-1-yl)-5-bromopyrimidin-4-yl]methyl}-5-[3,5-bis(trifluoromethyl)phenyl]-4-methyl-1,3-oxazolidin-2-one Step A: (4S,5R)-5-[3,5-bis(trifluoromethyl)phenyl]-3-{[5-bromo-2-(methylsulfonyl)pyrimidin-4-yl]methyl}-4-methyl-1,3-oxazolidin-2-one The mixture of the intermediate 45 (2.1 g, 3.96 mmol) and mCPBA (1.50 g, 8.71 mmol) in $CH_2Cl_2$ (20 mL) was stirred at 25° C. for 4 h. The solution was washed with $Na_2S_2O_3$ (5 mL), brine and dried ($Na_2SO_4$), filtered and the solvent was evaporated under reduced pressure. The residue was purified by column chromatography on silica gel Biotage 40M, eluting with EtOAc/hexane (1:1) to give the title compound as a colorless gum. $^1H$ NMR ($CDCl_3$, 500 MHz) δ 8.99 (s, 1H), 7.94 (s, 1H), 7.84 (s, 2H), 6.03 (d, J=8.0 Hz, 1H), 5.16 (d, J=18.5 Hz, 1H), 4.57 (m, 1H), 4.42 (d, J=18.5 Hz, 1H), 3.40 (s, 3H), 0.86 (d, J=7.0 Hz, 3H).

Step B: (4S,5R)-3-{[2-(azetidin-1-yl)-5-bromopyrimidin-4-yl]methyl}-5-[3,5-bis(trifluoromethyl)phenyl]-4-methyl-1,3-oxazolidin-2-one A mixture of the title compound from Step A (300 mg, 0.534 mmol) and azetidine (152 mg, 2.67 mmol) in THF (5 mL) was stirred at 25° C. overnight. The solvent was removed. The residue was purified by column chromatography on silica gel Biotage 40M, eluting with EtOAc/hexane to give the title compound as a colorless gum. $^1H$ NMR ($CDCl_3$, 500 MHz) δ 8.29 (s, 1H), 7.93 (s, 1H), 7.81 (s, 2H), 5.82 (d, J=8.5 Hz, 1H), 4.81 (d, J=18.0 Hz, 1H), 4.43 (m, 1H), 4.16 (m, 5H), 2.43 (m, 2H), 0.82 (d, J=6.5 Hz, 3H).

The following intermediates (Table 7) were synthesized using methods analogous to those described for INTERMEDIATE 46 from commercially available materials or intermediates whose syntheses are described above.

TABLE 7

| Intermediate | Molecular structure | LCMS (M + H)+ |
|---|---|---|
| 47 | 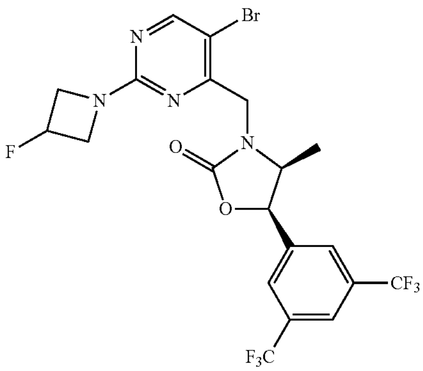 [SMILES: C[C@H]1[C@@H](c2cc(C(F)(F)F)cc(C(F)(F)F)c2)OC(=O)N1Cc1nc(N2CC(F)C2)ncc1Br] | 558.9 |
| 48 | 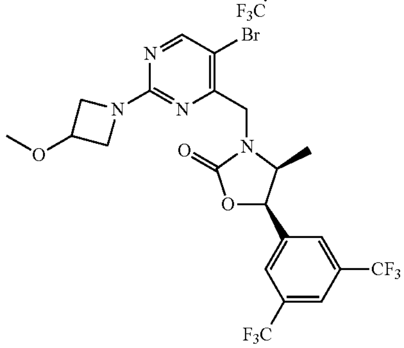 | 553.9 |
| 49 | 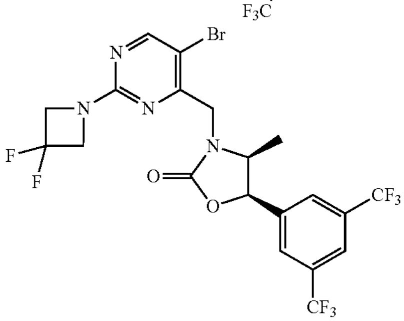 | 575.1 |

INTERMEDIATE 50

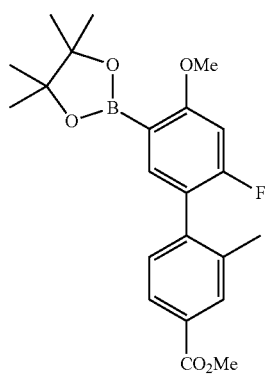

Methyl 2'-fluoro-4'-methoxy-2-methyl-5'-(4,4,5,5-tetramethyl-1,3,2-dioxaborolan-2-yl)biphenyl-4-carboxylate Step A: Methyl 2'-fluoro-4'-methoxy-2-methylbiphenyl-4-carboxylate A mixture of 4-bromo-3-fluoro anisole (2.0 g, 9.75 mmol), methyl 3-methyl-4-(4,4,5,5-tetramethyl-1-3,2-dioxaborolan-2-yl)benzoate (2.8 g, 10.14 mmol), $Cs_2CO_3$ (6.99 g, 21.46 mmol) and catalytic amount of $Pd(PPh_3)_4$ (1.13 g, 0.975 mmol) in dioxane (50 mL) was stirred at 80° C. overnight. The solvent was removed. Water was added. The mixture was extracted with $CH_2Cl_2$ (3×20 mL). Washed with brine and dried over $Na_2SO_4$. The residue was purified by column chromatography on silica gel Biotage 40M, eluting with EtOAc/hexane (1:9) to give the title compound as a colorless solid.

Step B: Methyl 2'-fluoro-5'-iodo-4'-methoxy-2-methylbiphenyl-4-carboxylate

To a mixture of $Ag_2SO_4$ (2.56 g, 8.22 mmol) and $I_2$ (2.088 g, 8.22 mmol) in MeOH (30 mL), a solution of the title compound from Step A (1.88 g, 6.85 mmol) in MeOH (30 mL) was added. The mixture was stirred at 25° C. overnight. The progression of reaction was monitored by crude $^1H$ NMR. Roughly in 24 h, the reaction was over. The mixture was filtered. The solvent was removed. The residue was purified by column chromatography on silica gel Biotage 40M, eluting with EtOAc/hexane (1:9) to give the title compound as a colorless solid. $^1H$ NMR ($CDCl_3$, 500 MHz) δ 7.99 (s, 1H), 7.93 (d, J=7.0 Hz, 1H), 7.68 (d, J=8.5 Hz, 1H), 7.29 (d, J=9 Hz, 1H), 6.70 (d, J=11.5 Hz, 1H), 4.00 (s, 6H), 2.30 (s, 3H).

Step C: Methyl 2'-fluoro-4'-methoxy-2-methyl-5'-(4,4,5,5-tetramethyl-1,3,2-dioxaborolan-2-yl)biphenyl-4-carboxylate A mixture of the title compound from Step B (2.00 g, 5.00 mmol), bis(pinacolato)diboron (1.523 g, 6.00 mmol), $PdCl_2(PPh_3)_2$ (0.702 g, 1.000 mmol) and KOAc (1.030 g, 10.50 mmol) in dioxane (20 mL) was divided into 4 parts. Each part was heated at 140° C. on microwave for 2 h. LC/MS showed no starting material. All parts were combined and the solvent was removed. Water (50 mL) was added and the mixture was extracted with $CH_2Cl_2$ (3×40 mL). The combined layers were washed with brine and dried over $Na_2SO_4$. The solvent was removed and the residue was purified via reverse phase HPLC to give the title compound as a brown solid. $^1H$ NMR ($CDCl_3$, 500 MHz) δ 8.00 (m, 2H), 7.60 (d, J=7.0 Hz, 1H), 7.29 (d, J=9 Hz, 1H), 6.70 (d, J=11.5 Hz, 1H), 4.00 (s, 3H), 3.90 (s, 3H), 2.30 (s, 3H), 1.50 (s, 12H).

INTERMEDIATE 51

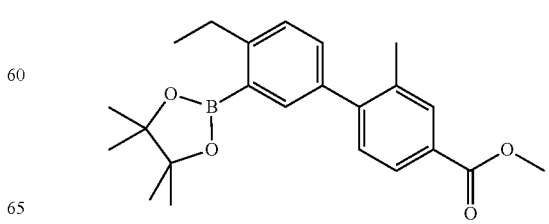

Methyl 4'-ethyl-2-methyl-3'-(4,4,5,5-tetramethyl-1,3, 2-dioxaborolan-2-yl)biphenyl-4-carboxylate Step A: 4-Chloro-1-ethenyl-2-nitrobenzene Bromo-4-chloro-2-nitrobenzene (3 g, 12.69 mmol), potassium vinyltrifluoroborate (2.039 g, 15.23 mmol), [1,1'-bis(diphenylphosphino)ferrocene]dichloropalladium(II) (1.857 g, 2.54 mmol), cesium carbonate (8.27 g, 25.4 mmol) and THF (50 mL) were heated in an 80° C. oil bath overnight. Volatiles were removed under reduced pressure. The pot residue was worked up with brine, extracted with ethyl acetate, dried over $Na_2SO_4$, filtered and evaporated to afford a dark mixture. The resulting crude mixture was purified by flash chromatography ($SiO_2$, Biotage 65i cartridge). The column was eluted by an EtOAc/hexane mixture (0% to 10%). Related fractions were pooled and evaporated to afford a yellow solid as the titled compound. $^1$H-NMR ($CDCl_3$, 600 MHz) δ 7.94 (d, J=2.4 Hz, 1H), 7.60-7.54 (m, 2H), 7.12 (dd, J=17.4, 10.8 Hz, 1H), 5.75 (d, J=16.8 Hz, 1H), 5.52 (d, J=10.8 Hz).

Step B: Methyl 4'-ethenyl-2-methyl-3'-nitrobiphenyl-4-carboxylate

4-Chloro-1-ethenyl-2-nitrobenzene (1.1406 g, 6.21 mmol), methyl 3-methyl-4-(4,4,5,5-tetramethyl-1,3,2-dioxaborolan-2-yl)benzoate (2.059 g, 7.46 mmol), 1,1bis(di-tert-butylphosphino)ferrocene palladium dichloride (0.422 g, 0.621 mmol), cesium carbonate (4.25 g, 13.05 mmol) and THF (30 mL) were heated in an 80° C. oil bath overnight. Volatiles were removed under reduced pressure. The pot residue was taken up by dichloromethane and filtered. The filtrate was concentrated in vacuo to afford a dark solid. The resulting solid was purified by flash chromatography ($SiO_2$, Biotage SNAP cartridge, silica gel, 100 g cartridge). The column was eluted by an EtOAc/hexanes mixture (0% to 40%). Related fractions were pooled and evaporated a light orange solid as the titled compound. LCMS calc.=297.10. found=298.10 $(M+H)^+$.

Step C: Methyl 3'-amino-4'-ethyl-2-methylbiphenyl-4-carboxylate

Methyl 4'-ethenyl-2-methyl-3'-nitrobiphenyl-4-carboxylate (1.6206 g, 5.45 mmol), palladium on carbon (0.290 g, 0.273 mmol) and MeOH (50 mL) were stirred under a balloon atmosphere of $H_2$ at room temperature overnight. The reaction crude was filtered and concentrated in vacuo to afford a light yellow oil. The resulting oil was purified by flash chromatography ($SiO_2$, Biotage SNAP Cartridge, silica gel 100 g cartridge). The column was eluted by an EtOAc/hexanes mixture (0% to 40%). Related fractions were pooled and evaporated to afford a light yellow oil as the titled compound. LCMS calc.=269.14. found=270.30 $(M+H)^+$.

Step D: Methyl 4'-ethyl-3'-iodo-2-methylbiphenyl-4-carboxylate

Methyl 3'-amino-4'-ethyl-2-methylbiphenyl-4-carboxylate (1.1263 g, 4.18 mmol) and iodine (0.258 ml, 5.02 mmol) were mixed in chloroform (40 mL) and immersed in a preheated oil bath (90° C. when immersed). To this hot mixture was added n-amyl nitrite (0.668 ml, 5.02 mmol). The reaction mixture was heated in an 80° C. oil bath for 2 hours then allowed to cool to ambient temperature overnight. The crude was stirred with a $Na_2S_2O_3$ solution. Volatiles were removed under reduced pressure. The pot residue was worked up with brine, extracted with ethyl acetate, dried over $Na_2SO_4$, filtered and evaporated. The resulting mixture was purified by flash chromatography ($SiO_2$, Isolute Flash Si; 100 g). The column was eluted by an EtOAc/hexane mixture (0% to 30%). Related fractions were pooled and evaporated to afford a light yellow solid as the titled compound. LCMS calc.=380.03. found=381.09 $(M+H)^+$.

Step E: Methyl 4'-ethyl-2-methyl-3'-(4,4,5,5-tetramethyl-1,3,2-dioxaborolan-2-yl)biphenyl-4-carboxylate Methyl 4'-ethyl-3'-iodo-2-methylbiphenyl-4-carboxylate (1.11 g, 2.92 mmol), 1,1'-bis(diphenylphosphino)ferrocenepalladium(ii) dichloride dichloromethane complex (0.238 g, 0.292 mmol), bis(pinacolato)diboron (0.890 g, 3.50 mmol), potassium acetate (0.430 g, 4.38 mmol), 1,4-dioxane (3.24 ml) and DMSO (11.35 mL) were sealed in a microwave reaction vessel and subject to microwave irradiation at 140° C. for 20 min. LCMS indicated complete consumption of the starting material and formation of the desired product. The crude was combined with the reaction crude from an identical probe reaction (38.5 mg scale) and purified by flash chromatography ($SiO_2$, Biotage SNAP Cartridge, silica gel, KP-Sil, 100 g cartridge). The column was eluted by an EtOAc/hexane mixture (0% to 10%). Related fractions were pooled and evaporated to afford a light purple gum. This purple gum was further purified by flash chromatography ($SiO_2$, Biotage SNAP Cartridge, silica gel, KP-Sil, 50 g cartridge). The column was eluted by an EtOAc/hexane mixture (0% to 10%). Related fractions were pooled and evaporated to afford a thick clear oil as the titled compound. LCMS calc.=380.22. found=381.28 $(M+H)^+$. $^1$H NMR ($CDCl_3$, 500 MHz) δ 7.93 (s, 1H), 7.87 (dd, J=8.0, 2.0 Hz, 1H), 7.70 (d, J=2.0 Hz, 1H), 7.32-7.30 (m, 1H), 7.30-7.28 (m, 1H), 7.26-7.24 (m, 1H), 3.93 (s, 3H), 2.96 (q, J=7.5 Hz, 2H), 2.31 (s, 3H), 1.34 (s, 12H), 1.25 (t, J=7.5 Hz, 3H).

INTERMEDIATE 52

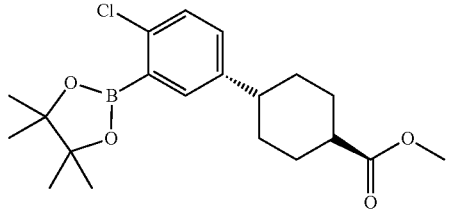

Methyl trans-4-[4-chloro-3-(4,4,5,5-tetramethyl-1,3, 2-dioxaborolan-2-yl)phenyl]cyclohexanecarboxylate Step A: Methyl trans-4-(4-chlorophenyl)cyclohexanecarboxylate Trimethylsilyldiazomethane (15.71 ml, 31.4 mmol) was slowly added into a solution of (e)-4-(4-chlorophenyl)cyclohexanecarboxylic acid (3 g, 12.57 mmol) in MeOH (75 mL) at room temperature. LCMS indicated complete conversion in 1 hr. Added a few drops of TFA to quench the reaction. Volatiles were removed under reduced pressure. The resulting pot residue was purified by flash chromatography ($SiO_2$, Biotage 65i cartridge). The column was eluted by an EtOAc/hexanes mixture (0% to 20%). Related fractions were pooled and evaporated to afford a white solid as the titled compound. LCMS calc.=252.09. found=253.20 (M+H)⁺.

Step B: Methyl trans-4-(4-chloro-3-iodophenyl)cyclohexanecarboxylate

Sulfuric acid (0.708 mL, 13.29 mmol) was added into a cold (ice bath) mixture of methyl trans-4-(4-chlorophenyl)cyclohexanecarboxylate (3.3588 g, 13.29 mmol) and n-iodosuccinimide (2.99 g, 13.29 mmol) in acetic acid (0.798 g, 13.29 mmol). The reaction mixture was stirred in an ice bath and was allowed to warm to ambient temperature overnight. The reaction crude was poured into an ice water and extracted with EtOAc. The separated organic phase was dried over $Na_2SO_4$, filtered and evaporated to afford a dark mixture. The resulting crude mixture was purified by flash chromatography ($SiO_2$, Biotage 65i cartridge). The column was eluted by a EtOAc/hexanes mixture (0% to 10%). Related fractions were pooled and evaporated to afford a crystalline solid as the titled compound. LCMS calc.=377.99. found=379.00 (M+H)⁺.

Step C: Methyl trans-4-[4-chloro-3-(4,4,5,5-tetramethyl-1,3,2-dioxaborolan-2-yl)phenyl]cyclohexanecarboxylate Methyl trans-4-(4-chloro-3-iodophenyl)cyclohexanecarboxylate (488.8 mg, 1.291 mmol), 1,1'-bis(diphenylphosphino)ferrocene-palladium(II)dichloride dichloromethane complex (211 mg, 0.258 mmol), potassium acetate (266 mg, 2.71 mmol), bis(pinacolato)diboron (393 mg, 1.549 mmol) and 1,4-dioxane (1.200 mL) were sealed in a microwave vessel and stirred in an 80° C. oil bath overnight. Volatiles were removed under reduced pressure. The pot residue was worked up with brine, extracted with ethyl acetate, dried over $Na_2SO_4$, filtered and evaporated to afford a dark mixture. The resulting mixture was purified by flash chromatography ($SiO_2$, Biotage SNAP Cartridge, silica gel, KP-Sil, 50 g cartridge). The column was eluted by an EtOAc/hexane mixture (0% to 40%). Related fractions were pooled and evaporated to afford a light green crystalline solid as the titled compound. LCMS calc.=378.18. found=379.20 (M+H)⁺. ¹H NMR (CDCl₃, 500 MHz) δ 7.49 (d, J=2.0 Hz, 1H), 7.28-7.25 (m, 1H), 7.17 (dd, J=8.3, 2.5 Hz, 1H), 3.69 (s, 3H), 2.51 (m 1H), 2.36 (m, 1H), 2.14-2.06 (m, 1H), 1.98-1.92 (m, 1H), 1.64-1.52 (m, 1H), 1.52-1.40 (m, 1H), 1.27 (s, 12H).

INTERMEDIATE 53

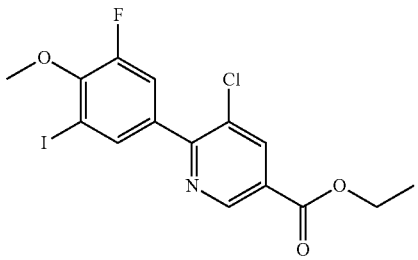

Ethyl 5-chloro-6-(3-fluoro-5-iodo-4-methoxyphenyl)pyridine-3-carboxylate

Step A: Ethyl 5-chloro-6-(3-fluoro-4-methoxyphenyl)pyridine-3-carboxylate

Ethyl 5,6-dichloronicotinate (1 g, 4.54 mmol), 3-fluoro-4-methoxyphenylboronic acid (0.965 g, 5.68 mmol), 1,1'-bis(diphenylphosphino)ferrocene-palladium(II)dichloride dichloromethane complex (0.371 g, 0.454 mmol), cesium carbonate (3.26 g, 10.00 mmol) and THF (30 mL) were refluxed in an 80° C. oil bath under $N_2$ for 2.5 hrs. Volatiles were removed under reduced pressure. The pot residue was worked up with brine, extracted with ethyl acetate, dried over $Na_2SO_4$, filtered and evaporated to afford a dark mixture. The resulting crude mixture was purified by flash chromatography ($SiO_2$, Biotage 65i cartridge). The column was eluted by an EtOAc/hexanes mixture (0% to 40%). Related fractions were pooled and evaporated to afford a white fluffy solid as the titled compound. LCMS calc.=309.06. found=310.01 (M+H)⁺.

Step B: Ethyl 5-chloro-6-(3-fluoro-5-iodo-4-methoxyphenyl)pyridine-3-carboxylate Sulfuric acid (2.5 mL) was added into a cold (ice bath) mixture of ethyl 5-chloro-6-(3-fluoro-4-methoxyphenyl)pyridine-3-carboxylate (500 mg, 1.614 mmol) and 1-iodopyrrolidine-2,5-dione (400 mg, 1.776 mmol) in acetic acid (7.5 mL). The reaction mixture was stirred in an ice bath and warmed up to room temperature in one hour before placed in a 55° C. oil bath overnight. The crude was combined with the crude from an identical probe reaction (33 mg scale). The combined crude was poured into an ice/water mixture and neutralized by $NaHCO_3$. The resulting mixture was extracted with EtOAc. The separated organic phase was dried over $Na_2SO_4$, filtered and evaporated to afford a dark mixture. This dark crude mixture was purified by flash chromatography ($SiO_2$, Biotage SNAP Cartridge, silica gel, KP-Sil, 100 g cartridge). The column was eluted by an EtOAc/hexanes mixture (0% to 30%). Related fractions were pooled and evaporated to afford a white solid as the titled compound. LCMS calc.=434.95. found=435.77 (M+H)⁺. ¹H NMR (CDCl₃, 500 MHz) δ 9.13 (d, J=2.0 Hz, 1H), 8.38 (d, J=1.5 Hz, 1H), 8.02 (s, 1H), 7.60 (dd, J=12.5, 2.0 Hz, 1H), 4.45 (q, J=7.0 Hz, 2H), 4.03 (s, 3H), 1.44 (t, J=7.0 Hz, 3H).

INTERMEDIATE 54

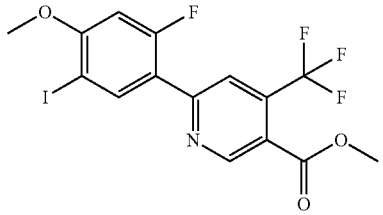

Methyl 6-(2-fluoro-5-iodo-4-methoxyphenyl)-4-(trifluoromethyl)pyridine-3-carboxylate Step A: Methyl 6-(2-fluoro-4-methoxyphenyl)-4-(trifluoromethyl)pyridine-3-carboxylate Methyl 6-chloro-4-(trifluoromethyl)nicotinate (963.6 mg, 4.02 mmol), 2-fluoro-4-methoxybenzeneboronic acid (854 mg, 5.03 mmol), cesium carbonate (2883 mg, 8.85 mmol), $PdCl_2(dppf)\cdot CH_2Cl_2$ adduct (328 mg, 0.402 mmol) and THF (30 mL) were refluxed in a 80° C. oil bath overnight. LCMS trace of the reaction aliquot indicated completion of reaction. The reaction crude was filtered through a bed of Celite® 521. The filtrate was concentrated in vacuo and purified by flash chromatography ($SiO_2$, Biotage SNAP Cartridge, silica gel, KP-Sil, 100 g cartridge). The column was eluted by an EtOAc/hexanes mixture (0% to 20%). Related fractions were pooled and evaporated to afford a colorless oil as the titled compound. LCMS calc.=329.07. found=330.17 (M+H)+.

Step B: Methyl 6-(2-fluoro-5-iodo-4-methoxyphenyl)-4-(trifluoromethylpyridine-3-carboxylate Methyl 6-(2-fluoro-4-methoxyphenyl)-4-(trifluoromethyl)pyridine-3-carboxylate (750 mg, 2.278 mmol), iodine (578 mg, 2.278 mmol), silver sulfate (710 mg, 2.278 mmol) and MeOH (20 mL) were stirred in a 70° C. oil bath and monitored by LCMS. The dark color disappeared and LCMS indicated >50% conversion when reaction time=1 hr. Additional I$_2$ (280 mg, 0.788 mmol) and Ag$_2$SO$_4$ (355 mg, 1.074 mmol) were added and resumed stirring/heating for 30 min. The reaction was cooled and quenched by adding Na$_2$S$_2$O$_3$ (sat.). Volatiles were removed under reduced pressure. The pot residue was worked up with brine, extracted with ethyl acetate, dried over Na$_2$SO$_4$, filtered and evaporated in vacuo. The resulting mixture was purified by flash chromatography (SiO$_2$, Biotage SNAP Cartridge, silica gel, KP-Sil, 100 g cartridge). The column was eluted by an EtOAc/hexanes mixture (0% to 40%). Pure fractions were pooled and evaporated to afford a white solid as the titled compound. LCMS calc.=454.96. found=456.03 (M+H)+. $^1$H NMR (CDCl$_3$, 600 MHz) δ 9.15 (s, 1H), 8.61 (d, J=9.0 Hz, 1H), 8.11 (s, 1H), 6.68 (d, J=11.0, 1H), 4.00 (s, 3H), 3.96 (s, 3H).

Step B: Ethyl 1-(3-iodo-4-methoxyphenyl)-5-(trifluoromethyl)-1H-pyrazole-4-carboxylate Ethyl 1-(4-methoxyphenyl)-5-(trifluoromethyl)-1H-pyrazole-4-carboxylate (1.1499 g, 3.66 mmol), iodine (0.929 g, 3.66 mmol), silver sulfate (1.141 g, 3.66 mmol) and MeOH (30 mL) were stirred at in a 75° C. oil bath. The reaction progress was followed by LCMS. Additional I$_2$/Ag$_2$SO$_4$ (1.5 eq. each) were added. LCMS indicated some unreacted starting material while de-methylation of the methoxy group was observed. Na$_2$S$_2$O$_3$ (sat., aq) was added to quench the reaction. Volatiles were removed under reduced pressure. The pot residue was taken up by EtOAc followed filtration. The separated aqueous phase was back extracted with EtOAc. The combined extracts were dried over Na$_2$SO$_4$, filtered and evaporated in vacuo. The resulting pot residue was purified by preparative HPLC (reverse phase, Kromasil® 100-5C18, 100×21.1 mm) eluting with acetonitrile/water+0.1% TFA (30% to 100% organic in 10 min, then to 100% for 2 min, 20 mL/min). Related fractions were pooled and evaporated under reduced pressure to afford a white solid as a TFA salt of the titled compound. LCMS calc.=439.98. found=441.05 (M+H)+. $^1$H NMR (CDCl$_3$, 500 MHz) δ 8.09 (s, 1H), 7.85 (d, J=2.0 Hz, 1H), 7.37 (dd, J=8.8, 2.0 Hz, 1H), 6.88 (d, J=8.5 Hz, 1H), 4.37 (q, J=7.0 Hz, 2H), 3.95 (s, 3H), 1.38 (t, J=7.0 Hz, 3H).

INTERMEDIATE 55

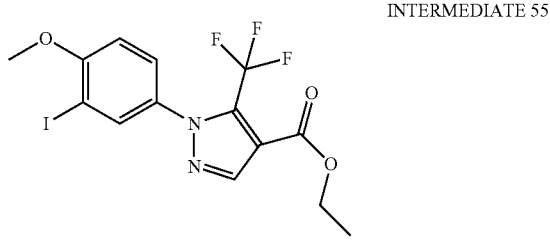 [SMILES: CCOC(=O)c1cnn(-c2ccc(OC)c(I)c2)c1C(F)(F)F]

Ethyl 1-(3-iodo-4-methoxyphenyl)-5-(trifluoromethyl)-1H-pyrazole-4-carboxylate

Step A: Ethyl 1-(4-methoxyphenyl)-5-(trifluoromethyl)-1H-pyrazole-4-carboxylate 4-Methoxy phenylhydrazine (1 g, 7.24 mmol) and ethyl 2-(ethoxymethylene)-4,4,4-trifluoro-3-oxobutyrate (1.408 ml, 7.24 mmol) were stirred in acetonitrile (40 mL) at room temperature. To this mixture was added triethylamine (1.0 mL, 7.24 mmol). LCMS trace of aliquot taken immediately after the addition indicated completion of reaction. The crude mixture was further aged for 1 hr. Volatiles were removed under reduce pressure. The resulting crude mixture was purified by flash chromatography (SiO$_2$, Isolute Flash Si; 100 g). The column was eluted by an EtOAc/hexanes mixture (0% to 20%). Related fractions were pooled and evaporated to afford a yellow oil of 1.4015 g. This oil was further purified by preparative HPLC (reverse phase, Kromasil® 100-5C18, 100×21.1 mm) eluting with acetonitrile/water+0.1% TFA (30% to 100% organic in 10 min, then to 100% for 2 min, 20 mL/min). Related fractions were pooled and evaporated under reduced pressure to afford an oil as a TFA salt of the titled compound.
LCMS calc.=314.09. found=315.22 (M+H)+.

INTERMEDIATE 56

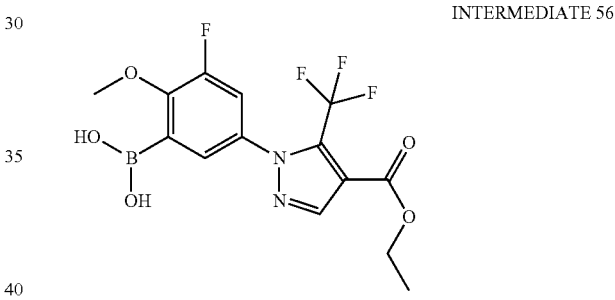

{5-[4-(Ethoxycarbonyl)-5-(trifluoromethyl)-1H-pyrazol-1-yl]-3-fluoro-2-methoxyphenyl}boronic acid

Step A: (3-Fluoro-4-methoxyphenyl)hydrazine hydrochloride

A suspension of 3-fluoro-4-methoxyaniline (1.5871 g, 11.24 mmol) in hydrochloric acid, 37% (14 ml) was diazotized with sodium nitrite (0.776 g, 11.24 mmol) in water (7 mL) and reduced with tin(ii) chloride dihydrate (1.873 mL, 22.49 mmol) in hydrochloric acid, 37% (5 ml) at 0° C. The reaction was then stirred for 20 min at room temperature. The precipitate was collected by filtration. The cake was triturated with ethanol (50 mL, room temp) followed by filtration to give a pale yellow solid as the titled compound. $^1$H NMR (DMSO-d$_6$, 500 MHz) δ 10.17 (br s, 2H), 8.12 (br s, 1H), 7.10 (dd, J=9.0, 9.0 Hz, 1H), 6.96 (dd, J=13.0, 2.5 Hz, 1H), 6.80-6.76 (m, 1H) 3.76 (s, 3H), 3.42 (br s, 1H).

Step B: Ethyl 1-(3-fluoro-4-methoxyphenyl)-5-trifluoromethyl)-1H-pyrazole-4-carboxylate (3-Fluoro-4-methoxyphenyl)hydrazine hydrochloride (1.7346 g, 9.01 mmol) and ethyl 2-(ethoxymethylene)-4,4,4- trifluoro-3-oxobutyrate (1.751 mL, 9.01 mmol) were stirred in acetonitrile (50 mL) at room temperature. To this mixture was added triethylamine (1.255 mL, 9.01 mmol). LCMS trace of reaction aliquot at reaction time 30 min indicated completion of reaction. Volatiles were removed under reduce pressure. The crude mixture was combined with the reaction crude from an identical probe reaction (112 mg scale). Volatiles were removed under reduced pressure. The resulting pot residue was purified by flash chromatography (SiO₂, Biotage 65i cartridge). The column was eluted by an EtOAc/hexanes mixture (0% to 25%). Related fractions were pooled and evaporated to afford a light yellow solid as the titled compound. LCMS calc.=332.08. found=333.22 (M+H)⁺.

Step C: Ethyl 1-(3-fluoro-5-iodo-4-methoxyphenyl)-5-(trifluoromethyl)-1H-pyrazole-4-carboxylate Sulfuric acid (3 mL) was added into a cold (ice bath) mixture of ethyl 1-(3-fluoro-4-methoxyphenyl)-5-(trifluoromethyl)-1H-pyrazole-4-carboxylate (500 mg, 1.505 mmol) and NIS (339 mg, 1.505 mmol) in acetic acid (10 mL). The resulting mixture was stirred in an ice bath and was allowed to warm to ambient temperature overnight. The reaction was then heated in a 55° C. oil bath for 5 hrs. The crude mixture was combined with the reaction crude from an identical probe reaction (32 mg scale). The combined crude was poured into an ice/water mixture and extracted with EtOAc. The separated organic phase was dried over Na₂SO₄, filtered and evaporated to afford a dark mixture. This dark mixture was purified by flash chromatography (SiO₂, Biotage SNAP Cartridge, silica gel, KP-Sil, 100 g cartridge). The column was eluted by an EtOAc/hexanes mixture (0% to 30%). Related fractions were pooled and evaporated to afford a colorless oil as the titled compound. LCMS calc.=457.98. found=459.06 (M+H)⁺.

Step D: {5-[4-(Ethoxycarbonyl)-5-(trifluoromethyl)-1H-pyrazol-1-yl]-3-fluoro-2-methoxyphenyl}boronic acid Ethyl 1-(3-fluoro-5-iodo-4-methoxyphenyl)-5-(trifluoromethyl)-1h-pyrazole-4-carboxylate (340 mg, 0.742 mmol), bis(hexyleneglycolato)diboron (283 mg, 1.113 mmol), tricyclohexylphosphine (62.4 mg, 0.223 mmol), potassium acetate (182 mg, 1.855 mmol), 1,1'-bis(diphenylphosphino)ferrocene-palladium(II)dichloride dichloromethane complex (121 mg, 0.148 mmol) and 1,4-dioxane (10 mL) were sealed in a microwave vessel and subject to microwave irradiation at 140° C. for a total of 2 hrs (1+1). The crude mixture was combined with the reaction crude from an identical probe reaction (32 mg scale). Volatiles were removed under reduced pressure. The resulting crude mixture was purified by flash chromatography (SiO₂, Biotage SNAP Cartridge, silica gel, KP-Sil, 100 g cartridge). The column was eluted by an EtOAc/hexanes mixture (0% to 40%). Related fractions were pooled and evaporated to afford a brown oil as a mixture of the titled compound and the de-iodinated reduced by-product (step B). LCMS calc.=376.09. found=377.18 (M+H)⁺.

INTERMEDIATE 57

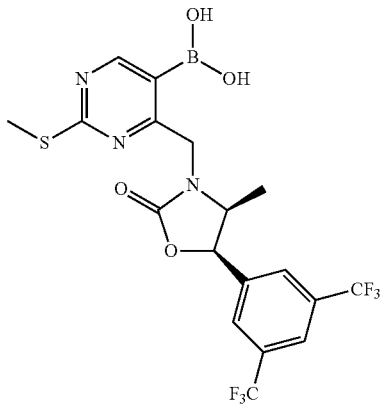

[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]boronic acid (4S,5R)-5-[3,5-bis(trifluoromethyl)phenyl]-3-{[5-bromo-2-(methylsulfanyl)pyrimidin-4-yl]methyl}-4-methyl-1,3-oxazolidin-2-one (400 mg, 0.754 mmol), bis(hexyleneglycolato)diboron (249 mg, 0.981 mmol), tricyclohexylphosphine (85 mg, 0.302 mmol), potassium acetate (163 mg, 1.659 mmol), 1,1bis(di-tert-butylphosphino)ferrocene palladium dichloride (51.3 mg, 0.075 mmol) and THF (10 mL) were sealed in a microwave vessel and subject to microwave irradiation at 140° C. for 60 min. LCMS indicated complete consumption of starting material and formation of the desired product. The resulting crude mixture was purified by flash chromatography (SiO₂, Biotage SNAP Cartridge, silica gel, KP-Sil, 50 g cartridge). The column was eluted by an EtOAc/hexanes mixture (0% to 40%). Related fractions were evaporated into a brown solid foam as the titled compound. LCMS calc.=495.09. found=495.91 (M+H)⁺.

INTERMEDIATE 58

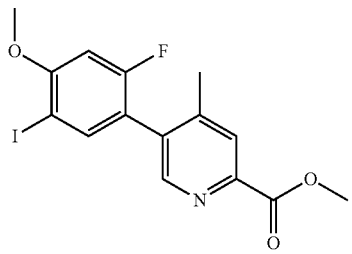

Methyl 5-(2-fluoro-5-iodo-4-methoxyphenyl)-4-methylpyridine-2-carboxylate

Step A: Methyl 5-(2-fluoro-4-methoxyphenyl)-4-methylpyridine-2-carboxylate (2-Fluoro-4-methoxyphenyl)boronic acid (177 mg, 1.043 mmol), methyl 5-bromo-4-methylpyridine-2-carboxylate (200 mg, 0.869 mmol), 1,1bis(di-tert-butylphosphino)ferrocene palladium dichloride (89 mg, 0.130 mmol), cesium carbonate (623 mg, 1.913 mmol) and THF (5 mL) were sealed in a microwave vessel and subject to microwave irradiation at 140° C. for 20 min. The reaction crude was combined with the crude from an identical probe reaction (44.3 mg scale). Volatiles were removed under reduced pressure. The resulting pot residue was purified by preparative HPLC (reverse phase, Kromasil® 100-5C18, 100×21.1 mm) eluting with acetonitrile/water+0.1% TFA (30% to 100% organic in 10 min, then to 100% for 2 min, 20 mL/min). Related fractions were pooled and evaporated under reduced pressure to afford a dark solid. This solid was further purified by flash chromatography (SiO$_2$, Biotage SNAP Cartridge, silica gel, KP-Sil, 50 g cartridge). The column was eluted with an EtOAc/hexanes mixture (0% to 100%). Related fractions were pooled and evaporated to afford a light yellow oil as the titled compound. LCMS calc.=275.10. found=276.11 (M+H)$^+$.

Step B: Methyl 5-(2-fluoro-5-iodo-4-methoxyphenyl-4-methylpyridine-2-carboxylate Methyl 5-(2-fluoro-4-methoxyphenyl)-4-methylpyridine-2-carboxylate (190 mg, 0.690 mmol), silver sulfate (430 mg, 1.380 mmol), iodine (0.071 ml, 1.380 mmol) and MeOH (10 mL) were stirred at room temperature overnight. The crude mixture was filtered. The filtrate was concentrated in vacuo. The resulting pot residue was purified by flash chromatography (SiO$_2$, Biotage SNAP Cartridge, silica gel, KP-Sil, 50 g cartridge). The column was eluted by an EtOAc/hexane mixture (0% to 40%). Related fractions were pooled and evaporated to afford a colorless oil as the titled compound. LCMS calc.=400.99. found=402.08 (M+H)$^+$.

INTERMEDIATE 59

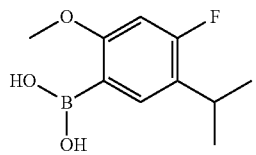

(4-fluoro-5-isopropyl-2-methoxyphenyl)boronic acid

INTERMEDIATE 59 was previously disclosed as INTERMEDIATE 2 in WO2007081569, and was synthesized by the method disclosed in WO2007081569.

INTERMEDIATE 60

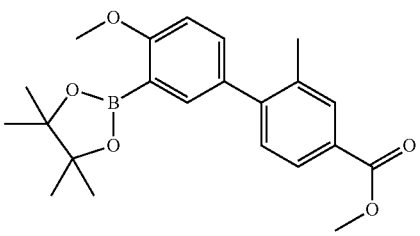

methyl 4'-methoxy-2-methyl-3'-(4,4,5,5-tetramethyl-1,3,2-dioxaborolan-2-yl)biphenyl-4-carboxylate Methyl 3'-iodo-4'-methoxy-2-methylbiphenyl-4-carboxylate (500 mg, 1.308 mmol), bis(pinacolato)diboron (353 mg, 1.57 mmol), 1,1'-bis(diphenylphosphino)ferrocene-palladium dichloride dichloromethane adduct (214 mg, 0.262 mmol), potassium acetate (257 mg, 2.616 mmol) and 1,4-dioxane (2.5 mL) were sealed in a microwave vessel. The reaction mixture was irradiated by microwave at 140° C. for 20 minutes, then at 130° C. for 30 minutes. The reaction crude was treated with brine followed by ethyl acetate extractions. The combined extracts were dried over Na$_2$SO$_4$ followed by filtration and concentration in vacuo to afford a dark oil as the crude mixture of methyl 4'-methoxy-2-methyl-3'-(4,4,5,5-tetramethyl-1,3,2-dioxaborolan-2-yl)biphenyl-4-carboxylate, which was used without further purification for the next coupling step. LCMS calc.=382.20. found=383.41 (M+1)$^+$.

The following intermediates (Table 8) were synthesized using commercially available materials by methods analogous to those described for INTERMEDIATE 1 of WO2007081569.

TABLE 8

| Intermediate | Molecular structure | LCMS (M + H)$^+$ |
|---|---|---|
| 61 | 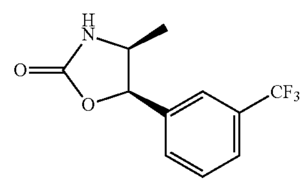 [SMILES: C[C@@H]1NC(=O)O[C@@H]1c1cccc(C(F)(F)F)c1] | 246.3 |
| 62 | 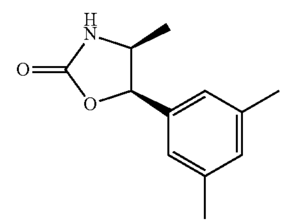 | 206.3 |
| 63 | 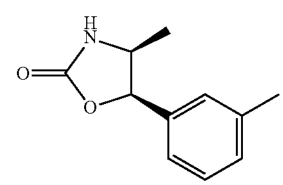 | 192.3 |
| 64 | 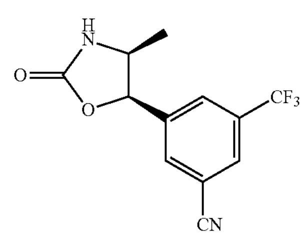 [SMILES: C[C@@H]1NC(=O)O[C@@H]1c1cc(C#N)cc(C(F)(F)F)c1] | 271.0 |
| 65 | 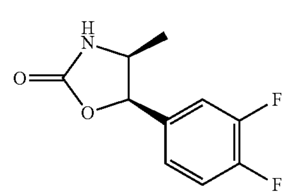 | 214.3 |

TABLE 8-continued

| Intermediate | Molecular structure | LCMS (M + H)+ |
|---|---|---|
| 66 | 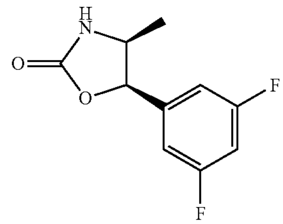 | 214.3 |
| 67 | 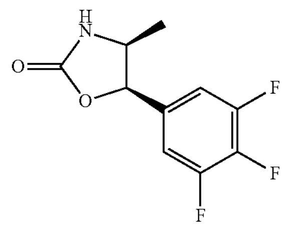 [SMILES: C[C@@H]1NC(=O)O[C@@H]1c1cc(F)c(F)c(F)c1] | 232.3 |
| 67(a) | 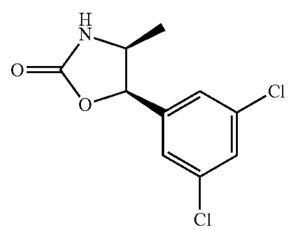 | 246.1 |
| 67(b) | 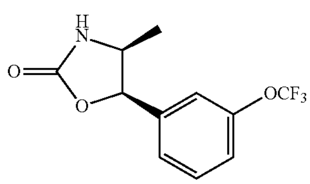 [SMILES: C[C@@H]1NC(=O)O[C@@H]1c1cccc(OC(F)(F)F)c1] | 262.1 |
| 67(c) | 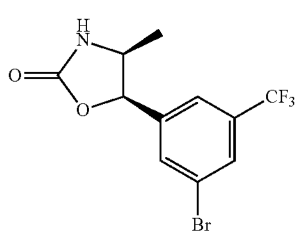 [SMILES: C[C@@H]1NC(=O)O[C@@H]1c1cc(Br)cc(C(F)(F)F)c1] | 324.2, 326.2 |

The following intermediates (Table 9) were synthesized using methods analogous to those described for INTERMEDIATE 35 from commercially available materials or intermediates whose syntheses are described above.

TABLE 9

| Intermediate | Molecular structure | LCMS (M + H)+ |
|---|---|---|
| 68 | 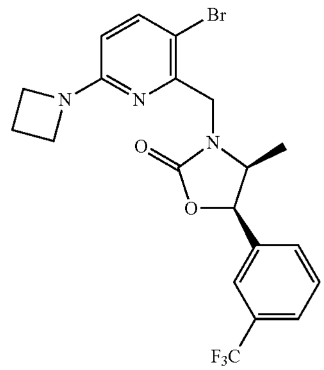 [SMILES: C[C@H]1[C@@H](c2cccc(C(F)(F)F)c2)OC(=O)N1Cc1nc(N2CCC2)ccc1Br] | 470.0, 472.0 |
| 69 | 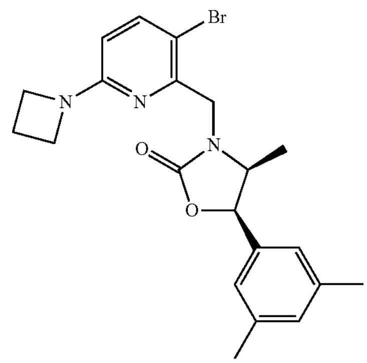 [SMILES: Cc1cc(C)cc([C@H]2OC(=O)N(Cc3nc(N4CCC4)ccc3Br)[C@H]2C)c1] | 430.1, 432.1 |
| 70 | 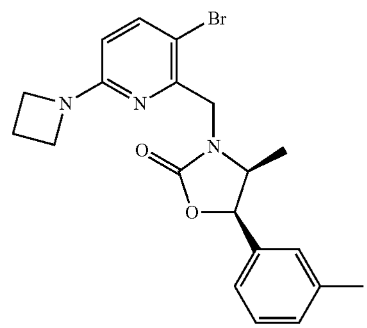 [SMILES: Cc1cccc([C@H]2OC(=O)N(Cc3nc(N4CCC4)ccc3Br)[C@H]2C)c1] | 416.1, 418.1 |
| 71 | 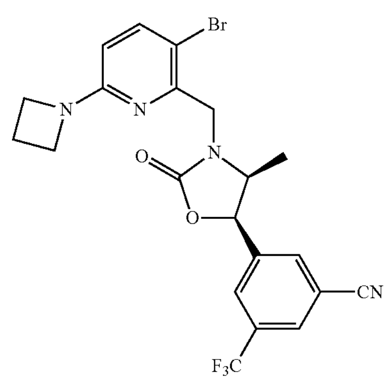 [SMILES: C[C@H]1[C@@H](c2cc(C#N)cc(C(F)(F)F)c2)OC(=O)N1Cc1nc(N2CCC2)ccc1Br] | 495.0, 497.0 |

TABLE 9-continued

| Intermediate | Molecular structure | LCMS (M + H)+ |
|---|---|---|
| 72 | 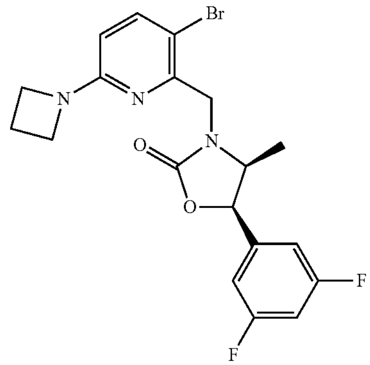 [SMILES: C[C@H]1[C@@H](c2cc(F)cc(F)c2)OC(=O)N1Cc1nc(N2CCC2)ccc1Br] | 439.8 (M + 3) |
| 73 | 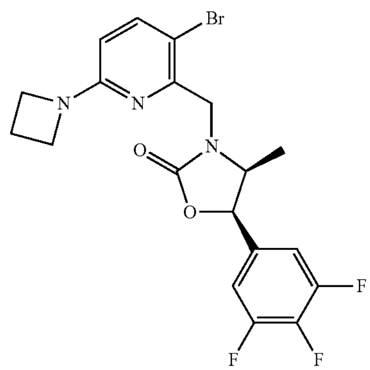 [SMILES: C[C@H]1[C@@H](c2cc(F)c(F)c(F)c2)OC(=O)N1Cc1nc(N2CCC2)ccc1Br] | 455.8, 457.8 |
| 73(a) | 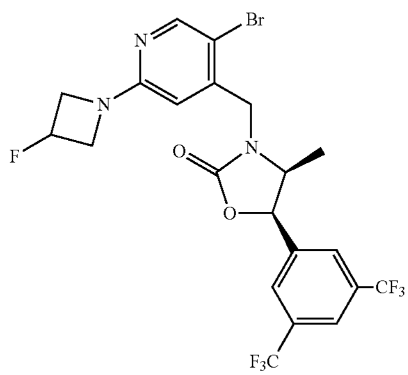 [SMILES: C[C@H]1[C@@H](c2cc(C(F)(F)F)cc(C(F)(F)F)c2)OC(=O)N1Cc1cc(N2CC(F)C2)ncc1Br] | 556.2, 558.2 |

INTERMEDIATE 74

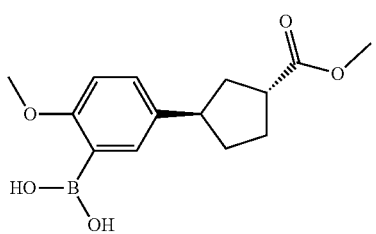

{2-methoxy-5-[trans-3-(methoxycarbonyl)cyclopentyl]phenyl}boronic acid

Step A: 2-iodo-4-(4-methoxyphenyl)cyclohexanone

To a solution of 4-(4-methoxyphenyl)cyclohexanone (INTERMEDIATE 7, Step A) (219.6 mg, 1.075 mmol) in DCM (5 ml), under nitrogen at 0° C., was added hexamethyldisilazane (0.272 ml, 1.290 mmol) followed by dropwise addition of iodotrimethylsilane (0.161 ml, 1.183 mmol). A solution of sodium iodide (161 mg, 1.075 mmol) in THF (3.3 ml) was then added, followed by addition of a cloudy mixture of m-CPBA (318 mg, 1.290 mmol) in DCM (3 ml). At 10 minutes, added ethyl acetate and washed with 1M aqueous hydrochloric acid (added brine to help break emulsion). The aqueous layer was extracted with EtOAc and the combined organics were washed with saturated aqueous sodium thiosulfate, followed by saturated aqueous sodium bicarbonate, and brine. The organic layer was dried over sodium sulfate, filtered, and the solvent was evaporated under reduced pressure. The residue was purified by flash column chromatography on silica gel, eluting with EtOAc in hexanes to afford each diastereomer of the titled compound. Either one can be used on Step B. $^1$H NMR (500 MHz, CDCl$_3$) (trans): δ 7.19-7.14 (m, 2H); 6.90-6.85 (m, 2H); 4.73-4.71 (m, 1H); 3.80 (s, 3H); 3.54 (td, J=14.6, 6.2 Hz, 1H); 3.46-3.40 (m, 1H); 2.42-2.37 (m, 1H); 2.30-2.25 (m, 1H); 2.23-2.09 (m, 2H); 1.93 (qd, J=13.3, 4.2 Hz, 1H). $^1$H NMR (500 MHz, CDCl$_3$) (cis): δ 7.16-7.11 (m, 2H); 6.88-6.83 (m, 2H); 5.05 (dd, J=13.5, 5.9 Hz, 1H); 3.78 (s, 3H); 3.12-3.08 (m, 1H); 2.88-2.77 (m, 2H); 2.68 (dd, J=14.1, 6.1 Hz, 1H); 2.48 (q, J=12.9 Hz, 1H); 2.29-2.25 (m, 1H); 1.98 (dd, J=13.2, 4.4 Hz, 1H).

Step B: methyl trans-3-(4-methoxyphenyl)cyclopentanecarboxylate

To a 0° C. solution of 2-iodo-4-(4-methoxyphenyl)cyclohexanone (Step A) (363 mg, 1.099 mmol) in diethyl ether (3 ml), under nitrogen, was added sodium methoxide (77 mg, 1.429 mmol) and the resulting mixture was stirred at RT for 30 minutes. Water was added and extracted 2 times with ethyl acetate. The combined organic layers were washed with brine, dried over sodium sulfate, filtered, and the solvent was evaporated under reduced pressure. The residue was purified by flash column chromatography on silica gel, eluting with EtOAc in hexanes to afford the titled compound. $^1$H NMR (500 MHz, CDCl$_3$): δ 7.15 (d, J=8.6 Hz, 1H); 6.84 (d, J=8.6 Hz, 1H); 3.79 (s, 3H); 3.70 (s, 3H); 3.17 (p, J=8.6 Hz, 1H); 3.06-2.91 (m, 1H); 2.34 (ddd, J=13.2, 8.1, 4.7 Hz, 1H); 2.19-2.06 (m, 2H); 2.03-1.80 (m, 2H); 1.70-1.58 (m, 1H).

Step C: methyl trans-3-(3-iodo-4-methoxyphenyl)cyclopentanecarboxylate

To a solution of methyl trans-3-(4-methoxyphenyl)cyclopentanecarboxylate (Step B) 60 mg, 0.256 mmol) in MeOH (2 ml), under nitrogen at RT, was added silver sulfate (80 mg, 0.256 mmol) followed by iodine (65.0 mg, 0.256 mmol). The resulting mixture was stirred at room temperature for 1 hour, then, filtered solids washing with MeOH and concentrated filtrate. The residue was purified by flash column chromatography on silica gel, eluting with EtOAc in hexanes to afford the titled compound. $^1$H NMR (500 MHz, CDCl$_3$): δ 7.63 (d, J=2.2 Hz, 1H); 7.15 (dd, J=8.4, 2.2 Hz, 1H); 6.75 (d, J=8.4 Hz, 1H); 3.85 (s, 3H); 3.70 (s, 3H); 3.12 (m, 1H); 3.00 (m, 1H);

2.33 (ddd, J=13.2, 8.0, 4.6 Hz, 1H); 2.17-2.10 (m, 2H); 1.94 (m, 1H); 1.83 (m, 1H); 1.61 (m, 1H).

Step D: {2-methoxy-5-[trans-3-(methoxycarbonyl)cyclopentyl]phenyl}boronic acid

A mixture of methyl trans-3-(3-iodo-4-methoxyphenyl)cyclopentanecarboxylate (Step C) (64 mg, 0.178 mmol), bis(neopentyl glycolato)diboron (48.2 mg, 0.213 mmol), potassium acetate (100 mg, 1.019 mmol), and 1,1'-bis(diphenylphosphino)ferrocene-palladium(II)dichloride dichloromethane complex (10 mg, 0.012 mmol) in DMSO (3 ml) was degassed flushing with nitrogen and heated at 80° C. for 1 hour. Then, added ethyl acetate and washed with water followed by brine, dried over sodium sulfate, filtered, and the solvent was evaporated under reduced pressure. The residue was purified by flash column chromatography on silica gel, eluting with EtOAc in hexanes to afford the titled compound. $^1$H NMR (500 MHz, CDCl$_3$): δ 7.71 (d, J=2.5 Hz, 1H); 7.29 (m, 1H); 6.85 (m, 1H); 6.10 (s, 2H); 3.90 (s, 3H); 3.70 (s, 3H); 3.19 (m, 1H); 3.02 (m, 1H); 2.35 (ddd, J=13.3, 8.0, 4.6 Hz, 1H); 2.19-2.11 (m, 2H); 2.01-1.85 (m, 2H); 1.72-1.63 (m, 1H).

INTERMEDIATE 75

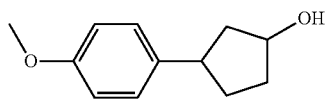

3-(4-methoxyphenyl)cyclopentanol

Step A: 3-(4-methoxyphenyl)cyclopent-2-en-1-one

To a 0° C. solution of 4-methoxyphenylmagnesium bromide (1M in THF) (30 ml, 30.0 mmol) was added dropwise 3-ethoxycyclopent-2-en-1-one (3.56 ml, 30.0 mmol). The reaction mixture was stirred at RT overnight. 1M aqueous hydrochloric acid and EtOAc were added. There was emulsion. The biphasic mixture was filtered through a Celite® pad. Extracted filtrate three times with EtOAc. The combined organics were washed with brine, dried over sodium sulfate, filtered, and the solvent was evaporated under reduced pressure. The Celite®/filtered solids were stirred in EtOAc/combined aqueous layers. The solids were filtered, separated filtrate layers, and extracted aqueous once more with EtOAc. The combined organics were washed with brine, dried over sodium sulfate, filtered, and the solvent was evaporated under reduced pressure. The two crude product batches were combined and purified by flash column chromatography on silica gel, eluting with EtOAc in hexanes to afford the title compound. Mass spectrum (ESI) 189.3 (M+1).

Step B: 3-(4-methoxyphenyl)cyclopentanone

To a RT solution of 3-(4-methoxyphenyl)cyclopent-2-en-1-one (Step A) (4.68 g, 24.86 mmol) in EtOAc (100 ml) was added Pd/C (Degussa E101 NE/W, 10% dry weight, 50% water) (2.65 g, 1.243 mmol). The reaction mixture was degassed and flushed with nitrogen, then, degassed and flushed with hydrogen using a balloon. After 2 hours filtered reaction mixture through a pad of Celite® washing with EtOAc. The filtrate was and purified by flash column chromatography on silica gel, eluting EtOAc in hexanes to afford the title compound as a racemic mixture. $^1$H NMR (500 MHz, CDCl$_3$): δ 7.18 (d, J=8.5 Hz, 1H); 6.88 (d, J=8.6 Hz, 1H); 3.80 (s, 3H); 3.42-3.32 (m, 1H); 2.65 (dd, J=18.1, 7.4 Hz, 1H); 2.48-2.36 (m, 2H); 2.34-2.23 (m, 2H); 2.00-1.90 (m, 1H).

Step C: 3-(4-methoxyphenyl)cyclopentanol

To a RT solution of 3-(4-methoxyphenyl)cyclopentanone (Step B) (482.5 mg, 2.54 mmol) in MeOH (5 ml) was added sodium borohydride (96 mg, 2.54 mmol). The reaction mixture was stirred under nitrogen for 30 minutes, then, concentrated, added water and extracted with ethyl acetate. The organic layer was washed with brine, dried over sodium sulfate, filtered, and the solvent was evaporated under reduced pressure to afford the title compound as a mixture of diastereomers that was used without further purification. Mass spectrum (ESI) 175.3 (M+1 minus 18).

INTERMEDIATE 76

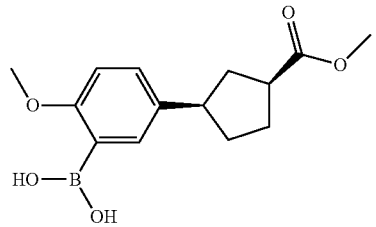

{2-methoxy-5-[cis-3-(methoxycarbonyl)cyclopentyl]phenyl}boronic acid

The title compound was synthesized from 3-(4-methoxyphenyl)cyclopentanone (INTERMEDIATE 75, Step B) and commercially available starting materials using an analogous method to that described for INTERMEDIATE 7. Bis(neopentyl glycolato)diboron was used instead of BISPIN to afford a mixture of the titled compound and methyl (1S,3R)-3-[3-(5,5-dimethyl-1,3,2-dioxaborinan-2-yl)-4-methoxyphenyl]cyclopentanecarboxylate. The mixture was used without further purification.

INTERMEDIATES 77 and 78

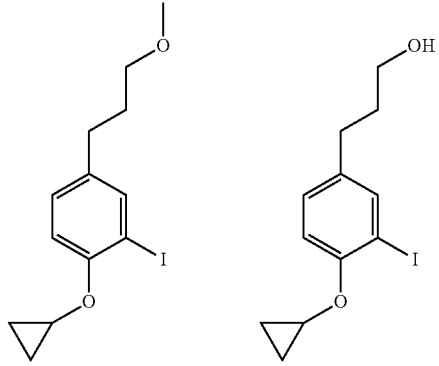

1-(cyclopropyloxy)-2-iodo-4-(3-methoxypropyl)benzene (INTERMEDIATE 77) and 3-[4-cyclopropyloxy)-3-iodophenyl]propan-1-ol (INTERMEDIATE 78)

Step A: 4-(3-hydroxypropyl)-2-iodophenol

To a solution of 4-(3-hydroxypropyl)phenol (2.00 g, 13.14 mmol) in MeOH (10 ml) under nitrogen at RT was added silver sulfate (4.10 g, 13.14 mmol) followed by iodine (3.34 g, 13.14 mmol). The resulting mixture was stirred at room temperature for 30 minutes, then, the solids were filtered washing with MeOH. The filtrate was concentrated and purified by flash column chromatography on silica gel, eluting with EtOAc in hexanes to afford the title compound. $^1$H NMR (500 MHz, CD$_3$OD): δ 7.51 (d, J=2.1 Hz, 1H); 7.02-6.97 (m, 1H); 6.73 (d, J=8.2 Hz, 1H); 3.53 (t, J=6.5 Hz, 2H); 2.59-2.51 (m, 2H); 1.80-1.71 (m, 2H).

Step B:
3-[4-(2-chloroethoxy)-3-iodophenyl]propan-1-ol

A mixture of 4-(3-hydroxypropyl)-2-iodophenol (Step A) (2.94 g, 10.57 mmol), 2-chloroethyl p-toluenesulfonate (2.88 ml, 15.86 mmol), and potassium carbonate (3.65 g, 26.4 mmol) in DMF (11 ml) was heated at 50° C. under nitrogen overnight. EtOAc was added and the mixture was washed 2 times with water, followed by brine. The organic layer was dried over sodium sulfate, filtered, and the solvent was evaporated under reduced pressure. The residue was purified by flash column chromatography on silica gel, eluting with EtOAc in hexanes to afford the title compound. $^1$H NMR (500 MHz, CD$_3$OD): δ 7.62 (d, J=2.1 Hz, 1H); 7.18-7.13 (m, 1H); 6.85 (d, J=8.3 Hz, 1H); 4.24 (t, J=5.5 Hz, 2H); 3.86 (t, J=5.5 Hz, 2H); 3.54 (t, J=6.4 Hz, 2H); 2.59 (t, J=7.7 Hz, 2H); 1.77 (p, J=7.2 Hz, 2H).

Step C: 3-[3-iodo-4-(vinyloxy)phenyl]propan-1-ol

To a 0° C. solution of 3-[4-(2-chloroethoxy)-3-iodophenyl]propan-1-ol (Step B) (1.00 g, 2.94 mmol) in THF (10 ml) was added potassium tert-butoxide (1M in THF) (6.61 ml, 6.61 mmol). The resulting solution was warmed to RT (turned cloudy) and stirred under nitrogen for 3 hours. Dilute HCl was added to the mixture and extracted 2 times with ethyl acetate. The combined organics were washed with brine and the solvent was evaporated under reduced pressure. The residue was purified by flash column chromatography on silica gel, eluting with EtOAc in hexanes to afford the title compound. $^1$H NMR (500 MHz, CD$_3$OD): δ 7.66 (s, 1H); 7.23-7.13 (m, 1H); 6.96-6.88 (m, 1H); 6.66 (ddd, J=28.0, 13.7, 6.2 Hz, 1H); 4.64-4.60 (m, 1H); 4.43 (dd, J=6.1, 1.6 Hz, 1H); 3.54 (t, J=6.4 2H); 2.62 (t, J=7.6 Hz, 3H); 1.81-1.74 (m, 3H).

Step D: 1-(cyclopropyloxy)-2-iodo-4-(3-methoxypropylbenzene (INTERMEDIATE 77) and 3-[4-(cyclopropyloxy)-3-iodophenyl]propan-1-ol (INTERMEDIATE 78)

To a 0° C. solution of 3-[3-iodo-4-(vinyloxy)phenyl]propan-1-ol (Step C) (786 mg, 2.58 mmol) in chloroiodomethane (0.600 ml, 8.27 mmol) and 1,2-dichloroethane (5 ml) was added slowly diethylzinc (0.424 ml, 4.14 mmol). The reaction was stirred at RT for 1 hour, then, added saturated aqueous ammonium chloride and tried to extract with dichloromethane. The organic layer was not clear. Separated layers and concentrated the organic layer. It was then combined with the aqueous layer from above and extracted three times with EtOAc. The combined organics were dried over sodium sulfate, filtered, and the solvent was evaporated under reduced pressure.
The residue was purified by flash column chromatography on silica gel, eluting with EtOAc in hexanes to afford the title compounds. INTERMEDIATE 77: $^1$H NMR (500 MHz, CD$_3$OD): δ 7.55 (s, 1H); 7.14 (s, 2H); 3.81 (m, 1H); 3.36 (t, J=6.4 Hz, 2H); 3.31 (s, 3H); 2.56 (t, J=7.7 Hz, 2H); 1.80 (m, 2H); 0.78 (m, 2H); 0.71 (m, 2H). INTERMEDIATE 78: $^1$H NMR (500 MHz, CD$_3$OD): δ 7.57 (s, 1H); 7.14 (m, 2H); 3.81 (m, 1H); 3.54 (t, J=6.4 Hz, 2H); 2.58 (t, J=7.8 Hz, 2H); 1.77 (m, 2H); 0.78 (m, 2H); 0.71 (m, 2H).

INTERMEDIATE 79

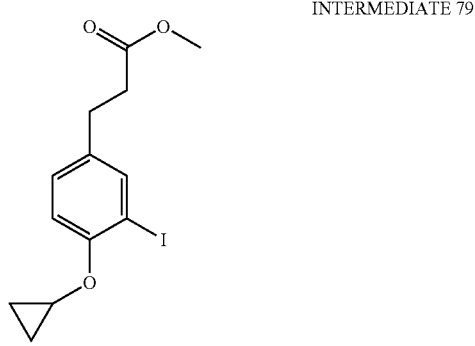 [SMILES: COC(=O)CCc1ccc(OC2CC2)c(I)c1]

methyl 3-[4-(cyclopropyloxy)-3-iodophenyl]propanoate

The title compound was synthesized from methyl 3-(4-hydroxyphenyl)propanoate using an analogous method to that described for INTERMEDIATE 78. $^1$H NMR (500 MHz, CDCl$_3$): δ 7.58 (s, 1H); 7.13 (d, J=8.5 Hz, 1H); 7.08 (d, J=8.4 Hz, 1H); 3.77 (m, 1H); 3.67 (s, 3H); 2.85 (t, J=7.8 Hz, 2H); 2.59 (t, J=7.8 Hz, 2H); 0.84-0.78 (m, 4H).

INTERMEDIATE 80

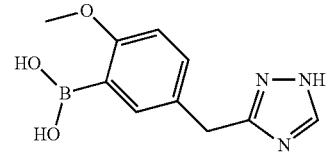

[2-methoxy-5-(1H-1,2,4-triazol-3-ylmethyl)phenyl]boronic acid

Step A: 3-(4-methoxybenzyl)-1H-1,2,4-triazole

A mixture of 2-(4-methoxyphenyl)acetamide (1.51 g, 9.14 mmol) and N,N-dimethylformamide dimethyl acetal (6 ml, 45.0 mmol) in a r.b.f, equipped with a Dean-Stark trap was placed in a 120° C. bath (turned to solution once heated) for 1.5 hours. The reaction was cooled and concentrated, then, added AcOH (18 ml), hydrazine hydrate (0.611 ml, 10.06 mmol), and heated at 90° C. for 1.5 hours. After cooling to RT, added 2M aqueous sodium hydroxide and extracted 3 times with ethyl acetate. The combined organics were washed with brine, dried over sodium sulfate, filtered, and the solvent was evaporated under reduced pressure. The residue was purified by flash column chromatography on silica gel, eluting with MeOH in DCM to afford the title compound. Mass spectrum (ESI) 190.3 (M+1).

Step B:
3-(3-iodo-4-methoxybenzyl)-1H-1,2,4-triazole

To a solution of 3-(4-methoxybenzyl)-1H-1,2,4-triazole (335 mg, 1.770 mmol) in MeOH (5 ml) under nitrogen at RT was added silver sulfate (552 mg, 1.770 mmol) followed by iodine (449 mg, 1.770 mmol). Added a second equivalent of silver sulfate and stirred for 3 days. The reaction did not go to completion. The solids were filtered washing with MeOH, the filtrate was concentrated, and the residue was purified by flash column chromatography on silica gel, eluting with MeOH in DCM to afford the title compound contaminated with ca. 20% of starting material. Mass spectrum (ESI) 316.1 (M+1).

Step C: [2-methoxy-5-(1H-1,2,4-triazol-3-ylmethyl) phenyl]boronic acid

A mixture of 3-(3-iodo-4-methoxybenzyl)-1H-1,2,4-triazole (Step B) (397 mg, 1.260 mmol), bis(neopentyl glycolato) diboron (342 mg, 1.512 mmol), potassium acetate (495 mg, 5.04 mmol), and 1,1'-bis(diphenylphosphino)ferrocene-palladium(II)dichloride dichloromethane complex (51.4 mg, 0.063 mmol) in DMSO (10 ml) was degassed flushing with nitrogen and heated at 80° C. overnight. The reaction was diluted with ethyl acetate and washed with water followed by brine, dried over sodium sulfate, filtered, and the solvent was evaporated under reduced pressure to afford the crude title product that was used without further purification. Mass spectrum (ESI) 234.3 (M+1).

The following intermediates (Table 10) were synthesized using methods analogous to those described for INTERMEDIATE 74, Steps C and D, or INTERMEDIATE 2, from commercially available materials or intermediates whose syntheses are described above. When bis(neopentyl glycolato)diboron was used, the product was a mixture of the borate noted below and the corresponding boronic acid.

TABLE 10

| Intermediate | Molecular structure |
|---|---|
| 81 | |
| 82 | |
| 83 | 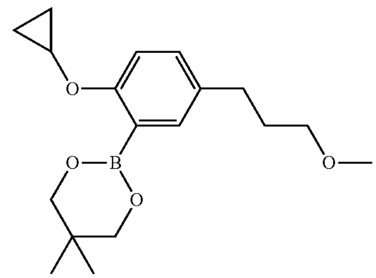 [SMILES: COCCCc1ccc(OC2CC2)c(B2OCC(C)(C)CO2)c1] |
| 84 | 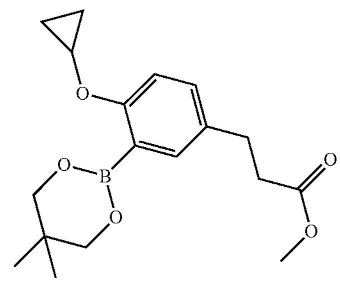 [SMILES: COC(=O)CCc1ccc(OC2CC2)c(B2OCC(C)(C)CO2)c1] |
| 85 | 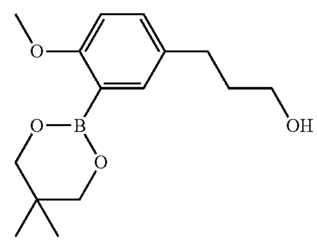 [SMILES: COc1ccc(CCCO)cc1B1OCC(C)(C)CO1] |
| 86 | 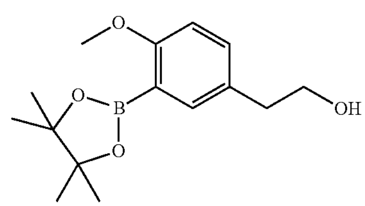 [SMILES: COc1ccc(CCO)cc1B1OC(C)(C)C(C)(C)O1] |

INTERMEDIATE 87 methyl 3-[4-chloro-3-(4,4,5,5-tetramethyl-1,3,2-dioxaborolan-2-yl)phenyl]propanoate Step A: methyl 3-(4-chlorophenyl)propanoate To a solution of 3-(4-chlorophenyl)propionic acid (2.45 g, 13.27 mmol) in toluene (65 mL) and methanol (10 mL) was added trimethylsilyldiazomethane (2M solution in hexane, 7.63 mL, 15.26 mmol). The mixture was allowed to stir for 1 hour and gas evolution was observed initially. After 1 hour, the mixture became homogeneous and was quenched via addition of 3.5 mL of acetic acid. The mixture was concentrated in vacuo, and purified via column chromatography on a Biotage 65i column eluting with 0% ethyl acetate in hexanes (1 CV) followed by a gradient to 50% ethyl acetate in hexanes (over 7 CV) to furnish the desired product. $^1$H NMR (CDCl$_3$, 500 MHz) δ 7.25 (d, J=8.2 Hz, 2H), 7.13 (d, J=8.3 Hz, 2H), 3.67 (s, 3H), 2.92 (t, J=7.7 Hz, 2H), 2.61 (t, J=7.7 Hz, 2H).

Step B: methyl 3-(4-chloro-3-iodophenyl)propanoate

Sodium metaperiodate (0.240 g, 1.121 mmol) was slowly added to a solution of iodine (0.846 g, 3.33 mmol) in sulfuric acid (21.1 ml). This was stirred at room temperature for 30 minutes. This dark brown iodinating solution was then slowly added to a solution of methyl 3-(4-chlorophenyl)propanoate (1.40 g, 7.05 mmol) in sulfuric acid (7.04 ml) (pre-cooled to 0° C.) taking care not to let the temperature rise above 30° C. This was stirred for 50 min. further, and then the reaction was quenched by pouring onto 100 mL of stirring ice water. This was extracted with ethyl acetate (2×100 mL) and the combined organic layers were washed with water (100 mL) and brine (100 mL). The organic layer was dried over sodium sulfate and purified via column chromatography on a Biotage 40M column eluting with hexanes (1 CV) followed by a gradient of 0-50% ethyl acetate in hexanes to provide the desired product as a clear colorless liquid. $^1$H NMR (CDCl$_3$, 500 MHz) δ 7.70 (t, J=1.6 Hz, 1H), 7.34 (d, J=8.3 Hz, 1H), 7.13 (dd, J=8.2 Hz, 1.8 Hz, 1H), 3.67 (s, 3H), 2.88 (t, J=7.7 Hz, 2H), 2.60 (t, J=7.7 Hz, 2H).

Step C: methyl 3-[4-chloro-3-(4,4,5,5-tetramethyl-1,32-dioxaborolan-2-yl)phenyl]propanoate To a solution of methyl 3-(4-chloro-3-iodophenyl)propanoate (1.0 g, 3.08 mmol) in dioxane (2 ml) and DMSO (9.5 ml) was added potassium acetate (0.605 g, 6.16 mmol), bis(pinacolato)diboron (0.978 g, 3.85 mmol), and 1,1'-bis(diphenylphosphino)ferrocene-palladium(II)dichloride dichloromethane complex (0.377 g, 0.462 mmol). The mixture was degassed, purged with nitrogen, and warmed to 80° C. for 15 hours. The mixture was then diluted with ethyl acetate (50 mL), and washed with water (50 mL) followed by brine (50 mL). The organic layer was dried over sodium sulfate, filtered, concentrated in vacuo, and purified via column chromatography on a Biotage 40M column eluting with 0% ethyl acetate in hexanes (1 CV) followed by a gradient to 50% ethyl acetate in hexanes (over 7 CV) to furnish the title compound. $^1$H NMR (CDCl$_3$, 500 MHz) δ 7.51 (d, J=2.3 Hz, 1H), 7.25 (d, J=8.2 Hz, 1H), 7.17 (dd, J=8.3 Hz, 2.3 Hz, 1H), 3.66 (s, 3H), 2.91 (t, J=7.9 Hz, 2H), 2.60 (t, J=7.8 Hz, 2H), 1.36 (s, 12H).

INTERMEDIATE 88

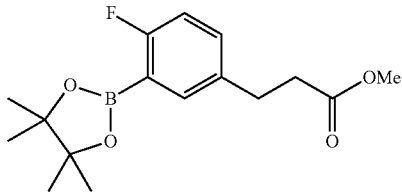

methyl 3-[4-fluoro-3-(4,4,5,5-tetramethyl-1,3,2-dioxaborolan-2-yl)phenyl]propanoate Step A: methyl 3-(4-fluorophenyl)propanoate To a solution of 3-(4-fluorophenyl)propionic acid (4.75 g, 28.2 mmol) in toluene (130 mL) and methanol (20 mL) was added trimethylsilyldiazomethane (2M solution in hexane, 16.24 mL, 32.5 mmol). The mixture was allowed to stir for 1 hour and gas evolution was observed initially. After 1 hour, the mixture became homogeneous and was quenched via addition of 3.5 mL of acetic acid. The mixture was concentrated in vacuo, and purified via column chromatography on a Biotage 65i column eluting with 0% ethyl acetate in hexanes (1 CV) followed by a gradient to 50% ethyl acetate in hexanes (over 7 CV) to furnish the desired product. $^1$H NMR (CDCl$_3$, 500 MHz) δ 7.16 (dd, J=8.0 Hz, 5.6 Hz, 2H), 6.97 (t, J=8.5 Hz, 2H), 3.66 (s, 3H), 2.92 (t, J=7.5 Hz, 2H), 2.61 (t, J=7.7 Hz, 2H).

Step B: methyl 3-(4-fluoro-3-iodophenyl)propanoate

Sodium metaperiodate (0.971 g, 4.54 mmol) was slowly added to a solution of iodine (3.43 g, 13.5 mmol) in sulfuric acid (86 ml). This was stirred at room temperature for 30 minutes. This dark brown iodinating solution was then slowly added to a solution of methyl 3-(4-fluorophenyl)propanoate (5.20 g, 28.5 mmol) in sulfuric acid (28.5 ml) (pre-cooled to 0° C.) taking care not to let the temperature rise above 30° C. This was stirred for 50 min. further, and then the reaction was quenched by pouring onto 100 mL of stirring ice water. This was extracted with ethyl acetate (2×100 mL) and the combined organic layers were washed with water (100 mL) and brine (100 mL). The organic layer was dried over sodium sulfate and purified via column chromatography on a Biotage 40M column eluting with hexanes (1 CV) followed by a gradient of 0-50% ethyl acetate in hexanes to provide the desired product as a clear colorless liquid. $^1$H NMR (CDCl$_3$, 500 MHz) δ 7.58 (dd, J=5.8 Hz, 1.9 Hz, 1H), 7.13 (m, 1H), 6.96 (t, J=8.2 Hz, 1H), 3.67 (s, 3H), 2.88 (t, J=7.7 Hz, 2H), 2.61 (t, J=7.7 Hz, 2H).

Step C: methyl 3-[4-fluoro-3-(4,4,5,5-tetramethyl-1,3,2-dioxaborolan-2-yl)phenyl]propanoate To a solution of methyl 3-(4-fluoro-3-iodophenyl)propanoate (2.0 g, 6.49 mmol) in dioxane (4.12 ml) and DMSO (20.10 ml) was added potassium acetate (1.274 g, 12.98 mmol), bis(pinacolato)diboron (2.06 g, 8.11 mmol), and 1,1'-bis(diphenylphosphino)ferrocene-palladium(II)dichloride dichloromethane complex (0.795 g, 0.974 mmol). The mixture was degassed, purged with nitrogen, and warmed to 80° C. for 15 hours. The mixture was then diluted with ethyl acetate (50 mL), and washed with water (50 mL) followed by brine (50 mL). The organic layer was dried over sodium sulfate, filtered, concentrated in vacuo, and purified via column chromatography on a Biotage 40M column eluting with 0% ethyl acetate in hexanes (1 CV) followed by a gradient to 50% ethyl acetate in hexanes (over 7 CV) to furnish the title compound. $^1$H NMR (CDCl$_3$, 500 MHz) δ 7.54 (dd, J=5.6 Hz, 2.4 Hz, 1H), 7.26 (m, 1H), 6.94 (t, J=8.7 Hz, 1H), 3.67 (s, 3H), 2.92 (t, J=7.9 Hz, 2H), 2.61 (t, J=7.8 Hz, 2H), 1.36 (s, 12H).

INTERMEDIATE 89

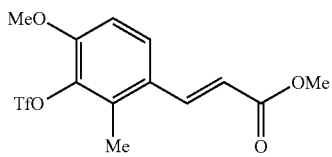

methyl (2E)-3-(4-methoxy-2-methyl-3-{[(trifluoromethyl)sulfonyl]oxy}phenyl)prop-2-enoate

Step A: methyl (2E)-3-(3-hydroxy-2-iodo-4-methoxyphenyl)prop-2-enoate

To a solution of 3-hydroxy-2-iodo-4-methoxybenzaldehyde (2.5 g, 8.99 mmol) in methanol (30 ml) was added potassium carbonate (3.11 g, 22.48 mmol) and methyl diethylphosphonoacetate (1.980 ml, 10.79 mmol). The initial cloudy mixture became clear with the addition of the base (although the base itself was mostly insoluble) The mixture was stirred overnight at 55° C. and became yellow and cloudy again. The solution was then concentrated in vacuo and the residue was taken up in ethyl acetate (20 mL) and 1M HCl (aq) (20 mL). The organic layer was separated and washed with brine (1×20 mL), dried over sodium sulfate, concentrated in vacuo, and purified via column chromatography on a Biotage 65i column eluting with 0% ethyl acetate in hexanes (1 CV) followed by a gradient to 50% ethyl acetate in hexanes (over 7 CV) to furnish the desired product as the E olefin. $^1$H NMR (CDCl$_3$, 500 MHz) $ 7.95 (d, J=15.9 Hz, 1H), 7.14 (d, J=8.4 Hz, 1H), 6.74 (d, J=8.6 Hz, 1H), 6.27 (d, J=15.8 Hz, 1H), 3.91 (s, 3H), 3.80 (s, 3H), 2.34 (s, 3H).

Step B: methyl (2E)-3-(3-hydroxy-4-methoxy-2-methylphenyl)prop-2-enoate

To a solution of methyl (2E)-3-(3-hydroxy-2-iodo-4-methoxyphenyl)prop-2-enoate (2.0 g, 5.99 mmol) in methanol (30 ml) was added trimethylboroxine (1.683 ml, 11.97 mmol), potassium carbonate (2.482 g, 17.96 mmol) and 1,1'-bis(di-tert-butylphosphino)ferrocene palladium dichloride (1.170 g, 1.796 mmol). The mixture was stirred overnight at 90° C. The solution was then filtered through a plug of silica gel (eluting with ethyl acetate), concentrated in vacuo and the residue was purified via column chromatography on a Biotage 65i column eluting with hexanes (1 CV) followed by a gradient of 0-50% ethyl acetate in hexanes (over 6.7 CVs) to furnish the desired compound. $^1$H NMR (CDCl$_3$, 500 MHz) δ 7.95 (d, J=15.9 Hz, 1H), 7.14 (d, J=8.4 Hz, 1H), 6.74 (d, J=8.6 Hz, 1H), 6.27 (d, J=15.8 Hz, 1H), 3.91 (s, 3H), 3.80 (s, 3H), 2.34 (s, 3H).

Step C: methyl (2E)-3-(4-methoxy-2-methyl-3-{[(trifluoromethyl)sulfonyl]oxy}phenyl)prop-2-enoate To a solution of methyl (2E)-3-(3-hydroxy-4-methoxy-2-methylphenyl)prop-2-enoate (722 mg, 3.25 mmol) in Pyridine (5592 μl) cooled to 0° C. was added trifluoromethanesulfonic anhydride (533 μl, 3.25 mmol). (one equivalent first, then warmed to room temperature and another equivalent at rt was added every 15 minutes until complete reaction observed via LC/MS). This ended up being about 5 equivalents (2.66 mL). The reaction mixture was then diluted with ethyl acetate (40 mL), cooled to 0° C. again and any excess reagent was quenched with addition of 40 mL of water. The organic layer was separated and washed with brine (2×30 mL), dried over sodium sulfate, concentrated in vacuo, and purified via column chromatography on a Biotage 65i column eluting with 0% ethyl acetate in hexanes (1 CV) followed by a gradient to 50% ethyl acetate in hexanes (over 7 CV) provided the desired product $^1$H NMR (CDCl$_3$, 500 MHz) δ 7.86 (d, J=15.9 Hz, 1H), 7.53 (d, J=8.7 Hz, 1H), 6.89 (d, J=8.7 Hz, 1H), 6.29 (d, J=15.8 Hz, 1H), 3.92 (s, 3H), 3.81 (s, 3H), 2.41 (s, 3H).

INTERMEDIATE 90

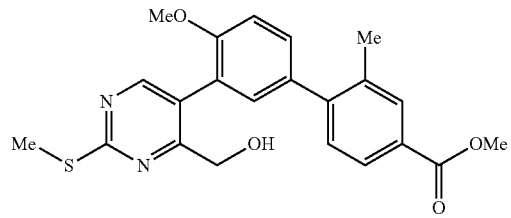

methyl 3'-[4-(hydroxymethyl)-2-(methylsulfanyl)pyrimidin-5-yl]-4'-methoxy-2-methylbiphenyl-4-carboxylate

Step A: methyl 4-bromo-3-methylbenzoate

Into a 10,000-mL 4-necked round-bottom flask was placed a solution of 4-bromo-3-methylbenzoic acid (500 g, 2.33 mol, 1.00 equiv) in methanol (5000 mL). This was followed by the addition of SOCl$_2$ (556 g, 4.67 mol, 2.00 equiv) dropwise with stirring at <10° C. over 120 min. The resulting solution was heated to reflux for 5 h in an oil bath. The resulting mixture was cooled and concentrated under vacuum. This resulted in 535 g (crude) of methyl 4-bromo-3-methylbenzoate as a dark red solid.

Step B: methyl 4'-methoxy-2-methylbiphenyl-4-carboxylate

Into a 10000-mL 4-necked round-bottom flask purged and maintained with an inert atmosphere of nitrogen was placed a solution of (4-methoxyphenyl)boronic acid (350 g, 2.30 mol, 1.00 equiv) in 1,4-dioxane (3500 mL), methyl 4-bromo-3-methylbenzoate (527 g, 2.30 mol, 1.00 equiv), Pd(PPh$_3$)$_4$ (79.8 g, 69.06 mmol, 0.03 equiv), Cs$_2$CO$_3$ (1501 g, 4.60 mol, 2.00 equiv), water (850 mL). The resulting solution was stirred overnight at 100° C. in an oil bath. The reaction was then cooled and quenched by the addition of 3000 mL of water. The resulting solution was extracted with 2×2000 mL of ethyl acetate. The organic layers were combined, washed with 1×2000 mL of brine, dried and concentrated under vacuum. The residue was applied onto a silica gel column and eluted with ethyl acetate/petroleum ether (1:50-1:20). This resulted in 471.6 g (crude) of methyl 4-(4-methoxyphenyl)-3-methylbenzoate as a red solid.

Step C: methyl 3'-iodo-4'-methoxy-2-methylbiphenyl-4-carboxylate

Into a 10000-mL 4-necked round-bottom flask was placed methyl 4-(4-methoxyphenyl)-3-methylbenzoate (470 g, 1.83 mol, 1.00 equiv), Ag$_2$SO$_4$ (572.8 g, 1.84 mol, 1.00 equiv), iodine (466.3 g, 1.84 mol, 1.00 equiv), methanol (4000 mL), ethyl acetate (1000 mL). The resulting solution was stirred for 3 h at room temperature. The resulting mixture was concentrated under vacuum. The residue was diluted with 3000/1500 mL of EtOAc/brine. The solid was filtered out. The filtrate was extracted with 2×1000 mL of ethyl acetate. The organic layers were combined, dried over anhydrous sodium sulfate and concentrated under vacuum. This resulted in 630 g (crude) of methyl 4-(3-iodo-4-methoxyphenyl)-3-methylbenzoate as a yellow solid.

Step D: [4-methoxy-4'-(methoxycarbonyl)-2'-methylbiphenyl-3-yl]boronic acid

Into a 10000-mL 4-necked round-bottom flask purged and maintained with an inert atmosphere of nitrogen was placed a solution of methyl 4-(3-iodo-4-methoxyphenyl)-3-methylbenzoate (600 g, 1.57 mol, 1.00 equiv) in tetrahydrofuran (5000 mL). This was followed by the addition of isopropyl magnesium chloride (960 mL, 1.20 equiv) dropwise with stirring at <−25° C. over 60 min. The reaction was maintained for 1 h at −15° C., followed by addition of trimethyl borate (329.2 g, 3.17 mol, 2.00 equiv) dropwise with stirring at <−20° C. over 30 min. The resulting solution was stirred for 60 min at <0° C., then quenched by the addition of 5000 mL of $H_3PO_4$ (aq. 1M). The bulk of THF was removed under vacuum. The solid was collected by filtration and washed with 2×200 ml of toluene. This resulted in 300 g (crude) of [2-methoxy-5-[4-(methoxycarbonyl)-2-methylphenyl]phenyl]boronic acid as a yellow solid.

Step E: methyl 3'-[4-(hydroxymethyl)-2-(methylsulfanyl)pyrimidin-5-yl]-4'-methoxy-2-methylbiphenyl-4-carboxylate Into a 3000-mL 4-necked round-bottom flask purged and maintained with an inert atmosphere of nitrogen was placed [5-bromo-2-(methylsulfanyl)pyrimidin-4-yl]methanol (130 g, 560 mmol, 1.00 equiv), [2-methoxy-5-[4-(methoxycarbonyl)-2-methylphenyl]phenyl]boronic acid (87.5 g, 0.5 equiv), $Pd(PPh_3)_4$ (32.3, 28 mmol, 0.05 equiv), $Cs_2CO_3$ (365.1 g, 2.00 equiv), water (300 mL), 1,4-dioxane (1200 mL). The resulting solution was stirred for 5 hour at 100° C., then added $2^{nd}$ batch of [2-methoxy-5-[4-(methoxycarbonyl)-2-methylphenyl]phenyl]boronic acid (50 g, 0.3 equiv). The last batch (37 g, 0.2 equiv) was added after 2 hours. The resulting solution was stirred for 3 h at 100° C. The reaction mixture was cooled to room temperature and diluted with 1000 mL of water. The resulting solution was extracted with 2×1000 mL of ethyl acetate. The organic layers were combined, washed with 1×1000 mL of brine, dried over anhydrous sodium sulfate and concentrated under vacuum. The residue was applied onto a silica gel column and eluted with ethyl acetate/petroleum ether (1:8). This resulted in 81 g (35.7%) of methyl 4-[3-[4-(hydroxymethyl)-2-(methylsulfanyl)pyrimidin-5-yl]-4-methoxyphenyl]-3-methylbenzoate as a yellow solid. LCMS (ES, m/z): 411 [M+H]$^+$. $^1$H NMR (CDCl$_3$, 300 MHz): δ 8.398 (1H, s), 7.976 (1H, s), 7.916 (2H, d), 7.410 (1H, d), 7.284-7.325 (1H, m), 7.066-7.114 (2H, m), 4.583 (2H, s), 3.954 (3H, s), 3.853 (3H, s), 2.663 (3H, s).

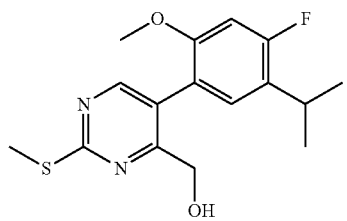

INTERMEDIATE 91

{5-[4-fluoro-2-methoxy-5-(propan-2-yl)phenyl]-2-(methylsulfanyl)pyrimidin-4-}methanol Into a 3000-mL 4-necked round-bottom flask purged and maintained with an inert atmosphere of nitrogen was placed [5-bromo-2-(methylsulfanyl)pyrimidin-4-yl]methanol (115.4 g, 490.85 mmol, 1.00 equiv), water (400 mL), 1,4-dioxane (1000 mL), (5-ethyl-4-fluoro-2-methylphenyl)boronic acid (115 g, 631.87 mmol, 1.20 equiv) and $Pd(PPh_3)_4$ (28.47 g, 24.64 mmol, 0.05 equiv). The resulting solution was stirred for 24 h at 90° C. The reaction mixture was cooled to room temperature, then quenched by the addition of 1000 mL of water. The resulting solution was extracted with 3×1000 mL of ethyl acetate. The organic layers were combined, washed with 2×1000 mL of brine, dried over anhydrous sodium sulfate and concentrated under vacuum. The residue was applied onto a silica gel column and eluted with ethyl acetate/petroleum ether (1:30-1:10). This resulted in 100.3 g (63%) of [5-[4-fluoro-2-methoxy-5-(propan-2-yl)phenyl]-2-(methylsulfanyl)pyrimidin-4-yl]methanol as light yellow oil. LCMS (ES, m/z): 323 [M+H]$^+$. $^1$H NMR (300 MHz, CDCl$_3$): δ 8.311 (1H, s), 6.954 (1H, d), 6.673 (1H, d), 4.484 (2H, s), 3.736 (3H, s), 3.196 (1H, m), 2.632 (3H, s), 1.249 (6H, m).

Example 1

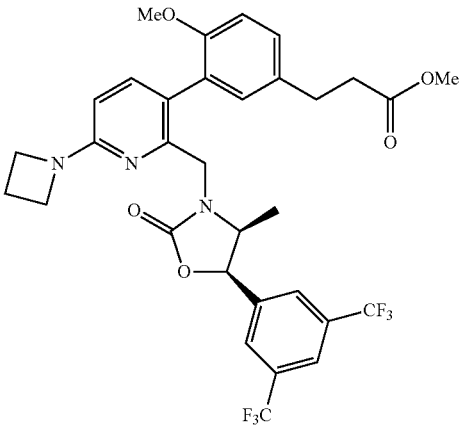 [SMILES: COC(=O)CCc1ccc(OC)c(-c2ccc(N3CCC3)nc2CN2C(=O)O[C@H](c3cc(C(F)(F)F)cc(C(F)(F)F)c3)[C@@H]2C)c1]

Methyl 3-{3-[6-azetidin-1-yl-2-({(4S,5R)-5-[3,5-bis(trifluoromethyl)phenyl]-4-methyl-2-oxo-1,3-oxazolidin-3-yl}methy)pyridin-3-yl]-4-methoxyphenyl}propanoate A flask was charged with (4S,5R)-3-[(6-azetidin-1-yl-3-bromopyridin-2-yl)methyl]-5-[3,5-bis(trifluoromethyl)phenyl]-4-methyl-1,3-oxazolidin-2-one (134 mg, 0.249 mmol), methyl 3-[4-methoxy-3-(4,4,5,5-tetramethyl-1,3,2-dioxaborolan-2-yl)phenyl]propanoate (100 mg, 0.312 mmol), 1,1'-bis(di-t-butylphosphino)ferrocene palladium dichloride (8.11 mg, 0.012 mmol), and THF (3 mL). The reaction was degassed with $N_2$ then 1M $K_2CO_3$ (3 mL, 3.00 mmol) was added. The reaction was stirred at room temperature for 45 min. The reaction was then diluted with ethyl acetate (20 mL), washed with water (2×15 mL) and brine (15 mL), dried over sodium sulfate, filtered, and concentrated. The residue was purified by flash chromatography on silica gel (0 to 100% ethyl acetate/hexanes) to afford methyl 3-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}propanoate. LCMS=652.2 (M+H)$^+$. $^1$H NMR (CDCl$_3$, 500 MHz) δ 7.84 (s, 1H), 7.72 (s, 2H), 7.29 (d, J=8.4 Hz, 1H), 7.15 (dd, J=8.3, 2.2 Hz, 1H), 6.97 (bs, 1H), 6.86 (d, J=8.5 Hz, 1H), 6.26 (d, J=8.4 Hz, 1H), 5.57 (bs, 1H), 4.75 (m, 1H), 4.33-3.95 (m, 6H), 3.75 (s, 3H), 3.64 (s, 3H), 2.91 (m, 2H), 2.62 (m, 2H), 2.40 (m, 2H), 0.66-0.59 (m, 3H).

The following compounds (Table 11) were synthesized using methods analogous to those described for EXAMPLE 1 from commercially available materials or intermediates whose syntheses are described above.

TABLE 11

| Example | Molecular structure | LCMS (M + H)$^+$ |
|---|---|---|
| 2 | 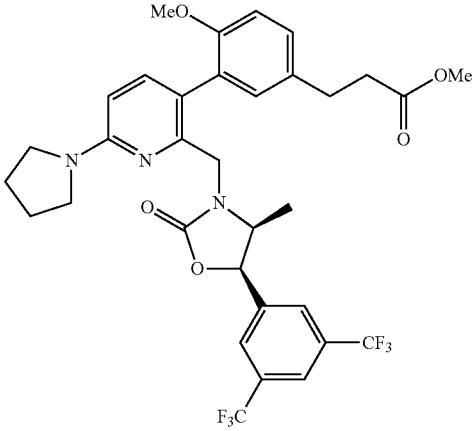 [SMILES: COC(=O)CCc1ccc(OC)c(-c2ccc(N3CCCC3)nc2CN2C(=O)O[C@H](c3cc(C(F)(F)F)cc(C(F)(F)F)c3)[C@@H]2C)c1] | 666.2 |
| 3 | 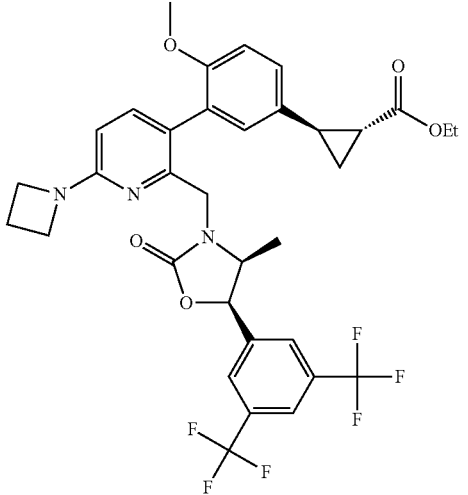 [SMILES: CCOC(=O)[C@@H]1C[C@H]1c1ccc(OC)c(-c2ccc(N3CCC3)nc2CN2C(=O)O[C@H](c3cc(C(F)(F)F)cc(C(F)(F)F)c3)[C@@H]2C)c1] | 678.2 |

TABLE 11-continued
| Example | Molecular structure | LCMS (M + H)+ |
|---|---|---|
| 4 | 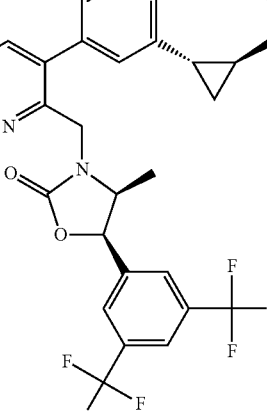 | 678.2 |
| 5 | 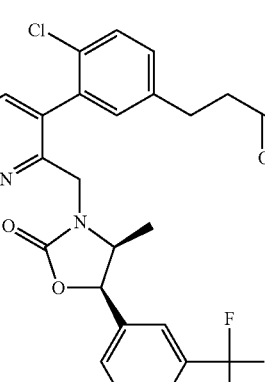 | 656.1 |
| 6 | 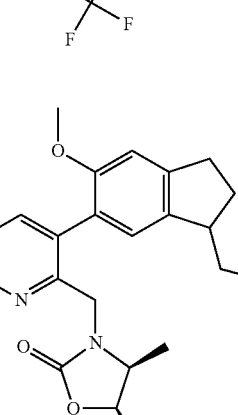 | 692.3 |

TABLE 11-continued

| Example | Molecular structure | LCMS (M + H)+ |
|---|---|---|
| 7 | 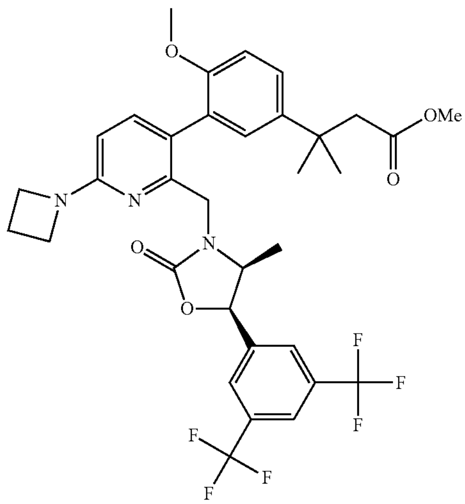 [SMILES: COC(=O)CC(C)(C)c1ccc(OC)c(-c2ccc(N3CCC3)nc2CN2C(=O)O[C@H](c3cc(C(F)(F)F)cc(C(F)(F)F)c3)[C@@H]2C)c1] | 680.2 |
| 8 | 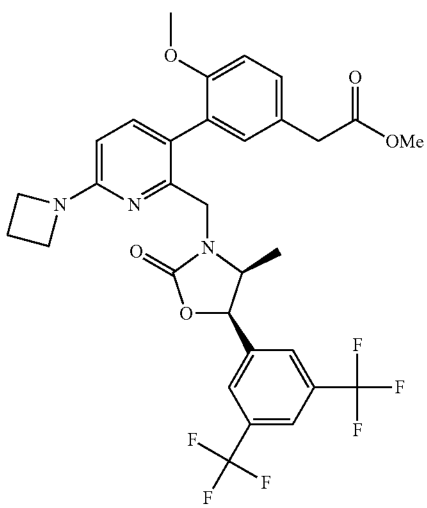 [SMILES: COC(=O)Cc1ccc(OC)c(-c2ccc(N3CCC3)nc2CN2C(=O)O[C@H](c3cc(C(F)(F)F)cc(C(F)(F)F)c3)[C@@H]2C)c1] | 638.1 |
| 9 | 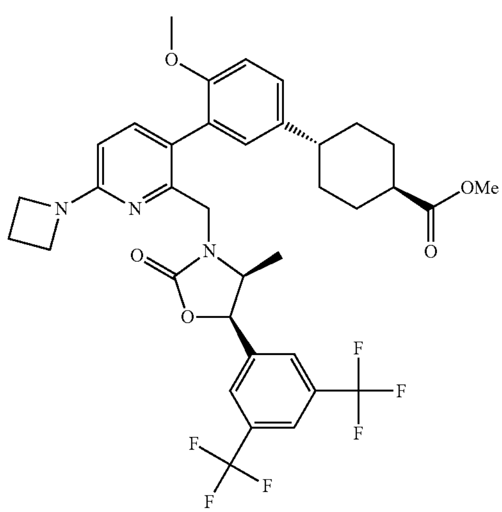 [SMILES: COc1ccc([C@H]2CC[C@H](C(=O)OC)CC2)cc1-c1ccc(N2CCC2)nc1CN1C(=O)O[C@H](c2cc(C(F)(F)F)cc(C(F)(F)F)c2)[C@@H]1C] | 706.3 |

TABLE 11-continued

| Example | Molecular structure | LCMS (M + H)+ |
|---|---|---|
| 10 | 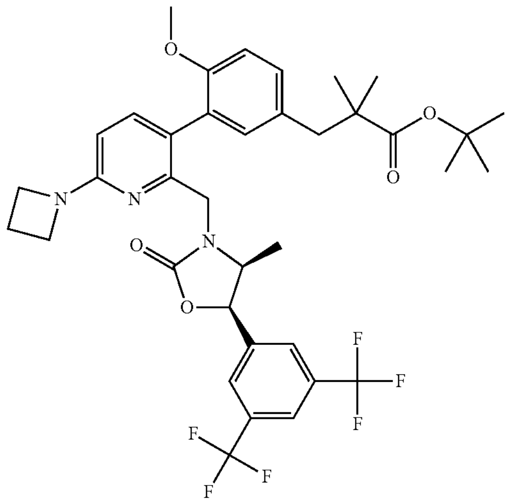 [SMILES: COc1ccc(CC(C)(C)C(=O)OC(C)(C)C)cc1-c1ccc(N2CCC2)nc1CN1C(=O)O[C@H](c2cc(C(F)(F)F)cc(C(F)(F)F)c2)[C@@H]1C] | 722.3 |
| 11 | 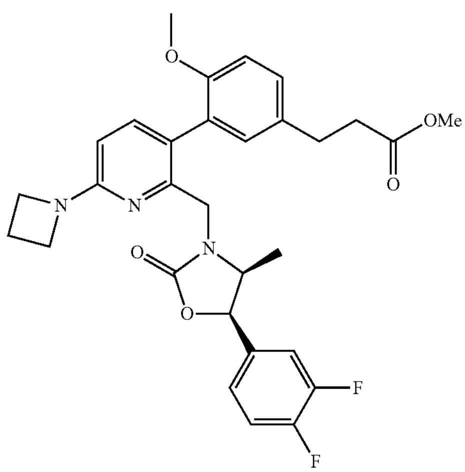 [SMILES: COC(=O)CCc1ccc(OC)c(-c2ccc(N3CCC3)nc2CN2C(=O)O[C@H](c3ccc(F)c(F)c3)[C@@H]2C)c1] | 552.1 |
| 12 | 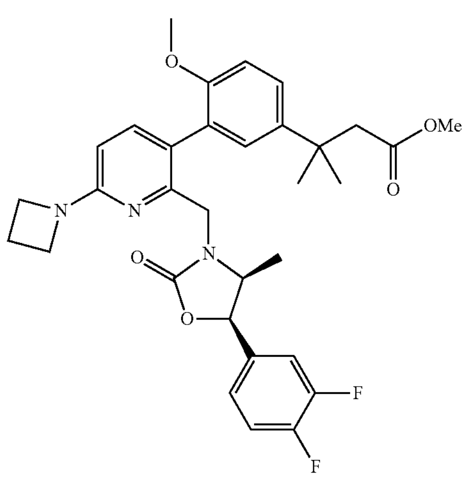 [SMILES: COC(=O)CC(C)(C)c1ccc(OC)c(-c2ccc(N3CCC3)nc2CN2C(=O)O[C@H](c3ccc(F)c(F)c3)[C@@H]2C)c1] | 580.1 |

TABLE 11-continued
| Example | Molecular structure | LCMS (M + H)+ |
|---|---|---|
| 13 | 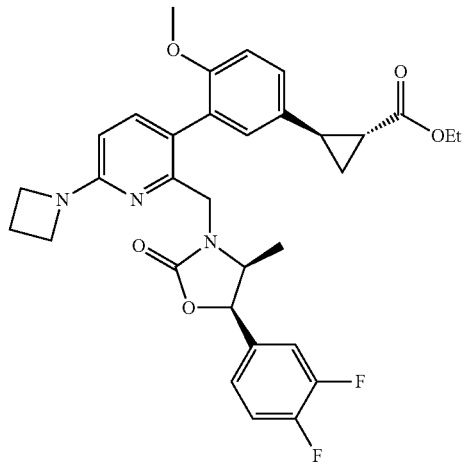 [SMILES: CCOC(=O)[C@@H]1C[C@H]1c1ccc(OC)c(-c2ccc(N3CCC3)nc2CN2C(=O)O[C@H](c3ccc(F)c(F)c3)[C@@H]2C)c1] | 578.1 |
| 14 | 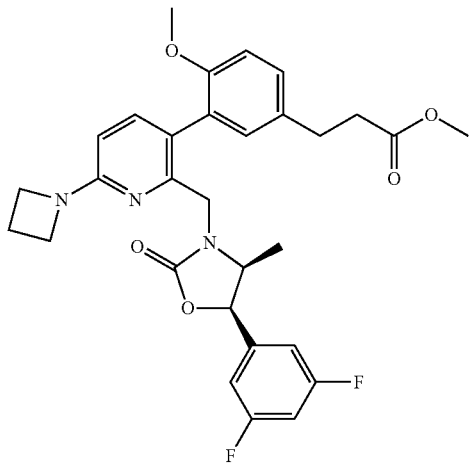 [SMILES: COC(=O)CCc1ccc(OC)c(-c2ccc(N3CCC3)nc2CN2C(=O)O[C@H](c3cc(F)cc(F)c3)[C@@H]2C)c1] | 552.09 |
| 15 | 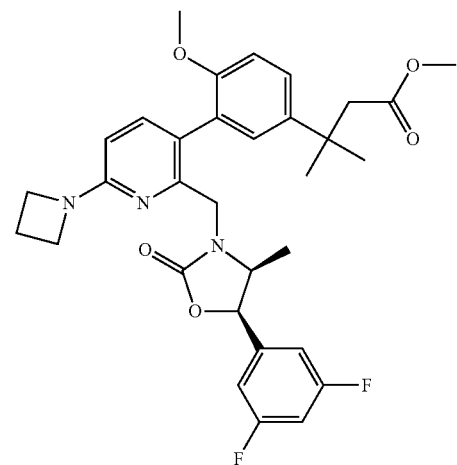 [SMILES: COC(=O)CC(C)(C)c1ccc(OC)c(-c2ccc(N3CCC3)nc2CN2C(=O)O[C@H](c3cc(F)cc(F)c3)[C@@H]2C)c1] | 580.13 |

TABLE 11-continued

| Example | Molecular structure | LCMS (M + H)+ |
| --- | --- | --- |
| 16 | 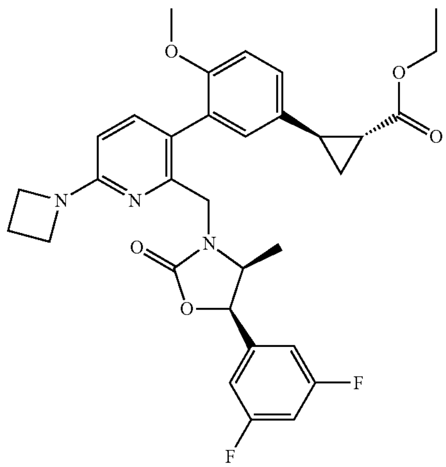 [SMILES: CCOC(=O)[C@@H]1C[C@H]1c1ccc(OC)c(-c2ccc(N3CCC3)nc2CN2C(=O)O[C@H](c3cc(F)cc(F)c3)[C@@H]2C)c1] | 578.10 |
| 17 | 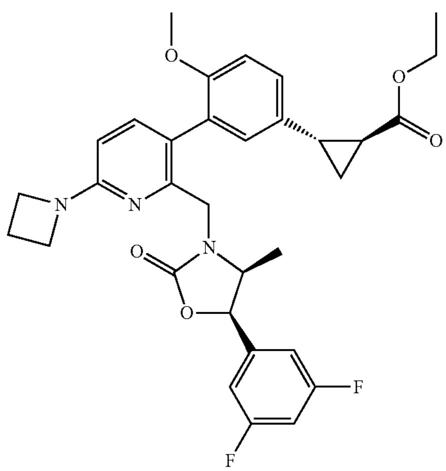 [SMILES: CCOC(=O)[C@H]1C[C@@H]1c1ccc(OC)c(-c2ccc(N3CCC3)nc2CN2C(=O)O[C@H](c3cc(F)cc(F)c3)[C@@H]2C)c1] | 578.16 |
| 18 | 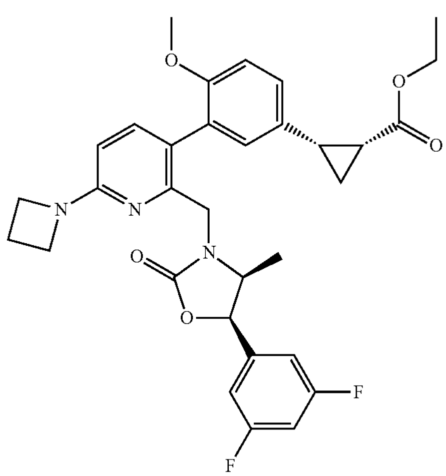 [SMILES: CCOC(=O)[C@@H]1C[C@@H]1c1ccc(OC)c(-c2ccc(N3CCC3)nc2CN2C(=O)O[C@H](c3cc(F)cc(F)c3)[C@@H]2C)c1] | 578.13 |

TABLE 11-continued

| Example | Molecular structure | LCMS (M + H)+ |
| --- | --- | --- |
| 19 | 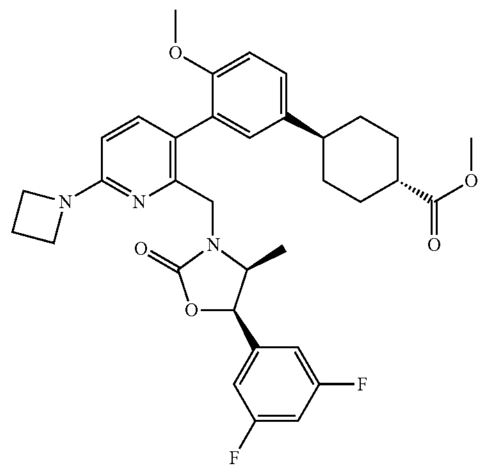 [SMILES: COc1ccc([C@H]2CC[C@H](C(=O)OC)CC2)cc1-c1ccc(N2CCC2)nc1CN1C(=O)O[C@H](c2cc(F)cc(F)c2)[C@@H]1C] | 606.15 |
| 20 | 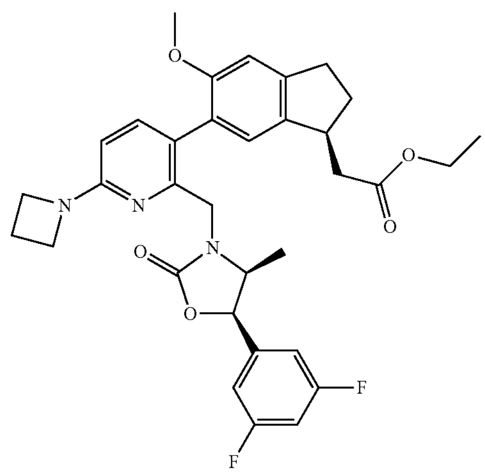 [SMILES: CCOC(=O)C[C@@H]1CCc2cc(OC)c(-c3ccc(N4CCC4)nc3CN3C(=O)O[C@H](c4cc(F)cc(F)c4)[C@@H]3C)cc21] | 592.14 |
| 21 | 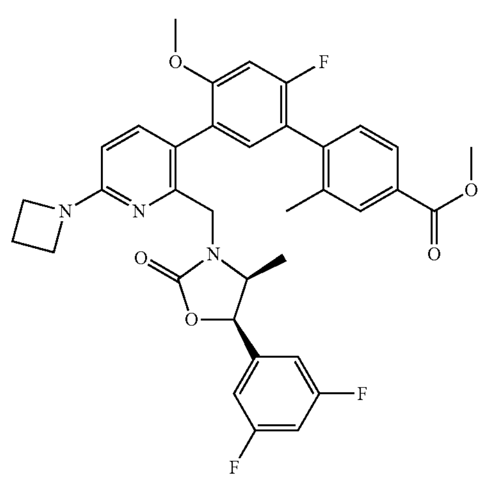 [SMILES: COC(=O)c1ccc(-c2cc(-c3ccc(N4CCC4)nc3CN3C(=O)O[C@H](c4cc(F)cc(F)c4)[C@@H]3C)c(OC)cc2F)c(C)c1] | 632.08 |

TABLE 11-continued
| Example | Molecular structure | LCMS (M + H)+ |
|---|---|---|
| 22 | 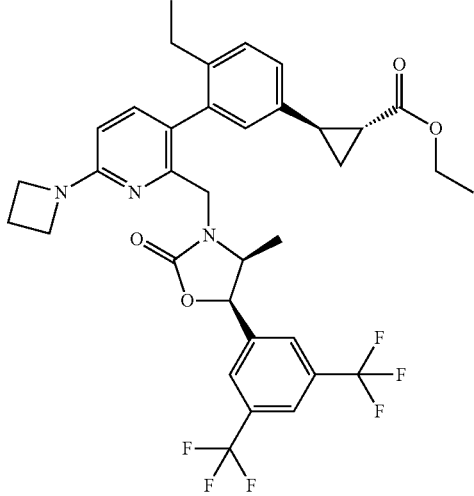 [SMILES: CCOC(=O)[C@@H]1C[C@H]1c1ccc(CC)c(-c2ccc(N3CCC3)nc2CN2C(=O)O[C@H](c3cc(C(F)(F)F)cc(C(F)(F)F)c3)[C@@H]2C)c1] | 676.24 |
| 23 | 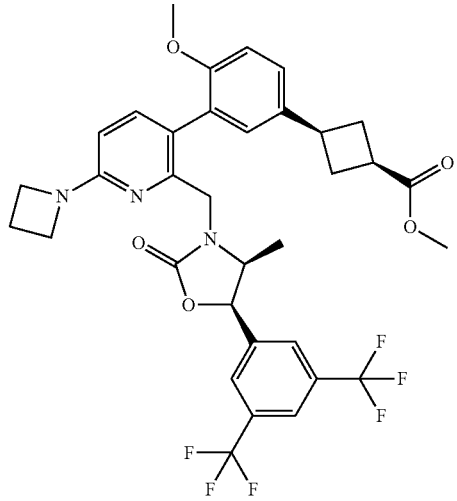 [SMILES: COc1ccc([C@H]2C[C@@H](C(=O)OC)C2)cc1-c1ccc(N2CCC2)nc1CN1C(=O)O[C@H](c2cc(C(F)(F)F)cc(C(F)(F)F)c2)[C@@H]1C] | 678.23 |
| 24 | 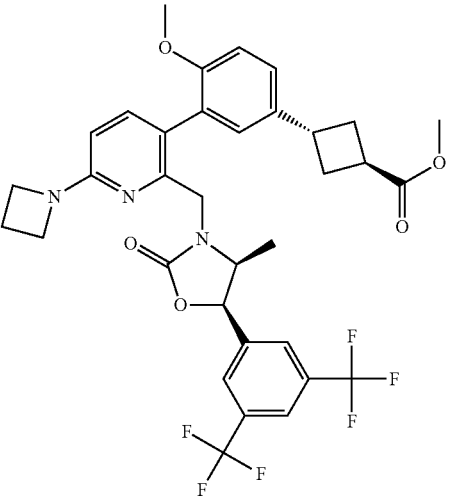 [SMILES: COc1ccc([C@H]2C[C@H](C(=O)OC)C2)cc1-c1ccc(N2CCC2)nc1CN1C(=O)O[C@H](c2cc(C(F)(F)F)cc(C(F)(F)F)c2)[C@@H]1C] | 678.33 |

TABLE 11-continued
| Example | Molecular structure | LCMS (M + H)+ |
|---|---|---|
| 25 | 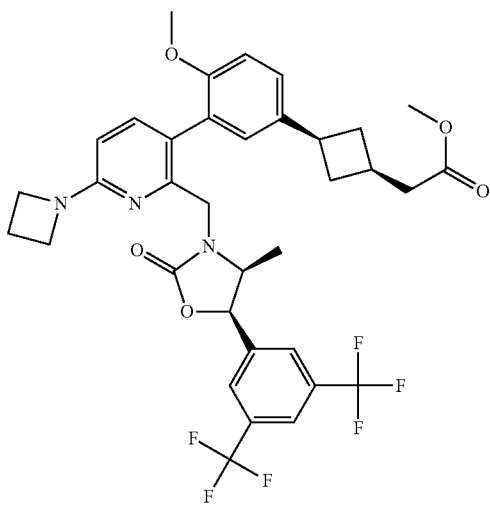 [SMILES: COC(=O)C[C@H]1C[C@@H](c2ccc(OC)c(-c3ccc(N4CCC4)nc3CN3C(=O)O[C@H](c4cc(C(F)(F)F)cc(C(F)(F)F)c4)[C@@H]3C)c2)C1] | 692.35 |
| 26 | 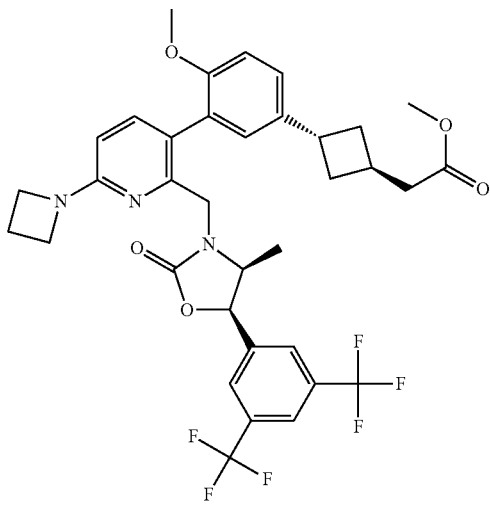 [SMILES: COC(=O)C[C@H]1C[C@H](c2ccc(OC)c(-c3ccc(N4CCC4)nc3CN3C(=O)O[C@H](c4cc(C(F)(F)F)cc(C(F)(F)F)c4)[C@@H]3C)c2)C1] | 692.29 |
| 27 | 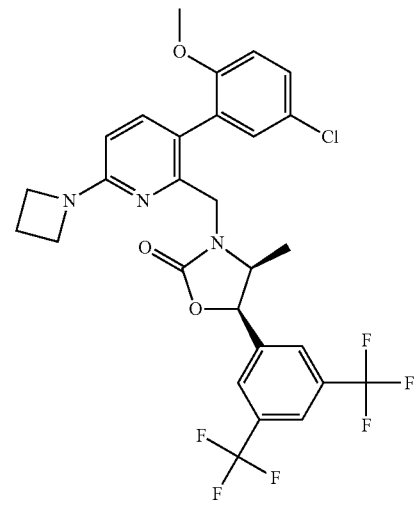 [SMILES: COc1ccc(Cl)cc1-c1ccc(N2CCC2)nc1CN1C(=O)O[C@H](c2cc(C(F)(F)F)cc(C(F)(F)F)c2)[C@@H]1C] | 600.08 |

TABLE 11-continued

| Example | Molecular structure | LCMS (M + H)+ |
|---|---|---|
| 28 | 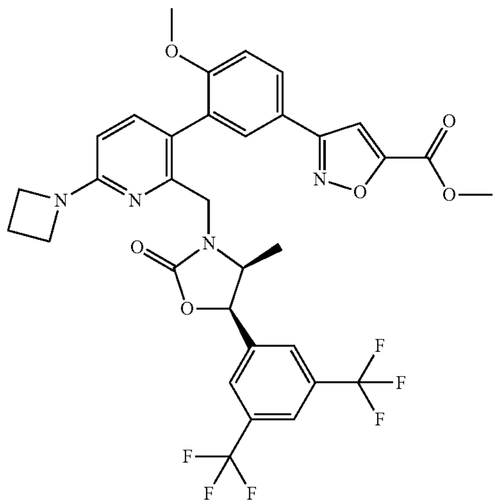 [SMILES: COC(=O)c1cc(-c2ccc(OC)c(-c3ccc(N4CCC4)nc3CN3C(=O)O[C@H](c4cc(C(F)(F)F)cc(C(F)(F)F)c4)[C@@H]3C)c2)no1] | 691.20 |
| 29 | 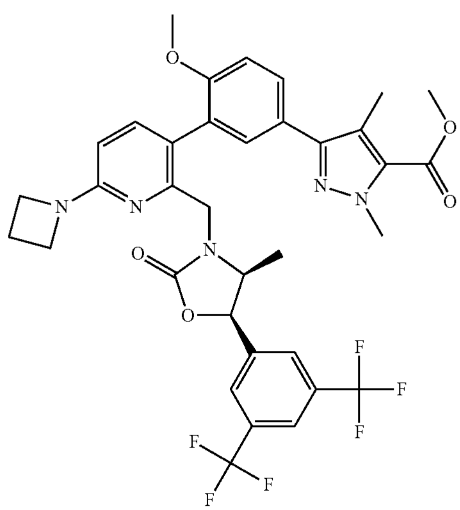 [SMILES: COC(=O)c1c(C)c(-c2ccc(OC)c(-c3ccc(N4CCC4)nc3CN3C(=O)O[C@H](c4cc(C(F)(F)F)cc(C(F)(F)F)c4)[C@@H]3C)c2)nn1C] | 718.22 |
| 30 | 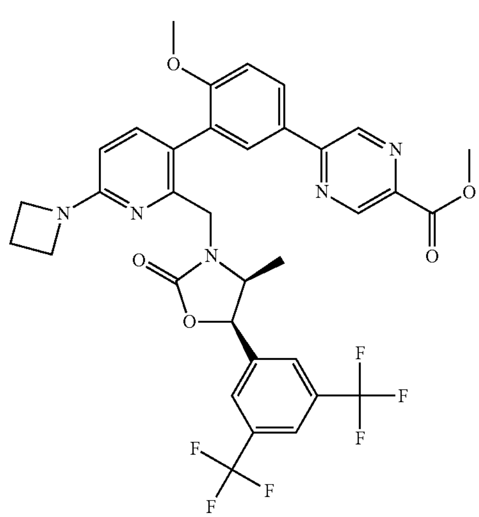 [SMILES: COC(=O)c1cnc(-c2ccc(OC)c(-c3ccc(N4CCC4)nc3CN3C(=O)O[C@H](c4cc(C(F)(F)F)cc(C(F)(F)F)c4)[C@@H]3C)c2)cn1] | 702.25 |

TABLE 11-continued
| Example | Molecular structure | LCMS (M + H)+ |
|---|---|---|
| 31 | 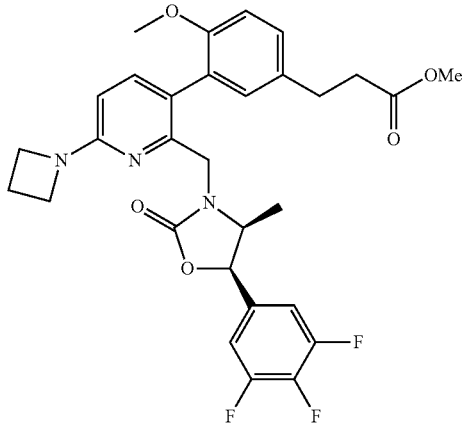 [SMILES: COC(=O)CCc1ccc(OC)c(-c2ccc(N3CCC3)nc2CN2C(=O)O[C@H](c3cc(F)c(F)c(F)c3)[C@@H]2C)c1] | 570.1 |
| 32 | 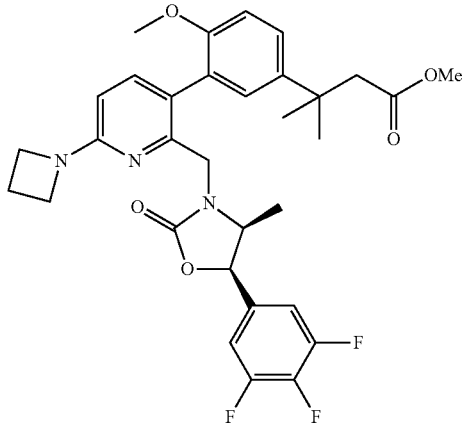 [SMILES: COC(=O)CC(C)(C)c1ccc(OC)c(-c2ccc(N3CCC3)nc2CN2C(=O)O[C@H](c3cc(F)c(F)c(F)c3)[C@@H]2C)c1] | 598.1 |
| 33 | 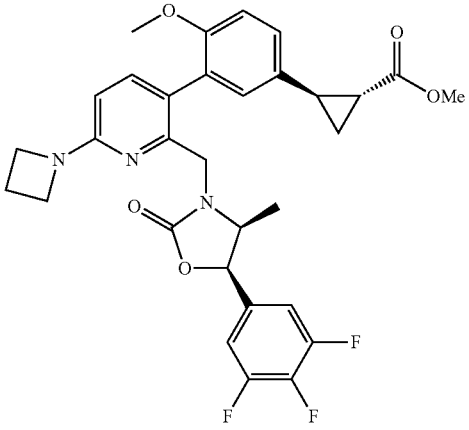 [SMILES: COC(=O)[C@@H]1C[C@H]1c1ccc(OC)c(-c2ccc(N3CCC3)nc2CN2C(=O)O[C@H](c3cc(F)c(F)c(F)c3)[C@@H]2C)c1] | 596.1 |

TABLE 11-continued
| Example | Molecular structure | LCMS (M + H)+ |
|---|---|---|
| 34 | 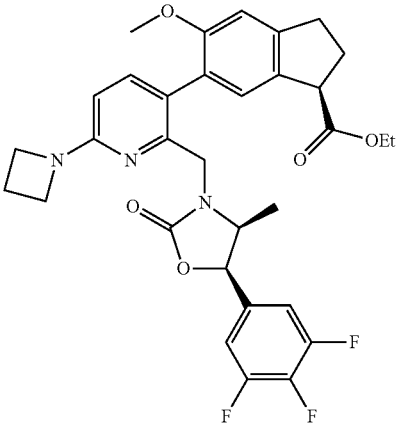 [SMILES: CCOC(=O)[C@@H]1CCc2cc(OC)c(-c3ccc(N4CCC4)nc3CN3C(=O)O[C@H](c4cc(F)c(F)c(F)c4)[C@@H]3C)cc21] | 610.2 |
| 35 | 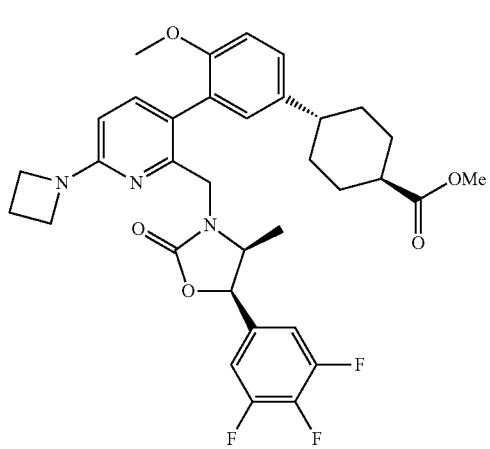 [SMILES: COc1ccc([C@H]2CC[C@H](C(=O)OC)CC2)cc1-c1ccc(N2CCC2)nc1CN1C(=O)O[C@H](c2cc(F)c(F)c(F)c2)[C@@H]1C] | 624.2 |
| 36 | 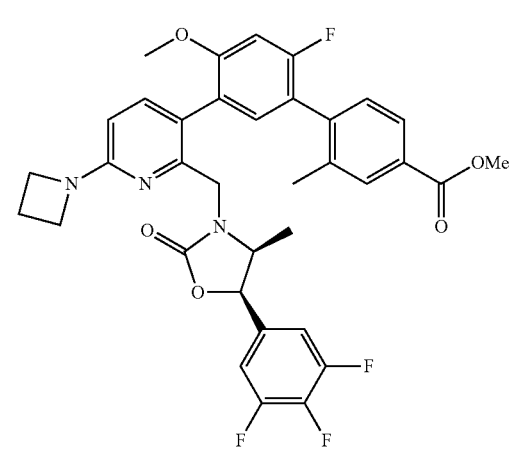 [SMILES: COC(=O)c1ccc(-c2cc(-c3ccc(N4CCC4)nc3CN3C(=O)O[C@H](c4cc(F)c(F)c(F)c4)[C@@H]3C)c(OC)cc2F)c(C)c1] | 650.1 |

TABLE 11-continued

| Example | Molecular structure | LCMS (M + H)+ |
|---|---|---|
| 37 | 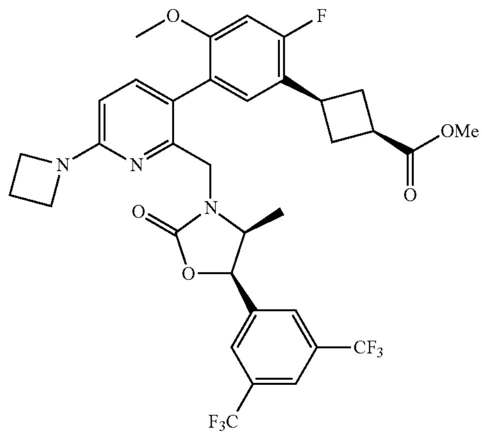 [SMILES: COc1cc(F)c([C@H]2C[C@@H](C(=O)OC)C2)cc1-c1ccc(N2CCC2)nc1CN1C(=O)O[C@H](c2cc(C(F)(F)F)cc(C(F)(F)F)c2)[C@@H]1C] | 696.3 |
| 38 | 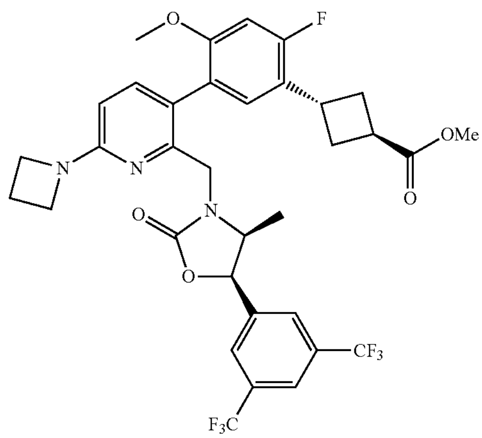 [SMILES: COc1cc(F)c([C@H]2C[C@H](C(=O)OC)C2)cc1-c1ccc(N2CCC2)nc1CN1C(=O)O[C@H](c2cc(C(F)(F)F)cc(C(F)(F)F)c2)[C@@H]1C] | 696.3 |

Example 39

Methyl 3-{3-[6-azetidin-1-yl-2-({(4S,5R)-5-[3,5-bis(trifluoromethyl)phenyl]-4-methyl-2-oxo-1,3-oxazolidin-3-yl}methyl)-4-methylpyridin-3-yl]-4-methoxyphenyl}propanoate A flask was charged with (4S,5R)-3-[(6-azetidin-1-yl-3-bromo-4-methylpyridin-2-yl)methyl]-5-[3,5-bis(trifluoromethyl)phenyl]-4-methyl-1,3-oxazolidin-2-one (460 mg, 0.833 mmol), methyl 3-[4-methoxy-3-(4,4,5,5,5-tetramethyl-1,3,2-dioxaborolan-2-yl)phenyl]propanoate (347 mg, 1.083 mmol), 1,1'-bis(di-t-butylphosphino)ferrocene palladium dichloride (27.1 mg, 0.042 mmol), and THF (9 mL) under nitrogen. The reaction was degassed with nitrogen for 5 minutes and then 1M potassium carbonate (9 mL, 9.00 mmol) was added via syringe. The reaction was stirred at room temperature for 45 minutes. The reaction was then diluted with ethyl acetate (50 mL), washed with water (2×25 mL) and brine (25 mL), dried over sodium sulfate, filtered, and concentrated. The residue was purified by flash chromatography on silica gel (0 to 100% ethyl acetate/hexanes) to afford methyl 3-{3-[6-azetidin-1-yl-2-({(4S,5R)-5-[3,5-bis(trifluoromethyl)phenyl]-4-methyl-2-oxo-1,3-oxazolidin-3-yl}methyl)-4-methylpyridin-3-yl]-4-methoxyphenyl}propanoate as a mixture of atropisomers. The atropisomers were separated by SFC on an AD chiral column using 20% IPA/CO$_2$. LCMS=666.3 (M+H)+. For Atropisomer A: ¹H NMR (CDCl₃, 500 MHz) δ 7.84 (s, 1H), 7.73 (s, 2H), 7.17 (dd, J=8.4, 2.0 Hz, 1H), 6.88 (m, 2H), 6.14 (s, 1H), 5.67 (d, J=8.5 Hz, 1H), 4.55 (d, J=16.4 Hz, 1H), 4.38 (m, 1H), 4.04 (m, 4H), 3.72 (m, 1H), 3.69 (s, 3H), 3.65 (s, 3H), 2.91 (m, 2H), 2.62 (m, 2H), 2.39 (m, 2H), 1.93 (s, 3H), 0.63 (d, J=6.6 Hz, 3H). For Atropisomer B: ¹H NMR (CDCl₃, 500 MHz) δ 7.84 (s, 1H), 7.71 (s, 2H), 7.16 (dd, J=8.4, 2.0 Hz, 1H), 6.87 (m, 2H), 6.14 (s, 1H), 5.61 (d, J=8.2 Hz, 1H), 4.57 (d, J=16.0 Hz, 1H), 4.28 (m, 1H), 4.04 (m, 4H), 3.76 (m, 1H), 3.75 (s, 3H), 3.61 (s, 3H), 2.89 (m, 2H), 2.60 (m, 2H), 2.38 (m, 2H), 1.94 (s, 3H), 0.65 (d, J=6.6 Hz, 3H).

The following compounds (Table 12) were synthesized using methods analogous to those described for EXAMPLE 39 from commercially available materials or intermediates whose syntheses are described above.

TABLE 12

| Example | Molecular structure | LCMS (M + H)⁺ |
|---|---|---|
| 40 | 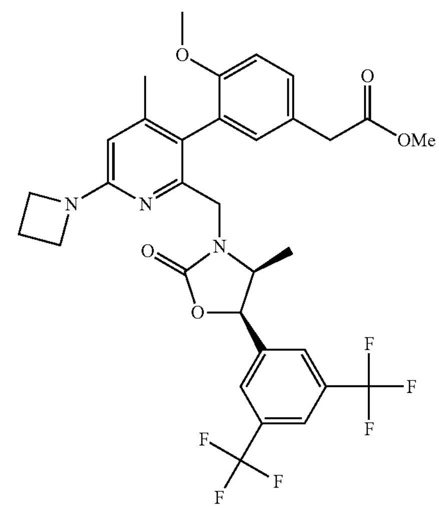 [SMILES: COC(=O)Cc1ccc(OC)c(-c2c(C)cc(N3CCC3)nc2CN2C(=O)O[C@H](c3cc(C(F)(F)F)cc(C(F)(F)F)c3)[C@@H]2C)c1] | 652.2 |
| 41 | Atropisomer A | 692.31 |
| 42 | Atropisomer B | 692.31 |
| 43 | Atropisomer A | 692.32 |

TABLE 12-continued

| Example | Molecular structure | LCMS (M + H)+ |
|---|---|---|
| 44 | 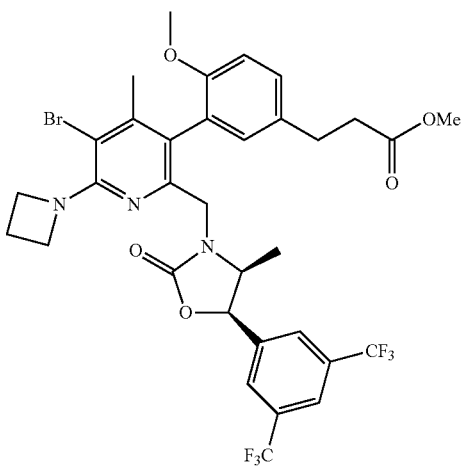 [SMILES: COC(=O)CCc1ccc(OC)c(-c2c(CN3C(=O)O[C@H](c4cc(C(F)(F)F)cc(C(F)(F)F)c4)[C@@H]3C)nc(N3CCC3)c(Br)c2C)c1] Atropisomer B | 692.30 |

Example 45

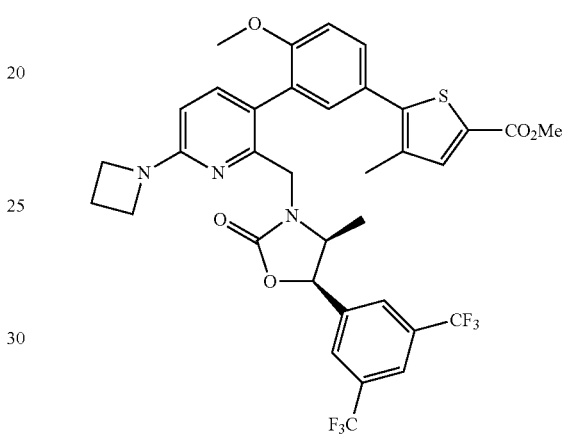

Methyl 3-{3-[6-azetidin-1-yl-2-({(4S,5R)-5-[3,5-bis (trifluoromethyl)phenyl]-4-methyl-2-oxo-1,3-oxazolidin-3-yl}methyl-5-bromo-4-methylpyridin-3-yl]-4-methoxyphenyl}propanoate An oven dried flask was charged with methyl 3-{3-[6-azetidin-1-yl-2-({(4S,5R)-5-[3,5-bis(trifluoromethyl)phenyl]-4-methyl-2-oxo-1,3-oxazolidin-3-yl}methyl)-4-methylpyridin-3-yl]-4-methoxyphenyl}propanoate (atropisomer A) (19.1 mg, 0.029 mmol) and $CH_2Cl_2$ (1 mL) under nitrogen. The solution was cooled to −10° C., N-bromosuccinimide (5.1 mg, 0.029 mmol) was added. The reaction was stirred for 15 minutes at −10° C. and then loaded directly onto a silica gel column and purified by flash chromatography on silica gel (0 to 100% ethyl acetate/hexanes) to afford methyl 3-{3-[6-azetidin-1-yl-2-({(4S,5R)-5-[3,5-bis(trifluoromethyl)phenyl]-4-methyl-2-oxo-1,3-oxazolidin-3-yl}methyl)-5-bromo-4-methylpyridin-3-yl]-4-methoxyphenyl}propanoate.
LCMS=744.4 and 746.4 (M+H)+. $^1$H NMR (CDCl$_3$, 500 MHz) δ 7.85 (s, 1H), 7.71 (s, 2H), 7.20 (dd, J=8.4 Hz, J=2.0 Hz, 1H), 6.88 (m, 2H), 5.65 (d, J=8.7 Hz, 1H), 4.50 (d, J=16.4 Hz, 1H), 4.41 (m, 2H), 4.32 (m, 1H), 4.18 (m, 2H), 3.69 (s, 3H), 3.67 (m, 1H), 3.66 (s, 3H), 2.91 (t, J=7.5 Hz, 2H), 2.62 (t, J=7.6 Hz, 2H), 2.29 (m, 2H), 2.02 (s, 3H), 0.62 (d, J=6.6 Hz, 3H).

Example 46

Methyl 5-{3-[6-azetidin-1-yl-2-({(4S,5R)-5-[3,5-bis (trifluoromethyl)phenyl]-4-methyl-2-oxo-1,3-oxazolidin-3-yl}methyl)pyridin-3-yl]-4-methoxyphenyl}-4-methylthiophene-2-carboxylate A solution of (4S,5R)-3-({6-azetidin-1-yl-3-[5-(5,5-dimethyl-1,3,2-dioxaborinan-2-yl)-2-methoxyphenyl]pyridin-2-yl}methyl)-5-[3,5-bis(trifluoromethyl)phenyl]-4-methyl-1,3-oxazolidin-2-one (27 mg, 0.040 mmol) and methyl 5-bromo-4-methyl-2-thiophene carboxylate (18.74 mg, 0.080 mmol) in THF (0.5 mL) was degassed with N$_2$ at 25° C. 1N K$_2$CO$_3$ (0.5 mL) was added followed by 1,1-bis(di-tert-butylphosphino) ferrocene palladium dichloride (2.60 mg, 3.99 mmol) and the reaction was stirred vigorously at 25° C. under N$_2$ overnight. The reaction was diluted with water and extracted with EtOAc (3×). The combined extracts were dried (Na$_2$SO$_4$) and concentrated in vacuo to afford the crude product. This was purified by preparative TLC (20×20, 1000 μm, hexanes/EtOAc (70/30)) to give methyl 5-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}-4-methylthiophene-2-carboxylate. LCMS calc.=719.2. found=720.2 (M+H)+. $^1$H NMR (500 MHz, CDCl$_3$): δ 7.86 (s, 1H); 7.73 (s, br, 2H); 7.62 (s, 1H); 7.47 (d, J=8.6 Hz, 1H); 7.35 (d, J=8.6 Hz, 1H); 7.33-7.23 (m, 1H); 7.03 (d, J=8.6 Hz, 1H); 6.31 (d, J=8.3 Hz, 1H); 5.74-5.31 (m, 1H); 4.87 (d, J=16.2 Hz, 1H); 4.24 (s, br, 1H); 4.23-3.97 (m, 5H); 3.88 (s, 3H); 3.87 (s, 3H); 2.47-2.41 (m, 2H); 2.33 (s, 3H); 0.75-0.53 (m, 3H).

Example 47

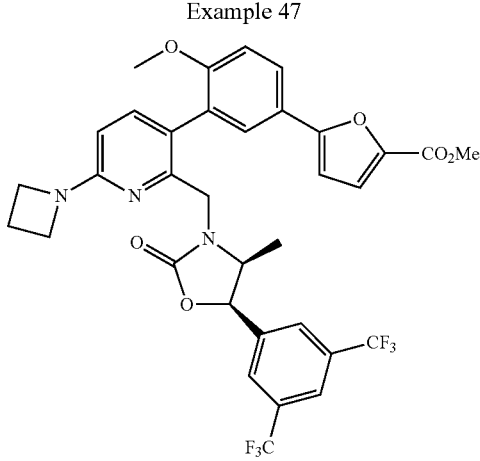

Methyl 5-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}-2-furoate A solution of (4S,5R)-3-{[6-azetidin-1-yl-3-(5-iodo-2-methoxyphenyl)pyridin-2-yl]methyl}-5-[3,5-bis(trifluoromethyl)phenyl]-4-methyl-1,3-oxazolidin-2-one (20 mg, 0.029 mmol) and [5-(methoxycarbonyl)-2-furyl]boronic acid (14.75 mg, 0.087 mmol) in THF (0.5 mL) was degassed with $N_2$ at 25° C. 1N $K_2CO_3$ (0.5 mL) was added followed by 1,1-bis(di-tert-butylphosphino)ferrocene palladium dichloride (1.885 mg, 2.89 μmol) and the reaction was stirred vigorously at 25° C. under $N_2$ overnight. The reaction was diluted with water and extracted with EtOAc (3×). The combined extracts were dried ($Na_2SO_4$) and concentrated in vacuo to afford the crude product. This was purified by preparative TLC (20×20, 1000 μm, hexanes/EtOAc (70/30)) to give methyl 5-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}-2-furoate.

LCMS calc.=689.2. found=690.2 (M+H)$^+$. $^1$H NMR (500 MHz, CDCl$_3$): δ 7.85 (s, 1H); 7.81-7.55 (m, 4H); 7.37 (d, J=8.3 Hz, 1H); 7.24 (d, J=3.7 Hz, 1H); 7.02 (d, J=8.6 Hz, 1H); 6.66 (s, 1H); 6.31 (d, J=8.3 Hz, 1H); 5.74-5.36 (m, 1H); 4.84 (d, J=16.1 Hz, 1H); 4.25 (s, 1H); 4.18-4.01 (m, 5H); 3.90 (s, 3H); 3.87 (s, 3H); 2.48-2.39 (m, 2H); 0.75-0.59 (m, 1H).

The following compounds (Table 13) were synthesized using methods analogous to those described in EXAMPLES 46 and 47 from commercially available materials or intermediates whose syntheses are described above.

TABLE 13

| Example | Structure | LCMS (M + H)$^+$ |
|---|---|---|
| 48 | 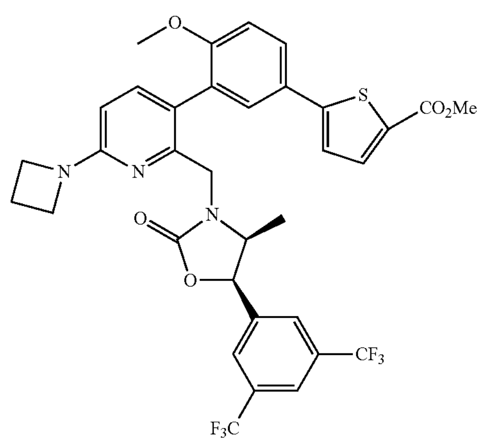 [SMILES: COC(=O)c1ccc(-c2ccc(OC)c(-c3ccc(N4CCC4)nc3CN3C(=O)O[C@H](c4cc(C(F)(F)F)cc(C(F)(F)F)c4)[C@@H]3C)c2)s1] | 706.2 |
| 49 | 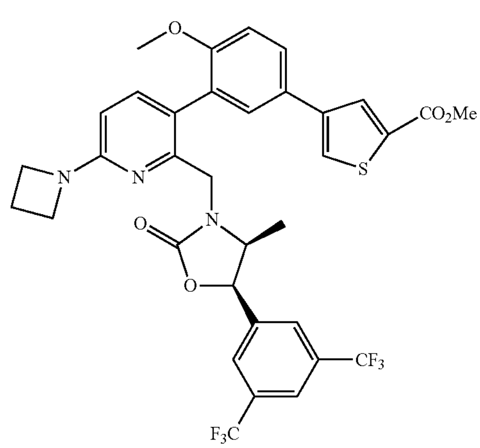 [SMILES: COC(=O)c1cc(-c2ccc(OC)c(-c3ccc(N4CCC4)nc3CN3C(=O)O[C@H](c4cc(C(F)(F)F)cc(C(F)(F)F)c4)[C@@H]3C)c2)cs1] | 706.3 |

TABLE 13-continued
| Example | Structure | LCMS (M + H)+ |
|---------|-----------|---------------|
| 50 | 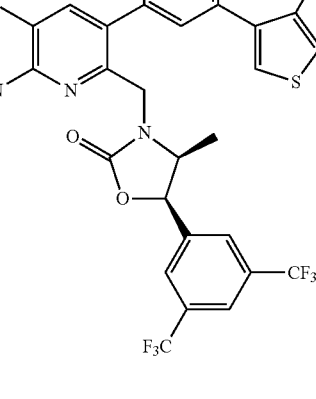 | 798.2 |
| 51 | 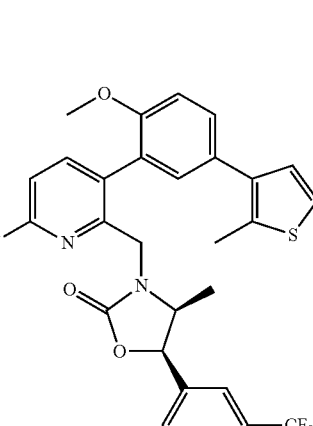 | 720.3 |
| 52 | 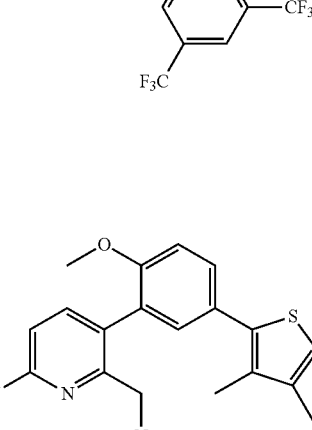 | 734.4 |

TABLE 13-continued

| Example | Structure | LCMS (M + H)+ |
| --- | --- | --- |
| 53 | 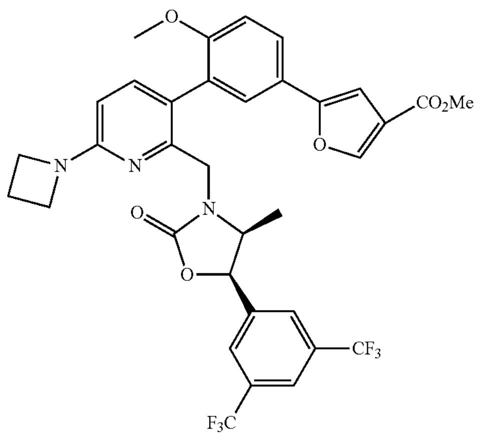 [SMILES: COC(=O)c1coc(-c2ccc(OC)c(-c3ccc(N4CCC4)nc3CN3C(=O)O[C@H](c4cc(C(F)(F)F)cc(C(F)(F)F)c4)[C@@H]3C)c2)c1] | 690.2 |
| 54 | 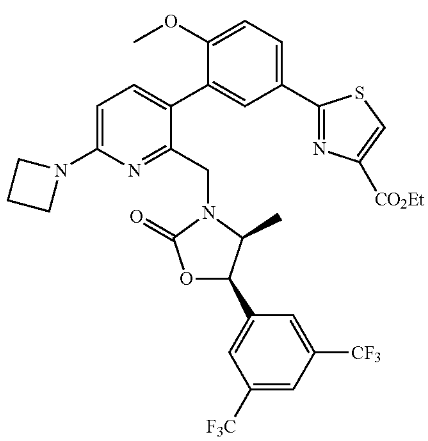 [SMILES: CCOC(=O)c1csc(-c2ccc(OC)c(-c3ccc(N4CCC4)nc3CN3C(=O)O[C@H](c4cc(C(F)(F)F)cc(C(F)(F)F)c4)[C@@H]3C)c2)n1] | 721.2 |
| 55 | 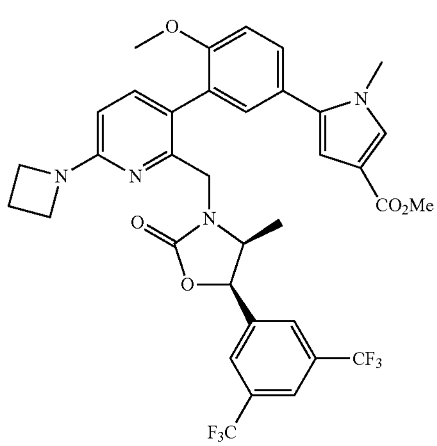 [SMILES: COC(=O)c1cc(-c2ccc(OC)c(-c3ccc(N4CCC4)nc3CN3C(=O)O[C@H](c4cc(C(F)(F)F)cc(C(F)(F)F)c4)[C@@H]3C)c2)n(C)c1] | 703.3 |

TABLE 13-continued
| Example | Structure | LCMS (M + H)+ |
| --- | --- | --- |
| 56 | 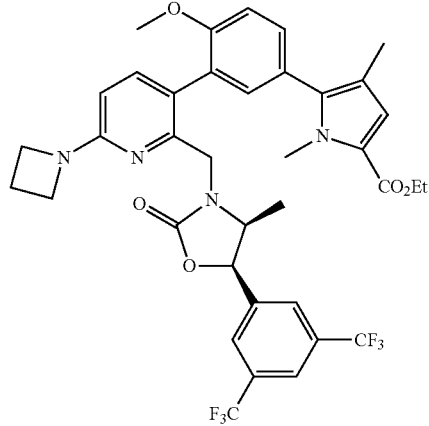 [SMILES: CCOC(=O)c1cc(C)c(-c2ccc(OC)c(-c3ccc(N4CCC4)nc3CN3C(=O)O[C@H](c4cc(C(F)(F)F)cc(C(F)(F)F)c4)[C@@H]3C)c2)n1C] | 731.4 |
| 57 | 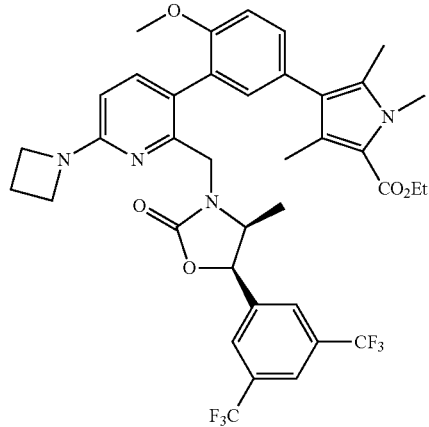 [SMILES: CCOC(=O)c1c(C)c(-c2ccc(OC)c(-c3ccc(N4CCC4)nc3CN3C(=O)O[C@H](c4cc(C(F)(F)F)cc(C(F)(F)F)c4)[C@@H]3C)c2)c(C)n1C] | 745.4 |
| 58 | 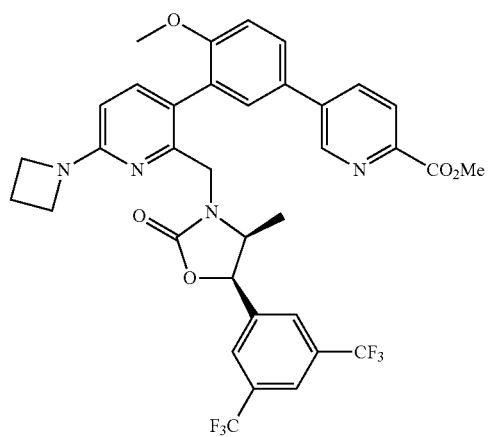 [SMILES: COC(=O)c1ccc(-c2ccc(OC)c(-c3ccc(N4CCC4)nc3CN3C(=O)O[C@H](c4cc(C(F)(F)F)cc(C(F)(F)F)c4)[C@@H]3C)c2)cn1] | 701.3 |

TABLE 13-continued

| Example | Structure | LCMS (M + H)+ |
|---|---|---|
| 59 | 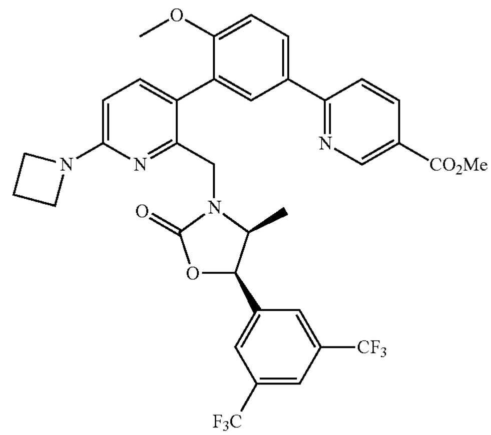 [SMILES: COC(=O)c1ccc(-c2ccc(OC)c(-c3ccc(N4CCC4)nc3CN3C(=O)O[C@H](c4cc(C(F)(F)F)cc(C(F)(F)F)c4)[C@@H]3C)c2)nc1] | 701.3 |

Example 60

3-{3-[6-Azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}propanoic acid Methyl 3-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}propanoate (93 mg, 0.143 mmol) was dissolved in dioxane (2 mL) and water (0.5 mL). As the solution was stirred vigorously, 1M lithium hydroxide (0.285 mL, 0.285 mmol) was added dropwise. The reaction was stirred at room temperature for 1 hr and then quenched with acetic acid (0.020 mL, 0.357 mmol). The reaction was diluted with ethyl acetate (15 mL) and washed with water (2×10 mL) and brine (10 mL). The organic layer was dried over sodium sulfate, filtered, and concentrated. The residue was redissolved in dichloromethane (2 mL) and heptanes (2 mL) and concentrated again. Purification of the residue by flash chromatography on silica gel (0 to 100% ethyl acetate/hexanes) afforded 3-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}propanoic acid. LCMS=638.2 (M+H)+. $^1$H NMR (CDCl$_3$, 500 MHz) δ 7.85 (s, 1H), 7.72 (s, 2H), 7.30 (d, J=8.7 Hz, 1H), 7.17 (dd, J=8.4, 2.2 Hz, 1H), 7.00 (bs, 1H), 6.87 (d, J=8.4 Hz, 1H), 6.27 (d, J=8.3 Hz, 1H), 5.61 (bs, 1H), 4.8-4.4 (m, 2H), 4.07 (m, 4H), 3.85 (m, 1H), 3.75 (s, 3H), 2.92 (m, 2H), 2.64 (m, 2H), 2.41 (m, 2H), 0.75-0.58 (m, 3H).

Example 61

3-{3-[6-Azetidin-1-yl-2-({(4S,5R)-5-[3,5-bis(trifluoromethyl)phenyl]-4-methyl-2-oxo-1,3-oxazolidin-3-yl}methyl)-4-methylpyridin-3-yl]-4-methoxyphenyl}propanoic acid Methyl 3-{3-[6-azetidin-1-yl-2-({(4S,5R)-5-[3,5-bis(trifluoromethyl)phenyl]-4-methyl-2-oxo-1,3-oxazolidin-3-yl}methyl)-4-methylpyridin-3-yl]-4-methoxyphenyl}propanoate (atropisomer A) (450 mg, 0.676 mmol) was dissolved in dioxane (8 mL) and water (2 mL). As the reaction stirred vigorously, 1M lithium hydroxide (1.352 mL, 1.352 mmol) was added dropwise. The reaction was stirred at room temperature for 1 hr and then quenched with acetic acid (0.097 mL, 1.690 mmol). The reaction was diluted with ethyl acetate (50 mL) and washed with water (2×25 mL) and brine (25 mL). The organic layer was dried over sodium sulfate, filtered, and concentrated. The residue was redissolved in dichloromethane (3 mL) and heptanes (3 mL) and concentrated again. Purification of the residue by flash chromatography on silica gel (0 to 100% ethyl acetate/hexanes) afforded 3-{3-[6-azetidin-1-yl-2-({(4S,5R)-5-[3,5-bis(trifluoromethyl)phenyl]-4-methyl-2-oxo-1,3-oxazolidin-3-yl})methyl)-4-methylpyridin-3-yl]-4-methoxyphenyl}propanoic acid as a single atropisomer. LCMS=652.5 (M+H)+. $^1$H NMR (CDCl$_3$, 500 MHz) δ 7.85 (s, 1H), 7.74 (s, 2H), 7.20 (dd, J=8.2, 2.2 Hz, 1H), 6.96 (bs, 1H), 6.89 (d, J=8.5 Hz, 1H), 6.15 (s, 1H), 5.76 (d, J=8.5 Hz, 1H), 4.70-4.50 (m, 2H), 4.08 (m, 4H), 3.70 (s, 3H), 3.67 (m, 1H), 2.94 (m, 2H), 2.70 (m, 1H), 2.58 (m, 1H), 2.41 (m, 2H), 1.95 (s, 3H), 0.67 (d, J=6.7 Hz, 3H).

The following compounds (Table 14) were synthesized using methods analogous to those described in EXAMPLES 60 and 61 from commercially available materials or intermediates whose syntheses are described above.

TABLE 14

| Example | Molecular structure | LCMS (M + H)+ |
|---|---|---|
| 62 | 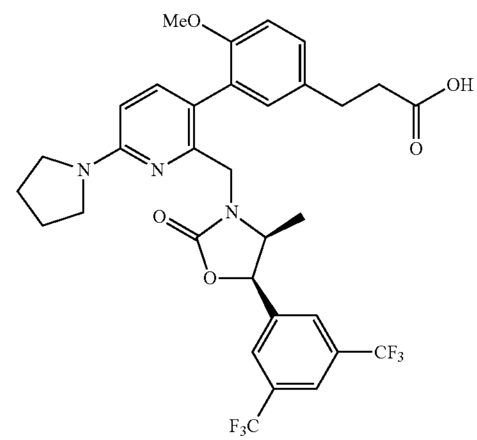 [SMILES: COc1ccc(CCC(=O)O)cc1-c1ccc(N2CCCC2)nc1CN1C(=O)O[C@H](c2cc(C(F)(F)F)cc(C(F)(F)F)c2)[C@@H]1C] | 652.2 |
| 63 | 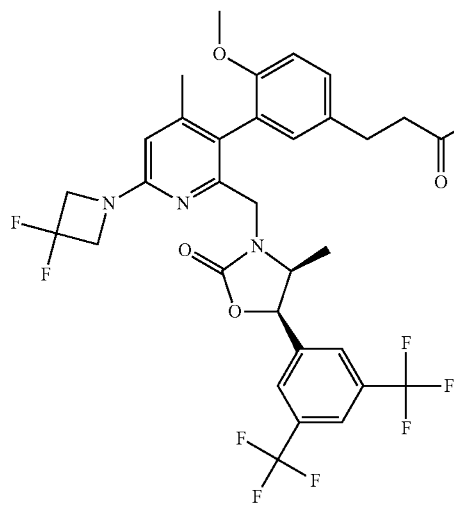 | 688.3 |
| 64 | 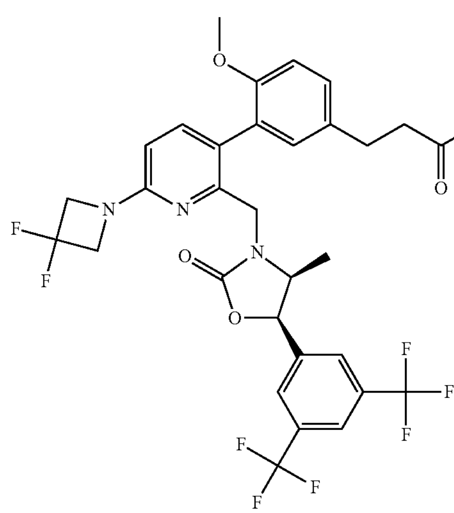 | 674.1 |

TABLE 14-continued

| Example | Molecular structure | LCMS (M + H)+ |
|---------|---------------------|---------------|
| 65 | 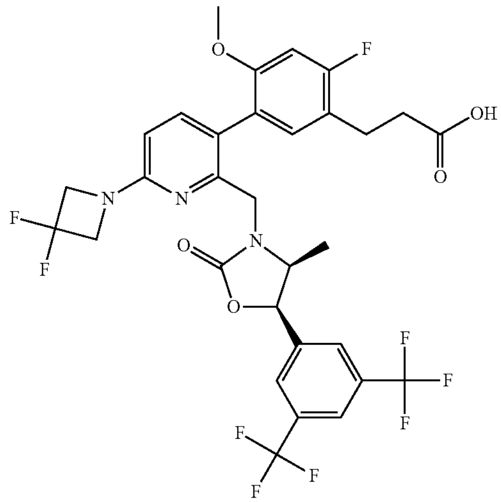 [SMILES: COc1cc(F)c(CCC(=O)O)cc1-c1ccc(N2CC(F)(F)C2)nc1CN1C(=O)O[C@H](c2cc(C(F)(F)F)cc(C(F)(F)F)c2)[C@@H]1C] | 692.3 |
| 66 | 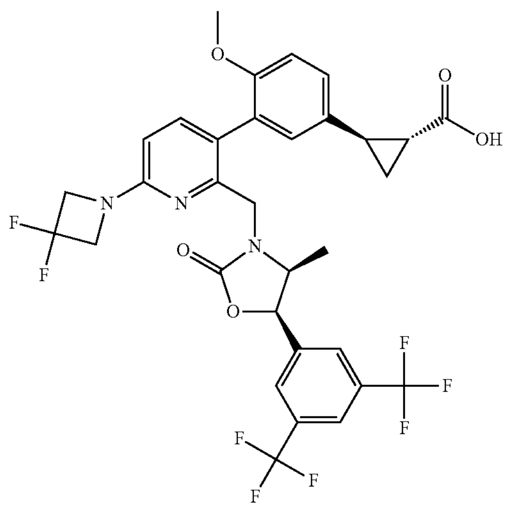 [SMILES: COc1ccc([C@@H]2C[C@H]2C(=O)O)cc1-c1ccc(N2CC(F)(F)C2)nc1CN1C(=O)O[C@H](c2cc(C(F)(F)F)cc(C(F)(F)F)c2)[C@@H]1C] | 686.1 |
| 67 | 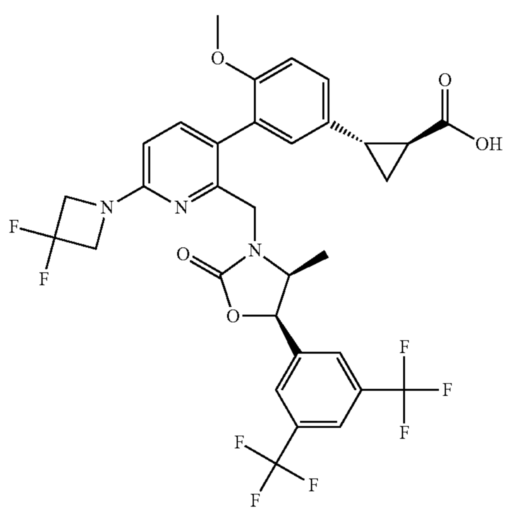 [SMILES: COc1ccc([C@H]2C[C@@H]2C(=O)O)cc1-c1ccc(N2CC(F)(F)C2)nc1CN1C(=O)O[C@H](c2cc(C(F)(F)F)cc(C(F)(F)F)c2)[C@@H]1C] | 686.2 |

TABLE 14-continued
| Example | Molecular structure | LCMS (M + H)+ |
|---|---|---|
| 68 | 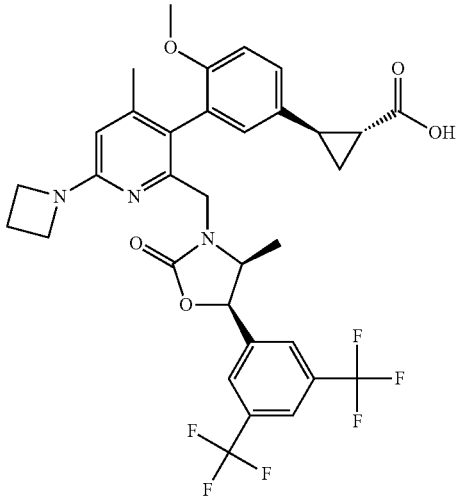 [SMILES: COc1ccc([C@@H]2C[C@H]2C(=O)O)cc1-c1c(C)cc(N2CCC2)nc1CN1C(=O)O[C@H](c2cc(C(F)(F)F)cc(C(F)(F)F)c2)[C@@H]1C] | 664.2 |
| 69 | 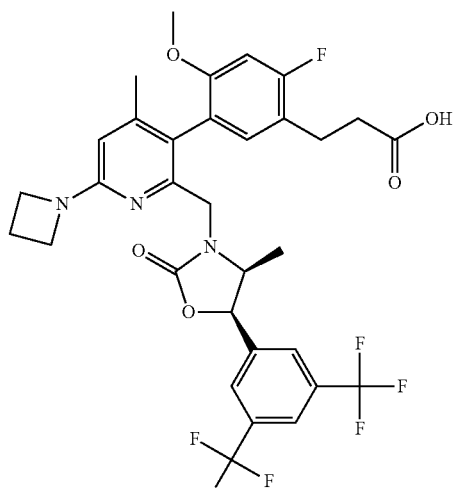 | 670.2 |
| 70 | 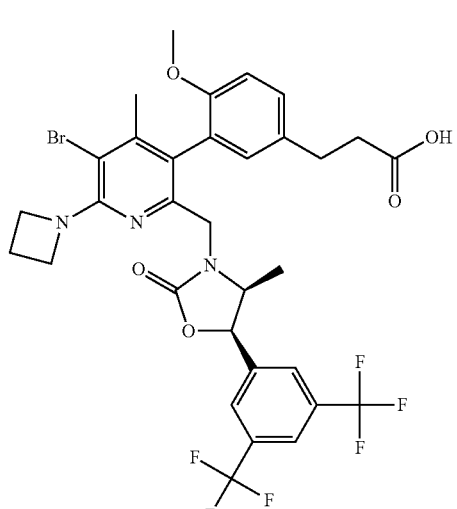 | 730.3, 732.3 |

TABLE 14-continued

| Example | Molecular structure | LCMS (M + H)+ |
|---|---|---|
| 71 | 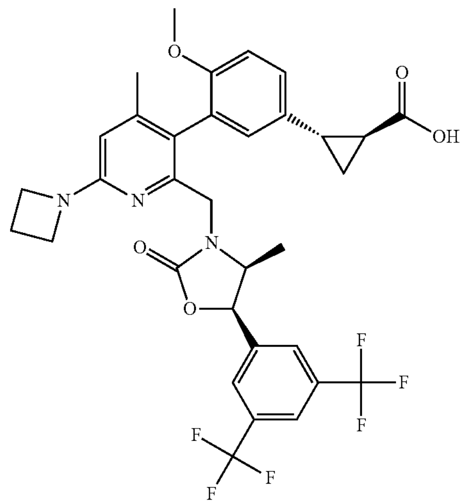 [SMILES: COc1ccc([C@H]2C[C@@H]2C(=O)O)cc1-c1c(C)cc(N2CCC2)nc1CN1C(=O)O[C@H](c2cc(C(F)(F)F)cc(C(F)(F)F)c2)[C@@H]1C] | 664.3 |
| 72 | 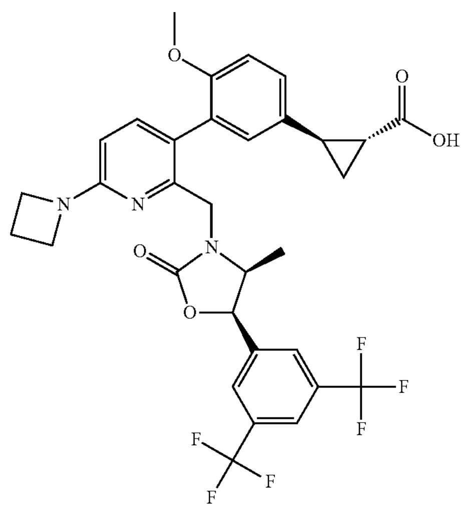 [SMILES: COc1ccc([C@@H]2C[C@H]2C(=O)O)cc1-c1ccc(N2CCC2)nc1CN1C(=O)O[C@H](c2cc(C(F)(F)F)cc(C(F)(F)F)c2)[C@@H]1C] | 650.2 |
| 73 | 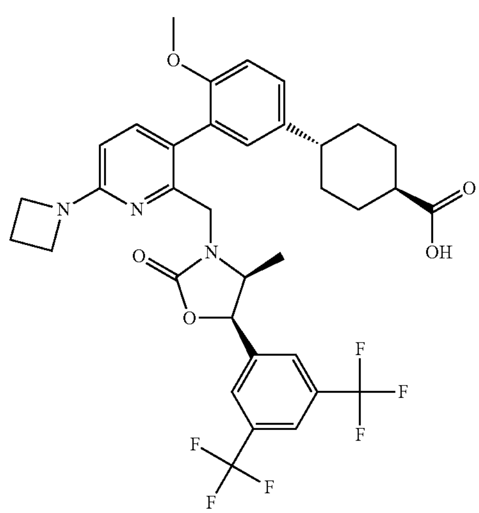 [SMILES: COc1ccc([C@H]2CC[C@H](C(=O)O)CC2)cc1-c1ccc(N2CCC2)nc1CN1C(=O)O[C@H](c2cc(C(F)(F)F)cc(C(F)(F)F)c2)[C@@H]1C] | 692.2 |

TABLE 14-continued

| Example | Molecular structure | LCMS (M + H)+ |
|---|---|---|
| 74 | 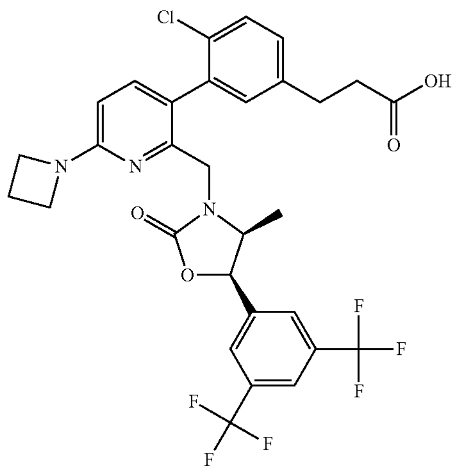 [SMILES: C[C@H]1[C@@H](c2cc(C(F)(F)F)cc(C(F)(F)F)c2)OC(=O)N1Cc1nc(N2CCC2)ccc1-c1cc(CCC(=O)O)ccc1Cl] | 642.1 |
| 75 | 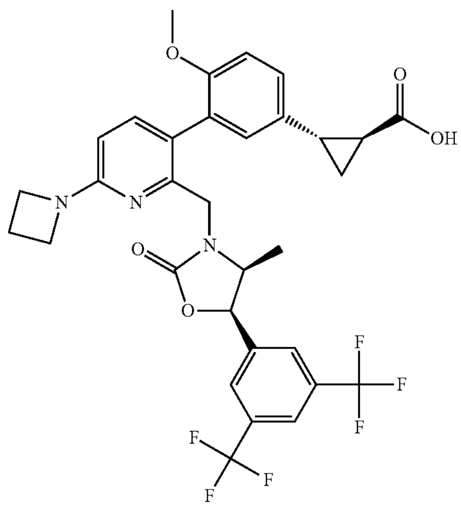 [SMILES: COc1ccc([C@H]2C[C@@H]2C(=O)O)cc1-c1ccc(N2CCC2)nc1CN1C(=O)O[C@H](c2cc(C(F)(F)F)cc(C(F)(F)F)c2)[C@@H]1C] | 650.2 |
| 76 | 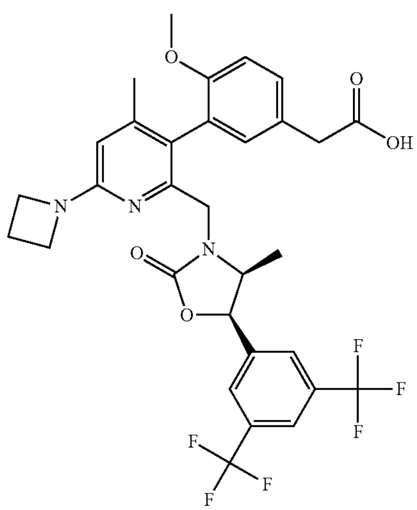 [SMILES: COc1ccc(CC(=O)O)cc1-c1c(C)cc(N2CCC2)nc1CN1C(=O)O[C@H](c2cc(C(F)(F)F)cc(C(F)(F)F)c2)[C@@H]1C] | 638.2 |

TABLE 14-continued

| Example | Molecular structure | LCMS (M + H)+ |
|---------|---------------------|---------------|
| 77 | 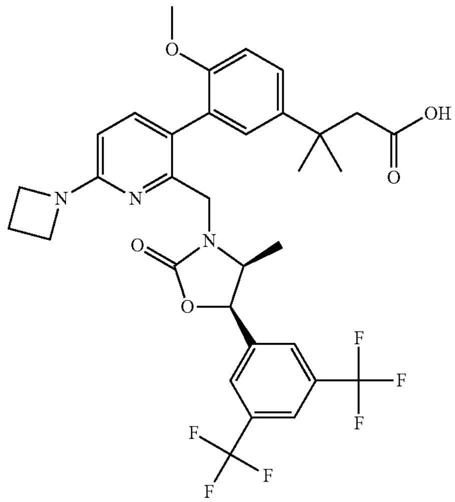 [SMILES: COc1ccc(C(C)(C)CC(=O)O)cc1-c1ccc(N2CCC2)nc1CN1C(=O)O[C@H](c2cc(C(F)(F)F)cc(C(F)(F)F)c2)[C@@H]1C] | 666.2 |
| 78 | 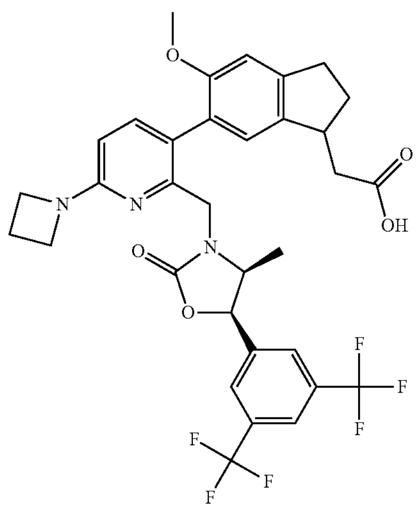 [SMILES: COc1cc2c(cc1-c1ccc(N3CCC3)nc1CN1C(=O)O[C@H](c3cc(C(F)(F)F)cc(C(F)(F)F)c3)[C@@H]1C)C(CC(=O)O)CC2] | 664.2 |
| 79 | 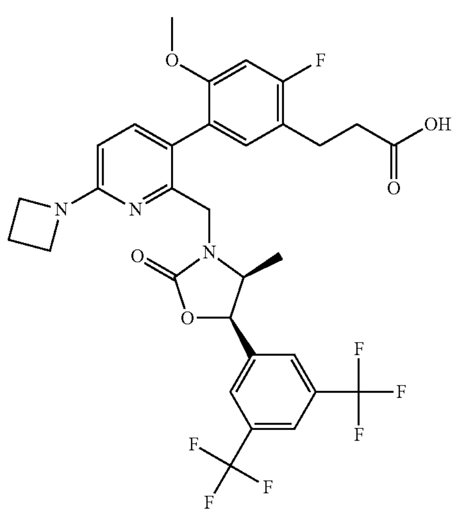 [SMILES: COc1cc(F)c(CCC(=O)O)cc1-c1ccc(N2CCC2)nc1CN1C(=O)O[C@H](c2cc(C(F)(F)F)cc(C(F)(F)F)c2)[C@@H]1C] | 656.2 |

TABLE 14-continued
| Example | Molecular structure | LCMS (M + H)+ |
|---|---|---|
| 80 | 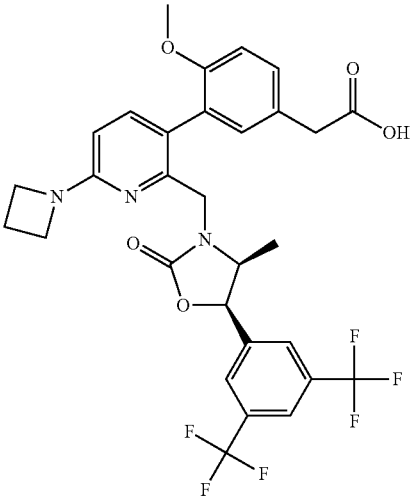 [SMILES: COc1ccc(CC(=O)O)cc1-c1ccc(N2CCC2)nc1CN1C(=O)O[C@H](c2cc(C(F)(F)F)cc(C(F)(F)F)c2)[C@@H]1C] | 624.1 |
| 81 | 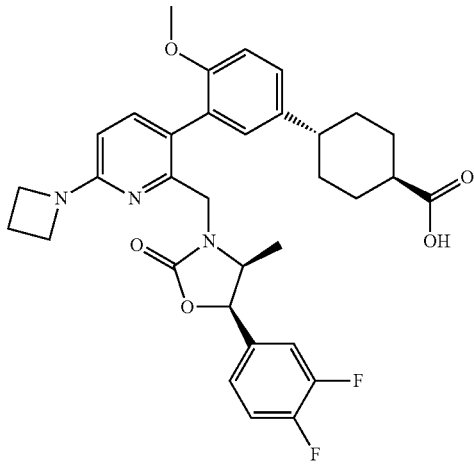 [SMILES: COc1ccc([C@H]2CC[C@H](C(=O)O)CC2)cc1-c1ccc(N2CCC2)nc1CN1C(=O)O[C@H](c2ccc(F)c(F)c2)[C@@H]1C] | 592.2 |
| 82 | 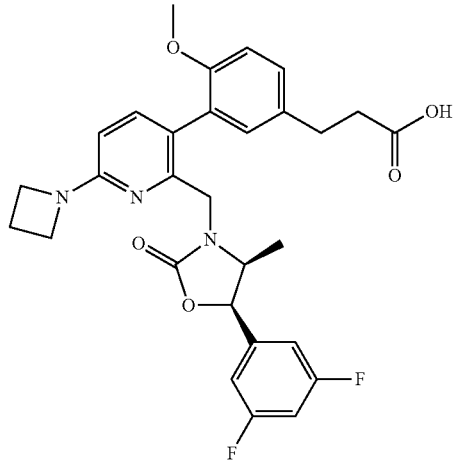 [SMILES: COc1ccc(CCC(=O)O)cc1-c1ccc(N2CCC2)nc1CN1C(=O)O[C@H](c2cc(F)cc(F)c2)[C@@H]1C] | 538.2 |

TABLE 14-continued

| Example | Molecular structure | LCMS (M + H)+ |
|---|---|---|
| 83 | 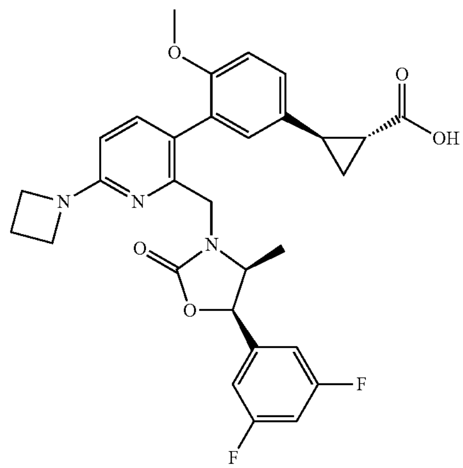 [SMILES: COc1ccc([C@@H]2C[C@H]2C(=O)O)cc1-c1ccc(N2CCC2)nc1CN1C(=O)O[C@H](c2cc(F)cc(F)c2)[C@@H]1C] | 550.0 |
| 84 | 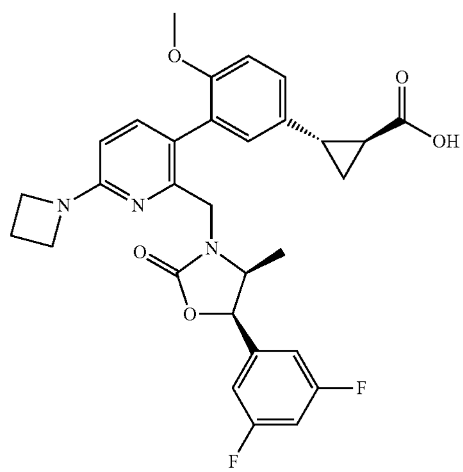 [SMILES: COc1ccc([C@H]2C[C@@H]2C(=O)O)cc1-c1ccc(N2CCC2)nc1CN1C(=O)O[C@H](c2cc(F)cc(F)c2)[C@@H]1C] | 550.0 |
| 85 | 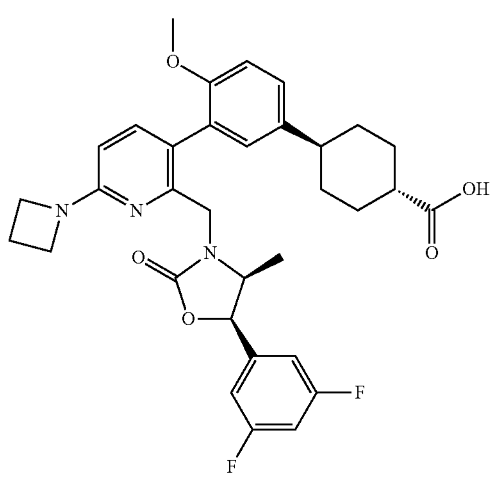 [SMILES: COc1ccc([C@H]2CC[C@H](C(=O)O)CC2)cc1-c1ccc(N2CCC2)nc1CN1C(=O)O[C@H](c2cc(F)cc(F)c2)[C@@H]1C] | 592.2 |

TABLE 14-continued
| Example | Molecular structure | LCMS (M + H)+ |
|---|---|---|
| 86 | 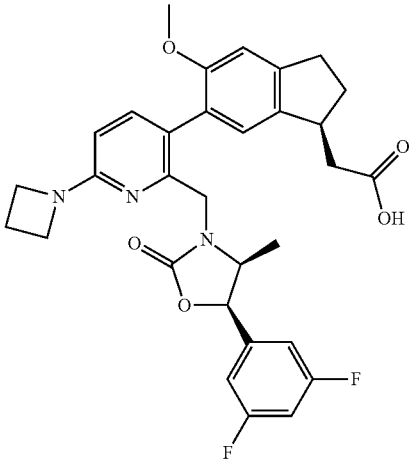 [SMILES: COc1cc2c(cc1-c1ccc(N3CCC3)nc1CN1C(=O)O[C@H](c3cc(F)cc(F)c3)[C@@H]1C)[C@H](CC(=O)O)CC2] | 564.2 |
| 87 | 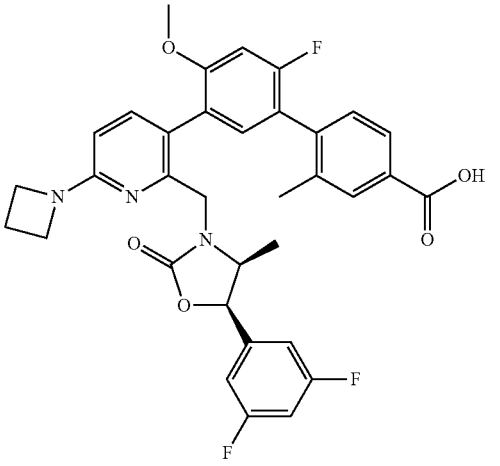 [SMILES: COc1cc(F)c(-c2ccc(C(=O)O)cc2C)cc1-c1ccc(N2CCC2)nc1CN1C(=O)O[C@H](c2cc(F)cc(F)c2)[C@@H]1C] | 618.1 |
| 88 | 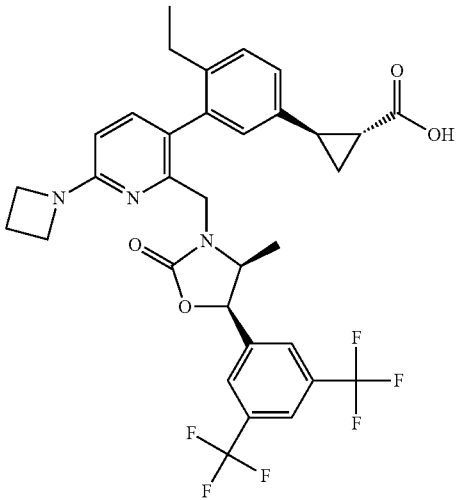 [SMILES: CCc1ccc([C@@H]2C[C@H]2C(=O)O)cc1-c1ccc(N2CCC2)nc1CN1C(=O)O[C@H](c2cc(C(F)(F)F)cc(C(F)(F)F)c2)[C@@H]1C] | 648.5 |

TABLE 14-continued

| Example | Molecular structure | LCMS (M + H)+ |
|---------|---------------------|---------------|
| 89 | 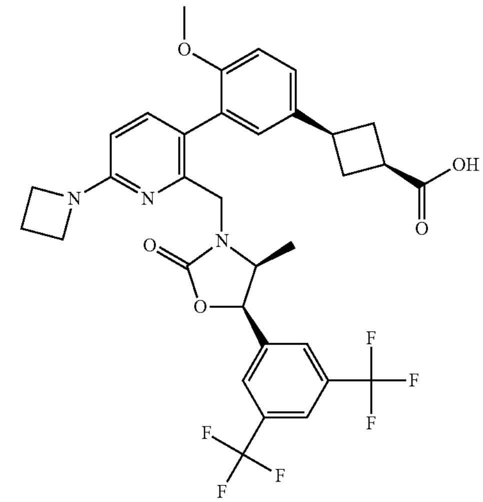 [SMILES: COc1ccc([C@H]2C[C@@H](C(=O)O)C2)cc1-c1ccc(N2CCC2)nc1CN1C(=O)O[C@H](c2cc(C(F)(F)F)cc(C(F)(F)F)c2)[C@@H]1C] | 664.2 |
| 90 | 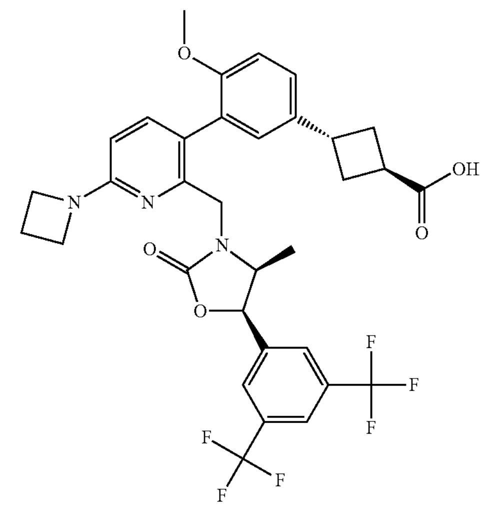 [SMILES: COc1ccc([C@H]2C[C@H](C(=O)O)C2)cc1-c1ccc(N2CCC2)nc1CN1C(=O)O[C@H](c2cc(C(F)(F)F)cc(C(F)(F)F)c2)[C@@H]1C] | 664.2 |
| 91 | 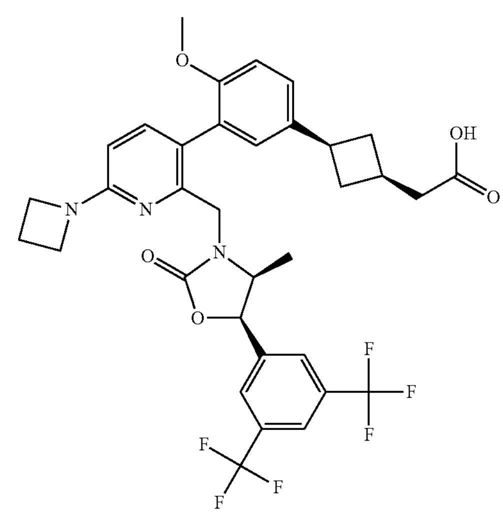 [SMILES: COc1ccc([C@H]2C[C@@H](CC(=O)O)C2)cc1-c1ccc(N2CCC2)nc1CN1C(=O)O[C@H](c2cc(C(F)(F)F)cc(C(F)(F)F)c2)[C@@H]1C] | 678.3 |

TABLE 14-continued

| Example | Molecular structure | LCMS (M + H)+ |
|---------|---------------------|---------------|
| 92 | 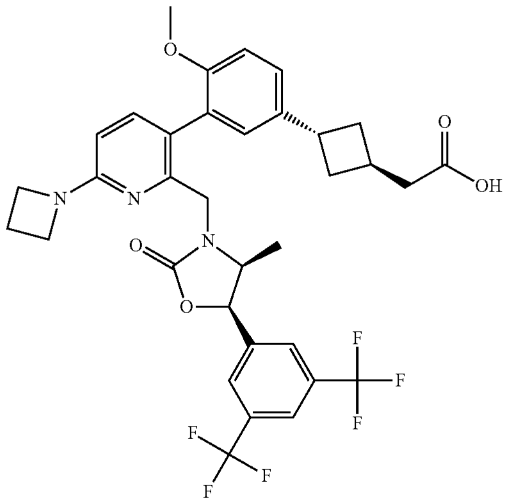 [SMILES: COc1ccc([C@H]2C[C@H](CC(=O)O)C2)cc1-c1ccc(N2CCC2)nc1CN1C(=O)O[C@H](c2cc(C(F)(F)F)cc(C(F)(F)F)c2)[C@@H]1C] | 678.3 |
| 93 | 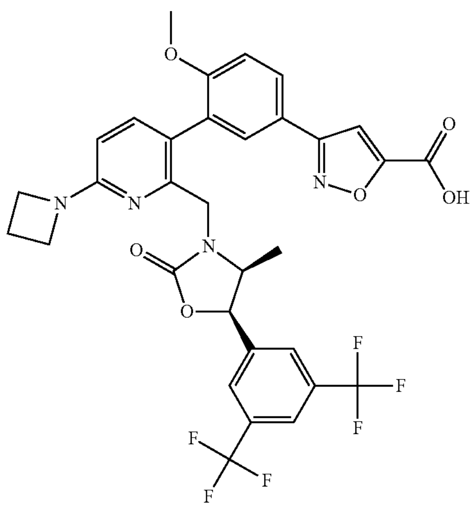 [SMILES: COc1ccc(-c2cc(C(=O)O)on2)cc1-c1ccc(N2CCC2)nc1CN1C(=O)O[C@H](c2cc(C(F)(F)F)cc(C(F)(F)F)c2)[C@@H]1C] | 677.2 |
| 94 | 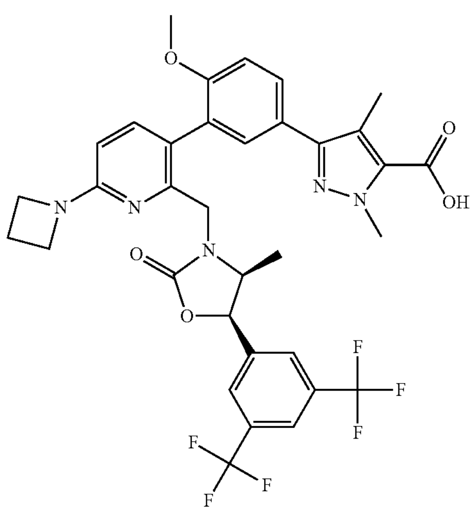 [SMILES: COc1ccc(-c2nn(C)c(C(=O)O)c2C)cc1-c1ccc(N2CCC2)nc1CN1C(=O)O[C@H](c2cc(C(F)(F)F)cc(C(F)(F)F)c2)[C@@H]1C] | 704.3 |

TABLE 14-continued
| Example | Molecular structure | LCMS (M + H)+ |
|---|---|---|
| 95 | 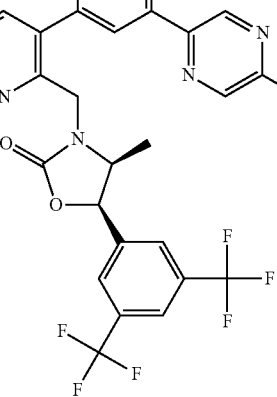 | 688.3 |
| 96 | 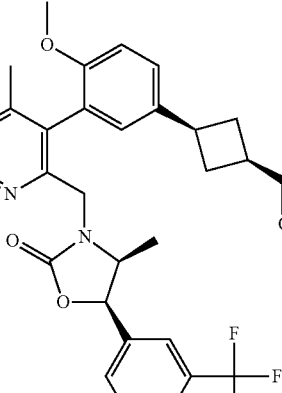 | 678.3 |
| 97 | 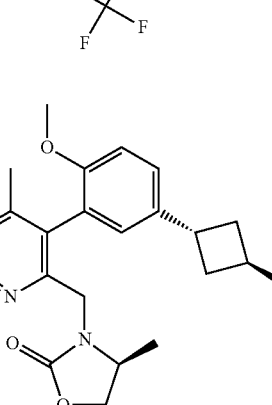 | 678.3 |

TABLE 14-continued
| Example | Molecular structure | LCMS (M + H)+ |
|---|---|---|
| 98 | 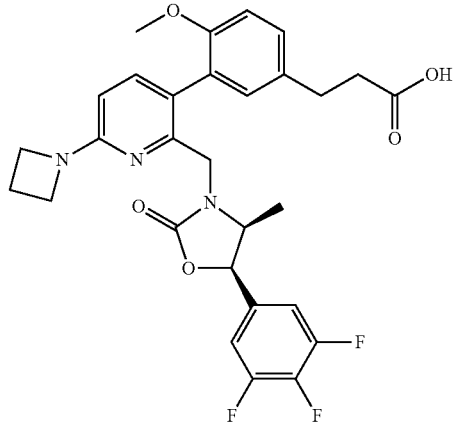 [SMILES: COc1ccc(CCC(=O)O)cc1-c1ccc(N2CCC2)nc1CN1C(=O)O[C@H](c2cc(F)c(F)c(F)c2)[C@@H]1C] | 556.0 |
| 99 | 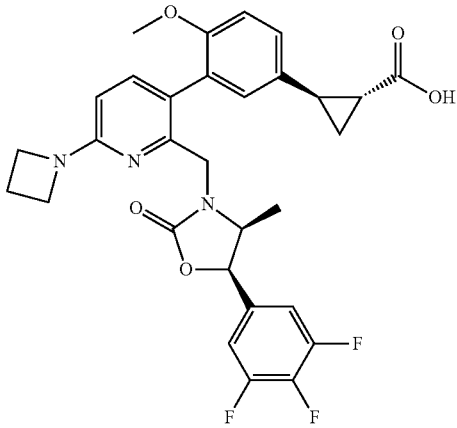 [SMILES: COc1ccc([C@@H]2C[C@H]2C(=O)O)cc1-c1ccc(N2CCC2)nc1CN1C(=O)O[C@H](c2cc(F)c(F)c(F)c2)[C@@H]1C] | 368.1 |
| 100 | 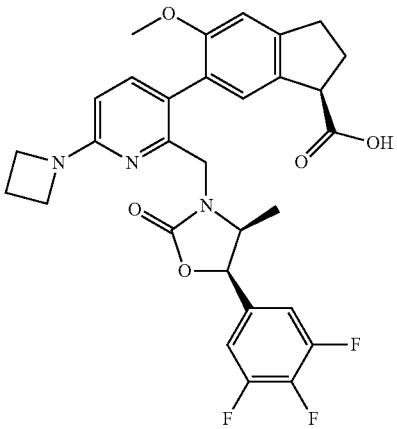 [SMILES: COc1cc2c(cc1-c1ccc(N3CCC3)nc1CN1C(=O)O[C@H](c3cc(F)c(F)c(F)c3)[C@@H]1C)[C@H](C(=O)O)CC2] | 582.1 |

TABLE 14-continued

| Example | Molecular structure | LCMS (M + H)+ |
|---|---|---|
| 101 | 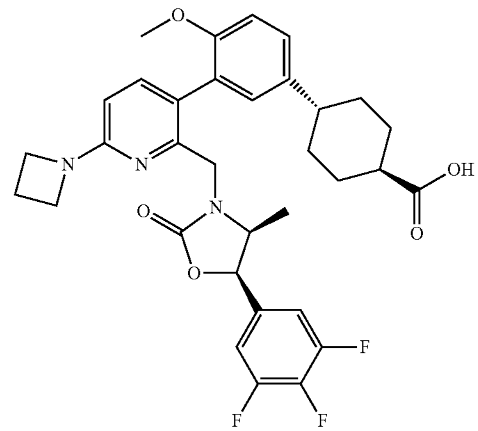 [SMILES: COc1ccc([C@H]2CC[C@H](C(=O)O)CC2)cc1-c1ccc(N2CCC2)nc1CN1C(=O)O[C@H](c2cc(F)c(F)c(F)c2)[C@@H]1C] | 610.2 |
| 102 | 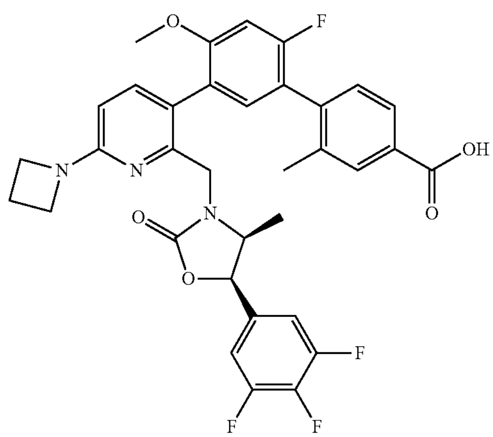 [SMILES: COc1cc(F)c(-c2ccc(C(=O)O)cc2C)cc1-c1ccc(N2CCC2)nc1CN1C(=O)O[C@H](c2cc(F)c(F)c(F)c2)[C@@H]1C] | 636.1 |
| 103 | 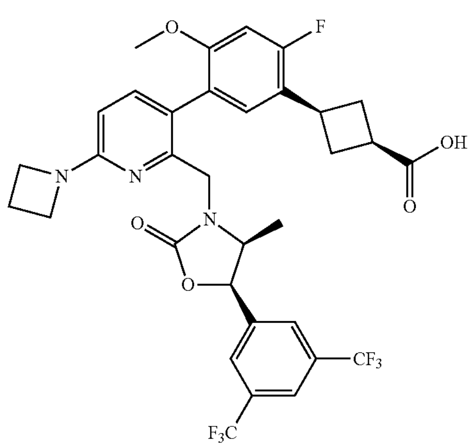 [SMILES: COc1cc(F)c([C@H]2C[C@@H](C(=O)O)C2)cc1-c1ccc(N2CCC2)nc1CN1C(=O)O[C@H](c2cc(C(F)(F)F)cc(C(F)(F)F)c2)[C@@H]1C] | 682.2 |

TABLE 14-continued

| Example | Molecular structure | LCMS (M + H)+ |
|---------|---------------------|---------------|
| 104 | 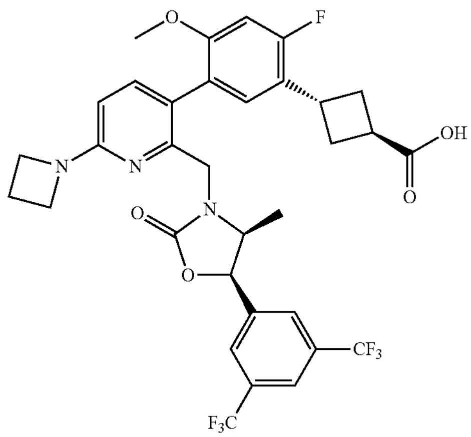 [SMILES: COc1cc(F)c([C@H]2C[C@H](C(=O)O)C2)cc1-c1ccc(N2CCC2)nc1CN1C(=O)O[C@H](c2cc(C(F)(F)F)cc(C(F)(F)F)c2)[C@@H]1C] | 682.3 |
| 105 | 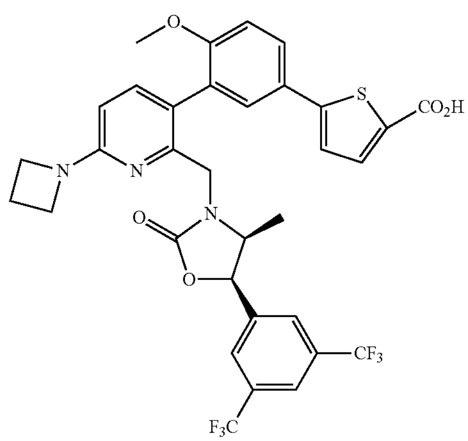 | 692.1 |
| 106 | 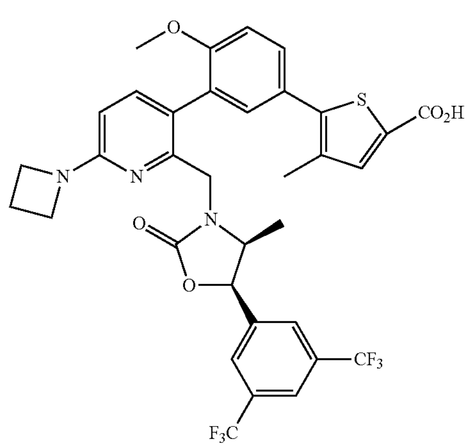 [SMILES: COc1ccc(-c2sc(C(=O)O)cc2C)cc1-c1ccc(N2CCC2)nc1CN1C(=O)O[C@H](c2cc(C(F)(F)F)cc(C(F)(F)F)c2)[C@@H]1C] | 706.3 |

TABLE 14-continued
| Example | Molecular structure | LCMS (M + H)+ |
|---|---|---|
| 107 | 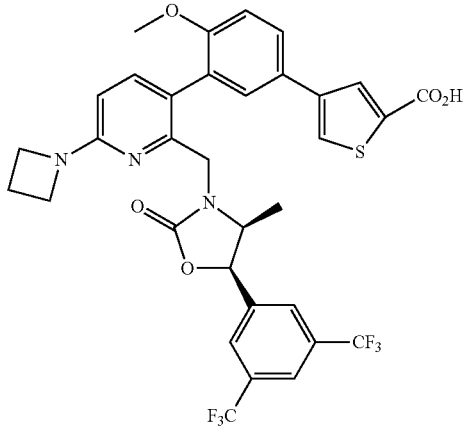 [SMILES: COc1ccc(-c2csc(C(=O)O)c2)cc1-c1ccc(N2CCC2)nc1CN1C(=O)O[C@H](c2cc(C(F)(F)F)cc(C(F)(F)F)c2)[C@@H]1C] | 692.2 |
| 108 | 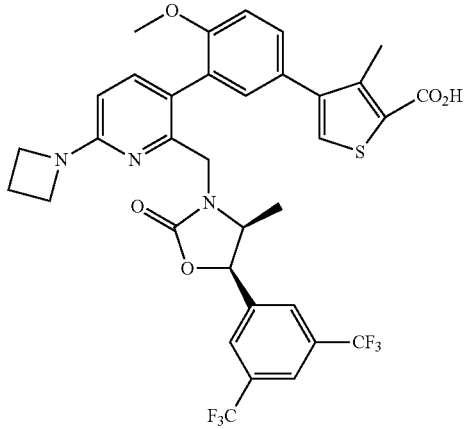 [SMILES: COc1ccc(-c2csc(C(=O)O)c2C)cc1-c1ccc(N2CCC2)nc1CN1C(=O)O[C@H](c2cc(C(F)(F)F)cc(C(F)(F)F)c2)[C@@H]1C] | 706.3 |
| 109 | 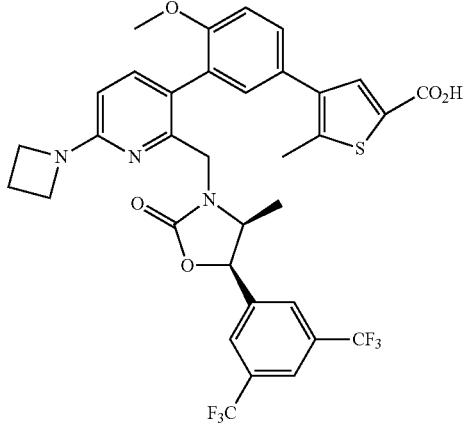 [SMILES: COc1ccc(-c2cc(C(=O)O)sc2C)cc1-c1ccc(N2CCC2)nc1CN1C(=O)O[C@H](c2cc(C(F)(F)F)cc(C(F)(F)F)c2)[C@@H]1C] | 706.3 |

TABLE 14-continued

| Example | Molecular structure | LCMS (M + H)+ |
|---|---|---|
| 110 | 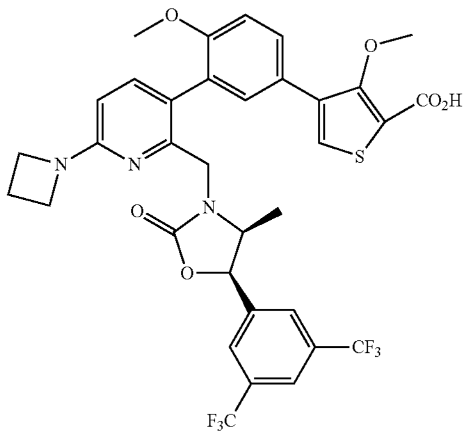 [SMILES: COc1ccc(-c2csc(C(=O)O)c2OC)cc1-c1ccc(N2CCC2)nc1CN1C(=O)O[C@H](c2cc(C(F)(F)F)cc(C(F)(F)F)c2)[C@@H]1C] | 722.3 |
| 111 | 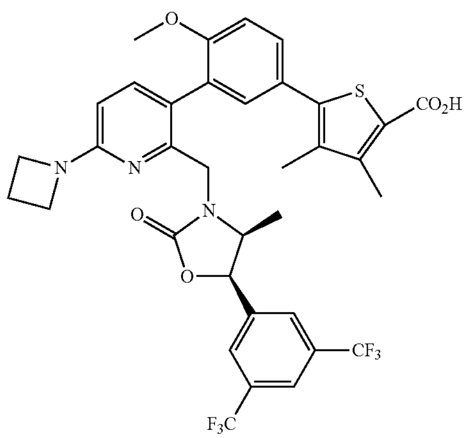 [SMILES: COc1ccc(-c2sc(C(=O)O)c(C)c2C)cc1-c1ccc(N2CCC2)nc1CN1C(=O)O[C@H](c2cc(C(F)(F)F)cc(C(F)(F)F)c2)[C@@H]1C] | 720.3 |
| 112 | 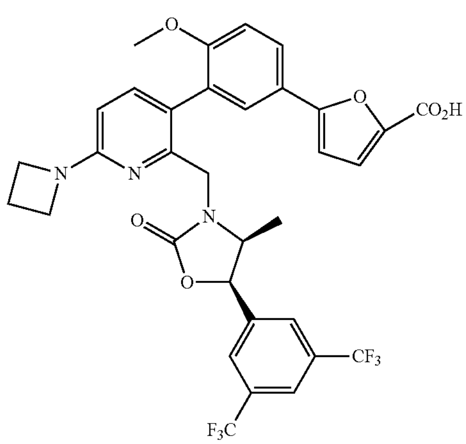 [SMILES: COc1ccc(-c2ccc(C(=O)O)o2)cc1-c1ccc(N2CCC2)nc1CN1C(=O)O[C@H](c2cc(C(F)(F)F)cc(C(F)(F)F)c2)[C@@H]1C] | 676.2 |

TABLE 14-continued
| Example | Molecular structure | LCMS (M + H)+ |
|---|---|---|
| 113 | 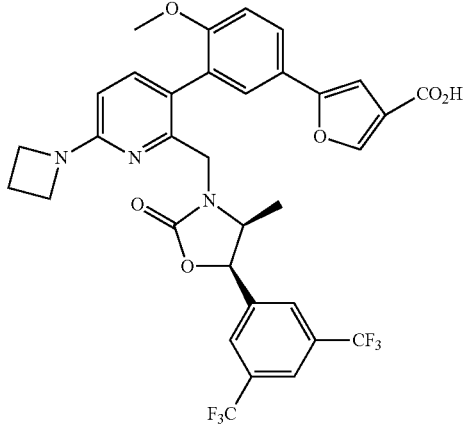 [SMILES: COc1ccc(-c2cc(C(=O)O)co2)cc1-c1ccc(N2CCC2)nc1CN1C(=O)O[C@H](c2cc(C(F)(F)F)cc(C(F)(F)F)c2)[C@@H]1C] | 676.2 |
| 114 | 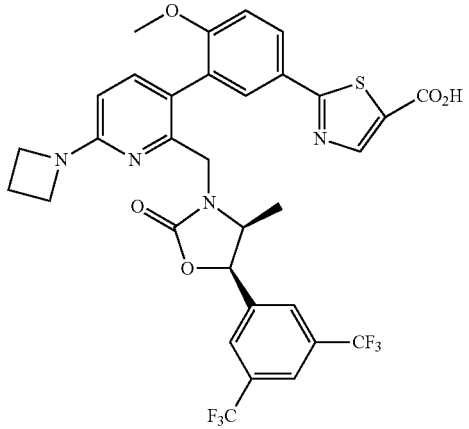 [SMILES: COc1ccc(-c2ncc(C(=O)O)s2)cc1-c1ccc(N2CCC2)nc1CN1C(=O)O[C@H](c2cc(C(F)(F)F)cc(C(F)(F)F)c2)[C@@H]1C] | 693.3 |
| 115 | 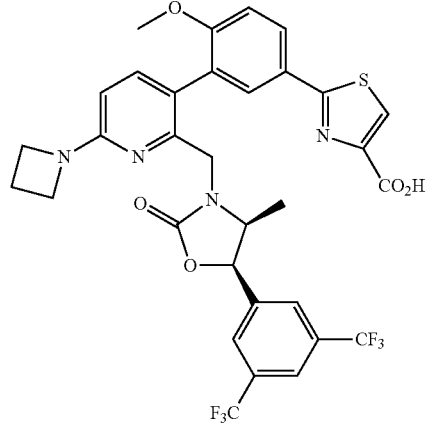 [SMILES: COc1ccc(-c2nc(C(=O)O)cs2)cc1-c1ccc(N2CCC2)nc1CN1C(=O)O[C@H](c2cc(C(F)(F)F)cc(C(F)(F)F)c2)[C@@H]1C] | 693.1 |

TABLE 14-continued

| Example | Molecular structure | LCMS (M + H)+ |
| --- | --- | --- |
| 116 | 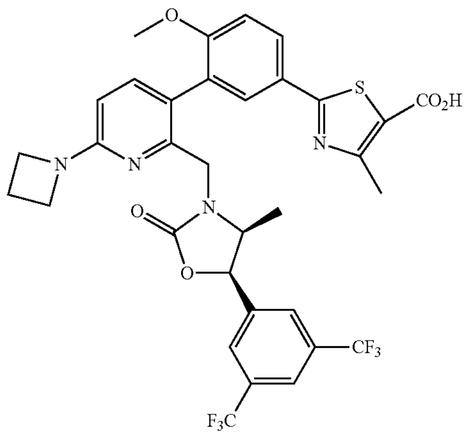 [SMILES: COc1ccc(-c2nc(C)c(C(=O)O)s2)cc1-c1ccc(N2CCC2)nc1CN1C(=O)O[C@H](c2cc(C(F)(F)F)cc(C(F)(F)F)c2)[C@@H]1C] | 707.3 |
| 117 | 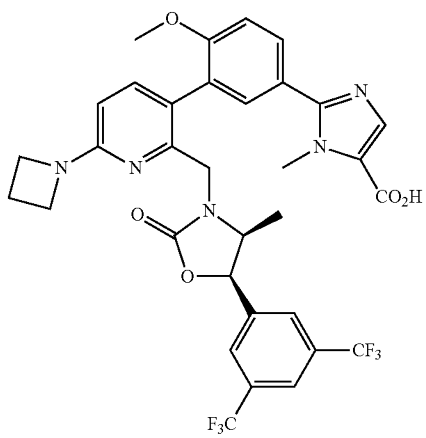 [SMILES: COc1ccc(-c2ncc(C(=O)O)n2C)cc1-c1ccc(N2CCC2)nc1CN1C(=O)O[C@H](c2cc(C(F)(F)F)cc(C(F)(F)F)c2)[C@@H]1C] | 690.3 |
| 118 | 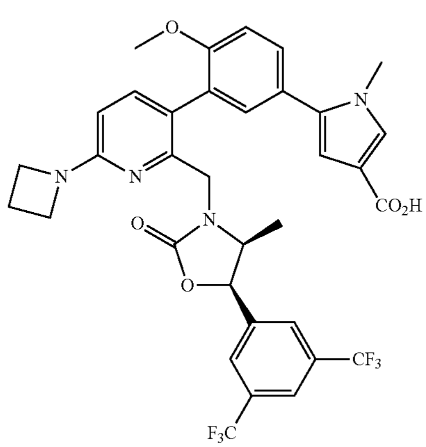 [SMILES: COc1ccc(-c2cc(C(=O)O)cn2C)cc1-c1ccc(N2CCC2)nc1CN1C(=O)O[C@H](c2cc(C(F)(F)F)cc(C(F)(F)F)c2)[C@@H]1C] | 689.3 |

TABLE 14-continued
| Example | Molecular structure | LCMS (M + H)+ |
|---------|---------------------|---------------|
| 119 | 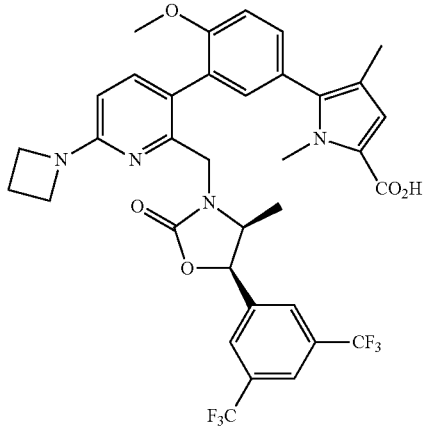 [SMILES: COc1ccc(-c2c(C)cc(C(=O)O)n2C)cc1-c1ccc(N2CCC2)nc1CN1C(=O)O[C@H](c2cc(C(F)(F)F)cc(C(F)(F)F)c2)[C@@H]1C] | 703.3 |
| 120 | 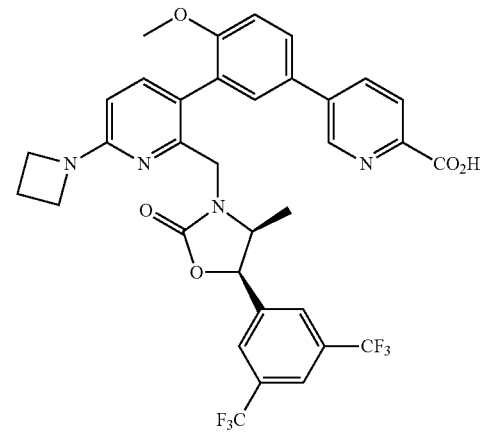 [SMILES: COc1ccc(-c2ccc(C(=O)O)nc2)cc1-c1ccc(N2CCC2)nc1CN1C(=O)O[C@H](c2cc(C(F)(F)F)cc(C(F)(F)F)c2)[C@@H]1C] | 687.3 |
| 121 | 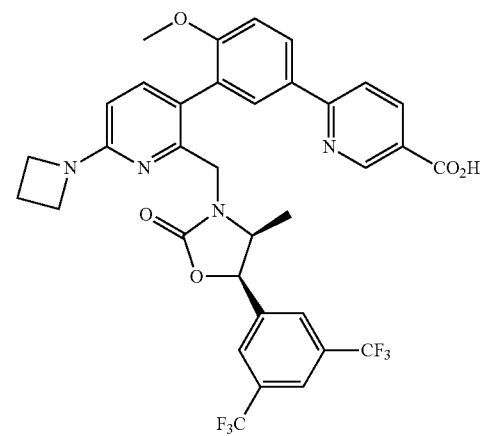 [SMILES: COc1ccc(-c2ccc(C(=O)O)cn2)cc1-c1ccc(N2CCC2)nc1CN1C(=O)O[C@H](c2cc(C(F)(F)F)cc(C(F)(F)F)c2)[C@@H]1C] | 687.4 |

Example 122

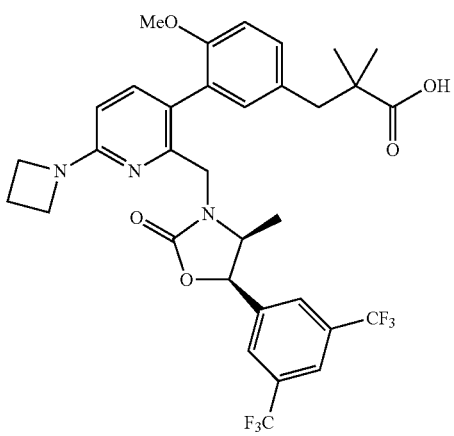 [SMILES: COc1ccc(CC(C)(C)C(=O)O)cc1-c1ccc(N2CCC2)nc1CN1C(=O)O[C@H](c2cc(C(F)(F)F)cc(C(F)(F)F)c2)[C@@H]1C]

3-{3-[6-Azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}-2,2-dimethylpropanoic acid Tert-butyl 3-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}-2,2-dimethylpropanoate (48 mg, 0.067 mmol) was dissolved in dichloromethane (1 mL). TFA (0.1 mL, 1.298 mmol) was added and the reaction was stirred at room temperature for 4 hours. The reaction was then concentrated and the residue was dissolved in methanol (1 mL). 4M KOH (0.333 mL, 1.330 mmol) was added, and the reaction was stirred for 10 min. at room temperature. Next, acetic acid (0.076 mL, 1.330 mmol) was added. The reaction was diluted with ethyl acetate (10 mL), washed with water (2×8 mL) and brine (8 mL), dried over sodium sulfate, filtered, and concentrated. The residue was purified by PTLC (50% ethyl acetate/hexanes) to afford 3-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}-2,2-dimethylpropanoic acid. LCMS=666.2 (M+H)$^+$. $^1$H NMR (CDCl$_3$, 500 MHz) δ 7.85 (s, 1H), 7.74 (s, 2H), 7.29 (d, J=7.6 Hz, 1H), 7.12 (dd, J=8.3, 2.2 Hz, 1H), 7.10-6.90 (m, 1H), 6.85 (d, J=8.5 Hz, 1H), 6.25 (d, J=8.2 Hz, 1H), 5.80-5.55 (m, 1H), 4.76 (m, 2H), 4.20-3.80 (m, 5H), 3.73 (s, 3H), 2.82 (m, 2H), 2.42 (bs, 2H), 1.35-1.15 (m, 6H), 0.75-0.58 (m, 3H).

Example 123

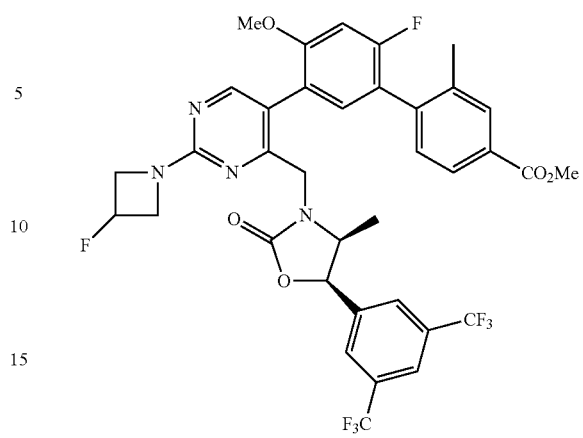

Methyl 5'-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-2'-fluoro-4'-methoxy-2-methylbiphenyl-4-carboxylate A mixture of intermediate 49 (50 mg, 0.09 mmol), intermediate 50 (45 mg, 0.112 mmol), K$_2$CO$_3$ (27.3 mg, 0.197 mmol) and catalytic amount of Pd(PPh$_3$)$_4$ was mixed in water/EtOH/toluene (1:2:4) (7 ml). The mixture was stirred at 80° C. for 1 h. The mixture was cooled, and the solvents were removed. Water (5 mL) was added and the mixture was extracted with dichloromethane (3×5 mL). The combined organic fractions were washed with brine (5 mL), dried (Na$_2$SO$_4$), filtered and the solvent was evaporated under reduced pressure. The residue was purified by column chromatography on silica gel Biotage 40S, eluting with EtOAc/hexane (2:8) to give the title compound as a yellow gum. $^1$H NMR (CDCl$_3$, 500 MHz) δ 8.18 (s, 1H), 7.99 (s, 1H), 7.92 (d, J=8.5 Hz, 1H), 7.91 (s, 1H), 7.75 (s, 2H), 7.31 (d, J=8.0 Hz, 1H), 7.06 (d, J=8.0 Hz, 1H), 6.83 (d, J=11.0 Hz, 1H), 5.66 (m, 1H), 5.54 (m, ½H), 5.42 (m, ½H), 4.79 (m, 1H), 4.28-4.56 (m, 5H), 3.96 (s, 3H), 3.88 (s, 3H), 2.31 (s, 3H), 0.78 (m, 3H).

The following compounds (Table 15) were synthesized using methods analogous to those described in EXAMPLE 123 from commercially available materials or intermediates whose syntheses are described above.

TABLE 15

| Example | Structure | LCMS (M + H)$^+$ |
|---|---|---|
| 124 | 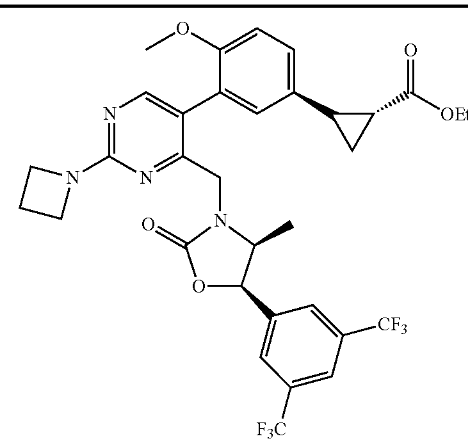 | 679.2 |

TABLE 15-continued
| Example | Structure | LCMS (M + H)+ |
|---|---|---|
| 125 | 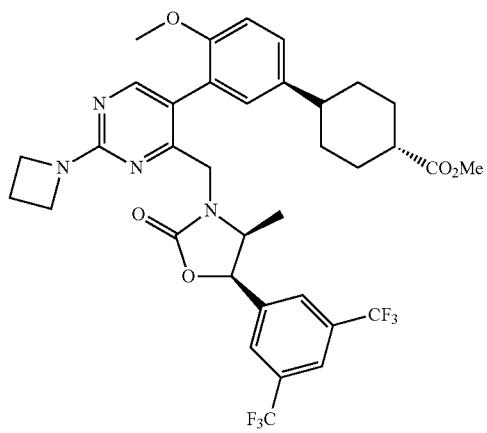 | 707.3 |
| 126 | 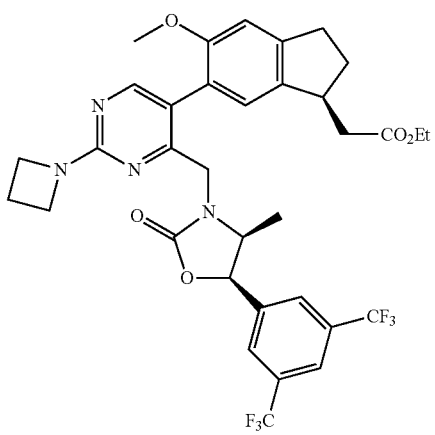 [SMILES: CCOC(=O)C[C@@H]1CCc2cc(OC)c(-c3cnc(N4CCC4)nc3CN3C(=O)O[C@H](c4cc(C(F)(F)F)cc(C(F)(F)F)c4)[C@@H]3C)cc21] | 693.2 |
| 127 | 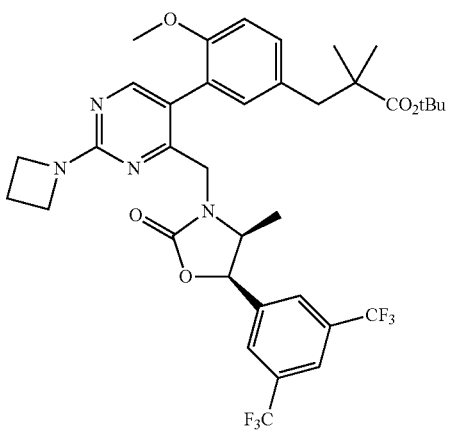 [SMILES: COc1ccc(CC(C)(C)C(=O)OC(C)(C)C)cc1-c1cnc(N2CCC2)nc1CN1C(=O)O[C@H](c2cc(C(F)(F)F)cc(C(F)(F)F)c2)[C@@H]1C] | 723.4 |

TABLE 15-continued
| Example | Structure | LCMS (M + H)+ |
| --- | --- | --- |
| 128 | 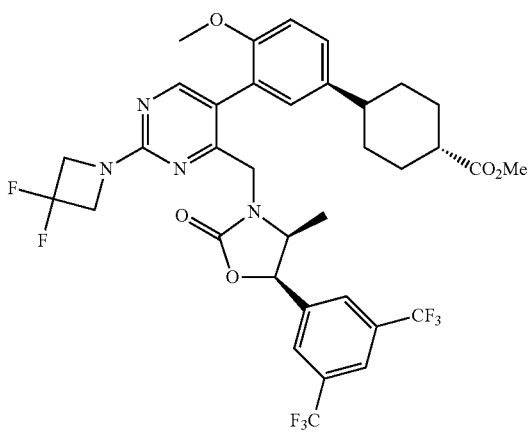 | 743.3 |
| 129 | 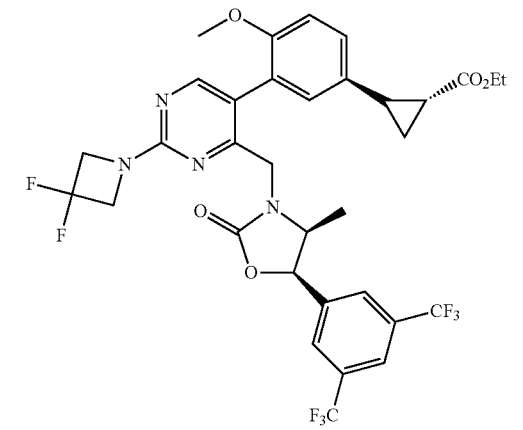 | 715.2 |
| 130 | 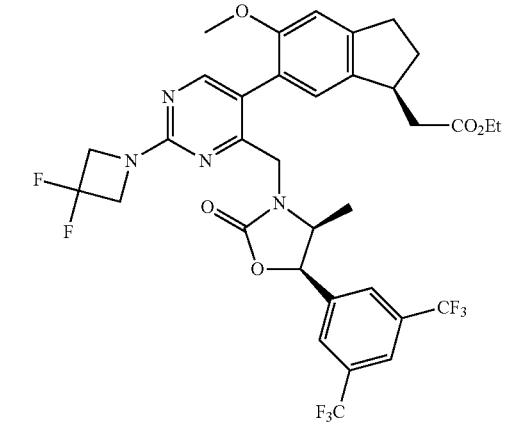 [SMILES: CCOC(=O)C[C@@H]1CCc2cc(OC)c(-c3cnc(N4CC(F)(F)C4)nc3CN3C(=O)O[C@H](c4cc(C(F)(F)F)cc(C(F)(F)F)c4)[C@@H]3C)cc21] | 729.3 |

TABLE 15-continued

| Example | Structure | LCMS (M + H)+ |
|---|---|---|
| 131 | 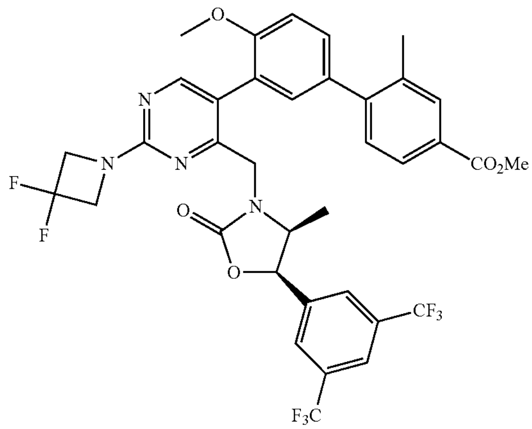 [SMILES: COC(=O)c1ccc(-c2ccc(OC)c(-c3cnc(N4CC(F)(F)C4)nc3CN3C(=O)O[C@H](c4cc(C(F)(F)F)cc(C(F)(F)F)c4)[C@@H]3C)c2)c(C)c1] | 751.3 |
| 132 | 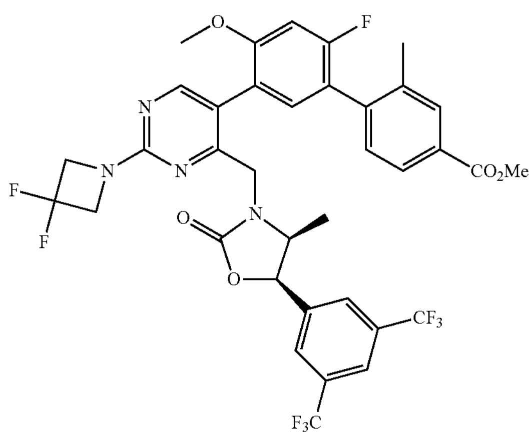 [SMILES: COC(=O)c1ccc(-c2cc(-c3cnc(N4CC(F)(F)C4)nc3CN3C(=O)O[C@H](c4cc(C(F)(F)F)cc(C(F)(F)F)c4)[C@@H]3C)c(OC)cc2F)c(C)c1] | 769.3 |
| 133 | 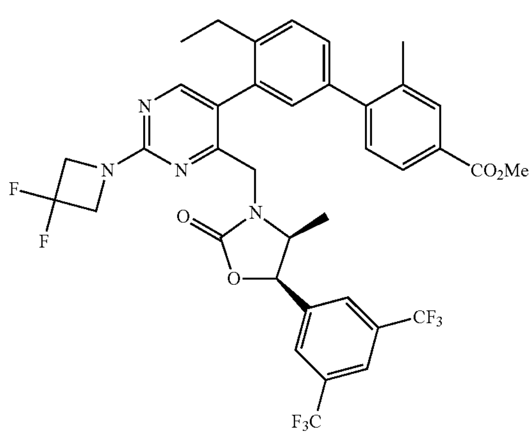 [SMILES: CCc1ccc(-c2ccc(C(=O)OC)cc2C)cc1-c1cnc(N2CC(F)(F)C2)nc1CN1C(=O)O[C@H](c2cc(C(F)(F)F)cc(C(F)(F)F)c2)[C@@H]1C] | 749.4 |

TABLE 15-continued

| Example | Structure | LCMS (M + H)+ |
|---------|-----------|---------------|
| 134 | 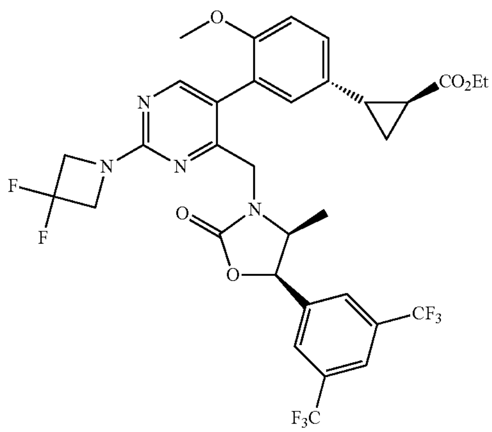 | 715.4 |
| 135 | 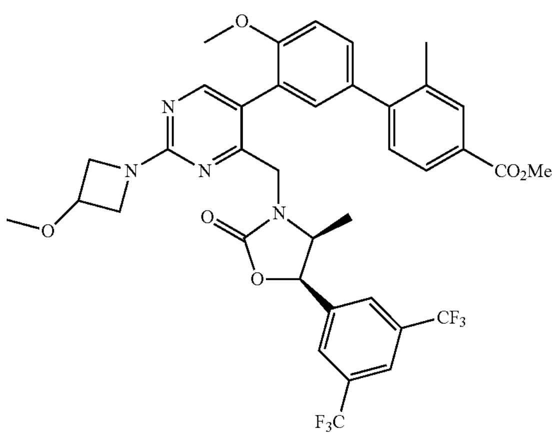 [SMILES: COC(=O)c1ccc(-c2ccc(OC)c(-c3cnc(N4CC(OC)C4)nc3CN3C(=O)O[C@H](c4cc(C(F)(F)F)cc(C(F)(F)F)c4)[C@@H]3C)c2)c(C)c1] | 745.4 |
| 136 | 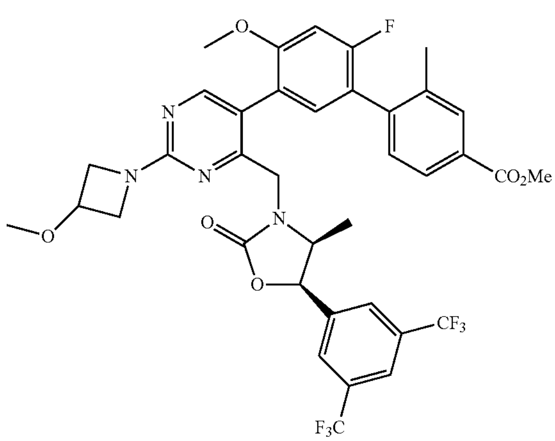 [SMILES: COC(=O)c1ccc(-c2cc(-c3cnc(N4CC(OC)C4)nc3CN3C(=O)O[C@H](c4cc(C(F)(F)F)cc(C(F)(F)F)c4)[C@@H]3C)c(OC)cc2F)c(C)c1] | 763.4 |

TABLE 15-continued

| Example | Structure | LCMS (M + H)+ |
|---------|-----------|---------------|
| 137 | 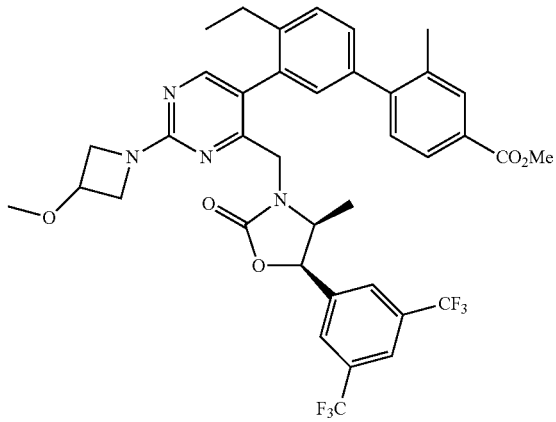 [SMILES: CCc1ccc(-c2ccc(C(=O)OC)cc2C)cc1-c1cnc(N2CC(OC)C2)nc1CN1C(=O)O[C@H](c2cc(C(F)(F)F)cc(C(F)(F)F)c2)[C@@H]1C] | 743.4 |
| 138 | 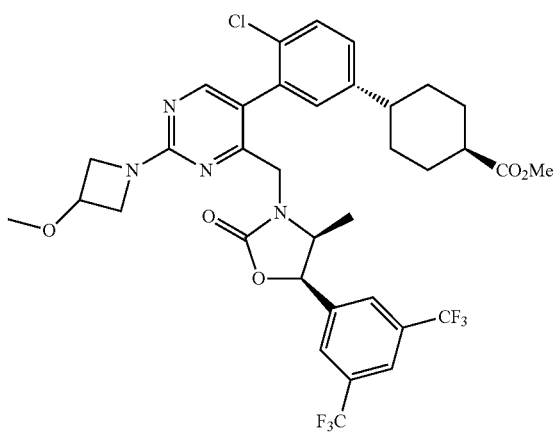 | 741.4 |

Example 139

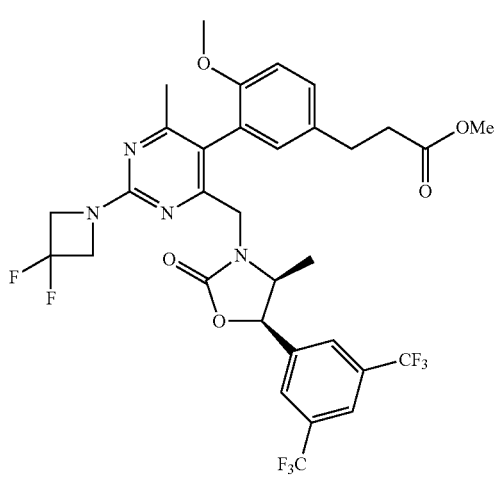 [SMILES: COC(=O)CCc1ccc(OC)c(-c2c(C)nc(N3CC(F)(F)C3)nc2CN2C(=O)O[C@H](c3cc(C(F)(F)F)cc(C(F)(F)F)c3)[C@@H]2C)c1]

Methyl 3-{3-[4-({(4S,5R)-5-[3,5-bis(trifluoromethyl)phenyl]-4-methyl-2-oxo-1,3-oxazolidin-3-yl}methyl)-2-(3,3-difluoroazetidin-1-yl)-6-methylpyrimidin-5-yl]-4-methoxyphenyl}propanoate Step A: Methyl 3-{3-[4-({(4S,5R)-5-[3,5-bis(trifluoromethyl)phenyl]-4-methyl-2-oxo-1,3-oxazolidin-3-yl}methyl)-6-methyl-2-(methylsulfanyl)pyrimidin-5-yl]-4-methoxyphenyl}propanoate A mixture of the INTERMEDIATE 44 (140 mg, 0.28 mmol), INTERMEDIATE 2 (120 mg, 0.375 mmol), $K_2CO_3$ (85 mg, 0.616 mmol) and a catalytic amount of Johnson Matthey catalyst for the coupling reaction in a mixture of aqueous THF (5 mL) was stirred at 140° C. under microwave for 1 h. The solvent was removed. Water was added. The mixture was extracted with $CH_2Cl_2$, washed with brine and dried over $Na_2SO_4$. The residue was purified by column chromatography on silica gel Biotage 40S, eluting with EtOAc/hexane (2:8) to give the title compound as a colorless solid. LCMS=658.3 (M+H)+.

Step B: Methyl 3-{3-[4-({(4S,5R)-5-[3,5-bis(trifluoromethyl)phenyl]-4-methyl-2-oxo-1,3-oxazolidin-3-yl}methyl)-2-(3,3-difluoroazetidin-1-yl)-6-methylpyrimidin-5-yl]-4-methoxyphenyl}propanoate A mixture of the title compound from Step A (20 mg, 0.030 mmol) and mCPBA (10.50 mg, 0.061 mmol) in CH$_2$Cl$_2$ (2 mL) was stirred at room temperature for 1 h. TLC showed no SM. The mixture was diluted with CH$_2$Cl$_2$ (10 mL) and washed with Na$_2$S$_2$O$_3$ and Na$_2$HCO$_3$, and dried over Na$_2$SO$_4$. The solvent was removed. A mixture of the residue, 3,3-difluoro-azetidine (19.70 mg, 0.152 mmol) and Et$_3$N (3.08 mg, 0.030 mmol) in THF was heated at 140° C. under microwave for 4 h. The solvent was removed and the title compound was purified by preparative TLC plate as a white solid using EtOAc/hexane as the elute (2/8). LCMS=703.4 (M+H)$^+$. The final compound was a mixture of two separable atropisomers, which could be separated by chiral OD column using EtOH/heptane as the elute.

Data for atropisomer A (faster fraction):
$^1$H NMR (CDCl$_3$, 500 MHz) δ 7.90 (s, 1H), 7.75 (s, 2H), 7.24 (dd, J=8.5, 2.5 Hz, 1H), 6.94 (d, J=2.5 Hz, 1H), 6.92 (d, J=8.5 Hz, 1H), 5.70 (d, J=8.5 Hz, 1H), 4.53 (m, 6H), 4.39 (m, 1H), 3.74 (s, 3H), 3.69 (s, 3H), 2.95 (t, J=8.0 Hz, 2H), 2.66 (t, J=8.0 Hz, 2H), 2.14 (s, 3H), 0.68 (d, J=7.0 Hz, 3H).

Data for atropisomer B (slower fraction):
$^1$H NMR (CDCl$_3$, 500 MHz) δ 7.89 (s, 1H), 7.75 (s, 2H), 7.23 (dd, J=8.5, 2.5 Hz, 1H), 6.94 (d, J=8.5 Hz, 1H), 6.90 (d, J=2.0 Hz, 1H), 5.66 (d, J=8.5 Hz, 1H), 4.53 (m, 6H), 4.30 (m, 1H), 3.79 (s, 3H), 3.64 (s, 3H), 2.93 (t, J=7.5 Hz, 2H), 2.63 (t, J=7.5 Hz, 2H), 2.15 (s, 3H), 0.68 (d, J=6.5 Hz, 3H).

Example 140

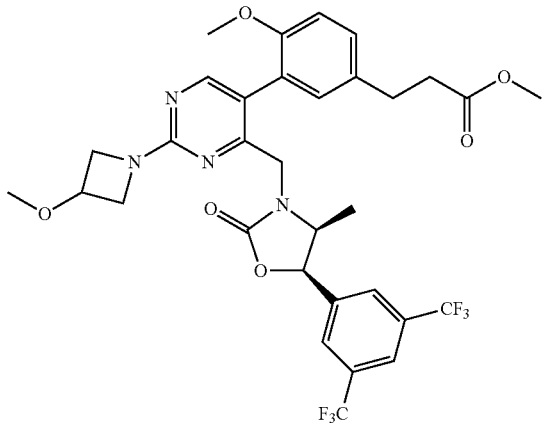

Methyl 3-{3-[4-({(4S,5R)-5-[3,5-bis(trifluoromethyl)phenyl]-4-methyl-2-oxo-1,3-oxazolidin-3-yl}methyl)-2-(3-methoxyazetidin-1-yl)pyrimidin-5-yl]-4-methoxyphenyl}propanoate Step A: Methyl 3-{3-[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]-4-methoxyphenyl}propanoate (4S,5R)-5-[3,5-bis(trifluoromethyl)phenyl]-3-{[5-bromo-2-(methylsulfanyl)pyrimidin-4-yl]methyl}-4-methyl-1,3-oxazolidin-2-one (INTERMEDIATE 45) (307 mg, 0.579 mmol), methyl 3-[4-methoxy-3-(4,4,5,5-tetramethyl-1,3,2-dioxaborolan-2-yl)phenyl]propanoate (INTERMEDIATE 2) (185 mg, 0.579 mmol), 1,1bis(di-tert-butylphosphino)ferrocene palladium dichloride (39.4 mg, 0.058 mmol), potassium carbonate (0.724 ml, 1.447 mmol) and THF (5 mL) were sealed in a uw vessel and subject to microwave irradiation at 140° C. for 20 min. The reaction crude was dried over Na$_2$SO$_4$, filtered and purified by preparative TLC (silica gel) developed with EtOAc/hexanes (40% ethyl acetate v/v) to give a brown solid as the titled compound. LCMS calc.=643.16. found=644.17 (M+H)$^+$.

Step B: Methyl 3-{3-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-4-methoxyphenyl}propanoate Methyl 3-({3-[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]-4-methoxyphenyl}propanoate (311 mg, 0.483 mmol) from Step A was dissolved in DCM (8 mL). To this solution was added chloroperoxybenzoic acid (250 mg, 1.450 mmol). The reaction mixture was stirred at room temperature for 2 hrs. The crude mixture was evaporated in vacuo. The pot residue was purified by preparative HPLC (reverse phase, SunFire Prep C18 OBD 5 um 19×150 mm) eluting with acetonitrile/water+0.05% HCOOH (30% to 100% organic in 10 min, hold 100% for 2 min, 20 mL/min) to give a colorless glass as the titled compound. LCMS calc.=675.15. found=676.15 (M+H)$^+$.

Step C: Methyl 3-{3-[4-({(4S,5R)-5-[3,5-bis(trifluoromethyl)phenyl]-4-methyl-2-oxo-1,3-oxazolidin-3-yl}methyl)-2-(3-methoxyazetidin-1-yl)pyrimidin-5-yl]-4-methoxyphenyl}propanoate 3-Methoxy-azetidine hydrochloride (60.4 mg, 0.488 mmol) was added into a stirred mixture of methyl 3-{3-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-4-methoxyphenyl}propanoate (66 mg, 0.098 mmol) and triethylamine (0.068 mL, 0.488 mmol) in THF (1 mL) at room temperature. The reaction mixture was stirred at room temperature overnight. The yellow reaction crude was concentrated in vacuo. The resulting pot residue was purified by preparative HPLC (reverse phase, SunFire Prep C18 OBD 5 um 19×150 mm) eluting with acetonitrile/water+0.05% HCOOH (20% to 100% organic in 10 min, hold 100% for 2 min, 20 mL/min) to give a colorless glass as the titled compound. LCMS calc.=682.22. found=683.27 (M+H)$^+$.
$^1$H-NMR (CDCl$_3$, 500 MHz) δ 8.12 (s, 1H), 7.86 (s, 1H), 7.73 (s, 2H), 7.20 (dd, J=8.5, 2.0 Hz, 1H), 6.97 (dd, J=1.5 Hz, 1H), 6.88 (d, J=8.5 Hz, 1H), 5.59 (br d, J=8.0 Hz, 1H), 4.73 (br d, J=17 Hz, 1H), 4.41-4.32 (m, 3H), 4.28 (br s, 1H), 4.11-4.03 (m, 2H), 3.91 (br s, 1H), 3.77 (s, 3H), 3.64 (s, 3H), 3.37 (s, 3H), 2.92 (t, J=7.5 Hz, 2H), 2.62 (t, J=7.5 Hz, 2H), 0.66 (br s, 3H).

The following compounds (Table 16) were synthesized using methods analogous to those described in EXAMPLES 139 and 140 from commercially available materials or intermediates whose syntheses are described above.

TABLE 16
| Example | Molecular structure | LCMS (M + H)+ |
|---------|---------------------|---------------|
| 141 | 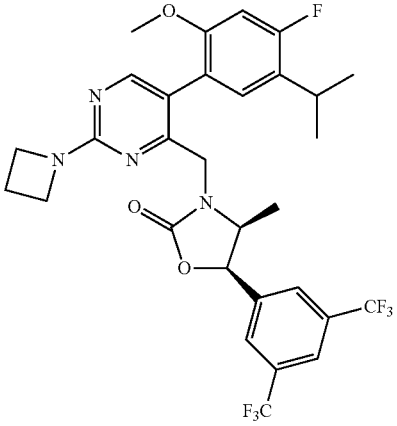 [SMILES: COc1cc(F)c(C(C)C)cc1-c1cnc(N2CCC2)nc1CN1C(=O)O[C@H](c2cc(C(F)(F)F)cc(C(F)(F)F)c2)[C@@H]1C] | 627.4 |
| 142 | 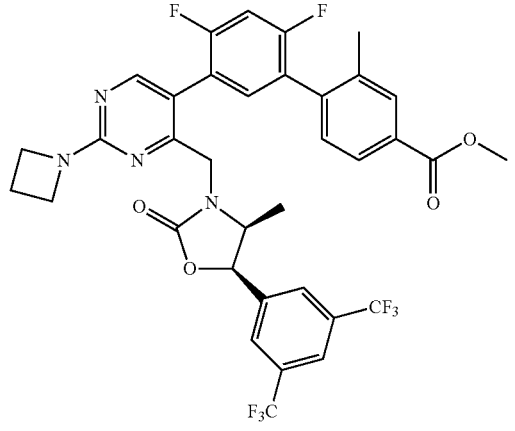 [SMILES: COC(=O)c1ccc(-c2cc(-c3cnc(N4CCC4)nc3CN3C(=O)O[C@H](c4cc(C(F)(F)F)cc(C(F)(F)F)c4)[C@@H]3C)c(F)cc2F)c(C)c1] | 721.3 |
| 143 | 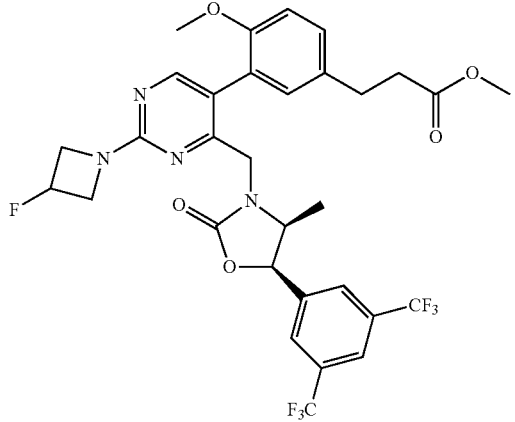 [SMILES: COC(=O)CCc1ccc(OC)c(-c2cnc(N3CC(F)C3)nc2CN2C(=O)O[C@H](c3cc(C(F)(F)F)cc(C(F)(F)F)c3)[C@@H]2C)c1] | 671.3 |

TABLE 16-continued

| Example | Molecular structure | LCMS (M + H)+ |
|---|---|---|
| 144 | 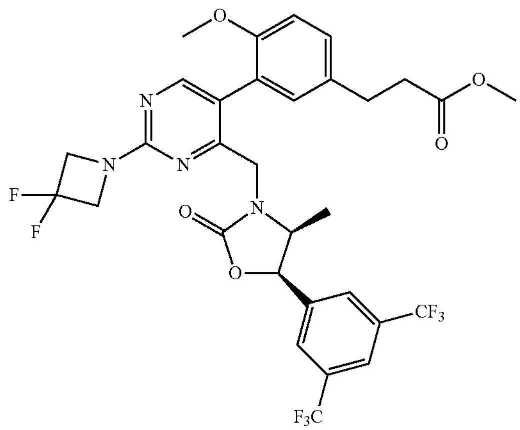 [SMILES: COC(=O)CCc1ccc(OC)c(-c2cnc(N3CC(F)(F)C3)nc2CN2C(=O)O[C@H](c3cc(C(F)(F)F)cc(C(F)(F)F)c3)[C@@H]2C)c1] | 689.2 |
| 145 | 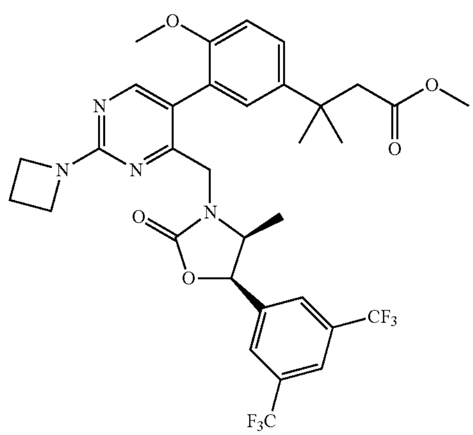 [SMILES: COC(=O)CC(C)(C)c1ccc(OC)c(-c2cnc(N3CCC3)nc2CN2C(=O)O[C@H](c3cc(C(F)(F)F)cc(C(F)(F)F)c3)[C@@H]2C)c1] | 681.2 |
| 146 | 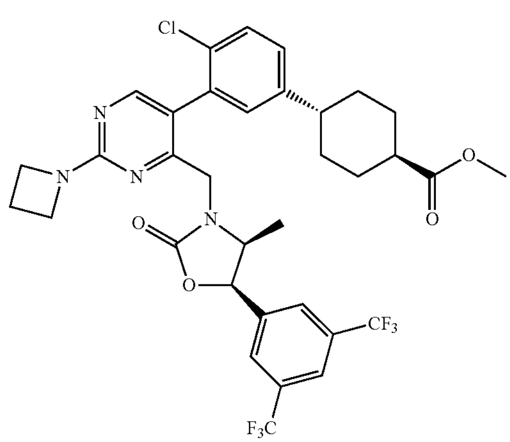 [SMILES: COC(=O)[C@H]1CC[C@H](c2ccc(Cl)c(-c3cnc(N4CCC4)nc3CN3C(=O)O[C@H](c4cc(C(F)(F)F)cc(C(F)(F)F)c4)[C@@H]3C)c2)CC1] | 711.2 |

TABLE 16-continued
| Example | Molecular structure | LCMS (M + H)+ |
|---|---|---|
| 147 | 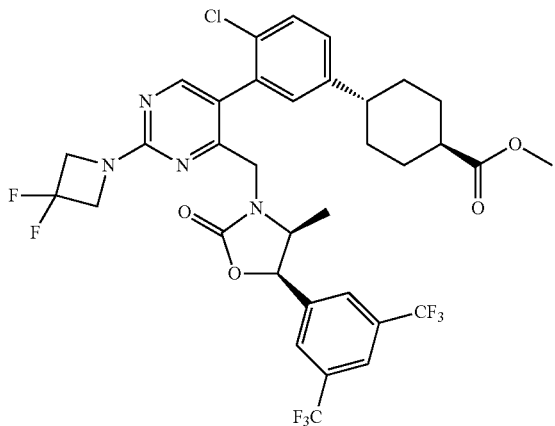 [SMILES: COC(=O)[C@H]1CC[C@H](c2ccc(Cl)c(-c3cnc(N4CC(F)(F)C4)nc3CN3C(=O)O[C@H](c4cc(C(F)(F)F)cc(C(F)(F)F)c4)[C@@H]3C)c2)CC1] | 747.2 |
| 148 | 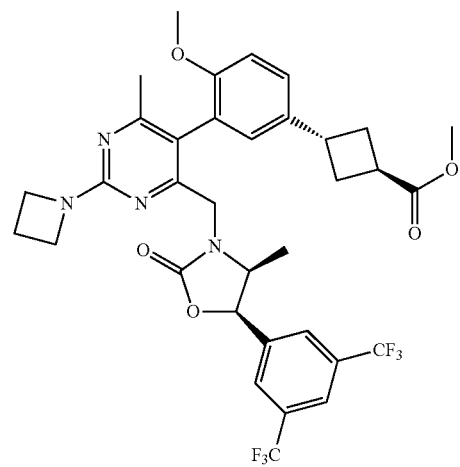  Atropisomer A | 693.4 |
| 149 | 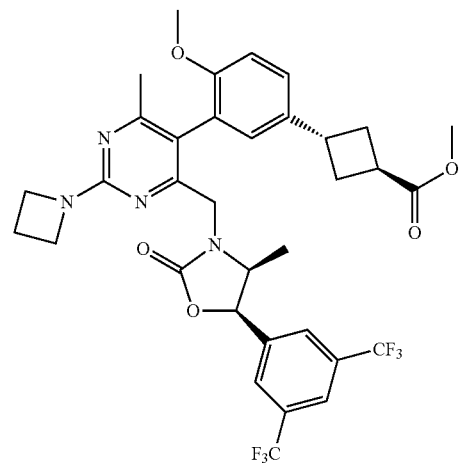  Atropisomer B | 693.4 |

TABLE 16-continued

| Example | Molecular structure | LCMS (M + H)+ |
|---|---|---|
| 150 | Atropisomer A | 729.4 |
| 151 | Atropisomer B | 729.5 |
| 151(a) | SPA = 417.3 nM | 593.4 |

Example 152

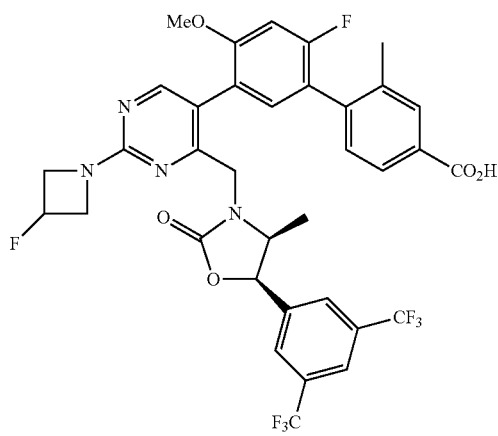 [SMILES: COc1cc(F)c(-c2ccc(C(=O)O)cc2C)cc1-c1cnc(N2CC(F)C2)nc1CN1C(=O)O[C@H](c2cc(C(F)(F)F)cc(C(F)(F)F)c2)[C@@H]1C]

5'-[4-({(4S,5R)-5-[3,5-bis(trifluoromethyl)phenyl]-4-methyl-2-oxo-1,3-oxazolidin-3-yl}methyl)-2-(3-fluoroazetidin-1-yl)pyrimidin-5-yl]-2'-fluoro-4'-methoxy-2-methylbiphen-4-carboxylic acid A mixture of EXAMPLE 123 (10 mg, 0.013 mmol) and LiOH (3.2 mg, 0.13 mmol) in aqueous dioxane (2 mL) was stirred at room temperature overnight. The solvent was removed. A few drops of 1N HCl and $CH_3CN$ (5 mL) were added. The title compound was purified by reverse phase HPLC as a colorless solid. $^1$H NMR ($CDCl_3$, 500 MHz) δ 8.26 (s, 1H), 8.04 (s, 1H), 7.97 (d, J=8 Hz, 1H), 7.92 (s, 1H), 7.76 (s, 2H), 7.34 (d, J=8 Hz, 1H), 7.08 (d, J=8 Hz, 1H), 6.85 (d, J=11 Hz, 1H), 5.70 (d, J=8.0 Hz, 1H), 5.55 (m, 0.5H), 5.44 (m, 0.5H), 4.80 (m, 2H), 4.56 (m, 2H), 4.38 (m, 2H), 4.14 (m, 1H), 3.89 (s, 3H), 1H), 2.33 (s, 3H), 0.75 (m, 3H). LCMS=737.4 $(M+H)^+$ The following compounds (Table 17) were synthesized using methods analogous to those described in EXAMPLE 152 from commercially available materials or intermediates whose syntheses are described above.

TABLE 17

| Example | Structure | LCMS $(M + H)^+$ |
|---|---|---|
| 153 | 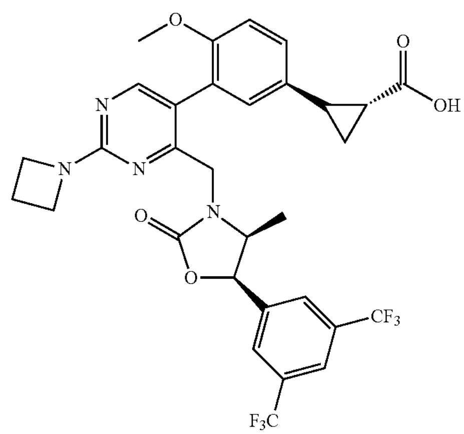 | 651.3 |
| 154 | 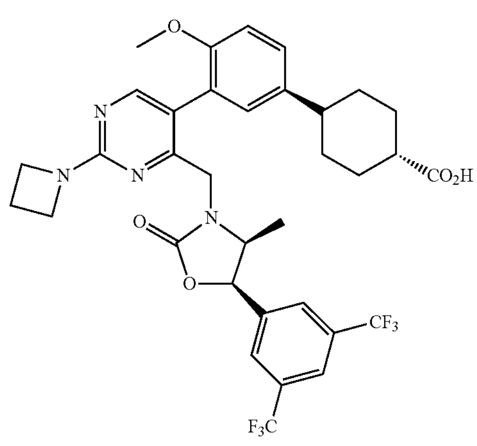 | 693.3 |

TABLE 17-continued

| Example | Structure | LCMS (M + H)+ |
|---------|-----------|---------------|
| 155 | 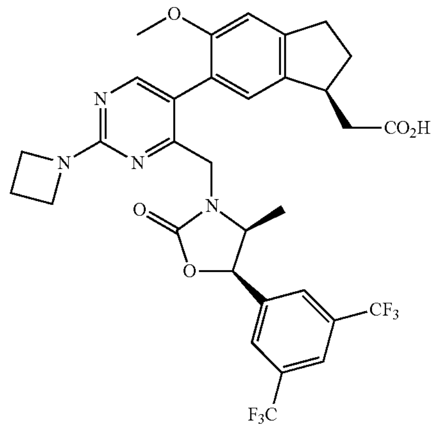 [SMILES: COc1cc2c(cc1-c1cnc(N3CCC3)nc1CN1C(=O)O[C@H](c3cc(C(F)(F)F)cc(C(F)(F)F)c3)[C@@H]1C)[C@H](CC(=O)O)CC2] | 665.2 |
| 156 | 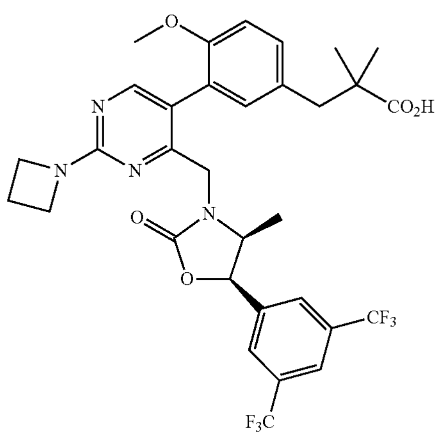 [SMILES: COc1ccc(CC(C)(C)C(=O)O)cc1-c1cnc(N2CCC2)nc1CN1C(=O)O[C@H](c2cc(C(F)(F)F)cc(C(F)(F)F)c2)[C@@H]1C] | 667.3 |
| 157 | 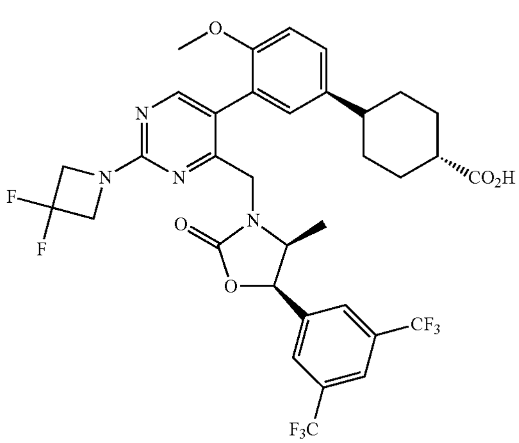 | 729.3 |

TABLE 17-continued

| Example | Structure | LCMS (M + H)+ |
|---------|-----------|---------------|
| 158 | 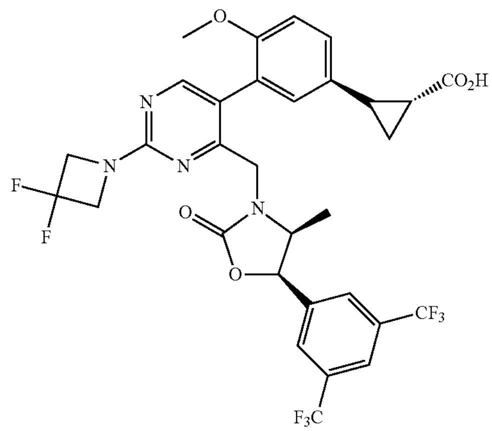 | 687.2 |
| 159 | 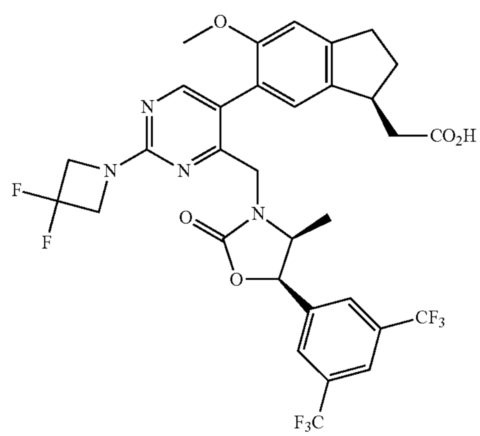 [SMILES: COc1cc2c(cc1-c1cnc(N3CC(F)(F)C3)nc1CN1C(=O)O[C@H](c3cc(C(F)(F)F)cc(C(F)(F)F)c3)[C@@H]1C)[C@H](CC(=O)O)CC2] | 701.3 |
| 160 | 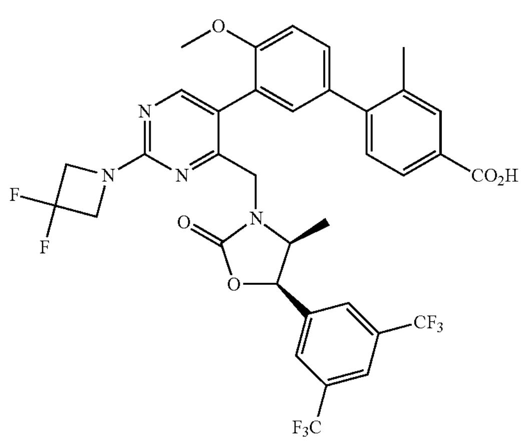 [SMILES: COc1ccc(-c2ccc(C(=O)O)cc2C)cc1-c1cnc(N2CC(F)(F)C2)nc1CN1C(=O)O[C@H](c2cc(C(F)(F)F)cc(C(F)(F)F)c2)[C@@H]1C] | 737.3 |

TABLE 17-continued

| Example | Structure | LCMS (M + H)+ |
| --- | --- | --- |
| 161 | 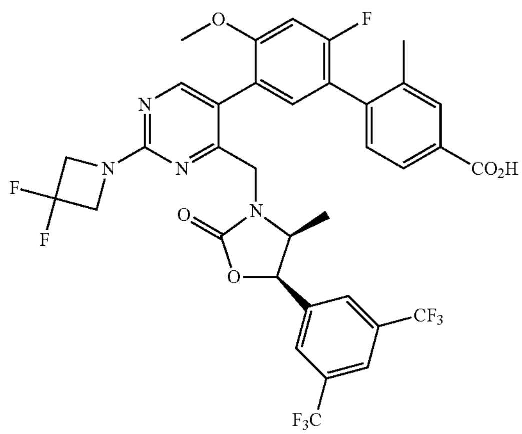 [SMILES: COc1cc(F)c(-c2ccc(C(=O)O)cc2C)cc1-c1cnc(N2CC(F)(F)C2)nc1CN1C(=O)O[C@H](c2cc(C(F)(F)F)cc(C(F)(F)F)c2)[C@@H]1C] | 755.3 |
| 162 | 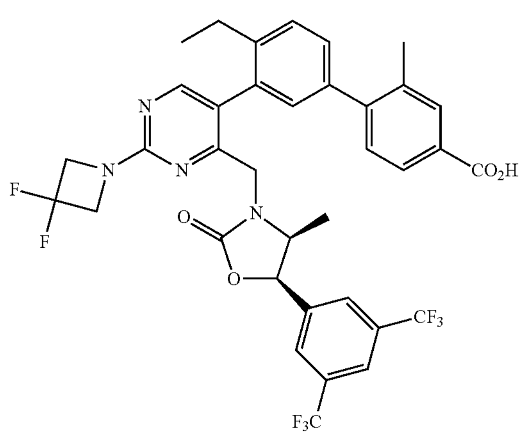 [SMILES: CCc1ccc(-c2ccc(C(=O)O)cc2C)cc1-c1cnc(N2CC(F)(F)C2)nc1CN1C(=O)O[C@H](c2cc(C(F)(F)F)cc(C(F)(F)F)c2)[C@@H]1C] | 735.3 |
| 163 | 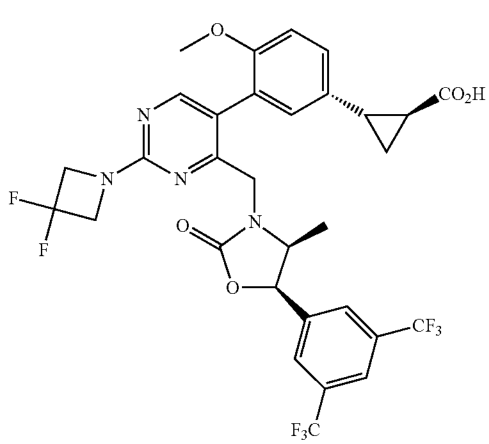 | 687.2 |

TABLE 17-continued
| Example | Structure | LCMS (M + H)+ |
|---|---|---|
| 164 | 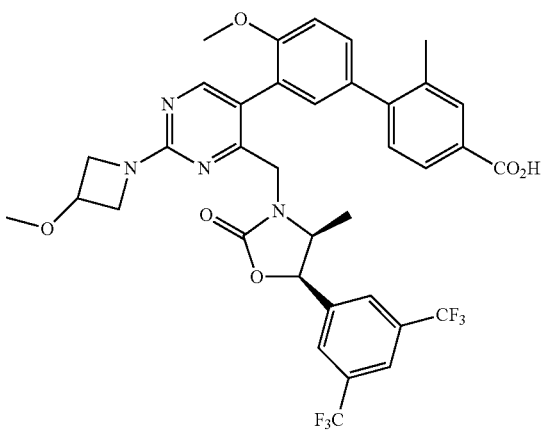 [SMILES: COc1ccc(-c2ccc(C(=O)O)cc2C)cc1-c1cnc(N2CC(OC)C2)nc1CN1C(=O)O[C@H](c2cc(C(F)(F)F)cc(C(F)(F)F)c2)[C@@H]1C] | 731.4 |
| 165 | 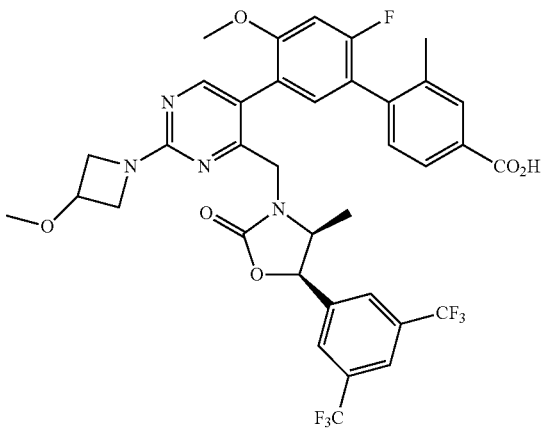 [SMILES: COc1cc(F)c(-c2ccc(C(=O)O)cc2C)cc1-c1cnc(N2CC(OC)C2)nc1CN1C(=O)O[C@H](c2cc(C(F)(F)F)cc(C(F)(F)F)c2)[C@@H]1C] | 749.4 |
| 166 | 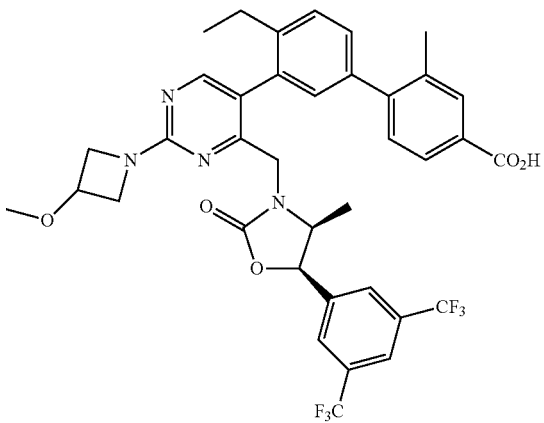 [SMILES: CCc1ccc(-c2ccc(C(=O)O)cc2C)cc1-c1cnc(N2CC(OC)C2)nc1CN1C(=O)O[C@H](c2cc(C(F)(F)F)cc(C(F)(F)F)c2)[C@@H]1C] | 729.4 |

TABLE 17-continued
| Example | Structure | LCMS (M + H)+ |
|---|---|---|
| 167 | 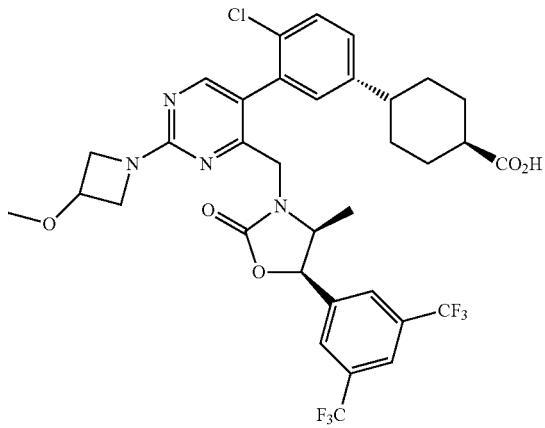 | 727.4 |
| 168 | 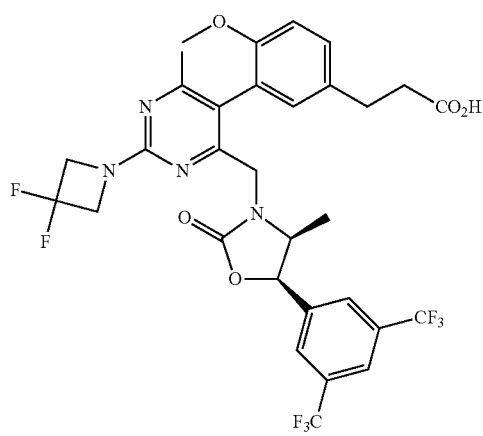  Atropisomer A | 689.4 |
| 169 | 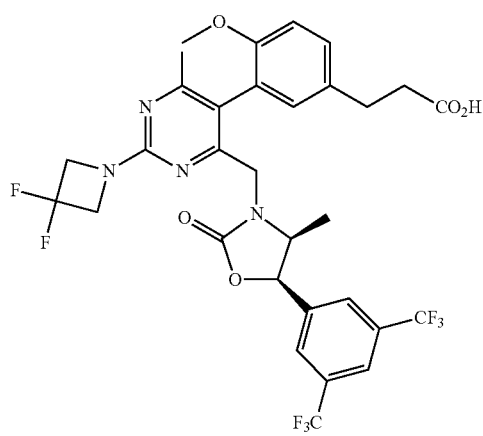  Atropisomer B | 689.4 |

TABLE 17-continued

| Example | Structure | LCMS (M + H)+ |
|---------|-----------|---------------|
| 170 | 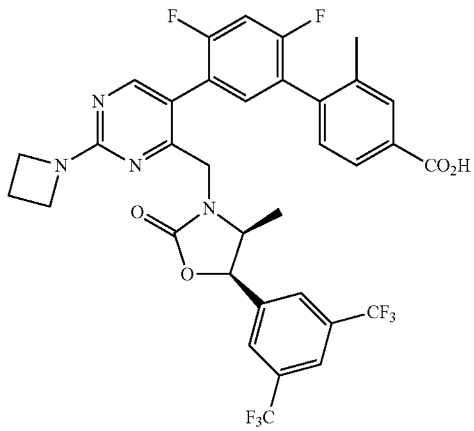 [SMILES: Cc1cc(C(=O)O)ccc1-c1cc(-c2cnc(N3CCC3)nc2CN2C(=O)O[C@H](c3cc(C(F)(F)F)cc(C(F)(F)F)c3)[C@@H]2C)c(F)cc1F] | 707.2 |
| 171 | 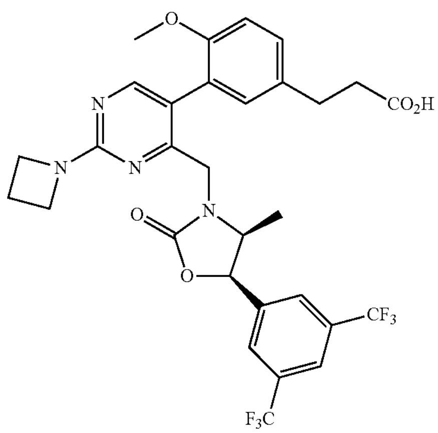 [SMILES: COc1ccc(CCC(=O)O)cc1-c1cnc(N2CCC2)nc1CN1C(=O)O[C@H](c2cc(C(F)(F)F)cc(C(F)(F)F)c2)[C@@H]1C] | 639.3 |
| 172 | 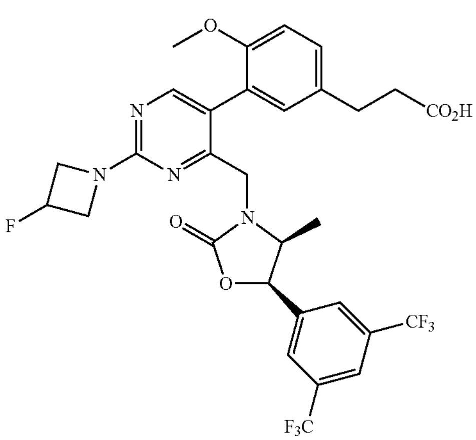 [SMILES: COc1ccc(CCC(=O)O)cc1-c1cnc(N2CC(F)C2)nc1CN1C(=O)O[C@H](c2cc(C(F)(F)F)cc(C(F)(F)F)c2)[C@@H]1C] | 657.2 |

TABLE 17-continued

| Example | Structure | LCMS (M + H)+ |
| --- | --- | --- |
| 173 | 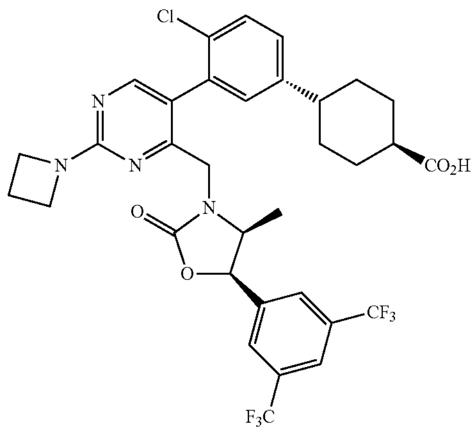 | 697.2 |
| 174 | 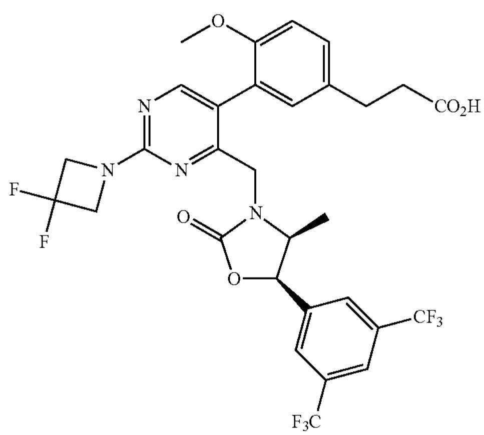 [SMILES: COc1ccc(CCC(=O)O)cc1-c1cnc(N2CC(F)(F)C2)nc1CN1C(=O)O[C@H](c2cc(C(F)(F)F)cc(C(F)(F)F)c2)[C@@H]1C] | 675.2 |
| 175 | 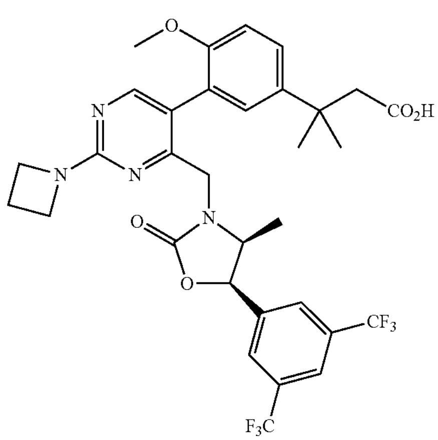 [SMILES: COc1ccc(C(C)(C)CC(=O)O)cc1-c1cnc(N2CCC2)nc1CN1C(=O)O[C@H](c2cc(C(F)(F)F)cc(C(F)(F)F)c2)[C@@H]1C] | 667.3 |

TABLE 17-continued
| Example | Structure | LCMS (M + H)+ |
|---|---|---|
| 176 | 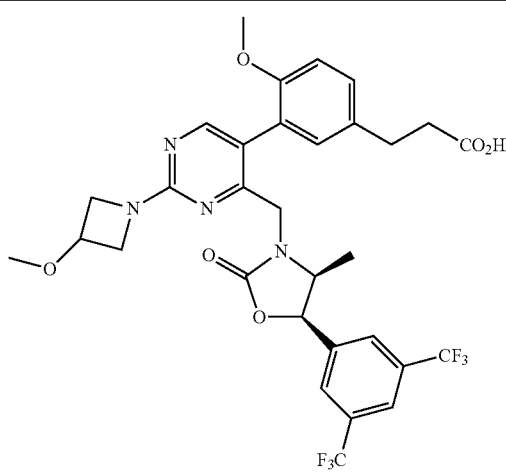 | 669.2 |
| 177 | 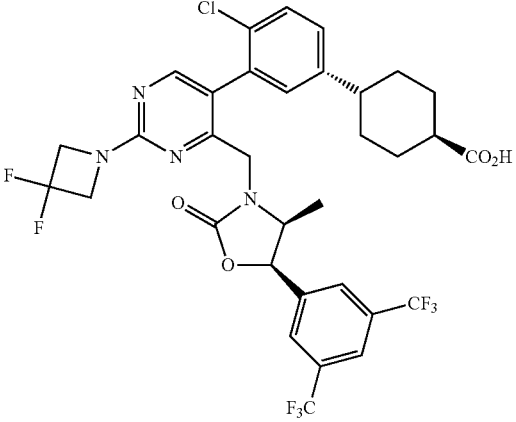 | 733.2 |
| 178 | 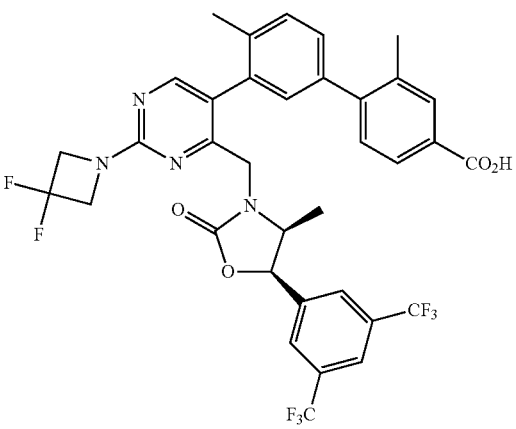 [SMILES: Cc1cc(C(=O)O)ccc1-c1ccc(C)c(-c2cnc(N3CC(F)(F)C3)nc2CN2C(=O)O[C@H](c3cc(C(F)(F)F)cc(C(F)(F)F)c3)[C@@H]2C)c1] | 721.4 |

TABLE 17-continued
| Example | Structure | LCMS (M + H)+ |
|---|---|---|
| 179 | 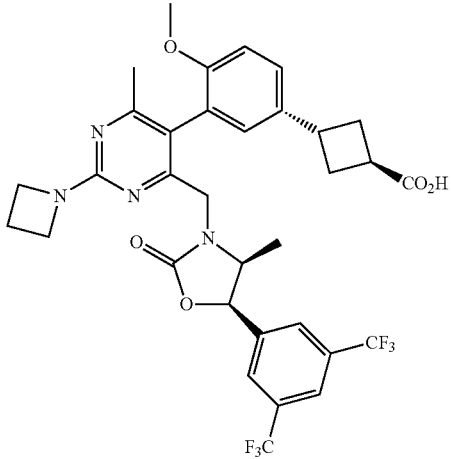<br>Atropisomer A | 679.3 |
| 180 | 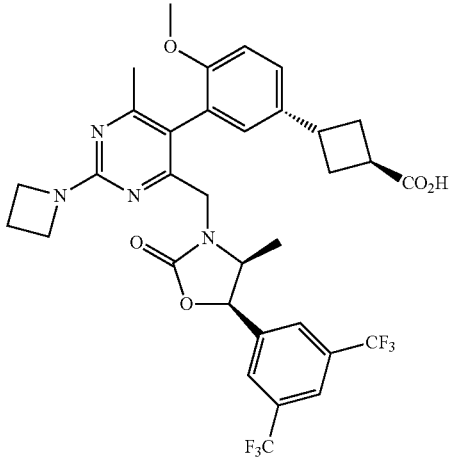<br>Atropisomer B | 679.3 |
| 181 | 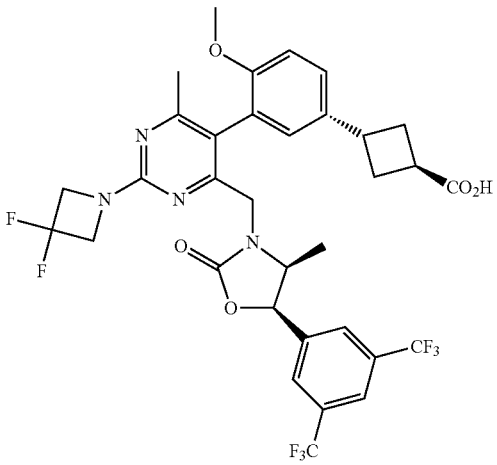<br>Atropisomer A | 715.4 |

TABLE 17-continued

| Example | Structure | LCMS (M + H)+ |
|---|---|---|
| 182 | 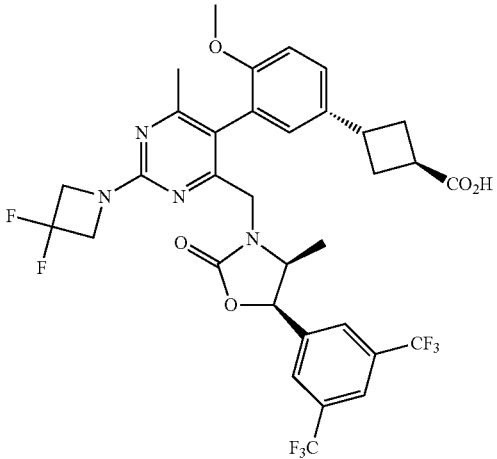<br>Atropisomer B | 715.4 |
| 183 | 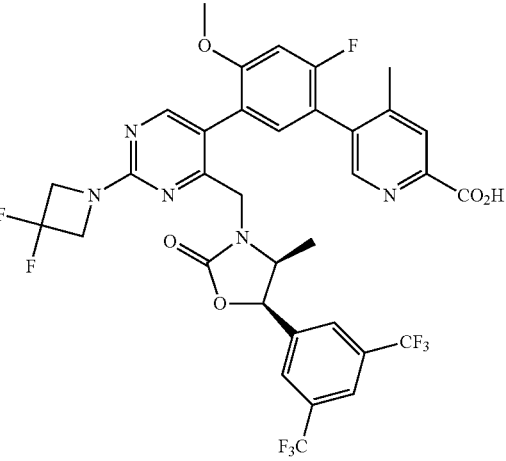 [SMILES: COc1cc(F)c(-c2cnc(C(=O)O)cc2C)cc1-c1cnc(N2CC(F)(F)C2)nc1CN1C(=O)O[C@H](c2cc(C(F)(F)F)cc(C(F)(F)F)c2)[C@@H]1C] | 756.4 |

Example 184

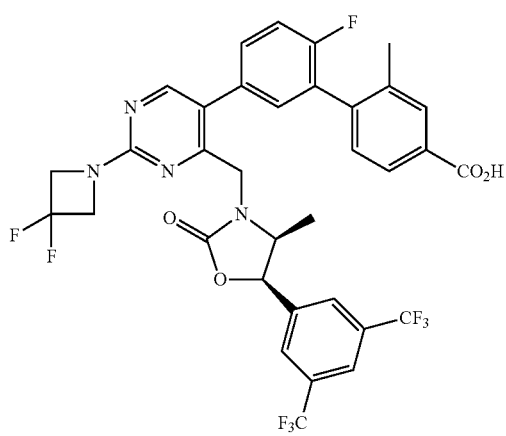 [SMILES: Cc1cc(C(=O)O)ccc1-c1cc(-c2cnc(N3CC(F)(F)C3)nc2CN2C(=O)O[C@H](c3cc(C(F)(F)F)cc(C(F)(F)F)c3)[C@@H]2C)ccc1F]

5'-[4-({(4S,5R)-5-[3,5-bis(trifluoromethyl)phenyl]-4-methyl-2-oxo-1,3-oxazolidin-3-yl}methyl)-2-(3,3-difluoroazetidin-1-yl)pyrimidin-5-yl]-2'-fluoro-2-methylbiphenyl-4-carboxylic acid Step A: (4S,5R)-3-{[5-(3-amino-4-fluorophenyl)-2-(methylsulfanyl)pyrimidin-4-yl]methyl}-5-[3,5-bis(trifluoromethyl)phenyl]-4-methyl-1,3-oxazolidin-2-one A mixture of the Intermediate 45 (2.0 g, 3.77 mmol), 3-amino-4-fluoro phenylboronic acid (0.92 g, 5.94 mmol), Na$_2$CO$_3$ (0.88 g, 8.3 mmol) and catalytic amount of Pd(PPh$_3$)$_4$ in a mixture of toluene/EtOH/water (4:2:1) (28 mL) was stirred at 80° C. for 1 h. The mixture was cooled, and the solvents were removed. Water (5 mL) was added and the mixture was extracted with dichloromethane (3×5 mL). The combined organic fractions were washed with brine (5 mL), dried (Na$_2$SO$_4$), filtered and the solvent was evaporated under reduced pressure. The residue was purified by column chromatography on silica gel Biotage 40M, eluting with EtOAc/isohexane to give the title compound as a yellow gum. $^1$H NMR (CDCl$_3$, 500 MHz) δ 8.42 (s, 1H), 7.91 (s, 1H), 7.77 (s, 2H), 7.10 (dd, J=11, 8 Hz, 1H), 6.77 (dd, J=8.5, 2.5 Hz, 1H), 6.64 (m, 1H), 5.72 (d, J=8.5 Hz, 1H), 4.98 (d, J=17.5 Hz, 1H), 4.40 (m, 1H), 4.10 (d, J=17.5 Hz, 1H), 2.64 (s, 3H), 0.74 (d, J=6.5 Hz, 3H). LCMS=561.5 (M+H)$^+$.

Step B: (4S,5R)-5-[3,5-bis(trifluoromethyl)phenyl]-3-{[5-(4-fluoro-3-iodophenyl)-2-(methylsulfanyl)pyrimidin-4-yl]methyl}-4-methyl-1,3-oxazolidin-2-one A mixture of the title compound from Step A (2.1 g, 3.75 mmol), n-pentyl nitrite (0.66 g, 5.62 mmol) and I$_2$ (1.24 g, 4.87 mmol) in chloroform (20 mL) was stirred at 80° C. for 1 h. The mixture was cooled, and the solvent was diluted with CH$_2$Cl$_2$. The mixture was washed with Na$_2$S$_2$O$_3$ (5 mL), and with brine (5 mL), dried (Na$_2$SO$_4$), filtered and the solvent was evaporated under reduced pressure. The residue was purified by column chromatography on silica gel Biotage 40M, eluting with EtOAc/hexane (10/90) to give the title compound as a yellow gum. $^1$H NMR (CDCl$_3$, 500 MHz) δ 8.41 (s, 1H), 7.92 (s, 1H), 7.78 (s, 2H), 7.77 (m, 1H), 7.35 (m, 1H), 7.22 (m, 1H), 5.76 (d, J=8.5 Hz, 1H), 4.91 (d, J=17 Hz, 1H), 4.45 (m, 1H), 4.06 (d, J=17.5 Hz, 1H), 2.64 (s, 3H), 0.76 (d, J=7 Hz, 3H). LCMS=672.1 (M+H)$^+$.

Step C: methyl 5'-[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]-2'-fluoro-2-methylbiphenyl-4-carboxylate A mixture of the title compound from Step B (400 mg, 0.596 mmol), methyl 3-methyl-4-(4,4,5,5-tetramethyl-1-3,2-dioxaborolan-2-yl)benzoate (247 mg, 0.894 mmol), Na$_2$CO$_3$ (139 mg, 1.31 mmol) and catalytic amount of Pd(PPh$_3$)$_4$ was mixed in water/EtOH/toluene (1:2:4) (7 mL). The mixture was stirred at 80° C. for 1 h. The mixture was cooled, and the solvents were removed. Water (5 mL) was added and the mixture was extracted with dichloromethane (3×5 mL). The combined organic fractions were washed with brine (5 mL), dried (Na$_2$SO$_4$), filtered and the solvent was evaporated under reduced pressure. The residue was purified by column chromatography on silica gel Biotage 40S, eluting with EtOAc/hexane (2:8) to give the title compound as a yellow gum. $^1$H NMR (CDCl$_3$, 500 MHz) δ 8.47 (s, 1H), 8.02 (s, 1H), 7.96 (d, J=8 Hz, 1H), 7.92 (s, 1H), 7.78 (s, 2H), 7.33 (m, 4H), 5.76 (d, J=8.0 Hz, 1H), 4.98 (d, J=17 Hz, 1H), 4.46 (m, 1H), 4.13 (d, J=17 Hz, 1H), 3.97 (s, 3H), 2.65 (s, 3H), 2.33 (s, 3H), 0.78 (d, J=6.5 Hz, 3H).

Step D: 5'-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-2'-fluoro-2-methylbiphenyl-4-carboxylic acid A mixture of the title compound from Step C (150 mg, 0.216 mmol) and LiOH (51.8 mg, 2.16 mmol) was stirred in dioxane and water overnight. The solvent was removed and water was added. A few drops of 1 N HCl were added. The organic material was extracted with EtOAc (3×10 mL). The combined EtOAc layers were dried over Na$_2$SO$_4$. The solvent was removed. The residue was dissolved in CH$_2$Cl$_2$ (5 mL) at 25° C. and mCPBA (82 mg, 0.476 mmol) was added. The solution was stirred at 25° C. for 3 h. The solution was washed with Na$_2$S$_2$O$_3$ and dried over Na$_2$SO$_4$. The residue was purified by reverse phase HPLC to give the title compound as a colorless solid. LCMS=712.6 (M+H)$^+$ Step E: 5'-[4-({(4S,5R)-5-[3,5-bis(trifluoromethyl)phenyl]-4-methyl-2-oxo-1,3-oxazolidin-3-yl}methyl)-2-(3,3-difluoroazetidin-1-yl)pyrimidin-5-yl]-2'-fluoro-2-methylbiphenyl-4-carboxylic acid A mixture of the title compound from Step D (22 mg, 0.031 mmol), 3,3-difluoro-azetidine hydrochloride (20 mg, 0.155 mmol) and Et$_3$N (31.3 mg, 0.309 mmol) in THF (5 mL) was stirred at 60° C. overnight. The solvent was removed. The residue was purified by preparative HPLC Reverse phase (C-18), eluting with Acetonitrile/Water+0.1% TFA, to give the title compound as a colorless solid. $^1$H NMR (CDCl$_3$, 500 MHz) δ 8.34 (s, 1H), 8.08 (s, 1H), 8.02 (d, J=8 Hz, 1H), 7.93 (s, 1H), 7.77 (s, 2H), 7.17-7.42 (m, 4H), 5.72 (d, J=8.0 Hz, 1H), 4.90 (d, J=17 Hz, 1H), 4.55 (m, 4H), 4.40 (m, 1H), 4.08 (d, J=17 Hz, 1H), 2.35 (s, 3H), 0.77 (d, J=7 Hz, 3H). LCMS=725.3 (M+H)$^+$ The following compounds (Table 18) were synthesized using methods analogous to those described in EXAMPLE 184 from commercially available materials or intermediates whose syntheses are described above. In some cases, step E can be run before step D, and step E can be run at higher temperatures (up to 100° C.) in the microwave.

TABLE 18

| Example | Structure | LCMS (M + H)$^+$ |
|---|---|---|
| 185 | 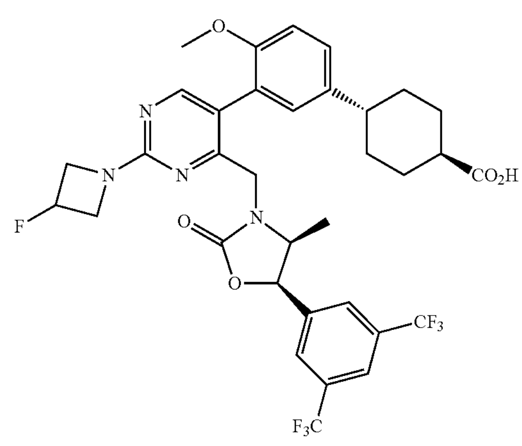 [SMILES: COc1ccc([C@H]2CC[C@H](C(=O)O)CC2)cc1-c1cnc(N2CC(F)C2)nc1CN1C(=O)O[C@H](c2cc(C(F)(F)F)cc(C(F)(F)F)c2)[C@@H]1C] | 711.3 |

TABLE 18-continued
| Example | Structure | LCMS (M + H)+ |
|---|---|---|
| 186 | 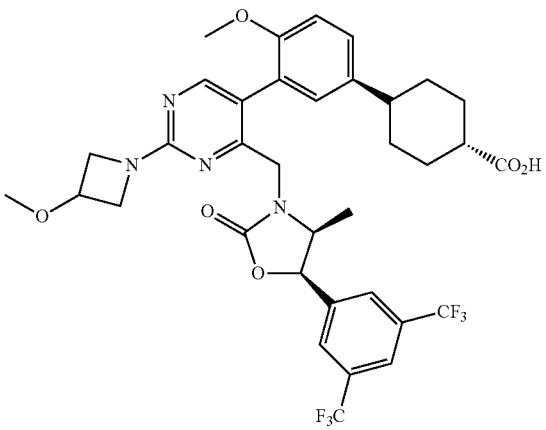 | 723.3 |
| 186(a) | 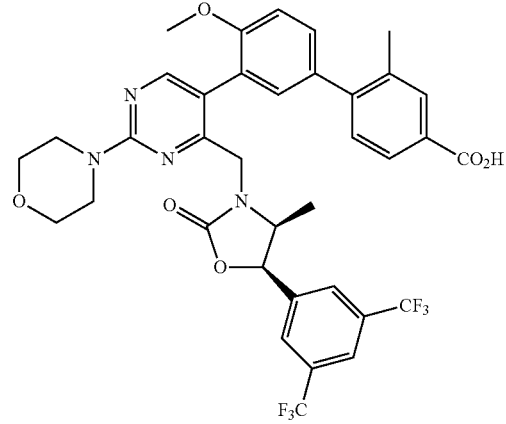  SPA = 15.8 nM | 731.5 |
| 186(b) | 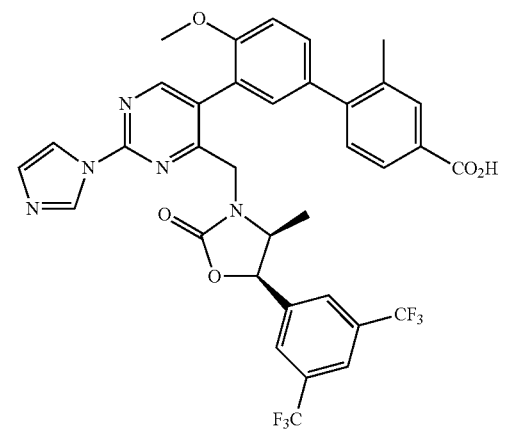  SPA = 8.8 nM | 712.2 |

TABLE 18-continued
| Example | Structure | LCMS (M + H)+ |
|---|---|---|
| 186(c) | 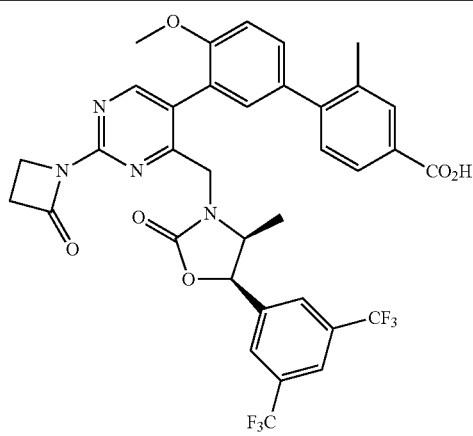 SPA = 24.5 nM | 715.3 |
| 186(d) | 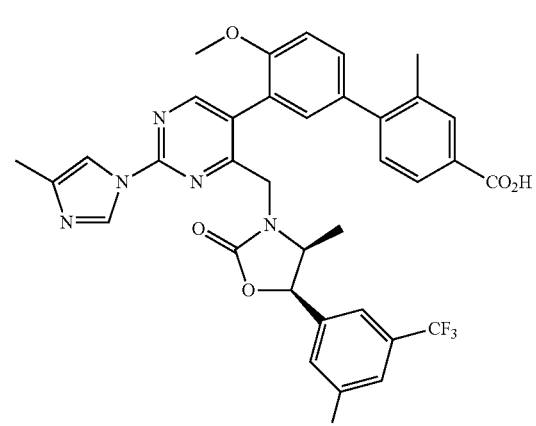 SPA = 331 nM | 726.2 |
| 186(e) | 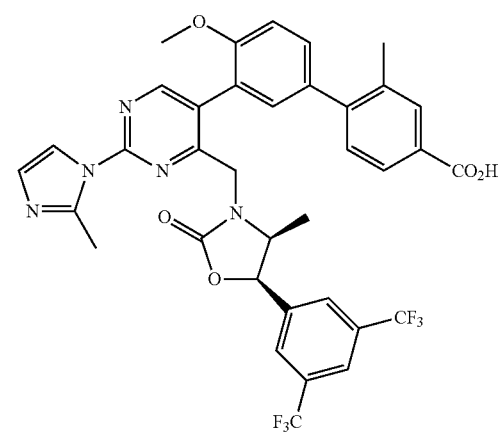 SPA = 15.6 nM | 726.2 |

TABLE 18-continued
| Example | Structure | LCMS (M + H)+ |
|---|---|---|
| 186(f) | 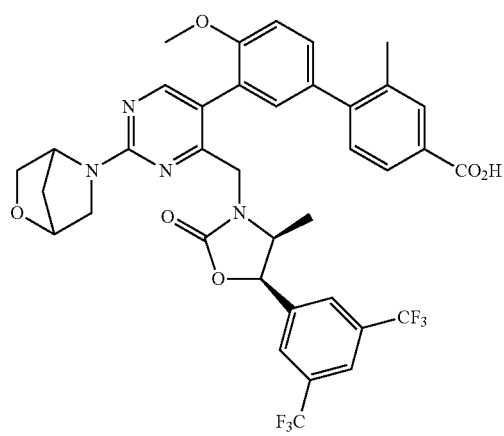<br>SPA = 68.7 nM | 743.3 |
| 186(g) | 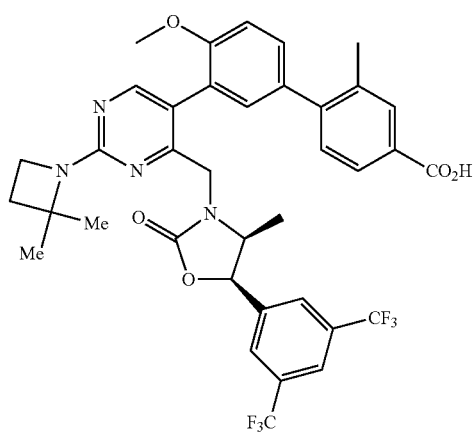<br>SPA = 10.9 nM | 729.3 |
| 186(h) | 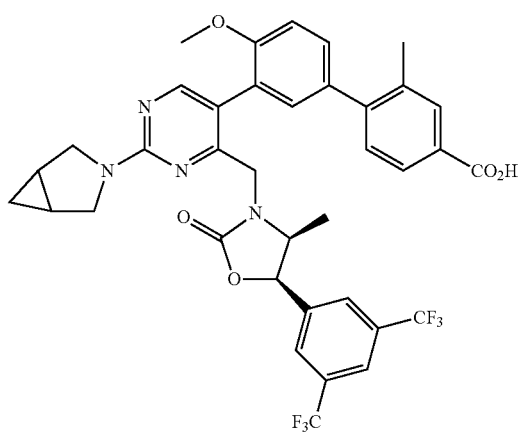<br>SPA = 55.6 nM | 727.3 |

TABLE 18-continued

| Example | Structure | LCMS (M + H)+ |
|---|---|---|
| 186(i) | SPA = 224 nM | 717.3 |
| 186(j) | SPA = 2121 nM | 765.3 |

Example 187

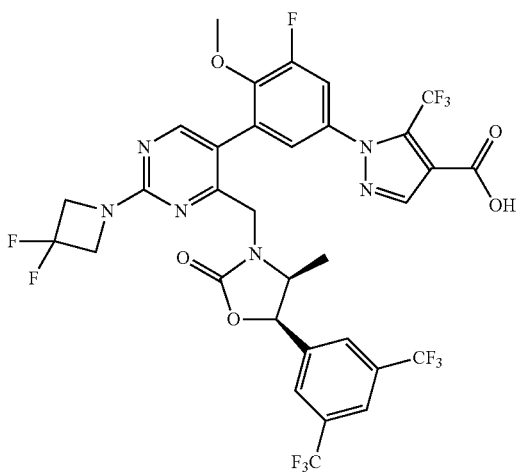 [SMILES: COc1c(F)cc(-n2ncc(C(=O)O)c2C(F)(F)F)cc1-c1cnc(N2CC(F)(F)C2)nc1CN1C(=O)O[C@H](c2cc(C(F)(F)F)cc(C(F)(F)F)c2)[C@@H]1C]

1-{3-[4-({(4S,5R)-5-[3,5-bis(trifluoromethyl)phenyl]-4-methyl-2-oxo-1,3-oxazolidin-3-yl}methyl-2-(3,3-difluoroazetidin-1-yl)pyrimidin-5-yl]-5-fluoro-4-methoxyphenyl}-5-(trifluoromethyl)-1H-pyrazole-4-carboxylic acid Step A: Methyl 3-{3-[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]-4-methoxyphenyl}propanoate

[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]boronic acid (INTERMEDIATE 57) (200 mg, 0.404 mmol), ethyl 1-(3-fluoro-5-iodo-4-methoxyphenyl)-5-(trifluoromethyl)-1H-pyrazole-4-carboxylate (Step C, INTERMEDIATE 56) (185 mg, 0.404 mmol), potassium carbonate (0.404 ml, 0.808 mmol), 1,1bis(di-tert-butylphosphino)ferrocene palladium dichloride (27.5 mg, 0.040 mmol) and THF (5 mL) were sealed in a microwave vessel and subject to microwave irradiation at 120° C. for 30 min. Volatiles were removed under reduced pressure. The resulting pot residue was purified by preparative HPLC (reverse phase, Waters SunFire PrepC18 OBD 5 um 19×150 mm) eluting with acetonitrile/water+0.1% TFA (30% to 100% organic in 10 min, then to 100% for 2 min, 20 mL/min). Related fractions were pooled and evaporated under reduced pressure to afford a dark solid. This dark solid was further purified by preparative TLC (silica gel) developed with EtOAc/hexanes (30% ethyl acetate v/v) to give the title compound as a colorless solid foam. LCMS calc.=781.14. found=782.25 (M+H)⁺.

Step B: 1-{3-[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]-5-fluoro-4-methoxyphenyl}-5-(trifluoromethyl)-1H-pyrazole-4-carboxylic acid A solution of lithium hydroxide monohydrate (7.57 mg, 0.180 mmol) in water (1 mL) was added into a solution of methyl 3-{3-[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]-4-methoxyphenyl}propanoate (47 mg, 0.060 mmol) in 1,4-dioxane (1 mL) at room temperature. The resulting mixture was stirred at room temperature overnight. LCMS trace indicated completion of reaction. To the crude was added HCl (1N) until the mixture turned cloudy. This cloudiness was dissolved by addition of MeCN. The resulting solution was purified by preparative HPLC (reverse phase, Kromasil® 100-5C18, 100×21.1 mm) eluting with acetonitrile/water+0.05% HCOOH (30% to 100% organic in 10 min, hold 100% for 2 min, 20 mL/min). Related fractions were pooled and evaporated under reduced pressure to afford a white solid as the titled compound. LCMS calc.=753.11. found=754.19 (M+H)⁺.

Step C: 1-{3-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-5-fluoro-4-methoxyphenyl}-5-(trifluoromethyl)-1H-pyrazole-4-carboxylic acid 1-{3-[4-({(4S,5R)-5-[3,5-bis(trifluoromethyl)phenyl]-4-methyl-2-oxo-1,3-oxazolidin-3-yl}methyl)-2-(methylsulfanyl)pyrimidin-5-yl]-5-fluoro-4-methoxyphenyl}-5-(trifluoromethyl)-1H-pyrazole-4-carboxylic acid (38 mg, 0.050 mmol), mCPBA (26.1 mg, 0.151 mmol) and DCM (1 mL) were stirred at room temp for 2 hrs. LCMS trace indicated completion of reaction. Volatiles were removed under reduced pressure. The resulting residue was purified by preparative HPLC (reverse phase, Kromasil® 100-5C18, 100× 21.1 mm) eluting with Acetonitrile/water+0.05% HCOOH (30% to 100% organic in 10 min, hold 100% for 2 min, 20 mL/min). Related fractions were pooled and evaporated under reduced pressure to afford a white solid as the titled compound. LCMS calc.=785.10. found=786.22 (M+H)⁺.

Step 4: 1-{3-[4-({(4S,5R)-5-[3,5-bis(trifluoromethyl)phenyl]-4-methyl-2-oxo-1,3-oxazolidin-3-yl}methyl)-2-(3,3-difluoroazetidin-1-yl)pyrimidin-5-yl]-5-fluoro-4-methoxyphenyl}-5-(trifluoromethyl)-1H-pyrazole-4-carboxylic acid 1-{3-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-5-fluoro-4-methoxyphenyl}-5-(trifluoromethyl)-1H-pyrazole-4-carboxylic acid (32 mg, 0.041 mmol), 3,3-difluoroazetidine hydrochloride (21.11 mg, 0.163 mmol), triethylamine (0.057 mL, 0.407 mmol) and THF (1 mL) were sealed in a uw vessel and subject to microwave irradiation at 120° C. for 20 min. The crude mixture was purified by flash chromatography (SiO₂, Biotage SNAP Cartridge, silica gel, KP-Sil, 50 g cartridge). The column was eluted by an EtOAc/hexanes mixture (0% to 40%). Related fractions were pooled and evaporated to afford a white solid glass as the titled compound. LCMS calc.=798.15. found=799.32 (M+L)⁺. ¹H-NMR (CDCl₃, 500 MHz) δ 8.25 (s, 1H), 8.16 (s, 1H), 7.89 (s, 1H), 7.75 (s, 2H), 7.20 (dd, J=11.3, 2.0 Hz, 1H), 7.11 (s, 1H), 5.66 (d, J=8.0 Hz, 1H), 4.77 (d, J=17.0 Hz, 1H), 4.54 (m, 4H), 4.25 (m, 1H), 4.05 (br s, 1H), 3.951 (s, 1.5H), 3.946 (s, 1.5H), 0.72 (s, 1.5H), 0.72 (s, 1.5H).

The following compounds (Table 19) were synthesized using methods analogous to those described in EXAMPLE 187 from commercially available materials or intermediates whose syntheses are described above.

TABLE 19

| Example | Molecular structure | LCMS (M + H)⁺ |
|---|---|---|
| 188 | 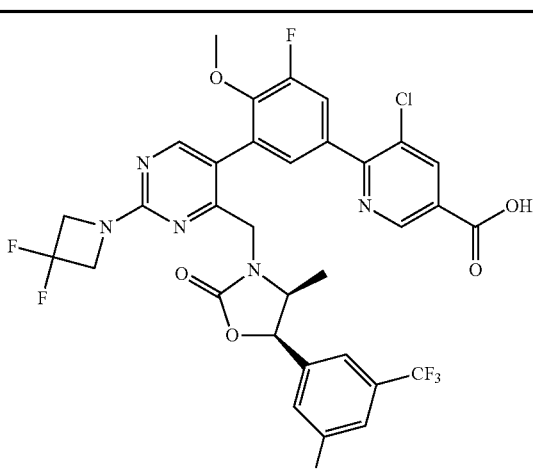 | 776.26 |

TABLE 19-continued

| Example | Molecular structure | LCMS (M + H)+ |
|---------|---------------------|---------------|
| 189 | 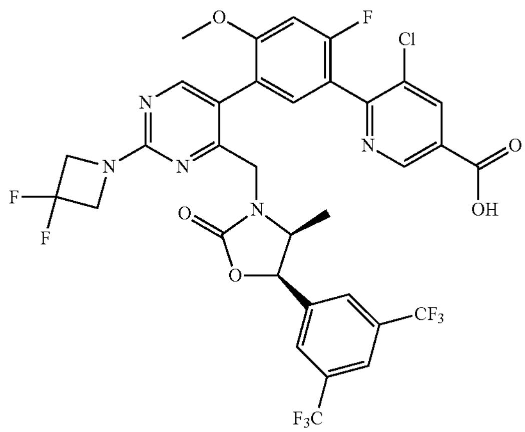 [SMILES: COc1cc(F)c(-c2ncc(C(=O)O)cc2Cl)cc1-c1cnc(N2CC(F)(F)C2)nc1CN1C(=O)O[C@H](c2cc(C(F)(F)F)cc(C(F)(F)F)c2)[C@@H]1C] | 776.30 |
| 190 | 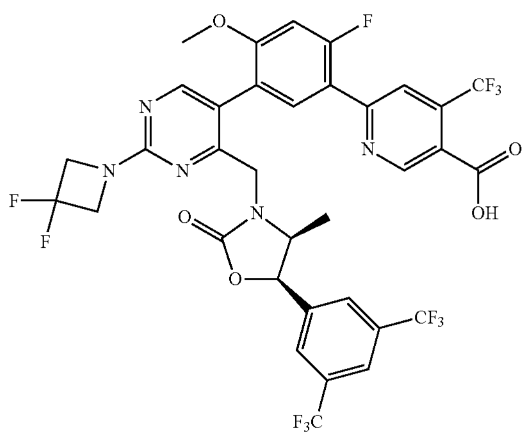 [SMILES: COc1cc(F)c(-c2cc(C(F)(F)F)c(C(=O)O)cn2)cc1-c1cnc(N2CC(F)(F)C2)nc1CN1C(=O)O[C@H](c2cc(C(F)(F)F)cc(C(F)(F)F)c2)[C@@H]1C] | 810.30 |
| 191 | 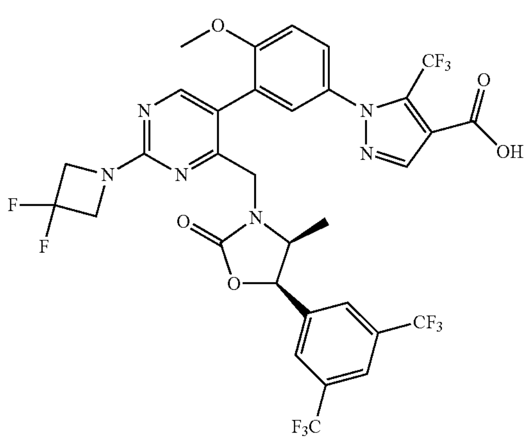 [SMILES: COc1ccc(-n2ncc(C(=O)O)c2C(F)(F)F)cc1-c1cnc(N2CC(F)(F)C2)nc1CN1C(=O)O[C@H](c2cc(C(F)(F)F)cc(C(F)(F)F)c2)[C@@H]1C] | 781.34 |

Example 192

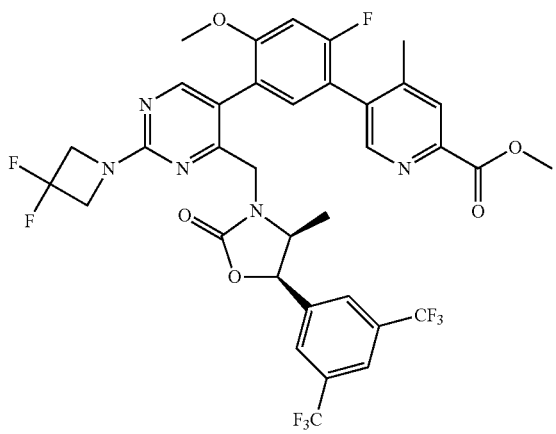 [SMILES: COC(=O)c1cc(C)c(-c2cc(-c3cnc(N4CC(F)(F)C4)nc3CN3C(=O)O[C@H](c4cc(C(F)(F)F)cc(C(F)(F)F)c4)[C@@H]3C)c(OC)cc2F)cn1]

Methyl 5-{5-[4-({(4S,5R)-5-[3,5-bis(trifluoromethyl)phenyl]-4-methyl-2-oxo-1,3-oxazolidin-3-yl}methyl)-2-(3,3-difluoroazetidin-1-yl)pyrimidin-5-yl]-2-fluoro-4-methoxyphenyl}-4-methylpyridine-2-carboxylate Step A: (4S,5R)-5-[3,5-bis(trifluoromethyl)phenyl]-3-{[5-bromo-2-(methylsulfonyl)pyrimidin-4-yl]methyl}-4-methyl-1,3-oxazolidin-2-one (4S,5R)-5-[3,5-bis(trifluoromethyl)phenyl]-3-{[5-bromo-2-(methylsulfanyl)pyrimidin-4-yl]methyl}-4-methyl-1,3-oxazolidin-2-one (INTERMEDIATE 45) (1.2544 g, 2.366 mmol) and 3-chloroperoxybenzoic acid (1.225 g, 7.10 mmol) were mixed in CH$_2$Cl$_2$ (20 mL) at room temperature overnight. The crude was purified by flash chromatography (SiO$_2$, Isolute Flash Si; 100 g prepacked cartridge). The column was eluted by an EtOAc/hexanes mixture (0% to 60%) to afford a colorless solid as the titled compound. LCMS calc.=560.98. found=564.04.

Step B: (4S,5R)-5-[3,5-bis(trifluoromethyl)phenyl]-3-{[5-bromo-2-(3,3-difluoroazetidin-1-yl)pyrimidin-4-yl]methyl}-4-methyl-1,3-oxazolidin-2-one (4S,5R)-5-[3,5-bis(trifluoromethyl)phenyl]-3-{[5-bromo-2-(methylsulfonyl)pyrimidin-4-yl]methyl}-4-methyl-1,3-oxazolidin-2-one (1.4428 g, 2.57 mmol) from Step A, 3,3-difluoroazetidine hydrochloride (0.997 g, 7.70 mmol), triethylamine (1.788 ml, 12.83 mmol) and THF (25 mL) were heated in a 63° C. oil bath overnight. The reaction crude was purified by flash chromatography (SiO$_2$, Isolute Flash Si; 100 g prepacked cartridge). The column was eluted by an EtOAc/hexanes mixture (0% to 40%). Related fractions were pooled and evaporated to afford a light yellow solid foam as the titled compound. LCMS calc.=574.03. found=575.09 (M+H)$^+$.

Step C: (4S,5R)-5-[3,5-bis(trifluoromethyl)phenyl]-3-{[2-(3,3-difluoroazetidin-1-yl)-5-(4,4,5,5-tetramethyl-1,3,2-dioxaborolan-2-yl)pyrimidin-4-yl]methyl}-4-methyl-1,3-oxazolidin-2-one (4S,5R)-5-[3,5-bis(trifluoromethyl)phenyl]-3-{[5-bromo-2-(3,3-difluoroazetidin-1-yl)pyrimidin-4-yl]methyl}-4-methyl-1,3-oxazolidin-2-one (574.7 mg, 0.999 mmol) from Step B, 1,1'-bis(diphenylphosphino)ferrocene-palladium(ii) dichloride dichloromethane complex (82 mg, 0.100 mmol), bis(pinacolato)diboron (304 mg, 1.199 mmol), potassium acetate (147 mg, 1.499 mmol), 1,4-dioxane (2.220 mL) and DMSO (7.770 mL) were sealed in a uw vessel and subject to microwave irradiation at 140° C. for 20 min. LCMS indicated complete consumption of the starting material and formation of the desired product and other impurities/by-products. Volatiles were removed under reduced pressure. The resulting pot residue was purified by preparative HPLC (reverse phase, Waters SunFire PrepC18 OBD 5 um 19×150 mm) eluting with acetonitrile/water+0.05% HCOOH (30% to 100% organic in 10 min, hold 100% for 2 min, 20 mL/min). Related fractions were pooled and evaporated under reduced pressure to afford a dark solid glass as a mixture of the titled compound (~40 a % pure) and other impurities/by-products. It was used without purification for the following step. LCMS calc.=622.20. found=623.28 (M+H)$^+$.

Step D: methyl 5-{5-[4-({(4S,5R)-5-[3,5-bis(trifluoromethyl)phenyl]-4-methyl-2-oxo-1,3-oxazolidin-3-yl}methyl)-2-(3,3-difluoroazetidin-1-yl)pyrimidin-5-yl]-2-fluoro-4-methoxyphenyl}-4-methylpyridine-2-carboxylate (4S,5R)-5-[3,5-bis(trifluoromethyl)phenyl]-3-{[2-(3,3-difluoroazetidin-1-yl)-5-(4,4,5,5-tetramethyl-1,3,2-dioxaborolan-2-yl)pyrimidin-4-yl]methyl}-4-methyl-1,3-oxazolidin-2-one (83 mg, 0.133 mmol) from Step C, INTERMEDIATE 58 (40 mg, 0.100 mmol), potassium carbonate (0.138 ml, 0.277 mmol), 1,1bis(di-tert-butylphosphino)ferrocene palladium dichloride (5 mg, 7.36 μmol) and tetrahydrofuran (1.5 mL) were sealed in a microwave vessel and subject to microwave irradiation at 140° C. for 25 min. Volatiles were removed under reduced pressure. The resulting pot residue was purified by preparative HPLC (reverse phase, Waters SunFire PrepC18 OBD 5 um 19×150 mm) eluting with acetonitrile/water+0.05% HCOOH (30% to 100% organic in 10 min, hold 100% for 2 min, 20 mL/min). Related fractions were pooled and evaporated under reduced pressure to afford a brown glass as a formate of the titled compound. LCMS calc.=769.19. found=770.35 (M+H)$^+$.

Example 193

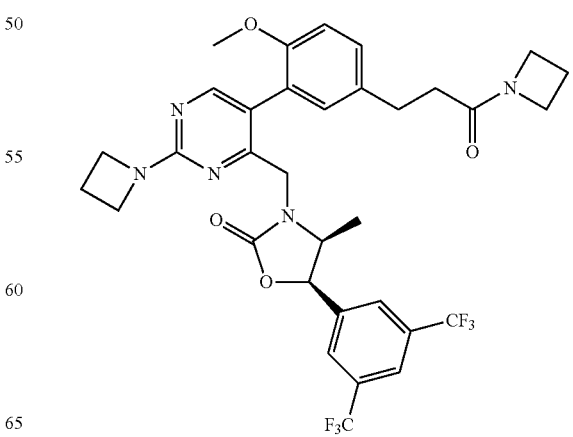

Azetidine 3-{3-[4-({(4S,5R)-5-[3,5-bis(trifluoromethyl)phenyl]-4-methyl-2-oxo-1,3-oxazolidin-3-yl}methyl)-2-(azetidin-1-yl)pyrimidin-5-yl]-4-methoxyphenyl}propanamide A mixture of methyl 3-{3-[4-({(4S,5R)-5-[3,5-bis(trifluoromethyl)phenyl]-4-methyl-2-oxo-1,3-oxazolidin-3-yl}methyl)-2-(methylsulfonyl)pyrimidin-5-yl]-4-methoxyphenyl}propanoate from Example 140, Step B (50 mg, 0.074 mmol), azetidine (21.1 mg, 0.37 mmol) in THF (5 mL) was stirred at 25° C. for overnight. The solvents were removed. The residue was purified by column chromatography on silica gel Biotage 405, eluting with EtOAc/hexane (2/8) to give the title compound as a yellow gum. $^1$H NMR (CDCl$_3$, 500 MHz) δ 8.13 (s, 1H), 7.90 (s, 1H), 7.77 (s, 2H), 7.41 (d, J=8 Hz, 1H), 7.02 (d, J=2 Hz, 1H), 6.91 (d, J=8 Hz, 1H), 5.65 (d, J=8.5 Hz, 1H), 4.74 (m, 1H), 4.38 (m, 1H), 4.24 (m, 4H), 3.80-4.08 (m, 5H), 3.81 (s, 3H), 2.94 (t, J=7.5 Hz, 2H), 2.45 (m, 2H), 2.38 (t, J=7.5 Hz, 1H), 2.24 (m, 2H), 0.71 (d, J=6.5 Hz, 3H). LCMS=678.7 (M+H)$^+$ The following compounds (Table 20) were synthesized using methods analogous to those described previously from commercially available materials or intermediates whose syntheses are described above.

TABLE 20

| Example | Molecular structure | LCMS (M + H)$^+$ |
|---|---|---|
| 194 | 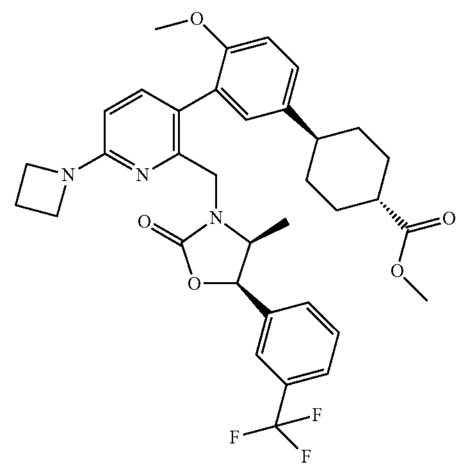 [SMILES: COc1ccc([C@H]2CC[C@H](C(=O)OC)CC2)cc1-c1ccc(N2CCC2)nc1CN1C(=O)O[C@H](c2cccc(C(F)(F)F)c2)[C@@H]1C] | 638.2 |
| 195 | 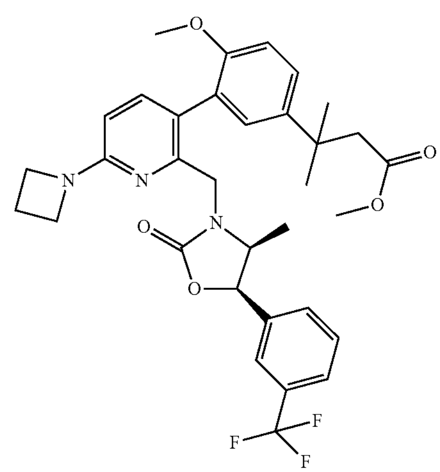 [SMILES: COC(=O)CC(C)(C)c1ccc(OC)c(-c2ccc(N3CCC3)nc2CN2C(=O)O[C@H](c3cccc(C(F)(F)F)c3)[C@@H]2C)c1] | 612.3 |

TABLE 20-continued
| Example | Molecular structure | LCMS (M + H)+ |
|---|---|---|
| 196 | 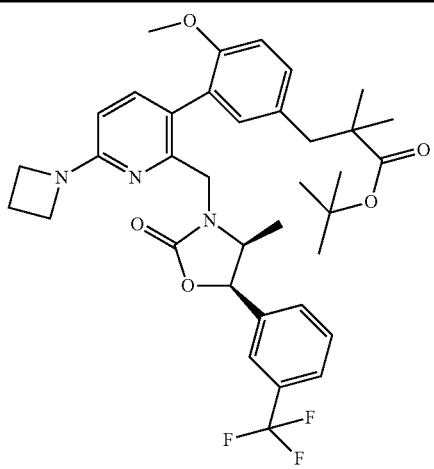 | 654.3 |
| 197 | 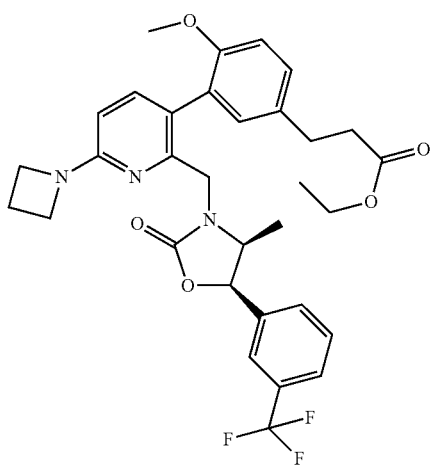 [SMILES: CCOC(=O)CCc1ccc(OC)c(-c2ccc(N3CCC3)nc2CN2C(=O)O[C@H](c3cccc(C(F)(F)F)c3)[C@@H]2C)c1] | 598.2 |
| 198 | 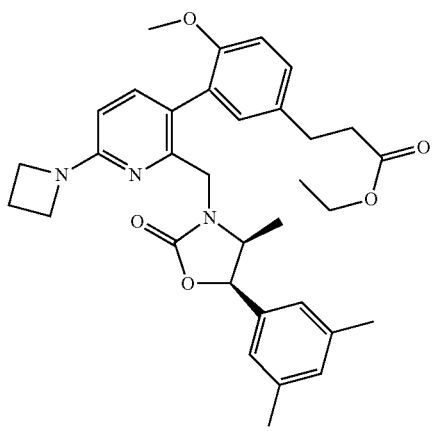 [SMILES: CCOC(=O)CCc1ccc(OC)c(-c2ccc(N3CCC3)nc2CN2C(=O)O[C@H](c3cc(C)cc(C)c3)[C@@H]2C)c1] | 558.3 |

TABLE 20-continued
| Example | Molecular structure | LCMS (M + H)+ |
|---|---|---|
| 199 | 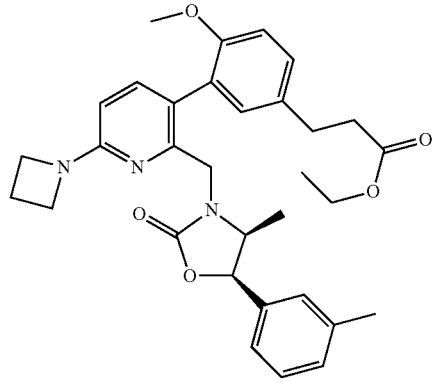 [SMILES: CCOC(=O)CCc1ccc(OC)c(-c2ccc(N3CCC3)nc2CN2C(=O)O[C@H](c3cccc(C)c3)[C@@H]2C)c1] | 544.2 |
| 200 | 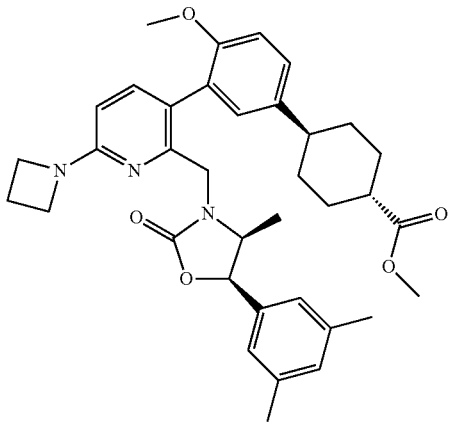 [SMILES: COc1ccc([C@H]2CC[C@H](C(=O)OC)CC2)cc1-c1ccc(N2CCC2)nc1CN1C(=O)O[C@H](c2cc(C)cc(C)c2)[C@@H]1C] | 598.3 |
| 201 | 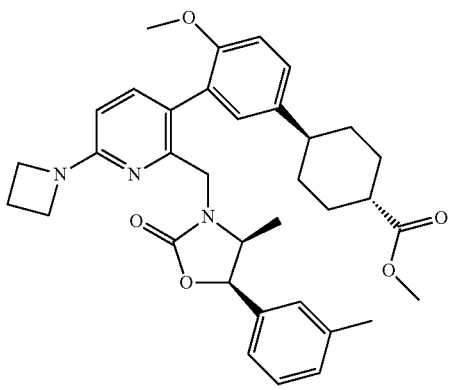 [SMILES: COc1ccc([C@H]2CC[C@H](C(=O)OC)CC2)cc1-c1ccc(N2CCC2)nc1CN1C(=O)O[C@H](c2cccc(C)c2)[C@@H]1C] | 584.4 |

TABLE 20-continued
| Example | Molecular structure | LCMS (M + H)+ |
|---|---|---|
| 202 | 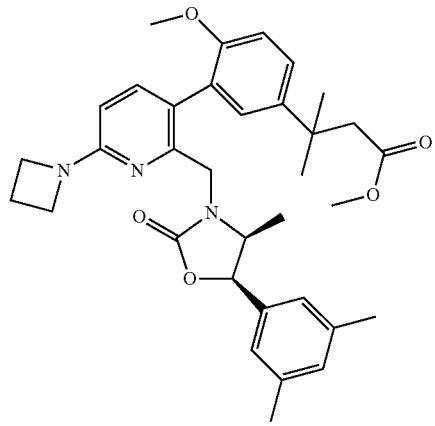 [SMILES: COC(=O)CC(C)(C)c1ccc(OC)c(-c2ccc(N3CCC3)nc2CN2C(=O)O[C@H](c3cc(C)cc(C)c3)[C@@H]2C)c1] | 572.3 |
| 203 | 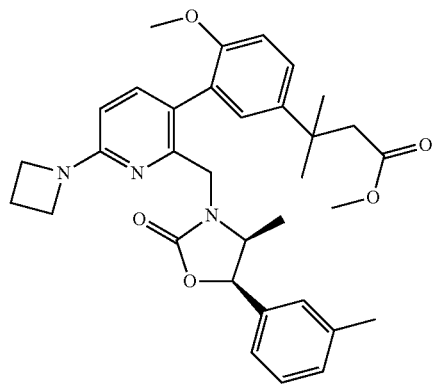 [SMILES: COC(=O)CC(C)(C)c1ccc(OC)c(-c2ccc(N3CCC3)nc2CN2C(=O)O[C@H](c3cccc(C)c3)[C@@H]2C)c1] | 558.3 |
| 204 | 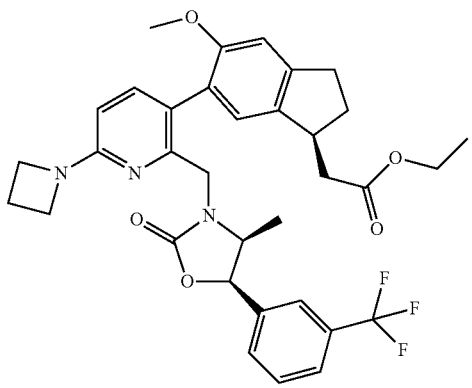 [SMILES: CCOC(=O)C[C@@H]1CCc2cc(OC)c(-c3ccc(N4CCC4)nc3CN3C(=O)O[C@H](c4cccc(C(F)(F)F)c4)[C@@H]3C)cc21] | 624.2 |

TABLE 20-continued
| Example | Molecular structure | LCMS (M + H)+ |
|---------|---------------------|---------------|
| 205 | 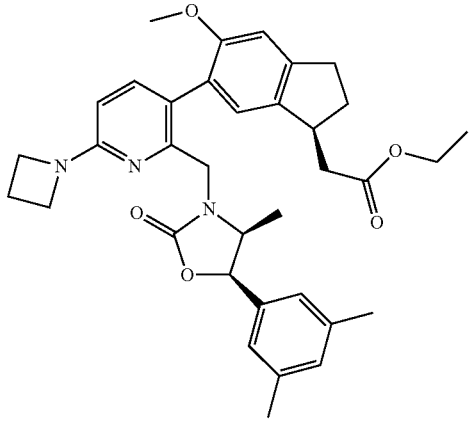 [SMILES: CCOC(=O)C[C@@H]1CCc2cc(OC)c(-c3ccc(N4CCC4)nc3CN3C(=O)O[C@H](c4cc(C)cc(C)c4)[C@@H]3C)cc21] | 584.3 |
| 206 | 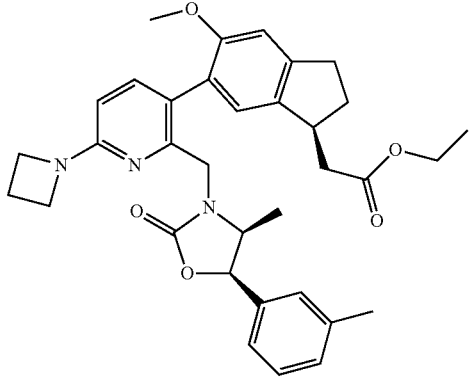 [SMILES: CCOC(=O)C[C@@H]1CCc2cc(OC)c(-c3ccc(N4CCC4)nc3CN3C(=O)O[C@H](c4cccc(C)c4)[C@@H]3C)cc21] | 570.4 |
| 207 | 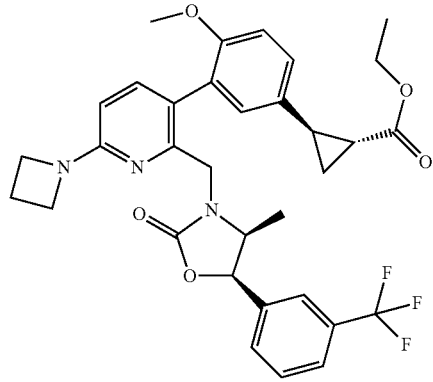 [SMILES: CCOC(=O)[C@@H]1C[C@H]1c1ccc(OC)c(-c2ccc(N3CCC3)nc2CN2C(=O)O[C@H](c3cccc(C(F)(F)F)c3)[C@@H]2C)c1] | 610.2 |

TABLE 20-continued
| Example | Molecular structure | LCMS (M + H)+ |
|---|---|---|
| 208 | 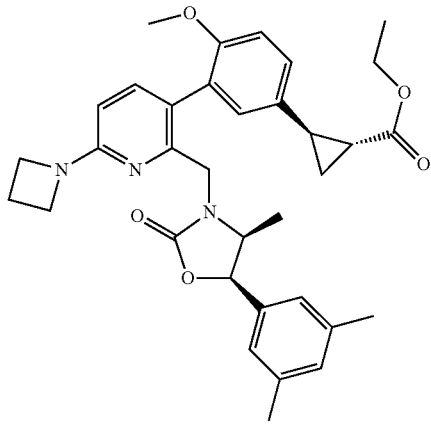 [SMILES: CCOC(=O)[C@@H]1C[C@H]1c1ccc(OC)c(-c2ccc(N3CCC3)nc2CN2C(=O)O[C@H](c3cc(C)cc(C)c3)[C@@H]2C)c1] | 570.4 |
| 209 | 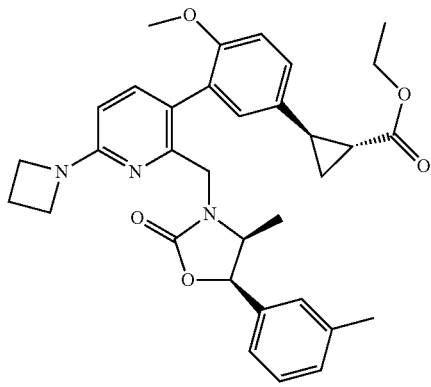 [SMILES: CCOC(=O)[C@@H]1C[C@H]1c1ccc(OC)c(-c2ccc(N3CCC3)nc2CN2C(=O)O[C@H](c3cccc(C)c3)[C@@H]2C)c1] | 556.2 |
| 210 | 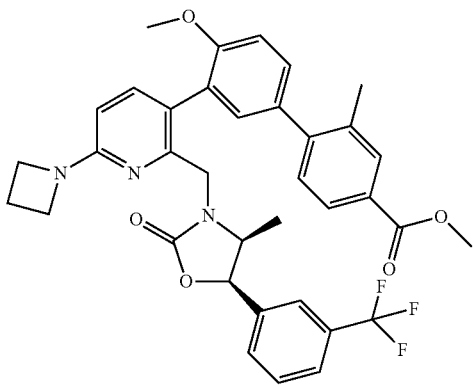 [SMILES: COC(=O)c1ccc(-c2ccc(OC)c(-c3ccc(N4CCC4)nc3CN3C(=O)O[C@H](c4cccc(C(F)(F)F)c4)[C@@H]3C)c2)c(C)c1] | 646.3 |

TABLE 20-continued
| Example | Molecular structure | LCMS (M + H)+ |
|---|---|---|
| 211 | 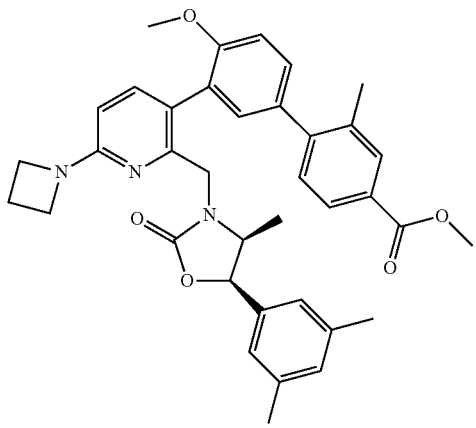 [SMILES: COC(=O)c1ccc(-c2ccc(OC)c(-c3ccc(N4CCC4)nc3CN3C(=O)O[C@H](c4cc(C)cc(C)c4)[C@@H]3C)c2)c(C)c1] | 606.3 |
| 212 | 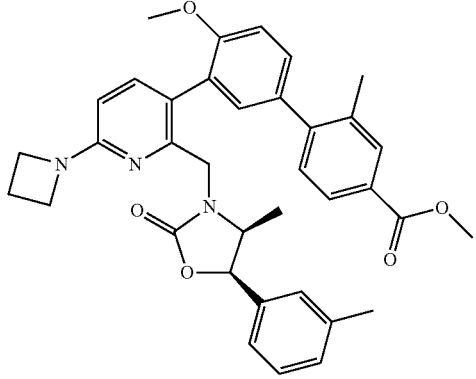 [SMILES: COC(=O)c1ccc(-c2ccc(OC)c(-c3ccc(N4CCC4)nc3CN3C(=O)O[C@H](c4cccc(C)c4)[C@@H]3C)c2)c(C)c1] | 592.3 |
| 213 | 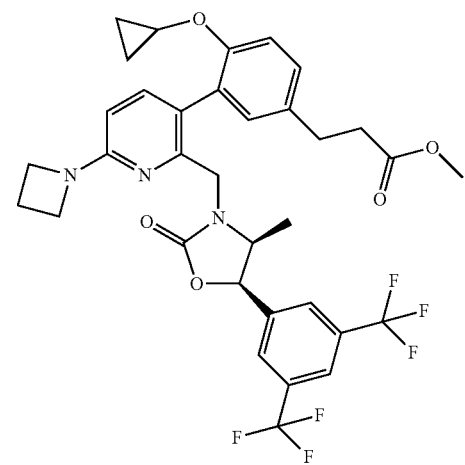 [SMILES: COC(=O)CCc1ccc(OC2CC2)c(-c2ccc(N3CCC3)nc2CN2C(=O)O[C@H](c3cc(C(F)(F)F)cc(C(F)(F)F)c3)[C@@H]2C)c1] | 678.4 |

TABLE 20-continued

| Example | Molecular structure | LCMS (M + H)+ |
|---------|---------------------|---------------|
| 214 | trans/racemic at cyclopentyl | 692.4 |
| 215 | 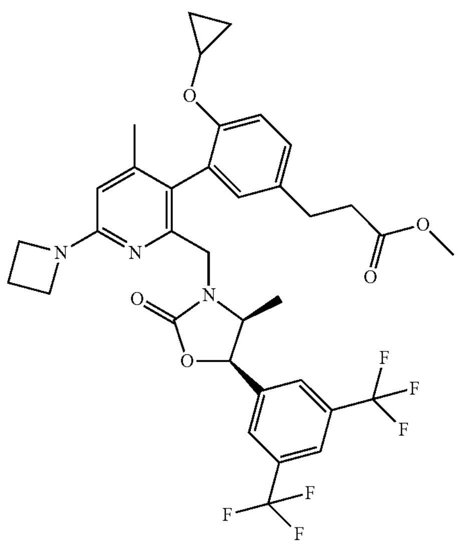 [SMILES: COC(=O)CCc1ccc(OC2CC2)c(-c2c(C)cc(N3CCC3)nc2CN2C(=O)O[C@H](c3cc(C(F)(F)F)cc(C(F)(F)F)c3)[C@@H]2C)c1] | 692.4 |
| 216 | trans/racemic at cyclopentyl; mixture of atropisomers | 706.4 |

TABLE 20-continued

| Example | Molecular structure | LCMS (M + H)+ |
|---------|---------------------|---------------|
| 217 | cis at cyclopentyl, enantiomer 1 | 692.4 |
| 218 | cis at cyclopentyl, enantiomer 2 | 692.4 |

The following compounds (Table 21) were synthesized using methods analogous to those described for EXAMPLES 60 and 61 from commercially available materials or intermediates whose syntheses are described above.

TABLE 21

| Example | Molecular structure | LCMS (M + H)+ |
|---------|---------------------|---------------|
| 219 | 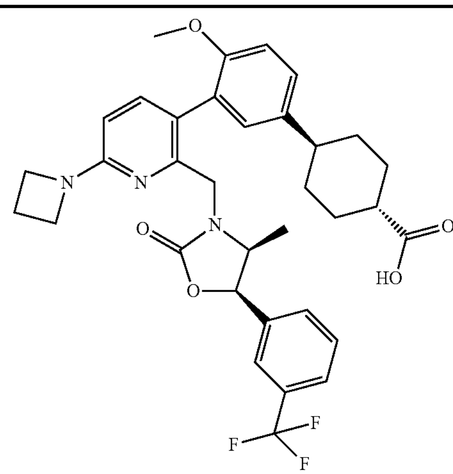 | 624.2 |

TABLE 21-continued
| Example | Molecular structure | LCMS (M + H)+ |
|---|---|---|
| 220 | 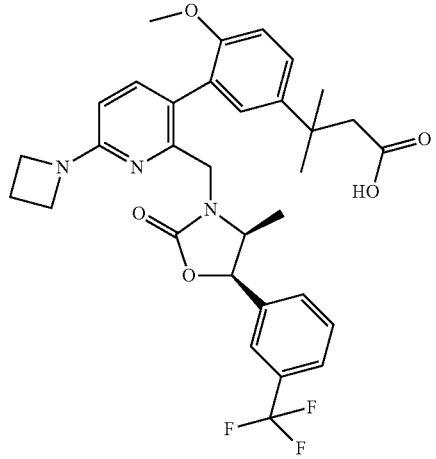 [SMILES: COc1ccc(C(C)(C)CC(=O)O)cc1-c1ccc(N2CCC2)nc1CN1C(=O)O[C@H](c2cccc(C(F)(F)F)c2)[C@@H]1C] | 598.2 |
| 221 | 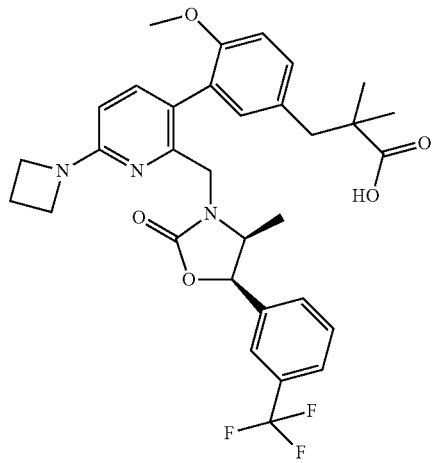 [SMILES: COc1ccc(CC(C)(C)C(=O)O)cc1-c1ccc(N2CCC2)nc1CN1C(=O)O[C@H](c2cccc(C(F)(F)F)c2)[C@@H]1C] | 598.2 |
| 222 | 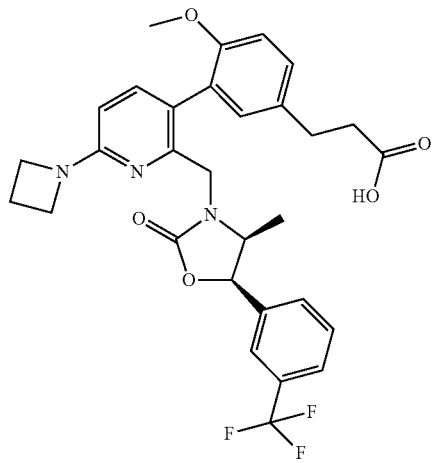 [SMILES: COc1ccc(CCC(=O)O)cc1-c1ccc(N2CCC2)nc1CN1C(=O)O[C@H](c2cccc(C(F)(F)F)c2)[C@@H]1C] | 570.2 |

TABLE 21-continued
| Example | Molecular structure | LCMS (M + H)+ |
|---------|---------------------|---------------|
| 223 | 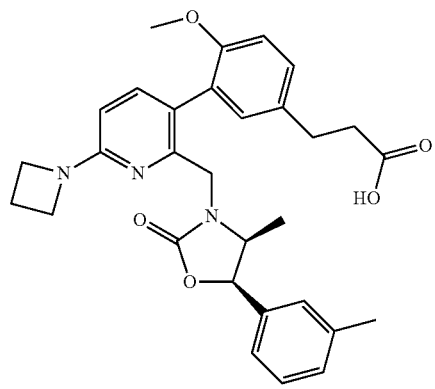 [SMILES: COc1ccc(CCC(=O)O)cc1-c1ccc(N2CCC2)nc1CN1C(=O)O[C@H](c2cccc(C)c2)[C@@H]1C] | 516.2 |
| 224 | 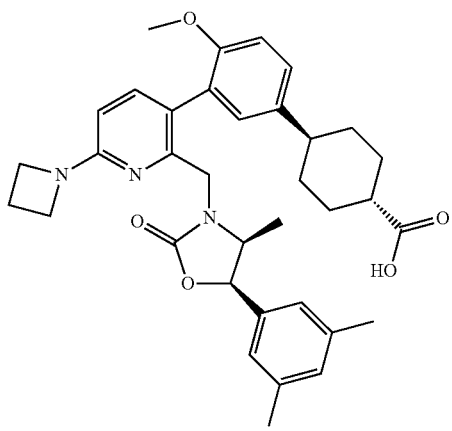 [SMILES: COc1ccc([C@H]2CC[C@H](C(=O)O)CC2)cc1-c1ccc(N2CCC2)nc1CN1C(=O)O[C@H](c2cc(C)cc(C)c2)[C@@H]1C] | 584.3 |
| 225 | 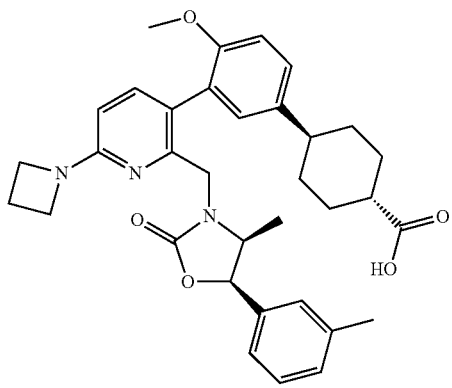 [SMILES: COc1ccc([C@H]2CC[C@H](C(=O)O)CC2)cc1-c1ccc(N2CCC2)nc1CN1C(=O)O[C@H](c2cccc(C)c2)[C@@H]1C] | 570.3 |

TABLE 21-continued
| Example | Molecular structure | LCMS (M + H)+ |
|---|---|---|
| 226 | 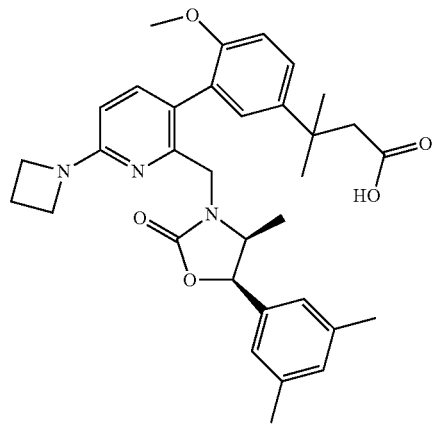 [SMILES: COc1ccc(C(C)(C)CC(=O)O)cc1-c1ccc(N2CCC2)nc1CN1C(=O)O[C@H](c2cc(C)cc(C)c2)[C@@H]1C] | 558.3 |
| 227 | 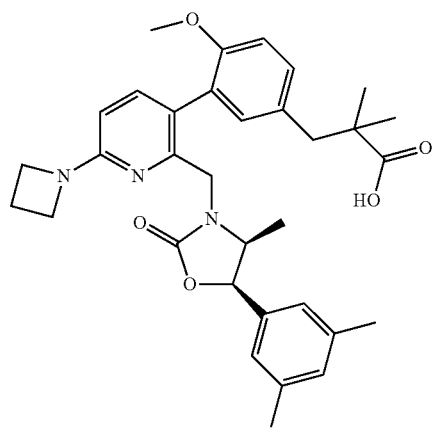 [SMILES: COc1ccc(CC(C)(C)C(=O)O)cc1-c1ccc(N2CCC2)nc1CN1C(=O)O[C@H](c2cc(C)cc(C)c2)[C@@H]1C] | 558.3 |
| 228 | 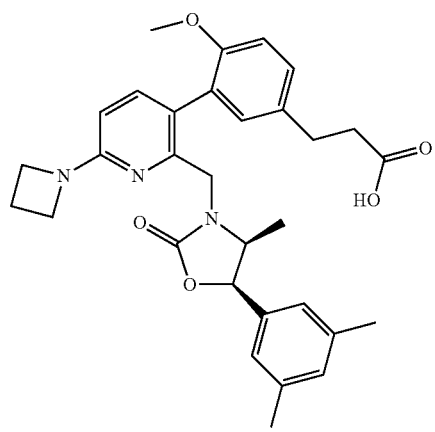 [SMILES: COc1ccc(CCC(=O)O)cc1-c1ccc(N2CCC2)nc1CN1C(=O)O[C@H](c2cc(C)cc(C)c2)[C@@H]1C] | 530.2 |

TABLE 21-continued
| Example | Molecular structure | LCMS (M + H)+ |
|---|---|---|
| 229 | 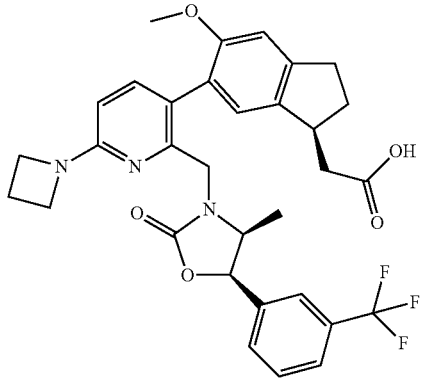 [SMILES: COc1cc2c(cc1-c1ccc(N3CCC3)nc1CN1C(=O)O[C@H](c3cccc(C(F)(F)F)c3)[C@@H]1C)[C@H](CC(=O)O)CC2] | 596.4 |
| 230 | 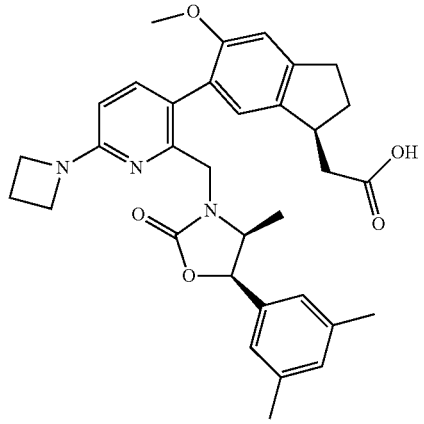 [SMILES: COc1cc2c(cc1-c1ccc(N3CCC3)nc1CN1C(=O)O[C@H](c3cc(C)cc(C)c3)[C@@H]1C)[C@H](CC(=O)O)CC2] | 556.3 |
| 231 | 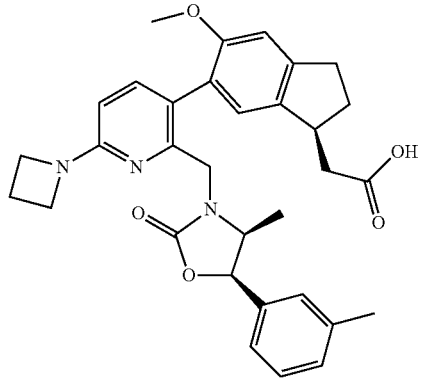 [SMILES: COc1cc2c(cc1-c1ccc(N3CCC3)nc1CN1C(=O)O[C@H](c3cccc(C)c3)[C@@H]1C)[C@H](CC(=O)O)CC2] | 542.3 |
| 232 | 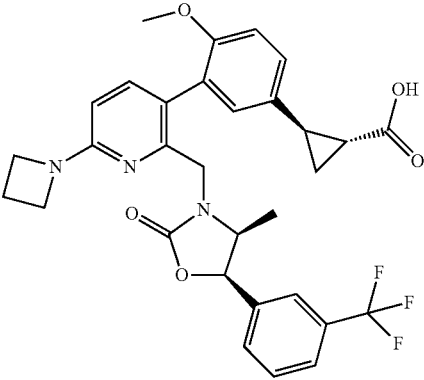 [SMILES: COc1ccc([C@@H]2C[C@H]2C(=O)O)cc1-c1ccc(N2CCC2)nc1CN1C(=O)O[C@H](c2cccc(C(F)(F)F)c2)[C@@H]1C] | 582.2 |

TABLE 21-continued
| Example | Molecular structure | LCMS (M + H)+ |
|---|---|---|
| 233 | 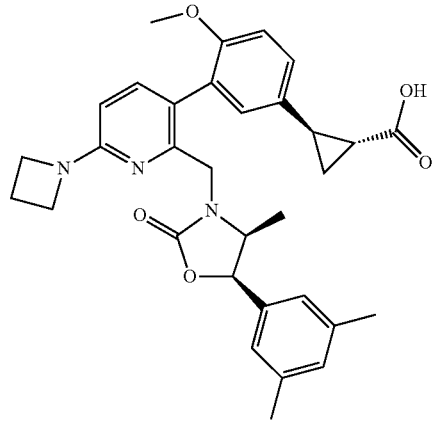 [SMILES: COc1ccc([C@@H]2C[C@H]2C(=O)O)cc1-c1ccc(N2CCC2)nc1CN1C(=O)O[C@H](c2cc(C)cc(C)c2)[C@@H]1C] | 542.2 |
| 234 | 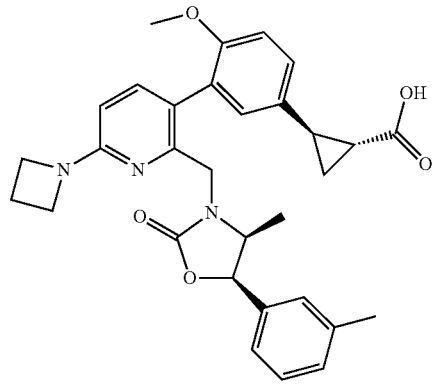 [SMILES: COc1ccc([C@@H]2C[C@H]2C(=O)O)cc1-c1ccc(N2CCC2)nc1CN1C(=O)O[C@H](c2cccc(C)c2)[C@@H]1C] | 528.5 |
| 235 | 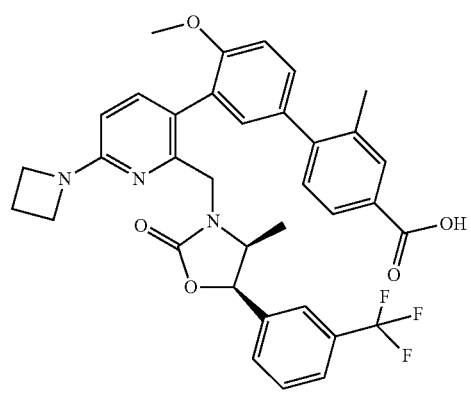 [SMILES: COc1ccc(-c2ccc(C(=O)O)cc2C)cc1-c1ccc(N2CCC2)nc1CN1C(=O)O[C@H](c2cccc(C(F)(F)F)c2)[C@@H]1C] | 632.3 |

TABLE 21-continued
| Example | Molecular structure | LCMS (M + H)+ |
|---|---|---|
| 236 | 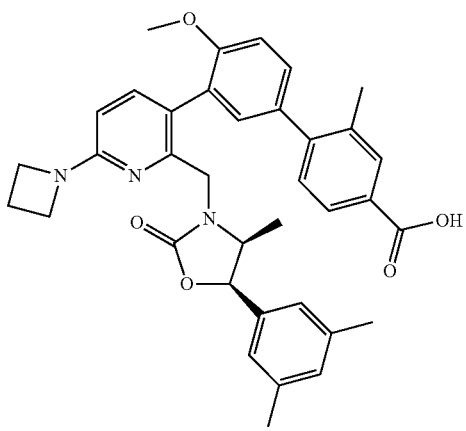 [SMILES: COc1ccc(-c2ccc(C(=O)O)cc2C)cc1-c1ccc(N2CCC2)nc1CN1C(=O)O[C@H](c2cc(C)cc(C)c2)[C@@H]1C] | 592.3 |
| 237 | 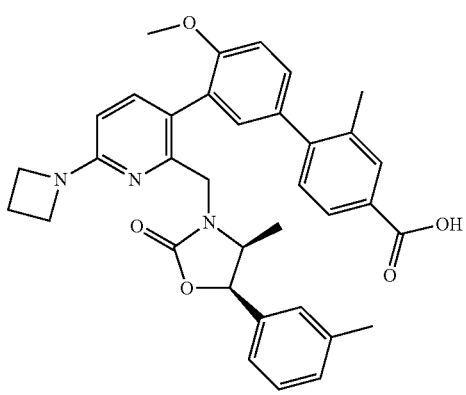 [SMILES: COc1ccc(-c2ccc(C(=O)O)cc2C)cc1-c1ccc(N2CCC2)nc1CN1C(=O)O[C@H](c2cccc(C)c2)[C@@H]1C] | 578.3 |
| 238 | 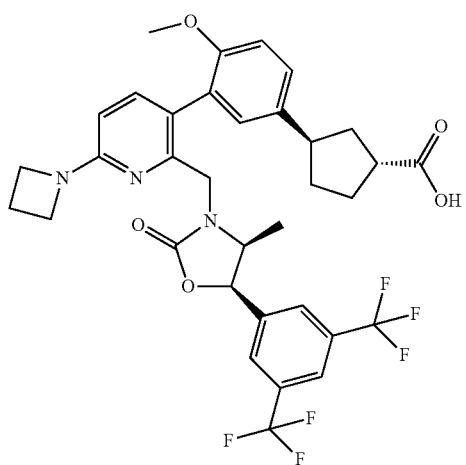<br>trans at cyclopentyl, enantiomer A | 678.3 |

TABLE 21-continued

| Example | Molecular structure | LCMS (M + H)+ |
|---|---|---|
| 239 | trans at cyclopentyl, enantiomer B | 678.3 |
| 240 | atropisomer A | 678.4 |
| 241 | atropisomer B | 678.4 |

TABLE 21-continued
| Example | Molecular structure | LCMS (M + H)+ |
|---|---|---|
| 242 | 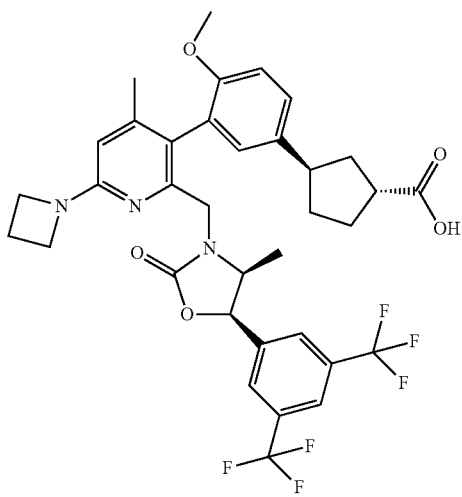 atropisomer A, enantiomer 1 | 692.4 |
| 243 | 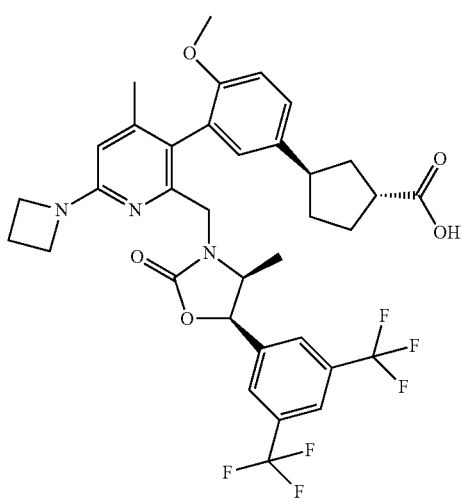 atropisomer A, enantiomer 2 | 692.4 |
| 244 | 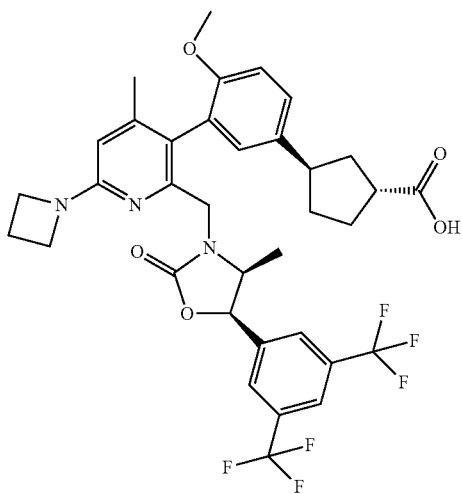 atropisomer B, enantiomer 2 | 692.4 |

TABLE 21-continued
| Example | Molecular structure | LCMS (M + H)+ |
| --- | --- | --- |
| 245 | 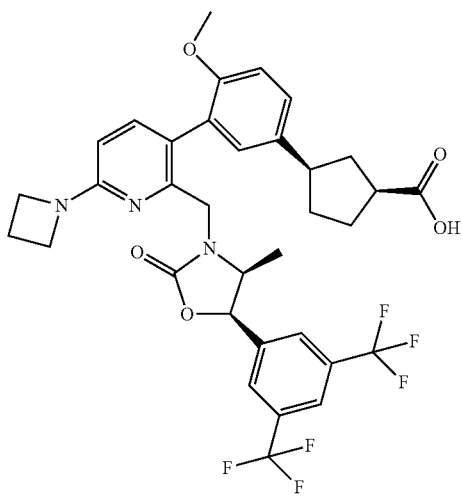 cis at cyclopentyl, enantiomer 1 | 678.3 |
| 246 | 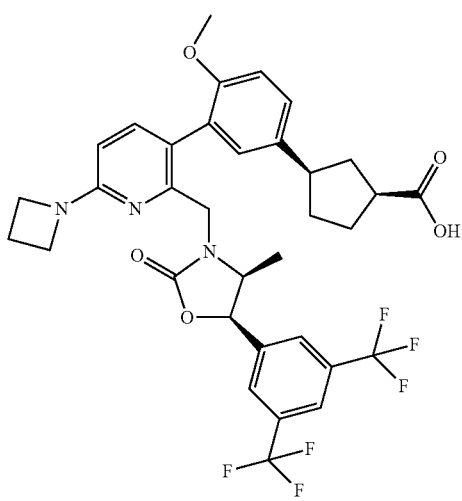 cis at cyclopentyl, enantiomer 2 | 678.3 |
| 247 | 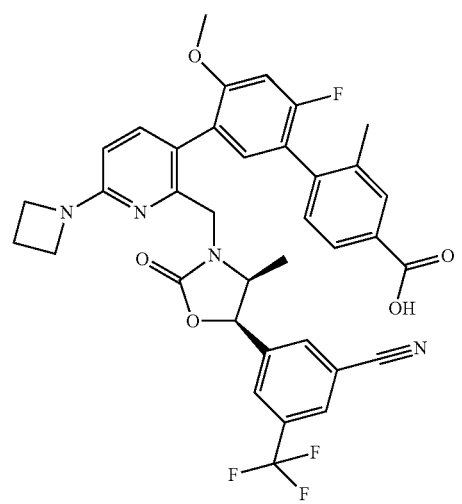 [SMILES: COc1cc(F)c(-c2ccc(C(=O)O)cc2C)cc1-c1ccc(N2CCC2)nc1CN1C(=O)O[C@H](c2cc(C#N)cc(C(F)(F)F)c2)[C@@H]1C] | 675.4 |

TABLE 21-continued

| Example | Molecular structure | LCMS (M + H)+ |
|---|---|---|
| 248 | 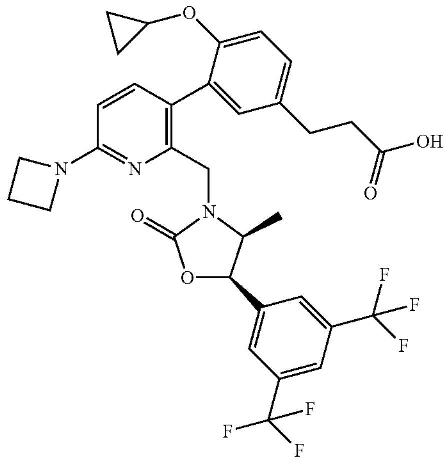 [SMILES: C[C@H]1[C@@H](c2cc(C(F)(F)F)cc(C(F)(F)F)c2)OC(=O)N1Cc1nc(N2CCC2)ccc1-c1cc(CCC(=O)O)ccc1OC1CC1] | 664.3 |
| 248(a) | SPA = 9.4 nM | 718.5 |

Example 249

3-[3-(6-azetidin-1-yl-2-{[(4S,5R)-5-(3,5-dimethylphenyl)-4-methyl-2-oxo-1,3-oxazolidin-3-yl]methyl}pyridin-3-yl)-4-methoxyphenyl]propanamide

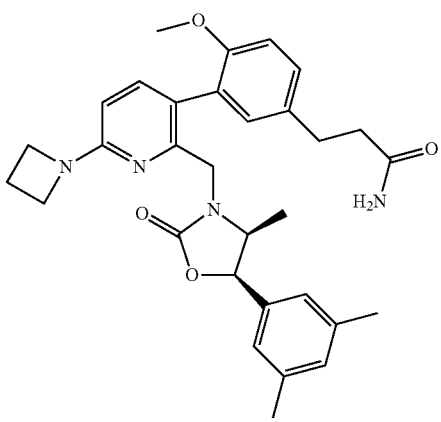 [SMILES: COc1ccc(CCC(N)=O)cc1-c1ccc(N2CCC2)nc1CN1C(=O)O[C@H](c2cc(C)cc(C)c2)[C@@H]1C]

To a solution of 3-[3-(6-azetidin-1-yl-2-{[(4S,5R)-5-(3,5-dimethylphenyl)-4-methyl-2-oxo-1,3-oxazolidin-3-yl]methyl}pyridin-3-yl)-4-methoxyphenyl]propanoic acid (EXAMPLE 228) (8 mg, 0.014 mmol) in DCM (2 ml) was added oxalyl chloride (2M in DCM) (100 μl, 0.200 mmol) and a drop of DMF. The solution was stirred for 30 minutes, concentrated, dissolved in THF (2 ml), added ammonium hydroxide (50 μl, 0.360 mmol) and stirred overnight. The mixture was acidified with 50 μl of TFA, concentrated, dissolved in MeOH, filtered, and purified by RP HPLC to afford the title compound. Mass spectrum (ESI) 529.5. $^1$H NMR (500 MHz, CD$_3$OD): δ 7.31 (d, J=8.3 Hz, 1H); 7.20 (dd, J=8.4, 2.3 Hz, 1H); 7.02 (s, 1H); 6.96 (s, 2H); 6.83 (s, 2H); 6.35 (d, J=8.4 Hz, 1H); 5.40 (d, J=8.5 Hz, 1H); 4.80-4.48 (m, 1H); 4.24-3.64 (m, 2H); 4.05 (t, J=7.4 Hz, 4H); 3.75 (s, 3H); 2.88 (m, 2H); 2.48 (m, 3H); 2.41 (m, 2H); 2.28 (s, 6H); 0.59 (m, 3H).

The following compounds (Table 22) were synthesized using methods analogous to those described for EXAMPLE 249 from commercially available materials or intermediates whose syntheses are described above.

TABLE 22
| Example | Molecular structure | LCMS (M + H)+ |
|---|---|---|
| 250 | 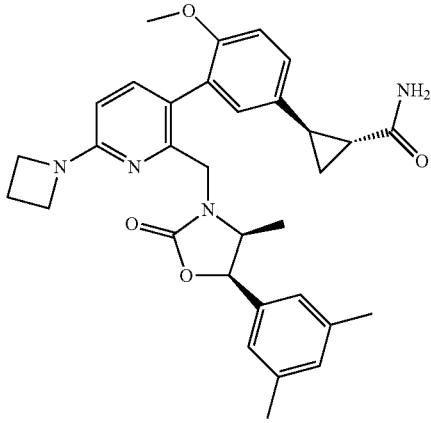 [SMILES: COc1ccc([C@@H]2C[C@H]2C(N)=O)cc1-c1ccc(N2CCC2)nc1CN1C(=O)O[C@H](c2cc(C)cc(C)c2)[C@@H]1C] | 541.5 |
| 251 | 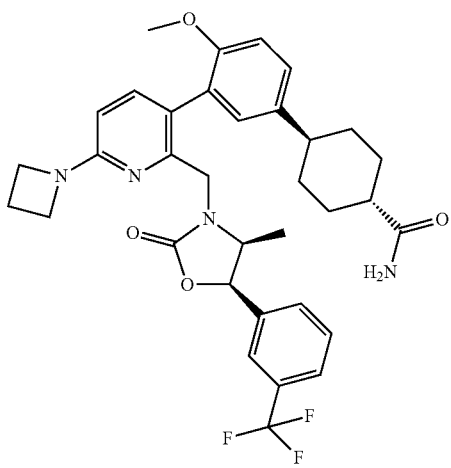 [SMILES: COc1ccc([C@H]2CC[C@H](C(N)=O)CC2)cc1-c1ccc(N2CCC2)nc1CN1C(=O)O[C@H](c2cccc(C(F)(F)F)c2)[C@@H]1C] | 623.5 |
| 252 | 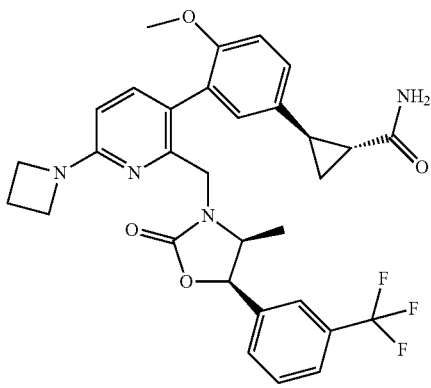 [SMILES: COc1ccc([C@@H]2C[C@H]2C(N)=O)cc1-c1ccc(N2CCC2)nc1CN1C(=O)O[C@H](c2cccc(C(F)(F)F)c2)[C@@H]1C] | 581.4 |

TABLE 22-continued

| Example | Molecular structure | LCMS (M + H)+ |
|---|---|---|
| 253 | 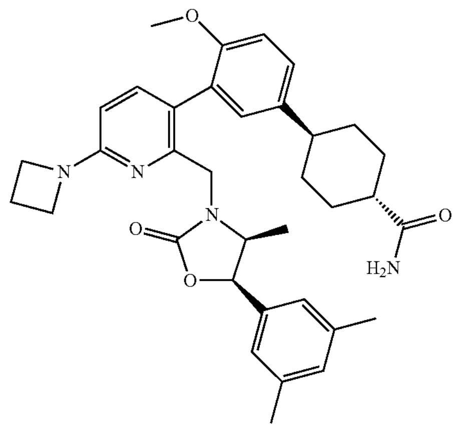 [SMILES: COc1ccc([C@H]2CC[C@H](C(N)=O)CC2)cc1-c1ccc(N2CCC2)nc1CN1C(=O)O[C@H](c2cc(C)cc(C)c2)[C@@H]1C] | 583.4 |
| 254 | 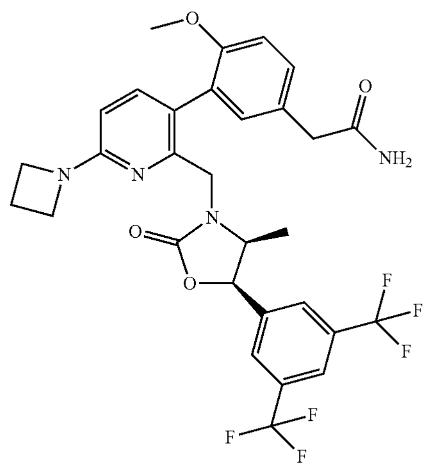 [SMILES: COc1ccc(CC(N)=O)cc1-c1ccc(N2CCC2)nc1CN1C(=O)O[C@H](c2cc(C(F)(F)F)cc(C(F)(F)F)c2)[C@@H]1C] | 623.3 |

Example 255

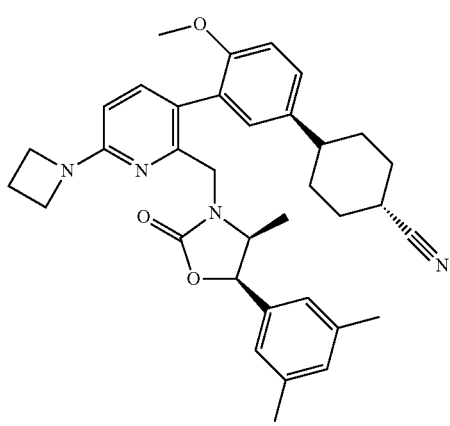

trans-4-[3-(6-azetidin-1-yl-2-{[(4S,5R)-5-(3,5-dimethylphenyl-4-methyl-2-oxo-1,3-oxazolidin-3-yl]methyl}pyridin-3-yl)-4-methoxyphenyl]cyclohexanecarbonitrile A solution of trans-4-[3-(6-azetidin-1-yl-2-{[(4S,5R)-5-(3,5-dimethylphenyl)-4-methyl-2-oxo-1,3-oxazolidin-3-yl]methyl}pyridin-3-yl)-4-methoxyphenyl]cyclohexanecarboxamide (EXAMPLE 253) (21 mg, 0.036 mmol) and cyanuric chloride (13.29 mg, 0.072 mmol) in DMF (2 ml) was stirred at RT under nitrogen. After 30 minutes added water and extracted with ethyl acetate. The organic was washed with brine, dried over sodium sulfate, filtered, and the solvent was evaporated under reduced pressure. The crude was purified by RP HPLC on a Kromasil®—5C18 21.2×100 mm column, eluting with a gradient of MeCN (0.1% TFA) in water (0.1% TFA) from 10% to 100% over 8 minutes, hold at 100% for 1 minute, at 20 ml/min flow rate to afford the title compound as the TFA salt. Mass spectrum (ESI) 565.3 (M+1). $^1$H NMR (500 MHz, CD$_3$OD): (atropisomers) δ 7.69 (d, J=8.9 Hz, 1H); 7.31 (m, 1H); 7.13-7.02 (m, 2H); 6.97 (s, 1H); 6.79 (d, J=8.9 Hz, 1H); 6.75 (s, 2H); 5.14 (dd, J=7.7, 33.1 Hz, 1H); 4.65 (m, 1H); 4.38 (t, J=7.7 Hz, 4H); 4.26 (dd, J=16.1, 61.4 Hz, 1H); 3.78 (d, J=8.5 Hz, 3H); 3.59 (m, 1H); 2.67-2.53 (m, 4H); 2.27 (s, 6H); 2.18 (d, J=11.2 Hz, 2H); 1.95-1.84 (m, 2H); 1.69 (q, J=12.6 Hz, 2H); 1.51 (q, J=12.5 Hz, 2H); 0.41 (d, J=6.6 Hz, 3H).

Example 256

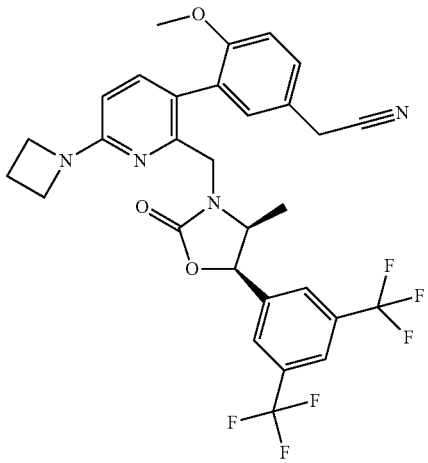 [SMILES: COc1ccc(CC#N)cc1-c1ccc(N2CCC2)nc1CN1C(=O)O[C@H](c2cc(C(F)(F)F)cc(C(F)(F)F)c2)[C@@H]1C]

{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}acetonitrile The title compound was synthesized from 2-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}acetamide (EXAMPLE 254) using an analogous method to that described on Example 255. Mass spectrum (ESI) 605.2 (M+1). $^1$H NMR (500 MHz, CD$_3$OD): δ 7.97 (s, 1H); 7.87 (s, 2H); 7.50 (d, J=8.6 Hz, 1H); 7.39 (d, J=8.5 Hz, 1H); 7.22 (s, 1H); 7.10 (d, J=8.3 Hz, 1H); 6.57 (d, J=8.6 Hz, 1H); 5.67 (m, 1H); 4.68 (d, J=16.0 Hz, 1H); 4.20 (t, J=7.4 Hz, 4H); 4.07 (m, 2H); 3.86 (s, 2H); 3.81 (s, 3H); 2.49 (m, 2H); 0.56 (m, 3H).

Example 257

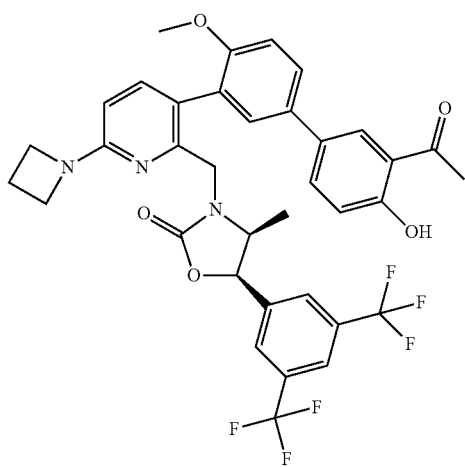 [SMILES: COc1ccc(-c2ccc(O)c(C(C)=O)c2)cc1-c1ccc(N2CCC2)nc1CN1C(=O)O[C@H](c2cc(C(F)(F)F)cc(C(F)(F)F)c2)[C@@H]1C]

(4S,5R)-3-{[3-(3'-acetyl-4'-hydroxy-4-methoxybiphenyl-3-yl)-6-azetidin-1-ylpyridin-2-yl]methyl}-5-[3,5-bis(trifluoromethyl)phenyl]-4-methyl-1,3-oxazolidin-2-one Step A: (4S,5R)-3-({3-[3'-acetyl-4'-(benzyloxy)-4-methoxybiphenyl-3-yl]-6-azetidin-1-ylpyridin-2-yl}methyl)-5-[3,5-bis(trifluoromethyl)phenyl]-4-methyl-1,3-oxazolidin-2-one To a mixture of 1-(5-bromo-2-hydroxyphenyl)ethanone (505 mg, 2.348 mmol) and cesium carbonate (1339 mg, 4.11 mmol) in DMF (5 ml) was added benzyl bromide (0.351 ml, 2.94 mmol) and the resulting mixture was stirred overnight. The reaction mixture was diluted with EtOAc and washed 2 times with water, followed by brine. The organic layer was dried over sodium sulfate, filtered, and the solvent was evaporated under reduced pressure. The residue was purified by flash column chromatography on silica gel, eluting with EtOAc in hexanes to afford 709 mg of 1-[2-(benzyloxy)-5-bromophenyl]ethanone, 703 mg (2.304 mmol) of which were combined with BISPIN (731 mg, 2.88 mmol), PdCl$_2$(dppf) (202 mg, 0.276 mmol), and potassium acetate (452 mg, 4.61 mmol) in 1,4-dioxane (2 ml)/DMSO (10 ml). The mixture was heated at 80° C. overnight. The solids were filtered through a silica plug washing with EtOAc. Water was added and the filtrate was extracted 3 times with EtOAc. The combined organics were washed with brine, dried over sodium sulfate, and concentrated. The residue was purified by flash column chromatography on silica gel, eluting with EtOAc in hexanes to afford 634 mg of 1-[2-(benzyloxy)-5-(4,4,5,5-tetramethyl-1,3,2-dioxaborolan-2-yl)phenyl]ethanone. A mixture of 64 mg (0.182 mmol) of 1-[2-(benzyloxy)-5-(4,4,5,5-tetramethyl-1,3,2-dioxaborolan-2-yl)phenyl]ethanone, 63 mg (0.105 mmol) of (4S,5R)-3-{[6-azetidin-1-yl-3-(5-chloro-2-methoxyphenyl)pyridin-2-yl]methyl}-5-[3,5-bis(trifluoromethyl)phenyl]-4-methyl-1,3-oxazolidin-2-one (EXAMPLE 27), potassium carbonate (1M aqueous) (0.400 ml, 0.400 mmol), and 1,1'-bis(di-t-butylphosphino)ferrocene palladium dichloride (15 mg, 0.023 mmol) in 1,4-dioxane (1.5 ml) was heated at 120° C. with microwaves for 4 hours, then transferred to an oil bath at 120° C. overnight. The mixture was filtered through a silica plug, washing with EtOAc. The filtrate was concentrated and purified by flash column chromatography on silica gel, eluting with EtOAc in hexanes to afford the title compound. Mass spectrum (ESI) 790.6 (M+1).

Step B: (4S,5R)-3-{[3-(3'-acetyl-4'-hydroxy-4-methoxybiphenyl-3-yl)-6-azetidin-1-ylpyridin-2-yl]methyl}-5-[3,5-bis(trifluoromethyl)phenyl]-4-methyl-1,3-oxazolidin-2-one A mixture of (4S,5R)-3-({3-[3'-acetyl-4'-(benzyloxy)-4-methoxybiphenyl-3-yl]-6-azetidin-1-ylpyridin-2-yl}methyl)-5-[3,5-bis(trifluoromethyl)phenyl]-4-methyl-1,3-oxazolidin-2-one (EXAMPLE 257 Step A) (42 mg, 0.053 mmol) and 10% Pd/C (20 mg, 0.053 mmol) in EtOAc (2 ml) was degassed and flushed with H$_2$ using a balloon. The mixture was stirred at RT under H$_2$ for 6 hours, then, flushed with nitrogen, and filtered washing with EtOAc. The filtrate was concentrated and the residue purified by TLC eluting with 3:2 hexanes/EtOAc to afford the title compound. Mass spectrum (ESI) 700.2 (M+1). $^1$H NMR (500 MHz, CD$_3$OD): (atropisomers) δ 8.05 (s, 1H); 7.96 (s, 1H); 7.91-7.70 (m, 3H); 7.61 (dd, J=2.3, 8.7 Hz, 1H); 7.49-7.36 (m, 2H); 7.13 (d, J=8.2 Hz, 1H); 6.98 (d, J=8.7 Hz, 1H); 6.38 (d, J=8.5 Hz, 1H); 5.70 (br d, J=75.7 Hz, 1H); 4.69 (m, 1H); 4.43-3.73 (m, 9H); 2.68 (s, 3H); 2.42 (m, 2H); 0.65 (br d, J=37.5 Hz, 3H).

Example 258

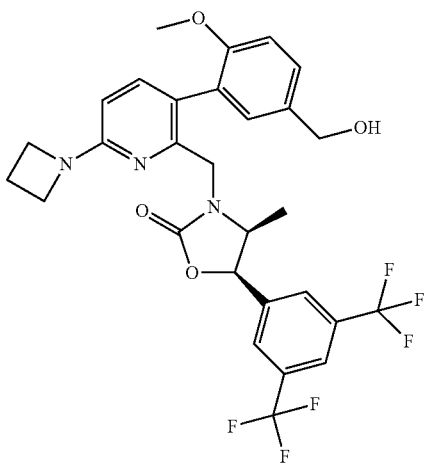 [SMILES: COc1ccc(CO)cc1-c1ccc(N2CCC2)nc1CN1C(=O)O[C@H](c2cc(C(F)(F)F)cc(C(F)(F)F)c2)[C@@H]1C]

(4S,5R)-3-({6-azetidin-1-yl-3-[5-(hydroxymethyl)-2-methoxyphenyl]pyridin-2-yl}methyl-5-[3,5-bis(trifluoromethyl)phenyl]-4-methyl-1,3-oxazolidin-2-one Step A: [4-methoxy-3-(4,4,5,5-tetramethyl-1,3,2-dioxaborolan-2-yl)phenyl]methanol A mixture of (3-iodo-4-methoxyphenyl)methanol (4.0 g, 15.15 mmol), BISPIN (4.81 g, 18.94 mmol), PdCl$_2$(dppf) (1.330 g, 1.818 mmol), and potassium acetate (2.97 g, 30.3 mmol) in 1,4-dioxane (10 ml)/DMSO (50 ml) was heated at 80° C. overnight. Filtered solids through a silica plug washing with EtOAc. Water was added to the filtrate and extracted 3 times with EtOAc. The combined organics were washed with brine, dried over sodium sulfate, filtered and concentrated. The residue was purified by flash column chromatography on silica gel, eluting with EtOAc in hexanes to afford the title compound that was carried on without further purification. $^1$H NMR (500 MHz, CD$_3$OD): δ 7.62 (d, J=2.1 Hz, 1H); 7.40 (dd, J=2.3, 8.5 Hz, 1H); 6.92 (d, J=8.5 Hz, 1H); 4.51 (s, 2H); 3.79 (s, 3H); 1.33 (s, 12H); 1.23 (s, 6H); 1.19 (s, 12H).

Step B: (4S,5R)-3-({6-azetidin-1-yl-3-[5-(hydroxymethyl)-2-methoxyphenyl]pyridin-2-yl}methyl)-5-[3,5-bis(trifluoromethyl)phenyl]-4-methyl-1,3-oxazolidin-2-one A mixture of (4S,5R)-3-[(6-Azetidin-1-yl-3-bromopyridin-2-yl)methyl]-5-[3,5-bis(trifluoromethyl)phenyl]-4-methyl-1,3-oxazolidin-2-one (INTERMEDIATE 35) (943 mg, 1.752 mmol), [4-methoxy-3-(4,4,5,5-tetramethyl-1,3,2-dioxaborolan-2-yl)phenyl]methanol (EXAMPLE 258, Step A) (555 mg, 2.102 mmol), potassium carbonate (1M aqueous) (4 ml, 4.00 mmol), and 1,1'-bis(di-t-butylphosphino)ferrocene palladium dichloride (114 mg, 0.175 mmol) in THF (12 ml) was stirred at 60° C. with microwaves for 1 hour. 125 mg of [4-methoxy-3-(4,4,5,5-tetramethyl-1,3,2-dioxaborolan-2-yl)phenyl]methanol were added and the heating continued for another 30 minutes. The reaction mixture was filtered through a silica plug washing with EtOAc and concentrated. The residue was purified by flash column chromatography on silica gel, eluting with EtOAc in hexanes. A second purification using RP HPLC afforded the pure title compound. Mass spectrum (ESI) 596.3 (M+1). $^1$H NMR (500 MHz, CD$_3$OD): δ 7.96 (s, 1H); 7.88 (s, 2H); 7.32 (d, J=8.2 Hz, 2H); 7.16 (s, 1H); 7.01 (d, J=8.2 Hz, 1H); 6.35 (d, J=8.3 Hz, 1H); 5.72 (m, 1H); 4.65 (d, J=16.3 Hz, 1H); 4.55 (s, 2H); 4.23 (s, 1H); 4.05 (t, J=7.3 Hz, 4H); 3.90 (br s, 1H); 3.77 (s, 2H); 2.43-2.36 (m, 2H); 0.60 (s, 3H).

The following compounds (Table 23) were synthesized using methods analogous to those described for EXAMPLE 258 from commercially available materials or intermediates whose syntheses are described above.

TABLE 23

| Example | Molecular structure | LCMS (M + H)+ |
|---|---|---|
| 259 | 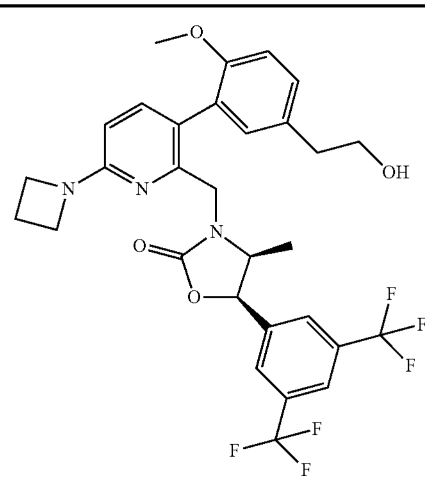 | 610.3 |

TABLE 23-continued

| Example | Molecular structure | LCMS (M + H)+ |
|---|---|---|
| 260 | 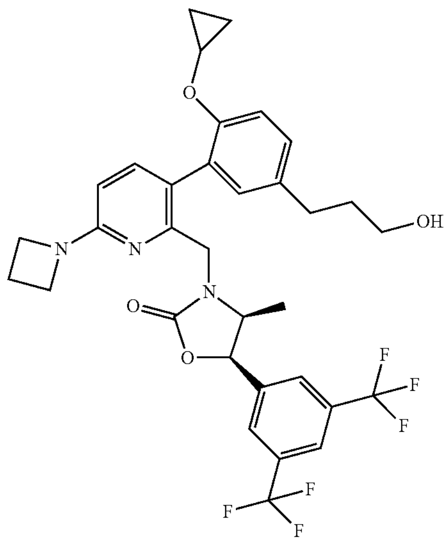 [SMILES: C[C@H]1[C@@H](c2cc(C(F)(F)F)cc(C(F)(F)F)c2)OC(=O)N1Cc1nc(N2CCC2)ccc1-c1cc(CCCO)ccc1OC1CC1] | 650.4 |
| 261 | 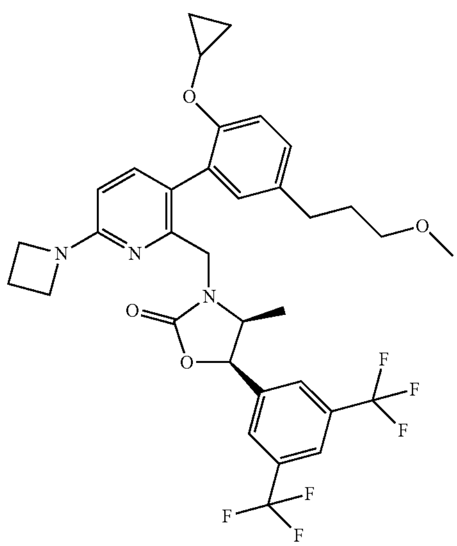 [SMILES: COCCCc1ccc(OC2CC2)c(-c2ccc(N3CCC3)nc2CN2C(=O)O[C@H](c3cc(C(F)(F)F)cc(C(F)(F)F)c3)[C@@H]2C)c1] | 664.4 |
| 262 | (diastereomer A, racemic) | 650.3 |

TABLE 23-continued
| Example | Molecular structure | LCMS (M + H)+ |
|---------|---------------------|---------------|
| 263 | 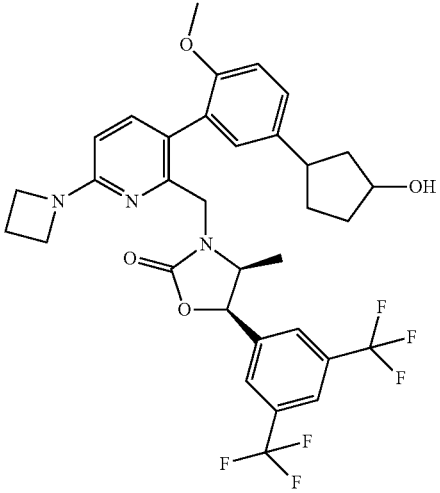 diastereomer B, racemic | 650.4 |
| 264 | 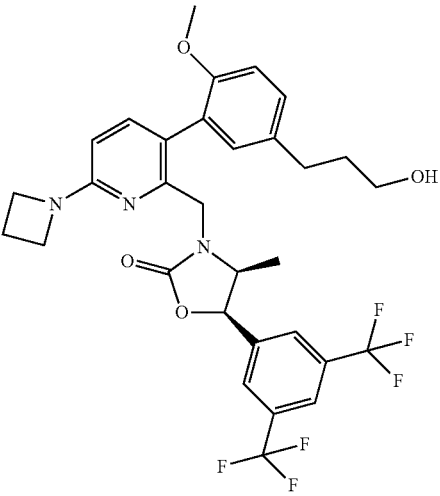 [SMILES: COc1ccc(CCCO)cc1-c1ccc(N2CCC2)nc1CN1C(=O)O[C@H](c2cc(C(F)(F)F)cc(C(F)(F)F)c2)[C@@H]1C] | 624.2 |
| 265 | 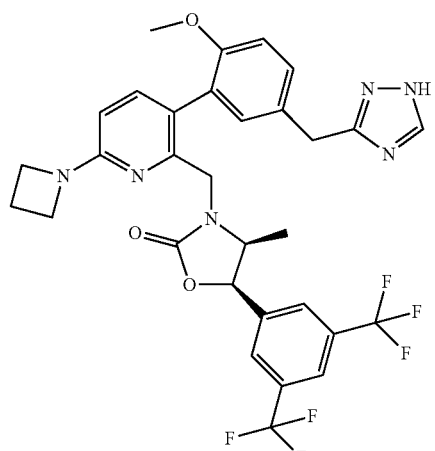 | 647.3 |

Example 266

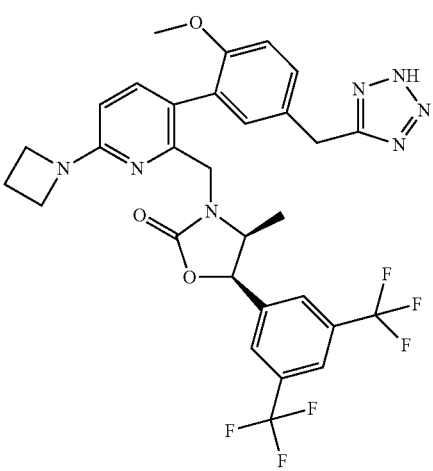 [SMILES: COc1ccc(Cc2nn[nH]n2)cc1-c1ccc(N2CCC2)nc1CN1C(=O)O[C@H](c2cc(C(F)(F)F)cc(C(F)(F)F)c2)[C@@H]1C]

(4S,5R)-3-({6-azetidin-1-yl-3-[2-methoxy-5-(2H-tetrazol-5-ylmethyl)phenyl]pyridin-2-yl}methyl)-5-[3,5-bis(trifluoromethyl)phenyl]-4-methyl-1,3-oxazolidin-2-one A mixture of 6-azetidin-1-yl-2-({(4S,5R)-5-[3,5-bis(trifluoromethyl)phenyl]-4-methyl-2-oxo-1,3-oxazolidin-3-yl}methyl)-3-[5-(cyanomethyl)-2-methoxyphenyl]pyridinium trifluoroacetate (EXAMPLE 256) (15 mg, 0.021 mmol), triethylamine hydrochloride (15 mg, 0.109 mmol), and sodium azide (30 mg, 0.461 mmol) in NMP (2 ml) was stirred at 150° C. under nitrogen for 3 days. Water was added and the mixture extracted 2 times with ethyl acetate. The combined organics were washed with brine, dried over sodium sulfate, filtered, and the solvent was evaporated under reduced pressure. The residue was purified by RP HPLC to afford the title compound. Mass spectrum (ESI) 648.3 (M+1). $^1$H NMR (500 MHz, CD$_3$OD): δ 7.97 (s, 1H); 7.88 (s, 2H); 7.30 (d, J=8.4 Hz, 1H); 7.26 (m, 1H); 7.08 (s, 1H); 7.01 (d, J=8.5 Hz, 1H); 6.34 (d, J=8.4 Hz, 1H); 5.70 (m, 1H); 4.62 (d, J=14.3 Hz, 1H); 4.25 (s, 2H); 4.20 (s, 1H); 4.04 (t, J=7.4 Hz, 4H); 3.86 (br s, 1H); 3.77 (s, 3H); 2.43-2.36 (m, 2H); 0.59 (m, 3H).

Example 267

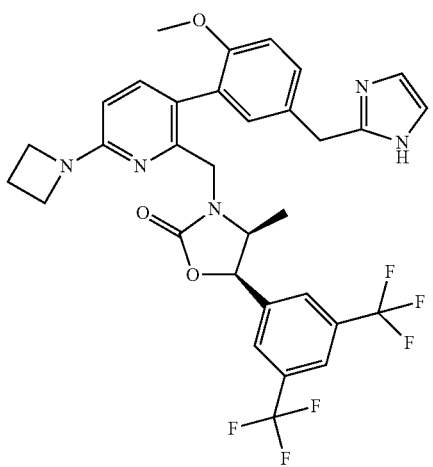 [SMILES: COc1ccc(Cc2ncc[nH]2)cc1-c1ccc(N2CCC2)nc1CN1C(=O)O[C@H](c2cc(C(F)(F)F)cc(C(F)(F)F)c2)[C@@H]1C]

(4S,5R)-3-({6-azetidin-1-yl-3-[5-(1H-imidazol-2-ylmethyl)-2-methoxyphenyl]pyridin-2-yl}methyl)-5-[3,5-bis(trifluoromethyl)phenyl]-4-methyl-1,3-oxazolidin-2-one To a solution of (4S,5R)-3-({6-azetidin-1-yl-3-[5-(2-hydroxyethyl)-2-methoxyphenyl]pyridin-2-yl}methyl)-5-[3,5-bis(trifluoromethyl)phenyl]-4-methyl-1,3-oxazolidin-2-one (EXAMPLE 259) (32 mg, 0.052 mmol) in DCM (2 ml) was added Dess-Martin periodinane (24.49 mg, 0.058 mmol) and the resulting mixture was stirred at RT for 40 minutes. The mixture was diluted with dichloromethane and washed with water. The organic was dried over sodium sulfate, filtered, and the solvent was evaporated under reduced pressure. The residue (32 mg, 0.053 mmol) was dissolved in MeOH (1 ml) and, at 0° C. under nitrogen, was added glyoxal (20 µl, 0.175 mmol) followed by ammonia (7M in MeOH) (60 µl, 0.420 mmol). The resulting mixture was stirred at RT for 2.5 hours, then, purified by RP HPLC, dissolved in EtOAc and washed with 2M NaOH, followed by brine. The organic was dried over sodium sulfate, filtered, and concentrated. It was then lyophilized from MeCN/water to afford the title compound. Mass spectrum (ESI) 646.2 (M+1). $^1$H NMR (500 MHz, CD$_3$OD): δ 7.97 (s, 1H); 7.86 (s, 2H); 7.29 (d, J=8.3 Hz, 1H); 7.21 (d, J=8.4 Hz, 1H); 7.02 (s, 1H); 6.98 (d, J=8.2 Hz, 1H); 6.87 (s, 2H); 6.34 (d, J=8.3 Hz, 1H); 5.64 (m, 1H); 4.62 (d, J=15.8 Hz, 1H); 4.18 (s, 1H); 4.06-3.66 (m, 10H); 2.40 (p, J=7.4 Hz, 2H); 0.57 (br s, 3H).

Example 268

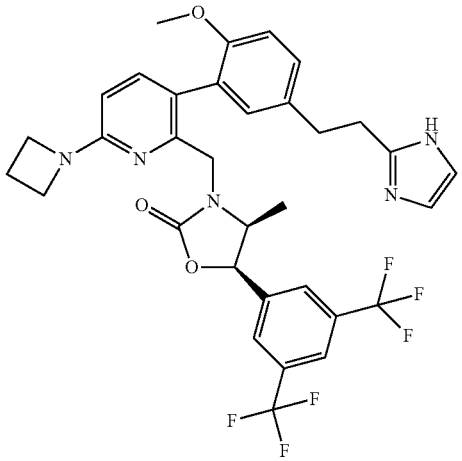 [SMILES: COc1ccc(CCc2ncc[nH]2)cc1-c1ccc(N2CCC2)nc1CN1C(=O)O[C@H](c2cc(C(F)(F)F)cc(C(F)(F)F)c2)[C@@H]1C]

(4S,5R)-3-[(6-azetidin-1-yl-3-{5-[2-1H-imidazol-2-yl)ethyl]-2-methoxyphenyl}pyridin-2-yl)methyl]-5-[3,5-bis(trifluoromethyl)phenyl]-4-methyl-1,3-oxazolidin-2-one The title compound was synthesized from (4S,5R)-3-({6-azetidin-1-yl-3-[5-(3-hydroxypropy)-2-methoxyphenyl]pyridin-2-yl}methyl)-5-[3,5-bis(trifluoromethyl)phenyl]-4-methyl-1,3-oxazolidin-2-one (EXAMPLE 264) using an analogous method to that described on EXAMPLE 267. Mass spectrum (ESI) 660.3 (M+1). $^1$H NMR (500 MHz, CD$_3$OD): δ 7.97 (s, 1H); 7.89 (s, 2H); 7.24 (d, J=8.3 Hz, 1H); 7.11 (dd, J=8.4, 2.3 Hz, 1H); 6.92 (d, J=8.4 Hz, 1H); 6.86 (s, 2H); 6.33 (d, J=8.3 Hz, 1H); 5.76 (d, J=8.5 Hz, 1H); 4.57 (m, 1H); 4.25 (m, 1H); 4.04 (t, J=7.4 Hz, 4H); 3.89 (s, 1H); 3.73 (s, 3H); 2.96 (s, 4H); 2.40 (p, J=7.4 Hz, 2H); 0.60 (s, 3H).

Example 269

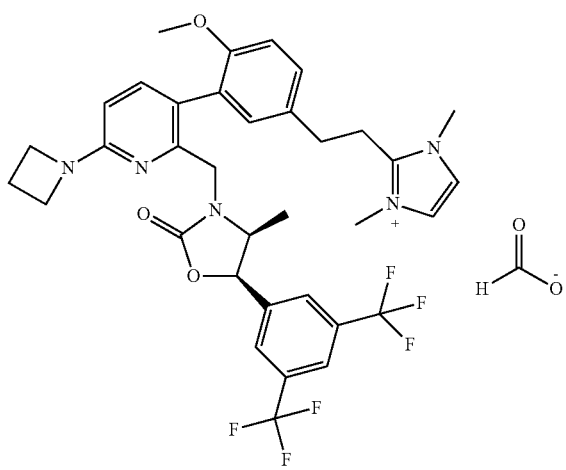

2-(2-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}ethyl)-1,3-dimethyl-1H-imidazol-3-ium formate To a solution of (4S,5R)-3-[(6-azetidin-1-yl-3-{5-[2-(1H-imidazol-2-yl)ethyl]-2-methoxyphenyl}pyridin-2-yl)methyl]-5-[3,5-bis(trifluoromethyl)phenyl]-4-methyl-1,3-oxazolidin-2-one (EXAMPLE 268) (19 mg, 0.029 mmol) in THF (2 ml) at RT under nitrogen was added NaHMDS (1M in THF) (0.027 ml, 0.027 mmol) dropwise followed by methyl iodide (3.60 µl, 0.058 mmol) and the resulting mixture was stirred at RT. At 45 minutes, added a drop of methyl iodide and stirred overnight. Added dichloromethane and washed with saturated aqueous sodium hydrogen carbonate followed by brine, dried over sodium sulfate, filtered, and the solvent was evaporated under reduced pressure. The residue was purified by RP HPLC using a SunFire—5C18 OBD 19×150 mm column, eluting with a gradient of MeCN (0.05% HCOOH) in water (0.05% HCOOH) from 10% to 100% over 8 minutes, hold at 100% for 1 minute, at 20 ml/min flow rate. The product was lyophilized from MeCN/water to afford the title compound. Mass spectrum (ESI) 688.4 (M+1). $^1$H NMR (500 MHz, CD$_3$OD): δ 8.45 (s, 1H); 7.99 (s, 1H); 7.91 (s, 2H); 7.43 (s, 2H); 7.22 (d, J=8.3 Hz, 1H); 7.11 (d, J=8.8 Hz, 1H); 6.99 (d, J=8.4 Hz, 1H); 6.86 (s, 1H); 6.33 (d, J=8.4 Hz, 1H); 5.83 (m, 1H); 4.72-3.69 (m, 3H); 4.04 (s, 4H); 3.76 (s, 3H); 3.63 (s, 6H); 3.36 (t, J=7.0 Hz, 2H); 3.02 (m, 2H); 2.41 (t, J=7.6 Hz, 2H); 0.71 (s, 3H).

Example 270

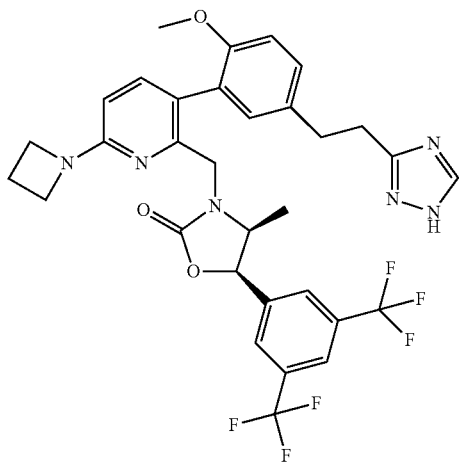 [SMILES: COc1ccc(CCc2nc[nH]n2)cc1-c1ccc(N2CCC2)nc1CN1C(=O)O[C@H](c2cc(C(F)(F)F)cc(C(F)(F)F)c2)[C@@H]1C]

(4S,5R)-3-[(6-azetidin-1-yl-3-{2-methoxy-5-[2-(1H-1,2,4-triazol-3-yl)ethyl]phenyl}pyridin-2-yl)methyl]-5-[3,5-bis(trifluoromethyl)phenyl]-4-methyl-1,3-oxazolidin-2-one To a solution of 3-{3-[6-Azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}propanoic acid (EXAMPLE 60) (66 mg, 0.104 mmol) in DCM (4 ml) was added oxalyl chloride (2M in DCM) (0.259 ml, 0.518 mmol) and a drop of DMF. The solution was stirred for 20 minutes, concentrated, dissolved in THF (3 ml), added ammonium hydroxide (0.144 ml, 1.035 mmol) and stirred overnight. The crude was concentrated, dissolved in MeOH, filtered and purified by RP HPLC to afford 38 mg (0.060 mmol) of 3-{3-[6-azetidin-1-yl-2-({(4S,5R)-5-[3,5-bis(trifluoromethyl)phenyl]-4-methyl-2-oxo-1,3-oxazolidin-3-yl}methyl)pyridin-3-yl]-4-methoxyphenyl}propanamide. This was combined with N,N-dimethylformamide dimethyl acetal (1 ml, 7.50 mmol) and heated at 120° C. for 40 minutes. The reaction mixture was concentrated, added AcOH (1 ml), hydrazine hydrate (7.26 µl, 0.119 mmol) and heated at 90° C. for 1.5 hours. Added saturated aqueous sodium hydrogen carbonate to the reaction mixture and extracted 3 times with ethyl acetate. The combined organics were washed with brine, dried over sodium sulfate, filtered, and the solvent was evaporated under reduced pressure. The residue was purified by TLC and RP HPLC and lyophilized from MeCN/water to afford the title compound. Mass spectrum (ESI) 661.3 (M+1). $^1$H NMR (500 MHz, CD$_3$OD): δ 8.07 (br s, 1H); 7.97 (s, 1H); 7.89 (s, 2H); 7.25 (d, J=8.3 Hz, 1H); 7.14 (d, J=8.4 Hz, 1H); 6.94 (d, J=8.4 Hz, 1H); 6.89 (s, 1H); 6.34 (d, J=8.3 Hz, 1H); 5.76 (s, 1H); 4.57 (m, 1H); 4.24 (m, 1H); 4.05 (t, J=7.4 Hz, 4H); 3.92 (m, 1H); 3.73 (s, 3H); 3.03 (d, J=14.7 Hz, 4H); 2.45-2.37 (m, 2H); 0.60 (s, 3H).

Example 271

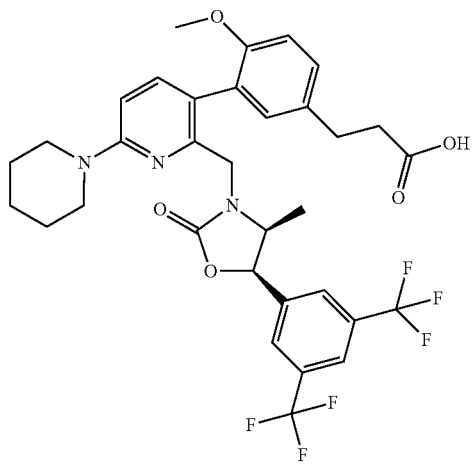 [SMILES: COc1ccc(CCC(=O)O)cc1-c1ccc(N2CCCCC2)nc1CN1C(=O)O[C@H](c2cc(C(F)(F)F)cc(C(F)(F)F)c2)[C@@H]1C]

3-{3-[2-({(4S,5R)-5-[3,5-bis(trifluoromethyl)phenyl]-4-methyl-2-oxo-1,3-oxazolidin-3-yl}methyl)-6-piperidin-1-ylpyridin-3-yl]-4-methoxyphenyl}propanoic acid A mixture of (4S,5R)-5-[3,5-Bis(trifluoromethyl)phenyl]-3-[(3-bromo-6-chloropyridin-2-yl)methyl]-4-methyl-1,3-oxazolidin-2-one (INTERMEDIATE 32) (500 mg, 0.966 mmol), methyl 3-[4-methoxy-3-(4,4,5,5-tetramethyl-1,3,2-dioxaborolan-2-yl)phenyl]propanoate (INTERMEDIATE 2)

(370 mg, 1.107 mmol), potassium carbonate (1M aqueous) (3 ml, 3.00 mmol), and 1,1'-bis(di-t-butylphosphino)ferrocene palladium dichloride (94 mg, 0.145 mmol) in THF (5 ml) was stirred at RT under nitrogen overnight. The reaction was diluted with water and extracted 3 times with ethyl acetate. The combined organics were washed with brine, dried over sodium sulfate, filtered, and the solvent was evaporated under reduced pressure. The residue was purified by flash column chromatography on silica gel, eluting EtOAc in hexanes to afford 582 mg of ethyl 3-{3-[2-({(4S,5R)-5-[3,5-bis(trifluoromethyl)phenyl]-4-methyl-2-oxo-1,3-oxazolidin-3-yl}methyl)-6-chloropyridin-3-yl]-4-methoxyphenyl}propanoate. 294 mg (0.456 mmol) of this ester was combined with LiOH (1M aqueous) (1 ml, 1.000 mmol) in THF (2 ml)/EtOH (0.5 ml) and stirred at RT under nitrogen overnight. The mixture was diluted with saturated aqueous ammonium chloride and extracted with ethyl acetate. The organic was dried over sodium sulfate and the solvent was evaporated under reduced pressure to afford 267 mg of 3-{3-[2-({(4S,5R)-5-[3,5-bis(trifluoromethyl)phenyl]-4-methyl-2-oxo-1,3-oxazolidin-3-yl}methyl)-6-chloropyridin-3-yl]-4-methoxyphenyl}propanoic acid, 30 mg of which were combined with copper (spatula tip) and piperidine (5 ml, 50.5 mmol) and was heated at 150° C. for 5 hours in a sealed tube. The reaction was concentrated and purified by RP HPLC to afford the title compound. Mass spectrum (ESI) 666.2 (M+1). $^1$H NMR (500 MHz, CD$_3$OD) (atropisomers) δ 7.96 (s, 1H); 7.88 (s, 2H); 7.30 (d, J=8.7 Hz, 1H); 7.20 (dd, J=2.2, 8.4 Hz, 1H); 7.02 (s, 1H); 6.95 (d, J=8.5 Hz, 1H); 6.73 (d, J=8.5 Hz, 1H); 5.76 (br s, 1H); 4.60 (br s, 1H); 3.49-4.34 (m, 9H); 2.87 (t, J=7.1 Hz, 2H); 2.57 (br s, 2H); 1.61-1.73 (m, 6H); 0.56 (br s, 3H).

The following compounds (Table 24) were synthesized using methods analogous to those described for EXAMPLES 60 and 61 from commercially available materials or intermediates whose syntheses are described above.

TABLE 24

| Example | Molecular structure | LCMS (M + H)$^+$ |
|---|---|---|
| 272 | 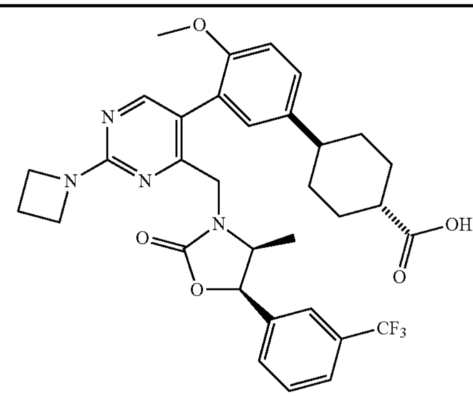 | 625.2 |
| 273 | 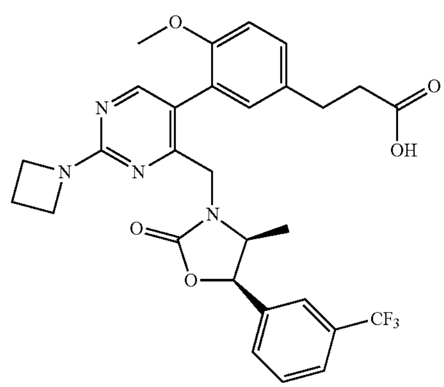 [SMILES: COc1ccc(CCC(=O)O)cc1-c1cnc(N2CCC2)nc1CN1C(=O)O[C@H](c2cccc(C(F)(F)F)c2)[C@@H]1C] | 571.2 |
| 274 | 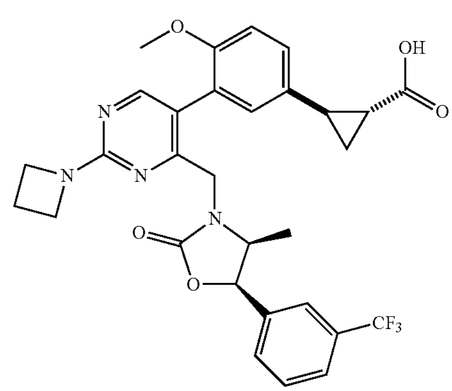 | 583.1 |

TABLE 24-continued
| Example | Molecular structure | LCMS (M + H)+ |
|---------|---------------------|---------------|
| 275 | 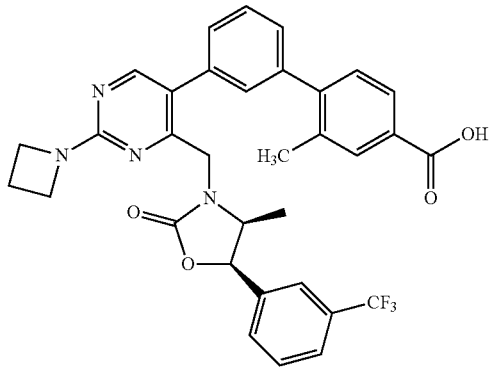 [SMILES: Cc1cc(C(=O)O)ccc1-c1cccc(-c2cnc(N3CCC3)nc2CN2C(=O)O[C@H](c3cccc(C(F)(F)F)c3)[C@@H]2C)c1] | 603.2 |
| 276 | 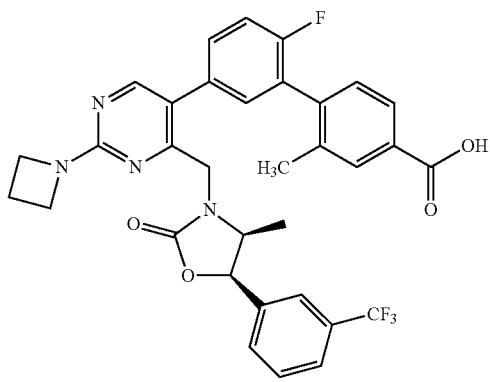 [SMILES: Cc1cc(C(=O)O)ccc1-c1cc(-c2cnc(N3CCC3)nc2CN2C(=O)O[C@H](c3cccc(C(F)(F)F)c3)[C@@H]2C)ccc1F] | 621.2 |
| 277 | 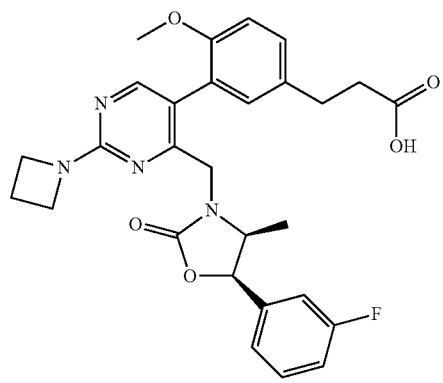 [SMILES: COc1ccc(CCC(=O)O)cc1-c1cnc(N2CCC2)nc1CN1C(=O)O[C@H](c2cccc(F)c2)[C@@H]1C] | 521.3 |
| 278 | 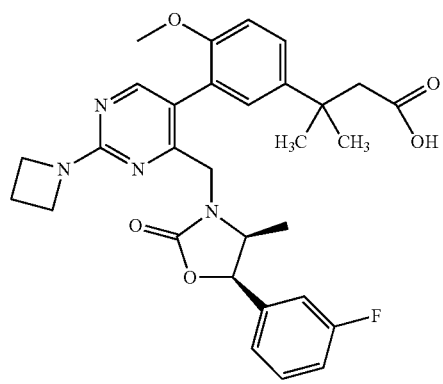 [SMILES: COc1ccc(C(C)(C)CC(=O)O)cc1-c1cnc(N2CCC2)nc1CN1C(=O)O[C@H](c2cccc(F)c2)[C@@H]1C] | 549.3 |

TABLE 24-continued
| Example | Molecular structure | LCMS (M + H)+ |
|---------|---------------------|---------------|
| 279 | 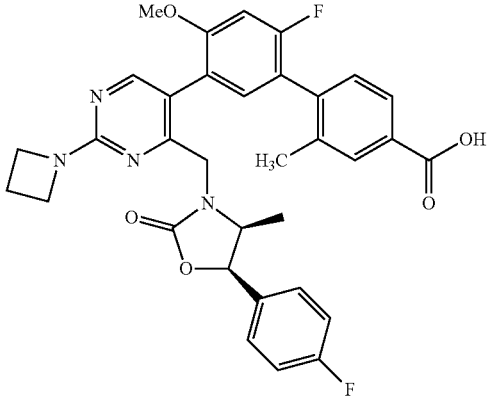 [SMILES: COc1cc(F)c(-c2ccc(C(=O)O)cc2C)cc1-c1cnc(N2CCC2)nc1CN1C(=O)O[C@H](c2ccc(F)cc2)[C@@H]1C] | 601.2 |
| 280 | 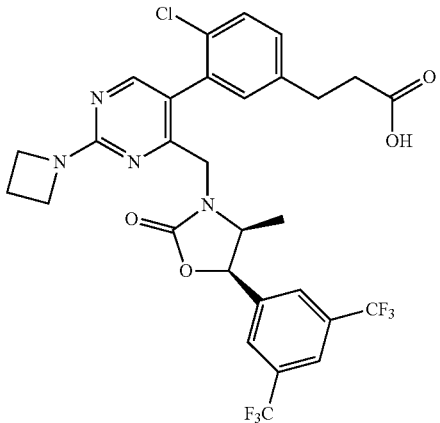 [SMILES: C[C@H]1[C@@H](c2cc(C(F)(F)F)cc(C(F)(F)F)c2)OC(=O)N1Cc1nc(N2CCC2)ncc1-c1cc(CCC(=O)O)ccc1Cl] | 643.1 |
| 281 | 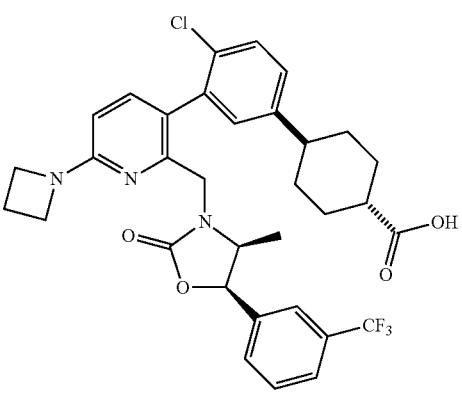 | 696.4 |

Example 282

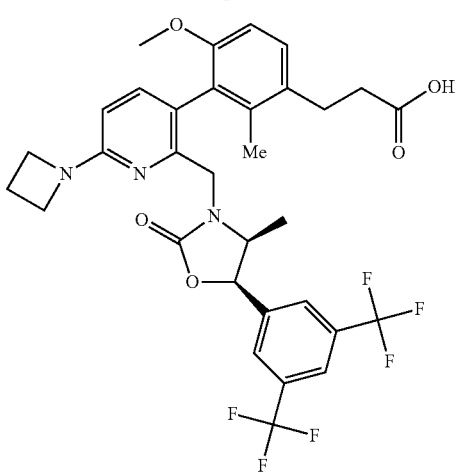 [SMILES: COc1ccc(CCC(=O)O)c(C)c1-c1ccc(N2CCC2)nc1CN1C(=O)O[C@H](c2cc(C(F)(F)F)cc(C(F)(F)F)c2)[C@@H]1C]

3-{3-[6-azetidin-1-yl)-2-({(4S,5R)-5-[3,5-bis(trifluoromethyl)phenyl]-4-methyl-2-oxo-1,3-oxazolidin-3-yl}methyl)pyridin-3-yl]-4-methoxy-2-methylphenyl}propanoic acid Step A: (4S,5R)-3-{[6-(azetidin-1-yl)-3-(4,4,5,5-tetramethyl-1,3,2-dioxaborolan-2-yl)pyridin-2-yl]methyl}-5-[3,5-bis(trifluoromethyl)phenyl]-4-methyl-1,3-oxazolidin-2-one To a solution of intermediate 32 (1140 mg, 2.118 mmol) in DMA (2.35 mL) was added bis(pinacolato)diboron (807 mg, 3.18 mmol), potassium acetate (416 mg, 4.24 mmol), 2-dicyclohexylphosphino-2',4',6'-tri-isopropyl-1,1'-biphenyl (606 mg, 1.271 mmol), and palladium(II) acetate (95 mg, 0.424 mmol). The mixture was then warmed to 85° C. for 15 hours. The mixture was then diluted with filtered though a plug of silica gel (eluting with ethyl acetate) and concentrated in vacuo. The residue was taken forward without further purification.

Step B: methyl (2E)-3-{3-[6-(azetidin-1-yl)-2-({(4S,5R)-5-[3,5-bis(trifluoromethyl)phenyl]-4-methyl-2-oxo-1,3-oxazolidin-3-yl}methyl)pyridin-3-yl]-4-methoxy-2-methylphenyl}prop-2-enoate To a solution of intermediate 89 (171 mg, 0.292 mmol) in Dioxane (3961 µl) and Water (990 µl) was added (4S,5R)-3-{[6-(azetidin-1-yl)-3-(4,4,5,5-tetramethyl-1,3,2-dioxaborolan-2-yl)pyridin-2-yl]methyl}-5-[3,5-bis(trifluoromethyl)phenyl]-4-methyl-1,3-oxazolidin-2-one (207 mg, 0.584 mmol), potassium carbonate (81 mg, 0.584 mmol), and 1,1'-bis(di-tert-butylphosphino)ferrocene palladium dichloride (38.1 mg, 0.058 mmol) The mixture was then warmed to 85° C. for 1 hour. The mixture was then diluted and filtered though a plug of silica gel (eluting with ethyl acetate) and concentrated in vacuo. The residue was purified via column chromatography on a Biotage 65i column eluting with 0% ethyl acetate in hexanes (1 CV) followed by a gradient to 50% ethyl acetate in hexanes (over 7 CV) provided the desired product. Mass spectrum (ESI) 664.3 (M+1).

Step C: 3-{3-[6-(azetidin-1-yl)-2-({(4S,5R)-5-[3,5-bis(trifluoromethyl)phenyl]-4-methyl-2-oxo-1,3-oxazolidin-3-yl}methyl)pyridin-3-yl]-4-methoxy-2-methylphenyl}propanoic acid To a solution of methyl (2E)-3-{3-[6-(azetidin-1-yl)-2-({(4S,5R)-5-[3,5-bis(trifluoromethyl)phenyl]-4-methyl-2-oxo-1,3-oxazolidin-3-yl}methyl)pyridin-3-yl]-4-methoxy-2-methylphenyl}prop-2-enoate (118 mg, 0.178 mmol) in methanol (2371 µl) was added palladium on carbon (10%) (59 mg, 0.178 mmol). This mixture was placed under a balloon of hydrogen gas and purged three times with vacuum, then allow to stir at 45° C. for 1.5 hours. LC/MS indicated complete conversion to desired product. The mixture was then diluted with filtered though a plug of Celite®. The residue was concentrated to furnish the desired product as a 53/47 mixture of atropisomers. To a solution of this mixture (98 mg, 0.147 mmol) in dioxane (1996 µl) and water (499 µl) was added lithium hydroxide (35.3 mg, 1.472 mmol). The reaction was stirred at room temp for 5 hours until complete. The mixture was then concentrated in vacuo and purified on reverse phase HPLC (C-18 column, 0-90% acetonitrile in water). The pure mixture of atropisomers was then separated on a Chiral SFC (Chiralcel AD-H column, 10% EtOH in $CO_2$). To provide both atropisomers. Atropisomer A: Mass spectrum (ESI) 652.3 (M+1). $^1$H NMR (500 MHz, $CDCl_3$) (atropisomers) δ 7.85 (s, 1H), 7.73 (s, 2H), 7.19 (d, J=8.4 Hz, 1H), 7.17 (d, J=8.4 Hz, 1H), 6.75 (d, J=8.4 Hz, 1H), 6.32 (d, J=8.4 Hz, 1H), 5.69 (d, J=8.7 Hz, 1H), 4.55 (m, 1H), 4.43 (d, J=15.8 Hz, 1H), 4.10 (m, 4H), 3.72 (m, 1H), 3.65 (s, 3H), 2.97 (m, 2H), 2.64 (t, J=7.6 Hz, 2H), 2.44 (t, J=7.2 Hz, 2H), 2.00 (s, 3H), 0.71 (d, J=6.6 Hz, 3H). Atropisomer B: Mass spectrum (ESI) 652.3 (M+1). $^1$H NMR (500 MHz, $CDCl_3$) (atropisomers) δ 7.84 (s, 1H), 7.68 (s, 2H), 7.20 (d, J=7.9 Hz, 1H), 7.16 (d, J=8.5 Hz, 1H), 6.77 (d, J=8.5 Hz, 1H), 6.32 (d, J=7.6 Hz, 1H), 5.51 (d, J=8.0 Hz, 1H), 4.62 (d, J=15.9 Hz, 1H), 4.22 (m, 1H), 4.09 (m, 4H), 3.73 (m, 1H), 2.95 (m, 2H), 2.64 (t, J=7.5 Hz, 2H), 2.43 (t, J=7.2 Hz, 2H), 2.02 (s, 3H), 0.68 (d, J=6.3 Hz, 3H).

Intermediate 92

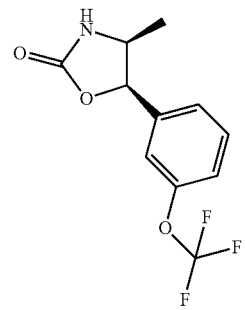 [SMILES: C[C@@H]1NC(=O)O[C@@H]1c1cccc(OC(F)(F)F)c1]

(4S,5R)-4-methyl-5-[3-(trifluoromethoxy)phenyl]-1,3-oxazolidin-2-one

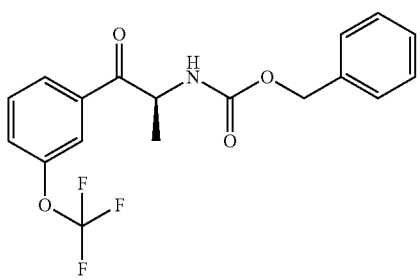 [SMILES: C[C@H](NC(=O)OCc1ccccc1)C(=O)c1cccc(OC(F)(F)F)c1]

Step 1: benzyl {(2S)-oxo-1-[3-(trifluoromethoxy) phenyl]propan-2-yl}carbamate To a solution of the commercially available benzyl {(2S)-1-[methoxy(methyl)amino]-1-oxopropan-2-yl}carbamate (5.52 g, 20.75 mmol) and 1-bromo-3-(trifluoromethoxy)benzene (5 g, 20.75 mmol) in THF (100 ml) cooled in an ice/methanol/dry ice cooling bath was added isopropylmagnesium chloride (20.75 ml, 41.5 mmol) dropwise under nitrogen while internal temperature was maintained between −35 and −15° C. (monitored w/ an immersed temperature probe). After addition, the reaction was stirred cold and allowed to warm to ambient overnight. The reaction crude was then cooled to −20° C. and slowly quenched into a stirred mixture of crushed ice and HCl (1N, ice bath cool). The resulting mixture was worked up with brine, extracted with ethyl acetate, dried over $Na_2SO_4$, filtered and evaporated under reduced pressure. The pot residue was purified by flash chromatography ($SiO_2$, Biotage SNAP Cartridge, silica gel, KP-Sil, 100 g cartridge). The column was eluted by an ethyl acetate/hexanes mixture (0% to 40% ethyl acetate). Related fractions were pooled and concentrated in vacuo to afford a colorless oil of 3.9824 g as the titled compound. LCMS calc.=367.1. found=390.00 $(M+Na)^+$.

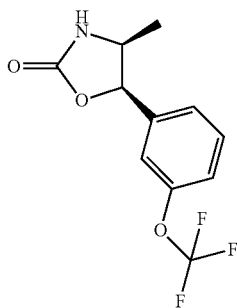 [SMILES: C[C@@H]1NC(=O)O[C@@H]1c1cccc(OC(F)(F)F)c1]

Step 2: (4S,5R)-4-methyl-5-[3-(trifluoromethoxy)phenyl]-1,3-oxazolidin-2-one Lithium tri-tert-butoxyaluminohydride (13.78 g, 54.2 mmol) was added into a cold (dry ice/acetone bath) solution of benzyl {(2S)-1-oxo-1-[3-(trifluoromethoxy)phenyl]propan-2-yl}carbamate (3.98 g, 10.84 mmol) in ethanol (100 ml). LCMS indicated the reaction was completed in 10 min. The reaction was quenched by HCl (1N). The crude mixture was diluted w/ ethyl acetate and filtered through a bed of Celite® 521 (slow filtration). Volatiles were removed from the filtrate under reduced pressure. The resulting pot residue was worked up with aqueous sodium hydrogen carbonate/brine, extracted with ethyl acetate, dried over $Na_2SO_4$, filtered and evaporated to afford a white solid. This solid was stirred with potassium hydroxide (7.22 ml, 54.2 mmol) in a THF (100 ml)/methanol (50 ml) mixture at room temperature for 2 hrs. LCMS indicated completion of reaction. HCl (1N) was added to acidify the reaction mixture. Volatiles were removed under reduced pressure. The pot residue was worked up with brine, extracted with ethyl acetate, dried over $Na_2SO_4$, filtered and evaporated to afford a dark mixture. The resulting crude mixture was purified by flash chromatography ($SiO_2$, Biotage 65i cartridge). The column was eluted by an ethyl acetate/hexanes mixture (0% to 100% ethyl acetate). Related fractions were pooled and evaporated to a white solid of 1.4170 g as the titled compound. LCMS calc.=261.06. found=260.21 $(M-1)^-$.

Intermediate 93

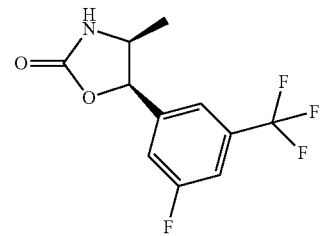 [SMILES: C[C@@H]1NC(=O)O[C@@H]1c1cc(F)cc(C(F)(F)F)c1]

(4S,5R)-5-[3-fluoro-5-(trifluoromethyl)phenyl]-4-methyl-1,3-oxazolidin-2-one

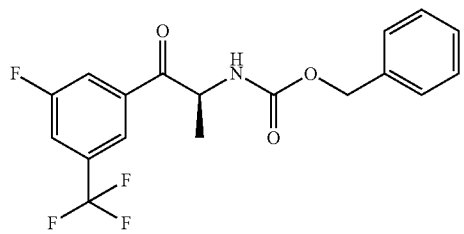 [SMILES: C[C@H](NC(=O)OCc1ccccc1)C(=O)c1cc(F)cc(C(F)(F)F)c1]

Step 1: benzyl {(2S)-1-[3-fluoro-5-(trifluoromethyl)phenyl]-1-oxopropan-2-yl}carbamate To a solution of the commercially available benzyl {(2S)-1-[methoxy(methyl)amino]-1-oxopropan-2-yl}carbamate (5.48 g, 20.58 mmol) and 3-bromo-5-fluorobenzotrifluoride (5 g, 20.58 mmol) in THF (52 ml) at −30° C. was added isopropylmagnesium chloride (20.58 ml, 41.2 mmol) dropwise under nitrogen. Removed the cold bath and allowed the reaction to age overnight to ambient temperature. The crude was cooled to −20° C. followed by addition of HC (1N, ice bath cold). The resulting mixture was worked up with brine, extracted with ethyl acetate, dried over $Na_2SO_4$, filtered and evaporated. The pot residue was purified by flash chromatography ($SiO_2$, Biotage 65i cartridge). The column was eluted by an ethyl acetate/hexanes mixture (0% to 40% ethyl acetate). Related fractions were pooled and evaporated under reduced pressure to afford a yellow oil of 5.4655 g as the titled compound. $^1$H-NMR (CDCl$_3$, 500 MHz) δ 8.03 (s, 1H), 7.86 (d, J=8.5 Hz, 1H), 7.57 (d, J=8 Hz, 1H), 7.38-7.30 (m, 5H), 5.7 (d, J=7.5 Hz, 1H), 5.3 (ps quintet, J=7.5 Hz, 1H), 1.45 (d, J=7 Hz, 3H).

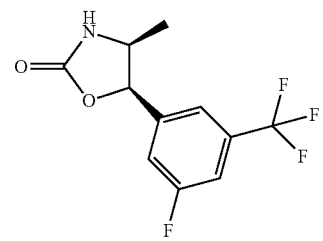 [SMILES: C[C@@H]1NC(=O)O[C@@H]1c1cc(F)cc(C(F)(F)F)c1]

Step 2: (4S,5R)-5-[3-fluoro-5-(trifluoromethyl)phenyl]-4-methyl-1,3-oxazolidin-2-one Lithium tri-tert-butoxyaluminohydride (18.27 ml, 74.0 mmol) was added into a cold (dry ice/acetone bath) solution of benzyl {(2S)-1-[3-fluoro-5-(trifluoromethyl)phenyl]-1-oxopropan-2-yl}carbamate (5.4655 g, 14.80 mmol) in ethanol (100 ml). LCMS indicated the reaction was completed in 10 min. The reaction was quenched by HCl (1N). The crude mixture was diluted with ethyl acetate and filtered through a bed of Celite® 521 (slow filtration). Volatiles were removed from the filtrate under reduced pressure. The resulting pot residue was worked up with aqueous sodium hydrogen carbonate/brine, extracted with ethyl acetate, dried over $Na_2SO_4$, filtered and evaporated to afford a white solid. This solid was stirred with potassium hydroxide (10 ml, 75 mmol) in a THF (100 ml)/methanol (50 ml) mixture at room temp for 2 hrs. LCMS indicated completion of reaction. HCl (1N) was added to acidify the reaction mixture. Volatiles were removed under reduced pressure. The pot residue was worked up with brine, extracted with ethyl acetate, dried over $Na_2SO_4$, filtered and evaporated to afford a dark mixture. The resulting mixture was purified by flash chromatography ($SiO_2$, Biotage 65i cartridge). The column was eluted by an ethyl acetate/hexanes mixture (0% to 100% ethyl acetate). Related fractions were pooled and evaporated under reduced pressure to afford a white solid of 2.6765 g as the titled compound. LCMS calc.=263.06. found=262.11 (M−1)⁻. ¹H-NMR (CDCl₃, 500 MHz) δ 7.36 (s, 1H), 7.34 (d, J=8.5 Hz, 1H), 7.27 (d, J=9 Hz, 1H), 5.8 (d, J=7.5 Hz, 2H), 4.3 (ps quintet, J=6.9 Hz, 1H), 0.85 (d, J=6.5 Hz, 3H).

Example 283

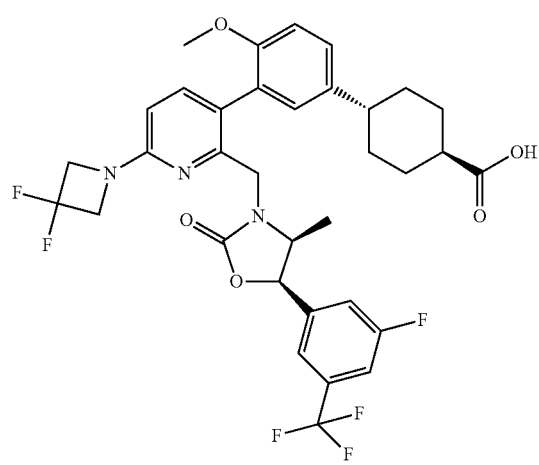 [SMILES: COc1ccc([C@H]2CC[C@H](C(=O)O)CC2)cc1-c1ccc(N2CC(F)(F)C2)nc1CN1C(=O)O[C@H](c2cc(F)cc(C(F)(F)F)c2)[C@@H]1C]

trans-4-{3-[6-(3,3-difluoroazetidin-1-yl)-2-({(4S,5R)-5-[3-fluoro-5-(trifluoromethyl)phenyl]-4-methyl-2-oxo-1,3-oxazolidin-3-yl}methyl)pyridin-3-yl]-4-methoxyphenyl}cyclohexanecarboxylic acid

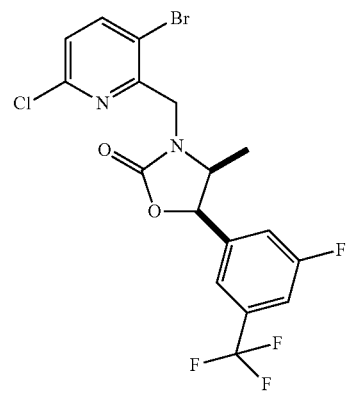

Step 1: (4S,5R)-3-[(3-bromo-6-chloropyridin-2-yl)methyl]-5-[3-fluoro-5-(trifluoromethyl)phenyl]-4-methyl-1,3-oxazolidin-2-one To a cold (ice/methanol bath) mixture of (4S,5R)-5-[3-fluoro-5-(trifluoromethyl)phenyl]-4-methyl-1,3-oxazolidin-2-one (INTERMEDIATE 93) (5000 mg, 19.00 mmol) in THF (100 ml) was added sodium hydride (912 mg, 22.80 mmol) all at once. The resulting mixture was stirred cold (ice bath) for 1.5 hrs followed by addition of 3-bromo-2-(bromomethyl)-6-chloropyridine (INTERMEDIATE 30) (5963 mg, 20.90 mmol). The reaction mixture was allowed to slowly warm to ambient in 3 hrs. The reaction was cooled (ice bath) and quenched by HCl (1N, aq.). The resulting mixture was extracted with ethyl acetate, dried over $Na_2SO_4$, filtered and evaporated under reduced pressure to afford an oil. This oil was purified by flash chromatography ($SiO_2$, Biotage 65i cartridge). The column was eluted by an ethyl acetate/hexanes mixture (0% to 40% ethyl acetate). Related fractions were pooled and concentrated in vacuo to afford a light amber gum of 8.2522 g as the titled compound. LCMS calc.=465.97. found=468.91.

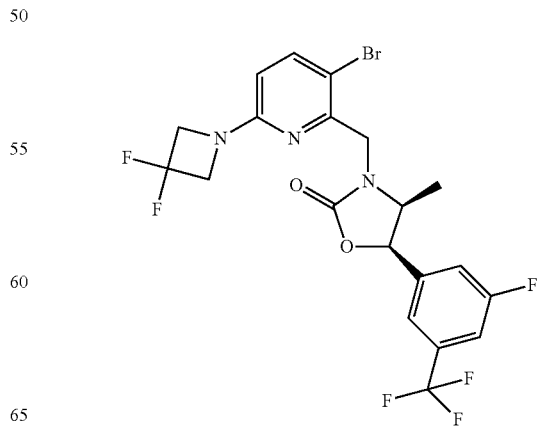

Step 2: (4S,5R)-3-{[3 bromo-6-(3,3-difluoroazetidin-1-yl)pyridin-2-yl]methyl}-5-[3-fluoro-5-(trifluoromethyl)phenyl]-4-methyl-1,3-oxazolidin-2-one (4S,5R)-3-[(3-bromo-6-chloropyridin-2-yl)methyl]-5-[3-fluoro-5-(trifluoromethyl)phenyl]-4-methyl-1,3-oxazolidin-2-one (1.0721 g, 2.293 mmol), 3,3-difluoroazetidine hydrochloride (1.336 g, 10.32 mmol), triethylamine (3.20 ml, 22.93 mmol) and THF (10 ml) were sealed in a microwave vessel and subject to microwave irradiation at 150° C. for 8 hrs. Volatiles were removed under reduced pressure. The resulting pot residue was worked up with brine/ethyl acetate. The combined extracts were dried over $Na_2SO_4$, filtered and evaporated to afford a dark mixture. This dark mixture was purified by flash chromatography ($SiO_2$, Biotage SNAP Cartridge, silica gel, KP-Sil, 100 g cartridge). The column was eluted by an ethyl acetate/hexanes mixture (0% to 40% ethyl acetate). Related fractions were pooled and evaporated under reduced pressure to afford a light amber glass of 530.8 mg as the titled compound. LCMS calc.=523.03. found=525.99.

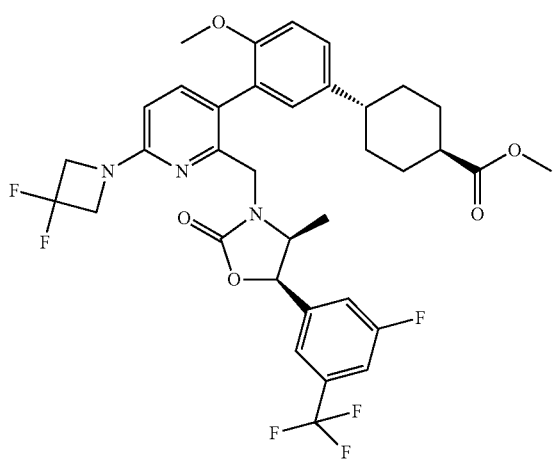 [SMILES: COc1ccc([C@H]2CC[C@H](C(=O)OC)CC2)cc1-c1ccc(N2CC(F)(F)C2)nc1CN1C(=O)O[C@H](c2cc(F)cc(C(F)(F)F)c2)[C@@H]1C]

Step 3: methyl trans-4-{3-[6-(3,3-difluoroazetidin-1-yl)-2-({(4S,5R)-5-[3-fluoro-5-(trifluoromethyl)phenyl]-4-methyl-2-oxo-1,3-oxazolidin-3-yl}methyl)pyridin-3-yl]-4-methoxyphenyl}cyclohexanecarboxylate (4S,5R)-3-{[3-bromo-6-(3,3-difluoroazetidin-1-yl)pyridin-2-yl]methyl}-5-[3-fluoro-5-(trifluoromethyl)phenyl]-4-methyl-1,3-oxazolidin-2-one (530.8 mg, 1.012 mmol), 1,1'-bis(di-tert-butylphosphino)ferrocene palladium dichloride (66.0 mg, 0.101 mmol), potassium carbonate (1.519 ml, 3.04 mmol), methyl trans-4-[4-methoxy-3-(4,4,5,5-tetramethyl-1,3,2-dioxaborolan-2-yl)phenyl]cyclohexanecarboxylate (INTERMEDIATE 7) (436 mg, 1.164 mmol) and THF (6 ml) were sealed in a reaction vessel and placed in a 90° C. oil bath for 4 hrs. LCMS indicated complete consumption of the starting material and formation of the desired product. Volatiles were removed under reduced pressure. The resulting pot residue was worked up with brine/ethyl acetate. The combined extracts were dried over $Na_2SO_4$, filtered and evaporated to afford a dark mixture. This mixture was purified by flash chromatography ($SiO_2$, Biotage SNAP Cartridge, silica gel, KP-Sil, 100 g cartridge). The column was eluted by an ethyl acetate/hexanes mixture (0% to 40%). Related fractions were pooled and evaporated in vacuo to afford a brown solid foam of 507 mg as the titled compound. LCMS calc.=691.25. found=692.49 (M+1)⁺.

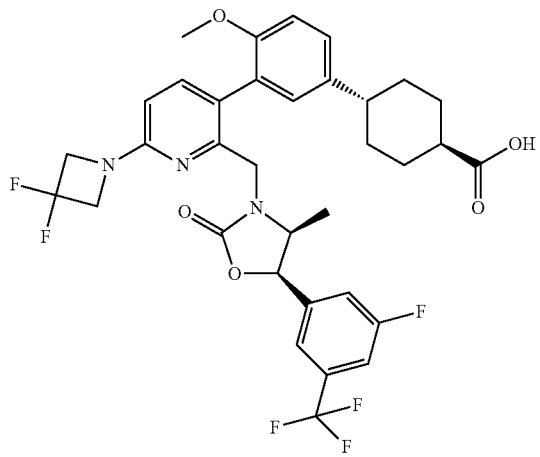 [SMILES: COc1ccc([C@H]2CC[C@H](C(=O)O)CC2)cc1-c1ccc(N2CC(F)(F)C2)nc1CN1C(=O)O[C@H](c2cc(F)cc(C(F)(F)F)c2)[C@@H]1C]

Step 4: trans-4-{3-[6-(3,3-difluoroazetidin-1-yl)-2-({(4S,5R)-5-[3-fluoro-5-(trifluoromethyl)phenyl]-4-methyl-2-oxo-1,3-oxazolidin-3-yl}methyl)pyridin-3-yl]-4-methoxyphenyl}cyclohexanecarboxylic acid A solution of lithium hydroxide monohydrate (154 mg, 3.67 mmol) in water (4 ml) was added into a solution of methyl trans-4-({3-[6-(3,3-difluoroazetidin-1-yl)-2-({(4S,5R)-5-[3-fluoro-5-(trifluoromethyl)phenyl]-4-methyl-2-oxo-1,3-oxazolidin-3-yl}methyl)pyridin-3-yl]-4-methoxyphenyl}cyclohexanecarboxylate (507 mg, 0.733 mmol) in 1,4-dioxane (6 ml) at room temperature and stirred overnight. To the resulting crude was added HCl (1N, aq.) until the mixture turned cloudy. This cloudiness was dissolved by addition of acetonitrile. This clear solution was purified by preparative HPLC (reverse phase, Waters SunFire PrepC18 OBD 5 um 19×150 mm) eluting with acetonitrile/water+0.05% HCOOH (30% to 100% organic in 10 min, hold 100% for 2 min, 20 mL/min). Related fractions were pooled and evaporated under reduced pressure to afford a colorless glass. This glass was re-dissolved in an acetonitrile/water mixture and lyophilized overnight to afford a fluffy white solid of 430.5 mg as the titled compound. LCMS calc.=677.23. found=678.44 (M+1)⁺. ¹H-NMR (CD₃OD, 500 MHz) δ 7.47-7.42 (m, 2H), 7.40 (d, J=8.5 Hz, 1H), 7.34 (br d, J=8.5 Hz, 1H), 7.22 (dd, J=8.5, 2.5 Hz, 1H), 7.06-6.94 (br m, 2H), 6.54 (d, J=8.5 Hz, 1H), 5.71-5.58 (br m, 1H), 4.68-4.53 (br m, 1H), 4.39 (d, J=12.5 Hz, 2H), 4.36 (d, J=12 Hz, 2H), 4.28-4.18 (br s, 0.5H), 4.16-4.02 (br m, 1H), 3.96-3.86 (br m, 0.5H), 3.74 (s, 3H), 2.50 (s, 1H), 2.32 (s, 1H), 2.11-2.04 (m, 2H), 1.96-1.88 (br m, 2H), 1.60-1.44 (m, 4H), 0.65 (br s, 1.6H), 0.54 (br s, 1.4H).

The following compounds (Table 25) were synthesized using methods analogous to those described above.

TABLE 25
| EXAMPLE | Molecular structure | LCMS (M + 1)+ |
|---|---|---|
| 284 | 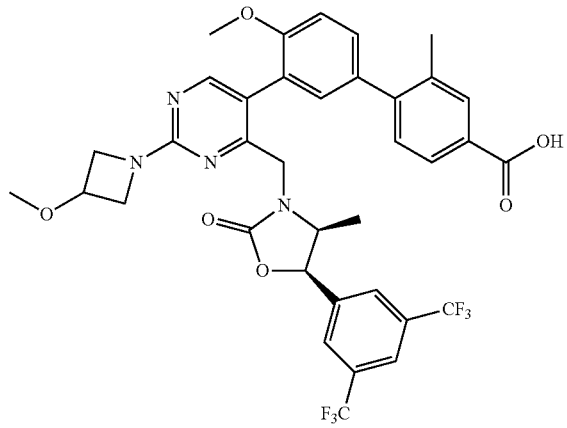 [SMILES: COc1ccc(-c2ccc(C(=O)O)cc2C)cc1-c1cnc(N2CC(OC)C2)nc1CN1C(=O)O[C@H](c2cc(C(F)(F)F)cc(C(F)(F)F)c2)[C@@H]1C] | 731.38 |
| 285 | 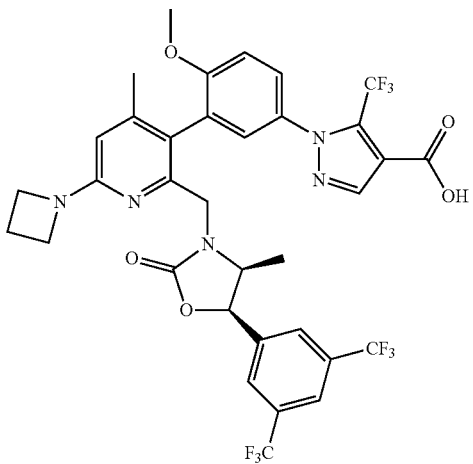 [SMILES: COc1ccc(-n2ncc(C(=O)O)c2C(F)(F)F)cc1-c1c(C)cc(N2CCC2)nc1CN1C(=O)O[C@H](c2cc(C(F)(F)F)cc(C(F)(F)F)c2)[C@@H]1C] | 758.32 |
| 286 | 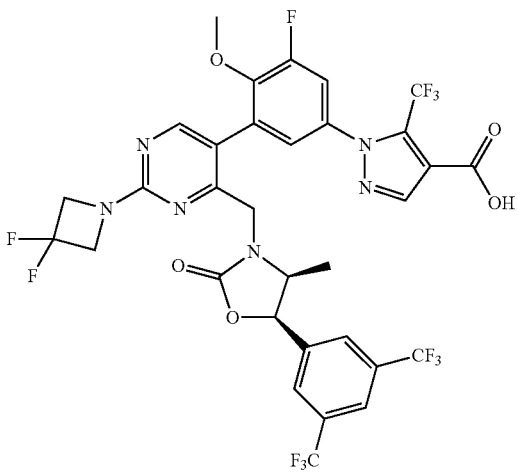 [SMILES: COc1c(F)cc(-n2ncc(C(=O)O)c2C(F)(F)F)cc1-c1cnc(N2CC(F)(F)C2)nc1CN1C(=O)O[C@H](c2cc(C(F)(F)F)cc(C(F)(F)F)c2)[C@@H]1C] | 799.32 |

TABLE 25-continued

| EXAMPLE | Molecular structure | LCMS (M + 1)+ |
|---------|---------------------|---------------|
| 287 | 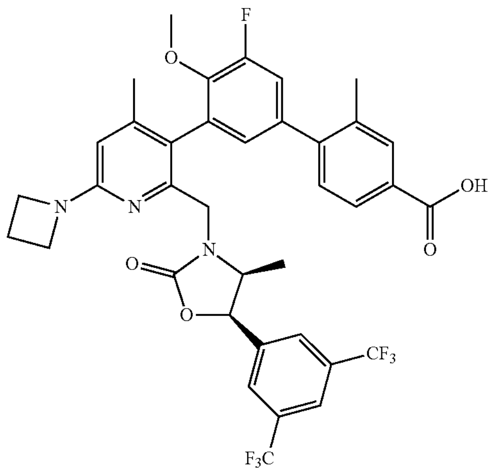 [SMILES: COc1c(F)cc(-c2ccc(C(=O)O)cc2C)cc1-c1c(C)cc(N2CCC2)nc1CN1C(=O)O[C@H](c2cc(C(F)(F)F)cc(C(F)(F)F)c2)[C@@H]1C] | 732.32 |
| 288 | 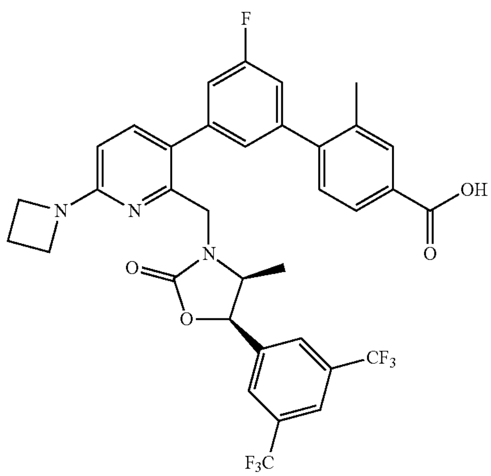 [SMILES: Cc1cc(C(=O)O)ccc1-c1cc(F)cc(-c2ccc(N3CCC3)nc2CN2C(=O)O[C@H](c3cc(C(F)(F)F)cc(C(F)(F)F)c3)[C@@H]2C)c1] | 688.39 |
| 289 | 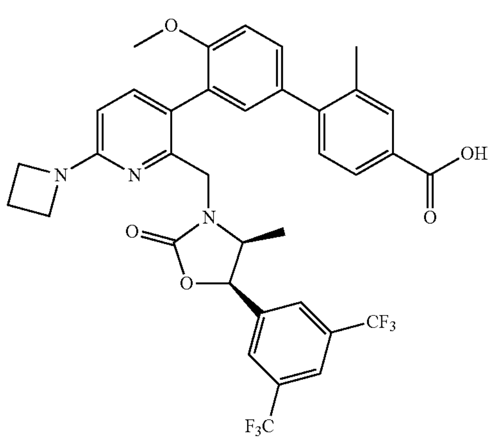 [SMILES: COc1ccc(-c2ccc(C(=O)O)cc2C)cc1-c1ccc(N2CCC2)nc1CN1C(=O)O[C@H](c2cc(C(F)(F)F)cc(C(F)(F)F)c2)[C@@H]1C] | 700.42 |

TABLE 25-continued
| EXAMPLE | Molecular structure | LCMS (M + 1)+ |
|---------|---------------------|---------------|
| 290 | 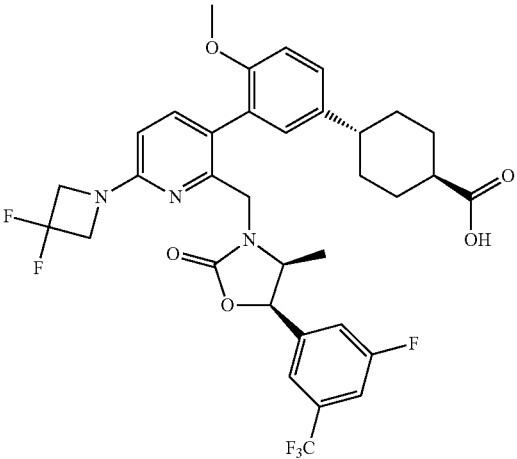 [SMILES: COc1ccc([C@H]2CC[C@H](C(=O)O)CC2)cc1-c1ccc(N2CC(F)(F)C2)nc1CN1C(=O)O[C@H](c2cc(F)cc(C(F)(F)F)c2)[C@@H]1C] | 678.48 |
| 291 | 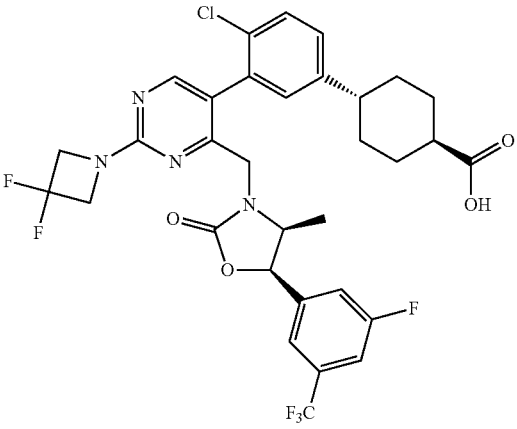 [SMILES: C[C@H]1[C@@H](c2cc(F)cc(C(F)(F)F)c2)OC(=O)N1Cc1nc(N2CC(F)(F)C2)ncc1-c1cc([C@H]2CC[C@H](C(=O)O)CC2)ccc1Cl] | 683.36 |
| 292 | 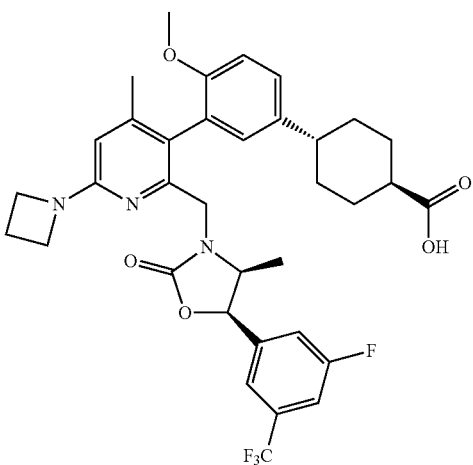 [SMILES: COc1ccc([C@H]2CC[C@H](C(=O)O)CC2)cc1-c1c(C)cc(N2CCC2)nc1CN1C(=O)O[C@H](c2cc(F)cc(C(F)(F)F)c2)[C@@H]1C] | 656.43 |

TABLE 25-continued

| EXAMPLE | Molecular structure | LCMS (M + 1)+ |
|---------|---------------------|---------------|
| 293 | 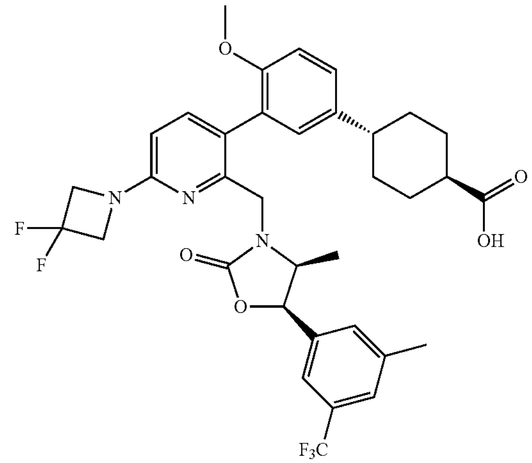 [SMILES: COc1ccc([C@H]2CC[C@H](C(=O)O)CC2)cc1-c1ccc(N2CC(F)(F)C2)nc1CN1C(=O)O[C@H](c2cc(C)cc(C(F)(F)F)c2)[C@@H]1C] | 674.45 |
| 294 | 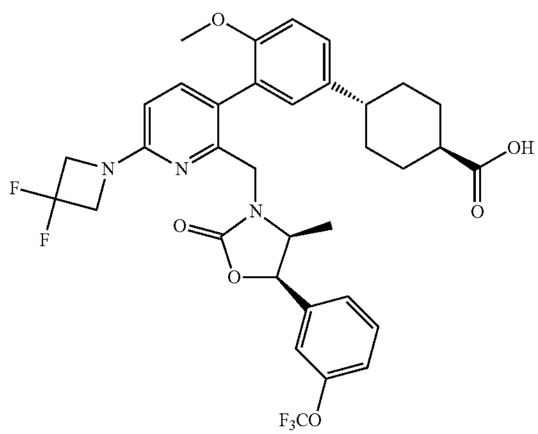 [SMILES: COc1ccc([C@H]2CC[C@H](C(=O)O)CC2)cc1-c1ccc(N2CC(F)(F)C2)nc1CN1C(=O)O[C@H](c2cccc(OC(F)(F)F)c2)[C@@H]1C] | 676.39 |
| 295 | 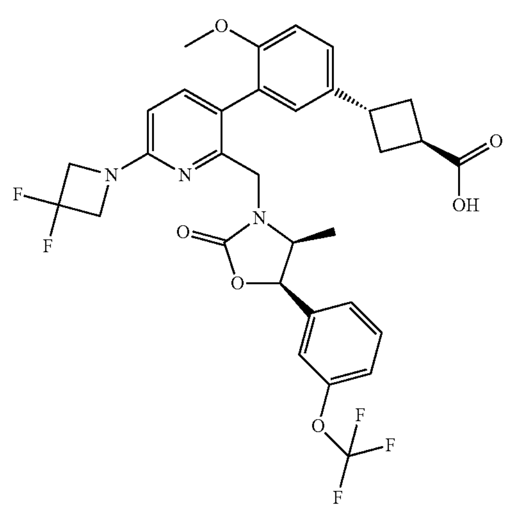 [SMILES: COc1ccc([C@H]2C[C@H](C(=O)O)C2)cc1-c1ccc(N2CC(F)(F)C2)nc1CN1C(=O)O[C@H](c2cccc(OC(F)(F)F)c2)[C@@H]1C] | 648.41 |

TABLE 25-continued

| EXAMPLE | Molecular structure | LCMS (M + 1)+ |
|---------|---------------------|---------------|
| 296 | 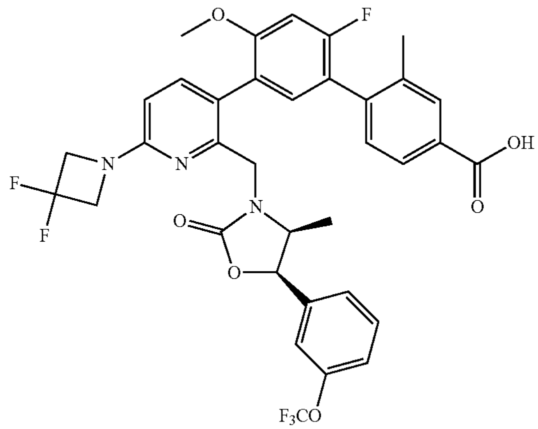 [SMILES: COc1cc(F)c(-c2ccc(C(=O)O)cc2C)cc1-c1ccc(N2CC(F)(F)C2)nc1CN1C(=O)O[C@H](c2cccc(OC(F)(F)F)c2)[C@@H]1C] | 702.43 |
| 297 | 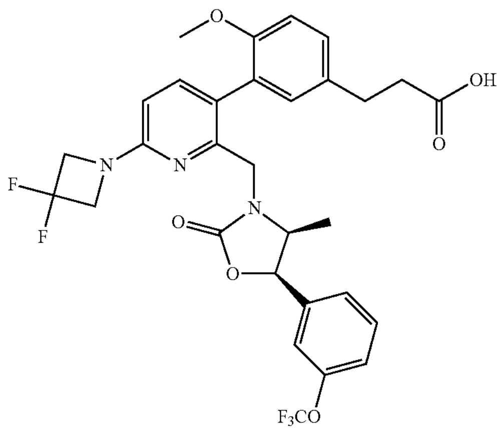 [SMILES: COc1ccc(CCC(=O)O)cc1-c1ccc(N2CC(F)(F)C2)nc1CN1C(=O)O[C@H](c2cccc(OC(F)(F)F)c2)[C@@H]1C] | 622.38 |
| 298 | 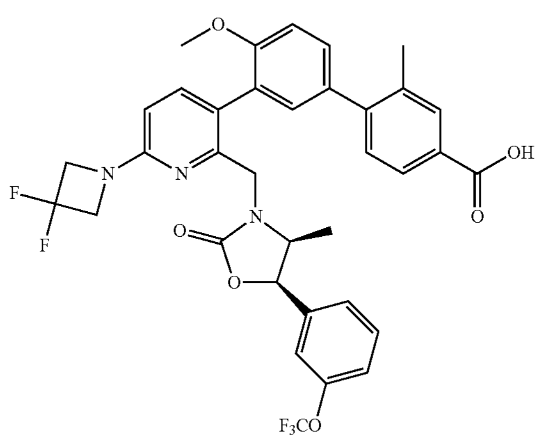 [SMILES: COc1ccc(-c2ccc(C(=O)O)cc2C)cc1-c1ccc(N2CC(F)(F)C2)nc1CN1C(=O)O[C@H](c2cccc(OC(F)(F)F)c2)[C@@H]1C] | 668.43 |

Example 299

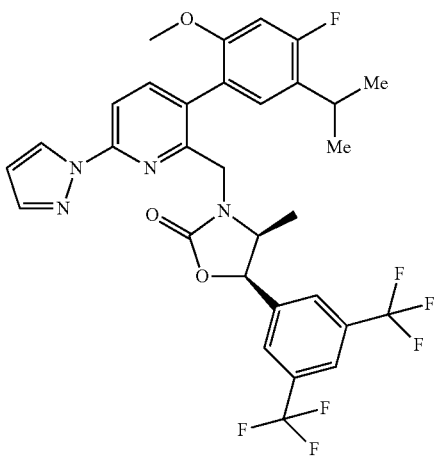 [SMILES: COc1cc(F)c(C(C)C)cc1-c1ccc(-n2cccn2)nc1CN1C(=O)O[C@H](c2cc(C(F)(F)F)cc(C(F)(F)F)c2)[C@@H]1C]

(4S,5R)-5-[3,5-bis(trifluoromethyl)phenyl]-3-({3-[4-fluoro-2-methoxy-5-(propan-2-yl)phenyl]-6-(1H-pyrazol-1-yl)pyridin-2-yl}methyl)-4-methyl-1,3-oxazolidin-2-one

Step 1: (4S,5R)-5-[3,5-bis(trifluoromethyl)phenyl]-3-({6-chloro-3-[4-fluoro-2-methoxy-5-(propan-2-yl)phenyl]pyridin-2-yl}methyl)-4-methyl-1,3-oxazolidin-2-one To (4S,5R)-5-[3,5-bis(trifluoromethyl)phenyl]-3-[(3-bromo-6-chloropyridin-2-yl)methyl]-4-methyl-1,3-oxazolidin-2-one (INTERMEDIATE 32) (460 mg, 0.889 mmol) in THF (10 mL) was added potassium carbonate (2 M in water, 1.3 mL, 2.67 mmol), 1,1'-bis(diphenylphosphino)ferrocene-palladium(II)dichloride dichloromethane complex (57.9 mg, 0.089 mmol) and (4-fluoro-5-isopropyl-2-methoxyphenyl)boronic acid (INTERMEDIATE 59) (283 mg, 1.33 mmol). The reaction was degassed with nitrogen and heated at 32° C. for 16 hr. The reaction was then poured into brine and extracted with ethyl acetate (2×10 mL). The combined extracts were dried over sodium sulfate, filtered, and concentrated. The residue was purified via flash chromatography on silica gel to afford (4S,5R)-5-[3,5-bis(trifluoromethyl)phenyl]-3-({6-chloro-3-[4-fluoro-2-methoxy-5-(propan-2-yl)phenyl]pyridin-2-yl}methyl)-4-methyl-1,3-oxazolidin-2-one (419.4 mg, 0.693 mmol) LCMS calc.=605.1. found=605.1.

Step 2: (4S,5R)-5-[3,5-bis(trifluoromethyl)phenyl]-3-({6-chloro-3-[4-fluoro-2-methoxy-5-(propan-2-yl)phenyl]pyridin-2-yl}methyl)-4-methyl-1,3-oxazolidin-2-one (4S,5R)-5-[3,5-Bis(trifluoromethyl)phenyl]-3-({6-chloro-3-[4-fluoro-2-methoxy-5-(propan-2-yl)phenyl]pyridin-2-yl}methyl)-4-methyl-1,3-oxazolidin-2-one chloride (40 mg, 0.066 mmol) and pyrazole (5.40 mg, 0.079 mmol) were dissolved in dioxane (0.7 mL) in a 2-5 mL microwave vial. Cesium carbonate (43.1 mg, 0.132 mmol) and copper(I) iodide (12.6 mg, 0.066 mmol) were added and the mixture was degassed. N,N-dimethylethylenediamine (23.3 mg, 0.264 mmol) was added before sealing the system and heating (thermally) to 110° C. overnight. The reaction was cooled and filtered over Celite® (ethyl acetate wash) and the filtrate was concentrated and was purified by reverse phase HPLC to yield (4S,5R)-5-[3,5-bis(trifluoromethyl)phenyl]-3-({6-chloro-3-[4-fluoro-2-methoxy-5-(propan-2-yl)phenyl]pyridin-2-yl}methyl)-4-methyl-1,3-oxazolidin-2-one (5.5 mg, 8.64 µmol). $^1$H NMR (CD$_3$OD, 500 MHz) δ 8.63 (s, 1H), 7.99 (s, 1H), 7.93 (m, 3H), 7.79 (s, 1H), 7.75 (d, J=8.2 Hz, 1H), 7.17 (br s, 1H), 6.88 (d, J=12.3 Hz, 1H), 6.57 (s, 1H), 5.84 (m, 1H), 4.85 (m, 1H), 4.21 (m, 2H), 3.81 (s, 3H), 3.21 (m, 1H), 1.29 (m, 6H), 0.64 (d, J=41.1 Hz, 3H). SPA=55.8 nM

Example 300

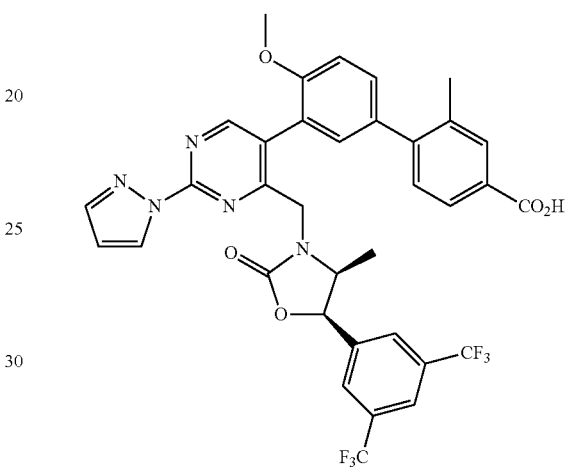

3'-[4-({(4S,5R)-5-[3,5-bis(trifluoromethyl)phenyl]-4-methyl-2-oxo-1,3-oxazolidin-3-yl}methyl)-2-(1H-pyrazol-1-yl)pyrimidin-5-yl]-4'-methoxy-2-methyl-biphenyl-4-carboxylic acid

Step 1: (4S,5R)-5-[3,5-bis(trifluoromethyl)phenyl]-3-{[3-bromo-6-(1H-pyrazol-1-yl)pyridin-2-yl]methyl}-4-methyl-1,3-oxazolidin-2-one To (4S,5R)-5-[3,5-bis(trifluoromethyl)phenyl]-3-[(3-bromo-6-chloropyridin-2-yl)methyl]-4-methyl-1,3-oxazolidin-2-one (INTERMEDIATE 32, 198 mg, 0.382 mmol) was added pyrazole (450 mg, 6.61 mmol) and p-toluenesulfonic acid (20 mg, 0.116 mmol). The mixture was heated by microwave irradiation to 180° C. for 30 minutes. The reaction was diluted with ethyl acetate and aqueous sodium hydroxide (1M). The organic was washed with water and brine and was dried over sodium sulfate, filtered and concentrated. The resultant residue was purified by column chromatography to yield (4S,5R)-5-[3,5-bis(trifluoromethyl)phenyl]-3-{[3-bromo-6-(1H-pyrazol-1-yl)pyridin-2-yl]methyl}-4-methyl-1,3-oxazolidin-2-one (173 mg, 0.316 mmol). LCMS calc.=549.0/551.0. found=549.0/551.0.

Step 2: methyl 3'-[2-({(4S,5R)-5-[3,5-bis(trifluoromethyl)phenyl]-4-methyl-2-oxo-1,3-oxazolidin-3-yl}methyl)-6-(1H-pyrazol-1-yl)pyridin-3-yl]-4'-methoxy-2-methylbiphenyl-4-carboxylate To (4S,5R)-5-[3,5-bis(trifluoromethyl)phenyl]-3-{[3-bromo-6-(1H-pyrazol-1-yl)pyridin-2-yl]methyl}-4-methyl- 1,3-oxazolidin-2-one (100 mg, 0.182 mmol) in THF (0.91 mL) was added methyl 4'-methoxy-2-methyl-3'-(4,4,5,5-tetramethyl-1,3,2-dioxaborolan-2-yl)biphenyl-4-carboxylate (84 mg, 0.218 mmol), 1,1'-bis(di-tert-butylphosphino)ferrocene palladium dichloride (17.8 mg, 0.027 mmol), and potassium carbonate (2 M in water, 0.273 mL, 0.546 mmol). The system was flushed with nitrogen, capped, and stirred at room temperature overnight. The reaction was diluted with ethyl acetate and the organic was washed with water (2×), brine, dried (Na$_2$SO$_4$), filtered, and concentrated. The crude material was purified by column chromatography to yield methyl 3'-[2-({(4S,5R)-5-[3,5-bis(trifluoromethyl)phenyl]-4-methyl-2-oxo-1,3-oxazolidin-3-yl}methyl)-6-(1H-pyrazol-1-yl)pyridin-3-yl]-4'-methoxy-2-methylbiphenyl-4-carboxylate (91.4 mg, 0.126 mmol). LCMS calc.=725.2. found=725.3.

Step 3: 3'-[2-({(4S,5R)-5-[3,5-bis(trifluoromethyl)phenyl]-4-methyl-2-oxo-1,3-oxazolidin-3-yl}methyl-6-(1H-pyrazol-1-yl)pyridin-3-yl]-4'-methoxy-2-methylbiphenyl-4-carboxylic acid To methyl 3'-[2-({(4S,5R)-5-[3,5-bis(trifluoromethyl)phenyl]-4-methyl-2-oxo-1,3-oxazolidin-3-yl}methyl)-6-(1H-pyrazol-1-yl)pyridin-3-yl]-4'-methoxy-2-methylbiphenyl-4-carboxylate (91.4 mg, 0.126 mmol) in dioxanes (2 mL) was added lithium hydroxide (0.5 M, 1.0 mL, 0.505 mmol). The system was heated to 40° C. and was stirred for 1.5 hrs. The reaction was cooled to room temperature and TFA (100 µL) was added to the reaction before volatiles were removed. The crude material was purified by reverse phase HPLC to yield 3'-[2-({(4S,5R)-5-[3,5-bis(trifluoromethyl)phenyl]-4-methyl-2-oxo-1,3-oxazolidin-3-yl}methyl)-6-(1H-pyrazol-1-yl)pyridin-3-yl]-4'-methoxy-2-methylbiphenyl-4-carboxylic acid (86.1 mg, 0.104 mmol). LCMS calc.=711.2. found=711.2. $^1$H NMR (CD$_3$OD, 500 MHz) δ 8.62 (s, 1H), 7.88 (m, 8H), 7.34 (m, 4H), 6.56 (s, 1H), 5.81 (m, 1H), 4.84 (m, 1H), 4.24 (m, 2H), 3.90 (br s, 3H), 3.36 (br s, 3H), 0.67 (d, J=33.5 Hz, 3H). RTA=14.8 nM The following compounds (Table 26) were synthesized using methods analogous to those described above.

Example 302

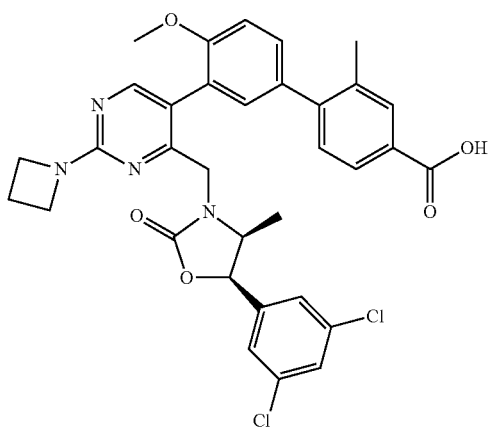 [SMILES: COc1ccc(-c2ccc(C(=O)O)cc2C)cc1-c1cnc(N2CCC2)nc1CN1C(=O)O[C@H](c2cc(Cl)cc(Cl)c2)[C@@H]1C]

3'-[2-(azetidin-1-yl)-4-{[(4S,5R)-5-(3,5-dichlorophenyl-4-methyl-2-oxo-1,3-oxazolidin-3-yl]methyl}pyrimidin-5-yl]-4'-methoxy-2-methylbiphenyl-4-carboxylic acid Step 1: methyl 4'-methoxy-2-methyl-3'-[2-(methylsulfanyl)-4-{[(methylsulfonyl)oxy]methyl}pyrimidin-5-yl]biphenyl-4-carboxylate To methyl 3'-[4-(hydroxymethyl)-2-(methylsulfanyl)pyrimidin-5-yl]-4'-methoxy-2-methylbiphenyl-4-carboxylate (INTERMEDIATE 90, 5.0 g, 12.18 mmol) in DCM (40.6 mL) was added TEA (2.55 mL, 18.27 mmol). The system was cooled in ice bath under a nitrogen atmosphere and methanesulfonyl chloride (1.14 mL, 14.62 mmol) was added. The reaction was stirred for 1 hour at 0° C. and was then diluted with DCM. The organic was washed with brine, dried over sodium sulfate and was concentrated to dryness before purification by column chromatography. Methyl 4'-methoxy-2-methyl-3'-[2-(methylsulfanyl)-4-{[(methylsulfonyl)oxy]methyl}pyrimidin-5-yl]biphenyl-4-carboxylate (5.67 g, 11.61 mmol). LCMS calc.=489.1. found=489.1.

TABLE 26

| EXAMPLE | Molecular structure | LCMS (M + 1)$^+$ |
|---|---|---|
| 301 | (structure: methoxy-biphenyl-methyl-CO$_2$H with pyridine-pyrazole(Me)-oxazolidinone-bis-CF$_3$-phenyl)  SPA = 260 nM | 725.2 |

Step 2: methyl 3'-[4-{[(4S,5R)-5-(3,5-dichlorophenyl)-4-methyl-2-oxo-1,3-oxazolidin-3-yl]methyl}-2-(methylsulfanyl)pyrimidin-5-yl]-4'-methoxy-2-methylbiphenyl-4-carboxylate To (4S,5R)-5-(3,5-dichlorophenyl)-4-methyl-1,3-oxazolidin-2-one (INTERMEDIATE XX—see table 18, 202 mg, 0.821 mmol) in THF (6 mL) at 0° C. was added sodium hydride (60 wt %, 37.3 mg, 0.933 mmol). The reaction was stirred at 0° C. for 1 hour and a solution of methyl 4'-methoxy-2-methyl-3'-[2-(methylsulfanyl)-4-{[(methylsulfonyl)oxy]methyl}pyrimidin-5-yl]biphenyl-4-carboxylate (364 mg, 0.746 mmol) in THF (500 μL) was added. The reaction was allowed to warm to room temperature overnight. The reaction was cooled to 0° C. and was quenched with HCl (1 N, 373 μL) and the reaction was poured into saturated aqueous NaHCO$_3$ and ethyl acetate. The organic was washed with brine, was dried (Na$_2$SO$_4$), filtered, and concentrated. The resultant residue was purified by column chromatography to yield methyl 3'-[4-{[(4S,5R)-5-(3,5-dichlorophenyl)-4-methyl-2-oxo-1,3-oxazolidin-3-yl]methyl}-2-(methylsulfanyl)pyrimidin-5-yl]-4'-methoxy-2-methylbiphenyl-4-carboxylate (295 mg, 0.462 mmol). LCMS calc.=638.1. found=638.2.

Step 3: methyl 3'-[4-{[(4S,5R)-5-(3,5-dichlorophenyl-4-methyl-2-oxo-1,3-oxazolidin-3-yl]methyl}-2-(methylsulfonyl)pyrimidin-5-yl]-4'-methoxy-2-methylbiphenyl-4-carboxylate To methyl 3'-[4-{[(4S,5R)-5-(3,5-dichlorophenyl)-4-methyl-2-oxo-1,3-oxazolidin-3-yl]methyl}-2-(methylsulfanyl)pyrimidin-5-yl]-4'-methoxy-2-methylbiphenyl-4-carboxylate (294 mg, 0.46 mmol) in DCM (5 mL) at 0° C. was added m-chloroperbenzoic acid (319 mg, 1.381 mmol). The reaction was allowed to warm to room temperature and was diluted with DCM and sat'd sodium thiosulfate solution. The organic was washed with sat'd NaHCO$_3$, brine, dried (Na$_2$SO$_4$) concentrate before purification by column chromatography to yield methyl 3'-[4-{[(4S,5R)-5-(3,5-dichlorophenyl)-4-methyl-2-oxo-1,3-oxazolidin-3-yl]methyl}-2-(methylsulfonyl)pyrimidin-5-yl]-4'-methoxy-2-methylbiphenyl-4-carboxylate (292 mg, 0.435 mmol). LCMS calc.=670.2. found=670.2.

Step 4: methyl 3'-[2-(azetidin-1-yl-4-{[(4S,5R)-5-(3,5-dichlorophenyl)-4-methyl-2-oxo-1,3-oxazolidin-3-yl]methyl}pyrimidin-5-yl]-4'-methoxy-2-methylbiphenyl-4-carboxylate To methyl 3'-[4-{[(4S,5R)-5-(3,5-dichlorophenyl)-4-methyl-2-oxo-1,3-oxazolidin-3-yl]methyl}-2-(methylsulfonyl)pyrimidin-5-yl]-4'-methoxy-2-methylbiphenyl-4-carboxylate (81 mg, 0.121 mmol) in THF (1.6 mL) was added azetidine (40.7 μL, 0.604 mmol). The reaction was subjected to microwave irradiation at 100° C. for 15 min. The reaction was concentrated, then dissolved in ethyl acetate and washed with water (2×), brine, dried (Na$_2$SO$_4$), filtered, concentrated. The crude reaction was purified by column chromatography to yield methyl 3'-[2-(azetidin-1-yl)-4-{[(4S,5R)-5-(3,5-dichlorophenyl)-4-methyl-2-oxo-1,3-oxazolidin-3-yl]methyl}pyrimidin-5-yl]-4'-methoxy-2-methylbiphenyl-4-carboxylate (78 mg, 0.121 mmol). LCMS calc.=647.2. found=647.4.

Step 5: 3'-[2-(azetidin-1-yl)-4-{[(4S,5R)-5-(3,5-dichlorophenyl)-4-methyl-2-oxo-1,3-oxazolidin-3-yl]methyl}pyrimidin-5-yl]-4'-methoxy-2-methylbiphenyl-4-carboxylic acid To methyl 3'-[2-(azetidin-1-yl)-4-{[(4S,5R)-5-(3,5-dichlorophenyl)-4-methyl-2-oxo-1,3-oxazolidin-3-yl]methyl}pyrimidin-5-yl]-4'-methoxy-2-methylbiphenyl-4-carboxylate (78 mg, 0.121 mmol) in dioxane (2.4 mL) was added LiOH (0.5 M, 1.2 mL, 0.605 mmol). The reaction was heated to 60° C. for 1 hour before cooling and acidifying with TFA. The volatiles were removed and the crude material was purified by reverse phase HPLC to yield 3'-[2-(azetidin-1-yl)-4-{[(4S,5R)-5-(3,5-dichlorophenyl)-4-methyl-2-oxo-1,3-oxazolidin-3-yl]methyl}pyrimidin-5-yl]-4'-methoxy-2-methylbiphenyl-4-carboxylic acid (70 mg, 0.110 mmol). LCMS calc.=633.2. found=–633.3. $^1$H NMR (CDCl$_3$, 500 MHz) 8.19 (s, 1H), 7.98 (m, 2H), 7.33 (m, 3H), 7.15 (m, 3H), 7.04 (d, J=8.6 Hz, 1H), 5.42 (br s, 1H), 4.75 (br s, 1H), 4.23 (m, 5H), 4.01 (br s, 1H), 3.87 (s, 3H), 2.43 (m, 2H), 2.36 (s, 3H), 0.73 (s, 3H). RTA=4.43 nM Example 303

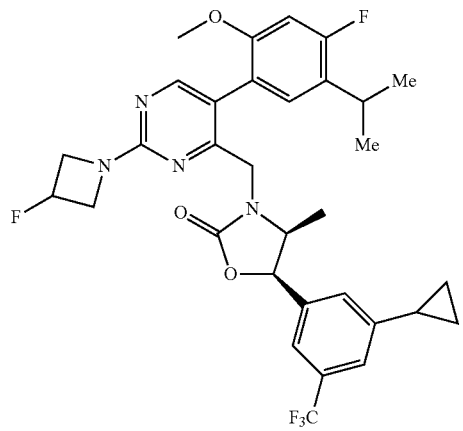 [SMILES: COc1cc(F)c(C(C)C)cc1-c1cnc(N2CC(F)C2)nc1CN1C(=O)O[C@H](c2cc(C3CC3)cc(C(F)(F)F)c2)[C@@H]1C]

(4S,5R)-5-[3-cyclopropyl-5-(trifluoromethyl)phenyl]-3-({2-(3-fluoroazetidin-1-yl)-5-[4-fluoro-2-methoxy-5-(propan-2-yl)phenyl]pyrimidin-4-yl}methyl)-4-methyl-1,3-oxazolidin-2-one

Step 1: {5-[4-fluoro-2-methoxy-5-(propan-2-yl)phenyl]-2-(methylsulfanyl)pyrimidin-4-yl}methyl methanesulfonate To {5-[4-fluoro-2-methoxy-5-(propan-2-yl)phenyl]-2-(methylsulfanyl)pyrimidin-4-yl}methanol (INTERMEDIATE 91, 3.22 g, 10.0 mmol) in DCM (40 mL) was added TEA (2.79 mL, 20.0 mmol). The system was cooled in ice bath under a nitrogen atmosphere and methanesulfonyl chloride (1.09 mL, 14.0 mmol) was added. The reaction was stirred for 30 minutes at 0° C. and was then diluted with DCM. The organic was washed with aqueous saturated sodium bicarbonate, water, brine, and was then dried over sodium sulfate, filtered, and concentrated to dryness before purification by column chromatography. {5-[4-Fluoro-2-methoxy-5-(propan-2-yl)phenyl]-2-(methylsulfanyl)pyrimidin-4-yl}methyl methanesulfonate (3.39 g, 8.46 mmol). LCMS calc.=401.1. found=401.2.

Step 2: (4S,5R)-5-[3-bromo-5-(trifluoromethyl)phenyl]-3-({5-[4-fluoro-2-methoxy-5-(propan-2-yl)phenyl]-2-(methylsulfanyl)pyrimidin-4-yl}methyl)-4-methyl-1,3-oxazolidin-2-one To (4S,5R)-5-[3-bromo-5-(trifluoromethyl)phenyl]-4-methyl-1,3-oxazolidin-2-one (INTERMEDIATE 67(c)—(Table 8), 145 mg, 0.447 mmol) in THF (4 mL) at 0° C. was added sodium hydride (60 wt %, 23.3 mg, 0.582 mmol). The reaction was stirred at 0° C. for 1 hour and a solution of {5-[4-fluoro-2-methoxy-5-(propan-2-yl)phenyl]-2-(methylsulfanyl)pyrimidin-4-yl}methyl methanesulfonate (188 mg, 0.470 mmol) in THF (500 µL) was added. The reaction was allowed to warm to room temperature and was stirred at room temperature for 6 hours. The reaction was quenched with HCl (1 N) and the reaction was poured into saturated aqueous NaHCO$_3$ and ethyl acetate. The organic was washed with brine, was dried (Na$_2$SO$_4$), filtered, and concentrated. The resultant residue was purified by column chromatography to yield (4S,5R)-5-[3-bromo-5-(trifluoromethyl)phenyl]-3-({5-[4-fluoro-2-methoxy-5-(propan-2-yl)phenyl]-2-(methylsulfanyl)pyrimidin-4-yl}methyl)-4-methyl-1,3-oxazolidin-2-one (190 mg, 0.302 mmol). LCMS calc.=628.1/630.1. found=628.2/630.2

Step 3: (4S,5R)-5-[3-bromo-5-(trifluoromethyl)phenyl]-3-({5-[4-fluoro-2-methoxy-5-propan-2-yl)phenyl]-2-(methylsulfonyl)pyrimidin-4-yl}methyl)-4-methyl-1,3-oxazolidin-2-one To (4S,5R)-5-[3-bromo-5-(trifluoromethyl)phenyl]-3-({5-[4-fluoro-2-methoxy-5-(propan-2-yl)phenyl]-2-(methylsulfanyl)pyrimidin-4-yl}methyl)-4-methyl-1,3-oxazolidin-2-one in water (0.75 mL) and acetonitrile (1.5 mL) was added Oxone® oxidizing agent (0.39 g, 0.634 mmol) at room temperature. The reaction was stirred overnight and was diluted with ethyl acetate and water. The organic was washed with 10% sodium thiosulfate and brine before drying over sodium sulfate, filtering, and concentrating. The crude material was carried forward without further purification (190 mg, 0.288 mmol). LCMS calc.=662.1. found=662.3.

Step 4: (4S,5R)-5-[3-bromo-5-(trifluoromethyl)phenyl]-3-({2-(3-fluoroazetidin-1-yl)-5-[4-fluoro-2-methoxy-5-(propan-2-yl)phenyl]pyrimidin-4-yl}methyl)-4-methyl-1,3-oxazolidin-2-one To (4S,5R)-5-[3-bromo-5-(trifluoromethyl)phenyl]-3-({5-[4-fluoro-2-methoxy-5-(propan-2-yl)phenyl]-2-(methylsulfonyl)pyrimidin-4-yl}methyl)-4-methyl-1,3-oxazolidin-2-one (175 mg, 0.265 mmol) in THF (1 mL) was added TEA (0.369 mL, 2.65 mmol) and 3-fluoroazetidine (236 mg, 2.120 mmol). The reaction was capped and heated at 100° C. for 10 min by microwave irradiation. The reaction was diluted with EtOAc, washed with sat. aqueous NaHCO$_3$, water and brine. The organic phase was dried over sodium sulfate, filtered and concentrated before purification by column chromatography to afford (4S,5R)-5-[3-bromo-5-(trifluoromethyl)phenyl]-3-({2-(3-fluoroazetidin-1-yl)-5-[4-fluoro-2-methoxy-5-(propan-2-yl)phenyl]pyrimidin-4-yl}methyl)-4-methyl-1,3-oxazolidin-2-one (160 mg, 0.244 mmol). LCMS calc.=655.2/657.2. found=655.4/657.4.

Step 5: (4S,5R)-5-[3-cyclopropyl-5-(trifluoromethyl)phenyl]-3-({2-(3-fluoroazetidin-1-yl)-5-[4-fluoro-2-methoxy-5-(propan-2-yl)phenyl]pyrimidin-4-yl}methyl)-4-methyl-1,3-oxazolidin-2-one To (4S,5R)-5-[3-bromo-5-(trifluoromethyl)phenyl]-3-({2-(3-fluoroazetidin-1-yl)-5-[4-fluoro-2-methoxy-5-(propan-2-yl)phenyl]pyrimidin-4-yl}methyl)-4-methyl-1,3-oxazolidin-2-one (0.031 g, 0.047 mmol) in dioxane (0.5 mL) was added tripotassium phosphate (0.071 mL, 0.142 mmol), cyclopropylboronic acid (6.10 mg, 0.071 mmol) and tetrakis(triphenylphosphine)palladium(0) (5.47 mg, 4.74 µmol). The system was flushed with nitrogen and was sealed before heating at 140° C. by microwave irradiation for 30 minutes. The reaction mixture was diluted with EtOAc, washed with sat. aqueous sodium bicarbonate, water and brine. The organic phase was dried over sodium sulfate, filtered, concentrated and the crude was purified by column chromatography to yield (4S,5R)-5-[3-cyclopropyl-5-(trifluoromethyl)phenyl]-3-({2-(3-fluoroazetidin-1-yl)-5-[4-fluoro-2-methoxy-5-(propan-2-yl)phenyl]pyrimidin-4-yl}methyl)-4-methyl-1,3-oxazolidin-2-one (13.3 mg, 0.022 mmol) as white solid. LCMS calc.=617.3. found=617.5.1H NMR (CDCl$_3$, 500 MHz) δ 8.15 (s, 1H), 7.29 (d, J=7.5 Hz, 2H), 7.19 (s, 1H), 7.01 (d, J=8.5 Hz, 1H), 6.69 (d, J=12 Hz, 1H), 5.54~5.33 (br m, 2H), 4.74 (d, J=17 Hz, 1H), 4.50 (m, 2H), 4.33 (m, 3H), 4.16~4.15 (br m, 1H), 3.97~3.94 (br m, 1H), 3.79 (s, 3H), 3.25~3.19 (m, 1H), 1.31~1.26 (m, 6H), 1.07 (m, 2H), 0.76 (m, 2H), 0.69 (m, 3H). RTA=98 nM.

What is claimed is:
1. A compound of Formula I, or a pharmaceutically acceptable salt thereof:

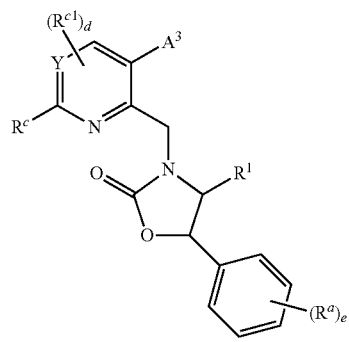

wherein $A^3$ is represented by Formula II:

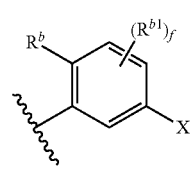

wherein Y is N or CH, wherein CH may be substituted with $R^{c1}$ if $R^{c1}$ is present in the structure;
$R^1$ is CH$_3$;
Each $R^a$ is independently CF$_3$, CH$_3$, —OCF$_3$, Cl, F, cyclopropyl, or —CN;
$R^c$ is (a) a 4-7 membered monocyclic heterocycle containing one N which is bonded to the heteroaromatic ring to which $R^c$ is connected, wherein the monocyclic heterocycle optionally contains 1-2 double bonds, one carbonyl, and 1-2 additional heteroatom groups which are each independently N, O, or S(O)$_2$, or (b) a 6-7 membered bicyclic heterocycle containing one N which is bonded to the heteroaromatic ring to which $R^c$ is connected, wherein the bicyclic heterocycle optionally contains 1-2 double bonds, one carbonyl, and 1-2 additional heteroatom groups which are each independently N, O, or S(O)$_2$, wherein $R^c$ as defined in (a) or (b) is optionally substituted with 1-2 substituent groups which are independently halogen, —OH, CH₃, —OCH₃, CF₃, or —OCF₃;

Each $R^{c1}$ is independently —CH₃ or Br;

$R^b$ is H, —C$_{1-2}$alkyl, —OCH₃, Cl, F, or —O-cyclopropyl;

Each $R^{b1}$ is F;

X is:
(a) Cl, —CH₂CN, —(CH₂)$_{1-3}$OH, —(CH₂)$_{1-3}$OCH₃, —CH(CH₃)₂ optionally substituted with 1-3 F and one —OH, -cyclopentyl-OH, -cyclohexyl-CN, or phenyl substituted with 2 substituents which are —OH and —C(=O)CH₃;
(b) D¹, wherein D¹ is —CO₂H or —CO₂C$_{1-4}$alkyl;
(c) —C$_{1-4}$alkyl-D², wherein D² is —CO₂H, —CO₂C$_{1-4}$alkyl, or —C(=O)NR²R³;
(d) —C$_{3-6}$cycloalkyl-D²;
(e) —C$_{3-6}$cycloalkyl-CH₂-D¹;
(f) -phenyl-D¹, wherein phenyl is optionally substituted with 1-3 substituents which are independently halogen or;
(g) -HET(1)-D¹-Het-D¹, wherein HET(1) is a 5-6-membered heteroaromatic ring having 1-2 heteroatom groups which are each independently N, O, or S, wherein HET(1) is optionally substituted with 1-3 groups which are independently halogen, —CH₃, —CF₃, —OCH₃, or —OCF₃; or
(h) —(CH2)$_{1-2}$-HET(2) wherein HET(2) is a 5-membered heteroaromatic ring having 2-4 N atoms, wherein HET(2) is optionally substituted with 1-2 groups which are independently —CH₃ or halogen;

R² and R³ are each independently H or —C$_{1-3}$alkyl, or R² and R³ are optionally joined to form a bridging group having 3-5 carbons, thereby yielding a 4-6 membered cyclic amide group;

d is an integer from 0-2;

e is an integer from 1-3; and f is an integer from 0-2.

2. The compound of claim 1 or a pharmaceutically acceptable salt thereof, wherein HET(1) is isoxazole, pyrazole, pyrazine, thiophene, furan, thiazole, pyrrole, pyridine, or imidazole.

3. The compound of claim 1 or a pharmaceutically acceptable salt thereof, wherein HET(2) is triazole, tetrazole, or imidazole.

4. The compound of claim 1 or a pharmaceutically acceptable salt thereof, wherein $R^c$ is (a) a 4-6 membered monocyclic heterocycle containing one N which is bonded to the heteroaromatic ring to which $R^c$ is connected, wherein the monocyclic heterocycle optionally comprises one carbonyl and 1 additional heteroatom group which is O, N, or —S(O)₂—; (b) a 5 membered monocyclic heteroaromatic ring containing one N which is bonded to the heteroaromatic ring to which $R^c$ is connected, wherein the 5 membered monocyclic heteroaromatic ring optionally contains 1 additional heteroatom group which is N; or (c) a 6-7 membered bicyclic heterocycle containing one N which is bonded to the heteroaromatic ring to which $R^c$ is connected, wherein the bicyclic heterocycle optionally contains 1 additional heteroatom group which is N or O; wherein $R^c$ as defined in (a), (b), or (c) is optionally substituted with 1-2 substituent groups which are each independently F, —OH, CH₃, —OCH₃, CF₃, or —OCF₃.

5. The compound of claim 1 or a pharmaceutically acceptable salt thereof, wherein the substituent $R^c$ is azetidine, azetidinone, pyrrolidine, piperidine, morpholine, imidazole, pyrazole, isothiazolidine 1,1-dioxide, a morpholine ring containing a methylene group bridging between two ring members, or a pyrrolidine ring containing a fused cyclopropyl ring, wherein $R^c$ is optionally substituted with 1-3 substituents which are each independently halogen, —OH, —CH₃, —OCH₃, —CF₃, or —OCF₃.

6. The compound of claim 5 or a pharmaceutically acceptable salt thereof, wherein $R^c$ is optionally substituted with 1-2 substituents which are each independently F, —CH₃, —OH, or —OCH₃.

7. The compound of claim 1, or a pharmaceutically acceptable salt thereof, having the structure below:

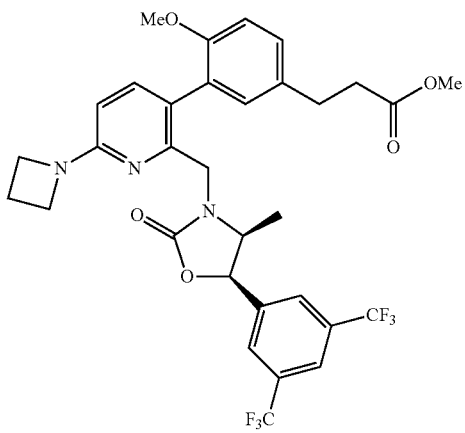

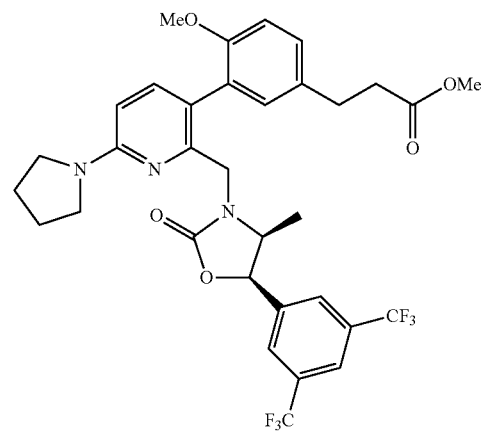

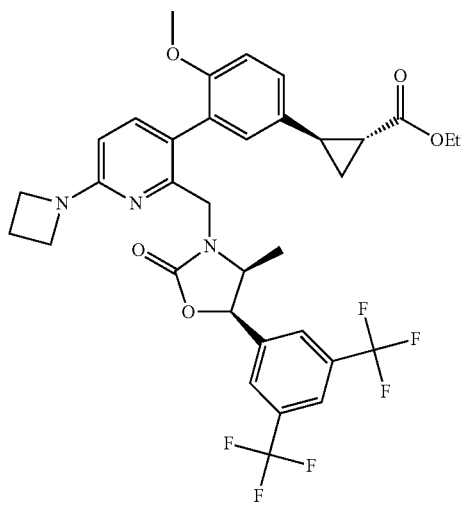

| 323 | 324 |
|---|---|
| -continued | -continued |
| 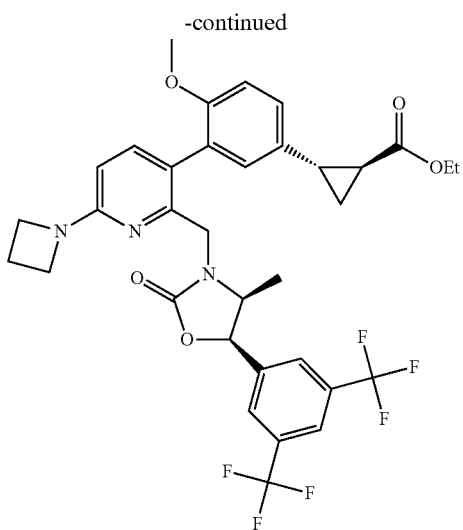 | 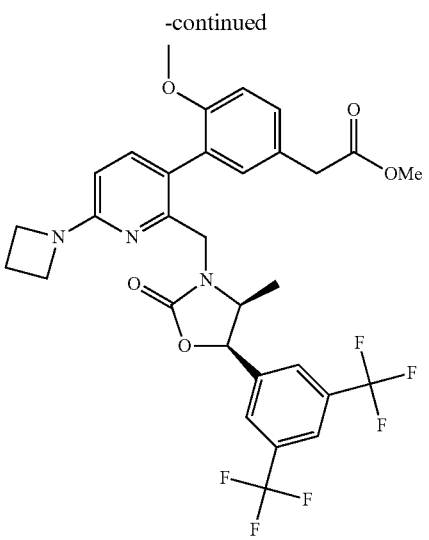 |
| 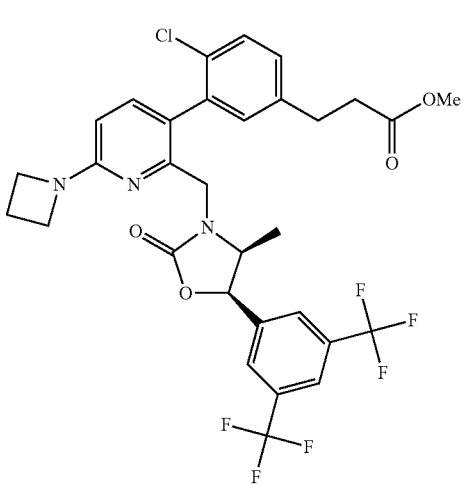 | 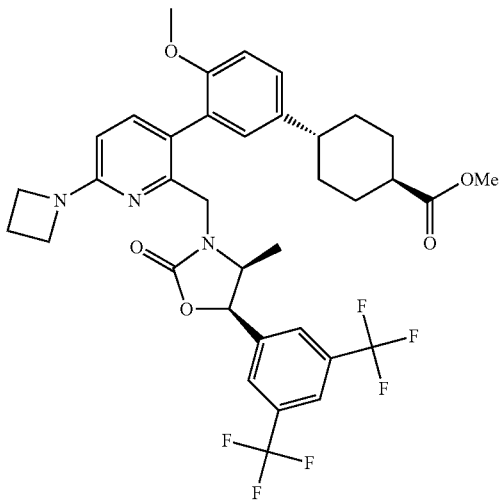 |
| 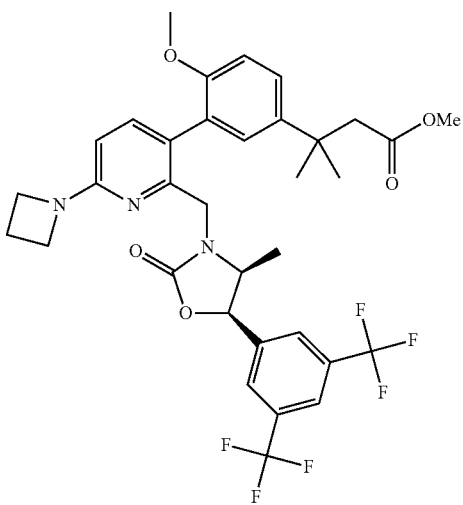 | 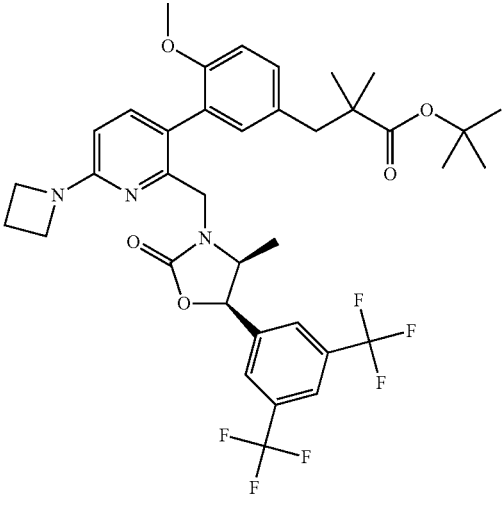 |

325
-continued
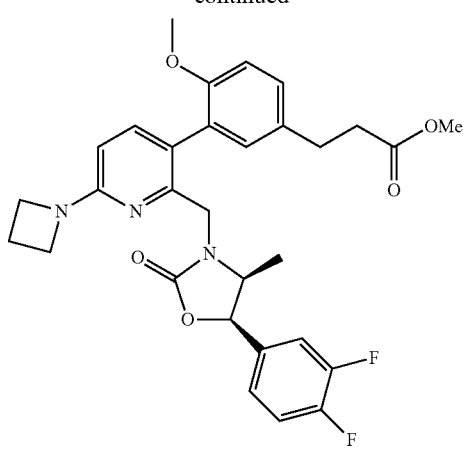
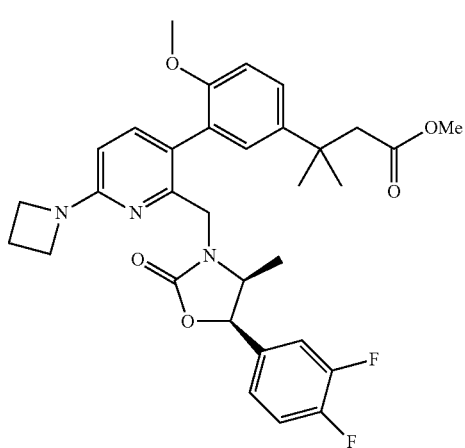
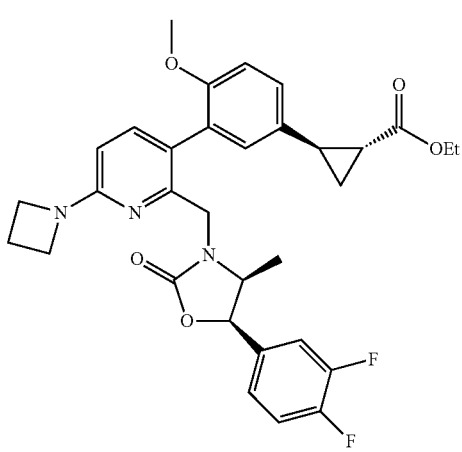
326
-continued
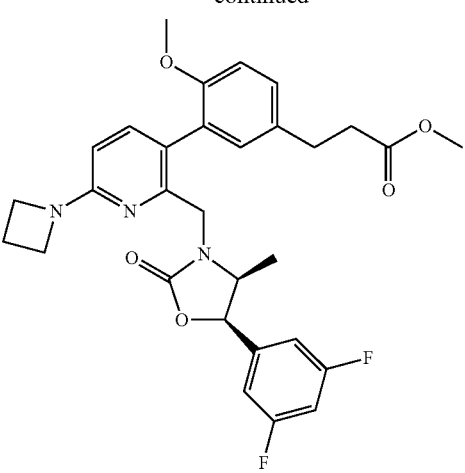
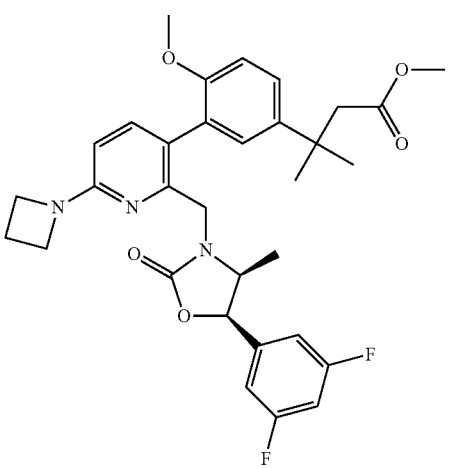
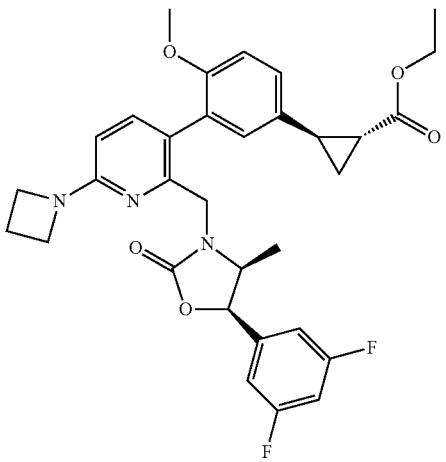

327
-continued
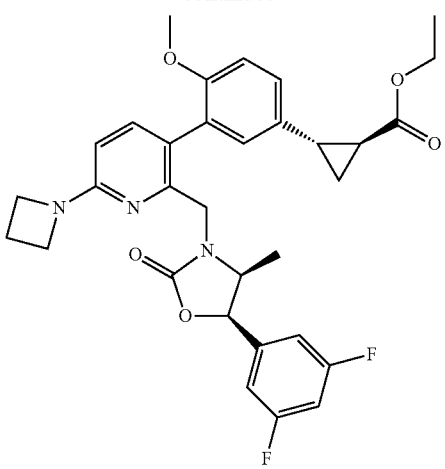
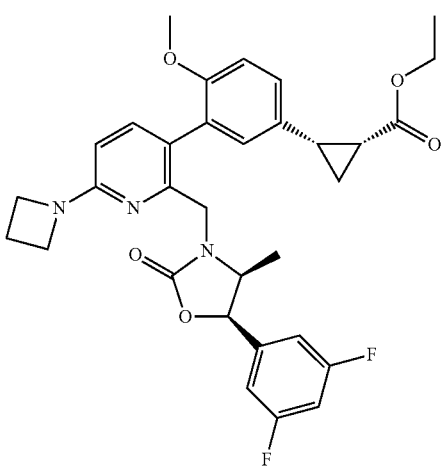
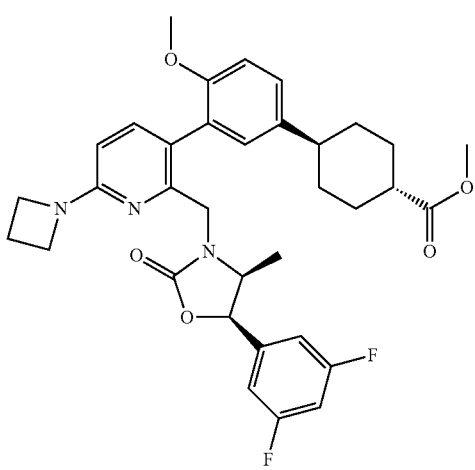
328
-continued
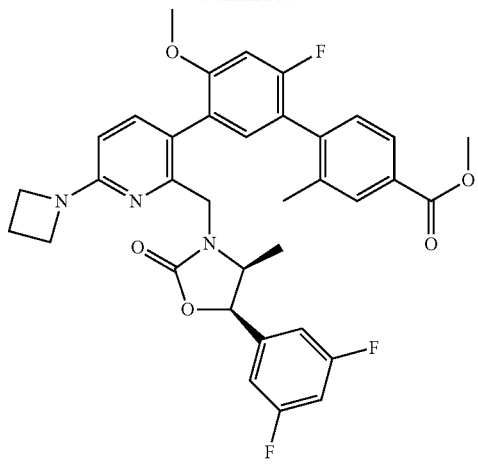
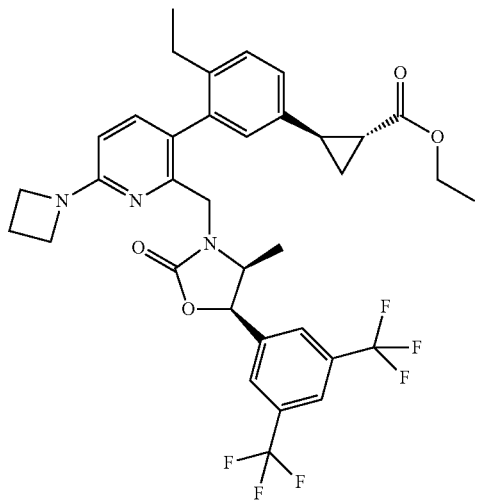
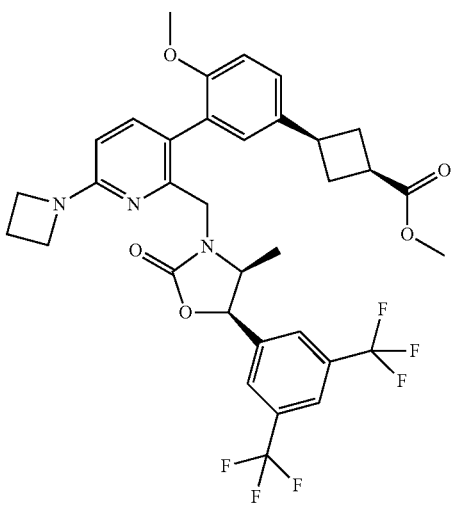

| 329 -continued | 330 -continued |
|---|---|
| 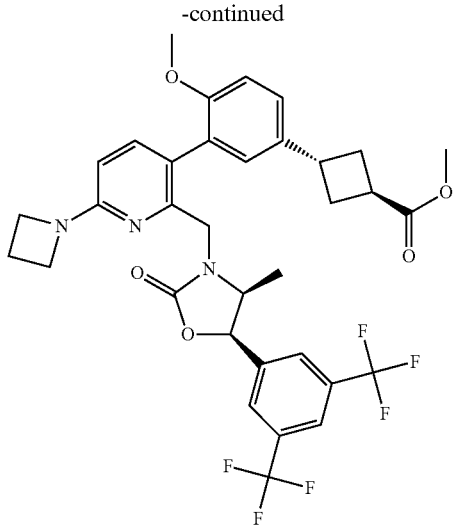 | 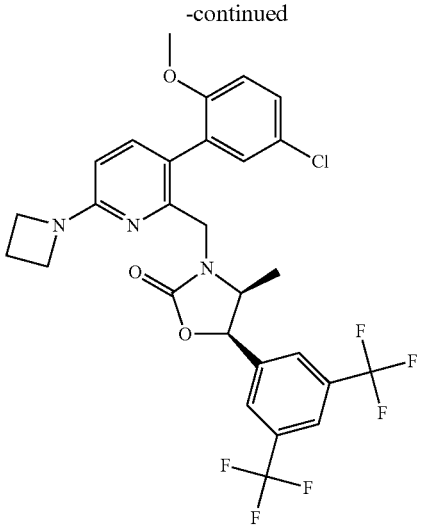 |
| 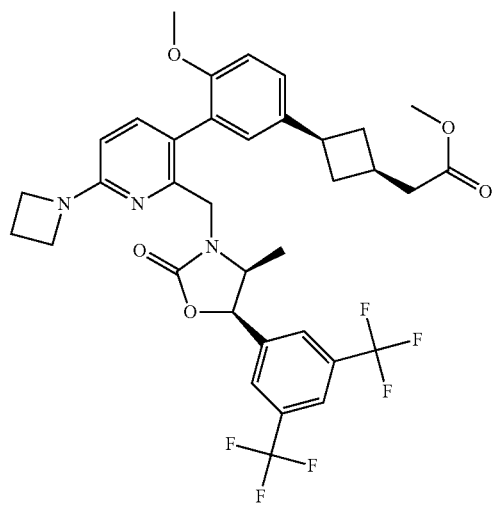 | 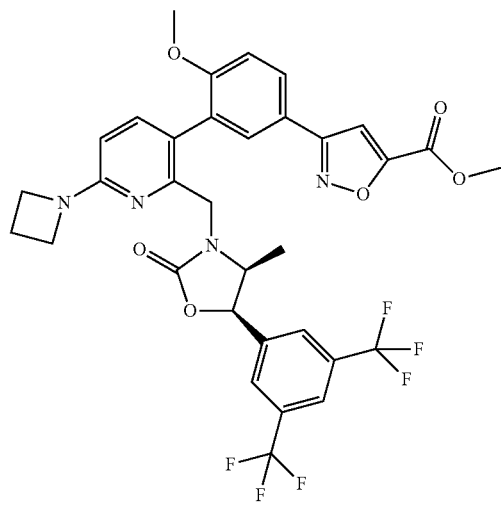 |
| 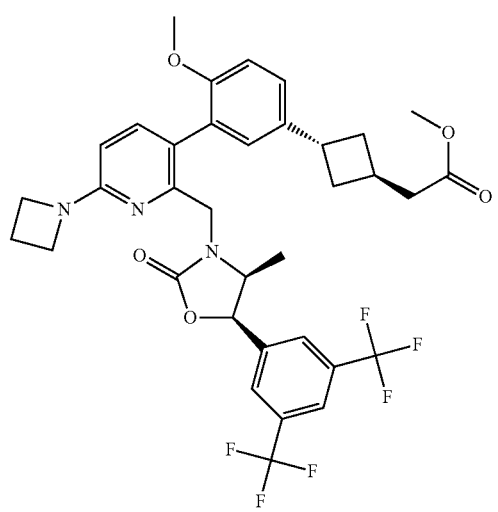 | 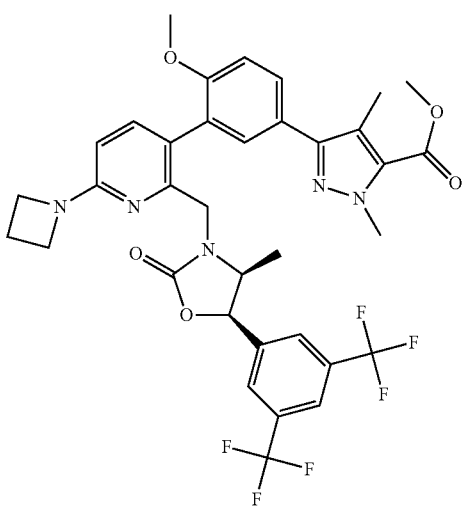 |

331
-continued
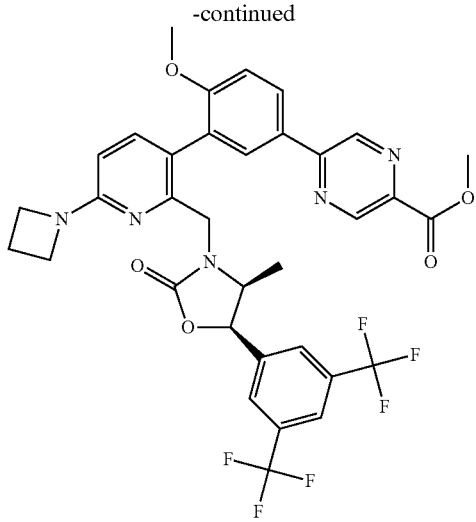
332
-continued
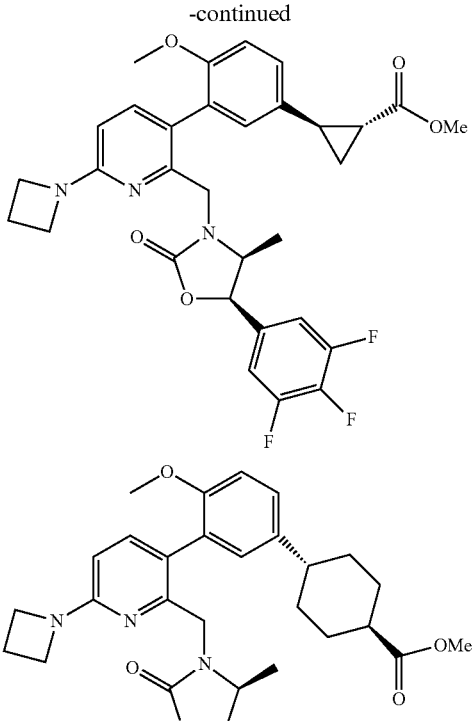
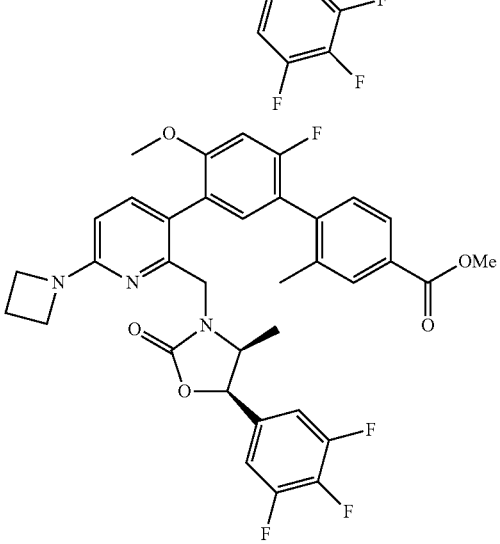
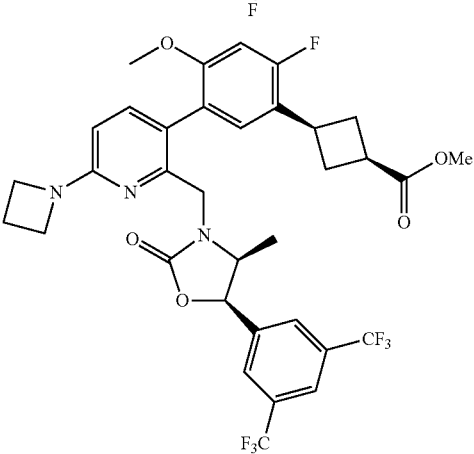

333
-continued
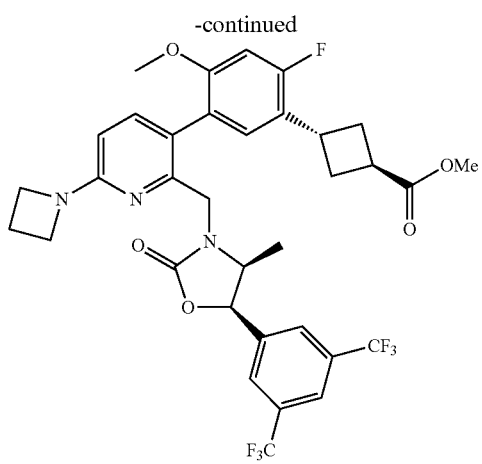
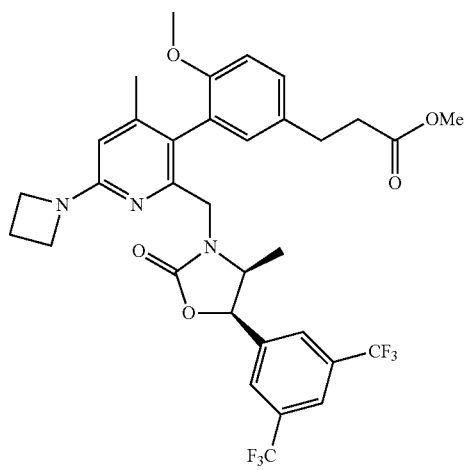
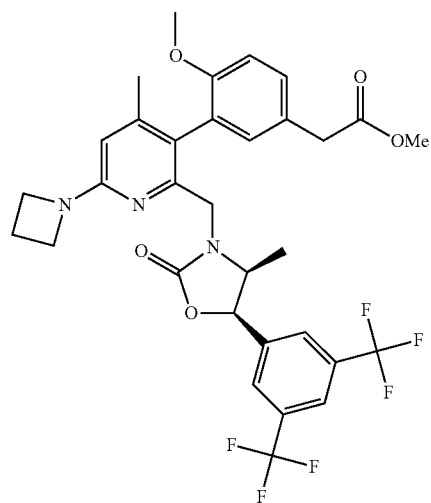
334
-continued
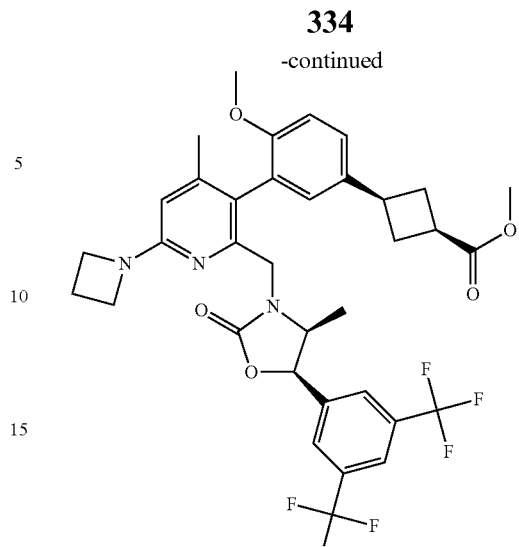
Atropisomers A and B
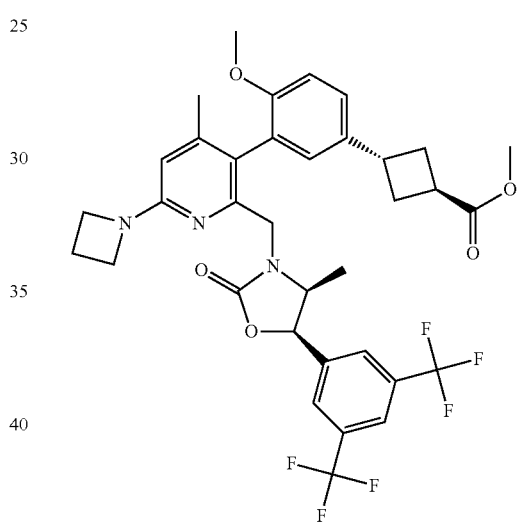
Atropisomers A and B
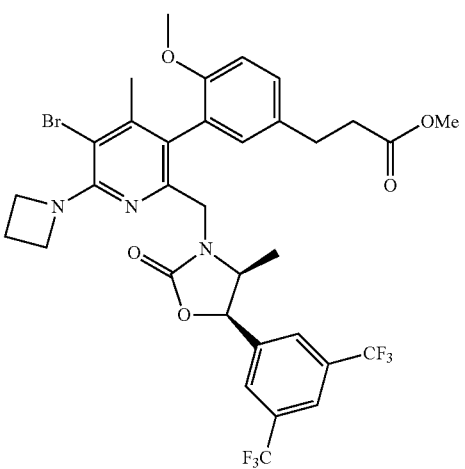

335
-continued
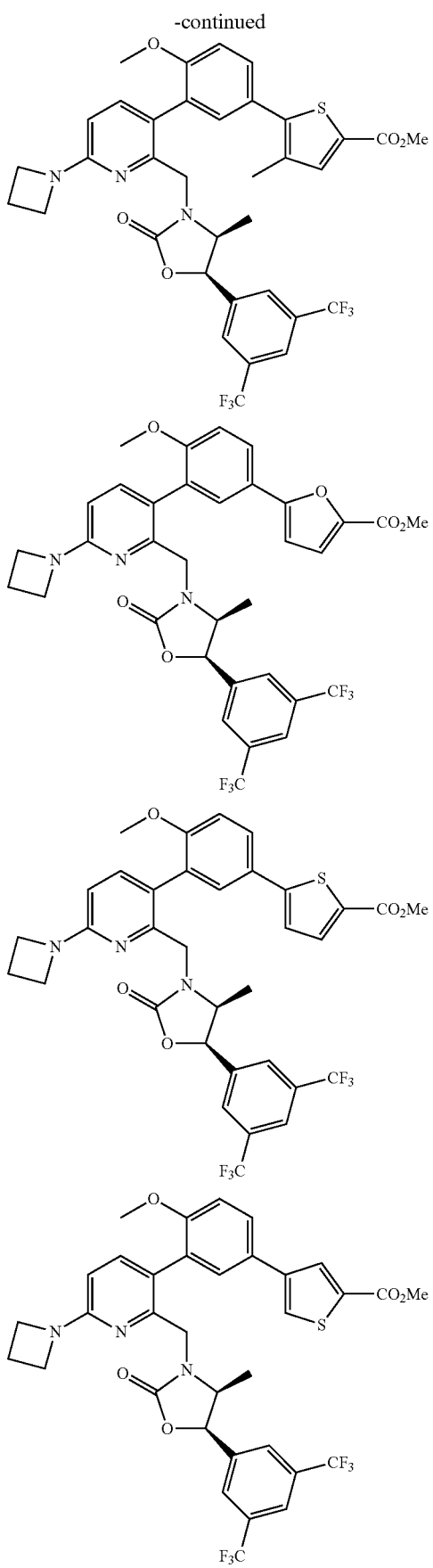
336
-continued
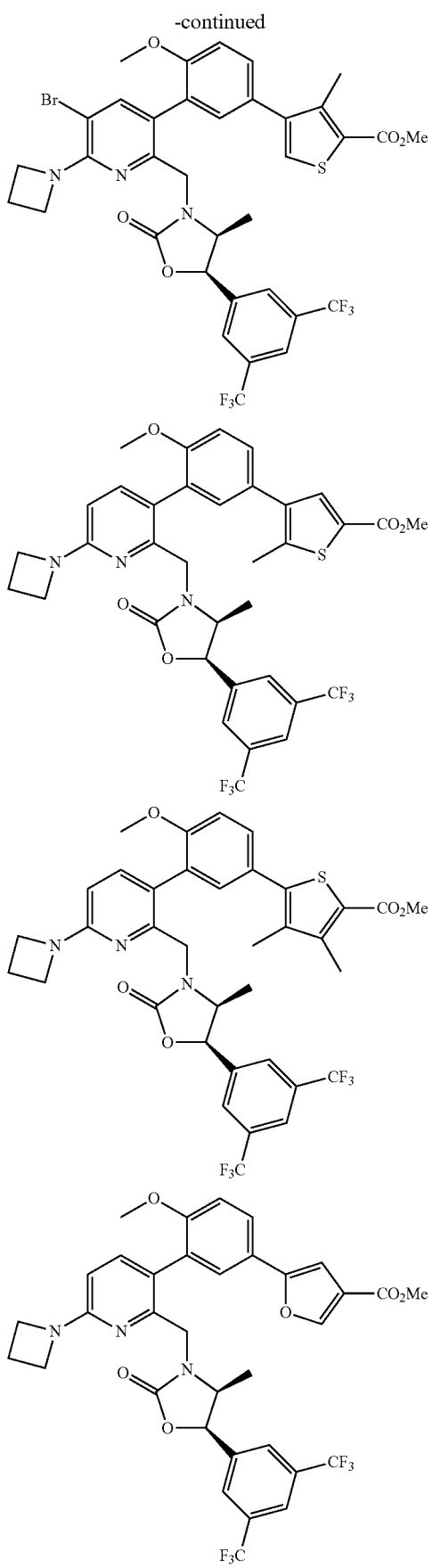

337
-continued
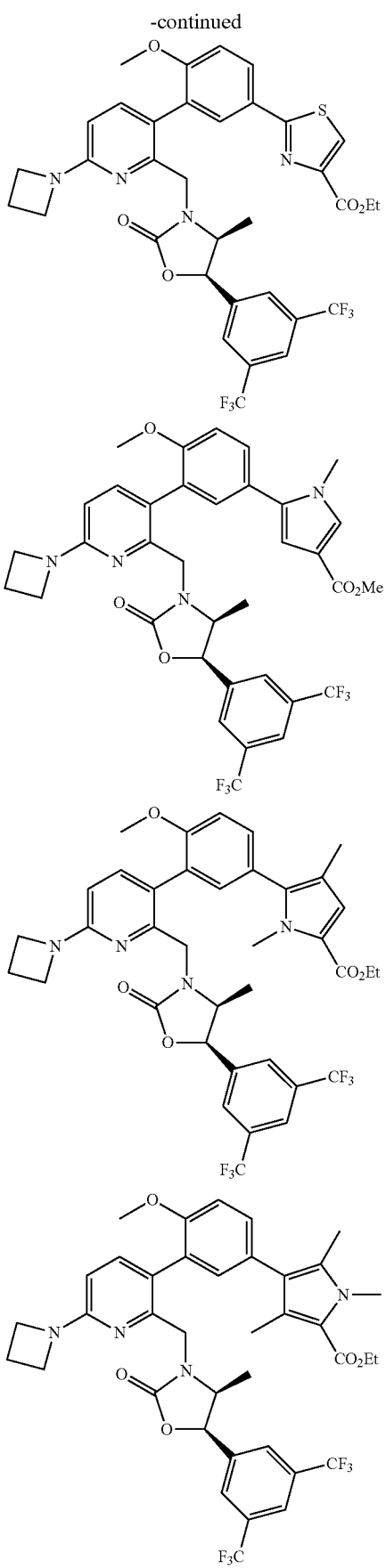
338
-continued
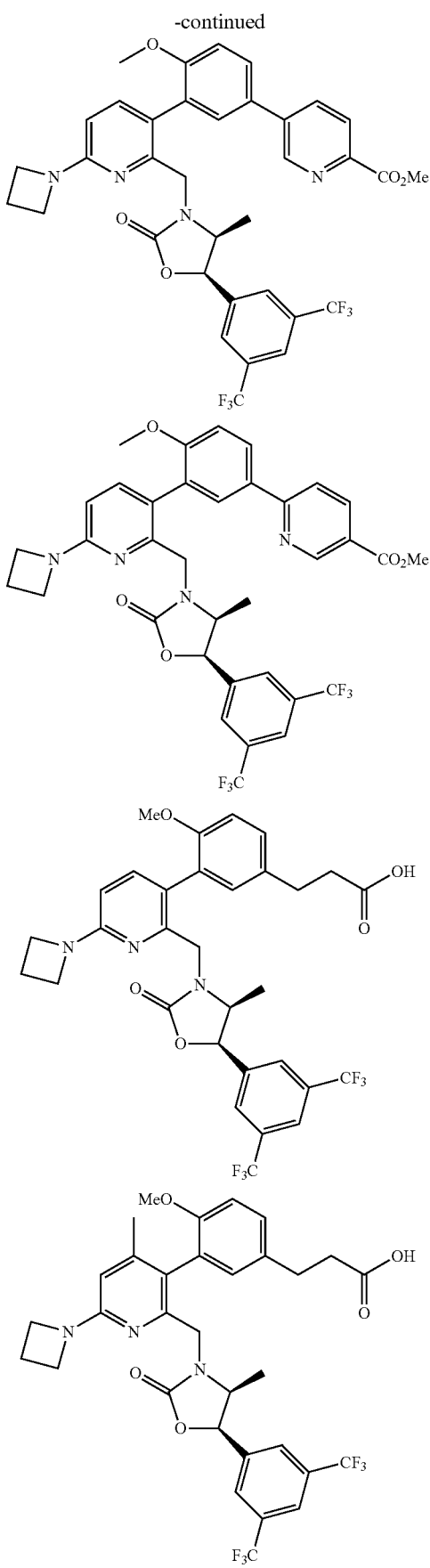

339
-continued
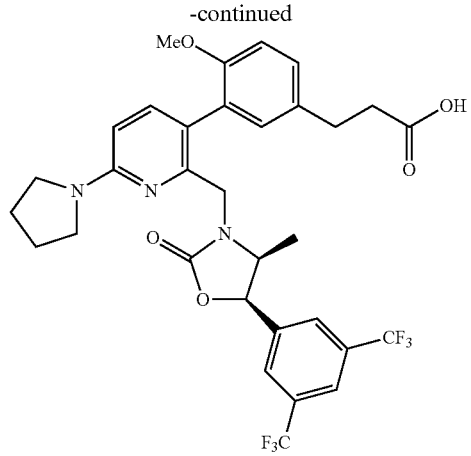
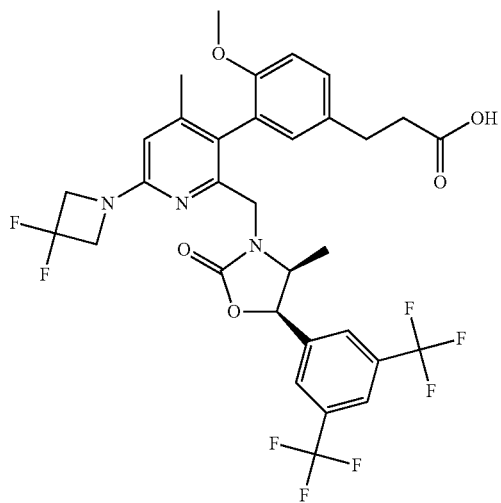
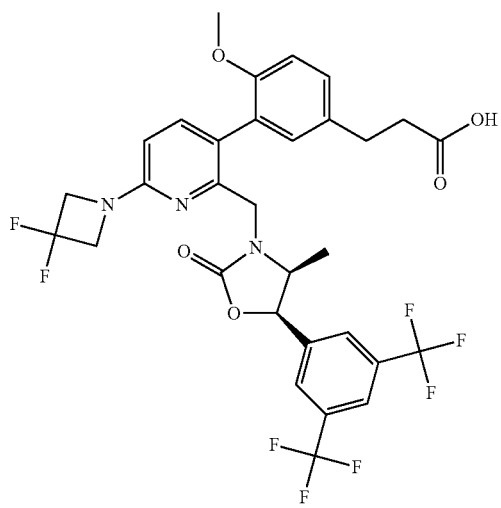
340
-continued
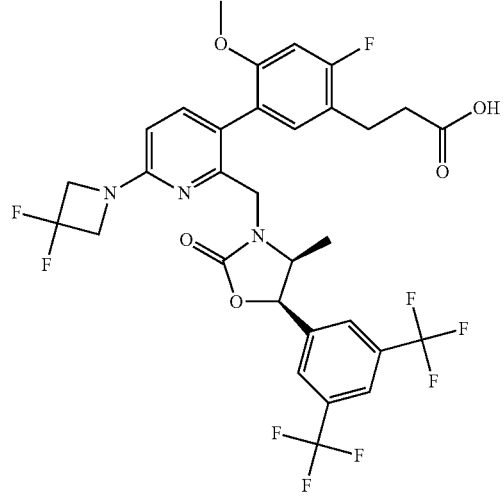
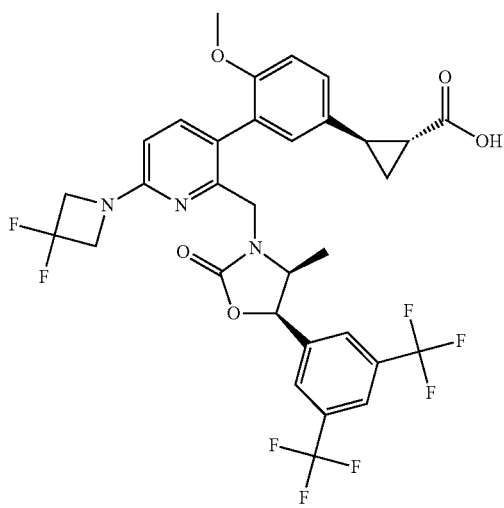
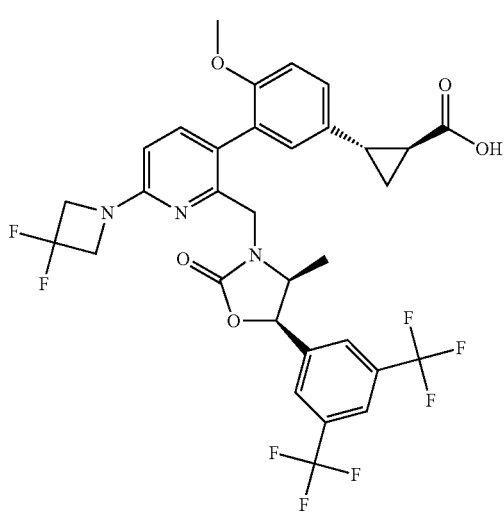

341
-continued
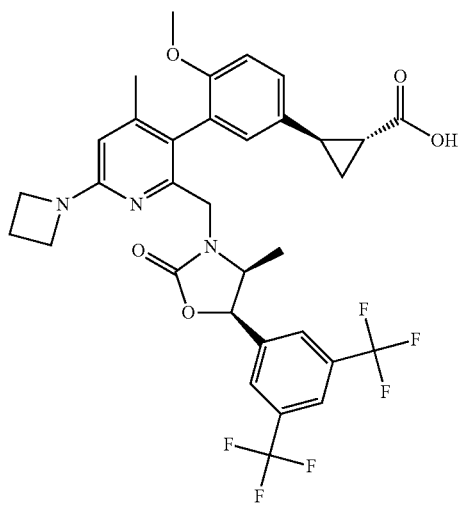
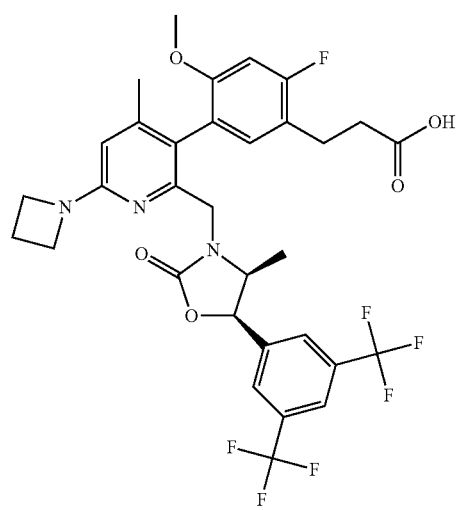
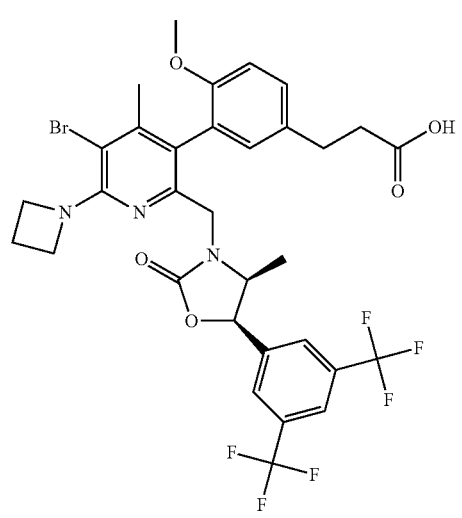
342
-continued
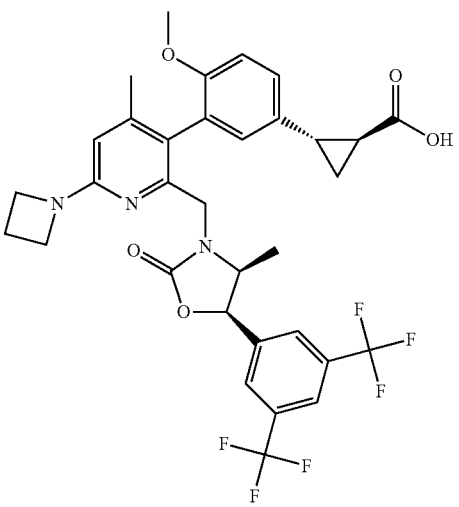
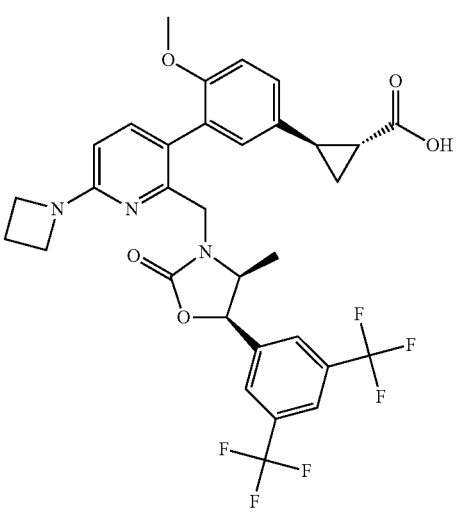
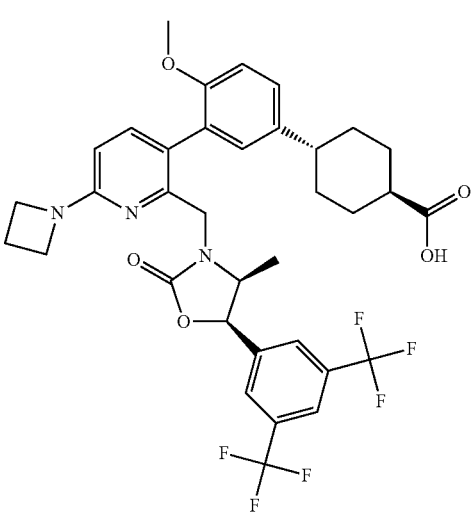

343
-continued
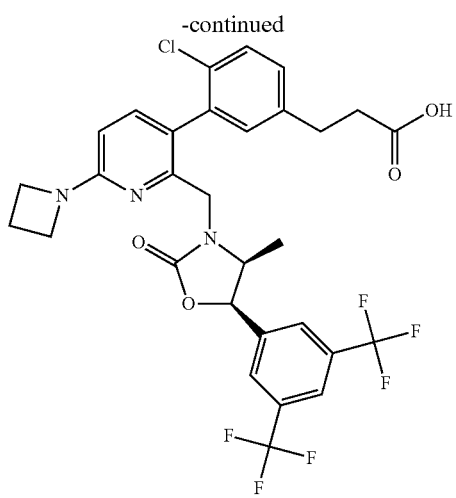
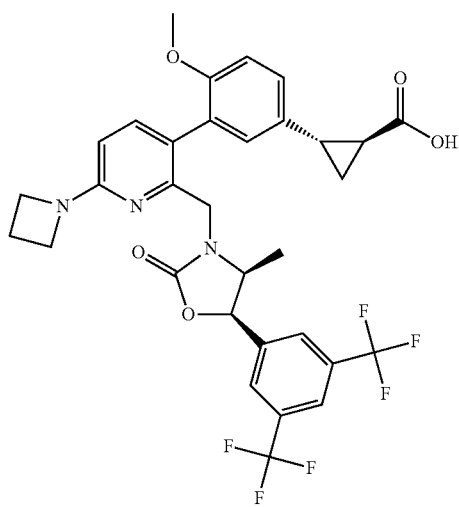
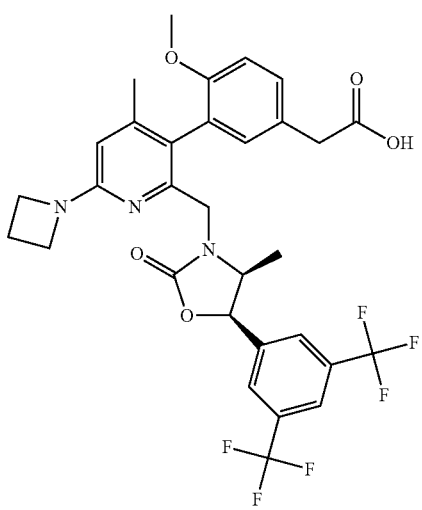
344
-continued
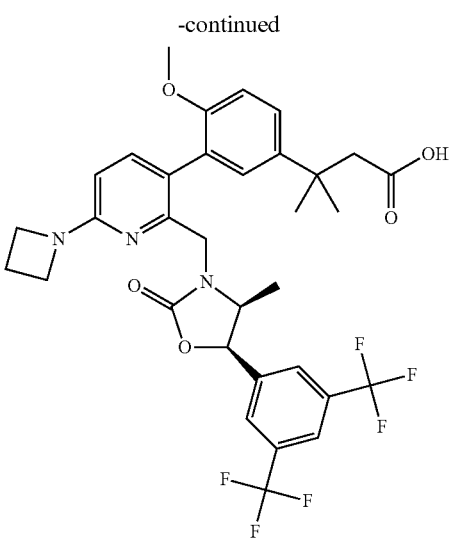
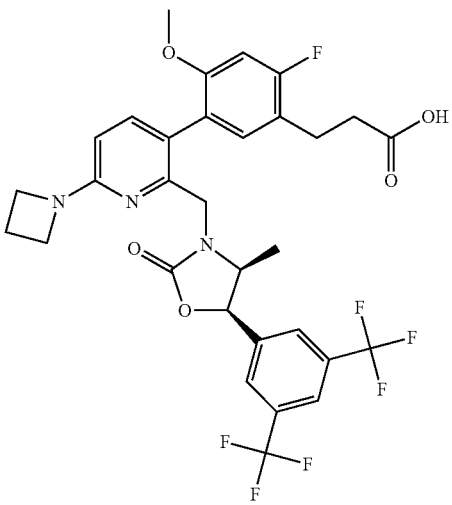
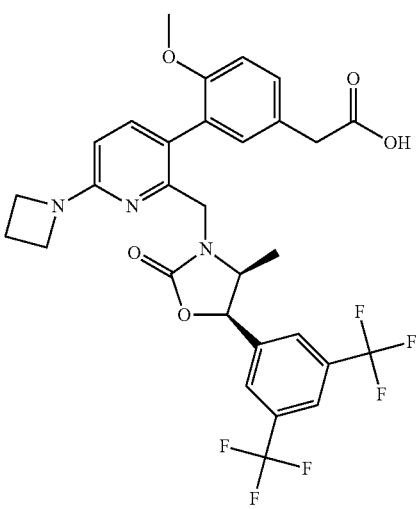

345
-continued
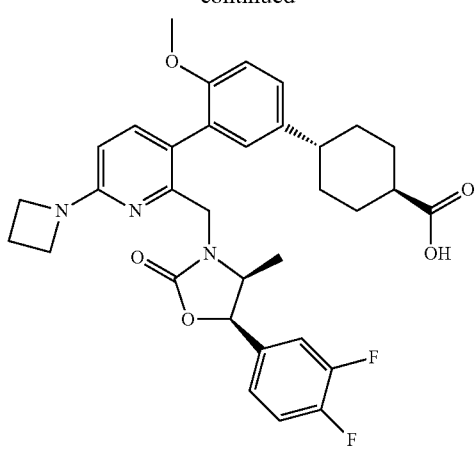
346
-continued
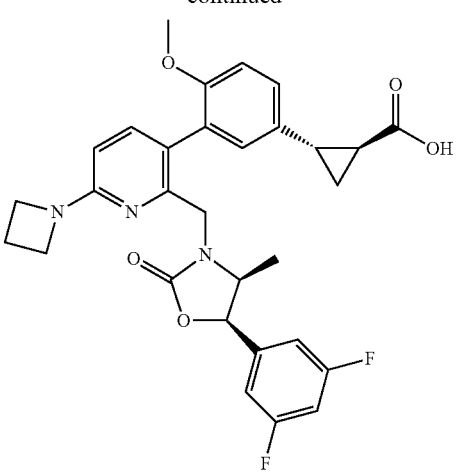
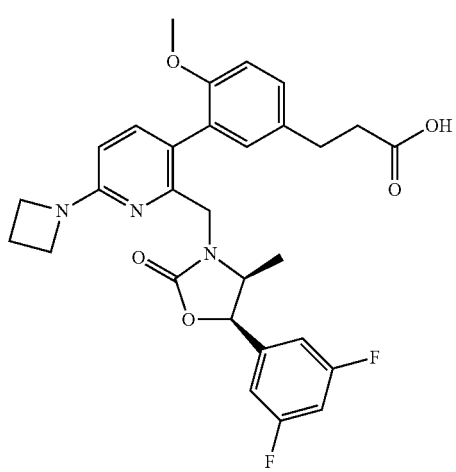
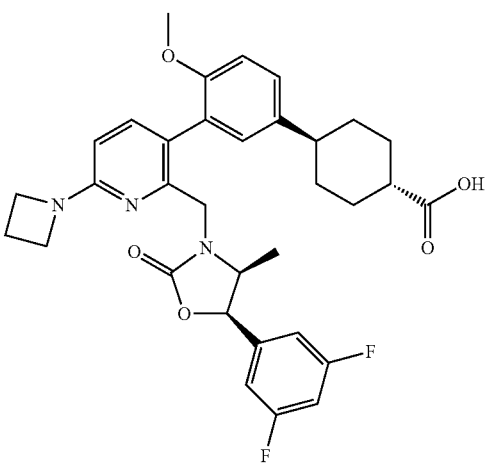
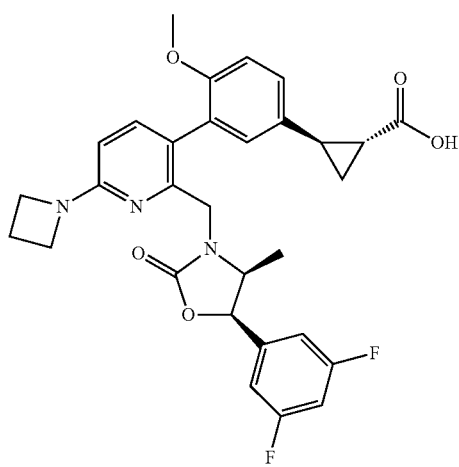
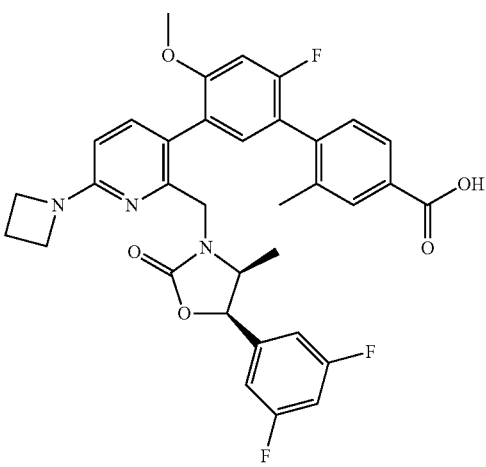

347
-continued
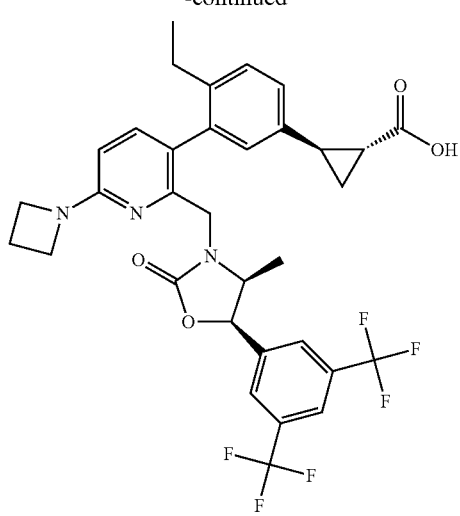
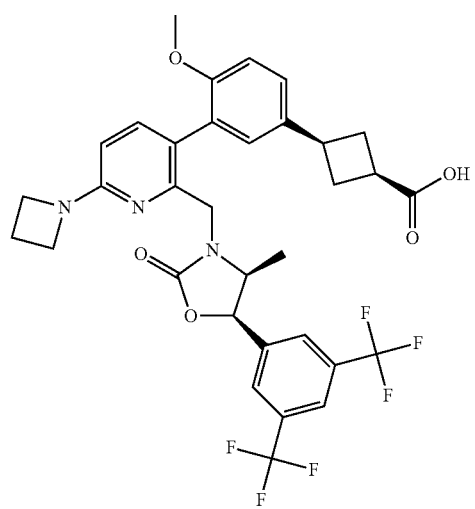
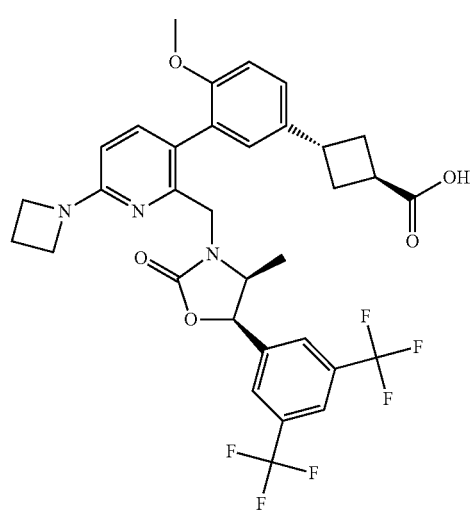
348
-continued
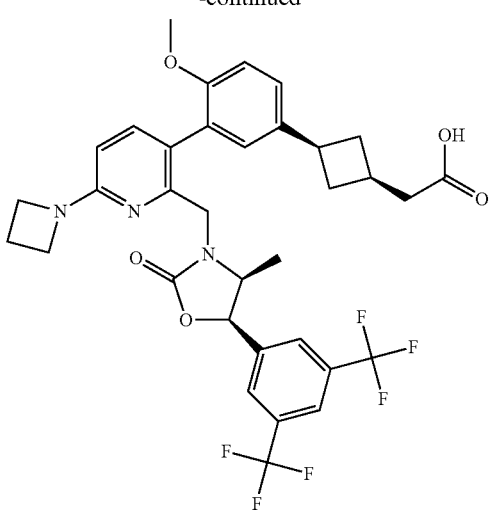
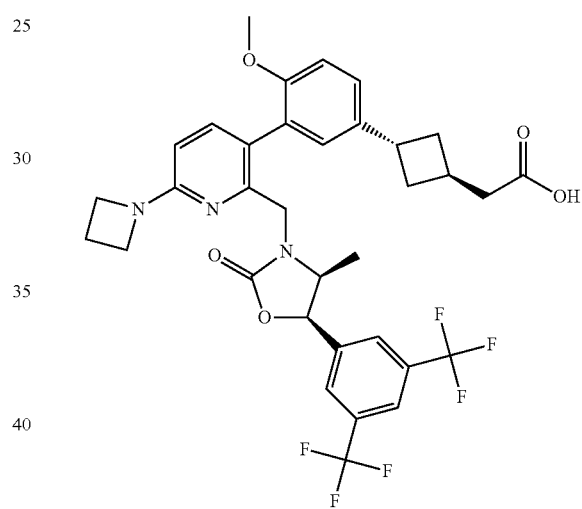
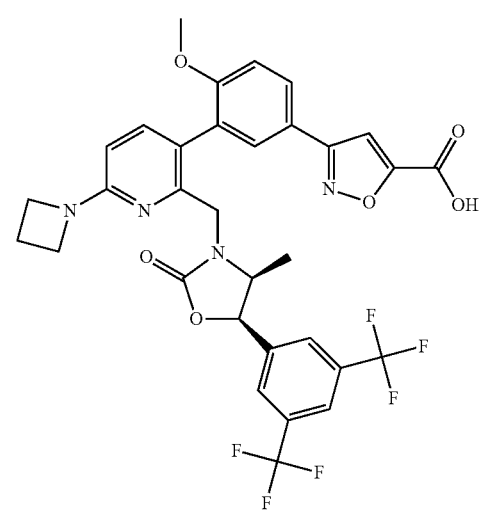

349
-continued
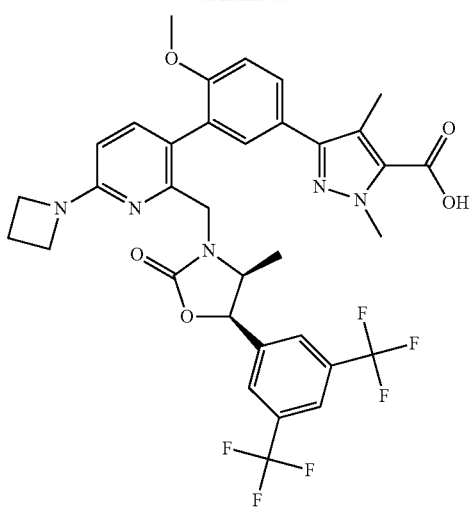
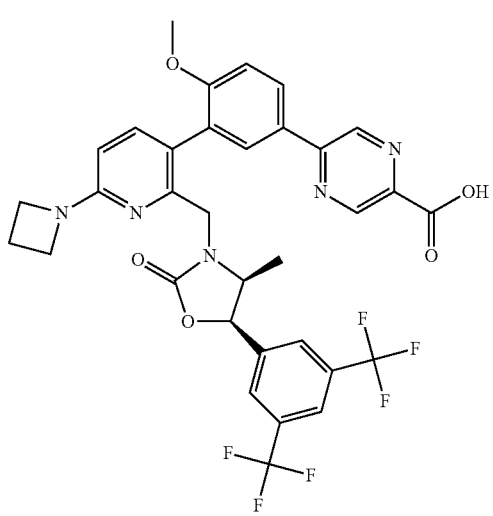
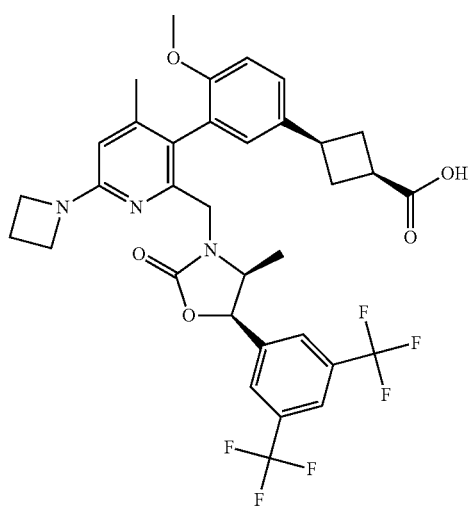
350
-continued
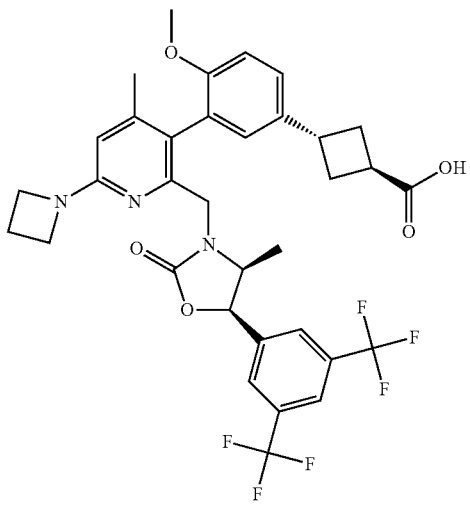
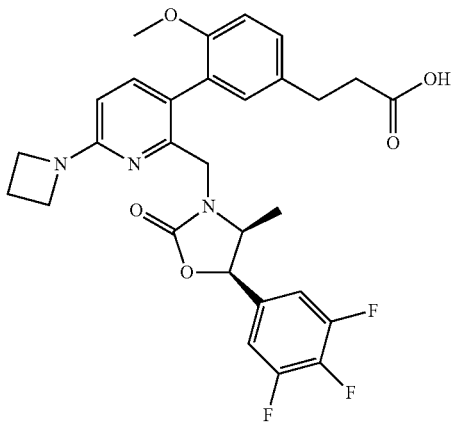
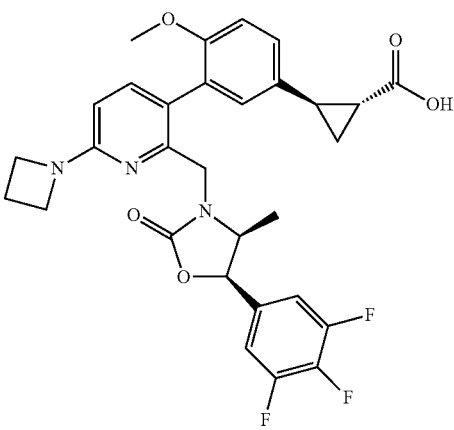

351
-continued
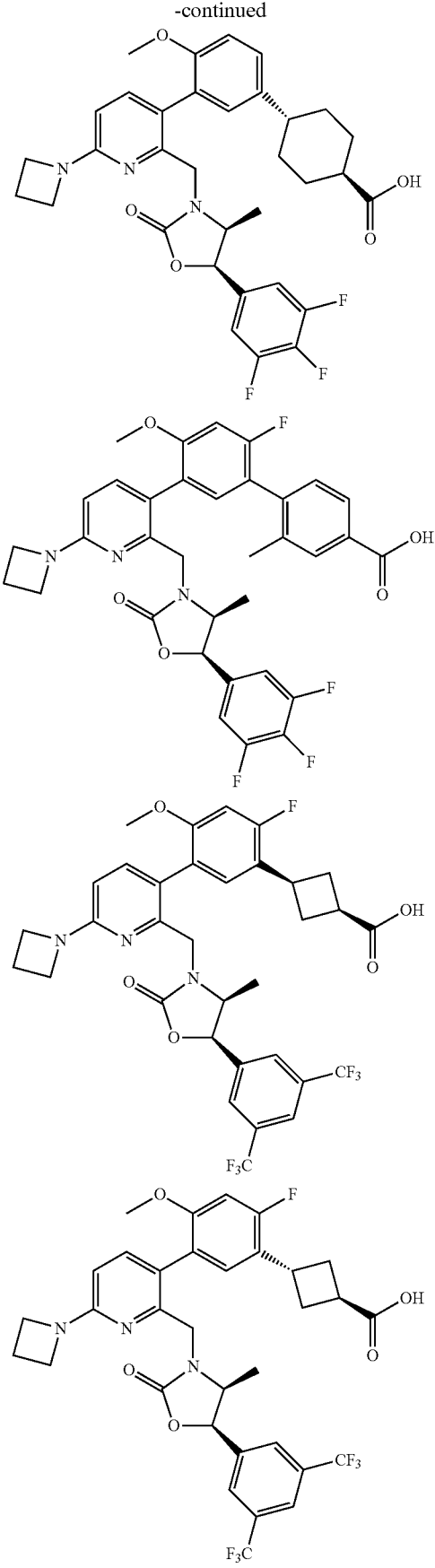
352
-continued
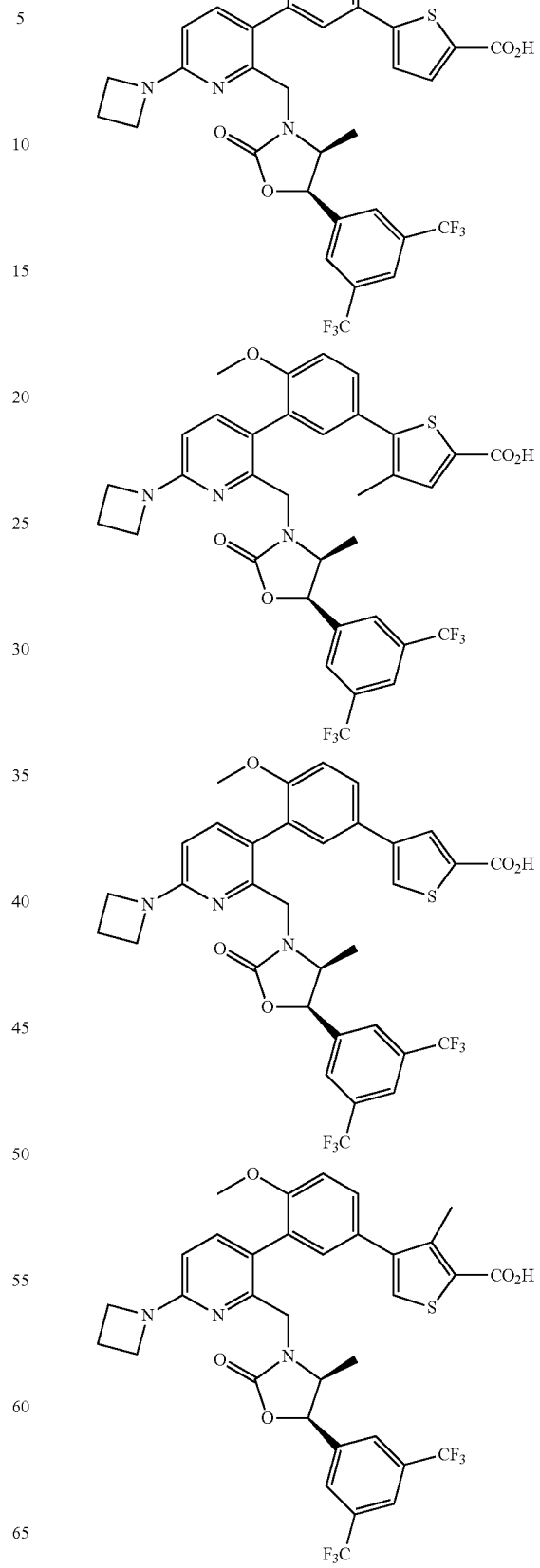

353
-continued
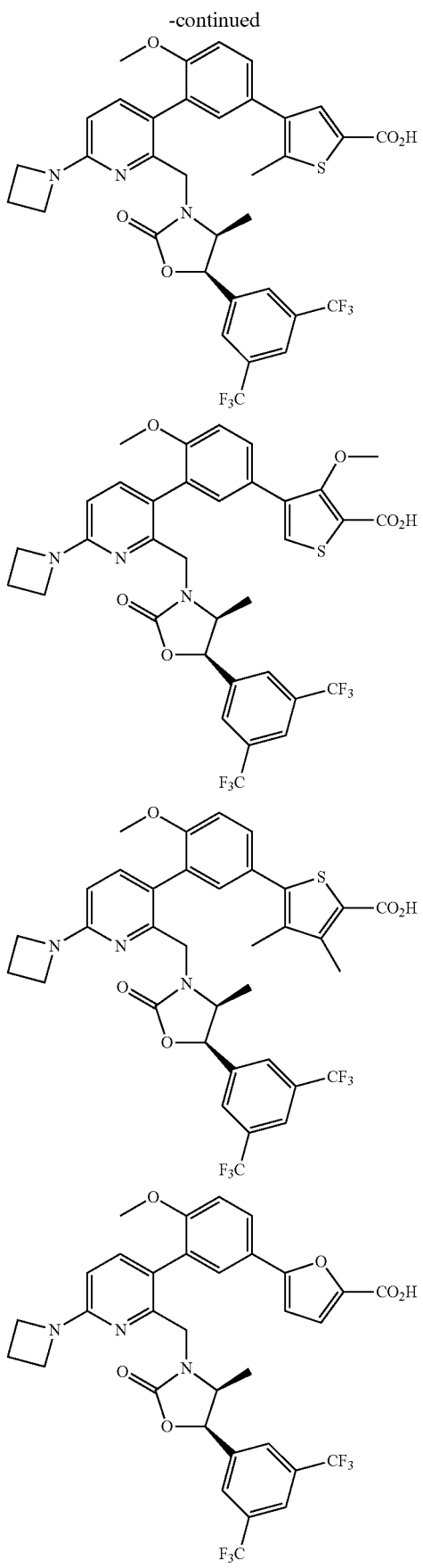
354
-continued
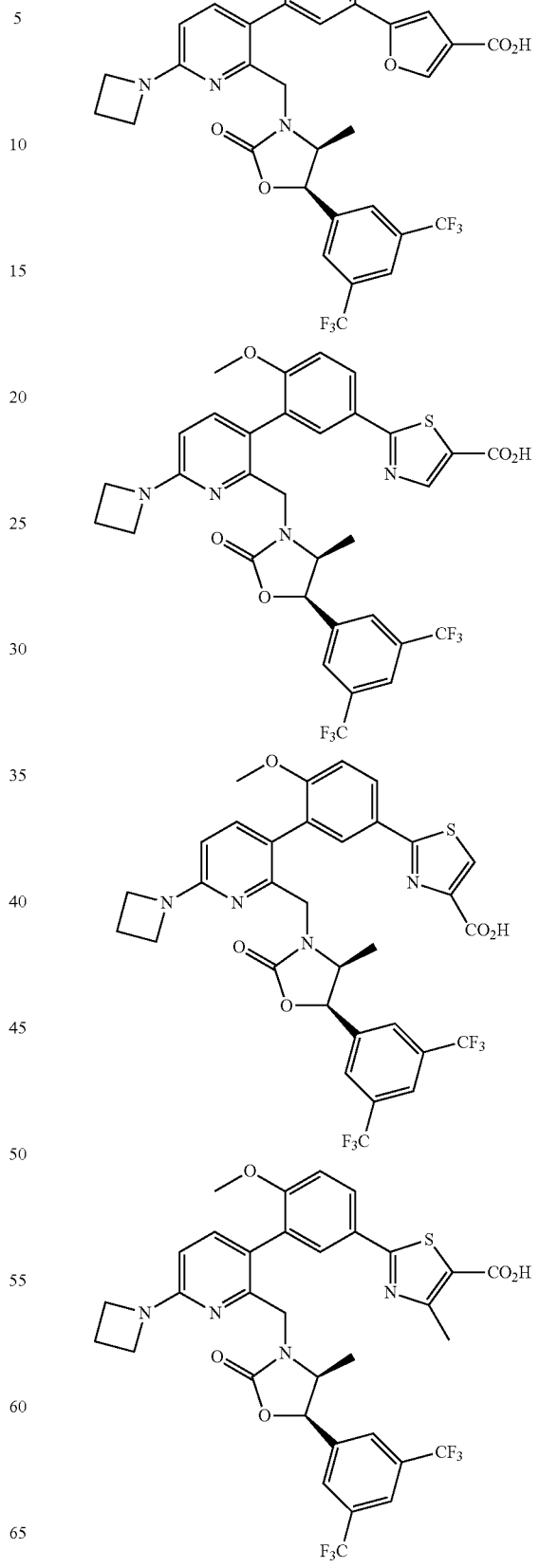

355
-continued
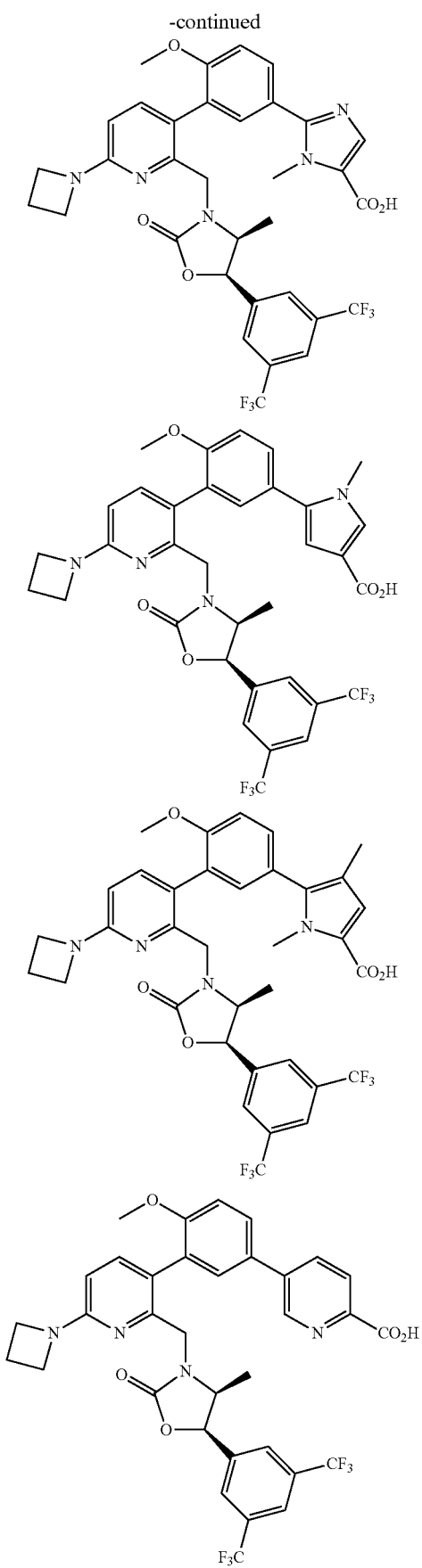
356
-continued
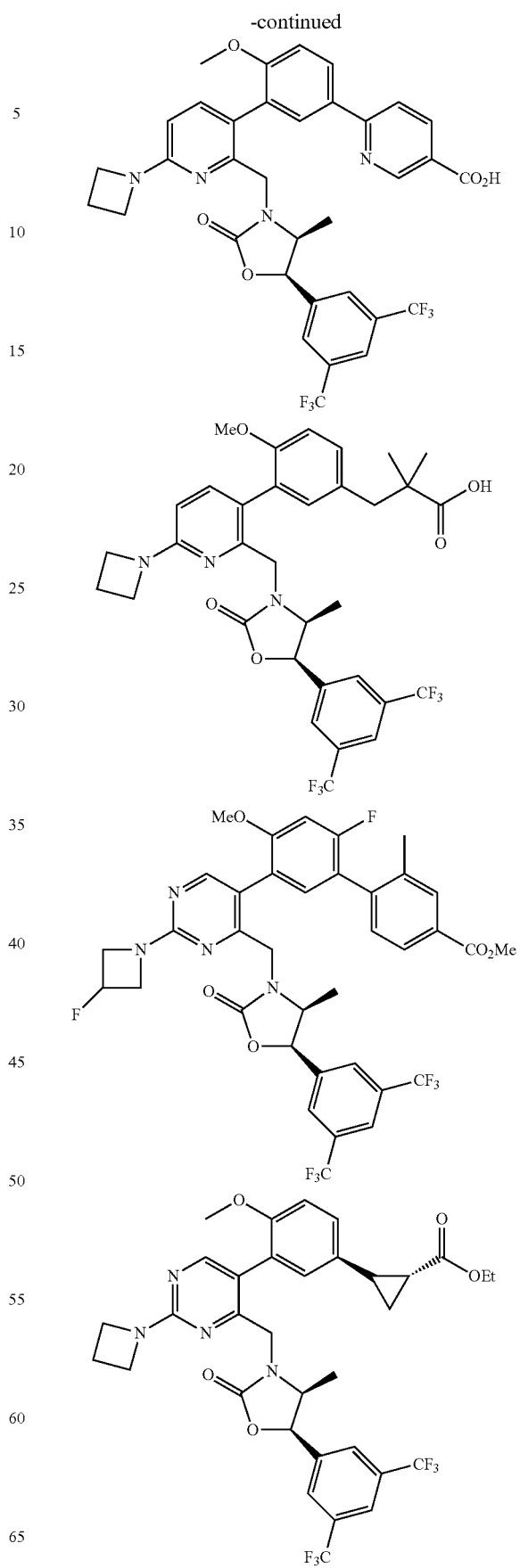

357
-continued
358
-continued
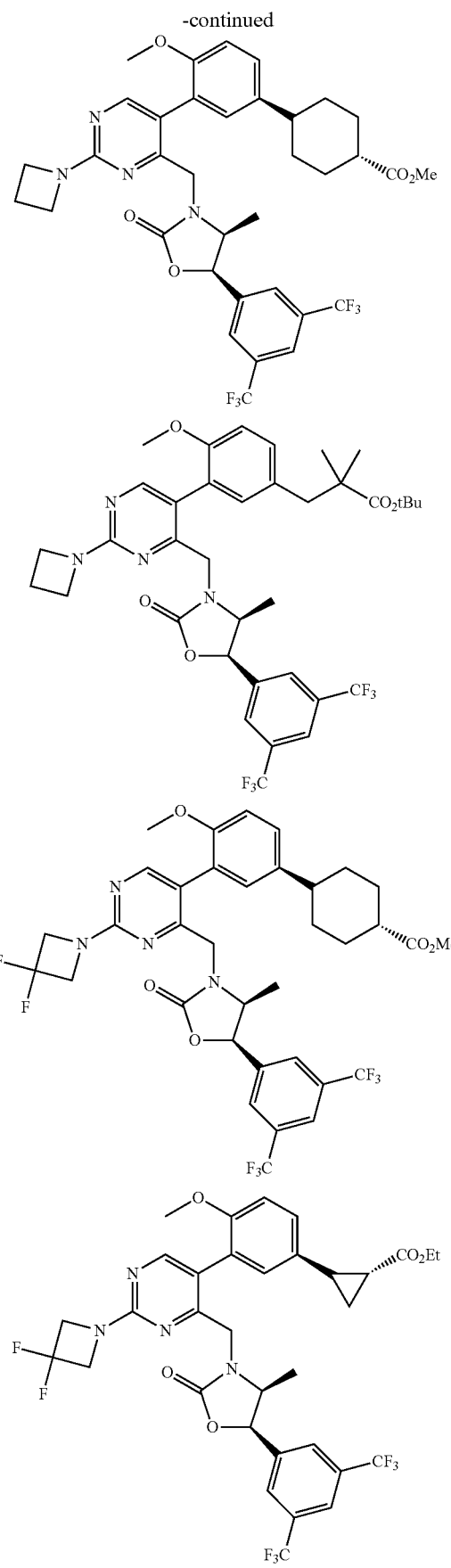
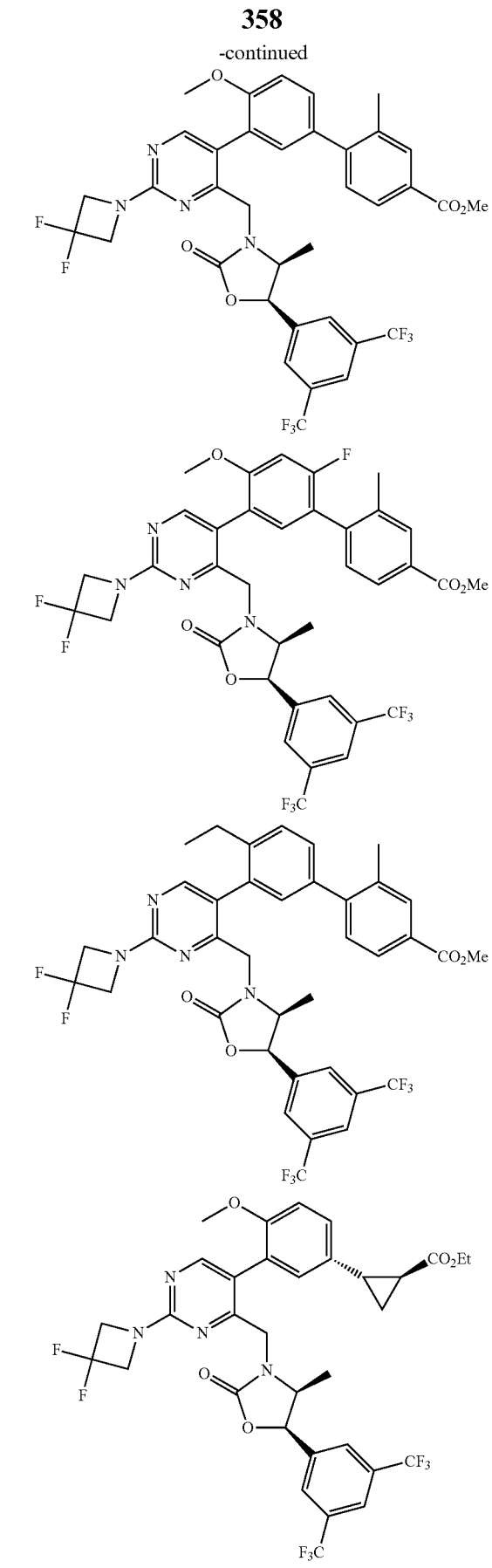

359
-continued
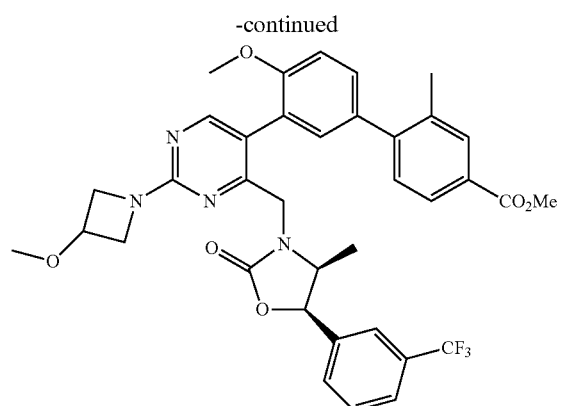
360
-continued
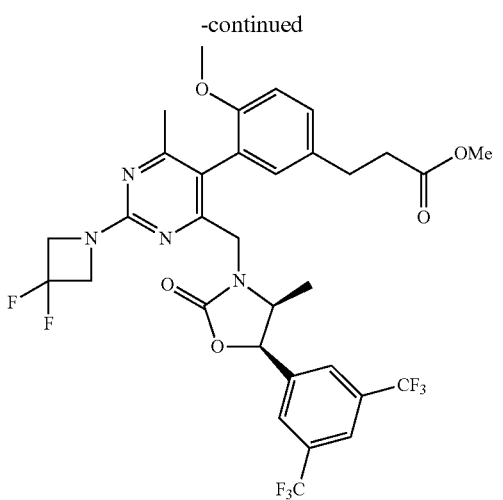
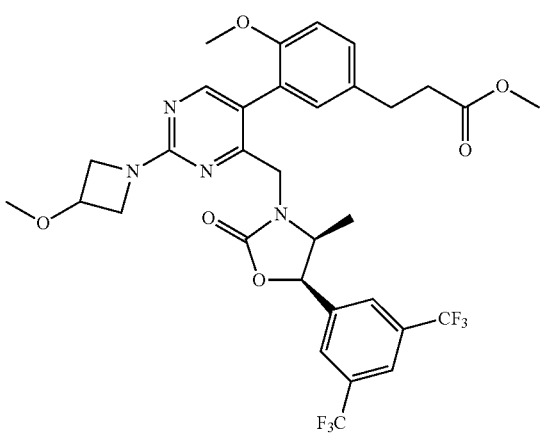
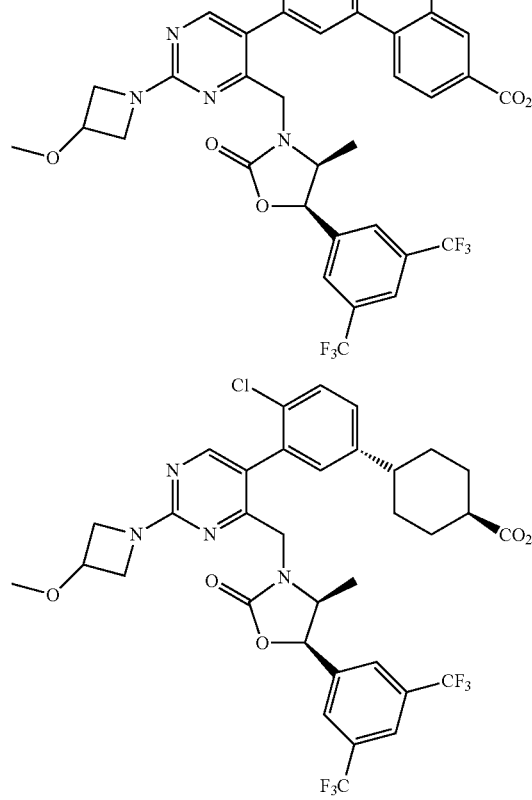
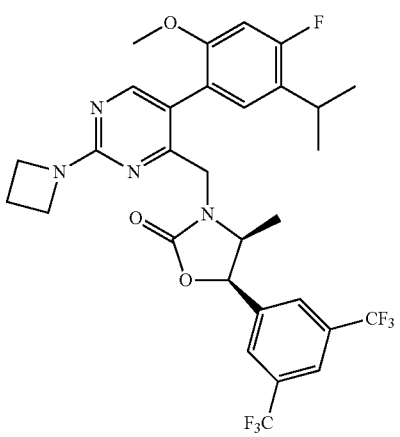

361
-continued
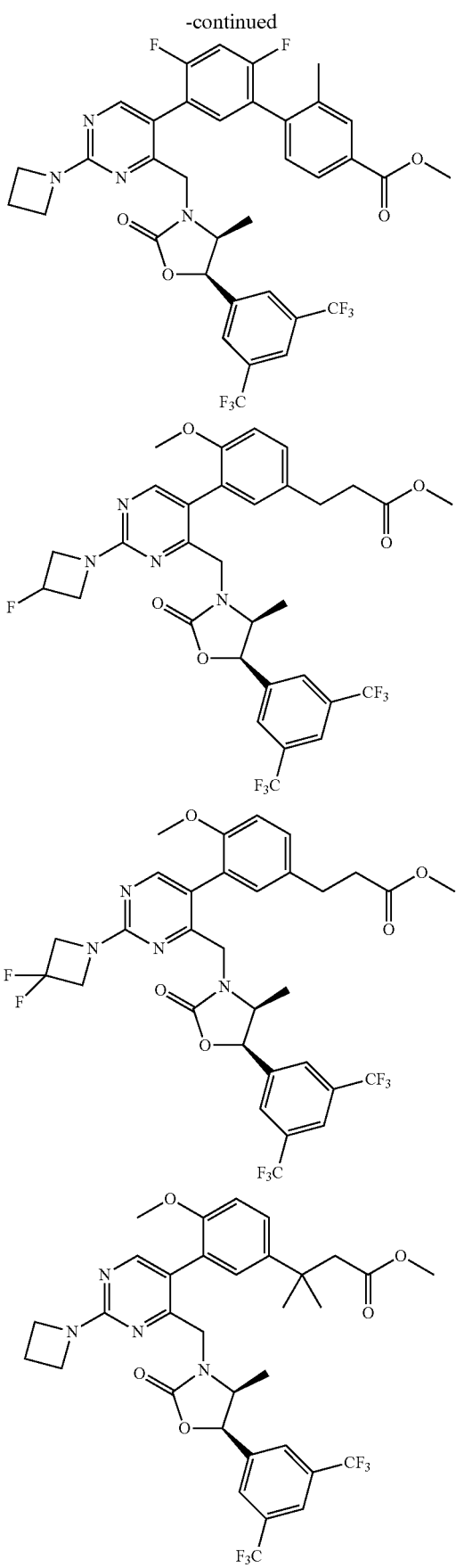
362
-continued
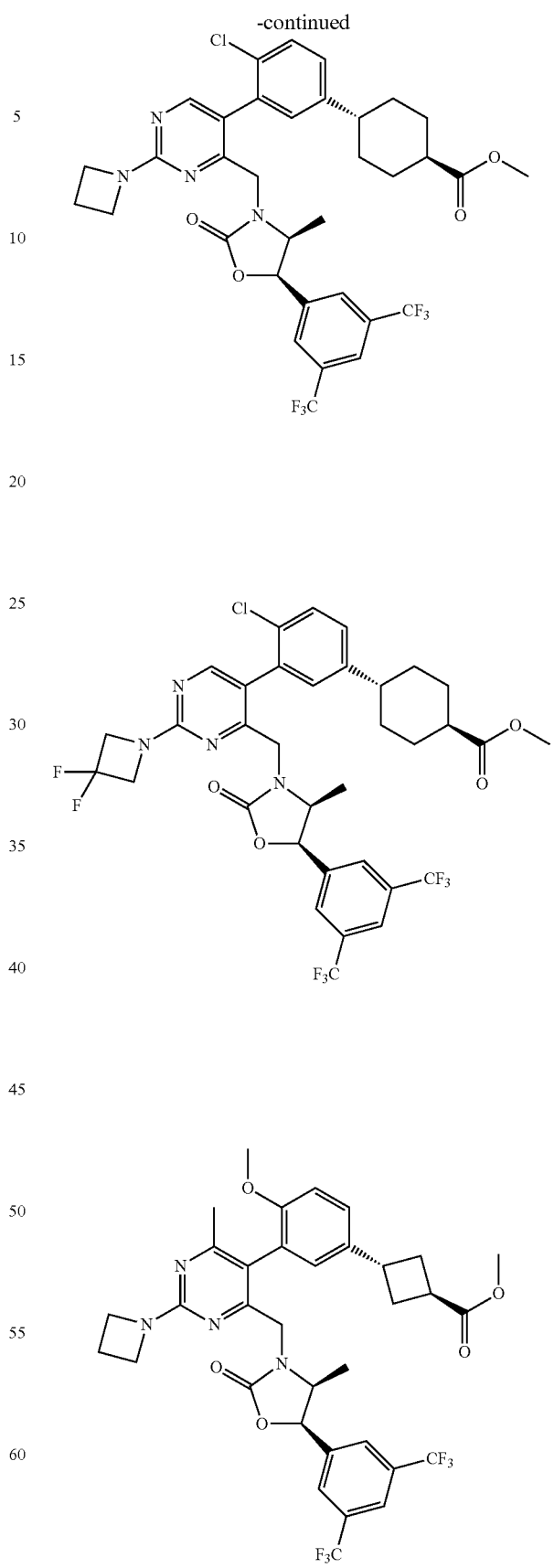
Atropisomers A and B

363
-continued
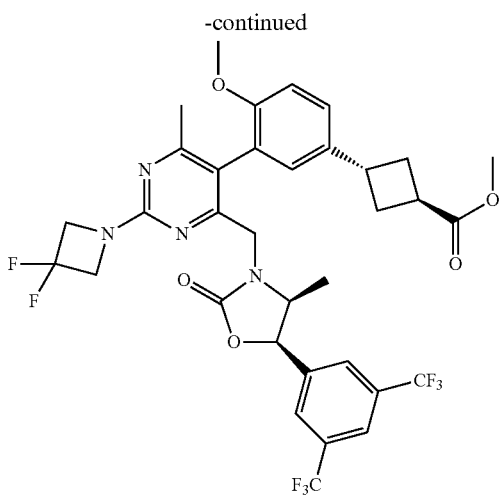
Atropisomers A and B
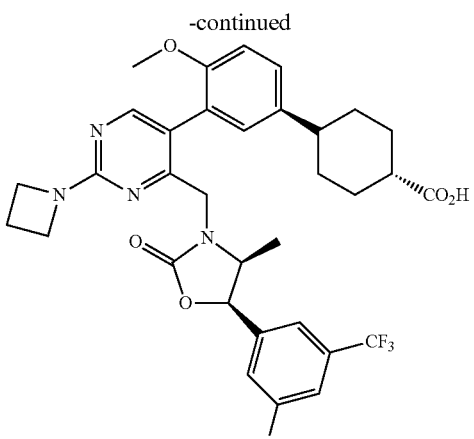
364
-continued
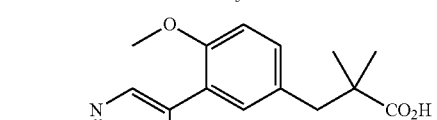
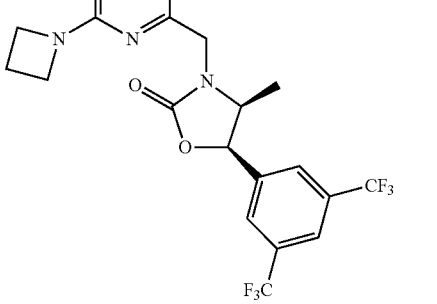
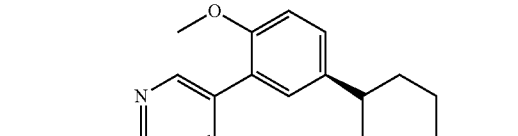
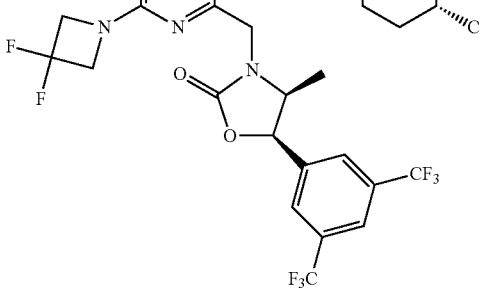
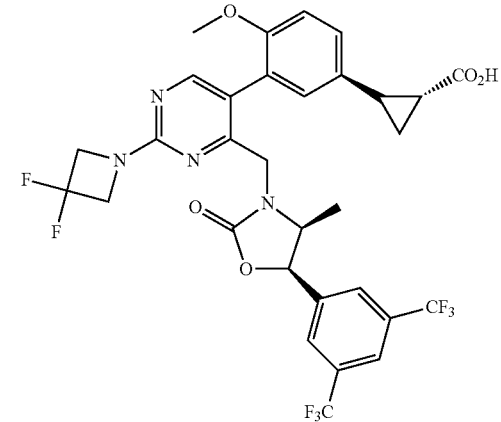

365
-continued
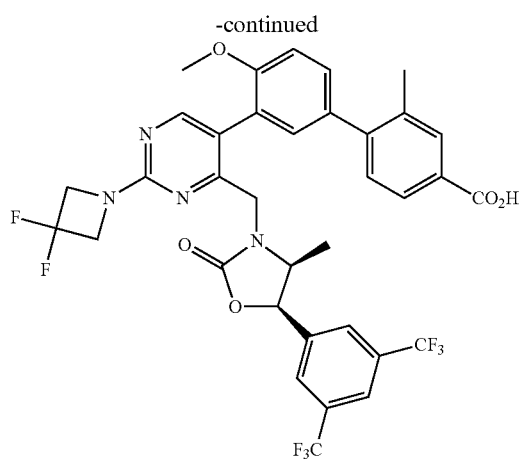
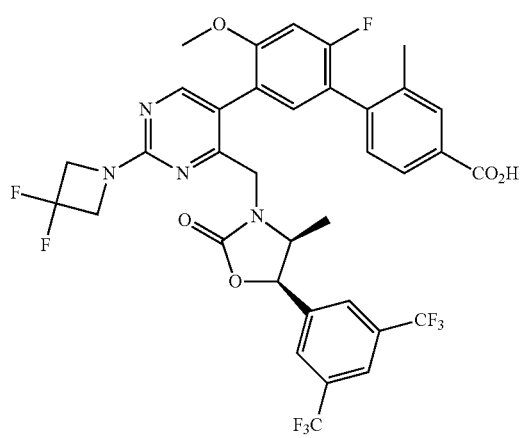
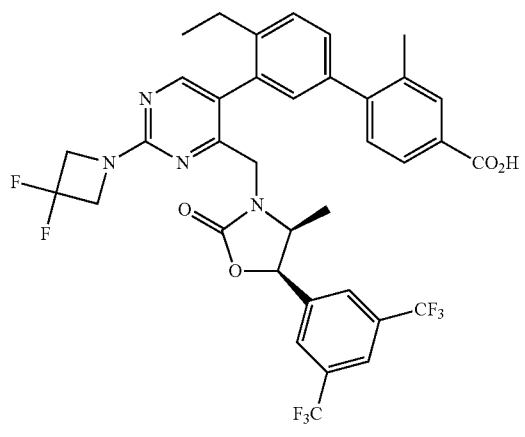
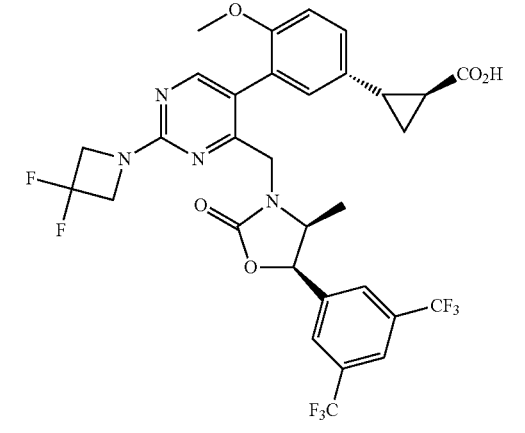
366
-continued
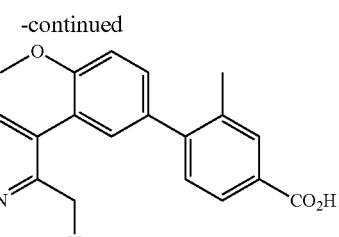
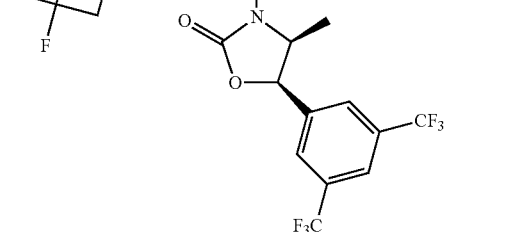
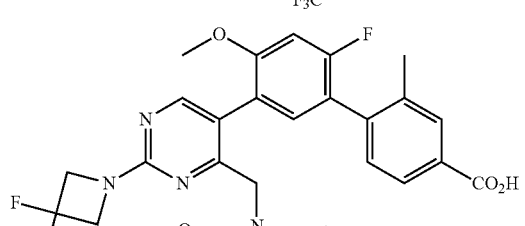
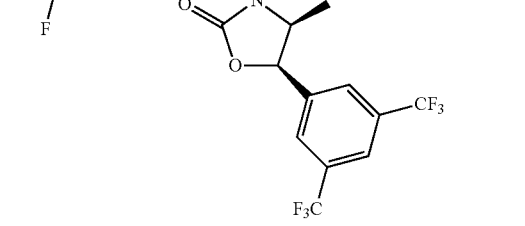

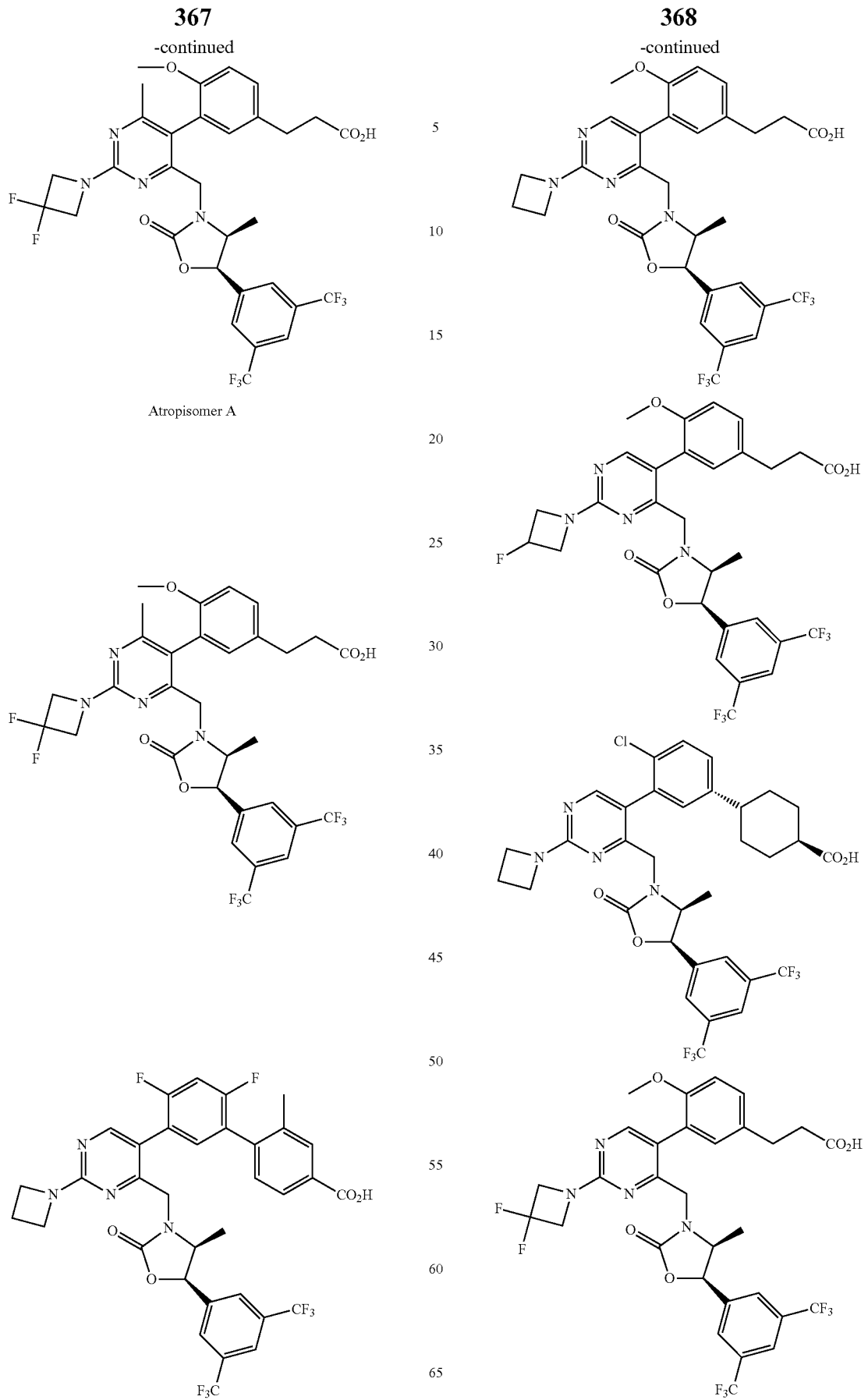

369
-continued
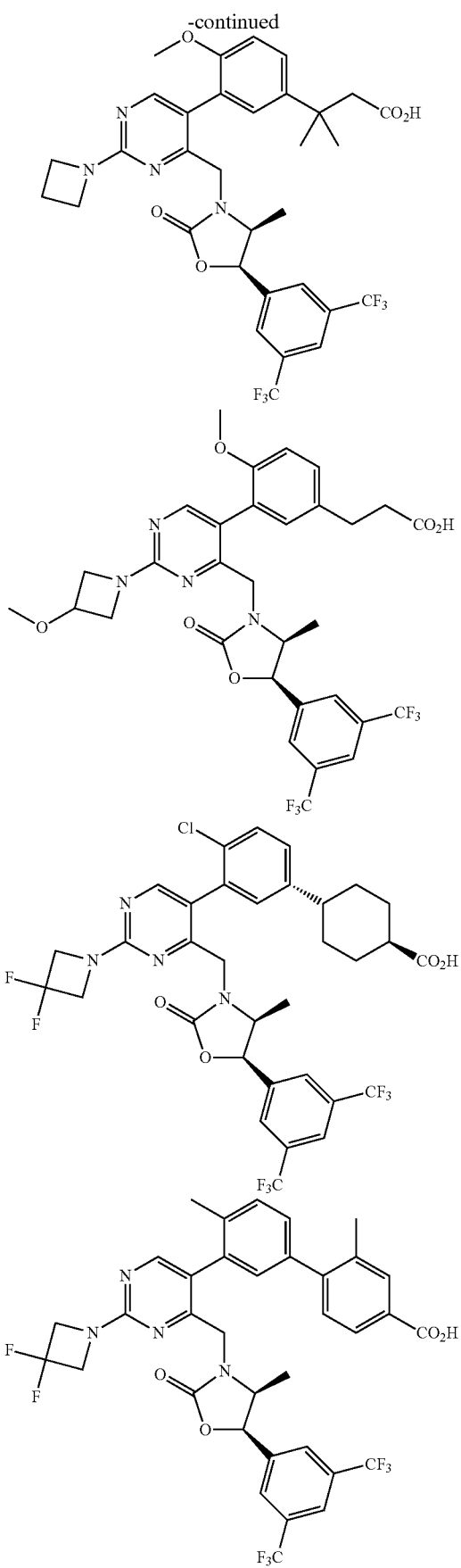
370
-continued
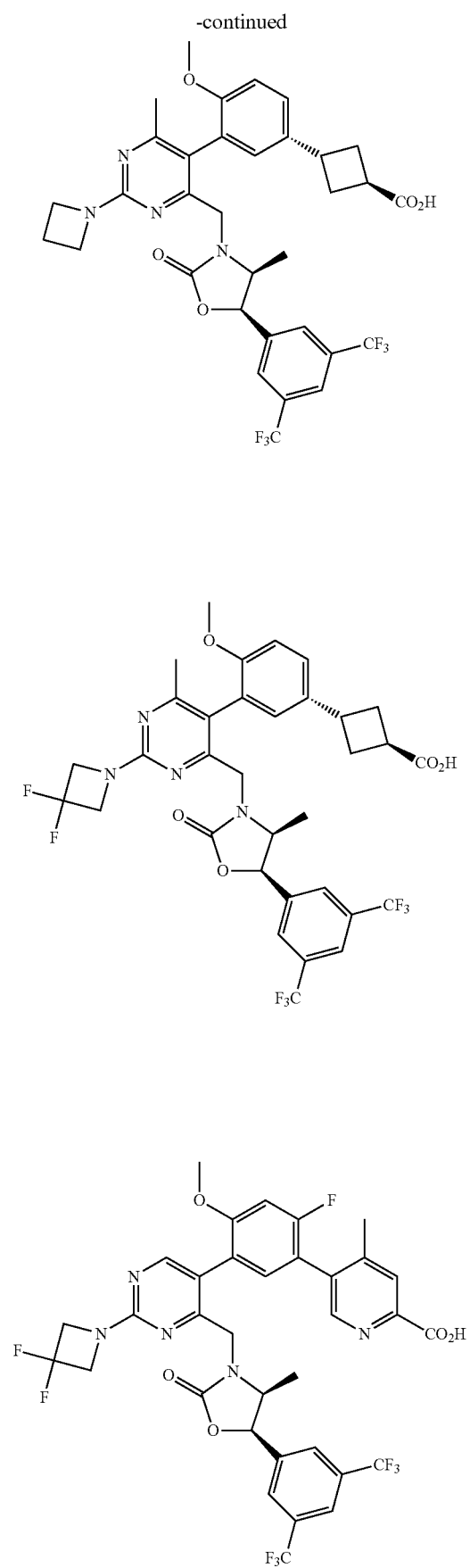

371
-continued
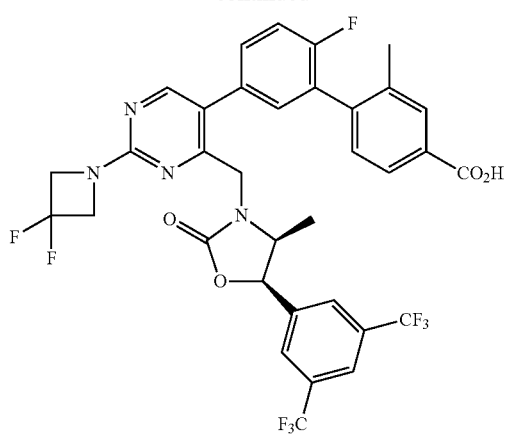
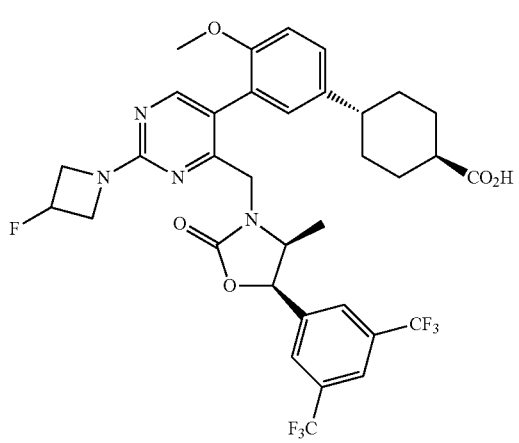
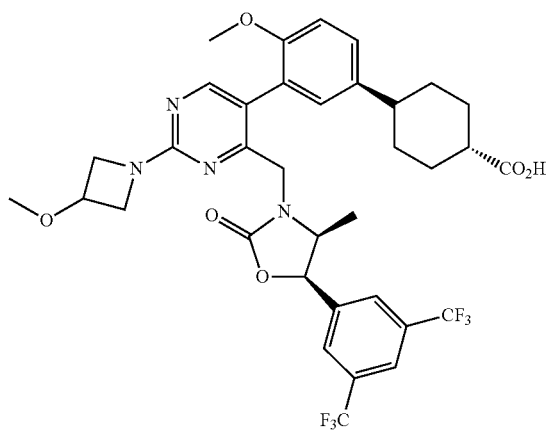
372
-continued
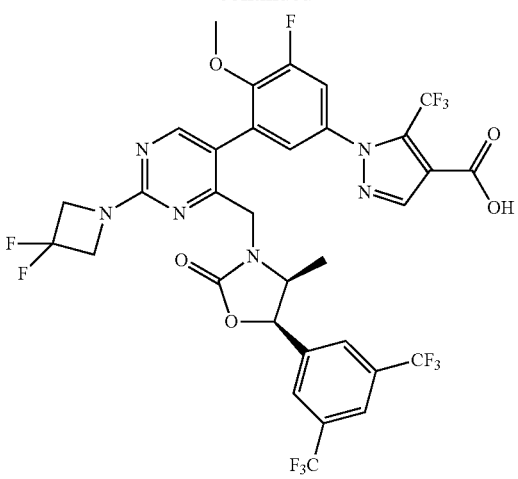
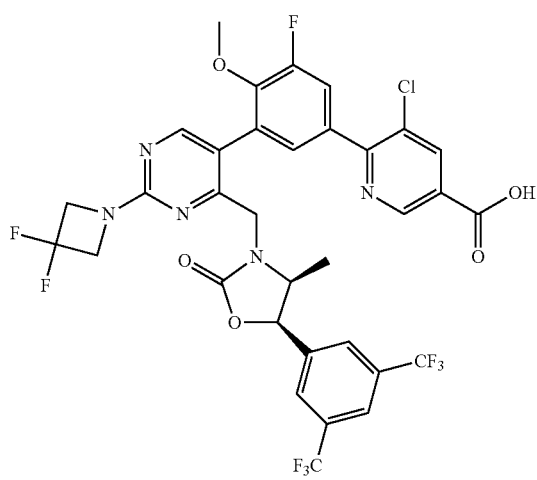
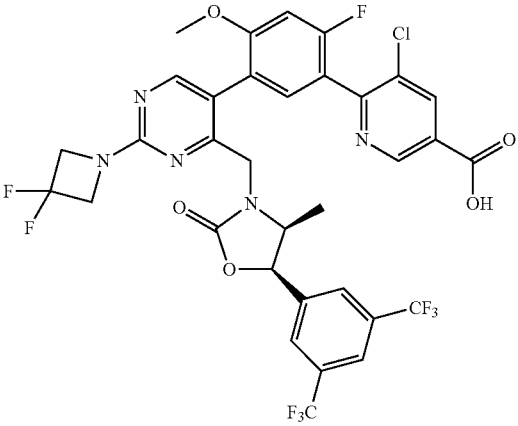

373
-continued
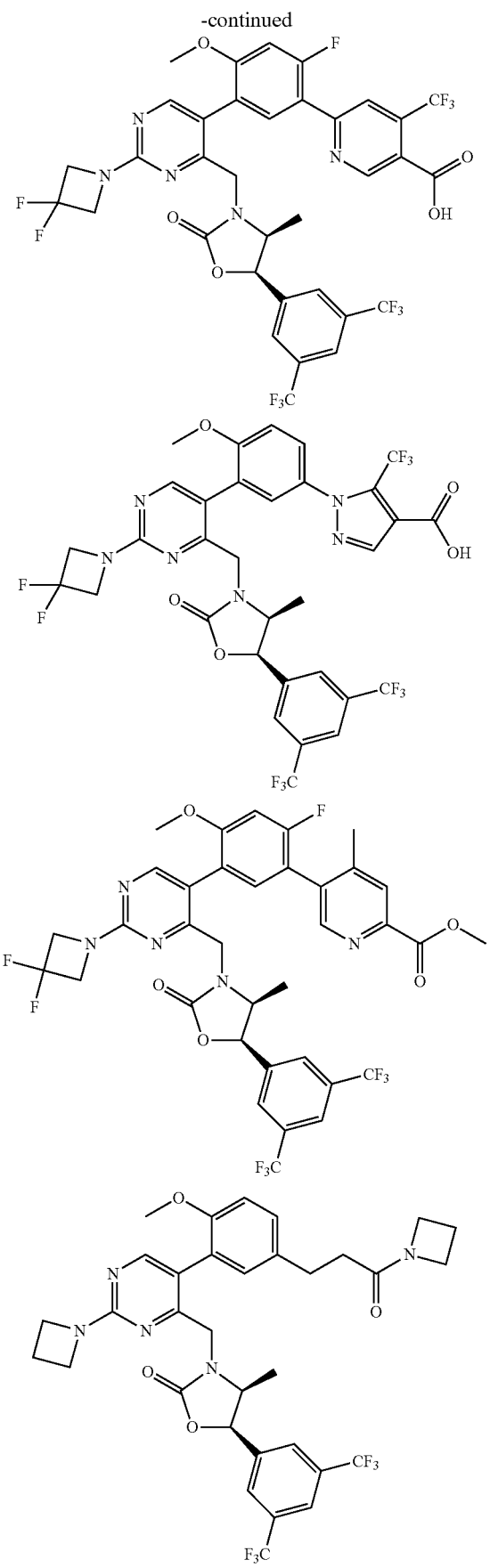
374
-continued
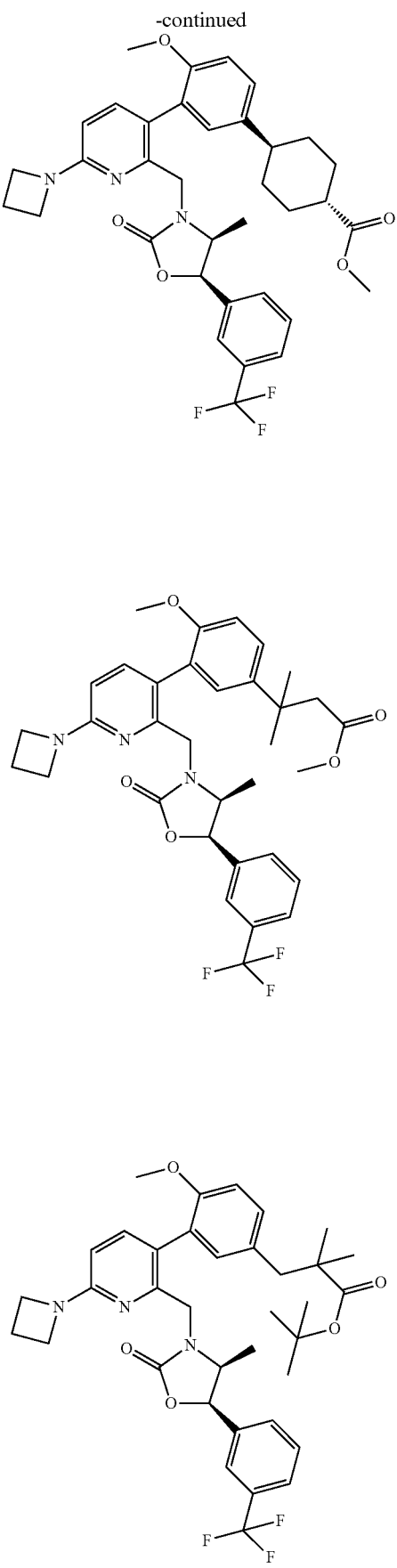

375
-continued
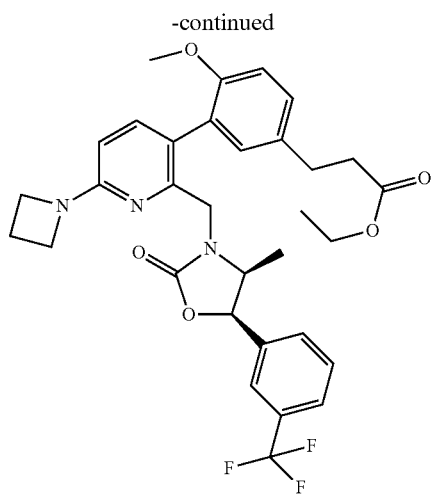
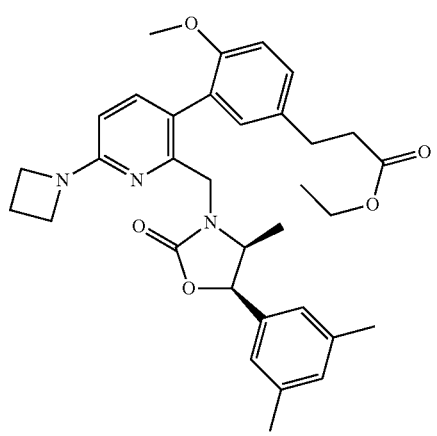
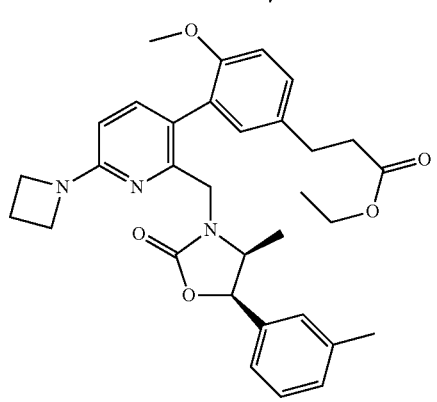
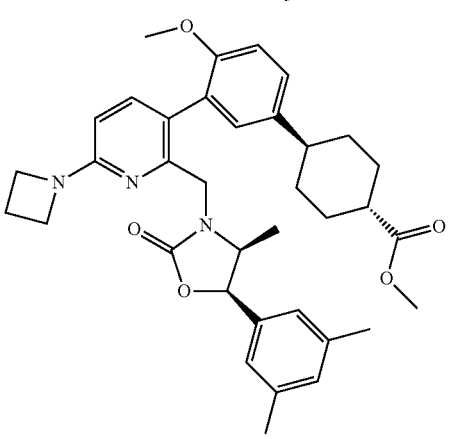
376
-continued
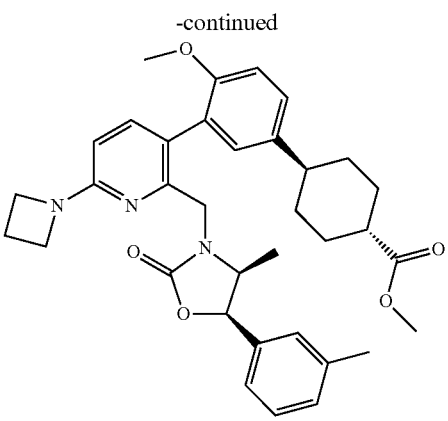
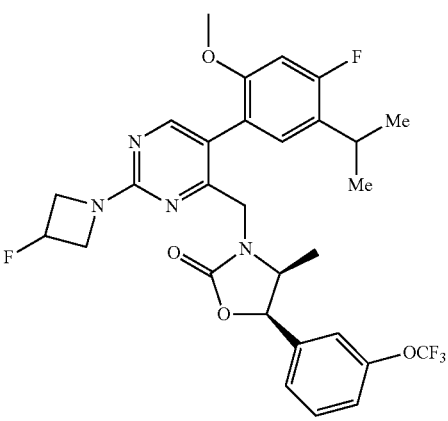
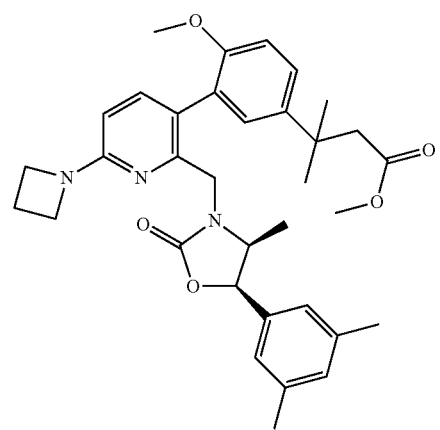
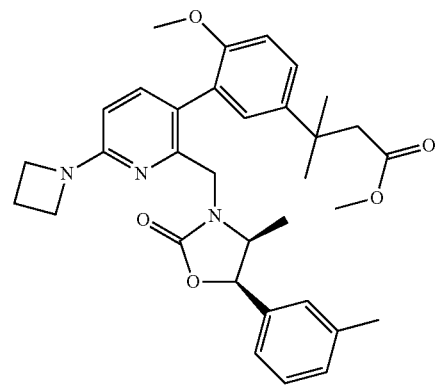

377
-continued
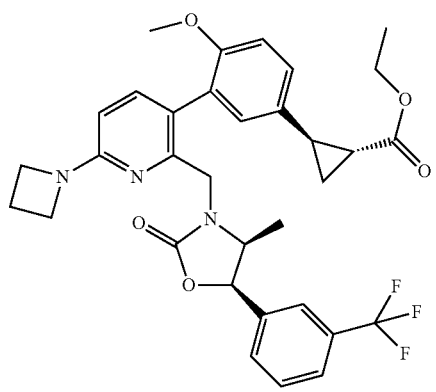
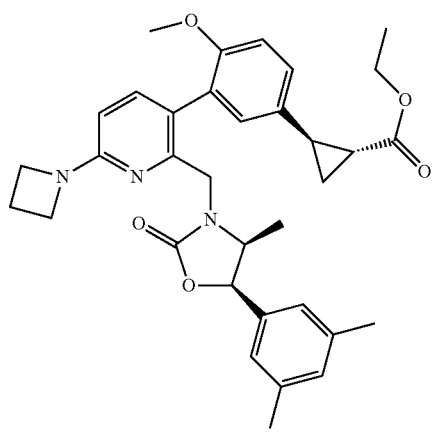
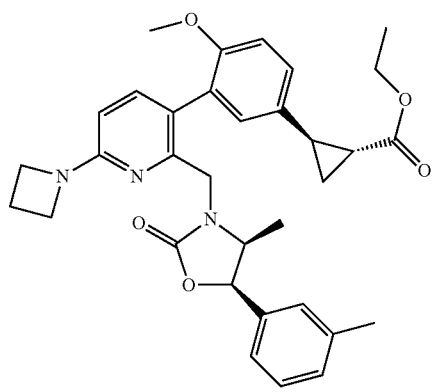
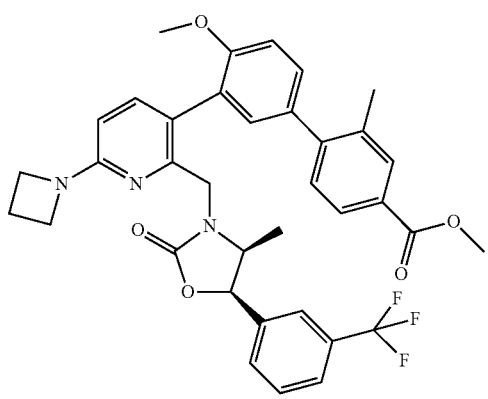
378
-continued
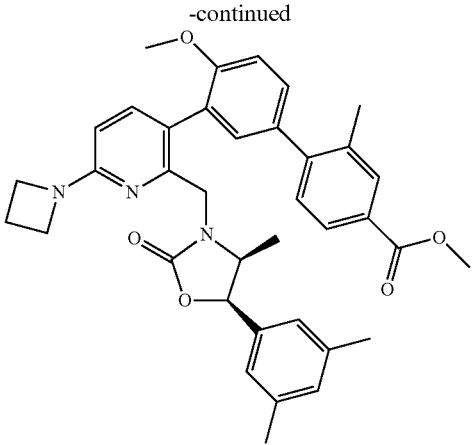
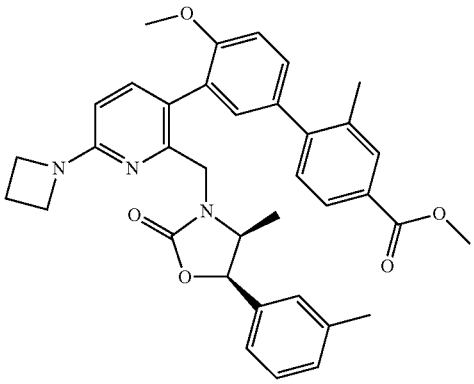
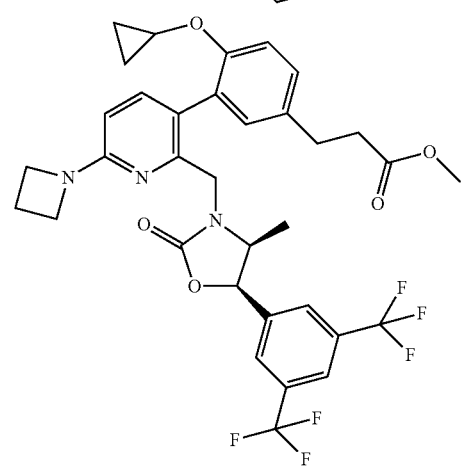
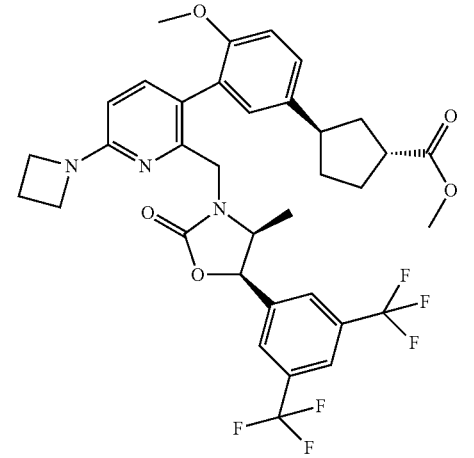

379
-continued
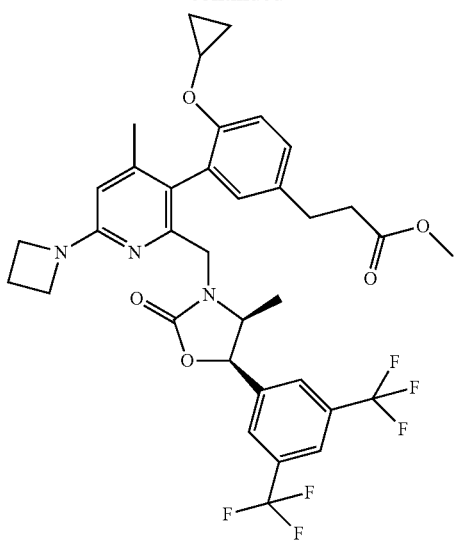
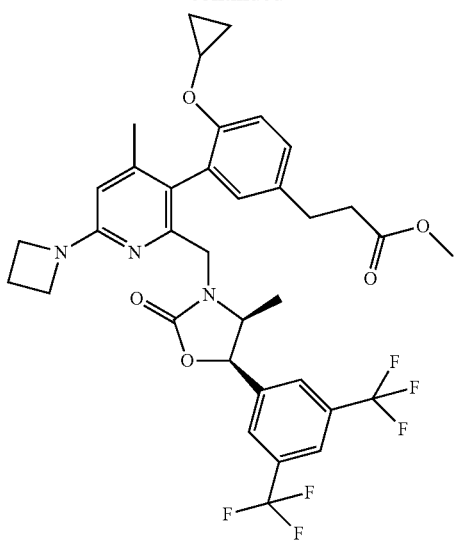
380
-continued
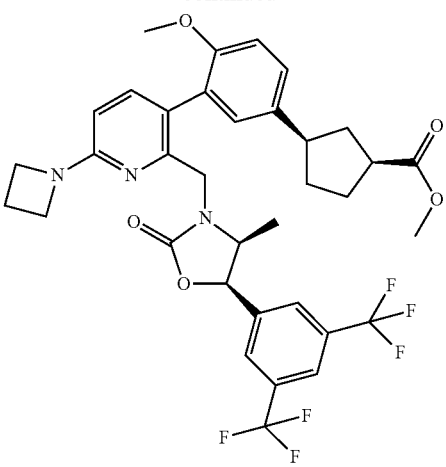
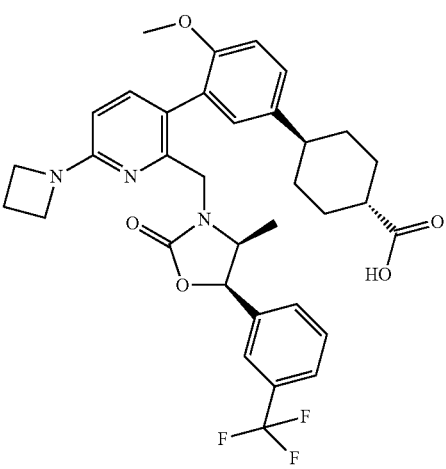
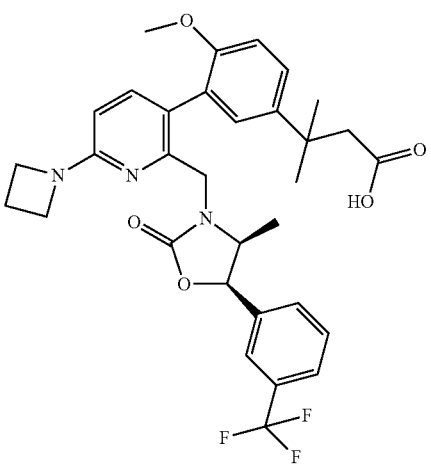

381
-continued
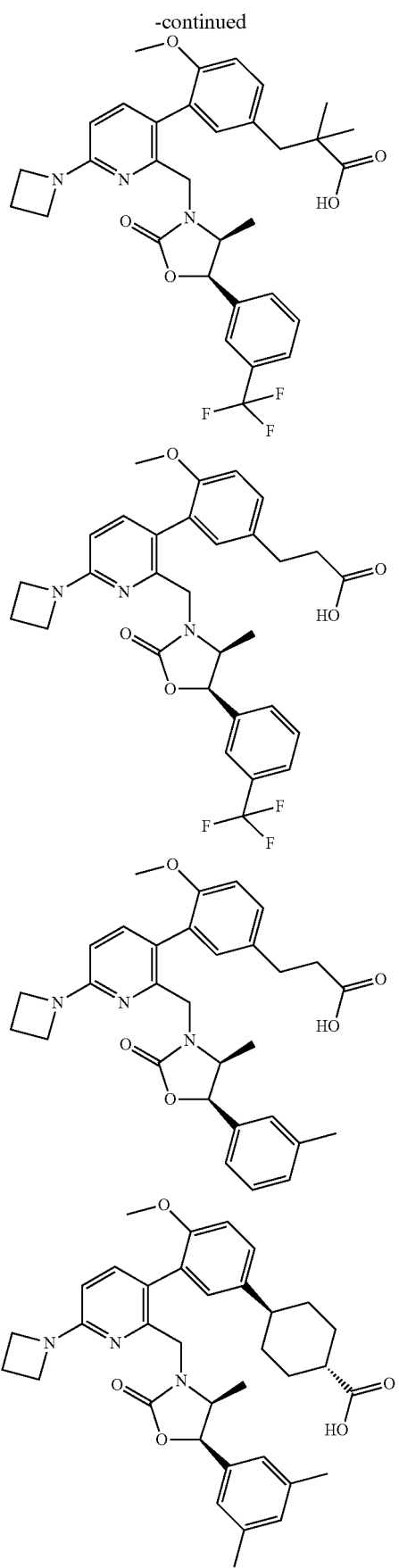
382
-continued
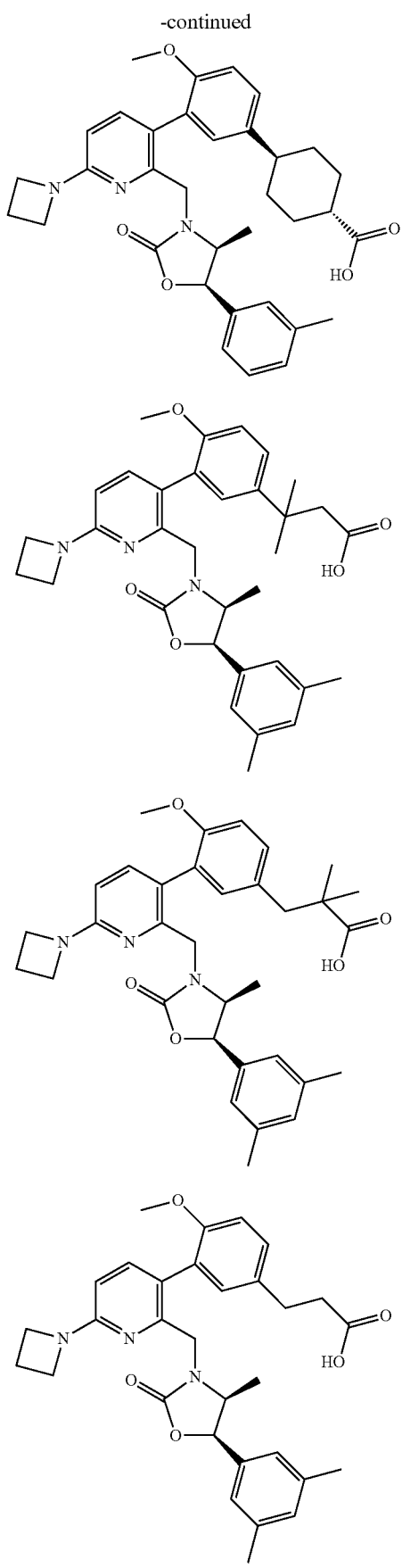

383
-continued
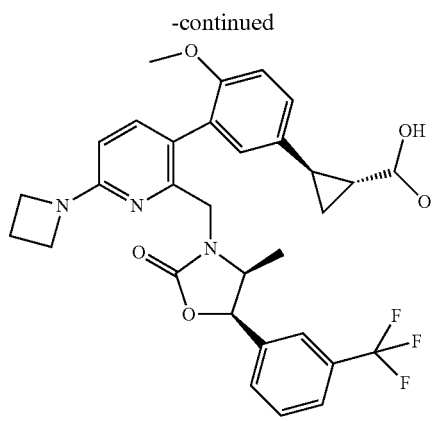
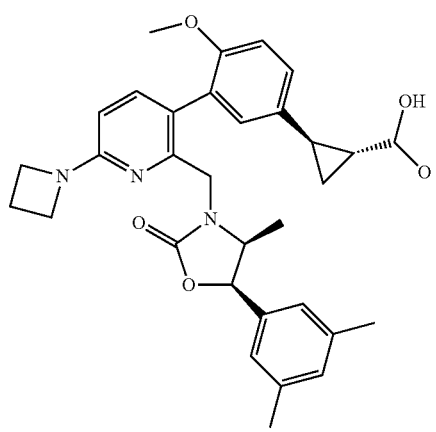
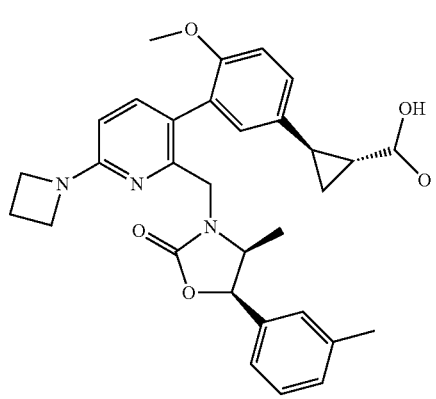
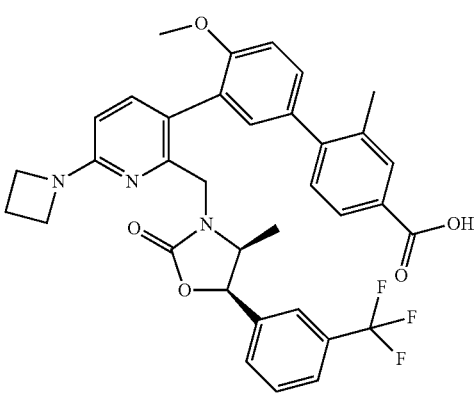
384
-continued
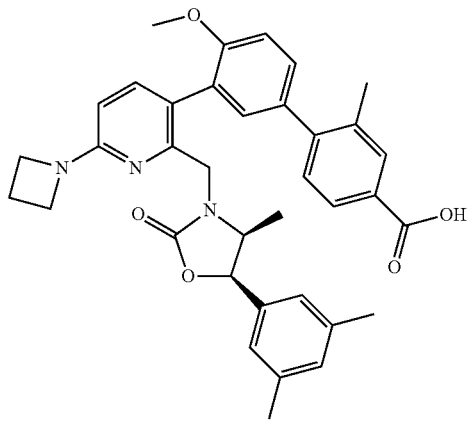
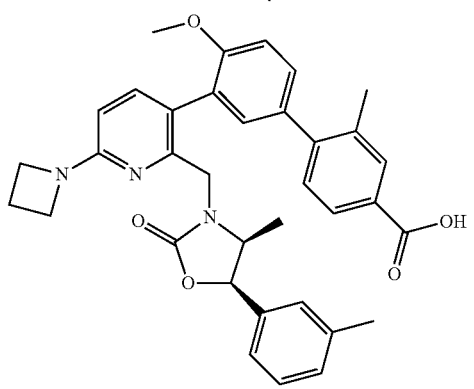
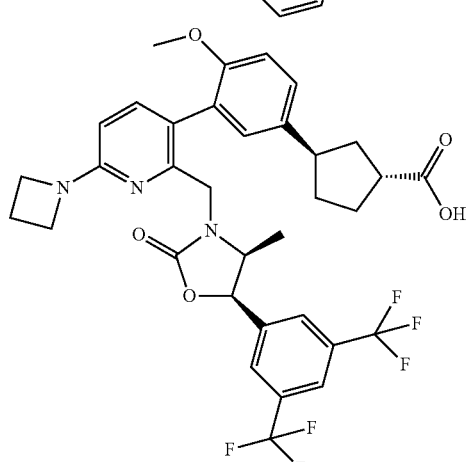
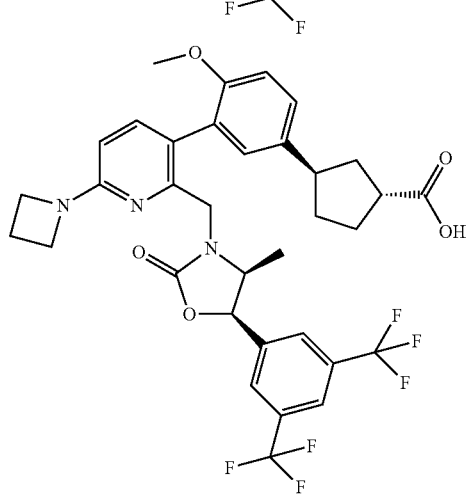

385
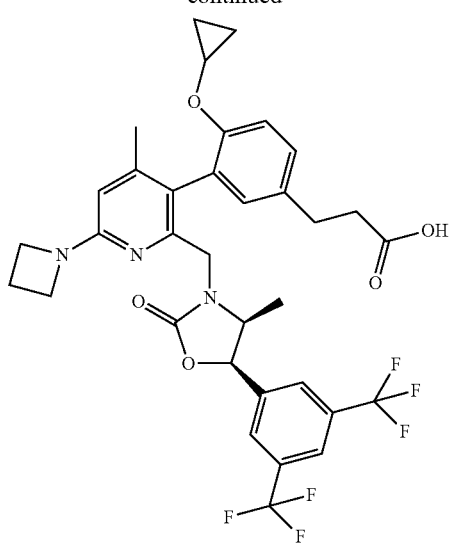
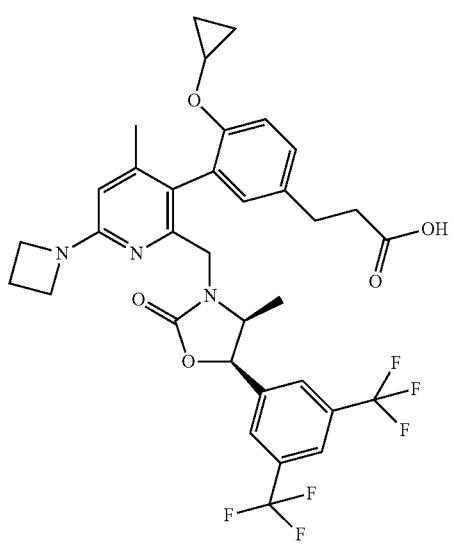
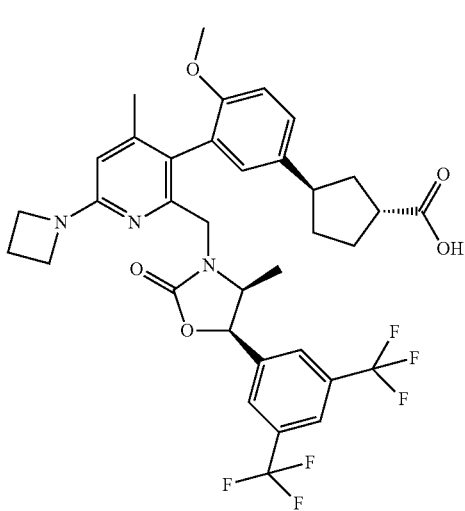
386
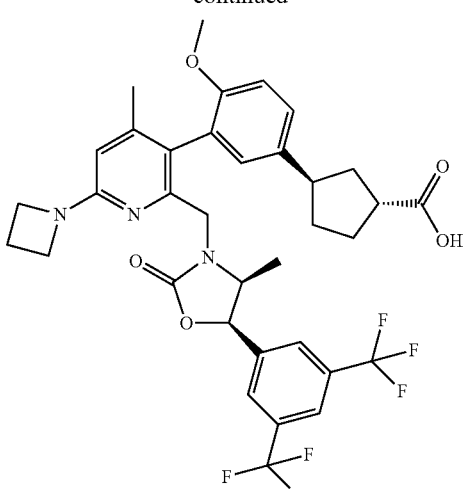
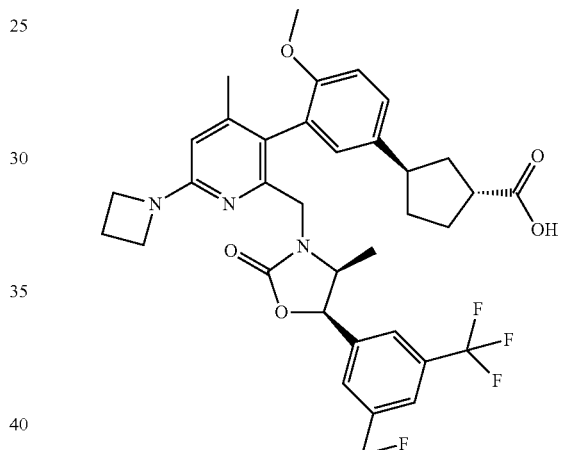
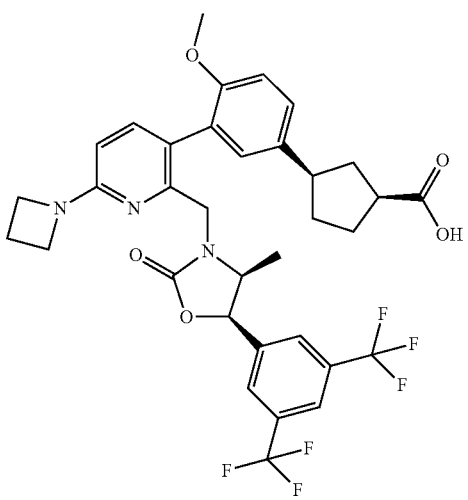

387
-continued
388
-continued
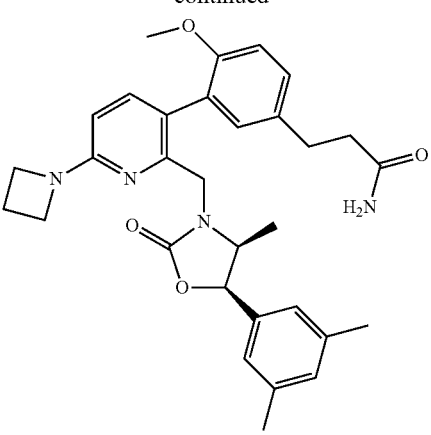
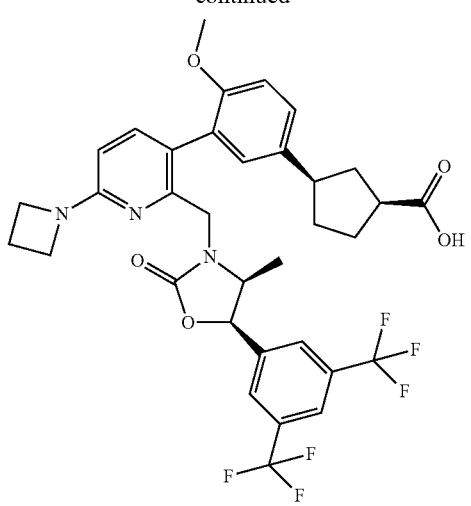
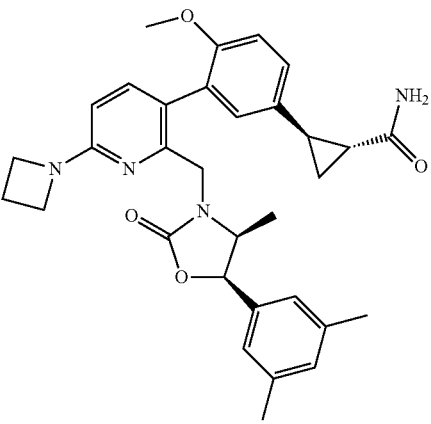
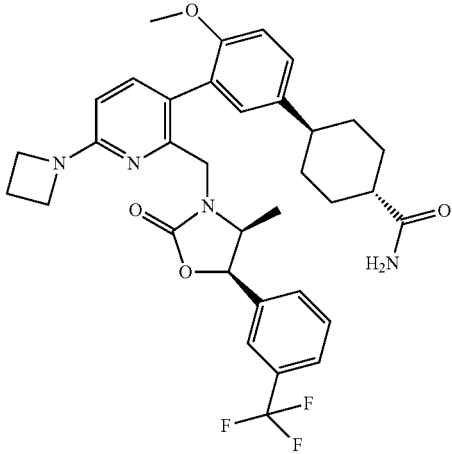
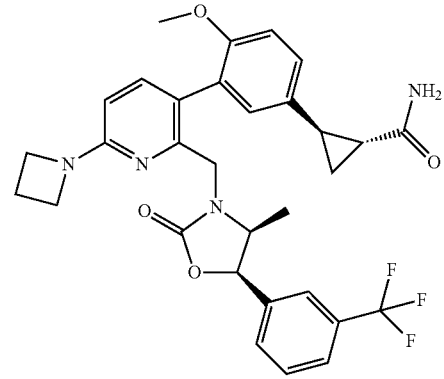

389
-continued
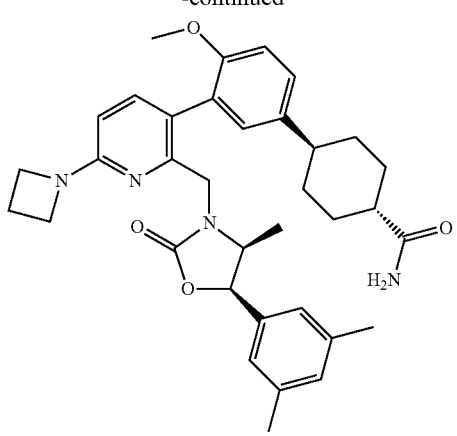
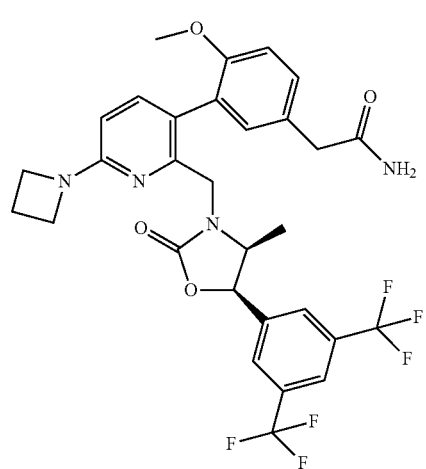
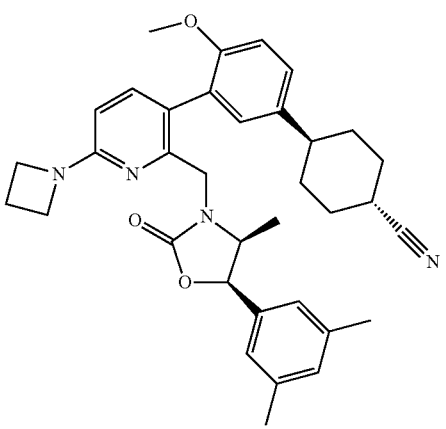
390
-continued
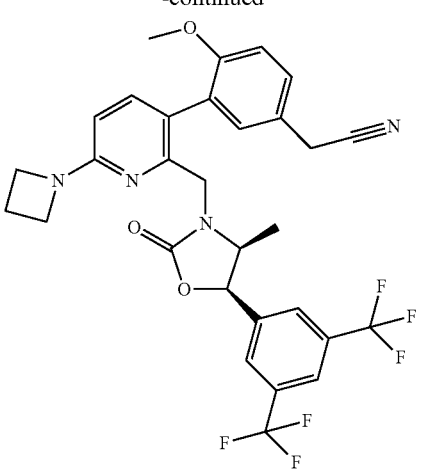
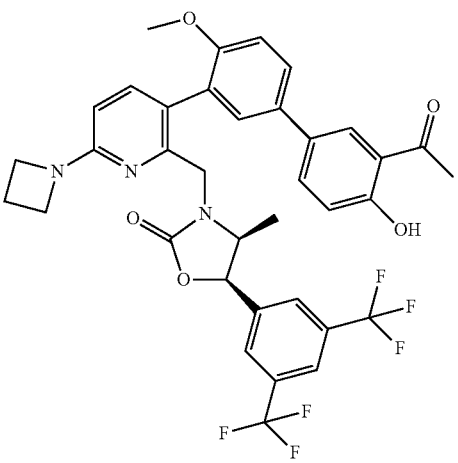
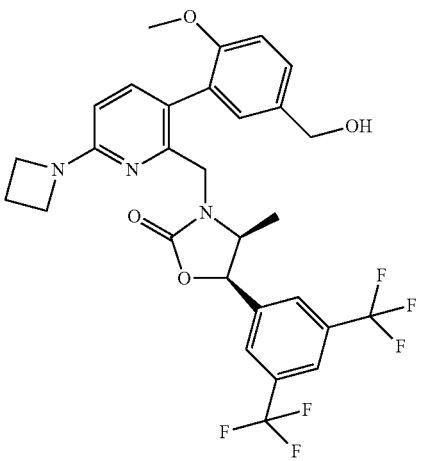

391
-continued
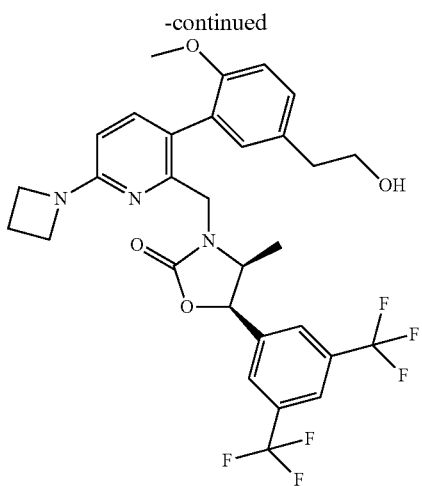
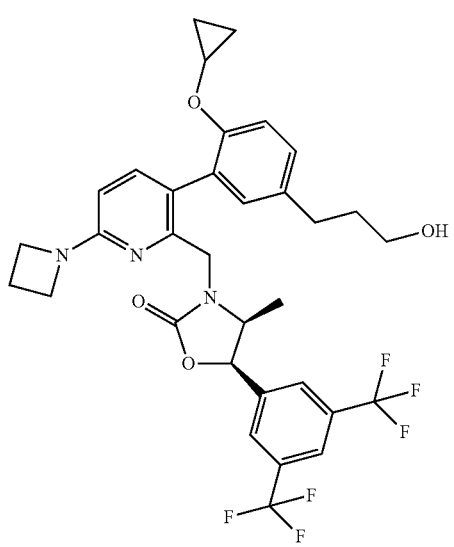
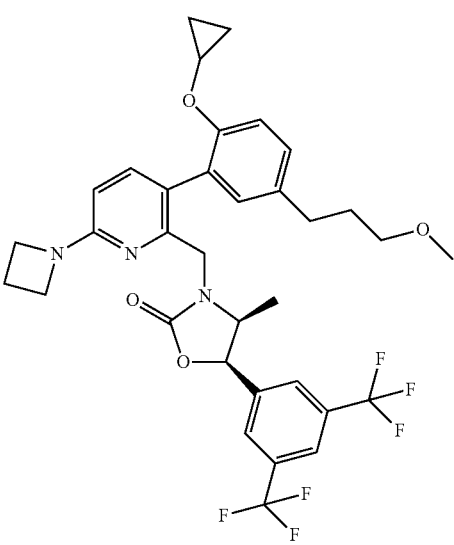
392
-continued
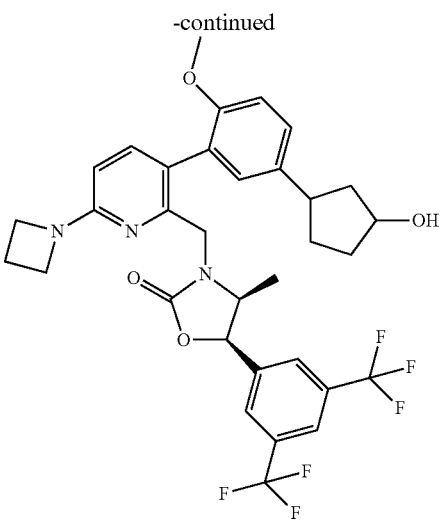
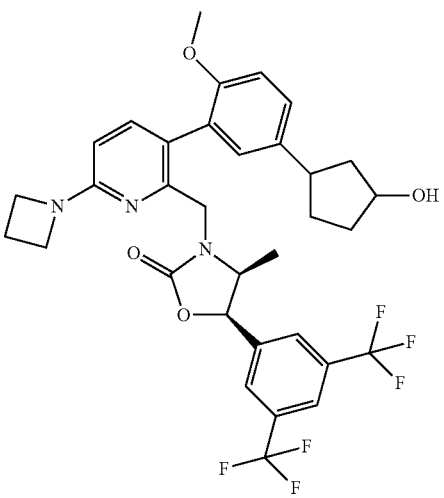
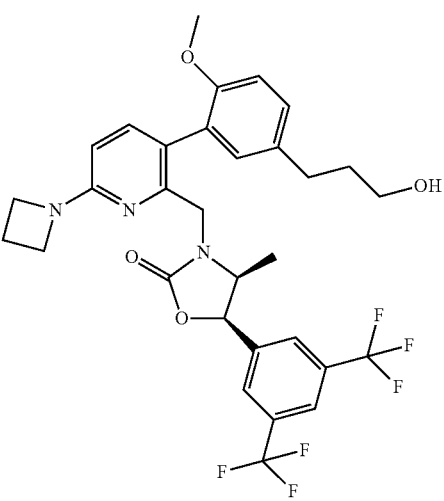

393
-continued
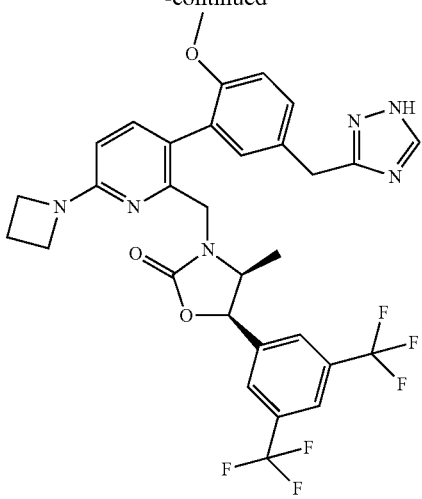
394
-continued
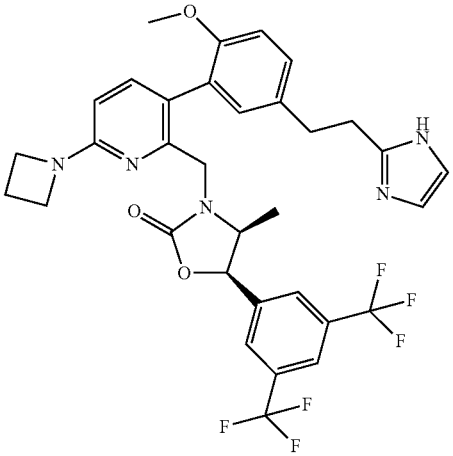
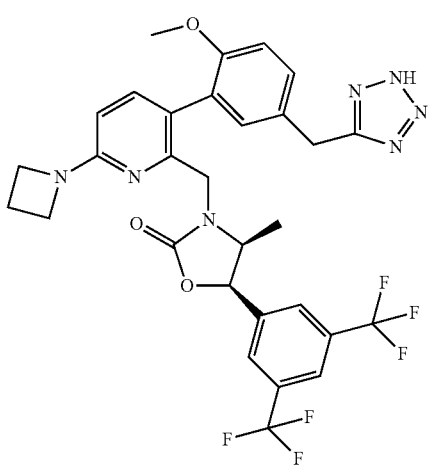
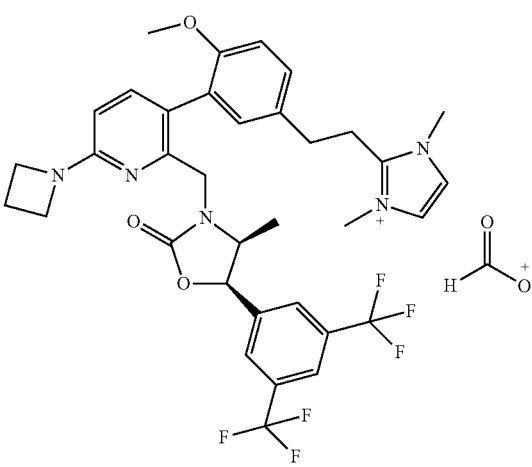
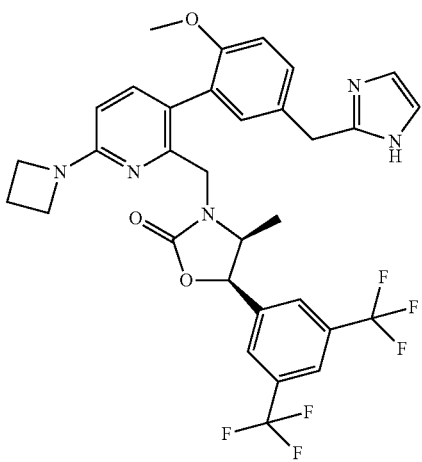
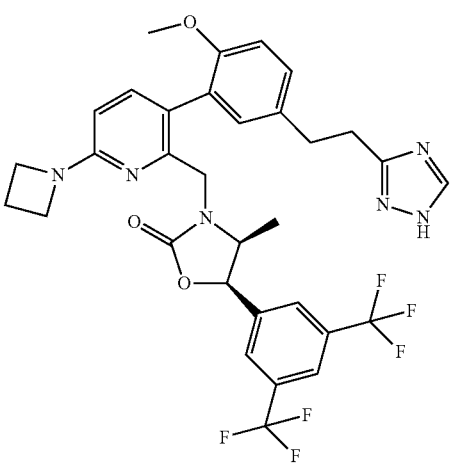

395
-continued
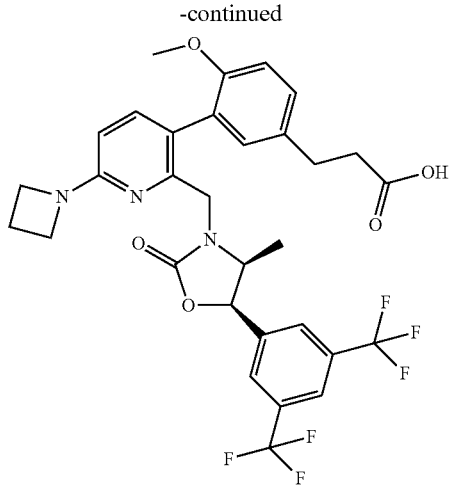
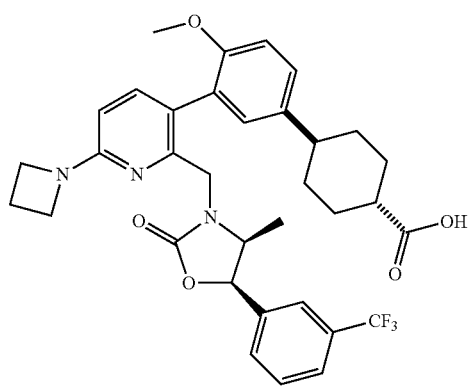
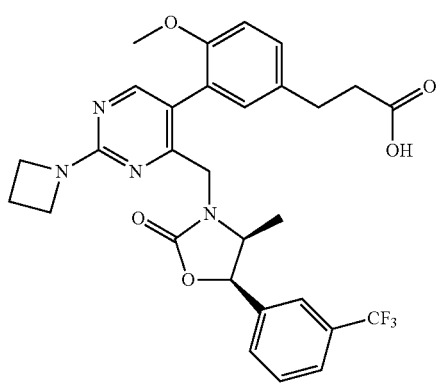
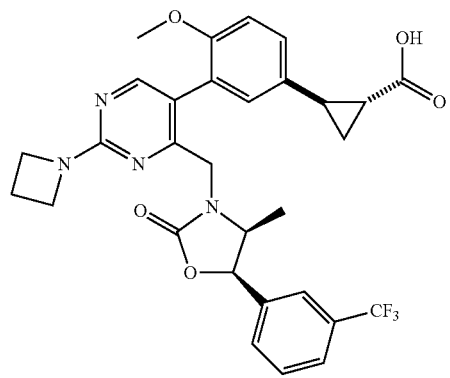
396
-continued
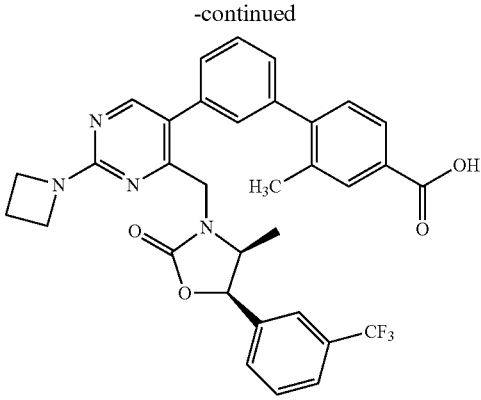
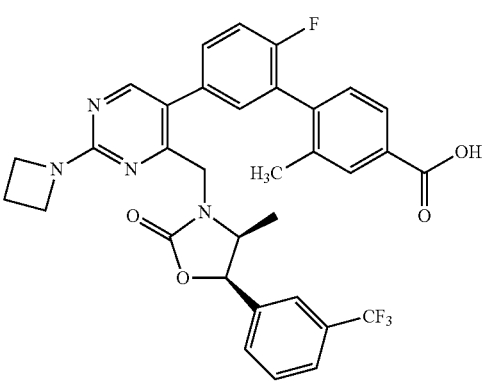
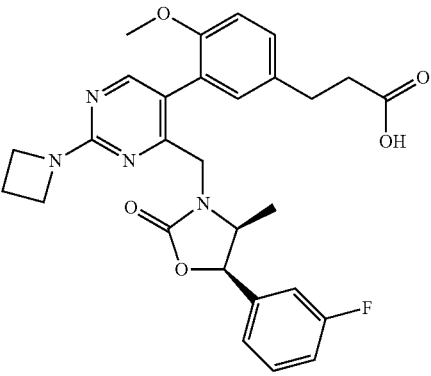
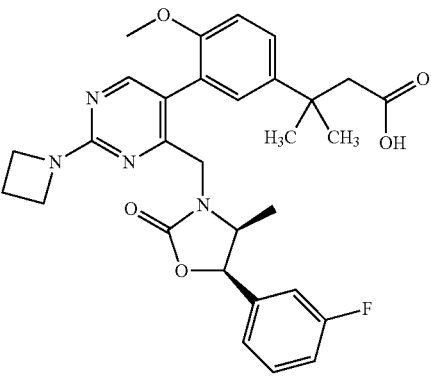

397
-continued
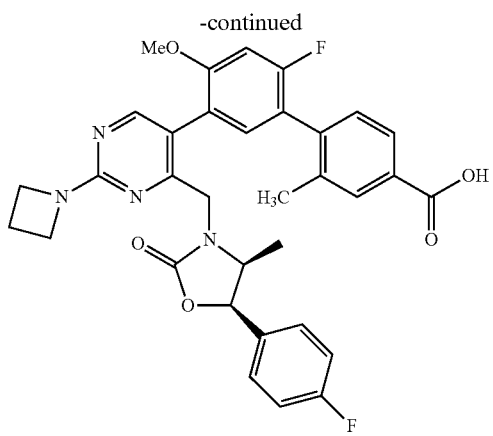
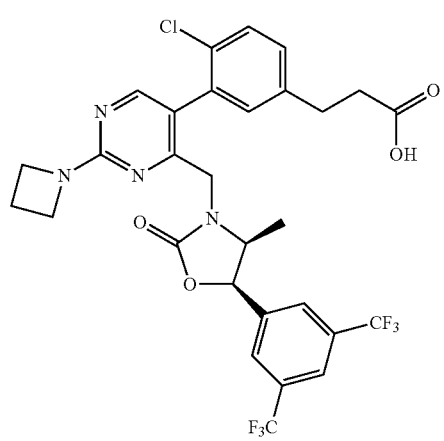
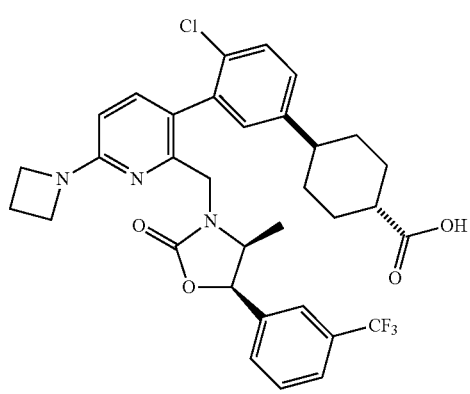
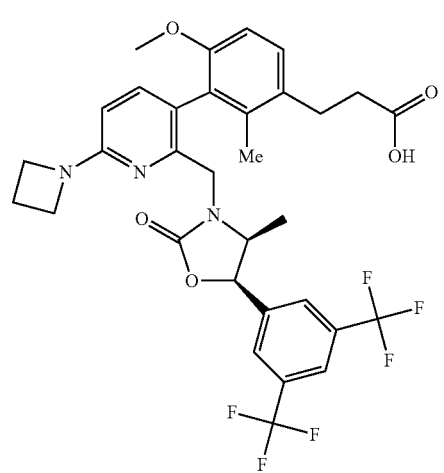
398
-continued
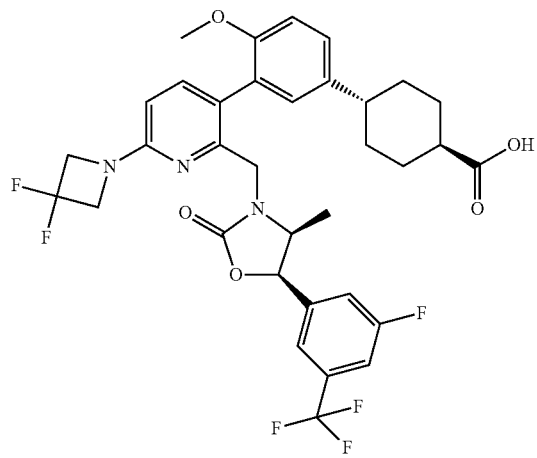
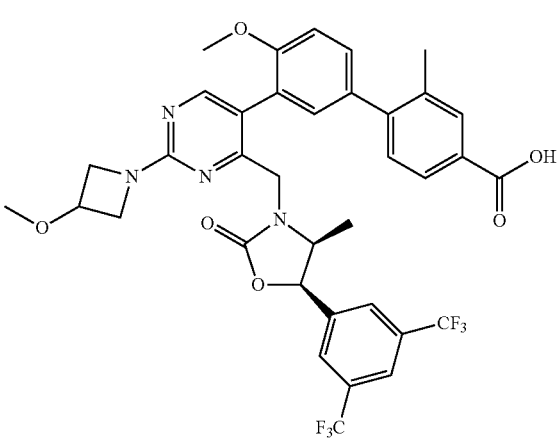
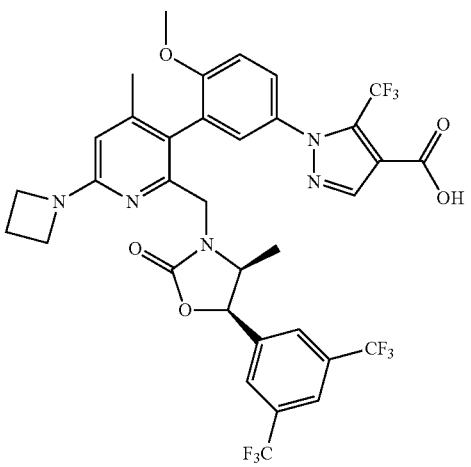

399
-continued
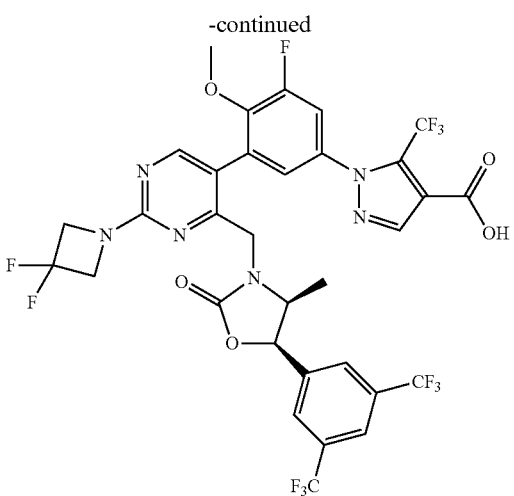
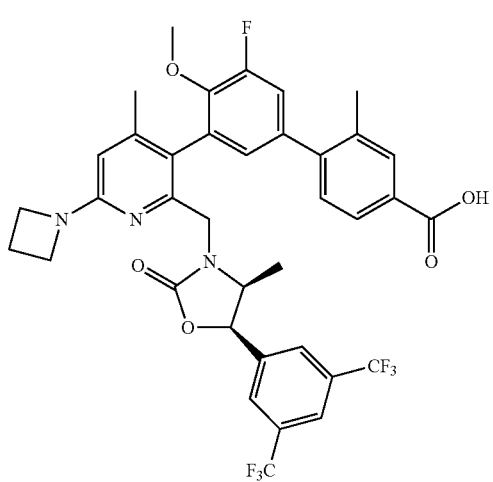
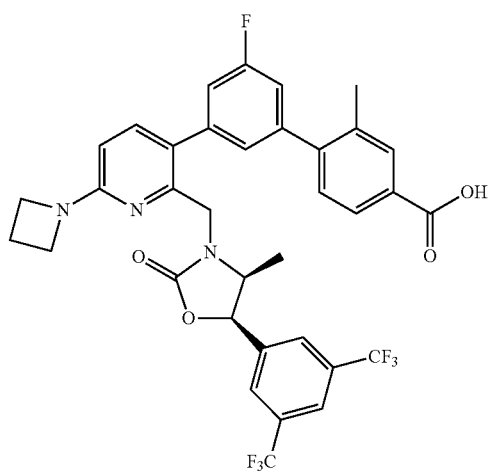
400
-continued
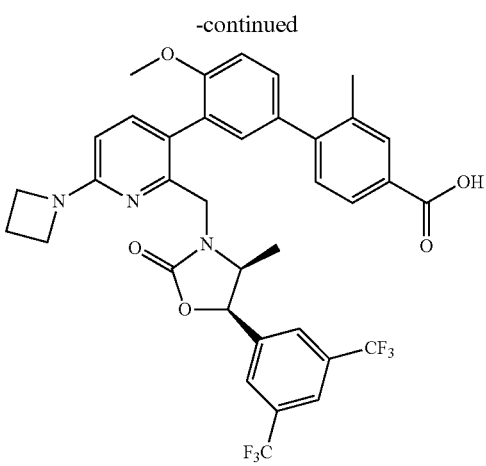
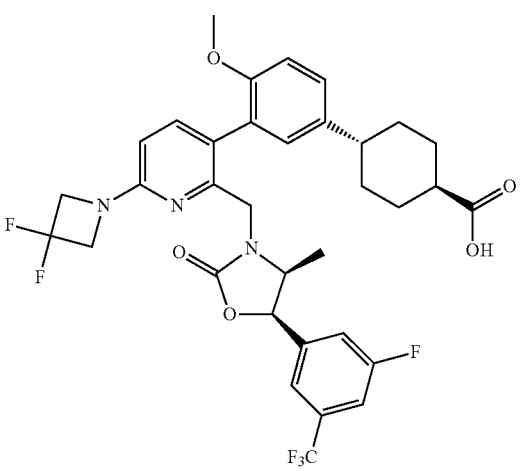
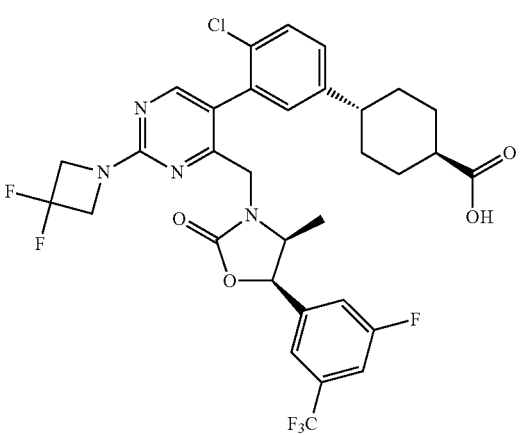

401
-continued
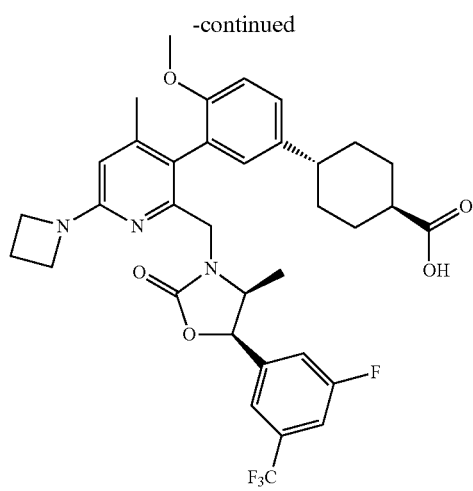
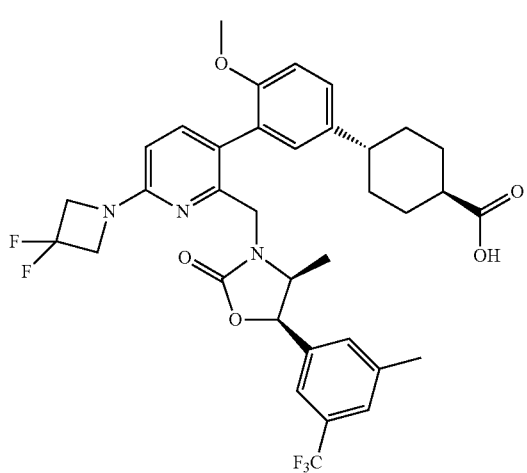
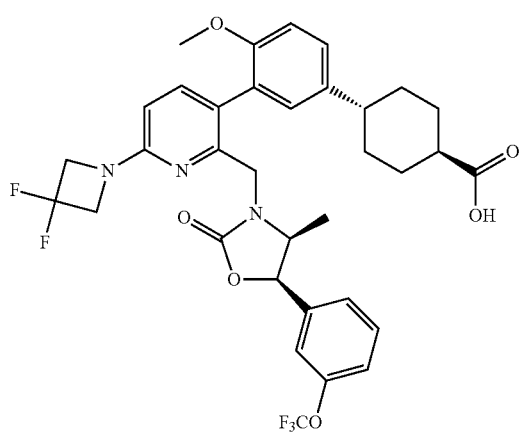
402
-continued
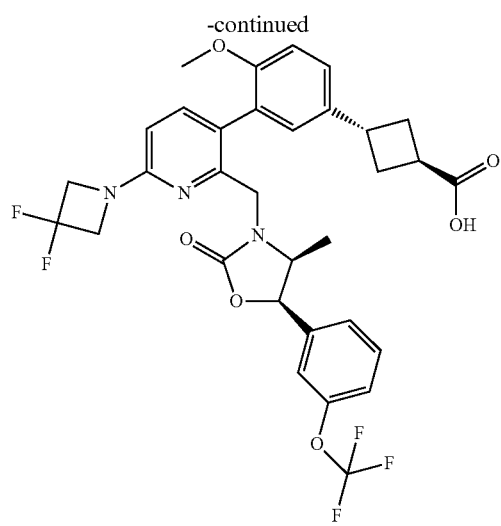
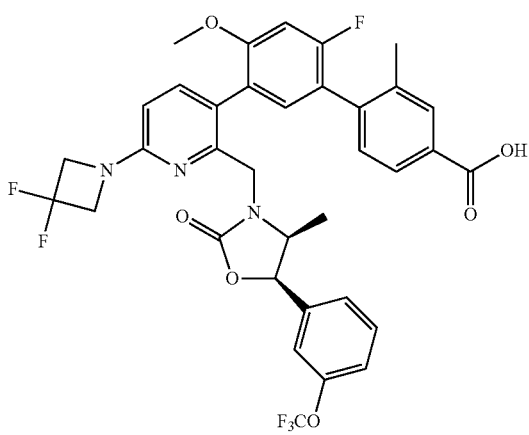
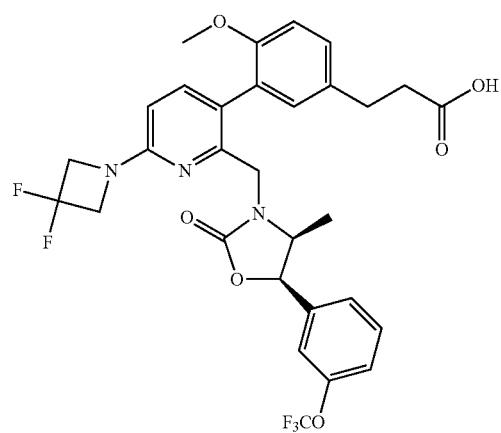

403
-continued
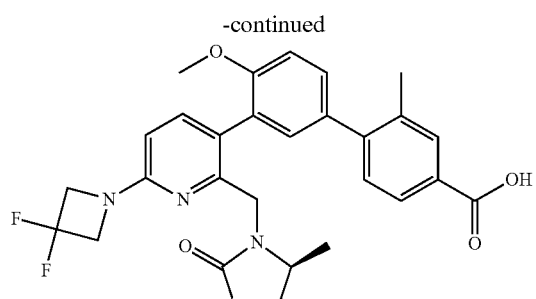
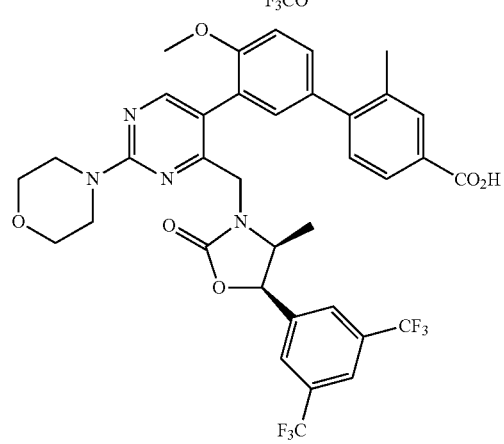
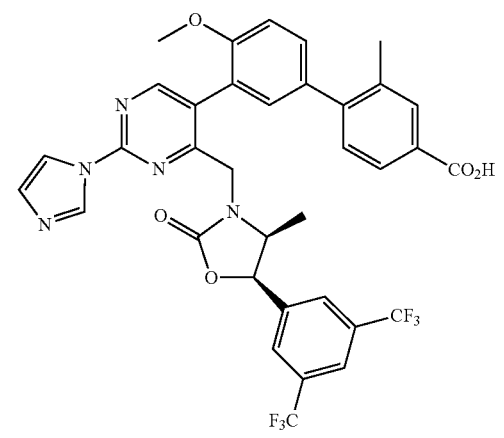
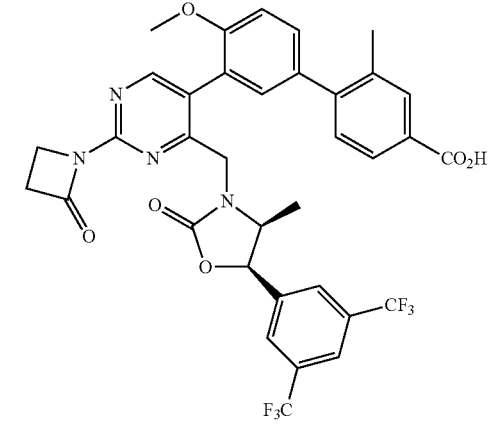
404
-continued
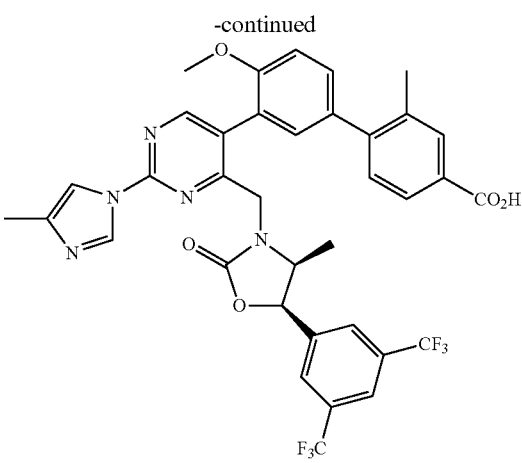
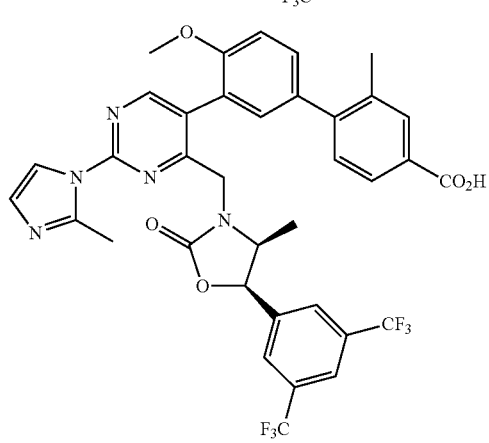
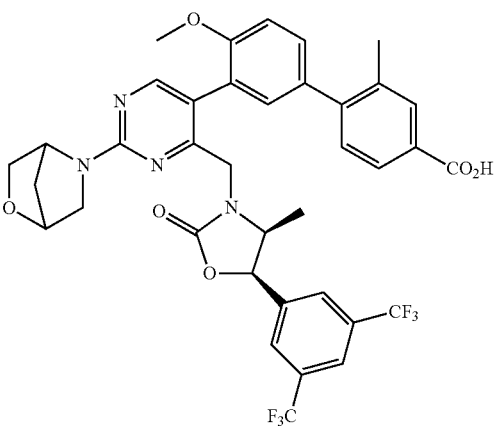
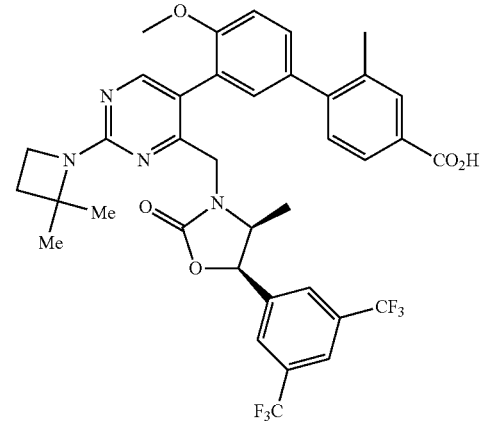

405
-continued
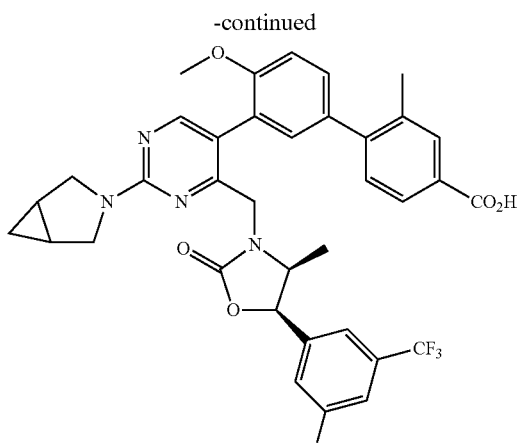
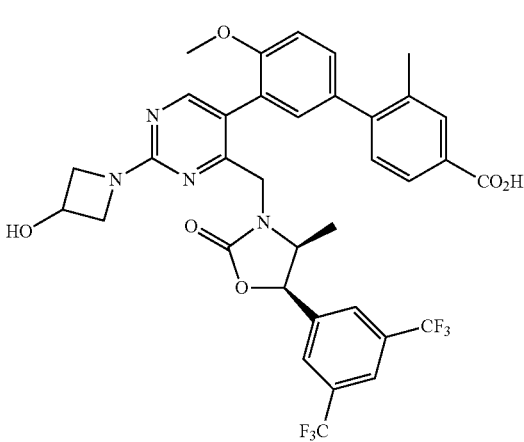
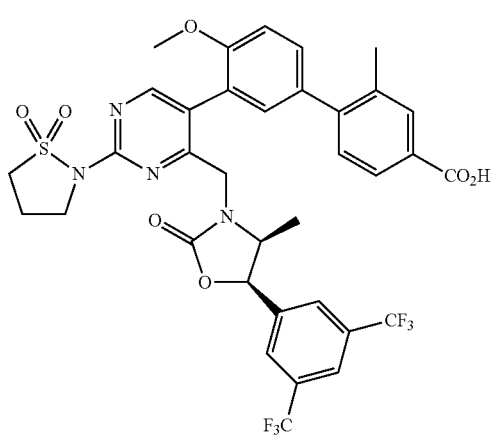
406
-continued
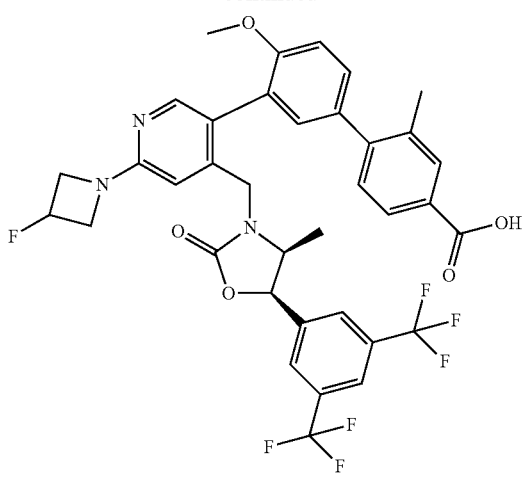
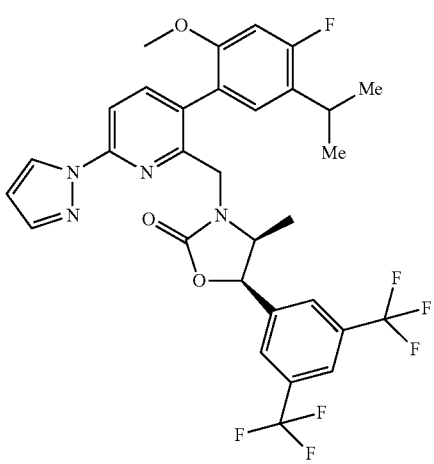
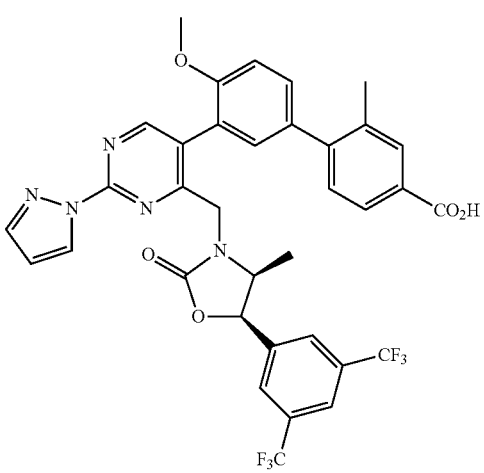

-continued

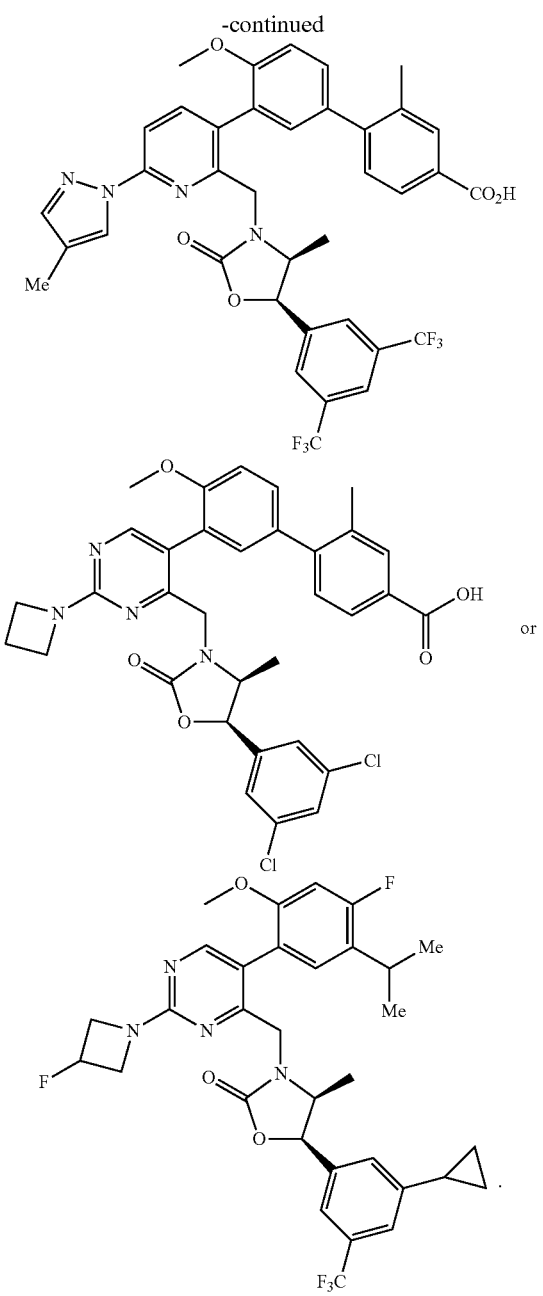

8. A pharmaceutical composition comprising the compound of claim 1, or a pharmaceutically acceptable salt thereof, and a pharmaceutically acceptable carrier.

9. A method of treating atherosclerosis in a patient in need of treatment comprising the administration of a therapeutically effective amount of the compound of claim 1 to said patient, or a pharmaceutically acceptable salt thereof.

10. A method of raising HDL-C in a patient in need of treatment comprising the administration of a therapeutically effective amount of the compound of claim 1 to said patient, or a pharmaceutically acceptable salt thereof.

11. A method of lowering LDL-C in a patient in need of treatment comprising the administration of a therapeutically effective amount of the compound of claim 1 to said patient, or a pharmaceutically acceptable salt thereof.

12. A method of treating dyslipidemia in a patient in need of treatment comprising the administration of a therapeutically effective amount of the compound of claim 1 to said patient, or a pharmaceutically acceptable salt thereof.

13. A pharmaceutical composition comprising the compound of claim 1 or a pharmaceutically acceptable salt thereof, a pharmaceutically acceptable carrier, and one or more active ingredients which are:
   (i) HMG-CoA reductase inhibitors;
   (ii) bile acid sequestrants;
   (iii) niacin and related compounds;
   (iv) PPARα agonists;
   (v) cholesterol absorption inhibitors;
   (vi) acyl CoA:cholesterol acyltransferase (ACAT) inhibitors;
   (vii) phenolic anti-oxidants;
   (viii) microsomal triglyceride transfer protein (MTP)/ApoB secretion inhibitors;
   (ix) anti-oxidant vitamins;
   (x) thyromimetics;
   (xi) LDL (low density lipoprotein) receptor inducers;
   (xii) platelet aggregation inhibitors;
   (xiii) vitamin B12 (also known as cyanocobalamin);
   (xiv) folic acid or a pharmaceutically acceptable salt or ester thereof;
   (xv) FXR and LXR ligands;
   (xvi) agents that enhance ABCA1 gene expression; or
   (xvii) ileal bile acid transporters.

14. The compound

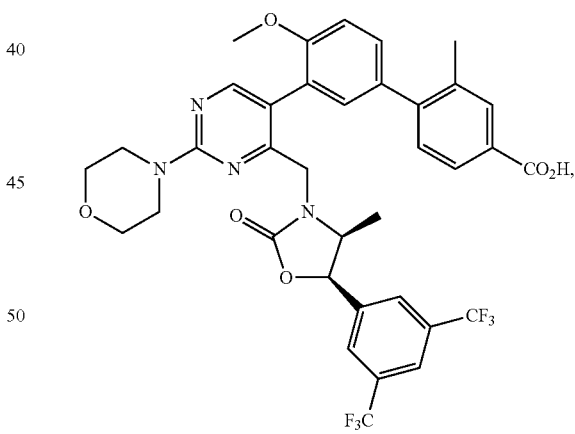

or a pharmaceutically acceptable salt thereof.

* * * * *